US012123030B2

(12) United States Patent
Benenato et al.

(10) Patent No.: US 12,123,030 B2
(45) **Date of Patent: *Oct. 22, 2024**

(54) POLYNUCLEOTIDES ENCODING LIPOPROTEIN LIPASE FOR THE TREATMENT OF HYPERLIPIDEMIA

(71) Applicant: ModernaTX, Inc., Cambridge, MA (US)

(72) Inventors: Kerry Benenato, Cambridge, MA (US); Stephen Hoge, Cambridge, MA (US); Paolo Martini, Boston, MA (US); Iain McFadyen, Medford, MA (US); Vladimir Presnyak, Manchester, NH (US); Ellalahewage Sathyajith Kumarasinghe, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,368

(22) PCT Filed: May 18, 2017

(86) PCT No.: PCT/US2017/033403

§ 371 (c)(1),
(2) Date: Nov. 16, 2018

(87) PCT Pub. No.: WO2017/201333

PCT Pub. Date: Nov. 23, 2017

(65) Prior Publication Data

US 2019/0390181 A1 Dec. 26, 2019

Related U.S. Application Data

(60) Provisional application No. 62/338,420, filed on May 18, 2016, provisional application No. 62/473,939, filed on Mar. 20, 2017.

(51) Int. Cl.
*A61K 48/00* (2006.01)
*A61K 9/127* (2006.01)
(Continued)

(52) U.S. Cl.
CPC .............. *C12N 9/20* (2013.01); *A61K 9/1274* (2013.01); *A61K 9/5123* (2013.01); *A61K 47/14* (2013.01);
(Continued)

(58) Field of Classification Search
CPC .......... A61K 48/00; A61K 9/51; A61K 47/16; A61K 47/22; A61K 47/14; A61K 9/5123; A61K 9/513; A61P 3/06
See application file for complete search history.

(56) References Cited

U.S. PATENT DOCUMENTS 8,691,966 B2 4/2014 Kariko et al.
9,095,552 B2 8/2015 Chakraborty et al.
(Continued)

FOREIGN PATENT DOCUMENTS

WO WO-2007075531 A2 * 7/2007 .......... C10M 141/12
WO WO2010053572 5/2010
(Continued)

OTHER PUBLICATIONS

Extended European Search Report in EP Application No. 17800198.8, dated Feb. 18, 2020, 9 pages.
(Continued)

*Primary Examiner* — Micah Paul Young
(74) *Attorney, Agent, or Firm* — Fish & Richardson P.C.

(57) ABSTRACT

The invention relates to mRNA therapy for the treatment of hyperlipidemia. mRNAs for use in the invention, when administered in vivo, encode human lipoprotein lipase (LPL), isoforms thereof, functional fragments thereof, and fusion proteins comprising LPL. mRNAs of the invention
(Continued)

A

SEQ ID NO: 1 (LPL; lipoprotein lipase, wt)

```
MESKALLVLTLAVWLQSLTASRGGVAAADQRRDFIDIESKFALRTPEDTAEDTCHLIPG
VAESVATCHFNHSSKTFMVIHGWTVTGMYESWVPKLVAALYKREPDSNVIVVDWLSRAQ
EHYPVSAGYTKLVGQDVARFINWMEEEFNYPLDNVHLLGYSLGAHAAGIAGSLTNKKVN
RITGLDPAGPNFEYAEAPSRLSPDDADFVDVLHTFTRGSPGRSIGIQKPVGHVDIYPNG
GTFQPGCNIGEAIRVIAERGLGDVDQLVKCSHERSIHLFIDSLLNEENPSKAYRCSSKE
AFEKGLCLSCRKNRCNNLGYEINKVRAKRSSKMYLKTRSQMPYKVFHYQVKIHFSGTES
ETHTNQAFEISLYGTVAESENIPFTLPEVSTNKTYSFLIYTEVDIGELLMLKLKWKSDS
YFSWSDWWSSPGFAIQKIRVKAGETQKKVIFCSREKVSHLQKGKAPAVFVKCHDKSLNK
KSG
```

lipoprotein lipase, Uniprot Acc. No. P06858. This isoform has been chosen as the 'canonical' sequence. All positional information in this entry refers to it.

B

| Feature | Position | Length | Description |
| --- | --- | --- | --- |
| Active site | 159-159 | 1 | Nucleophile |
| Active site | 183-183 | 1 | Charge relay system |
| Active site | 268-268 | 1 | Charge relay system |
| Signal peptide | 1-27 | 27 | Signal peptide |
| Domain | 28-475 | 448 | Lipoprotein lipase |

C are preferably encapsulated in lipid nanoparticles (LNPs) to effect efficient delivery to cells and/or tissues in subjects, when administered thereto, mRNA therapies of the invention increase and/or restore deficient levels of LPL expression and/or activity in subjects. mRNA therapies of the invention further decrease levels of triglycerides associated with deficient LPL activity in subjects.

55 Claims, 43 Drawing Sheets

Specification includes a Sequence Listing.

(51) Int. Cl.

| | |
|---|---|
| ***A61K 9/51*** | (2006.01) |
| ***A61K 47/14*** | (2017.01) |
| ***C12N 9/20*** | (2006.01) |
| *B82Y 5/00* | (2011.01) |
| *B82Y 30/00* | (2011.01) |

(52) U.S. Cl.

CPC ................ *B82Y 5/00* (2013.01); *B82Y 30/00* (2013.01); *C12Y 301/01034* (2013.01)

(56) References Cited

U.S. PATENT DOCUMENTS

| | | | | |
|---|---|---|---|---|
| 9,107,886 | B2 | 8/2015 | Chakraborty et al. | |
| 9,114,113 | B2 | 8/2015 | Chakraborty et al. | |
| 9,220,792 | B2 | 12/2015 | Chakraborty et al. | |
| 9,233,141 | B2 | 1/2016 | Chakraborty et al. | |
| 9,814,760 | B2 | 11/2017 | Bancel et al. | |
| 9,867,888 | B2 * | 1/2018 | Benenato | A61K 48/005 |
| 9,868,691 | B2 * | 1/2018 | Benenato | C07D 263/20 |
| 9,868,692 | B2 * | 1/2018 | Benenato | A61K 9/1272 |
| 9,868,693 | B2 * | 1/2018 | Benenato | C07K 14/505 |
| 10,702,478 | B2 | 7/2020 | Guild et al. | |
| 2011/0201673 | A1 | 8/2011 | Hayden et al. | |
| 2012/0295832 | A1 | 11/2012 | Constien et al. | |
| 2014/0148502 | A1 | 5/2014 | Bancel et al. | |
| 2014/0155472 | A1 | 6/2014 | Bancel et al. | |
| 2014/0155473 | A1 | 6/2014 | Bancel et al. | |
| 2014/0155474 | A1 | 6/2014 | Bancel et al. | |
| 2014/0155475 | A1 | 6/2014 | Bancel et al. | |
| 2014/0193482 | A1 | 7/2014 | Bancel et al. | |
| 2014/0194494 | A1 | 7/2014 | Bancel et al. | |
| 2014/0200263 | A1 | 7/2014 | Bancel et al. | |
| 2014/0275229 | A1 | 9/2014 | Bancel et al. | |
| 2018/0311381 | A1 | 11/2018 | Bancel et al. | |
| 2019/0175517 | A1 | 6/2019 | Martini et al. | |
| 2019/0298657 | A1 | 10/2019 | Martini et al. | |
| 2019/0298658 | A1 | 10/2019 | Martini et al. | |
| 2019/0300906 | A1 | 10/2019 | Martini et al. | |
| 2020/0078314 | A1 | 3/2020 | Martini et al. | |
| 2020/0085916 | A1 | 3/2020 | Martini et al. | |

FOREIGN PATENT DOCUMENTS

| | | | |
|---|---|---|---|
| WO | WO2011/068810 | 6/2011 | |
| WO | WO2013/086373 | 6/2013 | |
| WO | WO2013151666 | 10/2013 | |
| WO | WO-2013151666 A2 * | 10/2013 | A61K 38/17 |
| WO | WO2013151736 | 10/2013 | |
| WO | WO2015199952 | 12/2015 | |
| WO | WO-2015199952 A1 * | 12/2015 | A61K 38/4846 |
| WO | WO2017/049245 | 3/2017 | |
| WO | WO-2017049245 A2 * | 3/2017 | A61K 31/7105 |
| WO | WO2017070616 | 4/2017 | |
| WO | WO2017075531 | 5/2017 | |

OTHER PUBLICATIONS

Ferland et al., "Tissue-specific Responses of Lipoprotein Lipase to Dietary Macronutrient Composition as a Predictor of Weight Gain Over 4 Years", Obesity : A Research Journal, 2012, 20(5):1006-1011.

International Preliminary Report on Patentability in International Application No. PCT/US2017/033403, dated Nov. 29, 2018, 9 pages.

Lo et al., "Lipoprotein Lipase: Role of Intramolecular Disulfide Bonds in Enzyme Catalysis", Biochemical and Biophysical Research Communications, 1995, 206(1):266-271.

Mead et al., "Lipoprotein lipase: structure, function, regulation, and role in disease", Journal of Molecular Medicine, 2002, 80(12): 753-769.

Partial European Search Report in EP Application No. 17800198.8, dated Nov. 15, 2019, 11 pages.

PCT International Search Report in International Application No. PCT/US2017/033403, dated Oct. 17, 2017, 18 pages.

Ranganathan et al., "The lipoprotein lipase (LPL)S447X gain of function variant involves increased mRNA translation", Atherosclerosis, 2012, 221(1):143-147 (See the abstract; the section entitled "2.4. In Vitro translation" on p. 144; the section entitled "2.1. Preparation of constructs" on p. 144).

Ranganathan et al., "Tissue-specific expression of human lipoprotein lipase", The Journal of Biological Chemistry, 1995, 270(13):7149-7155 (See the sections entitled "Cloning and transcription of full length 3.2- and 3.6-kb LPL cDNAs" and "In vitro translation" on p. 7150).

Tavernier et al., "mRNA as gene therapeutic: How to control protein expression", Journal of Controlled Release, 2011, 150: 238-247.

Yamamoto et al., "Current prospects for mRNA gene delivery" European Journal of Pharmaceutics and Biopharmaceutics, 2018, 6 pages.

Youn et al., "Modified mRNA as an alternative to plasmid DNA (pDNA) for transcript replacement and vaccination therapy", Expert Opinion on Biological Therapy, Jun. 2015, 15(9): 1337-1348.

* cited by examiner

A

SEQ ID NO: 1 (LPL; lipoprotein lipase, wt)

MESKALLVLTLAVWLQSLTASRGGVAAADQRRDFIDIESKFALRTPEDTAEDTCHLIPG
VAESVATCHFNHSSKTFMVIHGWTVTGMYESWVPKLVAALYKREPDSNVIVVDWLSRAQ
EHYPVSAGYTKLVGQDVARFINWMEEEFNYPLDNVHLLGYSLGAHAAGIAGSLTNKKVN
RITGLDPAGPNFEYAEAPSRLSPDDADFVDVLHTFTRGSPGRSIGIQKPVGHVDIYPNG
GTFQPGCNIGEAIRVIAERGLGDVDQLVKCSHERSIHLFIDSLLNEENPSKAYRCSSKE
AFEKGLCLSCRKNRCNNLGYEINKVRAKRSSKMYLKTRSQMPYKVFHYQVKIHFSGTES
ETHTNQAFEISLYGTVAESENIPFTLPEVSTNKTYSFLIYTEVDIGELLMLKLKWKSDS
YFSWSDWWSSPGFAIQKIRVKAGETQKKVIFCSREKVSHLQKGKAPAVFVKCHDKSLNK
KSG lipoprotein lipase, Uniprot Acc. No. P06858. This isoform has been chosen as the 'canonical' sequence. All positional information in this entry refers to it.

| Feature | Position | Length | Description |
|---|---|---|---|
| Active site | 159-159 | 1 | Nucleophile |
| Active site | 183-183 | 1 | Charge relay system |
| Active site | 268-268 | 1 | Charge relay system |
| Signal peptide | 1-27 | 27 | Signal peptide |
| Domain | 28-475 | 448 | Lipoprotein lipase |

D SEQ ID NO: 2

ATGGAGAGCAAAGCCCTGCTCGTGCTGACTCTGGCCGTGTGGCTCCAGAGTCTGACCGCCTCCCGCG
GAGGGGTGGCCGCCGCCGACCAAAGAAGAGATTTTATCGACATCGAAAGTAAATTTGCCCTAAGGAC
CCCTGAAGACACAGCTGAGGACACTTGCCACCTCATTCCCGGAGTAGCAGAGTCCGTGGCTACCTGT
CATTTCAATCACAGCAGCAAAACCTTCATGGTGATCCATGGCTGGACGGTAACAGGAATGTATGAGA
GTTGGGTGCCAAAACTTGTGGCCGCCCTGTACAAGAGAGAACCAGACTCCAATGTCATTGTGGTGGA
CTGGCTGTCACGGGCTCAGGAGCATTACCCAGTGTCCGCGGGCTACACCAAACTGGTGGGACAGGAT
GTGGCCCGGTTTATCAACTGGATGGAGGAGGAGTTTAACTACCCTCTGGACAATGTCCATCTCTTGG
GATACAGCCTTGGAGCCCATGCTGCTGGCATTGCAGGAAGTCTGACCAATAAGAAAGTCAACAGAAT
TACTGGCCTCGATCCAGCTGGACCTAACTTTGAGTATGCAGAAGCCCCGAGTCGTCTTTCTCCTGAT
GATGCAGATTTTGTAGACGTCTTACACACATTCACCAGAGGGTCCCCTGGTCGAAGCATTGGAATCC
AGAAACCAGTTGGGCATGTTGACATTTACCCGAATGGAGGTACTTTTCAGCCAGGATGTAACATTGG
AGAAGCTATCCGCGTGATTGCAGAGAGAGGACTTGGAGATGTGGACCAGCTAGTGAAGTGCTCCCAC
GAGCGCTCCATTCATCTCTTCATCGACTCTCTGTTGAATGAAGAAAATCCAAGTAAGGCCTACAGGT
GCAGTTCCAAGGAAGCCTTTGAGAAAGGGCTCTGCTTGAGTTGTAGAAAGAACCGCTGCAACAATCT
GGGCTATGAGATCAATAAAGTCAGAGCCAAAAGAAGCAGCAAAATGTACCTGAAGACTCGTTCTCAG
ATGCCCTACAAAGTCTTCCATTACCAAGTAAAGATTCATTTTTCTGGGACTGAGAGTGAAACCCATA
CCAATCAGGCCTTTGAGATTTCTCTGTATGGCACCGTGGCCGAGAGTGAGAACATCCCATTCACTCT
GCCTGAAGTTTCCACAAATAAGACCTACTCCTTCCTAATTTACACAGAGGTAGATATTGGAGAACTA
CTCATGTTGAAGCTCAAATGGAAGAGTGATTCATACTTTAGCTGGTCAGACTGGTGGAGCAGTCCCG
GCTTCGCCATTCAGAAGATCAGAGTAAAAGCAGGAGAGACTCAGAAAAAGGTGATCTTCTGTTCTAG
GGAGAAAGTGTCTCATTTGCAGAAAGGAAAGGCACCTGCGGTATTTGTGAAATGCCATGACAAGTCT
CTGAATAAGAAGTCAGGC

Underlined nucleobases indicate region encoding the signal peptide (1-81)

SEQ ID NO: 3 (LPL-stop; lipoprotein lipase, S447Stop)

MESKALLVLTLAVWLQSLTASRGGVAAADQRRDFIDIESKFALRTPEDTAEDTCHLIPG
VAESVATCHFNHSSKTFMVIHGWTVTGMYESWVPKLVAALYKREPDSNVIVVDWLSRAQ
EHYPVSAGYTKLVGQDVARFINWMEEEFNYPLDNVHLLGYSLGAHAAGIAGSLTNKKVN
RITGLDPAGPNFEYAEAPSRLSPDDADFVDVLHTFTRGSPGRSIGIQKPVGHVDIYPNG
GTFQPGCNIGEAIRVIAERGLGDVDQLVKCSHERSIHLFIDSLLNEENPSKAYRCSSKE
AFEKGLCLSCRKNRCNNLGYEINKVRAKRSSKMYLKTRSQMPYKVFHYQVKIHFSGTES
ETHTNQAFEISLYGTVAESENIPFTLPEVSTNKTYSFLIYTEVDIGELLMLKLKWKSDS
YFSWSDWWSSPGFAIQKIRVKAGETQKKVIFCS

See Lipoprotein lipase, Uniprot Acc. No. P06858.

| Feature | Position | Length | Description |
|---|---|---|---|
| Active site | 159-159 | 1 | Nucleophile |
| Active site | 183-183 | 1 | Charge relay system |
| Active site | 268-268 | 1 | Charge relay system |
| Signal peptide | 1-27 | 27 | |
| Domain | 28-475 | 448 | Lipoprotein lipase |

C

D SEQ ID NO: 4

ATGGAGAGCAAGGCCCTGCTGGTGCTGACCCTGGCCGTGTGGCTGCAGAGCCTGACCGCCAGCAGAG
GCGGCGTGGCCGCCGCCGACCAGAGAAGAGACTTCATCGACATCGAGAGCAAGTTCGCCCTGAGAAC
CCCCGAGGACACCGCCGAGGACACCTGCCACCTGATCCCCGGCGTGGCCGAGAGCGTGGCCACCTGC
CACTTCAACCACAGCAGCAAGACCTTCATGGTGATCCACGGCTGGACCGTGACCGGCATGTACGAGA
GCTGGGTGCCCAAGCTGGTGGCCGCCCTGTACAAGAGAGAGCCCGACAGCAACGTGATCGTGGTGGA
CTGGCTGAGCAGAGCCCAGGAGCACTACCCCGTGAGCGCCGGCTACACCAAGCTGGTGGGCCAGGAC
GTGGCCAGATTCATCAACTGGATGGAGGAGGAGTTCAACTACCCCCTGGACAACGTGCACCTGCTGG
GCTACAGCCTGGGCGCCCACGCCGCCGGCATCGCCGGCAGCCTGACCAACAAGAAGGTGAACAGAAT
CACCGGCCTGGACCCCGCCGGCCCCAACTTCGAGTACGCCGAGGCCCCCAGCAGACTGAGCCCCGAC
GACGCCGACTTCGTGGACGTGCTGCACACCTTCACCAGAGGCAGCCCCGGCAGAAGCATCGGCATCC
AGAAGCCCGTGGGCCACGTGGACATCTACCCCAACGGCGGCACCTTCCAGCCCGGCTGCAACATCGG
CGAGGCCATCAGAGTGATCGCCGAGAGAGGCCTGGGCGACGTGGACCAGCTGGTGAAGTGCAGCCAC
GAGAGAAGCATCCACCTGTTCATCGACAGCCTGCTGAACGAGGAGAACCCCAGCAAGGCCTACAGAT
GCAGCAGCAAGGAGGCCTTCGAGAAGGGCCTGTGCCTGAGCTGCAGAAAGAACAGATGCAACAACCT
GGGCTACGAGATCAACAAGGTGAGAGCCAAGAGAAGCAGCAAGATGTACCTGAAGACCAGAAGCCAG
ATGCCCTACAAGGTGTTCCACTACCAGGTGAAGATCCACTTCAGCGGCACCGAGAGCGAGACCCACA
CCAACCAGGCCTTCGAGATCAGCCTGTACGGCACCGTGGCCGAGAGCGAGAACATCCCCTTCACCCT
GCCCGAGGTGAGCACCAACAAGACCTACAGCTTCCTGATCTACACCGAGGTGGACATCGGCGAGCTG
CTGATGCTGAAGCTGAAGTGGAAGAGCGACAGCTACTTCAGCTGGAGCGACTGGTGGAGCAGCCCCG
GCTTCGCCATCCAGAAGATCAGAGTGAAGGCCGGCGAGACCCAGAAGAAGGTGATCTTCTGCAGC

Underlined nucleobases indicate region encoding the signal peptide (1-81)

FIG. 2 (cont.)

```
LPL-WT      ATGGAGAGCAAAGCCCTGCTCGTGCTGACTCTGGCCGTGTGGCTCCAGAGTCTGACCGCC
LPL-CO01    ATGGAGAGCAAGGCTCTGCTGGTGCTGACGCTGGCCGTGTGGCTGCAGTCCCTGACCGCC
LPL-CO02    ATGGAGAGCAAGGCACTGCTGGTGCTGACACTGGCCGTGTGGCTGCAGAGCCTGACCGCC
LPL-CO03    ATGGAGTCCAAGGCCCTGCTGGTGCTCACACTCGCCGTGTGGCTGCAGAGCCTGACCGCC
LPL-CO18    ATGGAGTCCAAGGCCTTGCTGGTTCTGACCCTGGCCGTGTGGCTGCAGAGCCTGACGGCC
LPL-CO19    ATGGAGAGCAAAGCGCTACTGGTGCTGACCCTCGCCGTGTGGCTACAGAGCCTGACCGCC
LPL-CO21    ATGGAATCGAAGGCCCTGCTGGTGCTGACGCTGGCGGTGTGGCTGCAGAGCCTGACCGCC
LPL-CO14    ATGGAGTCCAAGGCCCTCCTGGTGCTGACCCTGGCCGTGTGGCTCCAGAGCCTAACCGCC
LPL-CO04    ATGGAGAGCAAGGCGCTGCTGGTGCTGACACTGGCGGTGTGGCTGCAAAGCCTGACCGCG
LPL-CO15    ATGGAGAGCAAGGCCCTGCTCGTGCTGACCCTCGCCGTCTGGCTGCAGAGCCTGACCGCC
LPL-CO10    ATGGAGTCAAAGGCCCTCCTGGTGCTTACCCTCGCCGTTTGGCTCCAGTCCCTGACCGCG
LPL-CO05    ATGGAAAGCAAGGCGCTGCTCGTCCTCACCCTGGCCGTCTGGCTGCAAAGCCTGACCGCC
LPL-CO22    ATGGAAAGCAAGGCCCTGCTGGTCCTGACCCTCGCCGTGTGGCTCCAGAGCCTGACCGCC
LPL-CO13    ATGGAGAGTAAGGCGCTGCTCGTGCTCACGCTGGCAGTGTGGCTCCAGTCCCTGACCGCC
LPL-CO08    ATGGAGAGCAAGGCCCTGCTGGTGCTGACCCTGGCCGTGTGGCTGCAGTCGCTGACCGCC
LPL-CO20    ATGGAGTCTAAAGCCCTGCTGGTGCTGACCCTCGCCGTGTGGCTGCAGTCGCTGACCGCC
LPL-CO07    ATGGAGAGCAAGGCGCTGCTGGTGCTGACCCTGGCGGTGTGGCTGCAGAGCCTCACCGCC
LPL-CO23    ATGGAGTCCAAAGCGCTTCTGGTGCTCACCCTGGCGGTGTGGCTGCAGAGCCTGACCGCC
LPL-CO25    ATGGAGAGCAAGGCCCTGCTGGTGCTGACCCTGGCCGTGTGGCTGCAGTCACTCACCGCA
LPL-CO09    ATGGAGAGCAAGGCCCTGCTGGTGCTGACGCTGGCGGTGTGGCTCCAGTCCCTGACCGCC
LPL-CO11    ATGGAGAGCAAGGCCCTGCTGGTGCTGACCCTGGCCGTTTGGCTGCAGTCCCTGACCGCC
LPL-CO12    ATGGAGTCCAAGGCCCTCCTGGTGCTGACCCTGGCCGTCTGGCTGCAGTCACTGACCGCG
LPL-CO16    ATGGAATCCAAGGCCCTACTCGTGCTCACCCTGGCCGTGTGGCTGCAGAGCCTGACCGCA
LPL-CO06    ATGGAGAGCAAGGCCCTGCTGGTCCTGACCCTGGCCGTCTGGCTGCAGAGCCTGACCGCC
LPL-CO24    ATGGAAAGCAAAGCCCTGCTGGTACTCACGCTCGCCGTCTGGCTGCAGTCCCTGACCGCC
LPL-CO17    ATGGAGTCCAAGGCCCTGCTGGTGCTGACCCTTGCCGTGTGGCTGCAGAGCCTGACCGCC
            *****.   **.**  .* ** ** ** ** ** ** ** ***** **.    ** ** **
```

FIG. 3

```
LPL-WT      TCCCGCGGAGGGGTGGCCGCCGCCGACCAAAGAAGAGATTTTATCGACATCGAAAGTAAA
LPL-CO01    AGCAGGGGAGGCGTGGCCGCCGCCGACCAGCGGCGCGACTTCATCGATATCGAGTCGAAG
LPL-CO02    TCCAGGGGCGGAGTGGCCGCCGCCGACCAGCGGCGGGACTTCATCGACATCGAATCGAAG
LPL-CO03    TCCCGGGGGGGCGTGGCGGCCGCCGACCAGCGGAGGGATTTCATCGACATCGAGAGCAAA
LPL-CO18    TCGAGGGGGGGCGTCGCGGCGGCCGACCAGCGGAGGGACTTCATCGACATCGAGAGCAAA
LPL-CO19    TCGCGGGGCGGCGTGGCCGCCGCTGACCAGAGGCGGGACTTCATCGACATCGAGAGCAAG
LPL-CO21    TCCCGCGGCGGCGTCGCCGCCGCCGACCAGAGGCGGGACTTCATCGATATCGAGAGCAAG
LPL-CO14    TCCCGGGGCGGCGTGGCCGCCGCCGATCAGAGGCGGGATTTCATCGACATAGAGAGCAAG
LPL-CO04    AGCAGGGGCGGCGTGGCCGCCGCCGACCAGAGGCGGGACTTCATTGACATCGAGTCCAAG
LPL-CO15    AGCAGGGGCGGCGTGGCCGCCGCCGATCAGAGGCGGGACTTCATAGATATCGAGAGCAAG
LPL-CO10    AGCCGCGGCGGGGTGGCCGCCGCCGACCAGAGGCGAGACTTTATCGACATTGAGTCCAAG
LPL-CO05    AGCAGAGGTGGCGTGGCGGCCGCCGACCAGCGGCGAGACTTCATCGATATCGAAAGCAAG
LPL-CO22    AGCCGGGGCGGGGTGGCCGCCGCCGACCAGCGACGGGACTTCATAGACATCGAGAGCAAG
LPL-CO13    AGCCGCGGGGGGGTGGCCGCGGCCGACCAGAGGAGGGACTTCATCGATATCGAGAGCAAG
LPL-CO08    AGCAGGGGCGGCGTGGCCGCGGCCGACCAGCGCCGGGACTTCATCGACATCGAGAGCAAG
LPL-CO20    TCCCGCGGCGGGGTGGCCGCAGCCGACCAGCGCCGGGACTTCATTGACATCGAGAGCAAG
LPL-CO07    TCGCGCGGTGGCGTGGCGGCCGCCGATCAACGGCGGGACTTCATCGATATCGAGAGCAAG
LPL-CO23    TCCAGAGGCGGCGTGGCCGCCGCCGACCAGCGGAGGGACTTCATCGACATCGAGAGCAAG
LPL-CO25    TCCAGGGGGGGAGTGGCCGCCGCCGACCAGAGGCGGGACTTCATCGATATCGAGAGCAAG
LPL-CO09    AGCCGGGGGGGCGTCGCCGCCGCCGACCAACGCCGCGACTTCATCGACATCGAAAGTAAA
LPL-CO11    AGCCGCGGTGGCGTGGCCGCCGCCGACCAGCGGCGGGATTTCATCGACATAGAATCTAAG
LPL-CO12    AGCAGGGGCGGCGTGGCCGCAGCGGACCAGCGCAGGGACTTCATCGACATCGAGAGCAAG
LPL-CO16    AGCAGGGGGGGCGTGGCCGCCGCGGACCAAAGGAGGGATTTCATTGATATCGAGAGCAAG
LPL-CO06    TCCCGGGGGGGCGTGGCCGCCGCCGACCAGAGGCGCGACTTTATAGACATCGAGTCGAAG
LPL-CO24    AGCAGAGGCGGCGTCGCGGCCGCCGATCAGAGAAGAGACTTCATCGACATCGAAAGCAAG
LPL-CO17    AGCAGGGGCGGCGTCGCCGCCGCGGACCAGCGCAGGGACTTTATCGATATCGAGAGCAAG
                  *  ** ** ** ** ** ** **.**. *  * **.**.** **.** **.   **.
```

FIG. 3 (cont.)

```
LPL-WT   TTTGCCCCTAAGGACCCCTGAAGACACAGCTGAGGACACTTGCCACCTCATTCCCGGAGTA
LPL-C001 TTCGCCCTGCGCACGCCCGAGGATACCGCCGAGGACACGTGCCACCTGATCCCGGGGTG
LPL-C002 TTCGCCCTGCGGACCCCGAGGAGACCCGCCGAAGACACCTGCCACCTCATCCCGGCGTC
LPL-C003 TTCGCCCTGAGGACCCCGAGGACACCGCCGAGGATACCTGCCATCTCATCCCGGCGTG
LPL-C018 TTCGCCCTGCGGACCCCGAGGACACCGCCGAGGAGACCTGTCACCTGATCCCGGCGTG
LPL-C019 TTCGCCCTGCGCACCCCAGAGGACACCGCCGAGGATACCTGTCACCTCATCCCGGCGTC
LPL-C021 TTCGCCCTGAGGACCCCGAAGATACCGCCGAAGACACGTGCCACCTGATCCCGGCGTG
LPL-C014 TTCGCCCCTCCGCACCCCGAAGACACCGCCGAAGACACTTGCCACCTGATTCCCGGAGTG
LPL-C004 TTCGCCCTTAGGACCCCGAGGAGACCGCCGAGGACACGTGCCACCTGATCCCGGGGTG
LPL-C015 TTCGCCCTGAGGACCCCGAAGACACCGCCGAGGACACCTGCCACCTGATCCCGGCGTG
LPL-C010 TTCGCCCTGAGGACCCCCGAGGAGACCGCCGAGGACACCTGCCACCTGATCCCGGCGTG
LPL-C005 TTCGCCCTGAGGACCCCCGAGGAGACCGCCGAGGACACCTGCCACCTGATCCCGGTGTG
LPL-C022 TTCGCCCTGAGGACCCCGAGGACACCGCCGAGGATACCGCCGAGGACACATGCCACCTGATCCCGGAGTG
LPL-C013 TTCGCCCTGCGCACGGACACCCCGAGGACACAGCCGAGGATACCGCCGAGGACACCTGCCACCTGATACCCGGCGTG
LPL-C008 TTTGCCCTGAGGACCCCCGAGGAGACCGCCGAGGATACCTGCCACCTGATCCCGGCGTG
LPL-C020 TTCGCCCTGCGAACCCCCGAGGAGACCGCCGAGGATACCTGCCACCTGATCCCGGAGTC
LPL-C007 TTCGCCCCTTCGCAGGACCCCCGAGGAGACCGCCGAGGATACTTGCCACCTGATCCCGGCGTG
LPL-C023 TTCGCACTCAGGACCCCGAGGAGACCGCCGAGGACACCTGCCACCTGATCCCGGTGTG
LPL-C025 TTCGCCCTCCGCACCCCGAGGAGACCGCCGAAGACACCTGCCACCTGATCCCGGGGTG
LPL-C009 TTCGCCCTGCGCACCCCCGAGGAGACCGCCGAGGACACGTGCCACCTGATCCCCTGAGTT
LPL-C011 TTTGCCCTGAGGACCCCGAGGAGACCGCCGAAGACACCTGCCACCTGATCCCGGGGTG
LPL-C012 TTCGCCCTCAGGACCCCGAGGAGACCAGCGCCGAGGACACCTGCCACCTGATCCCGGCGTA
LPL-C016 TTCGCCCTGCGCACCCCGAGGAGACAGCCGCCGAGGACACCTGCCACCTGATCCCGGCGTG
LPL-C006 TTTGCCCTGAGGACCCCGAGGAAGACAGCCGCCGAGGACACCTGCCACCTGATCCCGGCGTA
LPL-C024 TTCGCCCTGAGGACCCCGAGGACAGCCGCCGAAGACACCTGCCACCTGATCCCGGCGTG
LPL-C017 TTCGCCCGCTGAGGACACCCGAGGACACATGCCACCTGATCTGATCCCAGGCGTT
         ** *  ** **  **  ** *** *  ** * ** ** ** ***  ** * ** ****
```

FIG. 3 (cont.)

| | |
|---|---|
| LPL-WT | GCAGAGTCCGTGGCTACCTGTCATTCAATCACAGCAGCAAAACCTTCATGGTGATCCAT |
| LPL-C001 | GCGGAGAGCGTCGCCACCTGTCACTTCAACCATAGCAGCAAGAGCGTTCATGGTCATCCAC |
| LPL-C002 | GCCGAGAGCGTGGCCGTGCCACCTGCCACTTCAACCACAGCAGCAAGACCTTCATGGTGATCCAT |
| LPL-C003 | GCTGAGAGCGTGGCCGTGCCACCTGCCACTTCAACCACAGCAGCAAGAGACCTTCATGGTGATCCAC |
| LPL-C018 | GCTGAAAGCGTGGCCGTGCCAACCTGCCACTTCAACCACAGCAGCAAGACGTTATGGTCATACAC |
| LPL-C019 | GCCGAGAGCGTGGCGGTGCCGACCTGCCACTTGCCACTTTAACCACAGCAGCAAGACCTTCATGGTGATCCAC |
| LPL-C021 | GCGGAGTCGTGTGGCCACCTGCCACTTGCCACTTCAACCACAGCAGCAAGACCTTCATGGTGATCCAC |
| LPL-C014 | GCCGAGTCCGTGGCCACCTGCCACTTGCCACTTCAACCACAGCAGCAAGACCTTCATGGTGATCCAC |
| LPL-C004 | GCCGAGTCCGTGGCCGTGCCACCTGCCACTTCAACCACAGCAGCAAGACCTTCATGGTGATCCAC |
| LPL-C015 | GCCGAGTCCGTGGCCACCTGCCACATGCCACTTCAACCACAGCAGCAAGACGTTTATGGTGATCCAT |
| LPL-C010 | GCCGAGAGCGTCGCCACCTGCCACTGCCACTTCAACCACAGCAGCAAGACCTTCATGGTGATCCAC |
| LPL-C005 | GCCGAGAGCGTTGCCACCTGCCACTGCCACTTCAACCACAGCAGCAAGACCTTTATGGTGATACAC |
| LPL-C022 | GCCGAGAGCGTCGCCACCTGCCACTGCCACTGCCACTTTAACCACAGCAGCAAAACCTTCATGGTGATCCAC |
| LPL-C013 | GCCGAGAGCGTGGCCACCTGCCACTGCCACTTTAACCACAGCAGCAAGACCTTCATGGTCATCCAC |
| LPL-C008 | GCAGAGAGCGTCGCCACCTGCCACTGCCACTTGCCACTTCAACCATTCATAGCAGCAAGACCTTTATGGTGATCCAC |
| LPL-C020 | GCCGAGAGCGTGGCCACCTGCCACTGCCACTTGCCACTTCAACCACAGCAGCAAGACCTTCATGGTGATCCAC |
| LPL-C007 | GCCGAATCCGTGGCCGTGCCACCTGCCACTGCCACTTCAACCACAGCAGCAAGACCTTCATGGTGATCCAC |
| LPL-C023 | GCCGAGTCAGTGGCCGTCAGTGCCACCTGCCACTGTCATTCAACCACAGCAGCAAGACCTTCATGGTGATCCAC |
| LPL-C025 | GCCGAGTCAGTGGCCGTGCCGACCTGCCACTGCCACTTCAACCACAGCAGCAAGACCTTTATGGTGATCCAC |
| LPL-C009 | GCCGAGAGCGTGGCGTGCCGACCTGCCACTGCCACTTCAACCACAGCAGCAAGACGTTCATGGTGATCCAT |
| LPL-C011 | GCCGAGTCCGTGGCCGTGCCACCTGCCACTGTCACTTCAACCACAGCAGCAAGACCTTATGGTGATCCAC |
| LPL-C012 | GCCGAGTCCGTGGCCGTGCCACCTGCCACTGCCACTTCAACCACAGCAGCAAGACCTTTATGGTGATCCAC |
| LPL-C016 | GCCGAGTCCGTGGCCGTGCCACCTGCCACTGCCACTTAATCACTCCTCCAAGACCTTCATGGTGATACAC |
| LPL-C006 | GCCGAGAGCGTGGCCGTGCCACCTGCCACTGTCACTTCAACCACTCCTCCAAGACCTTCATGGTCATTCAT |
| LPL-C024 | GCCGAGAGCGTGGCCGTGCCACGTGCCACTGTCACTTCAACCACTCCTCCAAGACCTTATGGTGATCCAC |
| LPL-C017 | GCCGAGAGCGTGGCTACCTGCCACTTCAATCACAGCAGCAAAACCTTATGGTCATCCAC |
| | *** *. ** ** * ** * .*.** .**. ***.*. . *** *** * ****** * ** |

FIG. 3 (cont.)

```
LPL-WT      GGCTGGACGGTAACAGGAATGTATGAGAGTTGGGTGCCAAAACTTGTGGCCGCCCTGTAC
LPL-CO01    GGCTGGACCGTGACAGGAATGTACGAAAGCTGGGTGCCCAAGCTCGTGGCCGCCCTCTAC
LPL-CO02    GGCTGGACCGTGACAGGCATGTATGAGAGCTGGGTCCCCAAACTGGTGGCGGCCCTGTAC
LPL-CO03    GGCTGGACCGTGACCGGAATGTACGAGAGCTGGGTGCCCAAGCTGGTGGCCGCCCTGTAC
LPL-CO18    GGGTGGACCGTGACCGGAATGTACGAGAGTTGGGTGCCCAAACTGGTGGCCGCCCTGTAC
LPL-CO19    GGCTGGACCGTGACGGGCATGTACGAGTCCTGGGTGCCCAAACTGGTGGCGGCTCTGTAC
LPL-CO21    GGGTGGACCGTGACCGGCATGTACGAGAGCTGGGTGCCCAAGCTGGTCGCCGCGCTGTAC
LPL-CO14    GGCTGGACCGTTACCGGCATGTACGAAAGCTGGGTGCCGAAGCTCGTGGCCGCCCTGTAC
LPL-CO04    GGCTGGACCGTGACCGGGATGTACGAAAGCTGGGTGCCCAAGCTGGTGGCCGCCCTCTAC
LPL-CO15    GGCTGGACCGTCACCGGGATGTACGAGAGCTGGGTGCCCAAGCTGGTGGCCGCCCTCTAC
LPL-CO10    GGCTGGACTGTGACCGGGATGTACGAGTCCTGGGTCCCCAAGCTCGTGGCCGCCCTGTAC
LPL-CO05    GGCTGGACCGTCACGGGCATGTACGAGAGCTGGGTGCCCAAGCTGGTGGCCGCCCTGTAT
LPL-CO22    GGATGGACCGTGACCGGAATGTACGAGAGCTGGGTACCAAAGCTGGTCGCCGCCCTGTAC
LPL-CO13    GGCTGGACCGTCACCGGCATGTACGAGAGCTGGGTGCCCAAGCTGGTCGCCGCCCTGTAC
LPL-CO08    GGTTGGACCGTGACCGGAATGTACGAGTCCTGGGTCCCGAAACTGGTGGCCGCCCTGTAC
LPL-CO20    GGCTGGACGGTGACCGGGATGTACGAGAGCTGGGTCCCCAAGCTGGTGGCCGCCCTTTAT
LPL-CO07    GGCTGGACCGTGACCGGGATGTACGAGAGTTGGGTGCCCAAGCTGGTGGCCGCCCTGTAC
LPL-CO23    GGCTGGACCGTCACCGGCATGTACGAGAGCTGGGTGCCCAAGCTCGTCGCGGCGCTCTAC
LPL-CO25    GGCTGGACCGTGACCGGCATGTACGAGTCCTGGGTCCCCAAGCTGGTGGCCGCGCTGTAT
LPL-CO09    GGCTGGACCGTCACCGGCATGTACGAGAGCTGGGTGCCGAAGCTCGTGGCCGCGCTCTAC
LPL-CO11    GGCTGGACCGTGACTGGCATGTACGAGAGCTGGGTGCCCAAGCTCGTGGCCGCCCTGTAC
LPL-CO12    GGCTGGACCGTGACCGGAATGTATGAGAGCTGGGTGCCCAAGCTCGTGGCCGCCCTTTAC
LPL-CO16    GGGTGGACCGTGACCGGGATGTATGAAAGTTGGGTGCCAAAACTGGTGGCCGCCCTGTAC
LPL-CO06    GGCTGGACCGTCACCGGCATGTACGAGAGTTGGGTGCCGAAGCTGGTGGCCGCCCTCTAC
LPL-CO24    GGCTGGACGGTGACCGGAATGTACGAGAGCTGGGTGCCGAAGCTGGTGGCCGCCCTGTAC
LPL-CO17    GGCTGGACGGTGACCGGCATGTACGAGAGCTGGGTGCCAAAGCTGGTGGCCGCCCTGTAC
            ** ***** ** ** ** *****.**.  .***** ** **.** ** ** ** ** **.
```

FIG. 3 (cont.)

| | |
|---|---|
| LPL-WT | AAGAGAGAACCAGAGACTCCAATGTCATTGTGTGTGGACTGGCTGGCTGTGTCACGGCTCAGGAGCAT |
| LPL-C001 | AAGAGGGAGCCCGACAGAGCTCCGATAGTGATAGTGGTGGACTGGCTGTCCCGGCCCAGGAACAC |
| LPL-C002 | AAAAGGGAGCCCGACAGAGCTCCAATGTGATAGTCGTAGTGGACTGGCTGCTCCAGGCCCAGGAGCAC |
| LPL-C003 | AAGAGGGAGCCCGATAGCAACTCCGATAGTGATAGTGGTGGACTGGCTGGCTGAGCAGGCCAAGAGCAT |
| LPL-C018 | AAGAGGGAGCCCGACACAGCTCCAGCAGTAACGTGATAGTGGTGGACTGGCTGTCCCGGCCCAGGAGCAC |
| LPL-C019 | AAGAGGGAGCCCGACAGTAACGTGATTGTCGTGGACGTGGCTGGCTGAGCCGCTCAAGAACAC |
| LPL-C021 | AAAAGGGAGCCCGACACAGCTCATCGTCGTCGTGATTGTCGTGGACTGGCTGGCTGAGCAGGCACAGGAGCAT |
| LPL-C014 | AAGAGGGAGCCCGACTCCAACGTGATCGTGGTTGTGACTGGCTGGCTGTTGACTGGCTGTCCAGGCCCAGGAGCAC |
| LPL-C004 | AAAAGGGAGCCTGACTCCAACGTGATCGTCGTGGTTGTGACTGGCTGTCCAGGCCCAGGAGCAC |
| LPL-C015 | AAGCGGGAACCCGATAGCAACGTGATCGTGGTAGACGTGGCTGGCTGTCCAGGCCCAAGAACAC |
| LPL-C010 | AAGAGGGAGCCCGACAGCAACGTGATCGTGGTGGACTGGCTGGCTGTCCAGGCCCAGGAGCAC |
| LPL-C005 | AAGAGGGAGCCCGACAGCAACGTGATTGTGGTGGACTGGCTGGCTGTCCAGGCCCAAGAACAC |
| LPL-C022 | AAAAGGGAGCCGATAGCAACGTGATCGTCGTCGTGGACTGGCTGGCTGTCCCGGCCCAGGAGCAC |
| LPL-C013 | AAGCGCGAGCCTGATAGCAACTCCAACGTAACGTGATCGTCGTGGATTGGCTGTCCCAGGCCCAGGAGCAC |
| LPL-C008 | AAGCGGGAGCCCGATAGTAACAGCAACGTGATCGTCGTGGACTGGCTGTCCAGGCCCAGGAGCAC |
| LPL-C020 | AAAAGGGAGCCCGATAGCAACGTGATCGTGATCGTCGTGGACTGGCTGTCCAGGCCCAGGAGCAC |
| LPL-C007 | AAGCGGGAGCCCGATAGTAACGTGATCGTCGTGGACTGGCTGAGCAGGCCGCAGCCCAGGAGCAT |
| LPL-C023 | AAGCGGGAGCCCGACTCCAGCAACGTAACGTGATCGTCGTGGACTGGCTCAGCCGCTCAGCCCAGGAGCAC |
| LPL-C025 | AAGCGGGAACCCGACTCCAATGTAACGTGATCGTCGTGGATTGGCTGAGCCGTGCCCAGGAGCAT |
| LPL-C009 | AAGAGGGAGCCCGACTCCAATGTGATCGTGATCGTCGTGGATTGGCTGAGCCCGTGAGCCCAGGAGCAT |
| LPL-C011 | AAGAGGGAGCCCGACTCCAACGTGATCGTGATCGTCGTGGTCGTGGACTGGCTGAGCAGGCCCAGGAGCAC |
| LPL-C012 | AAGAGGGAGCCCGACTCCAACGTGATCGTCGTGGACTGGCTGAGCAGGCCCAGGAGCAC |
| LPL-C016 | AAGAGGGAGCCCGACTCCAACGTGATCGTCATAGTGGTCGTGGACTGGCTGAGCAGGCCCAGGAGCAC |
| LPL-C006 | AAGCGGGAGCCCGACAGCAACGTGATCGTCGTGGACTGGCTGAGCAGGCCCAGGAGCAC |
| LPL-C024 | AAGAGGGAACCCGACAGCAACGTGATCGTGATCGTAGTCGTGGACTGGCTGAGCAGGCCCAGGAGCAT |
| LPL-C017 | AAGAGGGAACCCGACAGCAACGTGATCGTGATCGTGGTTATCCAGGCGCAGGAGCAC |
| | ** * ** * *** ** *** *** *** * ** *** * |

FIG. 3 (cont.)

```
LPL-WT   TACCCAGTGTCCGCGGGCTACACCAAACTGTGTGGACAGGATGTGTGGCCCGGTTTATCAAC
LPL-C001 TATCCCGTGAGCGCCGGGTACACCAAGCTCGTGGGCCAGGACGTGGCCGGTTCATCAAT
LPL-C002 TACCCCGTCAGCGCCCGGCCGCCGGCTACACCAAGCTGTGGGCCAGGACGTGGCCAGTTCATCAAC
LPL-C003 TACCCCGTGAGCGCCCGGCCGCCGGCTATACCAAGCTGTGGGCCAGGACGTGGCCAGTTCATCAAC
LPL-C018 TACCCCGTGAGCGCCCGGCTACACCAAGCTGTGGGCCAGGACGTGGCCCGGTTCATCAAC
LPL-C019 TATCCCGTATCCGCCGGTTACACCAAGCTGTGGGCCAGGACGTGGCCGATTCATTAAC
LPL-C021 TACCCCGTCTCCGCCGGTTACACCAAACTGTGGGCCAGGACGTGGCGAGTTTATCAAC
LPL-C014 TACCCCGTGTCCGCCGGCTACACCAAGCTGGTCGGGCCAGGACGTGGCCAGTTCATCAAC
LPL-C004 TACCCCGTTTCCGCCGGATACACCAAGCTGTGGGCCAGGACGTGGCCCGGTTCATCAAT
LPL-C015 TACCCCGTGAGTGCCGCCGGCTACACCAAGCTGTGGGCCAGGACGTGGCCCGGTTCATCAAT
LPL-C010 TACCCCGTGAGCGCCGCCGGCTACACCAAGCTGTGGGCCAGGACGTGGCCCGCTTCATCAAC
LPL-C005 TACCCCGTGAGCGCCGCCGGCTACACCAAGCGAAGCTGTGGGCCAGGACGTTGCCCGCTTCATCAAT
LPL-C022 TACCCCGTGAGCGCCGCCGGCTACACCAAGCTGTGGGCCAGGACGTGGCCCGTTCAGATTCATAAAC
LPL-C013 TACCCCGTGAGCGCCGCCGGCTACACCAAGCTGGTCGTGGGCCAGGACGTGGCCCAGGTTCATCAAT
LPL-C008 TACCCCGTCTCCGCCGCCGGCTACACCAAACTGGTCGTGGGCCAGGACAAGACGTGGCCCAGGTTCATCAAC
LPL-C020 TACCCCGTGTCCGCCGCCGGCTACACCAAGCTGGTCGTGGGCCAGGACGTGGCCCAGGTTCATCAAT
LPL-C007 TATCCAGTGAGCGCCGCCGGCTACACCAAGCTGGTCGTGGGCCAGGACATGTCGCCAGGTTCATTAAC
LPL-C023 TACCCCGTGTCCGCCGCCGGGTACACCAAGCGAAGCTGGTCGTGGGCCAGGACGTGGCGCCCGCTTTATAAAC
LPL-C025 TACCCCGTCAGCGCCGCCGGCTACACCAAGTTGGTGTGGGCCAGGACGTGGCCAGGTTCATCAAC
LPL-C009 TACCCCGTCAGCGCCGCCGGGTACACCAAGCTGGTCGTGGGCCAGGACGTGGCGGTTTATAAAC
LPL-C011 TACCCCGTCAGCGCCGCCGGCTACACCAAGCTGTGGGCCAGGACTAGCGTGGCCAGTTCATCAAC
LPL-C012 TATCCCGTCAGCGCCGCCGGCTACACCAAGCTGGTCGTGGGCCAAGACGTGGCCAGGTTCATCAAC
LPL-C016 TATCCCGTGAGCGCCGCCGGCTATACGAAGCTGGTGTGGGCGTCCAGGACGTGGCCGATTCATCAAC
LPL-C006 TATCCCGTGAGCGCCGCCGGCTACACTAAGCTGGTGGGCCAGGACGTGGCCCGCTTCATCAAC
LPL-C024 TACCCCGTGAGCGCCGCCGGCTACACCAAGCTGGTCGTGGGCCAGGACGTGGCCCGCTTCATAAAC
LPL-C017 TATCCCGTCAGCGCCGCCGGCTACACCAAGCTGGTCGTGGGCCAGGACGTGGCGCCCAGGTTCATCAAT
         *  * **    **  **    * **  ** ** **    * **  **    ***    *  *  ***   *  ** ** ** **
```

FIG. 3 (cont.)

```
LPL-WT          TGGATGGAGGAGGAGTTTAACTACCCTCTGGACAATGTCCATCTCTTGGGATACAGCCTT
LPL-CO01        TGGATGGAGGAGGAGTTCAACTACCCCCTGGACAACGTGCATCTGCTCGGCTACTCCCTG
LPL-CO02        TGGATGGAGGAAGAGTTCAATTACCCCCTGGACAACGTGCATCTGCTCGGGTACTCCCTG
LPL-CO03        TGGATGGAGGAGGAGTTCAACTACCCCCTGGACAACGTCCACCTGCTGGGCTACAGCCTG
LPL-CO18        TGGATGGAGGAGGAGTTCAACTATCCCCTGGATAACGTGCACCTCCTGGGGTACAGCCTG
LPL-CO19        TGGATGGAGGAGGAGTTTAATTACCCCCTGGATAACGTGCATCTGCTGGGGTATAGCCTG
LPL-CO21        TGGATGGAGGAGGAGTTCAACTACCCCCTGGATAACGTGCACCTGCTGGGGTACAGCCTG
LPL-CO14        TGGATGGAAGAGGAGTTCAACTATCCTCTGGACAATGTGCACCTGCTGGGCTACAGCCTG
LPL-CO04        TGGATGGAGGAGGAATTCAATTACCCCCTGGACAACGTGCATCTGCTCGGCTACTCCCTG
LPL-CO15        TGGATGGAGGAGGAGTTCAACTACCCGCTCGATAACGTGCACCTGCTGGGCTATAGCCTG
LPL-CO10        TGGATGGAGGAGGAGTTCAACTACCCCCTGGACAACGTGCACCTGCTGGGCTACAGCCTG
LPL-CO05        TGGATGGAGGAGGAGTTCAACTATCCCCTCGACAACGTGCACCTCCTGGGCTACAGCCTG
LPL-CO22        TGGATGGAGGAGGAGTTCAATTACCCCCTGGACAACGTGCACCTGCTGGGCTACTCCCTG
LPL-CO13        TGGATGGAAGAGGAGTTTAACTACCCCCTGGACAACGTGCACCTGCTGGGCTATAGCCTG
LPL-CO08        TGGATGGAAGAGGAGTTCAACTATCCCCTGGACAACGTGCATCTCCTGGGCTACAGCCTC
LPL-CO20        TGGATGGAGGAGGAATTTAATTACCCCCTGGACAATGTGCACCTCCTGGGCTACTCGCTG
LPL-CO07        TGGATGGAGGAGGAATTCAACTACCCGCTGGATAACGTGCATCTGCTGGGGTACTCGCTG
LPL-CO23        TGGATGGAGGAAGAGTTCAACTACCCCCTGGACAACGTGCACCTGCTCGGTTACAGCCTC
LPL-CO25        TGGATGGAGGAGGAGTTCAACTACCCCCTGGATAACGTGCACCTGCTGGGCTACTCCCTG
LPL-CO09        TGGATGGAGGAGGAGTTCAACTATCCCCTGGATAACGTGCACCTGCTGGGCTACTCCCTG
LPL-CO11        TGGATGGAGGAGGAGTTTAACTACCCCCTCGACAACGTGCACCTCCTGGGCTACTCCCTG
LPL-CO12        TGGATGGAGGAGGAGTTCAACTACCCCCTGGACAACGTGCATCTGCTGGGGTACTCCCTG
LPL-CO16        TGGATGGAGGAGGAGTTCAACTACCCCCTGGACAACGTGCACCTGCTGGGCTATAGCCTC
LPL-CO06        TGGATGGAGGAAGAGTTTAACTATCCGCTCGACAACGTCCATCTGCTGGGGTACAGCCTG
LPL-CO24        TGGATGGAGGAAGAGTTCAACTACCCACTGGACAATGTCCACCTCCTGGGCTACAGCCTG
LPL-CO17        TGGATGGAGGAGGAATTCAATTATCCCCTGGATAACGTACACCTCCTGGGCTACAGCCTC
                ********.**.**.**.**.**.** ** **.**.** **.** .* ** **.    **
```

FIG. 3 (cont.)

| | |
|---|---|
| LPL-WT | GGAGCCCATGCTGCTGGCATTGCAGGAAGTCTGACCAATAAGAAAGTCAACAGAATTACT |
| LPL-CO01 | GGCGCTCACGCCGCCGGCATCGCCGGGCAGCCTGACAAACAACAAGAAGGTGAACAGGATCACC |
| LPL-CO02 | GGCGCCCACGCCGCCGGGGATCGCCGCCGGTAGCCTCACCAACAAGAAGTCAATCGAATCACC |
| LPL-CO03 | GGGGCCCACGCCGCCGCGGGCATCGCCGGCTCCCTCACCAACAAGAAGGTGAATAGGATAACG |
| LPL-CO18 | GGGGCCCACGCCGCCGGCATCGCCGCCGGAATCGCCGGCCTGACCAACAAGAAGGTGAACAGGATCACT |
| LPL-CO19 | GGCGCCCACGCCGCCGGCATAGCCGGCCTCCCTGACCAACAAGAAGGTCAACGGATCACC |
| LPL-CO21 | GGCGCCCACGCCGCCGGCAGGCATAGCCGGGGAGCCTGACCAATAAGAAAGTAAACCGATCACG |
| LPL-CO14 | GGCGCCCACGCCGCCGGCATCGCCGCCGGCAGCCTGACCAATAACAAGTGAATAGGATTACC |
| LPL-CO04 | GGCGCCCACGCCGCCGGCATCGCCGCCGCCGGGCAGCCTGACTAACCAACAAGAAGGTGAACAGGATCACC |
| LPL-CO15 | GGGGCCCACGCCGCCGGCATCGCCGCCGGCAGCCTCCCCTGACCAACAAGAAGGTGAACAGGATCACC |
| LPL-CO10 | GGCGCCCACGCCGCCGGCATCGCCGCCGGGGTCCCGGTTCGCTCACCAACAAATAAAAGGTGAACAGGATTACC |
| LPL-CO05 | GGCGCTCACGCCGCCGGCATCGCCGCCGGGCAGCCGGTTCGCTCACCAACAACAAGAAGGTCAACCGGATCACT |
| LPL-CO22 | GGAGCCCACGCCCGCCGGGATAGCCGCCGGGCAGCCTCACTAACAAGAAGGTGAATCGGATAACC |
| LPL-CO13 | GGCGCCCACGCCGCCGGCATCGCCGCCGGCAGCCTCCCTGACGAACAAGAAGGTGAACAGGATCACC |
| LPL-CO08 | GGCGCCCACGCCGCCGGCATCGCCGCCGGCAGTCGCCGCCGGCAGTCTGACCAGCCTGACCAGCCTGACCAACAAGAAGGTGAACAGGATCACC |
| LPL-CO20 | GGCGCCCACGCCGCCGGCATAGCCGGCCTCGCGGACCAACAAGAAAGTGAACAGGATCACG |
| LPL-CO07 | GGAGCCCATGCCGCCGGCATCGCCGGGGATCCCCTGACGAACAAGAAGGTCAATAGGATCACC |
| LPL-CO23 | GGCGCCCACGCTGCCGGCATCGCCGGGGGGCCGGTTCCCTCACCAACAAGAAGGTGAATAGGATCACC |
| LPL-CO25 | GGGGCCCACGCCGCATGCCGCCGGTATCGCTGGCCAGCCTGCAGCCTGCCAACAAGAAGGTGAATAGGATCACC |
| LPL-CO09 | GGCGCCCACGCCGCCGGGCTCGCCGCCGGAAGCCTGACCAACAAGAAAGTGAACCGGATCACC |
| LPL-CO11 | GGCGCCCACGCCGCCGGATCGCCGGGGGTCCCTGACTAACCAACAAGAAAAAGTCAATCGGATCACC |
| LPL-CO12 | GGCGCGCACGCTGCCGCCGGCATGCCGCCGGTGGCAGCCTCCCTAACCAACAAGAAGGTGAACAGGATCACC |
| LPL-CO16 | GGCGCCCACGCCGCCGGCATCGCCGGGGTCCCTGACGAACAAGAAGGTGAACCGGATCACC |
| LPL-CO06 | GGCGCCCATGCCGCCGGAATCGCCGCCGGGCTCCCCTCACCAACAAGAAGGTGAACCGGATCACC |
| LPL-CO24 | GGCGCCCACGCCGCCGGCATCGCCGCCGGTCCCCGTCCCTCACCAACAAGAAGGTCAACCGGATCACA |
| LPL-CO17 | GGAGCCCACGCCGCCGGGAATAGCCGGGGAGCCTCACGACGAATAAGAAGTTAACAGGATCACC |
| | ** *** ** * *** *  ** ** * *** * ** ** *** * ** |

FIG. 3 (cont.)

```
LPL-WT          GGCCTCGATCCAGCTGGACCTAACTTTGAGTATGCAGAAGCCCCGAGTCGTCTTTCTCCT
LPL-CO01        GGGCTCGACCCCGCCGGCCCCAACTTCGAGTACGCCGAGGCCCCCAGCAGGCTGAGCCCC
LPL-CO02        GGGCTGGACCCCGCCGGGCCCAACTTTGAATACGCCGAAGCCCCCAGCCGGCTCAGCCCC
LPL-CO03        GGCCTGGACCCCGCCGGTCCCAACTTCGAGTACGCCGAGGCCCCGTCCCGACTGTCTCCC
LPL-CO18        GGCCTCGACCCCGCCGGCCCGAACTTTGAGTATGCCGAGGCCCCGAGCCGGCTGTCCCCC
LPL-CO19        GGCCTGGACCCCGCCGGCCCCAACTTTGAGTACGCCGAGGCCCCCAGCAGGCTGTCCCCC
LPL-CO21        GGGCTGGACCCCGCCGGGCCCAATTTTGAGTATGCCGAGGCCCCCAGCCGGCTGTCCCCC
LPL-CO14        GGCCTGGACCCCGCGGGGCCCAACTTCGAGTACGCCGAAGCCCCCAGCAGGCTGAGCCCC
LPL-CO04        GGCCTGGACCCCGCCGGCCCCAACTTCGAATACGCCGAGGCCCCCTCCCGACTGTCCCCA
LPL-CO15        GGCCTCGACCCCGCCGGCCCCAACTTCGAATACGCCGAGGCCCCCAGCAGGCTGAGCCCG
LPL-CO10        GGCCTGGATCCGGCCGGACCCAACTTCGAATACGCCGAAGCCCCTAGCCGGCTGAGCCCC
LPL-CO05        GGTCTGGACCCCGCGGGCCCGAACTTCGAGTACGCCGAAGCCCCGAGCAGGCTGTCCCCG
LPL-CO22        GGCCTCGATCCCGCCGGACCCAACTTTGAGTACGCCGAAGCCCCCTCGAGGCTGAGCCCC
LPL-CO13        GGCCTGGATCCCGCCGGGCCCAATTTCGAGTACGCGGAAGCCCCCAGCCGGCTGAGCCCC
LPL-CO08        GGGCTGGACCCCGCCGGCCCGAATTTCGAGTACGCGGAGGCCCCGAGCAGGCTGAGCCCC
LPL-CO20        GGCCTGGACCCCGCCGGCCCCAACTTCGAGTACGCCGAGGCCCCCAGCCGTCTGAGCCCC
LPL-CO07        GGCCTGGACCCGGCCGGCCCCAACTTCGAGTACGCCGAGGCGCCCAGCCGTCTGAGCCCC
LPL-CO23        GGGCTGGACCCCGCCGGCCCCAATTTCGAGTACGCCGAGGCCCCCTCGCGGCTGAGCCCC
LPL-CO25        GGCCTGGATCCCGCCGGCCCGAACTTCGAGTACGCCGAGGCCCCCAGCAGGCTGAGCCCG
LPL-CO09        GGGCTGGACCCCGCCGGCCCCAACTTCGAGTACGCCGAGGCACCCAGCAGGCTGAGCCCG
LPL-CO11        GGCCTAGACCCCGCCGGGCCCAACTTCGAATACGCCGAGGCCCCCTCCAGGCTGAGCCCG
LPL-CO12        GGGCTGGACCCCGCCGGCCCCAATTTCGAATATGCCGAGGCCCCCAGCAGGCTGAGCCCC
LPL-CO16        GGCCTGGACCCGGCCGGCCCAAACTTTGAGTACGCCGAGGCCCCCTCCAGGCTGTCCCCC
LPL-CO06        GGGCTAGACCCCGCCGGGCCCAATTTCGAGTACGCCGAGGCGCCCAGCAGGCTGAGTCCC
LPL-CO24        GGCCTCGACCCCGCCGGCCCCAACTTTGAGTACGCCGAGGCCCCCTCAAGGCTGAGCCCC
LPL-CO17        GGCCTGGATCCCGCCGGCCCCAACTTCGAGTACGCAGAGGCACCGTCCAGGCTGTCCCCC
                ** ** **.** ** ** ** **.**.**.**.** **.** **      * **   .**
```

FIG. 3 (cont.)

```
LPL-WT      GATGATGCAGATTTTGTAGACGTCTTACACACATTCACCAGAGGGTCCCCTGGTCGAAGC
LPL-CO01    GACGATGCCGACTTCGTGGACGTGCTGCACACCTTCACCCGGGGCAGCCCCGGCAGGAGC
LPL-CO02    GACGATGCCGACTTTGTGGATGTGCTGCACACCTTCACCCGAGGTAGCCCCGGCAGGAGC
LPL-CO03    GACGACGCAGACTTCGTCGACGTCCTGCATACCTTCACCAGAGGCAGCCCCGGGAGGTCC
LPL-CO18    GACGACGCCGACTTCGTCGACGTGCTCCACACCTTCACGAGGGGGAGCCCCGGCCGGAGC
LPL-CO19    GATGATGCCGACTTCGTGGACGTGCTGCATACGTTCACCCGCGGGAGCCCCGGGAGGAGC
LPL-CO21    GACGACGCAGACTTCGTGGACGTGCTGCACACCTTCACCCGAGGCAGCCCGGGAAGAAGC
LPL-CO14    GACGATGCCGACTTCGTGGACGTCCTGCACACCTTCACCCGGGGCAGCCCCGGGAGGAGC
LPL-CO04    GACGACGCCGACTTCGTGGATGTGCTGCACACCTTCACCCGCGGCAGCCCCGGGCGAAGC
LPL-CO15    GATGACGCCGACTTTGTGGACGTGCTCCACACCTTCACCAGGGGCTCCCCCGGCCGGTCC
LPL-CO10    GACGACGCCGACTTCGTGGACGTCCTGCACACCTTCACAAGGGGGTCCCCTGGTCGCAGT
LPL-CO05    GACGACGCCGACTTCGTGGACGTGCTGCACACCTTTACCCGCGGCTCCCCCGGCCGGAGC
LPL-CO22    GACGACGCCGATTTTGTGGACGTCCTCCACACCTTCACCCGCGGGTCCCCCGGCAGGAGC
LPL-CO13    GATGACGCCGATTTCGTGGACGTGCTGCACACCTTCACGCGCGGCAGCCCCGGCCGGAGC
LPL-CO08    GACGACGCCGACTTCGTGGACGTGCTGCACACGTTCACCCGAGGAAGCCCCGGCCGGAGC
LPL-CO20    GACGACGCCGACTTTGTGGACGTGCTGCACACCTTCACCAGGGGGAGTCCTGGGCGGAGC
LPL-CO07    GACGACGCCGATTTCGTGGACGTGCTGCACACCTTCACCAGGGGCAGCCCCGGCCGCAGC
LPL-CO23    GACGACGCCGACTTTGTGGACGTGCTGCACACCTTCACCCGGGGCAGCCCTGGGAGATCC
LPL-CO25    GACGACGCCGACTTCGTGGACGTCCTCCACACCTTCACCAGGGGGAGCCCCGGGAGGAGC
LPL-CO09    GACGACGCTGACTTTGTGGACGTGCTGCACACCTTTACCAGGGGCAGCCCCGGTCGATCC
LPL-CO11    GACGACGCCGACTTTGTGGACGTCCTGCACACCTTCACGAGAGGGTCCCCGGGCCGGTCG
LPL-CO12    GACGACGCCGACTTCGTGGACGTGCTGCATACCTTCACCAGGGGCAGCCCCGGCCGGTCG
LPL-CO16    GACGACGCCGACTTCGTGGACGTCCTGCACACCTTCACCCGTGGGTCCCCCGGACGGAGC
LPL-CO06    GACGACGCCGACTTTGTGGACGTCCTGCATACCTTCACCCGCGGCAGCCCCGGGCGATCC
LPL-CO24    GACGACGCCGACTTCGTAGACGTGCTGCACACCTTTACTCGCGGCAGCCCGGGTAGGTCG
LPL-CO17    GACGACGCCGACTTCGTGGACGTCCTGCACACCTTCACCAGGGGCTCCCCCGGGCGTAGC
            **.**.** **.**.** **.** .* **.** **.**  * **   .** **  *
```

FIG. 3 (cont.)

```
LPL-WT          ATTGGAATCCAGAAACCAGTTGGGCATGTTGACATTTACCCGAATGGAGGTACTTTTCAG
LPL-CO01        ATCGGCATCCAGAAGCCCGTGGGCCATGTCGACATCTATCCCAATGGCGGCACCTTTCAG
LPL-CO02        ATCGGCATCCAGAAGCCCGTGGGCCACGTGGACATCTACCCCAACGGGGGTACCTTCCAG
LPL-CO03        ATCGGCATCCAGAAGCCCGTGGGCCATGTGGACATCTACCCGAATGGCGGCACCTTCCAG
LPL-CO18        ATCGGCATACAAAAGCCCGTGGGACACGTGGACATCTACCCCAACGGCGGCACCTTTCAG
LPL-CO19        ATCGGCATACAGAAACCCGTGGGCCACGTGGACATATACCCCAACGGCGGAACGTTCCAG
LPL-CO21        ATCGGCATCCAGAAGCCCGTGGGCCACGTGGACATCTACCCCAACGGAGGCACCTTCCAG
LPL-CO14        ATAGGCATACAGAAACCCGTGGGCCACGTGGACATCTACCCCAATGGCGGCACGTTCCAG
LPL-CO04        ATCGGAATCCAAAAGCCCGTGGGGCACGTGGATATCTACCCGAACGGGGGAACCTTCCAA
LPL-CO15        ATCGGGATCCAGAAGCCCGTCGGGCACGTGGACATCTACCCCAATGGGGGGACCTTCCAA
LPL-CO10        ATCGGGATCCAGAAGCCTGTCGGCCACGTCGATATCTACCCCAACGGCGGGACCTTCCAG
LPL-CO05        ATCGGAATCCAAAAGCCCGTCGGGCACGTGGATATCTACCCCAACGGCGGCACCTTCCAG
LPL-CO22        ATCGGCATCCAGAAGCCCGTGGGCCACGTGGACATCTATCCCAACGGCGGCACCTTCCAG
LPL-CO13        ATCGGTATCCAGAAACCAGTGGGCCATGTGGACATCTACCCAAATGGCGGAACCTTCCAG
LPL-CO08        ATCGGAATCCAGAAGCCCGTGGGCCACGTCGACATCTACCCCAATGGCGGAACCTTCCAG
LPL-CO20        ATCGGCATCCAAAAGCCGGTGGGCCACGTGGACATCTACCCGAACGGTGGTACGTTTCAG
LPL-CO07        ATCGGCATTCAGAAGCCCGTGGGCCACGTCGACATATATCCCAACGGCGGAACCTTCCAA
LPL-CO23        ATCGGCATACAGAAGCCCGTCGGCCACGTGGACATCTACCCCAACGGGGGACCTTTCAG
LPL-CO25        ATTGGAATCCAGAAGCCCGTGGGCCACGTGGACATCTATCCCAATGGCGGGACGTTCCAA
LPL-CO09        ATCGGTATACAGAAGCCCGTGGGCCACGTGGACATCTATCCCAACGGGGGCACATTTCAA
LPL-CO11        ATCGGAATCCAGAAACCCGTGGGGCATGTGGACATTTACCCCAACGGCGGCACCTTCCAG
LPL-CO12        ATTGGCATACAAAAGCCCGTGGGCCACGTGGACATCTACCCGAACGGGGGCACCTTCCAG
LPL-CO16        ATCGGGATTCAGAAACCCGTGGGCCATGTGGACATTTACCCCAACGGGGGGACCTTCCAA
LPL-CO06        ATCGGCATCCAGAAGCCGGTCGGCCACGTCGACATCTACCCCAACGGCGGCACATTCCAG
LPL-CO24        ATCGGGATCCAGAAGCCTGTCGGCCATGTGGACATCTACCCCAACGGCGGCACCTTCCAA
LPL-CO17        ATCGGCATCCAAAAGCCCGTGGGCCACGTGGACATCTACCCCAACGGCGGCACCTTCCAG
                ** ** ** **.**.** ** ** **.** **.** **.** **.** ** ** **.**.
```

FIG. 3 (cont.)

```
LPL-WT      CCAGGATGTAACATTGGAGAAGCTATCCGCGTGATTGCAGAGAGAGGACTTGGAGATGTG
LPL-CO01    CCCGGTTGCAACATCGGCGAGGCGATCAGGGTGATTGCCGAGAGGGGCCTGGGCGACGTC
LPL-CO02    CCCGGGTGCAACATCGGAGAGGCCATCAGGGTGATCGCAGAGAGGGGCCTGGGCGATGTG
LPL-CO03    CCTGGTTGCAACATTGGCGAGGCGATCAGGGTGATCGCCGAGCGTGGCCTCGGGGACGTG
LPL-CO18    CCGGGCTGTAATATCGGCGAGGCCATCCGCGTGATCGCCGAGAGGGGCCTGGGGGACGTG
LPL-CO19    CCGGGGTGCAACATCGGCGAGGCCATCCGGGTCATCGCCGAGAGGGGGCTGGGCGATGTG
LPL-CO21    CCAGGCTGTAACATCGGCGAGGCCATCAGGGTGATCGCCGAACGCGGCCTGGGCGACGTG
LPL-CO14    CCCGGGTGCAACATCGGGGAGGCCATCAGGGTGATCGCCGAGAGGGGACTTGGCGACGTG
LPL-CO04    CCCGGCTGCAACATTGGGGAGGCCATCAGAGTGATCGCCGAGCGCGGGCTGGGGGACGTC
LPL-CO15    CCCGGCTGCAACATCGGCGAGGCGATCAGGGTGATCGCCGAGCGCGGCCTGGGGGACGTG
LPL-CO10    CCCGGCTGCAACATCGGCGAGGCCATCCGGGTGATTGCCGAGAGGGGCCTGGGAGACGTC
LPL-CO05    CCCGGGTGCAACATCGGTGAGGCCATCAGGGTCATCGCCGAACGGGGCCTGGGCGACGTG
LPL-CO22    CCCGGCTGTAACATCGGCGAAGCCATCCGGGTGATCGCCGAACGGGGCCTGGGCGATGTG
LPL-CO13    CCGGGCTGTAACATCGGTGAAGCCATCCGGGTGATCGCCGAGAGGGGCCTGGGCGATGTG
LPL-CO08    CCCGGGTGCAACATAGGCGAAGCCATCAGGGTGATCGCCGAAAGGGGGCTGGGCGATGTG
LPL-CO20    CCCGGGTGCAACATCGGGGAAGCCATCAGGGTGATCGCCGAGAGGGGGCTGGGCGACGTG
LPL-CO07    CCCGGCTGTAACATCGGGGAGGCCATCCGGGTCATCGCCGAGAGGGGCCTGGGCGACGTG
LPL-CO23    CCCGGGTGCAATATCGGGGAAGCCATTAGGGTGATCGCCGAGAGGGGTCTGGGGGACGTC
LPL-CO25    CCTGGCTGCAACATCGGTGAAGCCATCCGCGTGATCGCCGAGCGCGGCCTGGGCGACGTG
LPL-CO09    CCCGGCTGCAACATCGGCGAAGCCATCAGGGTCATCGCCGAGCGCGGCCTGGGCGATGTG
LPL-CO11    CCAGGCTGCAACATCGGCGAAGCCATCAGGGTCATCGCCGAGAGGGGACTGGGCGACGTG
LPL-CO12    CCCGGGTGCAACATAGGAGAAGCCATCAGGGTGATCGCGGAGAGGGGCCTGGGCGATGTG
LPL-CO16    CCCGGGTGCAACATCGGAGAGGCGATCAGGGTGATCGCTGAGCGGGGCCTCGGGGACGTC
LPL-CO06    CCCGGCTGCAACATCGGCGAGGCCATCAGGGTGATCGCCGAGCGTGGGCTGGGCGACGTG
LPL-CO24    CCCGGATGTAACATCGGCGAGGCCATCCGGGTGATCGCCGAACGCGGGCTGGGAGACGTG
LPL-CO17    CCCGGGTGCAACATCGGCGAGGCGATCCGGGTGATAGCGGAACGCGGGCTGGGCGACGTG
            ** ** **.**.** ** **.** **. * ** ** ** **. * ** ** ** **.**
```

FIG. 3 (cont.)

```
LPL-WT      GACCAGCTAGTGAAGTGCTCCCACGAGCGCTCCATTCATCTCTTCATCGACTCTCTGTTG
LPL-CO01    GATCAGCTGGTGAAGTGTAGCCACGAGCGGTCCATCCATCTCTTCATAGACTCCCTTCTG
LPL-CO02    GACCAGCTGGTCAAGTGCAGCCACGAAAGGAGCATACACTTATTCATAGATAGCCTGCTC
LPL-CO03    GATCAGCTGGTGAAGTGTTCCCACGAGCGCAGCATCCACCTCTTCATCGACAGCCTGCTC
LPL-CO18    GACCAACTGGTGAAGTGTAGCCACGAAAGGTCCATCCACCTCTTCATCGACAGCCTCCTG
LPL-CO19    GACCAACTGGTGAAGTGCTCCCATGAACGGTCCATCCATCTGTTCATCGACAGCCTGCTG
LPL-CO21    GACCAACTCGTGAAGTGCTCCCACGAGCGCAGCATCCACCTCTTCATCGACAGCCTGCTG
LPL-CO14    GACCAGCTGGTGAAGTGCAGCCACGAGCGCAGCATACACCTGTTCATCGATAGCCTGCTT
LPL-CO04    GACCAGCTGGTGAAGTGCTCCCACGAGCGCAGCATCCACCTGTTCATCGACTCCCTACTG
LPL-CO15    GACCAGCTGGTGAAATGTTCCCATGAGCGGAGCATCCATCTGTTCATTGACTCCCTGCTG
LPL-CO10    GACCAGTTGGTGAAATGCAGCCACGAGAGGAGCATCCACCTGTTCATCGACTCCCTCCTG
LPL-CO05    GACCAGCTGGTCAAATGTAGCCATGAGAGGTCCATCCACCTGTTTATCGACTCCCTGCTG
LPL-CO22    GACCAGCTGGTGAAATGTAGCCACGAGAGGAGCATCCACCTGTTTATCGATAGCTTGCTG
LPL-CO13    GACCAGCTGGTGAAATGTAGCCACGAGCGCTCCATCCACCTCTTCATCGACTCCCTGCTG
LPL-CO08    GACCAGCTGGTGAAGTGTTCACACGAGAGGTCCATCCACCTGTTTATCGATAGCCTGCTG
LPL-CO20    GACCAGCTGGTGAAGTGCTCCCACGAGAGGTCCATCCACCTGTTCATCGACTCCCTTCTC
LPL-CO07    GACCAGCTGGTGAAGTGCTCCCACGAGCGTAGCATTCATCTGTTCATCGACTCCCTGCTG
LPL-CO23    GACCAGCTCGTGAAATGTTCCCACGAGAGGAGCATCCACCTGTTCATAGACAGCCTGCTG
LPL-CO25    GACCAGCTGGTGAAGTGCAGTCACGAGAGGAGCATCCACCTGTTCATCGATAGCCTGCTG
LPL-CO09    GATCAGCTGGTGAAGTGCTCCCACGAGAGGAGCATCCACCTGTTCATCGACAGCCTCCTC
LPL-CO11    GACCAGCTGGTGAAGTGCAGCCACGAGCGGAGCATCCACCTGTTCATCGACAGCCTGCTG
LPL-CO12    GACCAGCTGGTGAAATGCAGCCACGAAAGGTCCATCCACCTGTTTATCGACAGCCTGCTG
LPL-CO16    GACCAGCTGGTGAAGTGCAGCCACGAGCGCTCCATCCACCTGTTCATCGACAGCCTGCTG
LPL-CO06    GATCAGCTGGTGAAGTGCAGCCACGAGAGGAGCATCCATCTGTTCATCGATAGCCTGCTG
LPL-CO24    GACCAACTGGTGAAGTGCAGCCACGAGAGGAGCATCCACCTGTTCATCGACAGCCTGCTG
LPL-CO17    GATCAGCTGGTCAAGTGTAGCCATGAGCGCAGCATCCACCTGTTCATCGACTCCCTGCTC
            **.**..* ** **.**.   **.**. *   *** **..* **.** **.   ..* .*
```

FIG. 3 (cont.)

```
LPL-WT     AATGAAGAAAATCCAAGTAAGGCCTACAGGTGCAGTTCCAAGGAAGCCTTTGAGAAAGGG
LPL-CO01   AATGAAGAGAACCCCTCCAAAGCCTACCGATGCAGCAGCAAGGAGGCGTTCGAAAAGGGG
LPL-CO02   AACGAAGAGAACCCCAGCAAGGCCTACCGTTGTTCCTCTAAGGAGGCCTTCGAGAAGGGG
LPL-CO03   AACGAAGAGAACCCCTCCAAGGCCTACAGGTGCAGTTCCAAGGAGGCATTCGAGAAGGGC
LPL-CO18   AACGAGGAGAACCCCTCCAAGGCCTACAGGTGCAGCTCTAAAGAGGCGTTCGAGAAGGGG
LPL-CO19   AACGAGGAGAACCCCAGCAAGGCCTACAGGTGTAGCAGCAAGGAGGCCTTCGAGAAAGGC
LPL-CO21   AATGAGGAGAATCCCAGCAAGGCATATAGGTGCAGCAGCAAGGAGGCCTTTGAGAAGGGC
LPL-CO14   AACGAGGAAAACCCCTCCAAGGCCTACAGGTGCTCCTCAAAGGAAGCGTTCGAGAAGGGG
LPL-CO04   AATGAAGAGAACCCCAGCAAGGCGTACCGGTGCTCCTCCAAGGAGGCCTTCGAGAAGGGC
LPL-CO15   AACGAGGAGAACCCCTCCAAGGCCTACCGGTGCTCCAGCAAGGAGGCCTTCGAGAAGGGT
LPL-CO10   AACGAGGAGAACCCCAGCAAGGCCTACCGCTGCTCCTCCAAGGAGGCCTTCGAGAAAGGC
LPL-CO05   AACGAGGAGAACCCCAGCAAGGCCTACCGGTGCTCCAGCAAGGAGGCCTTCGAGAAAGGA
LPL-CO22   AACGAGGAGAACCCATCCAAAGCGTACAGGTGCAGCTCCAAGGAGGCCTTCGAAAAGGGC
LPL-CO13   AACGAAGAAAACCCCTCCAAGGCGTACAGGTGTAGCAGCAAGGAGGCCTTCGAGAAGGGC
LPL-CO08   AACGAGGAGAACCCATCCAAGGCCTACAGGTGCAGCAGCAAGGAGGCCTTTGAGAAGGGC
LPL-CO20   AACGAAGAAAACCCGAGCAAGGCCTACAGGTGTAGCAGCAAGGAAGCCTTCGAGAAGGGG
LPL-CO07   AACGAAGAGAACCCCTCCAAGGCCTACCGTTGCTCCAGCAAGGAGGCCTTCGAGAAGGGC
LPL-CO23   AATGAGGAGAACCCCTCCAAAGCCTACCGCTGCAGCAGCAAGGAGGCCTTCGAAAAGGGG
LPL-CO25   AACGAGGAGAACCCCAGCAAGGCCTACAGGTGCTCCAGCAAGGAGGCCTTCGAGAAGGGC
LPL-CO09   AATGAGGAGAATCCCAGCAAGGCCTACAGGTGCTCCAGCAAGGAGGCCTTCGAGAAGGGT
LPL-CO11   AATGAGGAGAATCCCAGCAAGGCCTACAGATGTTCCAGCAAAGAGGCCTTCGAGAAGGGA
LPL-CO12   AACGAGGAGAACCCCAGCAAGGCCTATAGGTGCAGCTCAAAGGAGGCCTTCGAGAAGGGA
LPL-CO16   AACGAGGAAAACCCCAGCAAGGCGTATAGGTGCTCGTCGAAGGAGGCCTTCGAAAAGGGC
LPL-CO06   AACGAGGAGAACCCGAGCAAGGCCTACAGGTGTAGCAGCAAGGAGGCCTTCGAGAAGGGC
LPL-CO24   AACGAGGAGAACCCCAGCAAAGCCTATAGGTGCAGCAGCAAGGAGGCCTTCGAAAAAGGC
LPL-CO17   AACGAAGAAAACCCCAGCAAGGCCTACCGGTGCTCGAGCAAGGAAGCGTTCGAGAAGGGC
           **.**.**.**.**   .**.** **. * **.      **.**.** **.**.**.**
```

FIG. 3 (cont.)

```
LPL-WT      CTCTGCTTGAGTTGTAGAAAGAACCGCTGCAACAATCTGGGCTATGAGATCAATAAAGTC
LPL-CO01    CTGTGCCTGTCCTGCAGGAAGAACAGGTGCAACAATCTGGGCTATGAGATCAACAAGGTA
LPL-CO02    CTCTGCCTGAGCTGCCGGAAAAACAGGTGCAACAACCTCGGCTACGAGATCAACAAGGTG
LPL-CO03    CTCTGCCTGAGCTGCAGGAAGAACAGGTGTAACAACCTAGGCTACGAGATCAACAAGGTC
LPL-CO18    CTTTGCCTGAGCTGCAGGAAGAATAGGTGCAACAACCTGGGCTACGAAATCAACAAGGTG
LPL-CO19    CTGTGTCTGAGCTGCAGAAAGAACAGGTGCAACAACCTCGGCTACGAGATCAACAAGGTG
LPL-CO21    CTGTGCCTGTCATGCCGGAAGAACAGGTGCAACAACCTGGGCTACGAGATCAACAAGGTC
LPL-CO14    CTGTGTCTCTCCTGCAGGAAGAACAGATGCAATAACCTGGGCTACGAGATCAACAAGGTG
LPL-CO04    CTCTGCCTGAGCTGCAGGAAGAACAGATGCAACAATCTGGGCTACGAGATCAATAAGGTC
LPL-CO15    CTGTGCCTGAGCTGCAGGAAGAATCGATGTAACAACCTGGGCTACGAGATCAACAAGGTG
LPL-CO10    CTGTGTCTGAGCTGCCGGAAGAACCGGTGCAATAACCTCGGGTACGAGATCAATAAGGTG
LPL-CO05    CTGTGCCTGAGCTGCAGGAAGAACCGTTGCAACAACCTGGGCTACGAGATCAACAAGGTG
LPL-CO22    CTGTGCCTCTCCTGCAGGAAGAACCGGTGCAACAACCTGGGGTATGAGATCAACAAAGTA
LPL-CO13    CTGTGCCTCTCCTGCCGTAAGAACAGGTGTAACAACCTGGGGTACGAGATCAACAAGGTG
LPL-CO08    CTGTGTCTGTCGTGTAGGAAGAACAGGTGCAACAATCTCGGCTACGAGATCAATAAGGTA
LPL-CO20    CTGTGCCTGTCCTGTAGGAAAAACAGGTGCAACAACCTCGGCTACGAGATCAACAAGGTG
LPL-CO07    CTCTGCCTCAGCTGCAGGAAGAACAGGTGTAACAACCTGGGCTACGAGATCAACAAGGTG
LPL-CO23    CTGTGCCTGAGCTGCAGGAAGAATAGGTGTAACAATCTGGGCTACGAGATCAACAAGGTG
LPL-CO25    CTCTGCCTGAGCTGCCGCAAGAACCGGTGCAACAACCTCGGGTACGAAATCAATAAGGTG
LPL-CO09    CTGTGCCTGTCCTGCAGAAAAAACAGGTGCAACAACCTGGGCTACGAGATCAACAAAGTG
LPL-CO11    CTGTGCCTGTCCTGCAGAAAGAACAGGTGCAATAACCTGGGTTACGAGATAAATAAGGTG
LPL-CO12    CTGTGCCTCTCCTGCAGGAAGAACCGCTGTAACAACCTGGGCTACGAGATAAACAAGGTG
LPL-CO16    CTGTGCCTGTCGTGCCGAAAGAACAGGTGTAACAACCTGGGTTACGAGATCAACAAGGTG
LPL-CO06    CTCTGTCTGTCATGCAGGAAGAATAGGTGCAACAACCTGGGCTACGAGATCAACAAGGTG
LPL-CO24    CTCTGCCTGTCCTGCAGGAAAAACCGTTGCAACAACCTGGGCTACGAAATCAACAAGGTG
LPL-CO17    CTGTGCCTGAGCTGCAGGAAGAATAGGTGCAATAATCTGGGCTATGAGATCAACAAGGTG
            ** **..*    **. * **.**. * **.**.**.** ** **.**.** **.**.**
```

FIG. 3 (cont.)

```
LPL-WT          AGAGCCAAAAGAAGCAGCAAAATGTACCTGAAGACTCGTTCTCAGATGCCCTACAAAGTC
LPL-CO01        CGCGCGAAGCGGAGCAGCAAGATGTATCTGAAGACCCGGTCGCAGATGCCCTATAAAGTG
LPL-CO02        CGGGCCAAACGGTCCAGCAAGATGTACCTGAAGACCAGGAGCCAGATGCCCTATAAGGTC
LPL-CO03        CGGGCCAAGCGGAGCTCAAAGATGTACCTGAAGACGCGGAGCCAGATGCCCTATAAGGTG
LPL-CO18        CGGGCCAAGCGCAGCAGCAAAATGTACCTGAAGACCCGTAGCCAGATGCCCTACAAGGTG
LPL-CO19        AGGGCCAAGAGGTCCAGCAAAATGTATCTGAAGACCAGGAGCCAGATGCCATACAAGGTC
LPL-CO21        AGGGCCAAACGCAGCTCCAAGATGTACCTGAAGACCCGGAGCCAAATGCCCTACAAGGTG
LPL-CO14        AGGGCCAAGAGGAGCAGCAAGATGTACCTGAAAACTAGGAGCCAAATGCCCTATAAGGTG
LPL-CO04        CGCGCCAAGAGAAGCAGCAAAATGTACCTGAAGACCCGGAGCCAGATGCCCTATAAGGTG
LPL-CO15        CGCGCCAAGAGGAGCAGCAAGATGTACCTGAAGACCAGGAGTCAAATGCCCTACAAGGTG
LPL-CO10        CGCGCCAAGCGGAGCAGCAAGATGTACCTGAAGACAAGGAGCCAGATGCCCTACAAGGTG
LPL-CO05        AGGGCAAAGCGGAGCTCAAAGATGTACCTGAAGACCCGGTCCCAAATGCCCTACAAAGTG
LPL-CO22        AGGGCGAAGAGGAGCTCCAAGATGTACCTGAAGACTAGGAGCCAGATGCCCTACAAGGTG
LPL-CO13        CGGGCCAAGAGGAGCAGCAAGATGTACCTGAAGACCCGGAGCCAGATGCCCTACAAGGTC
LPL-CO08        AGGGCCAAGCGGTCGAGCAAGATGTACCTCAAGACCAGGAGCCAGATGCCCTATAAGGTG
LPL-CO20        CGCGCTAAGCGCTCCAGCAAGATGTACCTGAAGACAAGGTCACAGATGCCCTACAAGGTG
LPL-CO07        AGGGCCAAGAGGAGCTCCAAGATGTATCTGAAGACACGGAGCCAGATGCCCTACAAGGTG
LPL-CO23        CGGGCGAAGAGGTCCTCTAAGATGTATCTTAAGACCCGAAGCCAAATGCCCTATAAGGTG
LPL-CO25        CGGGCCAAGAGGTCCAGCAAGATGTATCTGAAGACCCGGAGCCAGATGCCCTACAAGGTG
LPL-CO09        AGGGCCAAGAGGTCGAGCAAAATGTACCTGAAGACCAGGAGCCAGATGCCCTACAAGGTG
LPL-CO11        AGGGCCAAGAGGTCCTCCAAGATGTATCTGAAGACCCGCAGCCAGATGCCTTACAAGGTC
LPL-CO12        AGGGCCAAGCGGAGCAGCAAGATGTACCTGAAGACTCGCTCCCAGATGCCATACAAGGTG
LPL-CO16        AGGGCCAAAAGGAGCTCCAAGATGTATCTGAAGACCCGGTCCCAGATGCCCTATAAGGTG
LPL-CO06        AGGGCCAAAAGGAGCTCCAAGATGTATCTGAAGACCAGGTCCCAGATGCCGTACAAGGTG
LPL-CO24        CGAGCCAAAAGGAGCAGCAAGATGTACCTGAAGACCAGGTCCCAGATGCCGTATAAGGTG
LPL-CO17        CGGGCCAAGCGAAGCTCTAAAATGTACCTGAAGACTCGGTCCCAGATGCCGTACAAGGTG
                 * ** **. *       **.*****.** **.**  *    **.***** **.**.**
```

FIG. 3 (cont.)

```
LPL-WT   TTCCATTACCAAGTAAAGATTCATTTTTCTGGGACTGAGAGTGAAACCCATACCAATCAG
LPL-C001 TTCCACTACCAGGTAAAGATTCCACTTCTCCGGACTGAGAGCGAGACCCACACAAATCAG
LPL-C002 TTCCACTACCAGGTCAAGATCCACTTCTCCGGCACCGAGAGCGAGACCCACACTAACCAG
LPL-C003 TTCCACTACCAGGTGAAAATCCATTTCTCCGGCACCGAGTCCGAGACCCACACCAACCAA
LPL-C018 TTCCACTACCAGGTGAAAATCCATTTCTCCGGCACCGAGTCCGAAAGCGACACCAACCAG
LPL-C019 TTCCACTACCAGGTCAAGATCCATTTCTCCGGCACCGAGTCCGAAACCGACACCAACCAG
LPL-C021 TTCCACTACCAGGTGAAGATCCATTTCTCCGGCACCGAGTCCGAAACCGAGACCAACCAG
LPL-C014 TTTCACTACCAGGTGAAGATCCATTTCTCCGGCACCGAGAGCGAGACCCACACAAACCAG
LPL-C004 TTCCACTACCAGGTGAAGATCCACTTCCACTTCAGCGGCACCGAGAGCGAGACCCACACCAACCAG
LPL-C015 TTCCACTACCAGGTGAAGATCCACTTCCACTTCAGCGGCACCGAGAGTCTGAGACCCATACCAACCAG
LPL-C010 TTCCACTACCAGGTGAAGATCCACTTCCACTTCAGCGGCACCGAGAGCGAGACCCACACCAATCAG
LPL-C005 TTCCACTACCAGGTGAAAATTCATTTCAGCGGCACCGAGAGCGAGACCCACACGAACCAG
LPL-C022 TTCCACTATCAGGTGAAAATCCACTTCAGCGGCACCGAGACAGAGAGCGAGACCCACACCAACCAG
LPL-C013 TTCCACTACCAGGTCAAGATCCACTTCAGCGGCACCGAGAGCGAGACCCACACTAACCAA
LPL-C008 TTCCATTATCAGGTGAAGATCCACTTTAGCGGCACCGAGAGCGAAACCCACACCAACCAG
LPL-C020 TTCCACTACCAGGTGAAAATCCACTTTAGCGGCACCGAAAAGCGAAACCCACACCAACCAG
LPL-C007 TTCCACTACCAGGTGAAGATCCACTTCTCCGGGACCGAGAGCGGAATCAGAGACCCACGAACCAG
LPL-C023 TTCCACTACCAGGTGAAGATCCACTTCATTTTCCGGGACCGAGAGCGAGACCCATACCAACCAG
LPL-C025 TTCCACTATCAGGTGAAGATCCACTTTTTCGGTGACGAGTCCGAGACCCACACAAACCAG
LPL-C009 TTCCACTACCAGGTGAAGATCCACTTCTCGGCACAGAGGACGGAATCCGAGACGACACCAACCAG
LPL-C011 TTCCACTACCAGGTGAAGATCCACTTTAGCGGACGGAATCAGAGAGCGAGACCCACACCAACCAG
LPL-C012 TTCCACTACCAGGTGAAGATCCACTTCTCCGGCACCGAAACCGAGAGCGAAACCCACACAAACCAA
LPL-C016 TTCCACTACCAGGTGAAGATCCACTTCTCCGGCACCGAGAGCGAAACCCACACCAACCAG
LPL-C006 TTCCACTATCAGGTGAAGATCCACTTCTCCGGCACAGAGACGAGACGAGAGACGACACCAACCAG
LPL-C024 TTCCACTACCAGGTGAAGATCCACTTCTCATTTCTCCGGGAACCGAGTCGGAAACCCACACTAACCAG
LPL-C017 TTCCACTACCAGGTGAAGATCCACTTCAGCGGCGGGACCGAATCCGAAACGCACACCAACCAA
         ** **.***.**: ***.***.**: ** .*.**    *  **:**: **.**  **:**
```

FIG. 3 (cont.)

| | |
|---|---|
| LPL-WT | GCCTTTGAGAGATTTCTCTGTATGGCACCGTGTGGCCGAGAGTGAGAACATCCATTCACTCTG |
| LPL-C001 | GCCTTCGAGATCAGCCTGCGTGTACGGCACCGTGTGGCCGAGAGCGAGAATATCCCGTTCACCCTG |
| LPL-C002 | GCCTTCGAGATCTCGCTGTACGGACACCGTGTGGCCGGAATCCGAGAACATCCCGTTCACCCTG |
| LPL-C003 | GCATTCGAGATCTCCCTGTACGGACACCGTGTAGCCGGAGCGAGAACATCCCTTCACCCTC |
| LPL-C018 | GCCTTCGAGATCTCCCTGTACGGACACCGTGTCGCAGAGCGAGAACATCCCCTTCACGCTC |
| LPL-C019 | GCGTTCGAGATCAGCCTGTACGGACACCGTGTGGCCGAGAGCGAGAACATCCCCTTCACCCTT |
| LPL-C021 | GCGTTCGAAATCAGCCTGTACGGACACCGTGTGGCCGAGAGCGAGAACATCCCCTTCACCCTG |
| LPL-C014 | GCCTTCGAAATCTCGCTGTACGGACACCGTGTGGCCGAGAGCGAGAACATCCCGTTCACCCTG |
| LPL-C004 | GCTTTCGAAATCAGCCTGTACGGACACCGTGTGGCCGAGAGCGAGAACATCCCCTTTACCCTG |
| LPL-C015 | GCCTTCGAGATCAGCCTCTACGGACACCGTGTGGCCGAGAGCGAGAAACATCCCCTTCACCCTG |
| LPL-C010 | GCCTTCGAGATAAGCCTGTATGGCACCGTGTGGCCGAGAGCGAGAATATCCCCTTCACTCTC |
| LPL-C005 | GCCTTCGAGATCTCTCTGTATGGACACCGTGTGGCCGAGAGCGAGAACATCCCCTTCACCCTG |
| LPL-C022 | GCCTTCGAGATCAGCCTGTACGGACACTGTGTGCCGAGAGCGAGAACATCCCCTTCACCCTG |
| LPL-C013 | GCGTTCGAGATCAGCCTTATATGGACACCGTGTGGCCGAGTCCGAGAACATCCCCTTCACCCTG |
| LPL-C008 | GCCTTCGAGATCAGCCTGTACGGACACCGTGTGGCCGAGTCCGAGAACATCCCCTTCACCCTG |
| LPL-C020 | GCCTTCGAAATCAGCCTCCCCTGTACGGACACCGTGTGGCCGAGTCCGAAAACATCCCCTTCACCCTG |
| LPL-C007 | GCCTTTGAGATCAGCCTGTACGGACACAGTGTGGCCGAGTCCGAAAGCGAGAACATCCCCTTCACCCTG |
| LPL-C023 | GCCTTCGAGATCAGCCTGTACGGACACCGTGTGGCCGAGTCCGAAAGCGAGAACATCCCCTTCACCCTG |
| LPL-C025 | GCCTTCGAAATCAGCCTCCCCTGTACGGACACCGTGTGGCCGAGTCCGAGAGCGAGAATATCCCCTTTACCCTG |
| LPL-C009 | GCCTTCGAGATCTCCCTGTACGGACACCGTGTGGCCGAGTCCGAGAGCGAGAATATCCCCTTCACCCTG |
| LPL-C011 | GCTTTCGAGATCAGCCTGTACGGACACCGTGTGGCCGAGTCCGAGAGCGAGAACATCCCCTTCACCCTG |
| LPL-C012 | GCGTTCGAGATCAGCCTGTACGGACACCGTGTGGCCGAATCAGAGAGAACATCCCCTTTACCCTG |
| LPL-C016 | GCCTTCGAGATCTCCCTGTACGGACACCGTGTGGCCGAGTCCGAGAACATCCCCTTCACCCTG |
| LPL-C006 | GCCTTCGAGATCAGCCTGTACGGACACCGTGTGGCCGAGTCCGAAAACATATCCCCTTTTACCCTG |
| LPL-C024 | GCGTTCGAGATCAGCCTGTACGGACACGGTCGCCGCCGAGTCCGAGAGCGAGAACATCCCCTTCACCCTC |
| LPL-C017 | GCCTTCGAGATCAGCCTGTACGGACACCGTCGCCGCCGAGAGCGAGAACATCCCCTTCACCCTG |
| | *.* *** . * * ***** . * ** * ***** * *** ** *** * |

FIG. 3 (cont.)

| | |
|---|---|
| LPL-WT | CCTGAAGTTTCCACAAATAAGACCTACTCCTTCCTAATTTACACAGAGGTAGATATTGGA |
| LPL-C001 | CCTGAGGTGTCCACCAATAAGACCTACTCCTTCCTTCCTGATCTACACGGAGGTGGACATAGGC |
| LPL-C002 | CCCGAGGTGAGCACCAACAAACGTACAGCTTCCTGATCTACACCGAGGTCGACATCGGC |
| LPL-C003 | CCCGAGGTGAGCACTAACAGACGTACTCCTTCCTGATCTACACCGAGGTGGACATCGGC |
| LPL-C018 | CCTGAGGTGTCGACCAACAAGACCTATTCCTTCCTGATCTATACCGAGGTGGATATCGGA |
| LPL-C019 | CCCGAGGTGTCCACCAACAAGACCTACCTTCCTCATCTACACCGAGGTGGATATCGGC |
| LPL-C021 | CCCGAGGTGAGCACGAATAAGACCTACAGCTTCCTGATCTACACCGAGGTGGACATCGGC |
| LPL-C014 | CCCGAGGTGTCCACCAACAAGACCTACAGCTTCCTGATCTACACCGAGGTAGACATTGGT |
| LPL-C004 | CCAGAAGTGTCAACCAATAAGACCTACAGCTTCCTGATATACACTGAGGTGGATATCGGC |
| LPL-C015 | CCCGAGGTGTCCACCAACAACAAGACCTACTCCTTCCTGATCTACACCGAGGTGGATATCGGC |
| LPL-C010 | CCCGAGGTCTCCACCAACAAGACGACCTACAGCTTCCTGATCTACACCGAGGTAGATATCGGC |
| LPL-C005 | CCCGAGGTGAGCACGAACAAGACCTACTCCTTCCTGATCTACACGGAGGTCGATATCGGT |
| LPL-C022 | CCGAAGTGAGCACGAACAAAACCTACAGCTTCCTGATCTACACCGAGGTGGACATCGGC |
| LPL-C013 | CCCGAGGTGAGCACCAACAAACAAAACCTACTCCTTTCTGATCTACACGGAAGTGGACATCGGC |
| LPL-C008 | CCCGAGGTCAGCACCAACAAGACCTACAGCTTCCTGATCTACACGGAGGTCGACATCGGC |
| LPL-C020 | CCGAAGTGAGCACCAACAAGACCTATAGCTTCCTTCCTGATCTACACCGAGGTGGATATCGGG |
| LPL-C007 | CCCGAGGTGAGCACGAACAAACAAAACTTACTGCTTCCTCCTTCCTGATCTACACCGAGTGAAGTGGACATCGGC |
| LPL-C023 | CCCGAGGTGAGCACCAACAAGACCTATTCCTTCCTGATCTACACCGAGGTGGACATCGGC |
| LPL-C025 | CCGAAGTGTCCAGCACCAACAAGACCTACTCCTCATTTCTGATCTACACCGAGGTGGACATCGGC |
| LPL-C009 | CCCGAGGTGAGCACCAACAAGACCTACTCCTCCTGATCTACACGGAGGTGGACATCGGC |
| LPL-C011 | CCGGAGGTGTCCACCAACAAGACCTACTCCTTCCTGATATACGGAGGTCTATACAGGTCTATACAGAGGTGGACATCGGG |
| LPL-C012 | CCGGAGGTGAGCACCAACAAGACCTACTCCTTCCTGATCTACACACGTACACCGAGGTGGACATCGGG |
| LPL-C016 | CCCGAGGTGAGCACTAACAACAAGACCTACTCCTTCCTGATATACACCGAGGTGGACATAGGC |
| LPL-C006 | CCCGAGGTGTCCACCAACAAGACCTACAGCTTCCTGATATACACCGAGGTGGACATCGGC |
| LPL-C024 | CCCGAAGTGTCCACCAACAAAACGTACACATACAGCTTCCTGATCTACACCGAGGTGGACATCGGA |
| LPL-C017 | CCCGAGGTGTCCACCAACAACAAGACGTACAGCTTCCTCATCTATACCGAGGTCGACATCGGG |
|  | ** *. * * * ** ** * ** * * * * *. *** **. *** |

FIG. 3 (cont.)

```
LPL-WT          GAACTACTCATGTTGAAGCTCAAATGGAAGAGTGATTCATACTTTAGCTGGTCAGACTGG
LPL-CO01        GAGCTGCTGATGCTGAAGCTGAAGTGGAAGTCGGACAGCTACTTCTCCTGGAGCGACTGG
LPL-CO02        GAGCTCCTCATGCTCAAGCTCAAGTGGAAGAGCGATAGCTACTTCAGCTGGTCCGACTGG
LPL-CO03        GAGCTCCTGATGCTGAAGCTGAAGTGGAAGAGCGACTCCTACTTTTCCTGGTCCGACTGG
LPL-CO18        GAGCTGCTGATGCTGAAGCTCAAATGGAAAAGCGACAGCTATTTCTCATGGTCCGACTGG
LPL-CO19        GAGCTGCTGATGCTGAAGCTGAAGTGGAAGAGCGACAGCTACTTCAGCTGGTCGGACTGG
LPL-CO21        GAGCTGCTGATGCTGAAGCTGAAATGGAAATCCGACAGCTACTTCAGCTGGTCCGACTGG
LPL-CO14        GAGCTGCTGATGCTCAAACTCAAGTGGAAGAGCGACTCCTACTTCAGCTGGAGCGATTGG
LPL-CO04        GAGCTGCTGATGCTGAAGTTGAAGTGGAAGAGCGATAGCTACTTCAGCTGGAGCGATTGG
LPL-CO15        GAGCTGCTGATGCTGAAGCTGAAGTGGAAGAGCGATAGCTACTTCTCGTGGAGCGACTGG
LPL-CO10        GAGCTGCTGATGCTGAAGCTGAAATGGAAGAGCGACAGCTATTTCTCATGGAGCGACTGG
LPL-CO05        GAGCTGCTGATGCTGAAGCTGAAGTGGAAGAGCGACAGCTACTTCTCCTGGAGCGACTGG
LPL-CO22        GAGCTCCTCATGCTCAAGCTGAAGTGGAAGTCCGACAGCTACTTCTCGTGGAGCGACTGG
LPL-CO13        GAGCTGCTGATGCTGAAGCTGAAGTGGAAAAGCGACAGCTACTTTTCCTGGTCCGACTGG
LPL-CO08        GAACTGCTTATGCTGAAGCTGAAGTGGAAAAGCGACAGCTACTTCAGCTGGAGCGATTGG
LPL-CO20        GAGCTGCTGATGCTCAAACTGAAATGGAAGAGCGATAGCTACTTCTCCTGGAGCGATTGG
LPL-CO07        GAGCTGCTGATGCTGAAACTCAAATGGAAGAGCGACAGCTACTTTAGCTGGAGCGACTGG
LPL-CO23        GAGCTGCTGATGCTGAAGCTGAAGTGGAAGAGCGATAGCTACTTCAGCTGGTCAGACTGG
LPL-CO25        GAACTCCTGATGCTGAAGCTGAAGTGGAAGTCCGACAGCTACTTTTCCTGGAGCGACTGG
LPL-CO09        GAGCTGCTCATGCTGAAACTGAAGTGGAAGTCGGACAGCTACTTCAGCTGGAGCGATTGG
LPL-CO11        GAGCTGCTGATGCTGAAGCTGAAGTGGAAATCCGACAGCTACTTCAGCTGGAGCGACTGG
LPL-CO12        GAGCTGCTGATGCTGAAGCTGAAGTGGAAAAGCGACTCCTACTTCAGCTGGAGCGATTGG
LPL-CO16        GAGCTGCTGATGCTGAAGCTGAAGTGGAAGTCCGACTCCTATTTCAGCTGGAGCGACTGG
LPL-CO06        GAACTGCTGATGCTCAAGCTGAAATGGAAGTCCGACAGCTACTTCAGCTGGAGCGATTGG
LPL-CO24        GAGCTGCTGATGCTCAAGCTGAAGTGGAAGAGCGACAGCTACTTCAGCTGGAGCGACTGG
LPL-CO17        GAGCTGCTGATGTTAAAACTGAAGTGGAAGAGCGACTCCTATTTTAGCTGGTCCGACTGG
                **.** ** ***.* **..* **.*****.   **.   **.**.   ***   **.***
```

FIG. 3 (cont.)

```
LPL-WT     TGGAGCAGTCCCGGCTTCGCCATTCAGAAGATCAGAGTAAAAGCAGGAGAGACTCAGAAA ← SEQ ID NO:2
LPL-CO01   TGGTCCTCCCCCGGATTCGCCATCCAGAAGATCAGGGTGAAGGCCGGCGAGACCCAGAAA ← SEQ ID NO:5
LPL-CO02   TGGAGCAGCCCGGGCTTCGCCATCCAAAAGATTAGGGTGAAGGCCGGCGAGACCCAGAAG ← SEQ ID NO:6
LPL-CO03   TGGTCCAGCCCCGGGTTTGCGATTCAAAAGATCAGGGTGAAAGCCGGCGAAACCCAGAAG ← SEQ ID NO:7
LPL-CO18   TGGAGCAGCCCGGGATTCGCCATCCAGAAGATCAGGGTGAAGGCCGGGGAGACCCAGAAG ← SEQ ID NO:22
LPL-CO19   TGGAGCTCCCCCGGCTTCGCGATCCAGAAAATCCGTGTGAAAGCCGGGGAGACCCAGAAG ← SEQ ID NO:23
LPL-CO21   TGGAGCTCCCCCGGCTTCGCCATCCAGAAGATCAGGGTGAAGGCCGGGGAGACCCAGAAA ← SEQ ID NO:25
LPL-CO14   TGGTCCTCCCCGGGCTTCGCCATCCAGAAGATACGGGTCAAGGCTGGGGAAACCCAGAAG ← SEQ ID NO:18
LPL-CO04   TGGAGCAGCCCCGGATTCGCCATCCAGAAGATAAGGGTGAAGGCCGGAGAGACCCAGAAG ← SEQ ID NO:8
LPL-CO15   TGGAGCAGCCCCGGCTTCGCCATCCAGAAGATCAGGGTGAAGGCCGGCGAGACCCAAAAG ← SEQ ID NO:19
LPL-CO10   TGGAGCTCCCCGGGCTTCGCCATCCAGAAGATCAGGGTGAAGGCGGGCGAGACACAAAAG ← SEQ ID NO:14
LPL-CO05   TGGAGCAGCCCTGGGTTCGCCATCCAAAAAATCCGGGTGAAGGCCGGCGAGACCCAAAAG ← SEQ ID NO:9
LPL-CO22   TGGTCGAGCCCCGGCTTCGCCATCCAGAAGATCCGGGTGAAAGCCGGCGAGACCCAGAAG ← SEQ ID NO:26
LPL-CO13   TGGAGCAGCCCGGGCTTCGCGATCCAGAAGATCCGGGTGAAGGCCGGCGAGACCCAGAAG ← SEQ ID NO:17
LPL-CO08   TGGAGCAGCCCCGGCTTTGCCATCCAGAAAATCCGCGTGAAGGCAGGGGAGACCCAGAAG ← SEQ ID NO:12
LPL-CO20   TGGAGCAGCCCCGGCTTCGCGATCCAGAAGATCCGCGTGAAGGCGGGGGAGACCCAGAAG ← SEQ ID NO:24
LPL-CO07   TGGTCCAGCCCCGGCTTCGCCATCCAGAAAATCAGGGTCAAAGCCGGCGAGACCCAGAAA ← SEQ ID NO:11
LPL-CO23   TGGAGCAGCCCCGGCTTCGCAATCCAGAAGATCAGGGTGAAGGCCGGCGAGACGCAGAAG ← SEQ ID NO:27
LPL-CO25   TGGTCCAGCCCCGGGTTCGCCATACAGAAGATCCGGGTGAAGGCAGGGGAGACGCAGAAA ← SEQ ID NO:29
LPL-CO09   TGGAGCAGCCCCGGCTTCGCGATCCAGAAGATCAGGGTGAAGGCCGGGGAGACGCAGAAG ← SEQ ID NO:13
LPL-CO11   TGGAGCAGCCCCGGCTTTGCCATCCAGAAAATCAGGGTGAAGGCCGGAGAAACTCAAAAA ← SEQ ID NO:15
LPL-CO12   TGGTCCAGCCCCGGCTTTGCCATCCAGAAGATCAGGGTCAAGGCCGGCGAGACGCAGAAG ← SEQ ID NO:16
LPL-CO16   TGGTCCTCCCCCGGGTTTGCCATCCAAAAGATAAGGGTGAAGGCCGGCGAGACCCAAAAG ← SEQ ID NO:20
LPL-CO06   TGGAGCTCCCCGGGGTTCGCAATCCAAAAGATCAGGGTGAAGGCAGGGGAGACCCAGAAG ← SEQ ID NO:10
LPL-CO24   TGGTCCTCGCCGGGCTTCGCCATCCAAAAGATCCGCGTCAAGGCCGGGGAGACCCAGAAG ← SEQ ID NO:28
LPL-CO17   TGGAGCAGCCCCGGCTTCGCCATCCAGAAGATCAGGGTCAAGGCCGGTGAGACGCAGAAG ← SEQ ID NO:21
           ***      ** ** **.** ** **.**.**  * ** **.** ** **.** **.**.
```

FIG. 3 (cont.)

SEQUENCE LISTING

```
<160> NUMBER OF SEQ ID NOS: 203

<210> SEQ ID NO 1
<211> LENGTH: 475
<212> TYPE: PRT
<213> ORGANISM: Homo sapiens

<400> SEQUENCE: 1

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
        115                 120                 125

Lys Leu Val Gly Gln Asp Val Ala Arg Phe Ile Asn Trp Met Glu Glu
    130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
```

```
        195                 200                 205

Leu His Thr Phe Thr Arg Gly Ser Pro Gly Arg Ser Ile Gly Ile Gln
    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
        435                 440                 445

Lys Val Ser His Leu Gln Lys Gly Lys Ala Pro Ala Val Phe Val Lys
    450                 455                 460

Cys His Asp Lys Ser Leu Asn Lys Lys Ser Gly
465                 470                 475


<210> SEQ ID NO 2
<211> LENGTH: 1425
<212> TYPE: DNA
<213> ORGANISM: Homo sapiens

<400> SEQUENCE: 2

atggagagca aagccctgct cgtgctgact ctggccgtgt ggctccagag tctgaccgcc      60

tcccgcggag gggtggccgc cgccgaccaa agaagagatt ttatcgacat cgaaagtaaa     120

tttgccctaa ggacccctga agacacagct gaggacactt gccacctcat tcccggagta     180

gcagagtccg tggctacctg tcatttcaat cacagcagca aaaccttcat ggtgatccat     240

ggctggacgg taacaggaat gtatgagagt tgggtgccaa aacttgtggc cgccctgtac     300

aagagagaac cagactccaa tgtcattgtg gtggactggc tgtcacgggc tcaggagcat     360

tacccagtgt ccgcgggcta caccaaactg gtgggacagg atgtggcccg gtttatcaac     420

tggatggagg aggagtttaa ctaccctctg gacaatgtcc atctcttggg atacagcctt     480

ggagcccatg ctgctggcat tgcaggaagt ctgaccaata agaaagtcaa cagaattact     540
```

-continued

```
ggcctcgatc cagctggacc taactttgag tatgcagaag ccccgagtcg tctttctcct    600
gatgatgcag attttgtaga cgtcttacac acattcacca gagggtcccc tggtcgaagc    660
attggaatcc agaaaccagt tggcatgtt gacatttacc cgaatggagg tacttttcag    720
ccaggatgta acattggaga agctatccgc gtgattgcag agagaggact tggagatgtg    780
gaccagctag tgaagtgctc ccacgagcgc tccattcatc tcttcatcga ctctctgttg    840
aatgaagaaa atccaagtaa ggcctacagg tgcagttcca aggaagcctt tgagaaaggg    900
ctctgcttga gttgtagaaa gaaccgctgc aacaatctgg gctatgagat caataaagtc    960
agagccaaaa gaagcagcaa aatgtacctg aagactcgtt ctcagatgcc ctacaaagtc   1020
ttccattacc aagtaaagat tcatttttct gggactgaga gtgaaaccca taccaatcag   1080
gcctttgaga tttctctgta tggcaccgtg gccgagagtg agaacatccc attcactctg   1140
cctgaagttt ccacaaataa gacctactcc ttcctaattt acacagaggt agatattgga   1200
gaactactca tgttgaagct caaatggaag agtgattcat actttagctg gtcagactgg   1260
tggagcagtc ccggcttcgc cattcagaag atcagagtaa aagcaggaga gactcagaaa   1320
aaggtgatct tctgttctag ggagaaagtg tctcatttgc agaaaggaaa ggcacctgcg   1380
gtatttgtga aatgccatga caagtctctg aataagaagt caggc                     1425
```

<210> SEQ ID NO 3
<211> LENGTH: 446
<212> TYPE: PRT
<213> ORGANISM: Homo sapiens

<400> SEQUENCE: 3

```
Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
        115                 120                 125

Lys Leu Val Gly Gln Asp Val Ala Arg Phe Ile Asn Trp Met Glu Glu
    130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
        195                 200                 205

Leu His Thr Phe Thr Arg Gly Ser Pro Gly Arg Ser Ile Gly Ile Gln
    210                 215                 220
```

```
Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser
        435                 440                 445


<210> SEQ ID NO 4
<211> LENGTH: 1338
<212> TYPE: DNA
<213> ORGANISM: Homo sapiens

<400> SEQUENCE: 4

atggagagca aggccctgct ggtgctgacc ctggccgtgt ggctgcagag cctgaccgcc      60

agcagaggcg gcgtggccgc cgccgaccag agaagagact tcatcgacat cgagagcaag     120

ttcgccctga gaaccccccga ggacaccgcc gaggacacct gccacctgat ccccggcgtg     180

gccgagagcg tggccacctg ccacttcaac cacagcagca agaccttcat ggtgatccac     240

ggctggaccg tgaccggcat gtacgagagc tgggtgccca agctggtggc cgccctgtac     300

aagagagagc ccgacagcaa cgtgatcgtg gtggactggc tgagcagagc ccaggagcac     360

taccccgtga gcgccggcta caccaagctg gtgggccagg acgtggccag attcatcaac     420

tggatggagg aggagttcaa ctacccccctg gacaacgtgc acctgctggg ctacagcctg     480

ggcgcccacg ccgccggcat cgccggcagc ctgaccaaca agaaggtgaa cagaatcacc     540

ggcctggacc ccgccggccc caacttcgag tacgccgagg cccccagcag actgagcccc     600

gacgacgccg acttcgtgga cgtgctgcac accttcacca gaggcagccc cggcagaagc     660

atcggcatcc agaagcccgt gggccacgtg gacatctacc ccaacggcgg caccttccag     720

cccggctgca acatcggcga ggccatcaga gtgatcgccg agagaggcct gggcgacgtg     780

gaccagctgg tgaagtgcag ccacgagaga agcatccacc tgttcatcga cagcctgctg     840
```

aacgaggaga accccagcaa ggcctacaga tgcagcagca aggaggcctt cgagaagggc 900
ctgtgcctga gctgcagaaa gaacagatgc aacaacctgg gctacgagat caacaaggtg 960
agagccaaga gaagcagcaa gatgtacctg aagaccagaa gccagatgcc ctacaaggtg 1020
ttccactacc aggtgaagat ccacttcagc ggcaccgaga gcgagaccca caccaaccag 1080
gccttcgaga tcagcctgta cggcaccgtg gccgagagcg agaacatccc cttcaccctg 1140
cccgaggtga gcaccaacaa gacctacagc ttcctgatct acaccgaggt ggacatcggc 1200
gagctgctga tgctgaagct gaagtggaag agcgacagct acttcagctg gagcgactgg 1260
tggagcagcc ccggcttcgc catccagaag atcagagtga aggccggcga gacccagaag 1320
aaggtgatct tctgcagc 1338

<210> SEQ ID NO 5
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 5
atggagagca aggccctgct ggtgctgacc ctggccgtgt ggctgcagag cctgaccgcc 60
agccggggag gcgtggccgc cgccgaccag cggcgggact tcatcgacat cgagtccaag 120
ttcgccctgc ggacgcccga ggacaccgcc gaagacacct gccacctgat ccccggcgtc 180
gccgagagcg tggccacatg ccacttcaac cacagcagca agaccttcat ggtgatccac 240
ggctggaccg tgaccggcat gtacgagagc tgggtgccca agctggtggc cgctctgtac 300
aagcgggagc ccgacagcaa cgtgatcgtg gtggactggc tgagccgggc ccaggagcac 360
taccccgtga gcgccggcta caccaagctc gtcggccagg acgtggcccg gttcatcaac 420
tggatggagg aggagttcaa ctacccgctg gacaacgtgc acctgctggg ctacagcctg 480
ggcgcccacg ccgccggcat cgccggcagc ctcaccaaca agaaggtgaa ccggatcacc 540
ggcctggacc ccgccggccc caacttcgag tacgccgagg cgcccagcag gctctcgccc 600
gacgacgccg acttcgtgga cgtgctgcac accttcaccc ggggctctcc cggacggagc 660
atcggcatcc agaagcccgt gggccacgtg gacatctacc ccaacggcgg caccttccag 720
cccggctgca acatcggcga ggccatccgg gtgatcgccg agcggggtct gggcgacgtg 780
gaccagctgg tgaagtgcag ccacgagcgg agcattcacc tgttcatcga tagcctgctg 840
aacgaggaga acccctccaa agcataccgg tgcagtagta aggaggcctt cgagaagggc 900
ctgtgcctga gctgccggaa gaacagatgc aacaaccttg ggtacgagat caacaaggtg 960
cgggccaaga gatcttccaa gatgtacctg aagacccgga gccagatgcc ctacaaggtg 1020
ttccactacc aggtgaagat ccacttcagc ggcaccgaaa gcgaaactca caccaaccag 1080
gcctttgaaa tcagcctgta cggcaccgtg gccgagtctg agaacatccc tttcacactg 1140
cccgaggtga gcactaacaa gacctacagc ttcctgatct acaccgaggt ggacattggc 1200
gagctgctga tgctgaagct gaagtggaag tcagacagct acttcagctg gagcgactgg 1260
tggtctagcc ccggattcgc catccagaag atcagggtga aggccggaga gacacagaag 1320
aaagtgatct tctgcagccg ggagaaggta agccacctgc agaagggcaa ggctcccgcc 1380
gtgttcgtca agtgccacga caagtccctg aacaagaagt ccggc 1425

<210> SEQ ID NO 6
<211> LENGTH: 1425

<212> TYPE: DNA
<213> ORGANISM: Artificial Sequence
<220> FEATURE:
<223> OTHER INFORMATION: Synthetic Polynucleotide

<400> SEQUENCE: 6
atggagagca aggccctgct ggtgctgacc ctggccgtgt ggctgcagag cctgaccgcc 60
agccggggcg gcgtggccgc cgccgaccag cgccgcgact tcatcgacat cgagtccaag 120
ttcgccctcc gcacgcccga ggacaccgcc gaggacacct gccacctcat ccccggcgtc 180
gccgagtccg tcgccacctg ccacttcaac cactcctcca agaccttcat ggtcatccac 240
ggctggaccg tcaccggcat gtacgagtcc tgggtcccca agctcgtcgc cgccctctac 300
aagcgcgagc ccgactccaa cgtcatcgtc gtcgactggc tctcccgcgc ccaggagcac 360
taccccgtct ccgccggcta caccaagctc gtcggccagg acgtcgcccg cttcatcaac 420
tggatggagg aggagttcaa ctacccactc gacaacgtcc acctcctcgg ctactccctc 480
ggcgcccacg ccgccggcat cgccggctcc ctcaccaaca agaaggtcaa ccgcatcacc 540
ggcctcgacc ccgccggccc caacttcgag tacgccgagg cgccctcccg cctctcgccc 600
gacgacgccg acttcgtcga cgtcctccac accttcaccc gcggctcgcc cggccgctcc 660
atcggcatcc agaagcccgt cggccacgtc gacatctacc ccaacggcgg caccttccag 720
cccggctgca acatcggcga ggccatccgc gtcatcgccg agcgcggcct cggcgacgtc 780
gaccagctcg tcaagtgctc ccacgagcgc tccatccacc tcttcatcga ctccctcctc 840
aacgaggaga acccctccaa ggcctaccgc tgctcctcca aggaggcctt cgagaagggc 900
ctctgcctct cctgccgcaa gaaccgctgc aacaacctcg gctacgagat caacaaggtc 960
cgcgccaagc gctcctccaa gatgtacctc aagacccgct cccagatgcc ctacaaggtc 1020
ttccactacc aggtcaagat ccacttctcc ggcaccgagt ccgagaccca caccaaccag 1080
gccttcgaga tctccctcta cggcaccgtc gccgagtccg agaacatccc cttcaccctc 1140
cccgaggtct ccaccaacaa gacctactcc ttcctcatct acaccgaggt cgacatcggc 1200
gagctcctca tgctcaagct caagtggaag tccgactcct acttctcctg gtccgactgg 1260
tggtcctcgc ccggcttcgc catccagaag atccgcgtca aggccggcga gacccagaag 1320
aaggtcatct tctgctcccg cgagaaggtc tcccacctcc agaagggcaa ggcgcccgcc 1380
gtcttcgtca agtgccacga caagtccctc aacaagaagt ccggc 1425

<210> SEQ ID NO 7
<211> LENGTH: 1574
<212> TYPE: DNA
<213> ORGANISM: Artificial Sequence
<220> FEATURE:
<223> OTHER INFORMATION: Synthetic Polynucleotide

<400> SEQUENCE: 7
atggagagca aggccctgct ggtgctgacc ctggccgtgt ggctgcagag cctgaccgcc 60
agccggggag gcgtggccgc cgccgaccag cggcgggact tcatcgacat cgagtccaag 120
ttcgccctgc ggacccccga ggacaccgcc gaagacacct gccacctgat ccccggcgtc 180
gccgagagcg tggccacatg ccacttcaac cacagcagca agaccttcat ggtgatccac 240
ggctggactt catcgacatc gagtccaagt tcgccctgcg gacccccgag gacaccgccg 300
aagacacctg ccacctgatc cccggcgtcg ccgagagcgt ggccacatgc cacttcaacc 360
acagcagcaa gaccttcatg gtgatccacg gctggaccgt gaccggcatg tacgagagct 420
gggtgcccaa gctggtggcc gctctgtaca agcgggagcc cgacagcaac gtgatcgtgg 480
tggactggct gagccgggcc caggagcact accccgtgag cgccggctac accaagctcg 540
tcggccagga cgtggcccgg ttcatcaact ggatggagga ggagttcaac tacccccctgg 600 acaacgtgca cctgctgggc tacagcctgg gcgcccacgc cgccggcatc gccggcagcc 660
tcaccaacaa gaaggtgaac cggatcaccg gcctggaccc cgccggcccc aacttcgagt 720
acgccgaggc ccccagcagg ctctcccccg acgacgccga cttcgtggac gtgctgcaca 780
ccttcacccg gggctctccc ggacggagca tcggcatcca gaagcccgtg ggccacgtgg 840
acatctaccc caacggcggc accttccagc ccggctgcaa catcggcgag gccatccggg 900
tgatcgccga gcggggtctg ggcgacgtgg accagctggt gaagtgcagc cacgagcgga 960
gcattcacct gttcatcgat agcctgctga acgaggagaa cccctccaaa gcataccggt 1020
gcagtagtaa ggaggccttc gagaagggcc tgtgcctgag ctgccggaag aacagatgca 1080
acaaccttgg gtacgagatc aacaaggtgc gggccaagag atcttccaag atgtacctga 1140
agacccggag ccagatgccc tacaaggtgt tccactacca ggtgaagatc cacttcagcg 1200
gcaccgaaag cgaaactcac accaaccagg cctttgaaat cagcctgtac ggcaccgtgg 1260
ccgagtctga gaacatccct ttcacactgc ccgaggtgag cactaacaag acctacagct 1320
tcctgatcta caccgaggtg gacattggcg agctgctgat gctgaagctg aagtggaagt 1380
cagacagcta cttcagctgg agcgactggt ggtctagccc cggattcgcc atccaaaaga 1440
tcagggtgaa ggccggagag acacagaaga aagtgatctt ctgcagccgg gagaaggtaa 1500
gccacctgca gaagggcaag gctcccgccg tgttcgtcaa gtgccacgac aagtccctga 1560
acaagaagtc cggc 1574

<210> SEQ ID NO 8
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 8
atggagagca aggccctgct ggtgctgacc ctggccgtgt ggctgcagag cctgaccgcc 60
agccggggcg gcgtggccgc cgccgaccag cgccgcgact tcatcgacat cgagtccaag 120
ttcgccctcc gcacccccga ggacaccgcc gaggacacct gccacctcat ccccggcgtc 180
gccgagtccg tcgccacctg ccacttcaac cactcctcca agaccttcat ggtcatccac 240
ggctggaccg tcaccggcat gtacgagtcc tgggtcccca agctcgtcgc cgccctctac 300
aagcgcgagc ccgactccaa cgtcatcgtc gtcgactggc tctcccgcgc ccaggagcac 360
taccccgtct ccgccggcta caccaagctc gtcggccagg acgtcgcccg cttcatcaac 420
tggatggagg aggagttcaa ctacccccctc gacaacgtcc acctcctcgg ctactccctc 480
ggcgcccacg ccgccggcat cgccggctcc ctcaccaaca agaaggtcaa ccgcatcacc 540
ggcctcgacc ccgccggccc caacttcgag tacgccgagg ccccctcccg cctctccccc 600
gacgacgccg acttcgtcga cgtcctccac accttcaccc gcggctcccc cggccgctcc 660
atcggcatcc agaagcccgt cggccacgtc gacatctacc ccaacggcgg caccttccag 720
cccggctgca acatcggcga ggccatccgc gtcatcgccg agcgcggcct cggcgacgtc 780
gaccagctcg tcaagtgctc ccacgagcgc tccatccacc tcttcatcga ctccctcctc 840
aacgaggaga acccctccaa ggcctaccgc tgctcctcca aggaggcctt cgagaagggc 900

```
ctctgcctct cctgccgcaa gaaccgctgc aacaacctcg gctacgagat caacaaggtc    960
cgcgccaagc gctcctccaa gatgtacctc aagacccgct cccagatgcc ctacaaggtc   1020
ttccactacc aggtcaagat ccacttctcc ggcaccgagt ccgagaccca caccaaccag   1080
gccttcgaga tctccctcta cggcaccgtc gccgagtccg agaacatccc cttcaccctc   1140
cccgaggtct ccaccaacaa gacctactcc ttcctcatct acaccgaggt cgacatcggc   1200
gagctcctca tgctcaagct caagtggaag tccgactcct acttctcctg gtccgactgg   1260
tggtcctccc ccggcttcgc catccagaag atccgcgtca aggccggcga gacccagaag   1320
aaggtcatct tctgctcccg cgagaaggtc tcccacctcc agaagggcaa ggcccccgcc   1380
gtcttcgtca agtgccacga caagtccctc aacaagaagt ccggc                   1425
```

<210> SEQ ID NO 9
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 9

```
atggagagca aggctctgct ggtgctgacg ctggccgtgt ggctgcagtc cctgaccgcc     60
agcaggggag gcgtggccgc cgccgaccag cggcgcgact tcatcgatat cgagtcgaag    120
ttcgccctgc gcacgcccga ggataccgcc gaggacacgt gccacctgat ccccggggtg    180
gcggagagcg tcgccacctg tcacttcaac catagcagca agacgttcat ggtcatccac    240
ggctggaccg tgacaggaat gtacgaaagc tgggtgccca agctcgtggc cgccctctac    300
aagagggagc ccgacagcaa tgtgatagtg gtggactggc tgtcccgggc ccaggaacac    360
tatcccgtga gcgccgggta caccaagctc gtgggccagg acgtggcccg gttcatcaat    420
tggatggagg aggagttcaa ctacccccctg gacaacgtgc atctgctcgg ctactccctg    480
ggcgctcacg ccgccggcat cgcgggcagc ctgacaaaca agaaggtgaa caggatcacc    540
gggctcgacc ccgccggccc caacttcgag tacgccgagg cccccagcag gctgagcccc    600
gacgatgccg acttcgtgga cgtgctgcac accttcaccc ggggcagccc cggcaggagc    660
atcggcatcc agaagcccgt gggccatgtc gacatctatc ccaatggcgg cacctttcag    720
cccggttgca acatcggcga ggcgatcagg gtgattgccg agaggggcct gggcgacgtc    780
gatcagctgg tgaagtgtag ccacgagcgg tccatccatc tcttcataga ctcccttctg    840
aatgaagaga accccctccaa agcctaccga tgcagcagca aggaggcgtt cgaaaagggg    900
ctgtgcctgt cctgcaggaa gaacaggtgc aacaatctgg gctatgagat caacaaggta    960
cgcgcgaagc ggagcagcaa gatgtatctg aagacccggt cgcagatgcc ctataaagtg   1020
ttccactacc aggtaaagat ccacttctcc gggaccgaga gcgagaccca cacaaatcag   1080
gccttcgaga tcagcctgta cggcaccgtg gcggagagcg agaatatccc gttcaccctg   1140
cctgaggtgt ccaccaataa gacctactcc ttcctgatct acacggaggt ggacataggc   1200
gagctgctga tgctgaagct gaagtggaag tcggacagct acttctcctg gagcgactgg   1260
tggtcctccc ccggattcgc catccagaag atcagggtga aggccggcga gacccagaaa   1320
aaggtgatct tttgctcgcg cgagaaggtc tcgcacctgc agaaggggaa ggcccccgcc   1380
gtgttcgtga agtgccatga taagagtctc aataagaagt ccggg                   1425
```

<210> SEQ ID NO 10

<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 10
atggagagca aggcactgct ggtgctgaca ctggccgtgt ggctgcagag cctgaccgcc 60
tccaggggcg gagtggccgc cgccgaccag cggcgggact tcatcgacat cgaatcgaag 120
ttcgccctgc ggaccccgga ggacaccgcc gaagacacct gccacctcat ccccggcgtc 180
gccgagagcg tggccacgtg ccacttcaac cacagcagca agaccttcat ggtgatccat 240
ggctggaccg tgacaggcat gtatgagagc tgggtcccca aactggtggc ggccctgtac 300
aaaagggagc cggactccaa tgtgatcgta gtggactggc tctccagggc ccaggagcac 360
taccccgtca gcgccggcta caccaagctg gtgggccagg acgtggccag gttcatcaac 420
tggatggagg aagagttcaa ttacccctg gacaacgtgc atctgctcgg gtactccctg 480
ggcgcccacg ccgccgggat cgccggtagc ctcaccaaca agaaggtcaa tcgaatcacc 540
gggctggacc ccgccgggcc caactttgaa tacgccgaag cccccagccg gctcagcccc 600
gacgatgccg actttgtgga tgtgctgcac accttcaccc gaggtagccc cggcaggagc 660
atcggcatcc agaagcccgt gggccacgtg gacatctacc ccaacggggg taccttccag 720
cccgggtgca acatcggaga ggccatcagg gtgatcgcag agaggggcct gggcgatgtg 780
gaccagctgg tcaagtgcag ccacgaaagg agcatacact tattcataga tagcctgctc 840
aacgaagaga accccagcaa ggcctaccgt tgttcctcta aggaggcctt cgagaagggg 900
ctctgcctga gctgccggaa aaacaggtgc aacaacctcg gctacgagat caacaaggtg 960
cgggccaaac ggtccagcaa gatgtacctg aagaccagga gccagatgcc ctataaggtc 1020
ttccactacc aggtcaagat ccacttctcc ggcaccgaga gcgagaccca cactaaccag 1080
gccttcgaga tctcgctgta cgggacggtg gcggaatccg agaacatccc gttcaccctg 1140
cccgaggtga gcaccaacaa aacgtacagc ttcctgatct acaccgaggt cgacatcggc 1200
gagctcctca tgctcaagct caagtggaag agcgatagct acttcagctg gtccgactgg 1260
tggagcagcc cgggcttcgc catccaaaag attagggtga aggccggcga gacccagaag 1320
aaggtgatct tctgctcgag ggagaaagtg tcccatctgc agaagggcaa ggccccggcc 1380
gtgttcgtga agtgccacga taagtcgctg aacaagaagt ccggc 1425

<210> SEQ ID NO 11
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 11
atggagtcca aggccctgct ggtgctcaca ctcgccgtgt ggctgcagag cctgaccgcc 60
tcccgggggg gcgtggcggc cgccgaccag cggagggatt tcatcgacat cgagagcaaa 120
ttcgccctga ggacccccga ggacaccgcc gaggatacct gccatctcat ccccggcgtg 180
gctgagagcg tggccacctg ccacttcaac cacagcagca agaccttcat ggtgatccac 240
ggctggaccg tgaccggaat gtacgagagc tgggtgccca agctggtggc cgccctgtac 300
aagagggagc ccgatagcaa tgtgatagtg gtggattggc tgagcagggc ccaagagcat 360
taccccgtga gcgccggcta taccaagctg gtgggccagg acgtggccag gttcatcaac 420
tggatggagg aggagttcaa ctacccccctg gacaacgtcc acctgctggg ctacagcctg 480
ggggcccacg ccgcgggcat cgccggctcc ctcaccaaca agaaggtgaa taggataacg 540
ggcctggacc ccgccggtcc caacttcgag tacgccgagg ccccgtcccg actgtctccc 600
gacgacgcag acttcgtcga cgtcctgcat accttcacca gaggcagccc cgggaggtcc 660
atcggcatcc agaagcccgt gggccatgtg gacatctacc cgaatggcgg caccttccag 720
cctggttgca acattggcga ggcgatcagg gtgatcgccg agcgtggcct cggggacgtg 780
gatcagctgg tgaagtgttc ccacgagcgc agcatccacc tcttcatcga cagcctgctc 840
aacgaagaga acccctccaa ggcctacagg tgcagttcca aggaggcatt cgagaagggc 900
ctctgcctga gctgcaggaa gaacaggtgt aacaacctag gctacgagat caacaaggtc 960
cgggccaagc ggagctcaaa gatgtacctg aagacgcgga gccagatgcc ctataaggtg 1020
ttccactacc aggtgaaaat ccatttctcc ggcaccgagt ccgagaccca caccaaccaa 1080
gcattcgaga tctccctcta cggaaccgta gcagagagcg agaacatccc cttcaccctc 1140
cccgaggtga gcactaacaa gacgtactcc ttcctgatct acaccgaggt ggacatcggc 1200
gagctcctga tgctgaagct gaagtggaag agcgactcct acttttcctg gtccgactgg 1260
tggtccagcc ccgggtttgc gattcaaaag atcagggtga aagccggcga aacccagaag 1320
aaggtgatct tctgtagccg agagaaagtg agccacctgc agaaaggaaa ggcccccgcc 1380
gtcttcgtca agtgccacga caaaagcctc aataagaagt ccggg 1425

<210> SEQ ID NO 12
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 12
atggagagca aggcgctgct ggtgctgaca ctggcggtgt ggctgcaaag cctgaccgcg 60
agcaggggcg gcgtggccgc cgccgaccag aggcgggact tcattgacat cgagtccaag 120
ttcgccctta ggacccccga agacaccgcc gaggacacct gccacctgat accgggggtg 180
gccgagtccg tggccacctg ccactttaac cactcctcca agacgttcat ggtcatccac 240
ggctggaccg tgaccgggat gtacgaaagc tgggtgccca agctggtggc cgccctctac 300
aaaagggagc ctgactccaa cgtcatcgtg gtggactggc tgtccagggc ccaggagcac 360
taccccgttt ccgccggata caccaagctg gtgggccagg acgtggcccg gttcatcaat 420
tggatggagg aggaattcaa ttacccccctg gacaacgtgc atctgctcgg ctactccctg 480
ggcgcccacg ccgccggcat cgccggcagc ctgactaaca agaaggtgaa ccggatcacc 540
ggcctggacc ccgccggccc caacttcgaa tacgccgagg ccccctcccg actgtcccca 600
gacgacgccg acttcgtgga tgtgctgcac accttcaccc gcggcagccc cgggcgaagc 660
atcggaatcc aaaagcccgt ggggcacgtg gatatctacc cgaacggggg aaccttccaa 720
cccggctgca acattgggga ggccatcaga gtgatcgccg agcgcgggct gggggacgtc 780
gaccagctgg tgaagtgctc ccacgagcgc agcatccacc tgttcatcga ctccctactg 840
aatgaagaga accccagcaa ggcgtaccgg tgctcctcca aggaggcctt cgagaagggc 900
ctctgcctga gctgcaggaa gaacagatgc aacaatctgg gctacgagat caataaggtc 960
cgcgccaaga gaagcagcaa aatgtacctg aagacccgga gccagatgcc ctataaggtg 1020

```
ttccactacc aggtgaagat ccacttcagc ggtacggagt ctgagaccca taccaaccag   1080
gctttcgaaa tcagcctgta cggaaccgtg gccgagagcg agaacatccc ctttaccctg   1140
ccagaagtgt ccacaaacaa gacctactcc ttcctgatat acactgaggt ggacatcggc   1200
gagctgctga tgctgaagtt gaagtggaag agcgatagct acttcagctg gagcgattgg   1260
tggagcagcc ccggattcgc catccagaag ataagggtga aggccggaga gacccagaag   1320
aaggtcatct tttgcagcag ggagaaggtg agccacctgc agaagggcaa ggcgcccgcc   1380
gtgttcgtca agtgtcacga caagagcctg aataagaaga gcggg                   1425
```

<210> SEQ ID NO 13
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 13

```
atggaaagca aggcgctgct cgtcctcacc ctggccgtct ggctgcaaag cctgaccgcc     60
agcagaggtg gcgtggcggc cgccgaccag cggcgagact tcatcgatat cgaaagcaag    120
tttgccctga ggacccccga ggataccgcc gaggacacct gccacctgat tcccggagtg    180
gccgagagcg ttgccacctg ccacttcaac cactcgagca agacctttat ggtgatacac    240
ggctggaccg tcacgggcat gtacgagagc tgggtgccca agctggtggc cgccctgtat    300
aagagggagc cggacagcaa cgtcatcgtc gtggactggc tgtcgagggc ccaagaacac    360
taccccgtga gcgccgggta caccaagctg gtcggtcaag acgtggcccg cttcatcaat    420
tggatggagg aggagttcaa ctatcccctc gacaacgtgc acctcctggg ctacagcctg    480
ggcgcccacg ccgccggcat cgccggttcg ctcaccaata aaaaggtgaa caggattacc    540
ggtctggacc ccgcgggccc gaacttcgag tacgccgaag ccccgagcag gctgtccccg    600
gacgacgccg acttcgtgga cgtgctgcac acctttaccc gcggctcccc cggccggagc    660
atcggaatcc aaaagcccgt cgggcacgtg gatatctacc ccaacggcgg caccttccag    720
cccgggtgca acatcggtga ggccatcagg gtcatcgccg aacggggcct gggcgacgtg    780
gaccagctgg tcaaatgtag ccatgagagg tccatccacc tgtttatcga ctccctgctg    840
aacgaggaga accccagcaa ggcctaccgg tgctccagca aggaggcctt cgagaaagga    900
ctgtgcctga gctgcaggaa gaaccgttgc aacaacctgg gctacgagat caacaaggtg    960
agggcaaagc ggagctcaaa gatgtacctg aagacccggt cccaaatgcc ctacaaagtg   1020
ttccattacc aggtgaaaat tcatttcagc ggcaccgaga gcgaaaccca cacgaaccag   1080
gcctttgaga taagcctgta cgggaccgtg gcggagagcg agaatatccc cttcactctc   1140
cccgaggtga gcacgaacaa gacctactcc ttcctgatct acacggaggt cgatatcggt   1200
gagctgctga tgctgaagct gaagtggaag agcgacagct acttctcctg gagcgactgg   1260
tggagcagcc ctgggttcgc catccaaaaa atccgggtga aggccggcga gacccaaaag   1320
aaggtgatct tctgctctag ggagaaggtg tcccacctgc agaagggcaa ggcccccgcc   1380
gtatttgtga agtgccacga caagagcctg aataagaaga gcggc                   1425
```

<210> SEQ ID NO 14
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 14
atggagagca aggccctgct ggtcctgacc ctggccgtct ggctgcagag cctgaccgcc 60
tcccgggggg gcgtggccgc cgccgaccag aggcgcgact ttatagacat cgagtcgaag 120
tttgccctgc gcaccccga ggacacagcc gaagacacct gccacctgat ccccggggtg 180
gcggagagcg tggccacctg ccacttcaac cactcctcca agaccttcat ggtcattcat 240
ggctggaccg tcaccggcat gtacgagagt tgggtgccga agctggtggc cgccctctac 300
aagagggagc ccgactccaa cgtgatcgtg gtggactggc tgagcagggc ccaggagcac 360
tatccggtga gcgccgggta cacgaagctg gtcggacagg acgtggcccg cttcatcaac 420
tggatggagg aagagtttaa ctatccgctc gacaacgtcc atctgctggg gtacagcctg 480
ggcgcccatg ccgccggaat cgccggctcc ctgacgaaca agaaggtgaa ccggatcacc 540
gggctagacc ccgccgggcc caatttcgag tacgccgagg cgcccagcag gctgagtccc 600
gacgacgccg actttgtgga cgtcctgcat accttcaccc gcggcagccc cgggcgatcc 660
atcggcatcc agaagccggt cggccacgtc gacatctacc ccaacggcgg cacattccag 720
cccggctgca acatcggcga ggccatcagg gtgatcgccg agcgtgggct gggcgacgtg 780
gatcagctgg tgaagtgcag ccacgagagg agcatccatc tgttcatcga tagcctgctg 840
aacgaggaga acccgagcaa ggcctacagg tgtagcagca aggaggcctt cgagaagggc 900
ctctgtctgt catgcaggaa gaataggtgc aacaacctgg gctacgagat caacaaggtg 960
agggccaaaa ggagctccaa gatgtatctg aagaccaggt cccagatgcc gtacaaggtg 1020
ttccactatc aggtgaagat ccacttctcg ggcacagaga gcgagacgca caccaaccag 1080
gccttcgaga tcagcctgta cggcaccgtg gccgagtccg aaaacatccc ttttaccctg 1140
cccgaggtgt ccaccaacaa gacctacagc ttcctgatat acaccgaggt ggacatcggc 1200
gaactgctga tgctcaagct gaaatggaag tccgacagct acttcagctg gagcgattgg 1260
tggagctccc cggggttcgc aatccaaaag atcagggtga aggcagggga gacccagaag 1320
aaggtcatct tctgctcccg ggaaaaagtg agccatctcc agaagggcaa agcgcccgcc 1380
gtgttcgtca agtgccacga taagagcctg aacaagaaga gcggc 1425

<210> SEQ ID NO 15
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 15
atggagagca aggcgctgct ggtgctgacc ctggcggtgt ggctgcagag cctcaccgcc 60
tcgcgcggtg gcgtggcggc cgccgatcaa cggcgggact tcatcgatat cgagagcaag 120
ttcgcccttc ggaccccgga ggacaccgcc gaggatactt gccatctgat ccccggcgtg 180
gccgaatccg tggccacctg ccacttcaac cactccagca agaccttcat ggtgatccac 240
ggctggaccg tgaccgggat gtacgagagt tgggtgccca agctggtggc cgccctgtac 300
aagcgggagc ccgacagcaa tgtgatcgtg gtggactggc tgagcagggc ccaggagcat 360
tatccagtga gcgccgggta taccaaactc gtgggccagg atgtcgccag gttcattaac 420
tggatggagg aggaattcaa ctacccgctg gataacgtgc atctgctggg gtactcgctg 480
ggagcccatg ccgccggcat cgcgggatcc ctgacgaaca agaaggtcaa taggatcacc 540
ggcctggacc cggccggccc caacttcgag tacgccgagg cgcccagccg tctgagcccc 600
gacgacgccg atttcgtgga cgtgctgcac accttcacca ggggcagccc cggccgcagc 660
atcggcattc agaagcccgt gggccacgtc gacatatatc ccaacggcgg aaccttccaa 720
cccggctgta acatcgggga ggccatccgg gtcatcgccg agaggggcct gggcgacgtg 780
gaccagctgg tgaagtgctc ccacgagcgt agcattcatc tgttcatcga ctccctgctg 840
aacgaagaga accccctccaa ggcctaccgt tgctccagca aggaggcctt cgagaagggc 900
ctctgcctca gctgcaggaa gaacaggtgt aacaacctgg gctacgagat caacaaggtg 960
agggccaaga ggagctccaa gatgtatctg aagacacgga gccagatgcc ctacaaggtg 1020
ttccactacc aggtgaagat ccacttctcc gggacggaat cagagaccca cacgaaccag 1080
gcctttgaga tcagcctgta tgggaccgtg gccgagtccg agaacatccc cttcaccctg 1140
cccgaggtga gcaccaacaa aacttactcc ttcctgatct acactgaagt ggacatcggg 1200
gagctgctga tgctgaaact caaatggaag agcgacagct actttagctg gagcgactgg 1260
tggtccagcc ccggcttcgc catccagaaa atcagggtca aagccggcga gacccagaaa 1320
aaggtgatct tctgcagcag ggaaaaggtc agccacctgc agaaagggaa ggccccccgct 1380 gtgttcgtga aatgtcacga caagagcctg aacaaaaaga gcggc 1425

<210> SEQ ID NO 16
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 16
atggagagca aggccctgct ggtgctgacc ctggccgtgt ggctgcagtc gctgaccgcc 60
agcaggggcg gcgtggccgc ggccgaccag cgccgggact tcatcgacat cgagagcaag 120
tttgccctga ggacccccga ggataccgca gaggacacct gccatctgat ccccggcgtg 180
gcagagagcg tcgccacttg ccacttcaac cattccagca agacttttat ggtcatccac 240
ggttggaccg tgaccggaat gtacgagtcc tgggtcccga aactggtggc cgccctgtac 300
aagcgggagc cagactccaa cgtgatcgtc gtggattggc tgtccagggc ccaggagcac 360
taccccgtct ccgccggcta caccaagctg gtgggacaag acgtggccag gttcatcaac 420
tggatggaag aggagttcaa ctatcccctg gacaacgtgc atctcctggg ctacagcctc 480
ggcgcccacg ccgccggcat cgcgggcagt ctgacgaaca agaaggtgaa caggatcacc 540
gggctggacc ccgccggccc gaatttcgag tacgcggagg ccccgagcag gctgagcccc 600
gacgacgccg acttcgtgga cgtgctgcac acgttcaccc gaggaagccc cggccggagc 660
atcggaatcc agaagcccgt gggccacgtc gacatctacc ccaatggcgg aaccttccag 720
cccgggtgca acataggcga agccatcagg gtgatcgccg aaagggggct gggcgatgtg 780
gaccagctgg tgaagtgttc acacgagagg tccatccacc tgtttatcga tagcctgctg 840
aacgaggaga acccatccaa ggcctacagg tgcagcagca aggaggcctt tgagaagggc 900
ctgtgtctgt cgtgtaggaa gaacaggtgc aacaatctcg gctacgagat caataaggta 960
agggccaagc ggtcgagcaa gatgtacctc aagaccagga gccagatgcc ctataaggtg 1020
ttccattatc aggtgaaaat ccactttagc ggcaccgaga gcgaaaccca caccaaccag 1080
gccttcgaaa tctccctgta cggcactgtg gccgagagcg agaatatccc cttcaccctg 1140
cccgaggtca gcaccaacaa aacctacagc ttcctgatct acaccgaggt cgacatcggc 1200
gaactgctta tgctgaagct gaagtggaaa agcgacagct acttcagctg gagcgattgg 1260
tggagcagcc ccggctttgc catccagaaa atccgcgtga aggcagggga gacccagaag 1320
aaggtaatat tctgcagcag ggagaaggta agccacctgc agaaaggtaa ggcccccgcc 1380
gtgttcgtga aatgtcacga caagtccctg aataagaagt ccggg 1425

<210> SEQ ID NO 17
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 17
atggagagca aggccctgct ggtgctgacg ctggcggtgt ggctccagtc cctgaccgcc 60
agccgggggg gcgtcgccgc cgccgaccaa cgccgcgact tcatcgacat cgaaagtaaa 120
ttcgccctgc ggacccccga ggacaccgcc gaagacacgt gccacctgat ccctggagtt 180
gcggagagcg tggcgacctg ccacttcaac cactccagca agacgttcat ggtgatccat 240
ggctggaccg tcaccggcat gtacgagagc tgggtgccga agctcgtggc cgcgctctac 300
aagagggagc ccgactccaa cgtgatcgtg gtcgactggc tgagcagggc ccaggagcac 360
tacccagtca gcgccggcta caccaagctg gtgggccagg acgtggcgcg gtttataaac 420
tggatggagg aggagttcaa ctatcccctg gataacgtgc acctgctggg ctactccctg 480
ggcgcccacg ccgccgggat cgccggaagc ctgaccaaca agaaagtgaa ccgcattacc 540
gggctggacc ccgccggccc caacttcgag tacgccgagg cacccagcag gctgagcccg 600
gacgacgctg actttgtgga cgtgctgcac acctttacca ggggcagccc cggtcgatcc 660
atcggtatac agaagcccgt gggccacgtg gacatctatc ccaacggggg cacatttcaa 720
cccggctgca acatcggcga agccatcagg gtcatcgccg agcgcggcct gggcgatgtg 780
gatcagctgg tgaagtgctc ccacgagagg agcatccacc tgttcatcga cagcctcctc 840
aatgaggaga atcccagcaa ggcctacagg tgctccagca aggaggcctt cgagaagggt 900
ctgtgcctgt cctgcagaaa aaacaggtgc aacaacctgg gctacgagat caacaaagtg 960
agggccaaga ggtcgagcaa aatgtacctg aagaccagga gccagatgcc ctacaaggtg 1020
ttccactacc aggtgaagat ccacttcagc gggacggaat ccgagacgca caccaaccag 1080
gccttcgaga tctccctcta cggcaccgtg gccgagagcg agaatatccc cttcaccctg 1140
ccggaggtga gcacgaacaa gacctactca tttctgatct atacggaggt cgatatcggc 1200
gagctgctca tgctgaaact gaagtggaag tcggacagct acttcagctg gagcgattgg 1260
tggagcagcc ccggcttcgc gatccagaag atcagggtga aggccgggga gacgcagaag 1320
aaggtgattt tctgttccag agagaaagtc tcccacctcc aaaaaggcaa ggcccccgcc 1380
gtgttcgtga agtgccatga caagtccctg aacaagaaga gcggg 1425

<210> SEQ ID NO 18
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 18
atggagtcaa aggccctcct ggtgcttacc ctcgccgttt ggctccagtc cctgaccgcg 60

```
agccgcggcg gggtggccgc cgccgaccag aggcgagact ttatcgacat tgagtccaag    120

ttcgccctga ggacccccga ggacaccgcc gaggacacct gccacctgat ccccggtgtg    180

gccgagagcg tcgccacatg ccatttcaac cactcgagta aaaccttcat ggtgatccac    240

ggctggactg tgaccgggat gtacgagtcc tgggtcccca agctcgtggc cgccctgtac    300

aagagggagc ccgacagcaa cgtgattgtg gtggactggc tgtccagggc ccaggaacac    360

tacccggtga gcgccggcta caccaagctg gtgggccagg acgttgcccg cttcatcaac    420

tggatggagg aggagttcaa ctacccctg gacaacgtgc acctgctggg ctacagcctg    480

ggggcccacg ccgccgggat cgcggggtcc ctgaccaaca aaaaggtgaa caggatcacc    540

ggcctggatc cggccggacc caacttcgaa tacgccgaag cccctagccg gctgagcccc    600

gacgacgccg acttcgtgga cgtcctgcac accttcacaa gggggtcccc tggtcgcagt    660

atcgggatcc agaagcctgt cggccacgtc gatatctacc ccaacggcgg gaccttccag    720

cccggctgca acatcggcga ggccatccgg gtgattgccg agaggggcct gggagacgtc    780

gaccagttgg tgaaatgcag ccacgagagg agcatccacc tgttcatcga ctccctcctg    840

aacgaggaga accccagcaa ggcctaccgc tgctcctcca aggaggcctt cgagaaaggc    900

ctgtgtctga gctgccggaa gaaccggtgc aataacctcg ggtacgagat caataaggtg    960

cgcgccaagc ggagcagcaa gatgtacctg aagacaagga gccagatgcc ctacaaggtg   1020

ttccactacc aggtgaaaat ccacttcagc ggcaccgaga gcgagaccca caccaaccag   1080

gccttcgaga tcagcctgta tggcaccgtg gccgaaagcg agaacatccc ctttacactg   1140

cccgaggtct ccaccaacaa gacgtacagc ttcctgatct acaccgaggt ggatatcggc   1200

gagctgctga tgctgaagct gaaatggaag agcgacagct atttctcatg gagcgactgg   1260

tggagctccc cgggcttcgc catccagaag atcagggtga aggcgggcga gacacaaaag   1320

aaggtcatct tctgctccag ggagaaggtg agccacctgc agaagggcaa ggcccccgcc   1380

gtgttcgtga aatgccacga caagagcctg aataagaaga gcggc                   1425


<210> SEQ ID NO 19
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 19

atggagagca aggccctgct ggtgctgacc ctggccgttt ggctgcagtc cctgaccgcc     60

agccgcggtg gcgtggccgc cgccgaccag cggcgggatt tcatcgacat agaatctaag    120

tttgccctga ggacccccga ggacaccgcc gaggacacct gccacctgat ccccggggtg    180

gccgagtccg tggccacgtg tcacttcaac catagcagca agacctttat ggtcatccac    240

ggctggaccg tgactggcat gtacgagagc tgggtgccca agctcgtggc cgccctgtac    300

aagagggagc ccgacagcaa cgtgatcgtg gtggactggc tcagccgagc ccaggagcac    360

taccccgtca gcgccggcta caccaagctc gtgggccaag acgtagccag gttcatcaat    420

tggatggagg aggagtttaa ctacccctc gacaacgtgc acctcctggg ctactccctg    480

ggcgcccatg ccgccggcat agccggaagc ctgactaaca aaaaagtcaa tcggatcacc    540

ggcctagacc ccgccgggcc caacttcgaa tacgccgagg ccccctccag gctgagcccg    600

gacgacgccg actttgtgga cgtcctgcac accttcacga gagggtcccc gggccggtcg    660

atcggaatcc agaaacccgt ggggcatgtg gacatttacc ccaacggcgg caccttccag    720
```

```
ccaggctgca acatcggcga agccatcagg gtcatcgccg agaggggact gggcgacgtg     780

gaccagctgg tgaagtgcag ccacgagcgg agcatccacc tgttcatcga cagcctgctg     840

aatgaggaga atcccagcaa ggcctacaga tgttccagca aagaggcctt cgagaaggga     900

ctgtgcctgt cctgcagaaa gaacaggtgc aataacctgg gttacgagat aaataaggtg     960

agggccaaga ggtcctccaa gatgtatctg aagacccgca gccagatgcc ttacaaggtc    1020

ttccactacc aagtgaaaat ccactttagc gggaccgaat cagagacgca cacaaatcaa    1080

gctttcgaga tcagcctgta cggcaccgtg gccgagtccg agaacatccc cttcaccctc    1140

ccggaggtgt ccaccaacaa gacctactcc ttcctgatct atacagaggt ggacatcggg    1200

gagctgctga tgctgaagct gaagtggaaa tccgacagct acttcagctg gagcgactgg    1260

tggagcagcc ccggctttgc catccagaaa atcagggtga aggccggaga aactcaaaaa    1320

aaggtcatct tctgcagccg cgagaaggtg agccacctgc agaagggcaa ggcccccgcc    1380

gtgttcgtga agtgtcacga caagtcgctg aacaagaaga gcggt                    1425
```

<210> SEQ ID NO 20
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 20

```
atggagtcca aggccctcct ggtgctgacc ctggccgtct ggctgcagtc actgaccgcg      60

agcaggggcg gcgtggccgc agcggaccag cgcagggact tcatcgacat cgagagcaag     120

ttcgccctga ggacccccga ggacaccgcg gaagacacct gccacctgat ccccggcgtg     180

gccgagtccg tggccacctg ccacttcaat cacagctcca agacctttat ggtgatccac     240

ggctggaccg tgaccggaat gtatgagagc tgggtgccca agctcgtggc cgccctttac     300

aagagggagc ccgacagcaa tgtcatagtg gtggactggc tgagcagggc ccaggagcac     360

taccccgtga gtgccgggta caccaagctg gtgggccagg acgtcgcccg attcatcaac     420

tggatggagg aggagttcaa ctacccccctg gacaacgtgc atctgctggg gtactccctg     480

ggcgcgcacg ctgccggcat cgcggggtcc ctaaccaaca agaaggtgaa caggatcacc     540

gggctggacc ccgccggccc caatttcgaa tatgccgagg cccccagcag gctgagcccc     600

gacgacgccg acttcgtgga cgtgctgcat accttcacca ggggcagccc cggccggtcg     660

attggcatac aaaagcccgt gggccacgtg gacatctacc cgaacggggg caccttccag     720

cccgggtgca acataggaga agccatcagg gtgatcgcgg agaggggcct gggcgatgtg     780

gaccagctgg tgaaatgcag ccacgaaagg tccatccacc tgtttatcga cagcctgctg     840

aacgaggaga accccagcaa ggcctatagg tgcagctcaa aggaggcctt cgagaaggga     900

ctgtgcctct cctgcaggaa gaaccgctgt aacaacctgg gctacgagat aaacaaggtg     960

agggccaagc ggagcagcaa gatgtacctg aagactcgct cccagatgcc atacaaggtg    1020

ttccactacc aggtgaagat ccacttctcc ggcacggaga gcgagaccca caccaaccaa    1080

gcgttcgaga tctccctgta cgggacagtg gccgaatcag agaacatccc ctttaccctg    1140

cccgaggtga gcaccaataa gacctactcc ttcctgatct acacagaggt ggatatcggg    1200

gagctgctga tgctgaagct gaagtggaaa agcgactcct acttcagctg gagcgattgg    1260

tggtccagcc ccggctttgc catccagaag atcagggtca aggccggcga gacgcagaag    1320
```

aaggtgatct tctgctcccg ggaaaaggtg agccacctgc agaaaggcaa ggccccagcc 1380
gttttcgtga agtgccacga taagtccctg aacaagaaga gcggc 1425

<210> SEQ ID NO 21
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 21
atggagagta aggcgctgct cgtgctcacg ctggcagtgt ggctccagtc cctgaccgcc 60
agccgcgggg gggtggccgc ggccgaccag aggagggact tcatcgatat cgagagcaag 120
ttcgccctgc ggacacccga ggatacagcc gaggacacat gccacctgat acccggcgtg 180
gccgaaagcg tggccacgtg ccactttaac cactccagca agaccttcat ggtcatccac 240
ggctggaccg tcaccggcat gtacgagagc tgggtgccca agctggtcgc cgccctgtac 300
aagcgcgagc ctgatagcaa cgtgatcgtg gtggactggc tgtcccgggc ccaggagcac 360
taccccgtga gcgccggcta tacaaaactg gtgggtcagg acgtggccag attcataaac 420
tggatggaag aggagtttaa ctacccccctg gacaacgtgc acctgctggg ctatagcctg 480
ggcgcccacg ccgccggcat cgcgggcagc ctcactaaca agaaggtgaa tcggataacc 540
ggcctggatc ccgccgggcc caatttcgag tacgcggaag cccccagccg gctgagcccc 600
gatgacgccg atttcgtgga cgtgctgcac accttcacgc gcggcagccc cggccggagc 660
atcggtatcc agaaaccagt gggccatgtg gacatctacc caaatggcgg aaccttccag 720
ccgggctgta acatcggtga agccatccgg gtgatcgccg agaggggcct gggcgatgtg 780
gaccagctgg tgaaatgtag ccacgagcgc tccatccacc tcttcatcga ctccctgctg 840
aacgaagaaa accccctccaa ggcgtacagg tgtagcagca aggaggcctt cgagaagggc 900
ctgtgcctct cctgccgtaa gaacaggtgt aacaacctgg ggtacgagat caacaaggtg 960
cgggccaaga ggagcagcaa gatgtacctg aagacccgga gccagatgcc ctacaaggtc 1020
ttccactacc aggtcaagat ccacttcagc ggcaccgaga gcgagaccca cactaaccaa 1080
gccttcgaga tcagcctgta cgggaccgtc gccgagagcg agaacatccc cttcaccctg 1140
cccgaggtga gcaccaacaa aacctactcc tttctgatct acacggaagt ggacatcggc 1200
gagctgctga tgctgaagct gaagtggaaa agcgacagct acttttcctg gtccgactgg 1260
tggagcagcc cgggcttcgc gatccagaag atccgggtga aggccggcga gacccagaag 1320
aaggtcatct tttgcagcag ggagaaggtg agccacctgc agaagggtaa ggcccccgcc 1380
gtgttcgtga agtgccacga caagagcctg aacaagaagt ccgga 1425

<210> SEQ ID NO 22
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 22
atggagtcca aggccctcct ggtgctgacc ctggccgtgt ggctccagag cctaaccgcc 60
tcccggggcg gcgtggccgc cgccgatcag aggcgggatt tcatcgacat agagagcaag 120
ttcgccctcc gcacccccga agacaccgcc gaagacactt gccacctgat tcccggagtg 180
gccgagtccg tggccacttg ccacttcaac cacagcagca agaccttcat ggtgatccac 240
ggctggaccg ttaccggcat gtacgaaagc tgggtgccga agctcgtggc cgccctgtac 300
aagagggagc ccgactccaa cgtgatcgtg gttgactggc tgtccagggc ccaggagcac 360
taccccgtgt ccgccggcta caccaagctg gtcgggcagg acgtggccag gttcatcaac 420
tggatggaag aggagttcaa ctatcctctg gacaatgtgc acctgctggg ctacagcctg 480
ggcgcccacg ccgcgggcat cgccggcagc ctgaccaata agaaagtgaa taggattacc 540
ggcctggacc ccgcggggcc caacttcgag tacgccgaag cccccagcag gctgagcccc 600
gacgatgccg acttcgtgga cgtcctgcac accttcaccc ggggcagccc cgggaggagc 660
ataggcatac agaaacccgt gggccacgtg gacatctacc ccaatggcgg cacgttccag 720
cccgggtgca acatcgggga ggccatcagg gtgatcgccg agaggggact tggcgacgtg 780
gaccagctgg tgaagtgcag ccacgagcgc agcatacacc tgttcatcga tagcctgctt 840
aacgaggaaa acccctccaa ggcctacagg tgctcctcaa aggaagcgtt cgagaagggg 900
ctgtgtctct cctgcaggaa gaacagatgc aataacctgg gctacgagat caacaaggtg 960
agggccaaga ggagcagcaa gatgtacctg aaaactagga gccaaatgcc ctataaggtg 1020
tttcactacc aggtgaagat ccacttctcc ggcaccgaga gcgagaccca cacaaaccag 1080
gccttcgaaa tctcgctgta cgggaccgtg gccgagagcg aaaacatccc cttcaccctg 1140
cccgaggtgt ccaccaacaa gacctacagc ttcctgatct acaccgaggt agacattggt 1200
gagctgctga tgctcaaact caagtggaag agcgactcct acttcagctg gagcgattgg 1260
tggtcctccc cgggcttcgc catccagaag atacgggtca aggctgggga aacccagaag 1320
aaggtgatct tctgctcccg ggagaaggtc agccacctgc aaaaagggaa ggcgcccgcc 1380
gtcttcgtga agtgccacga taagagcctg aacaagaagt caggc 1425

<210> SEQ ID NO 23
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 23
atggagagca aggccctgct cgtgctgacc ctcgccgtct ggctgcagag cctgaccgcc 60
agcaggggcg gcgtggccgc cgccgatcag aggcgggact tcatagatat cgagagcaag 120
ttcgccctga ggacccccga agacaccgcg gaggacacct gccacctgat ccccggcgtg 180
gccgagtccg tggccacctg ccactttaac cactccagca aaacctttat ggtgatccat 240
ggctggaccg tcaccgggat gtacgagagc tgggtgccca agctggtggc cgccctctac 300
aagcgggaac ccgatagcaa cgtgatcgtg gtagactggc tgtccagggc ccaagagcac 360
taccccgtga gtgccggcta cacgaagctg gtgggccagg acgtggcccg cttcatcaat 420
tggatggagg aggagttcaa ctacccgctc gataacgtgc acctgctggg ctatagcctg 480
ggggcccacg ccgccgggat cgccggcagc ctcaccaaca agaaggtgaa caggatcacc 540
ggcctcgacc ccgccggccc caacttcgaa tacgccgagg cccccagcag gctgagcccg 600
gatgacgccg actttgtgga cgtgctccac accttcacca ggggctcccc cggccggtcc 660
atcgggatcc agaagcccgt cggcacgtg gacatctacc ccaatggggg gaccttccaa 720
cccggctgca acatcggcga ggcgatcagg gtgatcgccg agcgcggcct gggggacgtg 780
gaccagctgg tgaaatgttc ccatgagcgg agcatccatc tgttcattga ctccctgctg 840

-continued

```
aacgaggaga accccctccaa ggcctaccgg tgctccagca aggaggcctt cgagaagggt    900

ctgtgcctga gctgcaggaa gaatcgatgt aacaacctgg gctacgagat caacaaggtg    960

cgcgccaaga ggagcagcaa gatgtacctg aagaccagga gtcaaatgcc ctacaaggtg   1020

ttccactacc aggtgaagat ccacttcagc ggcacggaat ccgagaccca caccaatcag   1080

gccttcgaga tcagcctcta cgggaccgtg gccgagagcg aaaacatccc cttcaccctg   1140

cccgaggtgt caaccaataa gacctacagc ttcctgatct acaccgaggt ggatatcggc   1200

gagctgctga tgctgaagct gaagtggaag agcgatagct acttctcgtg gagcgactgg   1260

tggagcagcc ccggcttcgc catccagaag atcagggtga aggccggcga gacccaaaag   1320

aaagtgatct tttgcagcag ggagaaggtg tcccacctcc agaagggaaa ggcccccgcg   1380

gtgttcgtaa agtgccatga caagtccctg aacaaaaaga gcggg                   1425
```

```
<210> SEQ ID NO 24
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 24

atggaatcca aggccctact cgtgctcacc ctggccgtgt ggctgcagag cctgaccgca     60

agcagggggg gcgtggccgc cgcggaccaa aggagggatt tcattgatat cgagagcaag    120

ttcgccctca ggacccccga ggacacagcc gaggacacct gccacctgat ccccggcgta    180

gccgagtccg tggccacctg ccactttaat cactcctcca agaccttcat ggtgatacac    240

gggtggaccg tgaccgggat gtatgaaagt tgggtgccaa aactggtggc cgccctgtac    300

aagagggagc ccgactccaa cgtcatcgtc gtggattggc tgagccgggc ccaggagcac    360

tatcccgtca gcgctggcta tacgaagctg gtgggccagg acgtcgcccg gttcatcaat    420

tggatggagg aggagttcaa ctacccccctg gacaacgtgc acctgctggg ctatagcctc    480

ggcgcccacg ccgccggtat cgctggcagc ctgaccaaca agaaggtgaa ccggatcacc    540

ggcctggacc cggccggccc aaactttgag tacgccgagg ccccctccag gctgtccccc    600

gacgacgccg acttcgtgga cgtcctgcac accttcaccc gtgggtcccc cggacggagc    660

atcgggattc agaaacccgt gggccatgtg gacatttacc ccaacggggg gaccttccaa    720

cccgggtgca acatcggaga ggcgatcagg gtgatcgctg agcggggcct cggggacgtc    780

gaccagctgg tgaagtgcag ccacgagcgc tccatccacc tgttcatcga cagcctgctg    840

aacgaggaaa accccagcaa ggcgtatagg tgctcgtcga aggaggcctt cgaaaagggc    900

ctgtgcctgt cgtgccgaaa gaacaggtgt aacaacctgg gttacgagat caacaaggtg    960

agggccaaaa ggagctccaa gatgtatctg aagacccggt cccagatgcc ctataaggtg   1020

ttccactatc aggtgaagat ccactttagc ggaaccgaaa gcgaaaccca cacaaaccaa   1080

gccttcgaga tctccctgta cggcaccgtc gccgagtccg agaacatccc cttcaccctg   1140

cccgaggtga gcactaacaa gacctacagc ttcctcatct acacggaggt ggacataggc   1200

gagctgctga tgctgaagct gaagtggaag tccgactcct atttcagctg gagcgactgg   1260

tggtcctccc ccgggtttgc catccaaaag ataagggtga aggccggcga gacccaaaag   1320

aaggtgatct tctgttccag ggaaaaggtg agccacctgc agaagggcaa ggcccccgct   1380

gtgttcgtta agtgccacga caagtccctg aacaagaaga gcggc                   1425
```

<210> SEQ ID NO 25
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 25
atggagtcca aggccctgct ggtgctgacc cttgccgtgt ggctgcagag cctgaccgcc 60
agcaggggcg gcgtcgccgc cgcggaccag cgcagggact ttatcgatat cgagagcaag 120
ttcgccctga ggacacccga ggacaccgcc gaggacacat gccatctgat cccaggcgtt 180
gcggagagcg tggctacctg ccacttcaat cacagcagca aaacctttat ggtcatccac 240
ggctggacgg tgaccggcat gtacgagagc tgggtgccaa agctggtggc cgccctgtac 300
aagagggaac ccgacagcaa cgtgatcgtg gtggattggt tatccagggc gcaggagcac 360
tatcccgtca gcgccggcta caccaagctg gtgggccagg acgtcgccag gttcatcaat 420
tggatggagg aggaattcaa ttatcccctg gataacgtac acctcctggg ctacagcctc 480
ggagcccacg ccgcgggaat agccgggagc ctcacgaata agaaggttaa caggatcacc 540
ggcctggatc ccgccggccc caacttcgag tacgcagagg caccgtccag gctgtccccc 600
gacgacgccg acttcgtgga cgtcctgcac accttcacca ggggctcccc cgggcgtagc 660
atcggcatcc aaaagcccgt gggccacgtg gacatctacc ccaacggcgg caccttccag 720
cccgggtgca acatcggcga ggcgatccgg gtgatagcgg aacgcgggct gggcgacgtg 780
gatcagctgg tcaagtgtag ccatgagcgc agcatccacc tgttcatcga ctccctgctc 840
aacgaagaaa accccagcaa ggcctaccgg tgctcgagca aggaagcgtt cgagaagggc 900
ctgtgcctga gctgcaggaa gaataggtgc aataatctgg gctatgagat caacaaggtg 960
cgggccaagc gaagctctaa aatgtacctg aagactcggt cccagatgcc gtacaaggtg 1020
ttccactacc aggtgaagat ccacttcagc gggaccgaat ccgaaacgca caccaaccaa 1080
gccttcgaga tcagcctgta cgggaccgtc gccgagagcg agaacatccc cttcaccctg 1140
cccgaggtgt ccacaaacaa gacgtacagc ttcctcatct ataccgaggt cgacatcggg 1200
gagctgctga tgttaaaact gaagtggaag agcgactcct attttagctg gtccgactgg 1260
tggagcagcc ccggcttcgc catccagaag atcagggtca aggccggtga gacgcagaag 1320
aaggtgattt tctgcagcag ggaaaaagtg tcccatctcc agaagggtaa ggcgccggcc 1380
gtgtttgtaa aatgccacga caagagtctg aacaaaaaga gcggc 1425

<210> SEQ ID NO 26
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 26
atggagtcca aggccttgct ggttctgacc ctggccgtgt ggctgcagag cctgacggcc 60
tcgagggggg gcgtcgcggc ggccgaccag cggagggact tcatcgacat cgagagcaaa 120
tttgccctgc ggaccccccga agacaccgcg gaggatacct gtcacctgat tcccggcgtg 180
gctgaaagcg tggcaacctg ccacttcaac cactcaagca agacgtttat ggtcatacac 240
gggtggaccg tgaccggaat gtacgagagt tgggtgccca aactggtggc cgccctgtac 300
aagagggaac ccgacagcaa tgtgatagtg gtggactggc tgtcccgggc ccaggagcac 360

```
tacccggtga gcgccggcta caccaagctg gtgggccagg acgtggcccg gttcatcaac    420

tggatggagg aggagttcaa ctatcccctg gataacgtgc acctcctggg gtacagcctg    480

ggggcccacg ccgccggaat cgccggcagc ctgaccaaca agaaggtgaa caggatcact    540

ggcctcgacc ccgccggccc gaactttgag tatgccgagg ccccgagccg gctgtccccc    600

gacgacgccg acttcgtcga cgtgctccac accttcacga gggggagccc cggccggagc    660

atcggcatac aaaagcccgt gggacacgtg gacatctacc ccaacggcgg cacctttcag    720

ccgggctgta atatcggcga ggccatccgc gtgatcgccg agaggggcct gggggacgtg    780

gaccaactgg tgaagtgtag ccacgaaagg tccatccacc tcttcatcga cagcctcctg    840

aacgaggaga acccctccaa ggcctacagg tgcagctcta aagaggcgtt cgagaagggg    900

ctttgcctga gctgcaggaa gaataggtgc aacaacctgg gctacgaaat caacaaggtg    960

cgggccaagc gcagcagcaa aatgtacctg aagacccgta gccagatgcc ctacaaggtg   1020

tttcactacc aggtgaaaat ccatttcagc ggcaccgaaa gcgaaacgca caccaaccag   1080

gccttcgaga tctccctgta cgggaccgtc gcagagagcg agaacatccc cttcacgctc   1140

cctgaggtgt cgaccaacaa gacctattcc ttcctgatct ataccgaggt ggatatcgga   1200

gagctgctga tgctgaagct caaatggaaa agcgacagct atttctcatg gtccgactgg   1260

tggagcagcc cgggattcgc catccagaag atcagggtga aggccgggga gacccagaag   1320

aaggtgatct tttgcagccg cgaaaaggtg agccacctgc agaagggcaa ggcccccgcg   1380

gtgttcgtca agtgtcacga taaaagtctg aacaagaaga gcggc                  1425
```

<210> SEQ ID NO 27
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 27

```
atggagagca aagcgctact ggtgctgacc ctcgccgtgt ggctacagag cctgaccgcc     60

tcgcggggcg gcgtggccgc cgctgaccag aggcgggact tcatcgacat cgagagcaag    120

ttcgccctgc gcaccccaga ggacaccgcc gaggatacct gtcacctcat ccccggcgtc    180

gccgagagcg tggcgacctg ccactttaac cacagcagca agaccttcat ggtgatccac    240

ggctggaccg tgacgggcat gtacgagtcc tgggtgccca aactggtggc ggctctgtac    300

aagagggagc ccgacagtaa cgtgattgtc gtggactggc tgagccgcgc tcaagaacac    360

tatcccgtat ccgccggtta caccaagctg gtgggccagg acgtggcgcg attcattaac    420

tggatggagg aggagtttaa ttacccccctg gataacgtgc atctgctggg gtatagcctg    480

ggcgcccacg ccgccggcat agccggctcc ctgaccaaca agaaggtcaa ccgaatcacc    540

ggcctggacc ccgccggccc caactttgag tacgccgagg cccccagcag gctgtccccc    600

gatgatgccg acttcgtgga cgtgctgcat acgttcaccc gcgggagccc cgggaggagc    660

atcggcatac agaaacccgt gggccacgtg gacatatacc ccaacggcgg aacgttccag    720

ccggggtgca acatcggcga ggccatccgg gtcatcgccg agagggggct gggcgatgtg    780

gaccaactgg tgaagtgctc ccatgaacgg tccatccatc tgttcatcga cagcctgctg    840

aacgaggaga accccagcaa ggcctacagg tgtagcagca aggaggcctt cgagaaaggc    900

ctgtgtctga gctgcagaaa gaacaggtgc aacaacctcg gctacgagat caacaaggtg    960

agggccaaga ggtccagcaa aatgtatctg aagaccagga gccagatgcc atacaaggtc   1020
```

```
tttcactacc aggtcaagat ccatttctcc ggcaccgagt ccgaaaccca caccaaccag   1080

gcgttcgaaa tcagcctgta cggcaccgtg gccgagagcg agaacatccc cttcaccctt   1140

cccgaggtgt ccaccaacaa gacctacagc ttcctcatct acaccgaggt ggatatcggc   1200

gagctgctga tgctgaagct gaagtggaag agcgacagct acttcagctg gtcggactgg   1260

tggagctccc ccggcttcgc gatccagaaa atccgtgtga aagccgggga gacccagaag   1320

aaggtgatat tctgctcccg ggagaaggta agccacctgc agaaggggaa ggcccccgcc   1380

gtgttcgtta agtgccacga caagagccta aacaaaaagt ccggc                   1425
```

<210> SEQ ID NO 28
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 28

```
atggagtcta aagccctgct ggtgctgacc ctcgccgtgt ggctgcagtc gctgaccgcc     60

tcccgcggcg gggtggccgc agccgaccag cgccgggact tcattgacat cgagagcaag    120

ttcgccctgc gaacccccga ggataccgcc gaggacacct gccacctgat ccccggagtc    180

gccgagagcg tggccacctg ccactttaat catagcagca agaccttcat ggtgatccac    240

ggctggacgg tgaccgggat gtacgagagc tgggtcccca agctggtggc cgccctttat    300

aaaagggagc ccgatagtaa cgtgatcgtg gtggactggc tgtccagggc ccaagagcac    360

taccccgtgt ccgccggcta caccaagctg gtgggccagg acgtggccag gttcatcaat    420

tggatggagg aggaatttaa ttacccccctg gacaatgtgc acctcctggg ctactcgctg    480

ggcgctcacg ccgccggcat agccggcagc ctgaccaaca agaaagtgaa caggatcacg    540

ggcctggacc ccgccggccc caacttcgag tacgccgagg cccccagccg tctgagcccc    600

gacgacgccg actttgtgga cgtgctgcac accttcacca gggggagtcc tgggcggagc    660

atcggcatcc aaaagccggt gggccacgtg gacatctacc cgaacggtgg tacgtttcag    720

cccgggtgca acatcgggga agccatcagg gtgatcgccg agagggggct gggcgacgtg    780

gaccagctgg tgaagtgctc ccacgagagg tccatccacc tgttcatcga ctcccttctc    840

aacgaagaaa acccgagcaa ggcctacagg tgtagcagca aggaagcctt cgagaagggg    900

ctgtgcctgt cctgtaggaa aaacaggtgc aacaacctcg gctacgagat caacaaggtg    960

cgcgctaagc gctccagcaa gatgtacctg aagacaaggt cacagatgcc ctacaaggtg   1020

ttccactacc aggtgaaaat ccactttagc ggcaccgaaa gcgaaacgca caccaaccag   1080

gcgtttgaga tcagcttata tgggaccgtg gccgagtccg agaacatccc cttcaccctg   1140

cccgaagtga gcaccaacaa gacctatagc ttcctgatct acaccgaggt ggatatcggg   1200

gagctgctga tgctcaaact gaaatggaag agcgatagct acttctcctg gagcgattgg   1260

tggagcagcc ccggcttcgc gatccagaag atccgcgtga aggcggggga gacccagaag   1320

aaggtgatct tttgcagcag ggagaaggtg agccacctgc agaaaggcaa ggcccccgcg   1380

gtgtttgtca agtgccacga caagagcctc aacaagaaat ccggc                   1425
```

<210> SEQ ID NO 29
<211> LENGTH: 1425
<212> TYPE: DNA
<213> ORGANISM: Artificial Sequence
<220> FEATURE:

<223> OTHER INFORMATION: Synthetic Polynucleotide

<400> SEQUENCE: 29
atggaatcga aggccctgct ggtgctgacg ctggcggtgt ggctgcagag cctgaccgcc 60
tcccgcggcg gcgtcgccgc cgccgaccag aggcgggact tcatcgatat cgagagcaag 120
ttcgccctga ggacccccga agataccgcc gaagacacgt gccacctgat cccgggcgtg 180
gcggagtctg tggccacctg ccacttcaac cacagcagca agaccttcat ggtgatccac 240
gggtggaccg tgaccggcat gtacgagagc tgggtgccca agctggtcgc cgcgctgtac 300
aaaagggagc ccgacagcaa cgtcatcgtc gtggactggc tgagcagggc acaggagcat 360
taccccgtct ccgccggtta caccaaactg gtggggcagg acgtggcgag gtttatcaac 420
tggatggagg aggagttcaa ctaccccctg gataacgtgc acctgctggg gtacagcctg 480
ggggcccacg ccgcaggcat agccgggagc ctgaccaata agaaagtaaa ccggatcacg 540
gggctggacc ccgccgggcc caattttgag tatgccgagg cccccagccg gctgtccccc 600
gacgacgcag acttcgtgga cgtgctgcac accttcaccc gaggcagccc gggaagaagc 660
atcggcatcc agaagcccgt gggccacgtg gacatctacc ccaacggagg caccttccag 720
ccaggctgta acatcggcga ggccatcagg gtgatcgccg aacgcggcct gggcgacgtg 780
gaccaactcg tgaagtgctc ccacgagcgc agcatccacc tcttcatcga cagcctgctg 840
aatgaggaga atcccagcaa ggcatatagg tgcagcagca aggaggcctt tgagaagggc 900
ctgtgcctgt catgccggaa gaacaggtgc aacaacctgg gctacgagat caacaaggtc 960
agggccaaac gcagctccaa gatgtacctg aagacccgga gccaaatgcc ctacaaggtg 1020
tttcactacc aggtgaagat ccatttttcc ggcacggaga gtgaaaccca caccaaccag 1080
gccttcgaga taagcctgta cggcaccgtg gccgagagcg agaacatccc cttcaccctg 1140
cccgaggtga gcacgaataa gacctacagc ttcctgatct acacggaggt ggacatcggc 1200
gagctgctga tgctgaagct gaaatggaaa tccgacagct acttcagctg gtccgactgg 1260
tggagctccc ccggcttcgc catccagaag atcagggtga aggccgggga gacccagaaa 1320
aaggtgatct tctgcagcag ggagaaagtc agccatctgc agaaggggaa ggcccccgcg 1380
gtcttcgtga agtgccacga caagagcctg aacaagaaga gcggc 1425

<210> SEQ ID NO 30
<211> LENGTH: 87
<212> TYPE: RNA
<213> ORGANISM: Artificial Sequence
<220> FEATURE:
<223> OTHER INFORMATION: Synthetic Polynucleotide

<400> SEQUENCE: 30
gacagugcag ucacccauaa aguagaaagc acuacuaaca gcacuggagg guguaguguu 60
uccuacuuua uggaugagug uacugug 87

<210> SEQ ID NO 31
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 31
uguaguguuu ccuacuuuau gga 23

<210> SEQ ID NO 32
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 32
uccauaaagu aggaaacacu aca 23

<210> SEQ ID NO 33
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 33
cauaaaguag aaagcacuac u 21

<210> SEQ ID NO 34
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 34
aguagugcuu ucuacuuuau g 21

<210> SEQ ID NO 35
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 35
gggaaauaag agagaaaaga agaguaagaa gaaauauaag agccacc 47

<210> SEQ ID NO 36
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 36
gggagaucag agagaaaaga agaguaagaa gaaauauaag agccacc 47

<210> SEQ ID NO 37
<211> LENGTH: 145
<212> TYPE: RNA
<213> ORGANISM: Artificial Sequence
<220> FEATURE:
<223> OTHER INFORMATION: Synthetic Polynucleotide

<400> SEQUENCE: 37
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 38
<211> LENGTH: 42
<212> TYPE: RNA

<213> ORGANISM: Artificial Sequence
<220> FEATURE:
<223> OTHER INFORMATION: Synthetic Polynucleotide

<400> SEQUENCE: 38
gggagacaag cuuggcauuc cgguacuguu gguaaagcca cc 42

<210> SEQ ID NO 39
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 39
gggagaucag agagaaaaga agaguaagaa gaaauauaag agccacc 47

<210> SEQ ID NO 40
<211> LENGTH: 145
<212> TYPE: RNA
<213> ORGANISM: Artificial Sequence
<220> FEATURE:
<223> OTHER INFORMATION: Synthetic Polynucleotide

<400> SEQUENCE: 40
ggaauaaaag ucucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gcaac 145

<210> SEQ ID NO 41
<211> LENGTH: 42
<212> TYPE: RNA
<213> ORGANISM: Artificial Sequence
<220> FEATURE:
<223> OTHER INFORMATION: Synthetic Polynucleotide

<400> SEQUENCE: 41
gggagacaag cuuggcauuc cgguacuguu gguaaagcca cc 42

<210> SEQ ID NO 42
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 42
gggaauuaac agagaaaaga agaguaagaa gaaauauaag agccacc 47

<210> SEQ ID NO 43
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 43
gggaaauuag acagaaaaga agaguaagaa gaaauauaag agccacc 47

<210> SEQ ID NO 44
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 44
gggaaauaag agaguaaaga acaguaagaa gaaauauaag agccacc 47

<210> SEQ ID NO 45
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 45
gggaaaaaag agagaaaaga agacuaagaa gaaauauaag agccacc 47

<210> SEQ ID NO 46
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 46
gggaaauaag agagaaaaga agaguaagaa gauauauaag agccacc 47

<210> SEQ ID NO 47
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 47
gggaaauaag agacaaaaca agaguaagaa gaaauauaag agccacc 47

<210> SEQ ID NO 48
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 48
gggaaauuag agaguaaaga acaguaagua gaauuaaaag agccacc 47

<210> SEQ ID NO 49
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 49
gggaaauaag agagaauaga agaguaagaa gaaauauaag agccacc 47

<210> SEQ ID NO 50
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 50
gggaaauaag agagaaaaga agaguaagaa gaaaauuaag agccacc 47

<210> SEQ ID NO 51

<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 51
gggaaauaag agagaaaaga agaguaagaa gaaauuuaag agccacc 47

<210> SEQ ID NO 52
<211> LENGTH: 92
<212> TYPE: RNA
<213> ORGANISM: Artificial Sequence
<220> FEATURE:
<223> OTHER INFORMATION: Synthetic Polynucleotide

<400> SEQUENCE: 52
ucaagcuuuu ggacccucgu acagaagcua auacgacuca cuauagggaa auaagagaga 60
aaagaagagu aagaagaaau auaagagcca cc 92

<210> SEQ ID NO 53
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 53
ugauaauagu ccauaaagua ggaaacacua cagcuggagc cucgguggcc augcuucuug 60
ccccuugggc cuccccccag ccccuccucc ccuuccugca cccguacccc cgguggucuuu 120 gaauaaaguc ugagugggcg gc 142

<210> SEQ ID NO 54
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 54
ugauaauagg cuggagccuc gguggcucca uaaaguagga aacacuacac augcuucuug 60
ccccuugggc cuccccccag ccccuccucc ccuuccugca cccguacccc cguggucuuu 120
gaauaaaguc ugagugggcg gc 142

<210> SEQ ID NO 55
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 55
ugauaauagg cuggagccuc gguggccaug cuucuugccc cuuccauaaa guaggaaaca 60
cuacaugggc cuccccccag ccccuccucc ccuuccugca cccguacccc cguggucuuu 120
gaauaaaguc ugagugggcg gc 142

<210> SEQ ID NO 56
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 56
ugauaauagg cuggagccuc gguggccaug cuucuugccc cuugggccuc cccccagucc 60
auaaaguagg aaacacuaca ccccuccucc ccuuccugca cccguacccc cguggucuuu 120
gaauaaaguc ugagugggcg gc 142

<210> SEQ ID NO 57
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 57
ugauaauagg cuggagccuc gguggccaug cuucuugccc cuugggccuc cccccagccc 60
cuccuccccu ucuccauaaa guaggaaaca cuacacugca cccguacccc cguggucuuu 120
gaauaaaguc ugagugggcg gc 142

<210> SEQ ID NO 58
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 58
ugauaauagg cuggagccuc gguggccaug cuucuugccc cuugggccuc cccccagccc 60
cuccuccccu uccugcaccc guaccccuc cauaaaguag gaaacacuac agugguccuuu 120 gaauaaaguc ugagugggcg gc 142

<210> SEQ ID NO 59
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 59
ugauaauagg cuggagccuc gguggccaug cuucuugccc cuugggccuc cccccagccc 60
cuccuccccu uccugcaccc guacccccgu ggucuuugaa uaaaguucca uaaaguagga 120
aacacuacac ugagugggcg gc 142

<210> SEQ ID NO 60
<211> LENGTH: 371
<212> TYPE: RNA
<213> ORGANISM: Artificial Sequence
<220> FEATURE:
<223> OTHER INFORMATION: Synthetic Polynucleotide

<400> SEQUENCE: 60
gcgccugccc accugccacc gacugcugga acccagccag ugggagggcc uggcccacca 60
gaguccugcu cccucacucc ucgccccgcc cccuguccca gagucccacc ugggggcucu 120
cuccacccuu cucagaguuc caguuucaac cagaguucca accaaugggc uccauccucu 180
ggauucuggc caaugaaaua ucucccuggc aggguccucu ucuuuuccca gagcuccacc 240
ccaaccagga gcucuaguua auggagagcu cccagcacac ucggagcuug ugcuuugucu 300
ccacgcaaag cgauaaauaa aagcauuggu ggccuuuggu cuuugaauaa agccugagua 360
ggaagucuag a 371

<210> SEQ ID NO 61
<211> LENGTH: 568
<212> TYPE: RNA
<213> ORGANISM: Artificial Sequence
<220> FEATURE:
<223> OTHER INFORMATION: Synthetic Polynucleotide

<400> SEQUENCE: 61
gccccugccg cucccacccc cacccaucug ggccccgggu ucaagagaga gcggggucug 60
aucucgugua gccauauaga guuugcuucu gagugucugc uuuguuuagu agaggugggc 120
aggaggagcu gaggggcugg ggcuggggug uugaaguugg cuuugcaugc ccagcgaugc 180 gccuccccugu gggaugucau cacccuggga accgggagug gcccuuggcu cacuguguuc 240
ugcaugguuu ggaucugaau uaauuguccu uucuucuaaa ucccaaccga acuucuucca 300
accuccaaac uggcuguaac cccaaaucca agccauuaac uacaccugac aguagcaauu 360
gucugauuaa ucacuggccc cuugaagaca gcagaauguc ccuuugcaau gaggaggaga 420
ucugggcugg gcgggccagc uggggaagca uuugacuauc uggaacuugu gugugccucc 480
ucagguaugg cagugacuca ccugguuuua auaaaacaac cugcaacauc ucauggucuu 540
ugaauaaagc cugaguagga agucuaga 568

<210> SEQ ID NO 62
<211> LENGTH: 289
<212> TYPE: RNA
<213> ORGANISM: Artificial Sequence
<220> FEATURE:
<223> OTHER INFORMATION: Synthetic Polynucleotide

<400> SEQUENCE: 62
acacacucca ccuccagcac gcgacuucuc aggacgacga aucuucucaa ugggggggcg 60
gcugagcucc agccaccccg cagucacuuu cuuuguaaca acuuccguug cugccaucgu 120
aaacugacac aguguuuaua acguguacau acauuaacuu auuaccucau uuuguuauuu 180
uucgaaacaa agcccugugg aagaaaaugg aaaacuugaa gaagcauuaa agucauucug 240
uuaagcugcg uaaauggucu uugaauaaag ccugaguagg aagucuaga 289

<210> SEQ ID NO 63
<211> LENGTH: 379
<212> TYPE: RNA
<213> ORGANISM: Artificial Sequence
<220> FEATURE:
<223> OTHER INFORMATION: Synthetic Polynucleotide

<400> SEQUENCE: 63
caucacauuu aaaagcaucu cagccuacca ugagaauaag agaaagaaaa ugaagaucaa 60
aagcuuauuc aucuguuuuu cuuuuucguu gguguaaagc caacacccug ucuaaaaaac 120
auaaauuucu uuaaucauuu ugccucuuuu cucugugcuu caauuaauaa aaaauggaaa 180
gaaucuaaua gagugguaca gcacuguuau uuuucaaaga uguguugcua uccugaaaau 240
ucuguagguu cuguggaagu uccaguguuc ucucuuauuc cacuucggua gaggauuucu 300
aguuucuugu gggcuaauua aauaaaucau uaauacucuu cuaauggucu uugaauaaag 360
ccugaguagg aagucuaga 379

<210> SEQ ID NO 64
<211> LENGTH: 118

<212> TYPE: RNA
<213> ORGANISM: Artificial Sequence
<220> FEATURE:
<223> OTHER INFORMATION: Synthetic Polynucleotide

<400> SEQUENCE: 64
gcugccuucu gcggggcuug ccuucuggcc augcccuucu ucucucccuu gcaccuguac 60
cucuuggucu uugaauaaag ccugaguagg aaggcggccg cucgagcaug caucuaga 118

<210> SEQ ID NO 65
<211> LENGTH: 908
<212> TYPE: RNA
<213> ORGANISM: Artificial Sequence
<220> FEATURE:
<223> OTHER INFORMATION: Synthetic Polynucleotide

<400> SEQUENCE: 65
gccaagcccu ccccauccca uguauuuauc ucuauuuaau auuuaugucu auuuaagccu 60
cauauuuaaa gacagggaag agcagaacgg agccccaggc cucugugucc uucccugcau 120
uucugaguuu cauucuccug ccuguagcag ugagaaaaag cuccuguccu cccaucccu 180 ggacugggag guagauaggu aaauaccaag uauuuauuac uaugacugcu ccccagcccu 240
ggcucugcaa ugggcacugg gaugagccgc ugugagcccc ugguccugag gguccccacc 300
ugggacccuu gagaguauca ggucucccac gugggagaca agaaaucccu guuuaauauu 360
uaaacagcag uguuccccau cugggucuu gcaccccuca cucuggccuc agccgacugc 420
acagcggccc cugcaucccc uuggcuguga ggccccugga caagcagagg uggccagagc 480
ugggaggcau ggcccugggg ucccacgaau uugcuggga aucucguuuu ucuucuuaag 540
acuuuuggga caugguuuga cucccgaaca ucaccgacgc gucuccuguu uuucugggug 600
gccucgggac accugcccug cccccacgag ggucaggacu gugacucuuu uuagggccag 660
gcaggugccu ggacauuugc cuugcuggac ggggacuggg gaugugggag ggagcagaca 720
ggaggaauca ugucaggccu gugugugaaa ggaagcucca cugucacccu ccaccucuuc 780
accccccacu caccagugucc cccuccacug ucacauugua acugaacuuc aggauaauaa 840
aguguuugcc uccauggucu uugaauaaag ccugaguagg aaggcggccg cucgagcaug 900
caucuaga 908

<210> SEQ ID NO 66
<211> LENGTH: 835
<212> TYPE: RNA
<213> ORGANISM: Artificial Sequence
<220> FEATURE:
<223> OTHER INFORMATION: Synthetic Polynucleotide

<400> SEQUENCE: 66
acucaaucua aauuaaaaaa gaaagaaauu ugaaaaaacu uucucuuugc cauuucuucu 60
ucuucuuuuu uaacugaaag cugaauccuu ccauuucuuc ugcacaucua cuugcuuaaa 120
uugugggcaa aagagaaaaa gaaggauuga ucagagcauu gugcaauaca guuucauuaa 180
cuccuucccc cgcuccccca aaaauuugaa uuuuuuuuuc aacacucuua caccuguuau 240
ggaaaauguc aaccuuugua agaaaaccaa aauaaaaauu gaaaaauaaa aaccauaaac 300
auuugcacca cuuguggcuu uugaauaucu uccacagagg gaaguuuaaa acccaaacuu 360
ccaaagguuu aaacuaccuc aaaacacuuu cccaugagug ugauccacau uguuaggugc 420
ugaccuagac agagaugaac ugagguccuu guuuuguuuu guucauaaua caaaggugcu 480

```
aauuaauagu auuucagaua cuugaagaau guugauggug cuagaagaau uugagaagaa    540

auacuccugu auugaguugu aucguguggu guauuuuuua aaaaauuuga uuuagcauuc    600

auauuuucca ucuuauuccc aauuaaaagu augcagauua uuugcccaaa ucuucuucag    660

auucagcauu uguucuuugc cagucucauu uucaucuucu uccaugguuc cacagaagcu    720

uuguuucuug ggcaagcaga aaaauuaaau uguaccuauu uuguauaugu gagauguuua    780

aauaaauugu gaaaaaaaug aaauaaagca uguuugguuu uccaaaagaa cauau         835
```

<210> SEQ ID NO 67
<211> LENGTH: 297
<212> TYPE: RNA
<213> ORGANISM: Artificial Sequence
<220> FEATURE:
<223> OTHER INFORMATION: Synthetic Polynucleotide

<400> SEQUENCE: 67

```
cgccgccgcc cgggccccgc agucgagggu cgugagccca ccccguccau ggugcuaagc     60

gggcccgggu cccacacggc cagcaccgcu gcucacucgg acgacgcccu gggccugcac    120

cucuccagcu ccucccacgg gguccccgua gccccggccc ccgcccagcc ccaggucucc    180

ccaggcccuc cgcaggcugc ccggccuccc ucccccugca gccaucccaa ggcuccugac    240

cuaccuggcc ccugagcucu ggagcaagcc cugacccaau aaaggcuuug aacccau       297
```

<210> SEQ ID NO 68
<211> LENGTH: 602
<212> TYPE: RNA
<213> ORGANISM: Artificial Sequence
<220> FEATURE:
<223> OTHER INFORMATION: Synthetic Polynucleotide

<400> SEQUENCE: 68

```
ggggcuagag cccucuccgc acagcgugga gacggggcaa ggagggggu uauuaggauu      60

gguggguuuug uuuugcuuug uuuaaagccg ugggaaaaug gcacaacuuu accucugugg   120

gagaugcaac acugagagcc aaggggguggg aguugggaua auuuuuauau aaaagaaguu   180

uuuccacuuu gaauugcuaa aaguggcauu uuuccuaugu gcagucacuc cucucauuuc    240

uaaaauaggg acguggccag gcacgguggc ucaugccugu aaucccagca cuuugggagg    300

ccgaggcagg cggcucacga ggucaggaga ucgagacuau ccuggcuaac acgguaaaac    360

ccugucucua cuaaaaguac aaaaaauuag cugggcgugg uggugggcac cuguaguccc    420

agcuacucgg gaggcugagg caggagaaag gcaugaaucc aagaggcaga gcuugcagug    480

agcugagauc acgccauugc acuccagccu gggcaacagu guuaagacuc ugucucaaau    540

auaaauaaau aaauaaauaa auaaauaaau aaauaaaaau aaagcgagau guugcccuca    600

aa                                                                   602
```

<210> SEQ ID NO 69
<211> LENGTH: 785
<212> TYPE: RNA
<213> ORGANISM: Artificial Sequence
<220> FEATURE:
<223> OTHER INFORMATION: Synthetic Polynucleotide

<400> SEQUENCE: 69

```
ggcccugccc cgucggacug cccccagaaa gccuccugcc cccugccagu gaaguccuuc     60

agugagcccc ucccccagcca gcccuucccu ggccccgccg gauguauaaa uguaaaaaug   120

aaggaauuac auuuuauaug ugagcgagca agccggcaag cgagcacagu auuauuucuc    180
```

```
caucccucc cugccugcuc cuuggcaccc ccaugcugcc uucagggaga caggcaggga    240
gggcuugggg cugcaccucc uacccuccca ccagaacgca ccccacuggg agagcuggug    300
gugcagccuu ccccucccug uauaagacac uuugccaagg cucuccccuc ucgccccauc    360
ccugcuugcc cgcucccaca gcuuccugag ggcuaauucu gggaagggag aguucuuugc    420
ugccccuguc uggaagacgu ggcucugggu gagguaggcg ggaaaggaug gaguguuuua    480
guucuugggg gaggccaccc caaaccccag ccccaacucc aggggcaccu augagauggc    540
caugcucaac cccccuccca gacaggcccu cccugucucc agggccccca ccgagguucc    600
cagggcugga gacuuccucu gguaaacauu ccuccagccu ccccuccccu ggggacgcca    660
aggagguggg ccacacccag gaagggaaag cgggcagccc cguuuugggg acgugaacgu    720
uuuaauaauu uuugcugaau uccuuuacaa cuaaauaaca cagauauugu uauaaauaaa    780
auugu                                                                785
```

<210> SEQ ID NO 70
<211> LENGTH: 3001
<212> TYPE: RNA
<213> ORGANISM: Artificial Sequence
<220> FEATURE:
<223> OTHER INFORMATION: Synthetic Polynucleotide

<400> SEQUENCE: 70

```
auauuaagga ucaagcuguu agcuaauaau gccaccucug caguuuuggg aacaggcaaa     60
uaaaguauca guauacaugg ugauguacau cuguagcaaa gcucuuggag aaaaugaaga    120
cugaagaaag caaagcaaaa acuguauaga gagauuuuuc aaaagcagua aucccucaau    180
uuuaaaaaag gauugaaaau ucuaaauguc uuucugugca uauuuuuugu guuaggaauc    240
aaaaguauuu uauaaaagga gaaagaacag ccucauuuua gauguagucc uguuggauuu    300
uuuaugccuc cucaguaacc agaaauguuu uaaaaaacua aguguuuagg auuucaagac    360
aacauuauac auggcucuga aauaucugac acaauguaaa cauugcaggc accugcauuu    420
uauguuuuuu uuuucaacaa augugacuaa uuugaaacuu uuaugaacuu cugagcuguc    480
cccuugcaau ucaaccgcag uuugaauuaa ucauaucaaa ucaguuuuaa uuuuuuaaau    540
uguacuucag agucuauauu ucaagggcac auuuucucac uacuauuuua auacauuaaa    600
ggacuaaaua aucuuucaga gaugcuggaa acaaaucauu ugcuuuauau guuucauuag    660
aauaccaaug aaacauacaa cuugaaaauu aguaaauagua uuuuugaaga ucccauuucu    720
aauuggagau cucuuuaauu ucgaucaacu uauaaugugu aguacuauau uaagugcacu    780
ugaguggaau ucaacauuug acuaauaaaa ugaguucauc auguuggcaa gugauguggc    840
aauuaucucu ggugacaaaa gaguaaaauc aaauauuucu gccuguuaca aauaucaagg    900
aagaccugcu acuaugaaau agaugacauu aaucugucuu cacuguuuau aauacggaug    960
gauuuuuuuu caaaucagug uguguuuuga ggucuuaugu aauugaugac auuugagaga   1020
aaugguggcu uuuuuuagcu accucuuugu ucauuuaagc accaguaaag aucaugucuu   1080
uuuauagaag uguagauuuu cuuugugacu uugcuaucgu gccuaaagcu cuaaauauag   1140
gugaaugugu gaugaauacu cagauuauuu gucucucuau auaauuaguu ugguacuaag   1200
uuucucaaaa aauuauuaac acaugaaaga caaucucuaa accagaaaaa gaaguaguac   1260
aaauuuuguu acuguaaugc ucgcguuuag ugaguuuaaa acacacagua ucuuuugguu   1320
uuauaaucag uuucuauuuu gcugugccug agauuaagau cuguguaugu guguguguguu   1380
```

gugugugcgu uugugugua aagcagaaaa gacuuuuuua aaaguuuuaa gugauaaaug 1440
caauuuguua auugaucuua gaucacuagu aaacucaggg cugaauuaua ccauguauau 1500
ucuauuagaa gaaaguaaac accaucuuua uuccugcccu uuuucuucuc ucaaaguagu 1560
uguaguuaua ucuagaaaga agcaauuuug auuucuugaa aagguaguuc cugcacucag 1620
uuuaaacuaa aaauaaucau acuuggauuu uauuuauuuu ugucauagua aaaauuuuaa 1680
uuuauauaua uuuuuauuua guauuaucuu auucuuugcu auuugccaau ccuuugucau 1740
caauuguguu aaaugaauug aaaauucaug cccuguucau uuuauuuuac uuuauugguu 1800
aggauauuua aaggauuuuu guauauauaa uuucuuaaau uaauauucca aaagguuagu 1860
ggacuuagau uauaaauuau ggcaaaaauc uaaaaacaac aaaaaugauu uuuauacauu 1920
cuauuucauu auuccucuuu uuccaauaag ucauacaauu gguagauaug acuuauuuua 1980
uuuuuguauu auucacuaua ucuuuaugau auuuaaguau aaauaauuaa aaaaauuuau 2040
uguaccuuau agucugucac caaaaaaaaa aaauuaucug uagguaguga aaugcuaaug 2100
uugauuuguc uuuaagggcu uguuaacuau ccuuuauuuu cucauuuguc uuaaauuagg 2160
aguuuguguu uaaauuacuc aucuaagcaa aaaauguaua uaaaucccau uacuggguau 2220
auacccaaag gauuauaaau caugcugcua uaaagacaca ugcacacgua uguuuauugc 2280
agcacuauuc acaauagcaa agacuuggaa ccaacccaaa uguccaucaa ugauagacuu 2340
gauuaagaaa augugcacau auacaccaug gaauacuaug cagccauaaa aaaggaugag 2400
uucauguccu uuguagggac auggauaaag cuggaaacca ucauucugag caaacuauug 2460
caaggacaga aaaccaaaca cugcauguuc ucacucauag gugggaauug aacaaugaga 2520
acacuuggac acaagguggg gaacaccaca caccagggcc ugucaugggg ugggggggagu 2580 ggggagggau agcauuagga gauauaccua auguaaauga ugaguuaaug ggugcagcac 2640
accaacaugg cacauguaua cauauguagc aaaccugcac guugugcaca uguacccuag 2700
aacuuaaagu auaauuaaaa aaaaaaagaa aacagaagcu auuuauaaag aaguuauuug 2760
cugaaauaaa ugugaucuuu cccauuaaaa aaauaaagaa auuuuggggu aaaaaaacac 2820
aauauauugu auucuugaaa aauucuaaga gaguggaugu gaaguguucu caccacaaaa 2880
gugauaacua auugagguaa ugcacauauu aauuagaaag auuuugucau uccacaaugu 2940
auauauacuu aaaaauaugu uauacacaau aaauacauac auuaaaaaau aaguaaaugu 3000
a 3001

<210> SEQ ID NO 71
<211> LENGTH: 1037
<212> TYPE: RNA
<213> ORGANISM: Artificial Sequence
<220> FEATURE:
<223> OTHER INFORMATION: Synthetic Polynucleotide

<400> SEQUENCE: 71
cccacccugc acgccggcac caaacccugu ccucccaccc cuccccacuc aucacuaaac 60
agaguaaaau gugaugcgaa uuuucccgac caaccugauu cgcuagauuu uuuuuaagga 120
aaagcuugga aagccaggac acaacgcugc ugccugcuuu gugcaggguc cuccggggcu 180
cagcccugag uuggcaucac cugcgcaggg cccucugggg cucagcccug agcuagugc 240 accugcacag ggcccucuga ggcucagccc ugagcuggcg ucaccugugc agggcccucu 300
ggggcucagc ccugagcugg ccucaccugg guuccccacc ccgggcucuc cugcccugcc 360
cuccugcccg cccucccucc ugccugcgca gcuccuuccc uaggcaccuc ugugcugcau 420
cccaccagcc ugagcaagac gcccucucgg ggccugugcc gcacuagccu cccucuccuc 480
uguccccaua gcugguuuuu cccaccaauc cucaccuaac aguuacuuua caauuaaacu 540
caaagcaagc ucuucuccuc agcuuggggc agccauuggc cucugucucg uuuugggaaa 600
ccaaggucag gaggccguug cagacauaaa ucucggcgac ucggccccgu cuccugaggg 660
uccugcuggu gaccggccug gaccuuggcc cuacagcccu ggaggccgcu gcugaccagc 720
acugaccccg accucagaga guacucgcag gggcgcuggc ugcacucaag acccucgaga 780
uuaacggugc uaaccccguc ugcuccuccc ucccgcagag acuggggccu ggacuggaca 840
ugagagcccc uuggugccac agagggcugu gucuuacuag aaacaacgca aaccucuccu 900
uccucagaau agugaugugu ucgacguuuu aucaaaggcc cccuuucuau guucauguua 960
guuuugcucc uucuguguuu uuuucugaac cauauccaug uugcugacuu uuccaaauaa 1020
agguuuucac uccucuc 1037

<210> SEQ ID NO 72
<211> LENGTH: 577
<212> TYPE: RNA
<213> ORGANISM: Artificial Sequence
<220> FEATURE:
<223> OTHER INFORMATION: Synthetic Polynucleotide

<400> SEQUENCE: 72
agaggccugc cuccagggcu ggacugaggc cugagcgcuc cugccgcaga gcuggccgcg 60
ccaaauaaug ucucugugag acucgagaac uuucauuuuu uuccaggcug guucggauuu 120
gggguggauu uugguuuugu uccccuccuc cacucucccc caccccccucc ccgcccuuuu 180 uuuuuuuuuu uuuuaaacug guauuuuauc uuugauucuc cuucagcccu caccccuggu 240
ucucaucuuu cuugaucaac aucuuuucuu gccucugucc ccuucucuca ucucuuagcu 300
ccccuccaac cugggggggca guggugugga gaagccacag gccugagauu ucaucugcuc 360
uccuuccugg agcccagagg agggcagcag aagggggugg ugucuccaac cccccagcac 420
ugaggaagaa cggggcucuu cucauuucac cccucccuuu cuccccugcc cccaggacug 480
ggccacuucu ggguggggca gugggucccca gauuggcuca cacugagaau guaagaacua 540
caaacaaaau uucuauuaaa uuaaauuuug ugucucc 577

<210> SEQ ID NO 73
<211> LENGTH: 2212
<212> TYPE: RNA
<213> ORGANISM: Artificial Sequence
<220> FEATURE:
<223> OTHER INFORMATION: Synthetic Polynucleotide

<400> SEQUENCE: 73
cucccuccau cccaaccugg cucccuccca cccaaccaac uuuccccccca acccggaaac 60 agacaagcaa cccaaacuga acccccucaa aagccaaaaa augggagaca auuucacaug 120
gacuuuggaa aauauuuuuu uccuuugcau ucaucucuca aacuuaguuu uuaucuuuga 180
ccaaccgaac augaccaaaa accaaaagug cauucaaccu uaccaaaaaa aaaaaaaaaa 240
aaagaauaaa uaaauaacuu uuuaaaaaag gaagcuuggu ccacuugcuu gaagacccau 300
gcggggguaa gucccuuucu gcccguuggg cuuaugaaac ccccaaugcug cccuuucugc 360 uccuuucucc acacccccccu uggggccucc ccuccacucc uucccaaauc ugucuccccca 420 gaagacacag gaaacaaugu auugucugcc cagcaaucaa aggcaaugcu caaacaccca 480 agugqccccc acccucagcc cgcuccugcc cgcccagcac ccccaggccc ugggggaccu 540
gggguucuca gacugccaaa gaagccuugc caucuggcgc ucccauggcu cuugcaacau 600
cuccccuucg uuuuugaggg ggucaugccg ggggagccac cagccccuca cuggguucgg 660
aggagaguca ggaagggcca cgacaaagca gaaacaucgg auuuggggaa cgcgugucaa 720
ucccuugugc cgcagggcug ggcgggagag acuguucugu uccuugugua acuguguugc 780
ugaaagacua ccucguucuu gucuugaugu gucaccgggg caacugccug ggggcgggga 840
ugggggcagg guggaagcgg cuccccauuu uauaccaaag gugcuacauc uaugugaugg 900 guggggugg gagggaauca cuggugcuau agaaauugag augcccccc aggccagcaa 960 auguuccuuu uuguucaaag ucuauuuuua uuccuugaua uuuuucuuuu uuuuuuuuuu 1020
uuuuugugga uggggacuug ugaauuuuuc uaaaggugcu auuuaacaug ggaggagagc 1080
gugugcggcu ccagcccagc ccgcugcuca cuuuccaccc ucucuccacc ugccucuggc 1140
uucucaggcc ucugcucucc gaccucucuc cucugaaacc cuccuccaca gcugcagccc 1200
auccucccgg cucccuccua gucuguccug cguccucugu ccccggguuu cagagacaac 1260
uucccaaagc acaaagcagu uuuuccccu agggguggga ggaagcaaaa gacucuguac 1320
cuauuuugua uguguauaau aauuugagau guuuuuaauu auuuugauug cuggaauaaa 1380
gcauguggaa augacccaaa cauaauccgc aguggccucc uaauuuccuu cuuuggaguu 1440
gggggagggg uagacauggg gaaggggcuu uggggugaug ggcuugccuu ccauuccugc 1500
ccuuucccuc cccacuauuc ucuucuagau cccuccauaa ccccacuccc cuuucucuca 1560
cccuucuuau accgcaaacc uuucuacuuc cucuuucauu uucuauucuu gcaauuuccu 1620
ugcaccuuuu ccaaauccuc uucuccccug caauaccaua caggcaaucc acgugcacaa 1680
cacacacaca cacucuucac aucuggggu guccaaaccu cauacccacu ccccuucaag 1740
cccauccacu cuccacccc uggaugcccu gcacuuggug gcggugggau gcucauggau 1800
acugggaggg ugaggggagu ggaacccgug aggaggaccu gggggccucu ccuugaacug 1860
acaugaaggg ucaucuggcc ucugcucccu ucucacccac gcugaccucc ugccgaagga 1920
gcaacgcaac aggagagggg ucugcugagc cuggcgaggg ucugggaggg accaggagga 1980
aggcgugcuc ccugcucgcu guccuggccc ugggggagug agggagacag acaccuggga 2040
gagcuguggg gaaggcacuc gcaccgugcu cuugggaagg aaggagaccu ggcccugcuc 2100
accacggacu gggugccucg accuccugaa uccccagaac acaaccccc ugggcugggg 2160 uggucugggg aaccaucgug cccccgccuc ccgccuacuc cuuuuuaagc uu 2212

<210> SEQ ID NO 74
<211> LENGTH: 729
<212> TYPE: RNA
<213> ORGANISM: Artificial Sequence
<220> FEATURE:
<223> OTHER INFORMATION: Synthetic Polynucleotide

<400> SEQUENCE: 74
uuggccaggc cugacccucu uggaccuuuc uucuuugccg acaaccacug cccagcagcc 60
ucugggaccu cgggguccca gggaacccag uccagccucc uggcuguuga cuucccauug 120
cucuuggagc caccaaucaa agagauucaa agagauuccu gcaggccaga ggcggaacac 180
accuuuaugg cuggggcucu ccgugguguu cuggacccag ccccuggaga caccauucac 240
uuuuacugcu uuguagugac ucgugcucuc caaccugucu uccugaaaaa ccaaggcccc 300
cuucccccac cucuuccaug gggugagacu ugagcagaac aggggcuucc ccaaguugcc 360
cagaaagacu gucuggguga gaagccaugg ccagagcuuc ucccaggcac agguguugca 420
ccagggacuu cugcuucaag uuuuggggua aagacaccug gaucagacuc caagggcugc 480
ccugagucug ggacuucugc cuccauggcu ggucaugaga gcaaaccgua guccccugga 540
gacagcgacu ccagagaacc ucuugggaga cagaagaggc aucugugcac agcucgaucu 600
ucuacuugcc uguggggagg ggagugacag guccacacac cacacugggu cacccugucc 660
uggaugccuc ugaagagagg gacagaccgu cagaaacugg agaguuucua uuaaagguca 720
uuuaaacca 729

<210> SEQ ID NO 75
<211> LENGTH: 847
<212> TYPE: RNA
<213> ORGANISM: Artificial Sequence
<220> FEATURE:
<223> OTHER INFORMATION: Synthetic Polynucleotide

<400> SEQUENCE: 75
uccuccggga ccccagcccu caggauuccu gaugcuccaa ggcgacugau gggcgcugga 60
ugaaguggca cagucagcuu cccugggggc uggugucaug uugggcuccu ggggcggggg 120
cacggccugg cauuucacgc auugcugcca ccccaggucc accugucucc acuuucacag 180
ccuccaaguc uguggcucuu cccuucuguc cuccgagggg cuugccuucu cucgugucca 240
gugaggugcu cagugaucgg cuuaacuuag agaagcccgc ccccuccccu ucuccgucug 300
ucccaagagg gucugcucug agccugcguu ccuagguggc ucggccucag cugccugggu 360
uguggccgcc cuagcauccu guaugcccac agcuacugga auccccgcug cugcuccggg 420
ccaagcuucu gguugauuaa ugagggcaug ggguggucc ucaagaccuu ccccuaccuu 480
uuguggaacc agugaugccu caaagacagu guccccucca cagcugggug ccaggggcag 540
gggauccuca guauagccgg ugaacccuga uaccaggagc cugggccucc cugaaccccu 600
ggcuuccagc caucucaucg ccagccuccu ccuggaccuc uuggccccca gccccuuccc 660
cacacagccc cagaagggucс ccagagcuga ccccacucca ggaccuaggc ccagccccuc 720
agccucaucu ggagccccug aagaccaguc ccacccaccu uucuggccuc aucugacacu 780
gcuccgcauc cugcugugug uccuguucca uguuccgguu ccauccaaau acacuuucug 840
gaacaaa 847

<210> SEQ ID NO 76
<211> LENGTH: 110
<212> TYPE: RNA
<213> ORGANISM: Artificial Sequence
<220> FEATURE:
<223> OTHER INFORMATION: Synthetic Polynucleotide

<400> SEQUENCE: 76
gcuggagccu cgguggccau gcuucuugcc ccuugggccu ccccccagcc ccuccucccc 60
uuccugcacc cguacccccg uggucuuuga auaaagucug agugggcggc 110

<210> SEQ ID NO 77
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 77

-continued ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 78
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 78
attgggcacc cgtaaggg 18

<210> SEQ ID NO 79
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 79
tcaagctttt ggaccctcgt acagaagcta atacgactca ctatagggaa ataagagaga 60
aaagaagagt aagaagaaat ataagagcca cc 92

<210> SEQ ID NO 80
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 80
atggaaagca aggccctgct ggtcctgacc ctcgccgtgt ggctccagag cctgaccgcc 60
agccggggcg gggtggccgc cgccgaccag cgacgggact tcatagacat cgagagcaag 120
tttgccctgc gcacgcccga ggacacggcc gaggacacct gccatctgat ccccggcgtg 180
gccgagagcg tcgccacctg ccactttaac cacagcagca aaaccttcat ggtgatccac 240
ggatggaccg tgaccggaat gtacgagagc tgggtaccaa agctggtcgc cgccctgtac 300
aaaagggaac ccgatagcaa cgtgatcgtg gtggactggc tctccagggc ccaagagcac 360
taccccgtca gcgccggcta caccaagctg gtgggacagg acgtggcccg tttcatcaat 420
tggatggagg aggagttcaa ttacccccctg gacaacgtgc acctgctggg ctactccctg 480
ggagcccacg ccgccgggat agccggctcc ctcaccaaca agaaggtcaa ccggatcact 540
ggcctcgatc ccgccggacc caactttgag tacgccgaag ccccctcgag gctgagcccc 600
gacgacgccg attttgtgga cgtcctccac accttcaccc gcgggtcccc cggcaggagc 660
atcggcatcc agaagcccgt gggccacgtg gacatctatc ccaacggcgg caccttccag 720
cccggctgta acatcggcga agccatccgg gtgatcgccg aacggggcct gggcgatgtg 780
gaccagctgg tgaaatgtag ccacgagagg agcatccacc tgtttatcga tagcttgctg 840
aacgaggaga acccatccaa agcgtacagg tgcagctcca aggaggcctt cgaaaagggc 900
ctgtgcctct cctgcaggaa gaaccggtgc aacaacctgg ggtatgagat caacaaagta 960
agggcgaaga ggagctccaa gatgtacctg aagactagga gccagatgcc ctacaaggtg 1020
ttccactatc aggtgaaaat ccacttcagc ggcacagaaa gcgagaccca caccaaccag 1080
gccttcgaga tctctctgta tggcaccgtg gccgagagcg agaacatacc cttcaccctg 1140
cccgaagtga gcaccaacaa aacctacagc ttcctgatct acaccgaggt ggacatcggc 1200
gagctcctca tgctcaagct gaagtggaag tccgacagct acttctcgtg gagcgactgg 1260
tggtcgagcc ccggcttcgc catccagaag atccgggtga aagccggcga gacccagaag 1320
aaggtcatct tttgcagcag ggagaaggtg agccatctcc agaagggcaa agctccagcc 1380
gtgttcgtca agtgccacga caagtccctg aacaagaaga gcggc 1425

<210> SEQ ID NO 81
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 81
atggagtcca aagcgcttct ggtgctcacc ctggcggtgt ggctgcagag cctgaccgcc 60
tccagaggcg gcgtggccgc cgccgaccag cggagggact tcatcgacat cgagagcaag 120
ttcgcactca ggaccccgga ggataccgcc gaggacacct gccacctgat ccccggtgtg 180
gccgagtcag tggccacctg tcatttcaac cacagcagca agaccttcat ggtgatccac 240
ggctggaccg tcaccggcat gtacgagagc tgggtgccca agctcgtcgc ggcgctctac 300
aagcgggagc cagacagcaa tgtgatcgtg gtggactggc tcagccgggc ccaggagcac 360
tacccggtgt ccgccgggta cacgaagctg gtgggccagg acgtcgcccg ctttataaac 420
tggatggagg aagagttcaa ctacccctg gacaacgtgc acctgctcgg ttacagcctc 480
ggggcccacg ccgccggaat cgcgggttcc ctcaccaaca agaaggtgaa taggatcacc 540
gggctggacc ccgccggccc caatttcgag tacgccgagg ccccctcgcg gctgagcccc 600
gacgacgccg actttgtgga cgtgctgcac accttcaccc ggggcagccc tgggagatcc 660
atcggcatac agaagcccgt cggccacgtg gacatctacc ccaacggggg gacctttcag 720
cccgggtgca atatcgggga agccattagg gtgatcgccg agaggggtct gggggacgtc 780
gaccagctcg tgaaatgttc ccacgagagg agcatccacc tgttcataga cagcctgctg 840
aatgaggaga accccctccaa agcctaccgc tgcagcagca aggaggcctt cgaaaagggg 900
ctgtgcctga gctgcaggaa gaataggtgt aacaatctgg gctacgagat caacaaggtg 960
cgggcgaaga ggtcctctaa gatgtatctt aagacccgaa gccaaatgcc ctataaggtg 1020
ttccactacc aagtgaagat ccatttttcc gggaccgaga gcgagaccca taccaaccag 1080
gccttcgaga tctccctgta cgggacagtg gccgagtccg aaaacatccc cttcaccctg 1140
cccgaagtga gcaccaacaa gacctactcc tttctgatct acaccgaggt ggacatcggc 1200
gagctgctga tgctgaagct gaagtggaag agcgatagct acttcagctg gtcagactgg 1260
tggagcagcc ccggcttcgc aatccagaag atcagggtga aggccggcga gacgcagaag 1320
aaagtgatct tctgcagcag ggagaaggta agccatctcc agaagggcaa agccccccgcc 1380 gtgttcgtga agtgtcacga caagtccctg aacaaaaaaa gcggt 1425

<210> SEQ ID NO 82
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 82
atggaaagca aagccctgct ggtactcacg ctcgccgtct ggctgcagtc cctgaccgcc 60

-continued

```
agcagaggcg gcgtcgcggc cgccgatcag agaagagact tcatcgacat cgaaagcaag    120
ttcgcgctga ggaccccgga agacaccgcc gaggacacgt gccacctgat ccccggcgtg    180
gccgagagcg tggccacgtg tcacttcaac cactcctcca agacctttat ggtgatccac    240
ggctggacgg tgaccggaat gtacgagagc tgggtgccga agctggtggc cgccctgtac    300
aagcgggagc cggacagcaa cgtgatcgta gtggactggc tgagcagggc ccaggagcat    360
tatcccgtga gcgccggcta cactaagctg gtgggccagg acgtggcccg gttcataaac    420
tggatggagg aagagttcaa ctacccactg gacaatgtcc acctcctggg ctacagcctg    480
ggcgcccacg ccgccggcat cgccgggtcc ctcaccaaca agaaggtcaa ccggatcaca    540
ggcctcgacc ccgccggccc caactttgag tacgccgagg ccccctcaag gctgagcccc    600
gacgacgccg acttcgtaga cgtgctgcac acctttactc gcggcagccc gggtaggtcg    660
atcgggatcc agaagcctgt cggccatgtg gacatctacc ccaacggcgg caccttccaa    720
cccggatgta acatcggcga ggccatccgg gtgatcgccg aacgcgggct gggagacgtg    780
gaccaactgg tgaagtgcag ccacgagagg agcatccacc tgttcatcga cagcctgctg    840
aacgaggaga accccagcaa agcctatagg tgcagcagca aggaggcctt cgaaaaaggc    900
ctctgcctgt cctgcaggaa aaaccgttgc aacaacctgg gctacgaaat caacaaggtg    960
cgagccaaaa ggagcagcaa gatgtacctg aagaccaggt cccagatgcc gtataaggtg   1020
ttccactacc aggtgaagat ccatttctcc ggaaccgagt cggaaaccca cactaaccag   1080
gccttcgaga tcagcctgta cggcacggtc gccgagtccg aaaatatccc cttcaccctc   1140
cccgaagtgt ccaccaacaa gacatacagc ttcctgatct acaccgaggt ggacatcgga   1200
gagctgctga tgctcaagct gaagtggaag agcgacagct acttcagctg gagcgactgg   1260
tggtcctcgc cgggcttcgc catccaaaag atccgcgtca aggccgggga gacccagaag   1320
aaggtcatct tctgttccag ggagaaggtg agccacctcc agaagggcaa ggcccccgcc   1380
gtgttcgtga agtgccatga caagagcctg aacaagaaga gcggc                   1425
```

<210> SEQ ID NO 83
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 83

```
atggagagca aggccctgct ggtgctgacc ctggccgtgt ggctgcagtc actcaccgca     60
tccagggggg gagtggccgc cgccgaccag aggcgggact tcatcgatat cgagagcaag    120
ttcgccctcc ggacccccga ggacacagcc gaggacacct gccacctgat ccccggggtg    180
gccgagtcag tggcgacctg ccatttcaac cactccagca agacctttat ggtcatccac    240
ggctggaccg tgaccggcat gtacgagtcc tgggtcccca agctggtggc cgcgctgtat    300
aagcgggaac ccgactccaa tgtgatcgtc gtggattggc tgagccgtgc ccaggagcat    360
taccccgtga gcgccggcta caccaagttg gtgggacagg acgtggccag gttcatcaac    420
tggatggagg aggagttcaa ctaccccctg gataacgtgc acctgctggg ctactccctg    480
ggggcgcatg ccgcgggcat cgccgggagc ctgaccaaca agaaggtgaa taggatcacc    540
ggcctggatc ccgccggccc gaacttcgag tacgccgagg cccccagcag gctgagcccg    600
gacgacgccg acttcgtgga cgtcctccac accttcacca gggggagccc cgggaggagc    660
attggaatcc agaagcccgt gggccacgtg gacatctatc ccaatggcgg gacgttccaa    720
```

```
cctggctgca acatcggtga agccatccgc gtgatcgccg agcgcggcct gggcgacgtg    780
gaccagctgg tgaagtgcag tcacgagagg agcatccacc tgttcatcga tagcctgctg    840
aacgaggaga accccagcaa ggcctacagg tgctccagca aggaggcctt cgagaagggc    900
ctctgcctga gctgccgcaa gaaccggtgc aacaacctcg ggtacgaaat caataaggtg    960
cgggccaaga ggtccagcaa gatgtatctg aagacccgga gccagatgcc ctacaaggtg   1020
ttccactacc aagtgaagat ccacttttcg ggtacggagt ccgagacgca caccaaccag   1080
gcctttgaaa tcagcctcta cggcaccgtg gccgaaagcg agaacatccc ctttaccctg   1140
cccgaggtca gcaccaacaa gacctattcc ttcctgatct acaccgaggt ggacatcggc   1200
gaactcctga tgctgaagct gaagtggaag tccgacagct acttttcctg gagcgactgg   1260
tggtccagcc ccgggttcgc catacagaag atccgggtga aggcagggga gacgcagaaa   1320
aaggtcatct tctgcagccg tgaaaaggtg agtcacctcc aaaagggcaa ggcgcccgcc   1380
gtgttcgtaa agtgccacga taagagcctg aacaaaaaaa gcggc                   1425
```

<210> SEQ ID NO 84
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 84

```
ccrccaugg                                                              9
```

<210> SEQ ID NO 85
<211> LENGTH: 3846
<212> TYPE: DNA
<213> ORGANISM: Artificial Sequence
<220> FEATURE:
<223> OTHER INFORMATION: Synthetic Polynucleotide

<400> SEQUENCE: 85

```
tttaacgtga atcgatgtaa acctgtgttt ggtgcttaga caggggggccc ccgggtagag     60
tggaacccct taagctaagc gaacaggagc ctaacaaagc aaatttttcc gtctgccctt    120
tccccctctt ctcgttggca gggttgatcc tcattactgt ttgctcaaac gtttagaagt    180
gaatttaggt ccctcccccc aacttatgat tttatagcca ataggtgatg aggtttattt    240
gcatatttcc agtcacataa gcagccttgg cgtgaaaaca gtgtcagact cgattccccc    300
tcttcctcct cctcaaggga aagctgccca cttctagctg ccctgccatc ccctttaaag    360
ggcgacttgc tcagcgccaa accgcggctc cagccctctc cagcctccgg ctcagccggc    420
tcatcagtcg gtccgcgcct tgcagctcct ccagagggac gcgccccgag atggagagca    480
aagccctgct cgtgctgact ctggccgtgt ggctccagag tctgaccgcc tcccgcggag    540
gggtggccgc cgccgaccaa agaagagatt ttatcgacat cgaaagtaaa tttgccctaa    600
ggacccctga agacacagct gaggacactt gccacctcat tcccggagta gcagagtccg    660
tggctacctg tcatttcaat cacagcagca aaaccttcat ggtgatccat ggctggacgg    720
taacaggaat gtatgagagt tgggtgccaa aacttgtggc cgccctgtac aagagagaac    780
cagactccaa tgtcattgtg gtggactggc tgtcacgggc tcaggagcat tacccagtgt    840
ccgcgggcta caccaaactg gtgggacagg atgtggcccg gtttatcaac tggatggagg    900
aggagtttaa ctaccctctg gacaatgtcc atctcttggg atacagcctt ggagcccatg    960
```

-continued

```
ctgctggcat tgcaggaagt ctgaccaata agaaagtcaa cagaattact ggcctcgatc   1020
cagctggacc taactttgag tatgcagaag ccccgagtcg tctttctcct gatgatgcag   1080
attttgtaga cgtcttacac acattcacca gagggtcccc tggtcgaagc attggaatcc   1140
agaaaccagt tgggcatgtt gacatttacc cgaatggagg tacttttcag ccaggatgta   1200
acattggaga agctatccgc gtgattgcag agagaggact tggagatgtg gaccagctag   1260
tgaagtgctc ccacgagcgc tccattcatc tcttcatcga ctctctgttg aatgaagaaa   1320
atccaagtaa ggcctacagg tgcagttcca aggaagcctt tgagaaaggg ctctgcttga   1380
gttgtagaaa gaaccgctgc aacaatctgg gctatgagat caataaagtc agagccaaaa   1440
gaagcagcaa aatgtacctg aagactcgtt ctcagatgcc ctacaaagtc ttccattacc   1500
aagtaaagat tcatttttct gggactgaga gtgaaaccca taccaatcag gcctttgaga   1560
tttctctgta tggcaccgtg gccgagagtg agaacatccc attcactctg cctgaagttt   1620
ccacaaataa gacctactcc ttcctaattt acacagaggt agatattgga gaactactca   1680
tgttgaagct caaatggaag agtgattcat actttagctg gtcagactgg tggagcagtc   1740
ccggcttcgc cattcagaag atcagagtaa aagcaggaga gactcagaaa aaggtgatct   1800
tctgttctag ggagaaagtg tctcatttgc agaaaggaaa ggcacctgcg gtatttgtga   1860
aatgccatga caagtctctg aataagaagt caggctgaaa ctgggcgaat ctacagaaca   1920
aagaacggca tgtgaattct gtgaagaatg aagtggagga agtaactttt acaaaacata   1980
cccagtgttt ggggtgtttc aaaagtggat ttcctgaat attaatccca gccctaccct   2040
tgttagttat tttaggagac agtctcaagc actaaaaagt ggctaattca atttatgggg   2100
tatagtggcc aaatagcaca tcctccaacg ttaaaagaca gtggatcatg aaaagtgctg   2160
ttttgtcctt tgagaaagaa ataattgttt gagcgcagag taaaataagg ctccttcatg   2220
tggcgtattg ggccatagcc tataattggt tagaacctcc tattttaatt ggaattctgg   2280
atctttcgga ctgaggcctt ctcaaacttt actctaagtc tccaagaata cagaaaatgc   2340
ttttccgcgg cacgaatcag actcatctac acagcagtat gaatgatgtt ttagaatgat   2400
tccctcttgc tattggaatg tggtccagac gtcaaccagg aacatgtaac ttggagaggg   2460
acgaagaaag ggtctgataa acacagaggt tttaaacagt ccctaccatt ggcctgcatc   2520
atgacaaagt tacaaattca aggagatata aaatctagat caattaattc ttaataggct   2580
ttatcgttta ttgcttaatc cctctctccc ccttcttttt tgtctcaaga ttatattata   2640
ataatgttct ctgggtaggt gttgaaaatg agcctgtaat cctcagctga cacataattt   2700
gaatggtgca gaaaaaaaaa aagaaaccgt aattttatta ttagattctc caaatgattt   2760
tcatcaattt aaaatcattc aatatctgac agttactctt cagttttagg cttaccttgg   2820
tcatgcttca gttgtacttc cagtgcgtct cttttgttcc tggctttgac atgaaaagat   2880
aggtttgagt tcaaattttg cattgtgtga gcttctacag attttagaca aggaccgttt   2940
ttactaagta aaagggtgga gaggttcctg ggtggattc ctaagcagtg cttgtaaacc   3000
atcgcgtgca atgagccaga tggagtacca tgagggttgc tatttgttgt ttttaacaac   3060
taatcaagag tgagtgaaca actatttata aactagatct cctatttttc agaatgctct   3120
tctacgtata aatatgaaat gataaagatg tcaaatatct cagaggctat agctgggaac   3180
ccgactgtga aagtatgtga tatctgaaca catactagaa agctctgcat gtgtgttgtc   3240
cttcagcata attcggaagg gaaaacagtc gatcaaggga tgtattggaa catgtcggag   3300
tagaaattgt tcctgatgtg ccagaacttc gaccctttct ctgagagaga tgatcgtgcc   3360
```

tataaatagt aggaccaatg ttgtgattaa catcatcagg cttggaatga attctctcta 3420
aaaataaaat gatgtatgat ttgttgttgg catccccttt attaattcat taaatttctg 3480
gatttgggtt gtgacccagg gtgcattaac ttaaaagatt cactaaagca gcacatagca 3540
ctgggaactc tggctccgaa aaactttgtt atatatatca aggatgttct ggctttacat 3600
tttatttatt agctgtaaat acatgtgtgg atgtgtaaat ggagcttgta catattggaa 3660
aggtcattgt ggctatctgc atttataaat gtgtggtgct aactgtatgt gtctttatca 3720
gtgatggtct cacagagcca actcactctt atgaaatggg ctttaacaaa acaagaaaga 3780
aacgtactta actgtgtgaa gaaatggaat cagcttttaa taaaattgac aacattttat 3840
taccac 3846

<210> SEQ ID NO 86
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 86
atggagagca aggccctgct ggtgctgacc ctggccgtgt ggctgcagag cctgaccgcc 60
agccgcggcg gcgtggccgc cgccgaccag cgccgcgact tcatcgacat cgagagcaag 120
ttcgccctgc gcacccccga ggacaccgcc gaggacacct gccacctgat ccccggcgtg 180
gccgagagcg tggccacctg ccacttcaac cacagcagca agaccttcat ggtgatccac 240
ggctggaccg tgaccggcat gtacgagagc tgggtgccca agctggtggc cgccctgtac 300
aagcgcgagc ccgacagcaa cgtgatcgtg gtggactggc tgagccgcgc ccaggagcac 360
taccccgtga gcgccggcta caccaagctg gtgggccagg acgtggcccg cttcatcaac 420
tggatggagg aggagttcaa ctacccccg gacaacgtgc acctgctggg ctacagcctg 480
ggcgcccacg ccgccggcat cgccggcagc ctgaccaaca agaaggtgaa ccgcatcacc 540
ggcctggacc ccgccggccc caacttcgag tacgccgagg cccccagccg cctgagcccc 600
gacgacgccg acttcgtgga cgtgctgcac accttcaccc gcggcagccc cggccgcagc 660
atcggcatcc agaagcccgt gggccacgtg gacatctacc ccaacggcgg caccttccag 720
cccggctgca acatcggcga ggccatccgc gtgatcgccg agcgcggcct gggcgacgtg 780
gaccagctgg tgaagtgcag ccacgagcgc agcatccacc tgttcatcga cagcctgctg 840
aacgaggaga accccagcaa ggcctaccgc tgcagcagca aggaggcctt cgagaagggc 900
ctgtgcctga gctgccgcaa gaaccgctgc aacaacctgg gctacgagat caacaaggtg 960
cgcgccaagc gcagcagcaa gatgtacctg aagacccgca gccagatgcc ctacaaggtg 1020
ttccactacc aggtgaagat ccacttcagc ggcaccgaga gcgagaccca caccaaccag 1080
gccttcgaga tcagcctgta cggcaccgtg gccgagagcg agaacatccc cttcaccctg 1140
cccgaggtga gcaccaacaa gacctacagc ttcctgatct acaccgaggt ggacatcggc 1200
gagctgctga tgctgaagct gaagtggaag agcgacagct acttcagctg gagcgactgg 1260
tggagcagcc ccggcttcgc catccagaag atccgcgtga aggccggcga gacccagaag 1320
aaggtgatct tctgcagccg cgagaaggtg agccacctgc agaagggcaa ggcccccgcc 1380
gtgttcgtga agtgccacga caagagcctg aacaagaaga gcggc 1425

<210> SEQ ID NO 87

<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 87
atggagagca aggccctgct ggtgctgacc ctggccgtgt ggctgcagag cctgaccgcc 60
agcagaggcg gcgtggccgc cgccgaccag agaagagact tcatcgacat cgagagcaag 120
ttcgccctga gaacccccga ggacaccgcc gaggacacct gccacctgat ccccggcgtg 180
gccgagagcg tggccacctg ccacttcaac cacagcagca agaccttcat ggtgatccac 240
ggctggaccg tgaccggcat gtacgagagc tgggtgccca agctggtggc cgccctgtac 300
aagagagagc ccgacagcaa cgtgatcgtg gtggactggc tgagcagagc ccaggagcac 360
taccccgtga gcgccggcta caccaagctg gtgggccagg acgtggccag attcatcaac 420
tggatggagg aggagttcaa ctacccctg gacaacgtgc acctgctggg ctacagcctg 480
ggcgcccacg ccgccggcat cgccggcagc ctgaccaaca agaaggtgaa cagaatcacc 540
ggcctggacc ccgccggccc caacttcgag tacgccgagg cccccagcag actgagcccc 600
gacgacgccg acttcgtgga cgtgctgcac accttcacca gaggcagccc cggcagaagc 660
atcggcatcc agaagcccgt gggccacgtg gacatctacc ccaacggcgg caccttccag 720
cccggctgca acatcggcga ggccatcaga gtgatcgccg agagaggcct gggcgacgtg 780
gaccagctgg tgaagtgcag ccacgagaga agcatccacc tgttcatcga cagcctgctg 840
aacgaggaga accccagcaa ggcctacaga tgcagcagca aggaggcctt cgagaagggc 900
ctgtgcctga gctgcagaaa gaacagatgc aacaacctgg gctacgagat caacaaggtg 960
agagccaaga gaagcagcaa gatgtacctg aagaccagaa gccagatgcc ctacaaggtg 1020
ttccactacc aggtgaagat ccacttcagc ggcaccgaga gcgagaccca caccaaccag 1080
gccttcgaga tcagcctgta cggcaccgtg gccgagagcg agaacatccc cttcaccctg 1140
cccgaggtga gcaccaacaa gacctacagc ttcctgatct acaccgaggt ggacatcggc 1200
gagctgctga tgctgaagct gaagtggaag agcgacagct acttcagctg gagcgactgg 1260
tggagcagcc ccggcttcgc catccagaag atcagagtga aggccggcga gacccagaag 1320
aaggtgatct tctgcagcag agagaaggtg agccacctgc agaagggcaa ggcccccgcc 1380
gtgttcgtga agtgccacga caagagcctg aacaagaaga gcggctag 1428

<210> SEQ ID NO 88
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 88
atggagtcca aagcactgct cgttctcacc ctagcagtgt ggctgcagag cctgactgcc 60
tcgcggggag gagttgctgc ggccgaccag cgccgggact ttatcgacat cgagtctaaa 120
ttcgccctgc gcaccccaga ggatactgcc gaagacacct gtcatctaat cccaggggtt 180
gccgagagcg tagccacatg ccatttcaac cactcttcca aaacattcat ggtcatccac 240
ggttggacag tgactggtat gtacgagagc tgggtgccaa agctcgtggc agctctgtac 300
aagagagaac cggattctaa cgtgatcgtc gtggattggc tgagcagagc ccaggaacac 360
tatccagtgt ctgccgggta tacaaaactc gtcggccagg atgtggccag gttcattaac 420
tggatggagg aagaattcaa ttaccctttg gacaacgttc atctgcttgg gtactcactg 480
ggtgcacatg ccgccggtat cgccggttct ttgactaaca aaaaggtgaa caggatcact 540
gggttagacc cggcaggccc taactttgag tacgccgaag caccaagccg gctctcccca 600
gatgatgctg atttcgttga tgtcctacac actttcacac gcgggtcccc cggccgttct 660
atcggaattc agaagccagt tggccatgtt gatatctacc ctaatggggg tacttttcag 720
ccaggctgta acatcgggga ggccattaga gttatagcag agaggggcct cggagacgtc 780
gaccagttgg tgaagtgcag tcatgaacgc tcgatccatc tgttcatcga ttccctgctg 840
aatgaggaga acccgagcaa ggcatataga tgttcctcca aagaggcctt tgagaagggg 900
ctctgcttgt cctgtaggaa gaaccgatgc aacaacttgg gttacgagat aaacaaggta 960
cgtgctaaga ggtcttctaa aatgtatctg aagacgcgga gtcagatgcc ctacaaggtc 1020
tttcattacc aagtcaaaat acatttctct gggactgaat cagagacgca tacgaaccaa 1080
gcctttgaaa tcagcttgta tggtactgtg gctgagagtg agaatatccc gtttaccctt 1140
ccagaagttt caaccaataa aacttatagc tttctgatct acactgaggt agacattgga 1200
gaactgctga tgttgaaatt gaagtggaaa agcgacagct acttctcctg gagcgactgg 1260
tggtcctcgc ccggcttcgc cattcagaag atcagggtta aggccgggga gacgcagaag 1320
aaagttattt tctgttctag ggagaaggtt tctcaccttc aaaagggaaa agcccccgca 1380
gttttcgtga aatgccatga taaaagcttg aacaaaaagt ccggatag 1428

<210> SEQ ID NO 89
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 89
atggagagca aggccctgct ggtgctgacc ctggccgtgt ggctgcagag cctgacagcc 60
agcagaggag gagtggccgc tgctgaccag aggcgggact tcattgatat tgagagcaag 120
tttgccctgc ggaccccaga ggacacagct gaggacacct gccacctgat ccctggggtg 180
gccgagagcg tggccacctg ccacttcaac cacagcagca agaccttcat ggtgatccac 240
ggctggacag tgacaggcat gtatgagagc tgggtgccca agctggtggc cgccctgtac 300
aagcgggagc cagacagcaa tgtgattgtg gtggactggc tgagccgggc ccaggagcac 360
taccctgtgt ctgctggcta caccaagctg gtgggccagg atgtggcccg cttcatcaac 420
tggatggagg aggagttcaa ctacccccctg gacaacgtgc acctgctggg ctacagcctg 480
ggcgcccacg ccgccggcat tgctggcagc ctgaccaaca agaaggtgaa ccgcatcacc 540
ggcctggacc ctgctggccc caactttgaa tatgcagagg cccccagccg gctgagccca 600
gatgatgctg actttgtgga tgtgctgcac accttcaccc ggggcagccc tggccgcagc 660
atcggcatcc agaagcctgt gggccacgtg gacatctacc caaatggagg caccttccag 720
cccggctgca acattggaga ggccatccgg gtgattgctg agcggggcct gggagatgtg 780
gaccagctgg tgaagtgcag ccatgagagg agcatccacc tgttcatcga cagcctgctg 840
aatgaggaga accccagcaa ggcctaccgc tgcagcagca aggaggcctt tgagaagggc 900
ctgtgcctga gctgcaggaa gaaccgctgc aacaacctgg gctatgagat caacaaggtg 960
cgggccaaga ggagcagcaa gatgtacctg aagaccagga gccagatgcc ctacaaggtg 1020

-continued

```
ttccactacc aggtgaagat ccacttcagc ggcacagaga gcgagaccca caccaaccag   1080

gcctttgaga tcagcctgta tggaacagtg gccgagagcg agaacatccc cttcaccctg   1140

cctgaggtgt ccaccaacaa gacctacagc ttcctgatct acacagaggt ggacattgga   1200

gagctgctga tgctgaagct gaagtggaag agtgacagct acttctcctg gagcgactgg   1260

tggagcagcc ctggctttgc catccagaag atccgggtga aggccgggga gacccagaag   1320

aaggtgatct tctgcagccg ggagaaggtg agccacctgc agaagggcaa ggccccagct   1380

gtgtttgtga agtgccacga caagagcctg aacaagaaga gcggctag                1428
```

<210> SEQ ID NO 90
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 90

```
atggagagca aggccctgct ggtgctgacc ctggccgtgt ggctgcagtc actgactgct     60

tctagaggag gagtggcggc agccgaccag cgccgggact tcattgacat tgaatcaaag    120

tttgctctcc gcactccaga ggacacagca gaagatacct gccatctgat tccaggggtc    180

gccgagtcag ttgctacatg ccatttcaat catagctcca agacattcat ggtgatccac    240

gggtggacag tgacaggcat gtatgaaagc tgggttccta aattggtcgc cgcgctatat    300

aaacgagagc cagatagcaa cgtgattgta gtggattggt tgtcacgggc tcaggaacat    360

taccccgtat ctgccggcta caccaagctc gtgggacaag atgtggcaag attcatcaac    420

tggatggagg aggaattcaa ttaccccttg gacaatgttc atctgctggg atattcactg    480

ggagcgcatg ctgccgggat cgctggaagc ctgacaaaca agaaagtgaa tagaattacc    540

ggcctggacc ctgcggggcc aaactttgaa tatgcagaag ctcctagcag actgagtccg    600

gacgacgcag attttgtaga cgtccttcat actttcacta ggggctctcc cggcagatcc    660

attggcatcc agaagcccgt tggacatgtg gatatctatc ccaacggagg gacatttcag    720

cccggttgta acatcgggga agccatcagg gtaattgccg aacgcggtct cggcgatgtg    780

gatcagcttg tgaagtgctc tcacgaacgc tccatacatc tatttatcga tagccttcta    840

aatgaggaga acccttcaaa agcataccgt tgcagttcca aggaggcatt tgagaagggt    900

ctgtgtctgt cttgccgaaa gaatcggtgt aataacctcg gatacgagat taataaggtt    960

cgggccaaga ggtcctctaa gatgtattta aagaccagat cacagatgcc atacaaagtc   1020

ttccattatc aggtgaaaat tcacttcagt ggaaccgaat cagagacaca tactaaccag   1080

gcctttgaaa ttagccttta tggtaccgtc gcggagtcag agaacattcc tttcacgtta   1140

cccgaggtgt ccaccaacaa gacatactcc tttctcatct acacagaggt agatatcgga   1200

gagttgctga tgctgaagct gaaatggaaa agcgattcct atttttcttg gtcggattgg   1260

tggagcagcc ccgggtttgc aatccagaag attcgggtga aggctggcga gacccagaag   1320

aaggtcattt tttgctctcg tgaaaaagtc tcgcaccttc aaaaaggcaa ggctcccgca   1380

gtatttgtga agtgccatga caaaagtctt aataaaaaat ccggatag                1428
```

<210> SEQ ID NO 91
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 91
atggagtcta aggccctcct tgtacttaca ctggctgtgt ggcttcagtc cctgacagct 60
tccaggggtg gcgttgctgc agcagatcag cgacgggatt ttattgacat tgagagtaaa 120
tttgccctgc gtactcccga ggatacagcc gaagatacct gtcatttgat ccctggagtc 180
gccgagagcg tggctacctg tcatttcaac cattctagca aaacatttat ggtgatacac 240
gggtggacag tcacaggaat gtatgagagc tgggtgccca aattagtggc tgctctgtac 300
aagagggaac ctgactctaa cgtcattgtc gtagattggc tgtcccgggc tcaagagcat 360
taccccgtgt ctgccggtta taccaagctg gtcggccagg atgttgctcg cttcataaat 420
tggatggagg aagagttcaa ttaccctctg gataacgttc acctgctagg gtactcacta 480
ggggctcacg ctgctggaat cgcgggatcg ttgaccaaca aaaaagtcaa ccgaatcacc 540
ggcctcgacc ctgcaggccc aaattttgag tatgccgaag ccccaagcag actgtccccc 600
gacgatgcgg acttcgtgga tgtgctgcac acgtttacaa gaggaagccc agggagaagc 660
atcggcatcc agaagccagt gggacatgtg gacatttacc caaacggcgg tactttccag 720
ccagggtgta atatagggga ggccatacgg gtgatcgccg aacgcggtct gggggatgtg 780
gaccagttag tgaaatgttc ccatgaacgt agcatccatt tatttatcga ttccctcctg 840
aacgaggaga accccagcaa ggcataccgg tgctccagta aggaggcgtt tgaaaagggg 900
ctttgtctga gctgtcgaaa gaataggtgc aacaatttgg gatacgagat caataaagtc 960
agggcaaagc gttctagcaa gatgtacctt aaaactagaa gccagatgcc ttataaggtg 1020
tttcattatc aagttaagat ccacttctct ggaacagaat cggagacaca caccaatcaa 1080
gcttttgaaa tttctcttta tggtacagtc gctgaaagcg aaaatattcc tttcaccctg 1140
cccgaggtca gtaccaataa aacctattcc tttctgatct atacagaagt cgacattgga 1200
gagctgctga tgctgaagct caagtggaaa tcagacagct acttctcctg gagcgattgg 1260
tggagcagcc ccggattcgc cattcagaag atcagagtca aggccggtga aacccagaaa 1320
aaagtgatct tttgttccag agagaaagtc agtcacttgc agaagggaaa agcccctgcg 1380
gtcttcgtaa aatgtcacga taagagcctg aacaaaaaaa gtgggtag 1428

<210> SEQ ID NO 92
<211> LENGTH: 1428
<212> TYPE: RNA
<213> ORGANISM: Artificial Sequence
<220> FEATURE:
<223> OTHER INFORMATION: Synthetic Polynucleotide

<400> SEQUENCE: 92
auggagucca aggcacugcu agugcugaca cuagccgucu gguugcagag ccuaaccgca 60
agcagaggag gggucgcagc ugcagaccaa cgacgggauu uuauugauau cgaauccaaa 120
uucgcccuua ggacaccaga agauacagcc gaggacacau gucacuugau cccuggggu u 180
gccgaguccg uugccacuug ccacuucaau cacaguagca aaaccuuuau ggucauacac 240
ggcuggacag uuacuggaau guacgaaagu uggguuccaa agcugguugc ggccuuauau 300
aaaagagaac cagauucaaa cgucaucguc guugacuggc ugucaagagc ucaggagcau 360
uaucccguuu ccgcagggua cacuaaguua gugggucagg auguggcucg cuucaucaac 420
uggauggaag aagaguuuaa uuacccauua gauaacgugc accuuuuggg cuauucccug 480
ggugcccacg cugcuggcau ugcuggcucc cucacaaaca agaaagugaa uagaaucacc 540
ggccuggacc cagcagggcc gaacuuugaa uaugccgaag cgcccaguag acucucuccg 600
gacgaugcgg auuucgucga cguccugcau accuuuacac gaggaucccc uggucgaucg 660
auaggcauac agaagccggu uggucacgug gacaucuauc ccaaugggggg gacguuccag 720 cccgggugua acauuggaga agccaucaga guuaucgccg agcggggccu uggggacgug 780
gaucagcucg ugaaaugcag ucacgaacgu uccauacacc uguuuaucga uagucuacug 840
aacgaagaaa aucccagcaa ggccuaccgg ugcagcagua aagaagcuuu ugaaaaaggc 900
uuaugucuga gcugccgaaa aaaucggugc aauaauuugg gguacgaaau aaacaaaguu 960
cgcgcuaaga gaagcuccaa gauguaccug aagacuagau cccagaugcc uuacaaggua 1020
uuccauuacc aagugaagau ccauuuuucc ggaacagaaa gcgaaaccca caccaaccag 1080
gccuuugaga uuagccugua uggcaccgua gcugaauccg agaacauccc cuuuacgcug 1140
cccgaaguaa guacuaauaa aaccuacagc uuucugauuu auacagaagu ggauauuggc 1200
gaacugcuga ugcugaagcu gaaguggaag ucagacagcu acuuuucgug gagcgacugg 1260
uggucuuccc ccggauuugc aauacagaaa aucagggguga aagccggaga gacacagaaa 1320
aaggugaucu ucuguagcag agaaaaggua agucaucugc agaagggguaa ggcuccagcg 1380 guguuuguca agugccauga caaaucccug aauaaaaagu ccggcuag 1428

<210> SEQ ID NO 93
<211> LENGTH: 1428
<212> TYPE: RNA
<213> ORGANISM: Artificial Sequence
<220> FEATURE:
<223> OTHER INFORMATION: Synthetic Polynucleotide

<400> SEQUENCE: 93
auggagucaa aagcucuucu uguguugacu cucgccgucu ggcugcaguc ccugaccgcc 60
ucgagaggag gaguggcagc agccgaccag agacgcgauu uuauugauau agaauccaag 120
uuugcccucc guacccccga agauacugca gaggauaccu gucaucuuau cccaggugu 180 gcagaguccg uugcuaccug ucacuucaau cauaguucca aaaccuucau ggugauccac 240
ggauggacug uaacaggaau guacgaguca ugggucccaa aacugguggc cgcucucuau 300
aaaagagaac cggauucuaa cguuauugug guugacuggc ugucuagggc ucaagaacau 360
uaccccguga gugcagguua uaccaagcug guugggcagg acguugcgag auuuauuaau 420
uggauggaag aagaguucaa uuacccacug gacaaugugc accugcucgg cuacucccuu 480
ggcgcacacg ccgcaggcau ugccgggguca cugaccaaua aaaaaguaaa ccgcaucaca 540
ggucuggacc cagccggucc gaacuuugaa uaugccgagg cucccucacg acuguccccc 600
gaugacgcag auuucgucga uguucugcac acguuuacua gaggaagccc ugggcgcagc 660
auagguauuc aaaaacccgu aggacaugug gauaucuacc caaauggagg cacguuccag 720
ccuggaugua auaucgguga ggcuauccgc gucauagccg aaagaggccu gggggacgua 780
gaccagcuag ugaagugcag ccacgagcgc aguauccauu uauucaucga uucccugcug 840
aaugaagaga auccaucuaa ggcuuauagg ugcucaagca aagaagccuu cgaaaaagga 900
cuuugccuuu cgugcagaaa aaaucguugc aauaaccucg guuaugagau uaauaaaguc 960
agagcuaaga gaucuucuaa gauguaucug aagacccgau cucaaaugcc uuauaaaguu 1020
uuccacuacc aggucaagau acacuucagc ggcaccgaau cagagacuca cacuaaucag 1080
gcuuuugaga ucuccuugua uggcacaguu gccgagucag aaaauauucc cuuuacacuc 1140
ccagaaguca gcacgaacaa aaccuauucc uuuuuaauuu auaccgaggu cgacaucggu 1200
gaacugcuca ugcuaaaacu gaaauggaag ucagauucuu acuucucgug gagcgauugg 1260
uggagcagcc caggauuugc uauacagaaa auuagaguua aagccgguga aacccagaag 1320
aaagugaucu uuuguucaag agaaaagguu ucucaccugc aaaaggguaa agccccugcc 1380
guguucguga aaugccauga uaagucacug aauaaaaagu ccggcuag 1428

<210> SEQ ID NO 94
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 94
atggagtcga aggcgttgct tgtcctgacc cttgcggtct ggctccagtc cctgaccgcg 60
tcgagaggtg gagtggctgc agctgatcag cgaagagatt tcattgacat cgaatcgaag 120
tttgccctga gaactcccga agatacggca gaggatacgt gtcatctgat cccaggcgtt 180
gcagaatcgg tcgcaacttg tcatttcaat cactcgagca agaccttcat ggtaatccac 240
gggtggaccg tgactggaat gtatgaaagc tgggtcccaa agctggtcgc ggccctgtac 300
aagcgagagc cagattcgaa cgttatcgtg gtggattggc tttccagagc acaagaacac 360
tatcctgtct cggcaggtta cactaagctc gtgggacaag acgtggcccg cttcatcaac 420
tggatggaag aagaattcaa ttacccgctg gacaacgtcc accttttggg ttactcactg 480
ggtgcacacg cggcaggcat tgctgggtcg ttgaccaaca agaaagtgaa tcgtattacc 540
ggccttgatc cagcaggtcc aaactttgaa tacgcggaag ccccttcgag actgagtcct 600
gacgatgcag attttgtgga cgtgctgcac acctttacta ggggttcacc aggccggtcc 660
ataggcattc agaagcctgt gggacatgtg gacatctacc caaacggagg cacctttcaa 720
cccggatgca atatcggtga agcaattagg gtcatagcag aaagggggtt gggtgacgtg 780
gatcagcttg tgaaatgttc ccatgagcgc tctatacacc tgttcatcga ctcacttctg 840
aatgaagaaa atccgtcgaa ggcctacaga tgctcctcga aggaagcatt cgaaaagggg 900
ctgtgtctgt cctgccgcaa gaacagatgc aataaccttg gttacgagat caacaaagtg 960
cgcgccaagc ggtcctcaaa aatgtacctt aaaacgcgat cacagatgcc ctacaaggtt 1020
tttcattacc aagtcaaaat tcacttttcg ggcactgagt cggagactca taccaaccaa 1080
gcatttgaaa ttagcctgta cggaactgtg gcggagagcg aaaacattcc ctttaccctc 1140
cccgaagtct ctaccaacaa aacctactcg ttcttgatct acaccgaagt ggacattgga 1200
gagcttttga tgctcaaact caagtggaag tccgattctt acttctcctg gagcgattgg 1260
tggagctctc caggtttcgc aattcaaaag attcgcgtca aggcgggcga gactcagaaa 1320
aaagtcatct tttgttccag agagaaagtg tcgcatttgc aaaagggaaa agcgcctgcg 1380
gtgttcgtga aatgtcatga taagagcctt aacaagaagt cagga 1425

<210> SEQ ID NO 95
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 95
atggagtcta aggcacttct cgtgctgacc ctcgctgtct ggctgcagag tctgaccgcg 60

```
tcacgcggcg gggtggcggc agcagatcaa cgacgagact ttattgacat tgagtcaaaa    120
tttgccctga gaactccaga ggacaccgcc gaagacacgt gtcatctaat ccccggcgtg    180
gccgagtcag ttgccacctg tcacttcaac cactccagca aaacattcat ggtaattcat    240
ggatggaccg tgacaggaat gtacgaaagt tgggttccta agttagtcgc tgccctatat    300
aagcgggagc ccgacagtaa cgttatcgtg gtcgattggc tgagcagggc gcaggagcat    360
tatcctgtga gtgctggata taccaagtta gttgggcaag acgtggcccg cttcataaat    420
tggatggagg aggaatttaa ttaccctctg gacaacgtgc accttttggg ttactccttg    480
ggtgcacacg ctgctggtat agcagggtcc ctcaccaata agaaggttaa tcgaatcacc    540
ggactagacc ctgctggacc aaacttcgaa tatgctgagg caccgtcccg cctgtccccc    600
gatgatgccg atttcgttga cgtgctgcac acctttacca ggggaagtcc gggaagaagc    660
attggcatcc aaaaaccggt cggtcacgtg gacatctatc ccaatggagg caccttccag    720
cccggatgta acatcgggga ggcaattcgc gttatcgccg agagaggcct cggcgacgtc    780
gaccagctgg tcaagtgtag tcatgagcgc tccattcacc tgttcattga ctccctcctc    840
aatgaggaga atccgagtaa agcttacaga tgttcatcga aggaggcatt cgagaagggc    900
ctttgcctgt cctgtcggaa gaataggtgt aataatcttg gttacgagat aaataaggtc    960
cgggccaagc gctcttccaa gatgtacctc aaaactcggt cccagatgcc atataaagtg   1020
tttcactatc aagtgaaaat tcatttctcc ggtactgaat ctgagactca caccaaccag   1080
gccttcgaga tcagcctgta tggcactgtt gcagaaagtg aaaacattcc cttcacactc   1140
cccgaggtgt ctaccaacaa gacctacagt tttctaatct acacggaggt ggatattggc   1200
gaactgttga tgcttaagct gaagtggaaa agcgacagct attttagttg gagcgactgg   1260
tggagttccc cggggtttgc cattcagaaa attagagtca aggcggggga aactcagaag   1320
aaggtgatct tctgcagtag ggaaaaggtg agccatctgc agaaggggaa ggcccctgca   1380
gtattcgtaa agtgccacga caaaagtttg aacaaaaagt caggt                   1425
```

<210> SEQ ID NO 96
<211> LENGTH: 560
<212> TYPE: DNA
<213> ORGANISM: Artificial Sequence
<220> FEATURE:
<223> OTHER INFORMATION: Synthetic Polynucleotide

<400> SEQUENCE: 96

```
aacagtttgt atgctggaag agttctgaaa agatctctga gggctggaag tgctaaggac     60
aatttcataa agaagaaaga agagatttta tcgacatcga aagtaaattt gccctaagga    120
cccctgaaga cacagctgag gacacttgcc acctcattcc cggagtagca gagtccgtgg    180
ctacctgtca tttcaatcac agcagcaaaa ccttcatggt gatccatggc tggacggtaa    240
caggaatgta tgagagttgg gtgccaaaac ttgtggccgc cctgtacaag agagaaccag    300
actccaatgt cattgtggtg gactggctgt cacgggctca ggagcattac ccagtgtccg    360
cgggctacac caaactggtg ggacaggatg tggcccggtt tatcaactgg atggaggagg    420
agtttaacta ccctctggac aatgtccatc tcttgggata cagccttgga gcccatgctg    480
ctggcattgc aggaagtctg accaataaga aagtcaacag aattactggc ctcgatccag    540
ctggacctaa ctttgagtat                                                560
```

<210> SEQ ID NO 97
<211> LENGTH: 345

<212> TYPE: DNA
<213> ORGANISM: Artificial Sequence
<220> FEATURE:
<223> OTHER INFORMATION: Synthetic Polynucleotide

<400> SEQUENCE: 97
atggtgatcc acggctggac cgtgaccggc atgtacgaga gctgggtgcc caagctggtg 60
gccgccctgt acaagcgcga gcccgacagc aacgtgatcg tggtggactg gctgagccgc 120
gcccaggagc actaccccgt gagcgccggc tacaccaagc tggtgggcca ggacgtggcc 180
cgcttcatca actggatgga ggaggagttc aactaccccc tggacaacgt gcacctgctg 240
ggctacagcc tgggcgccca cgccgccggc atcgccggca gcctgaccaa caagaaggtg 300
aaccgcatca ccggcctgga ccccgccggc cccaacttcg agtac 345

<210> SEQ ID NO 98
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 98
atggtgatcc acggctggac cgtgaccggc atgtacgaga gctgggtgcc caagctggtg 60
gccgccctgt acaagagaga gcccgacagc aacgtgatcg tggtggactg gctgagcaga 120
gcccaggagc actaccccgt gagcgccggc tacaccaagc tggtgggcca ggacgtggcc 180
agattcatca actggatgga ggaggagttc aactaccccc tggacaacgt gcacctgctg 240
ggctacagcc tgggcgccca cgccgccggc atcgccggca gcctgaccaa caagaaggtg 300
aacagaatca ccggcctgga ccccgccggc cccaacttcg agtactag 348

<210> SEQ ID NO 99
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 99
atggtcattc atgggtggac tgtgacaggt atgtatgaat cttgggtccc caaattagtc 60
gcggctcttt ataagcggga gcctgatagc aacgtgatag ttgtcgactg gttgagtcga 120
gcccaggagc actatcctgt gagcgcagga tataccaaat tggtcggcca agacgtcgcg 180
agatttatca actggatgga agaggaattt aactatcccc ttgataacgt gcacctcctg 240
gggtactcct tgggcgctca tgctgccggc atcgctggca gcttaaccaa taagaaggtc 300
aaccggatta ctggcctgga tcccgccggc ccaaacttcg agtactag 348

<210> SEQ ID NO 100
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 100
atggtgatcc acggctggac agtgacaggc atgtatgaga gctgggtgcc caagctggtg 60
gccgccctgt acaagcggga gccagacagc aatgtgattg tggtggactg gctgagccgg 120
gcccaggagc actaccctgt gtctgctggc tacaccaagc tggtgggcca ggatgtggcc 180
cgcttcatca actggatgga ggaggagttc aactacccccc tggacaacgt gcacctgctg 240
ggctacagcc tgggcgccca cgccgccggc attgctggca gcctgaccaa caagaaggtg 300
aaccgcatca ccggcctgga ccctgctggc cccaactttg agtactag 348

<210> SEQ ID NO 101
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 101
atggtgatcc acggctggac cgtgaccggc atgtacgaga gctgggtacc taagctggtg 60
gctgccctct ataaacgcga acctgatagc aatgtcatcg tggtggattg gttgtccaga 120
gcacaggaac attacccagt ttccgcagga tacaccaagc tcgtcggaca ggacgtggcc 180
cgctttatca attggatgga agaagagttt aactaccctc tcgataacgt gcaccttctg 240
ggctacagcc tcggcgccca cgctgcagga atagcaggaa gcctgactaa taaaaaggtg 300
aaccgcatca ctggcctcga cccagcaggc cccaattttg agtactag 348

<210> SEQ ID NO 102
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 102
atggttattc acggatggac tgtgactggt atgtacgagt catgggttcc caaactcgtc 60
gcggcactgt acaagcgaga gccagattca aacgtgatcg ttgtggattg gctgagcagg 120
gctcaagagc attaccccgt ttctgctggc tacaccaaac ttgtcggcca agatgtagcg 180
aggtttatca actggatgga ggaggaattt aactaccctt tggacaatgt ccaccttctg 240
ggctactctt taggcgcaca tgcagccgga attgccggaa gcctcaccaa taagaaggtt 300
aacaggatca ccggcttgga ccccgctggg ccaaattttg aatactag 348

<210> SEQ ID NO 103
<211> LENGTH: 348
<212> TYPE: RNA
<213> ORGANISM: Artificial Sequence
<220> FEATURE:
<223> OTHER INFORMATION: Synthetic Polynucleotide

<400> SEQUENCE: 103
augguuaucc auggcuggac ugugacuggc auguacgaaa guuggguucc aaaacuggug 60
gccgcccuuu acaaacgcga gccggauucu aaugugauug ucgucgauug gcuuucucgc 120
gcacaggagc auuaccccgu gucggcagga uauacuaaau ugguugguca ggauguggca 180
agauuuauua acuggaugga ggaggaauuc aacuaccccc uugauaacgu gcaccuguua 240
ggguauaguc ugggugccca cgccgccggu aucgcuggcu cacucacaaa uaagaagguc 300
aaucgaauca ccggccuuga cccugccggg cccaauuuug aguauuag 348

<210> SEQ ID NO 104
<211> LENGTH: 348
<212> TYPE: RNA
<213> ORGANISM: Artificial Sequence
<220> FEATURE:
<223> OTHER INFORMATION: Synthetic Polynucleotide

<400> SEQUENCE: 104
augguuaucc auggcuggac ugugacuggc auguacgaaa guuggguucc aaaacuggug 60
gccgcccuuu acaaacgcga gccggauucu aaugugauug ucgucgauug gcuuucucgc 120
gcacaggagc auuaccccgu gucggcagga uauacuaaau ugguugguca ggauguggca 180
agauuuauua acuggaugga ggaggaauuc aacuacccc uugauaacgu gcaccuguua 240
ggguauaguc ugggugccca cgccgccggu aucgcuggcu cacucacaaa uaagaagguc 300
aacagaauca ccggcuuaga uccagcaggc ccaaacuuug aauacuag 348

<210> SEQ ID NO 105
<211> LENGTH: 559
<212> TYPE: DNA
<213> ORGANISM: Artificial Sequence
<220> FEATURE:
<223> OTHER INFORMATION: Synthetic Polynucleotide

<400> SEQUENCE: 105
aaactttccc tccttggaaa acagtcacat aagcagcctt ggcgtgaaaa cagtgtcaga 60
ctcgattccc cctcttcctc ctcctcaagg gaaagctgcc cacttctagc tgccctgcca 120
tcccctttaa agggcgactt gctcagcgcc aaaccgcggc tccagccctc tccagcctcc 180
ggctcagccg gctcatcagt cggtccgcgc cttgcagctc ctccagaggg acgcgccccg 240
agatggagag caaagccctg ctcgtgctga ctctggccgt gtggctccag agtctgaccg 300
cctcccgcgg aggggtggcc gccgccgacc aaagaagaga ttttatcgac atcgaaagta 360
aatttgccct aaggacccct gaagacacag ctgaggacac ttgccacctc attcccggag 420
tagcagagtc cgtggctacc tgtcatttca atcacagcag caaaaccttc atggtgatcc 480
atggctggac ggtaacagga atgtatgaga gttgggtgcc aaaacttgtg gccgccctgt 540
acaagagaga accagactc 559

<210> SEQ ID NO 106
<211> LENGTH: 318
<212> TYPE: DNA
<213> ORGANISM: Artificial Sequence
<220> FEATURE:
<223> OTHER INFORMATION: Synthetic Polynucleotide

<400> SEQUENCE: 106
atggagagca aggccctgct ggtgctgacc ctggccgtgt ggctgcagag cctgaccgcc 60
agccgcggcg gcgtggccgc cgccgaccag cgccgcgact tcatcgacat cgagagcaag 120
ttcgccctgc gcacccccga ggacaccgcc gaggacacct gccacctgat ccccggcgtg 180
gccgagagcg tggccacctg ccacttcaac cacagcagca agaccttcat ggtgatccac 240
ggctggaccg tgaccggcat gtacgagagc tgggtgccca agctggtggc cgccctgtac 300
aagcgcgagc ccgacagc 318

<210> SEQ ID NO 107
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 107
atggagagca aggccctgct ggtgctgacc ctggccgtgt ggctgcagag cctgaccgcc 60
agcagaggcg gcgtggccgc cgccgaccag agaagagact tcatcgacat cgagagcaag 120
ttcgccctga gaaccccga ggacaccgcc gaggacacct gccacctgat ccccggcgtg 180
gccgagagcg tggccacctg ccacttcaac cacagcagca agaccttcat ggtgatccac 240
ggctggaccg tgaccggcat gtacgagagc tgggtgccca agctggtggc cgccctgtac 300
aagagagagc ccgacagcta g 321

<210> SEQ ID NO 108
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 108
atggaatcta aggcactact ggtgctaact ctcgcagtgt ggctgcagag tctgaccgcc 60
tcacgagggg gagttgccgc cgctgaccag cggagggact tcattgacat cgaatctaaa 120
tttgcattga gaactccgga agatacagct gaggatacat gccacttaat tccgggtgtt 180
gccgagtccg tcgccacttg ccacttcaac cattcctcca aaaccttcat ggtgatccat 240
ggatggacag ttacggggat gtacgagtct tgggtgccta aactggtcgc tgccttgtac 300
aagagagagc ccgacagcta g 321

<210> SEQ ID NO 109
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 109
atggagagca aggccctgct ggtgctgacc ctggccgtgt ggctgcagag cctgacagcc 60
agcagaggag gagtggccgc tgctgaccag aggcgggact tcattgatat tgagagcaag 120
tttgccctgc ggaccccaga ggacacagct gaggacacct gccacctgat ccctggggtg 180
gccgagagcg tggccacctg ccacttcaac cacagcagca agaccttcat ggtgatccac 240
ggctggacag tgacaggcat gtatgagagc tgggtgccca agctggtggc cgccctgtac 300
aagcgggagc cagacagcta g 321

<210> SEQ ID NO 110
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 110
atggagagca aggccctgct ggtgctgacc ctggccgtgt ggctgcagtc tctgaccgca 60
agtcgcggtg gtgttgccgc tgcagaccag cgaagggact ttatagatat cgaatctaaa 120
ttcgctcttc gaacccccga agataccgca gaggacactt gtcacctcat tcccggcgtt 180
gccgaatctg tggctacttg tcatttcaat cattcctcaa aaactttcat ggtgattcat 240
ggttggaccg ttacagggat gtatgaaagt tgggtcccaa agcttgttgc tgccctgtat 300
aagagagagc ccgactccta g 321

<210> SEQ ID NO 111
<211> LENGTH: 321

<212> TYPE: DNA
<213> ORGANISM: Artificial Sequence
<220> FEATURE:
<223> OTHER INFORMATION: Synthetic Polynucleotide

<400> SEQUENCE: 111
atggagagca aggcactcct cgtcttgact ctggccgtgt ggctgcagtc cctcaccgcc 60
agtcggggtg gggttgcagc cgctgaccag cgtcgcgact ttattgacat cgaatcaaag 120
ttcgcccttc gcaccccga agacacagct gaggacacct gccatctgat acccggagta 180
gctgagagtg tcgccacttg tcacttcaat cactccagca agactttcat ggtgatccac 240
ggatggacgg taaccggaat gtatgagagc tgggtgccca agttagtagc cgcactgtac 300
aagagagagc cggattccta g 321

<210> SEQ ID NO 112
<211> LENGTH: 321
<212> TYPE: RNA
<213> ORGANISM: Artificial Sequence
<220> FEATURE:
<223> OTHER INFORMATION: Synthetic Polynucleotide

<400> SEQUENCE: 112
auggaaucga aagcuuuacu gguccugacg cuggccgucu ggcuucaaag uuuaaccgcc 60
uccaggggag gcguugccgc cgcagaucag aggcgugauu uuauugacau cgagucuaaa 120
uuugcauuac gcacaccaga ggauacugcc gaagauaccu gucacuuaau ccccggcgua 180
gccgagagcg uggccacuug ccauuucaac cauaguucaa aaaccuuuau ggucauucac 240
ggcuggaccg ucaccgguau guacgaaucu ugggugccua aacuggucgc ugcacuguac 300
aagcgggaac cagauucuua g 321

<210> SEQ ID NO 113
<211> LENGTH: 321
<212> TYPE: RNA
<213> ORGANISM: Artificial Sequence
<220> FEATURE:
<223> OTHER INFORMATION: Synthetic Polynucleotide

<400> SEQUENCE: 113
auggaaucga aagcuuuacu gguccugacg cuggccgucu ggcuucaaag uuuaaccgcc 60
uccaggggag gcguugccgc cgcagaucag aggcgugauu uuauugacau cgagucuaaa 120
uuugcauuac gcacaccaga ggauacugcc gaagauaccu gucacuuaau ccccggcgua 180
gccgagagcg uggccacuug ccauuucaac cauaguucaa aaaccuuuau ggucauucac 240
ggcuggaccg ucaccgguau guacgaaucu ugggugccua aacuggucgc ugcacuguac 300
aaacgcgaac cagauucuua g 321

<210> SEQ ID NO 114
<211> LENGTH: 629
<212> TYPE: DNA
<213> ORGANISM: Artificial Sequence
<220> FEATURE:
<223> OTHER INFORMATION: Synthetic Polynucleotide

<400> SEQUENCE: 114
gacaaacagg attcgtcaaa agagaggtgt attaaagtgc cgatcaaatg taatttaaca 60
gctaaacttt ccctccttgg aaaacaggga aagctgccca cttctagctg ccctgccatc 120
ccctttaaag ggcgacttgc tcagcgccaa accgcggctc cagccctctc cagcctccgg 180

-continued

```
ctcagccggc tcatcagtcg gtccgcgcct tgcagctcct ccagagggac gcgccccgag    240

atggagagca aagccctgct cgtgctgact ctggccgtgt ggctccagag tctgaccgcc    300

tcccgcggag gggtggccgc cgccgaccaa agaagagatt ttatcgacat cgaaagtaaa    360

tttgccctaa ggacccctga agacacagct gaggacactt gccacctcat tcccggagta    420

gcagagtccg tggctacctg tcatttcaat cacagcagca aaaccttcat ggtgatccat    480

ggctggacgg taacaggaat gtatgagagt tgggtgccaa aacttgtggc cgccctgtac    540

aagagagaac cagactccaa tgtcattgtg gtggactggc tgtcacgggc tcaggagcat    600

tacccagtgt ccgcgggcta caccaaact                                     629
```

<210> SEQ ID NO 115
<211> LENGTH: 390
<212> TYPE: DNA
<213> ORGANISM: Artificial Sequence
<220> FEATURE:
<223> OTHER INFORMATION: Synthetic Polynucleotide

<400> SEQUENCE: 115

```
atggagagca aggccctgct ggtgctgacc ctggccgtgt ggctgcagag cctgaccgcc     60

agccgcggcg gcgtggccgc cgccgaccag cgccgcgact tcatcgacat cgagagcaag    120

ttcgccctgc gcacccccga ggacaccgcc gaggacacct gccacctgat ccccggcgtg    180

gccgagagcg tggccacctg ccacttcaac cacagcagca agaccttcat ggtgatccac    240

ggctggaccg tgaccggcat gtacgagagc tgggtgccca agctggtggc cgccctgtac    300

aagcgcgagc ccgacagcaa cgtgatcgtg gtggactggc tgagccgcgc ccaggagcac    360

taccccgtga gcgccggcta caccaagctg                                     390
```

<210> SEQ ID NO 116
<211> LENGTH: 393
<212> TYPE: DNA
<213> ORGANISM: Artificial Sequence
<220> FEATURE:
<223> OTHER INFORMATION: Synthetic Polynucleotide

<400> SEQUENCE: 116

```
atggagagca aggccctgct ggtgctgacc ctggccgtgt ggctgcagag cctgaccgcc     60

agcagaggcg gcgtggccgc cgccgaccag agaagagact tcatcgacat cgagagcaag    120

ttcgccctga gaacccccga ggacaccgcc gaggacacct gccacctgat ccccggcgtg    180

gccgagagcg tggccacctg ccacttcaac cacagcagca agaccttcat ggtgatccac    240

ggctggaccg tgaccggcat gtacgagagc tgggtgccca agctggtggc cgccctgtac    300

aagagagagc ccgacagcaa cgtgatcgtg gtggactggc tgagcagagc ccaggagcac    360

taccccgtga gcgccggcta caccaagctg tag                                 393
```

<210> SEQ ID NO 117
<211> LENGTH: 393
<212> TYPE: DNA
<213> ORGANISM: Artificial Sequence
<220> FEATURE:
<223> OTHER INFORMATION: Synthetic Polynucleotide

<400> SEQUENCE: 117

```
atggagagca aagccttgtt agtgctcaca ctggcggttt ggctccagag cctgacggcc     60

tcaagagggg gcgttgcagc cgccgatcag aggcgcgatt tcatcgacat tgaatctaaa    120

tttgcactcc gaacgcccga ggatacggcc gaggacacat gtcacttgat tcccggcgtc    180
```

gctgagagcg tggctacttg tcactttaat catagcagta aaactttcat ggtgattcat 240
gggtggaccg tgaccggcat gtatgagtca tgggtaccta aactggtggc ggcactgtac 300
aaacgggagc cagattctaa cgtcatcgtc gtcgattggt tgtcccgtgc acaggaacac 360
tacccagtga gtgcaggata caccaagctg tag 393

<210> SEQ ID NO 118
<211> LENGTH: 393
<212> TYPE: DNA
<213> ORGANISM: Artificial Sequence
<220> FEATURE:
<223> OTHER INFORMATION: Synthetic Polynucleotide

<400> SEQUENCE: 118
atggagagca aggccctgct ggtgctgacc ctggccgtgt ggctgcagag cctgacagcc 60
agcagaggag gagtggccgc tgctgaccag aggcgggact tcattgatat tgagagcaag 120
tttgccctgc ggaccccaga ggacacagct gaggacacct gccacctgat ccctggggtg 180
gccgagagcg tggccacctg ccacttcaac cacagcagca agaccttcat ggtgatccac 240
ggctggacag tgacaggcat gtatgagagc tgggtgccca agctggtggc cgccctgtac 300
aagcgggagc cagacagcaa tgtgattgtg gtggactggc tgagccgggc ccaggagcac 360
taccctgtgt ctgctggcta caccaagctg tag 393

<210> SEQ ID NO 119
<211> LENGTH: 393
<212> TYPE: DNA
<213> ORGANISM: Artificial Sequence
<220> FEATURE:
<223> OTHER INFORMATION: Synthetic Polynucleotide

<400> SEQUENCE: 119
atggagagca aggccctgct ggtgctgacc ctggccgtgt ggctgcaatc tcttaccgcc 60
tctaggggag gcgtggccgc agccgaccaa aggcgcgatt ttatcgacat agagtcgaag 120
ttcgctctga ggacccccga ggacacagct gaggatacat gtcacctcat tccgggagtg 180
gcggaatccg tcgccacttg ccactttaac cattcatcca aaactttcat ggtaattcat 240
ggatggaccg tcactggaat gtatgaaagc tgggtgccta agctggtcgc cgccctttac 300
aagagagaac cagacagcaa cgtgattgtt gttgattggt tgtccagagc ccaagaacac 360
tacccagtgt ccgccgggta taccaagctt tag 393

<210> SEQ ID NO 120
<211> LENGTH: 393
<212> TYPE: DNA
<213> ORGANISM: Artificial Sequence
<220> FEATURE:
<223> OTHER INFORMATION: Synthetic Polynucleotide

<400> SEQUENCE: 120
atggaaagca aagccctgct tgtgctgact ctggccgtgt ggttgcagag tctgaccgcc 60
tccaggggcg gtgttgcagc ggcagaccaa aggagagact ttattgatat cgaatcaaaa 120
tttgctctga gaactccaga ggataccgcc gaggacacct gccaccttat tccgggtgtc 180
gccgaatccg tggccacttg ccacttcaac catagttcaa agactttcat ggtgatacac 240
ggctggactg tcacaggcat gtacgagagt tgggtgccaa agctggtcgc tgcactgtat 300
aagagggagc ccgactccaa cgtcattgtg gtggactggc tgtctcgggc acaggagcat 360
tatcccgttt ctgctgggta caccaaactc tag 393

<210> SEQ ID NO 121
<211> LENGTH: 393
<212> TYPE: RNA
<213> ORGANISM: Artificial Sequence
<220> FEATURE:
<223> OTHER INFORMATION: Synthetic Polynucleotide

<400> SEQUENCE: 121
auggaaagua aagcacuacu gguccucacc uuagcuguau ggcugcaguc uuugacagcg 60
agccgcgggg ggguggcagc ugcagaccaa cgccgggauu ucauugacau agaaagcaaa 120
uuugccuuac gcaccccaga agacacagcu gaagauacuu gccaucucau ccccggcgua 180
gcugaaagcg uggcuaccug ucacuuuaac cacaguucca agaccuucau ggugauccac 240
ggcuggacug ucacaggaau guacgaguca ugggugccga agcugguggc ggccuuguau 300
aaacgcgagc cugacaguaa ugucauagug guggacuggc ugagccgagc ccaagagcac 360
uaccccguga gugcuggaua uacaaaacug uag 393

<210> SEQ ID NO 122
<211> LENGTH: 393
<212> TYPE: RNA
<213> ORGANISM: Artificial Sequence
<220> FEATURE:
<223> OTHER INFORMATION: Synthetic Polynucleotide

<400> SEQUENCE: 122
auggaaagca aagcccuguu agugcucacc cuggccguau ggcugcaguc ucugacagcu 60
agccguggug gcguugccgc ugcugaccag cguagggacu uuaucgauau ugaguccaaa 120
uuugcccucc gcacaccuga agauaccgcc gaggacaccu gucaucucau acccggcguc 180
gcugaaagcg uugcuaccug ccacuuuaac cauucgucca agaccuuuau ggugauccac 240 gggugga cag uuaccgguau guacgagucg ugggucccca aacuagucgc ugcccuuuac 300
aagagagagc cugauucuaa cgugaucguc guugacuggu ugagcagagc ccaggagcac 360
uaccccguau cggcugggua cacaaagcug uag 393

<210> SEQ ID NO 123
<211> LENGTH: 3335
<212> TYPE: DNA
<213> ORGANISM: Artificial Sequence
<220> FEATURE:
<223> OTHER INFORMATION: Synthetic Polynucleotide

<400> SEQUENCE: 123
atggagagca aagccctgct cgtgctgact ctggccgccg ccgaccaaag aagagatttt 60
atcgacatcg aaagtaaatt tgccctaagg acccctgaag acacagctga ggacacttgc 120
cacctcattc ccggagtagc agagtccgtg gctacctgtc atttcaatca cagcagcaaa 180
accttcatgg tgatccatgg ctggacggta acaggaatgt atgagagttg ggtgccaaaa 240
cttgtggccg ccctgtacaa gagagaacca gactccaatg tcattgtggt ggactggctg 300
tcacgggctc aggagcatta cccagtgtcc gcgggctaca ccaaactggt gggacaggat 360
gtggcccggt ttatcaactg gatggaggag gagtttaact accctctgga caatgtccat 420
ctcttgggat acagccttgg agcccatgct gctggcattg caggaagtct gaccaataag 480
aaagtcaaca gaattactgg cctcgatcca gctggaccta actttgagta tgcagaagcc 540
ccgagtcgtc tttctcctga tgatgcagat tttgtagacg tcttacacac attcaccaga 600

```
gggtcccctg gtcgaagcat tggaatccag aaaccagttg ggcatgttga catttacccg    660
aatggaggta cttttcagcc aggatgtaac attggagaag ctatccgcgt gattgcagag    720
agaggacttg gagatgtgga ccagctagtg aagtgctccc acgagcgctc cattcatctc    780
ttcatcgact ctctgttgaa tgaagaaaat ccaagtaagg cctacaggtg cagttccaag    840
gaagcctttg agaaagggct ctgcttgagt tgtagaaaga accgctgcaa caatctgggc    900
tatgagatca ataaagtcag agccaaaaga agcagcaaaa tgtacctgaa gactcgttct    960
cagatgccct acaaagtctt ccattaccaa gtaaagattc atttttctgg gactgagagt   1020
gaaacccata ccaatcaggc ctttgagatt tctctgtatg gcaccgtggc cgagagtgag   1080
aacatcccat tcactctgcc tgaagtttcc acaaataaga cctactcctt cctaatttac   1140
acagaggtag atattggaga actactcatg ttgaagctca aatggaagag tgattcatac   1200
tttagctggt cagactggtg gagcagtccc ggcttcgcca ttcagaagat cagagtaaaa   1260
gcaggagaga ctcagaaaaa ggtgatcttc tgttctaggg agaaagtgtc tcatttgcag   1320
aaaggaaagg cacctgcggt atttgtgaaa tgccatgaca agtctctgaa taagaagtca   1380
ggctgaaact gggcgaatct acagaacaaa gaacggcatg tgaattctgt gaagaatgaa   1440
gtggaggaag taacttttac aaaacatacc cagtgtttgg ggtgtttcaa aagtggattt   1500
tcctgaatat taatcccagc cctacccttg ttagttattt taggagacag tctcaagcac   1560
taaaaagtgg ctaattcaat ttatggggta tagtggccaa atagcacatc ctccaacgtt   1620
aaaagacagt ggatcatgaa aagtgctgtt ttgtcctttg agaaagaaat aattgtttga   1680
gcgcagagta aaataaggct ccttcatgtg gcgtattggg ccatagccta taattggtta   1740
gaacctccta ttttaattgg aattctggat ctttcggact gaggccttct caaactttac   1800
tctaagtctc caagaataca gaaaatgctt ttccgcggca cgaatcagac tcatctacac   1860
agcagtatga atgatgtttt agaatgattc cctcttgcta ttggaatgtg gtccagacgt   1920
caaccaggaa catgtaactt ggagagggac gaagaaaggg tctgataaac acagaggttt   1980
taaacagtcc ctaccattgg cctgcatcat gacaaagtta caaattcaag gagatataaa   2040
atctagatca attaattctt aataggcttt atcgtttatt gcttaatccc tctctccccc   2100
ttcttttttg tctcaagatt atattataat aatgttctct gggtaggtgt tgaaaatgag   2160
cctgtaatcc tcagctgaca cataatttga atggtgcaga aaaaaaaaaa gaaaccgtaa   2220
ttttattatt agattctcca aatgatttc atcaatttaa aatcattcaa tatctgacag    2280
ttactcttca gttttaggct taccttggtc atgcttcagt tgtacttcca gtgcgtctct   2340
tttgttcctg gctttgacat gaaaagatag gtttgagttc aaattttgca ttgtgtgagc   2400
ttctacagat tttagacaag gaccgttttt actaagtaaa agggtggaga ggttcctggg   2460
gtggattcct aagcagtgct tgtaaaccat cgcgtgcaat gagccagatg gagtaccatg   2520
agggttgcta tttgttgttt ttaacaacta atcaagagtg agtgaacaac tatttataaa   2580
ctagatctcc tatttttcag aatgctcttc tacgtataaa tatgaaatga taaagatgtc   2640
aaatatctca gaggctatag ctgggaaccc gactgtgaaa gtatgtgata tctgaacaca   2700
tactagaaag ctctgcatgt gtgttgtcct tcagcataat tcggaaggga aaacagtcga   2760
tcaagggatg tattggaaca tgtcggagta gaaattgttc ctgatgtgcc agaacttcga   2820
ccctttctct gagagagatg atcgtgccta taaatagtag gaccaatgtt gtgattaaca   2880
tcatcaggct tggaatgaat tctctctaaa aataaaatga tgtatgattt gttgttggca   2940
```

tccccttat taattcatta aatttctgga tttgggttgt gacccagggt gcattaactt 3000
aaaagattca ctaaagcagc acatagcact gggaactctg gctccgaaaa actttgttat 3060
atatatcaag gatgttctgg ctttacattt tatttattag ctgtaaatac atgtgtggat 3120
gtgtaaatgg agcttgtaca tattggaaag gtcattgtgg ctatctgcat ttataaatgt 3180
gtggtgctaa ctgtatgtgt ctttatcagt gatggtctca cagagccaac tcactcttat 3240
gaaatgggct ttaacaaaac aagaaagaaa cgtacttaac tgtgtgaaga aatggaatca 3300
gcttttaata aaattgacaa cattttatta ccaca 3335

<210> SEQ ID NO 124
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 124
atggagagca aggccctgct ggtgctgacc ctggccgccg ccgaccagag aagagacttc 60
atcgacatcg agagcaagtt cgccctgaga acccccgagg acaccgccga ggacacctgc 120
cacctgatcc ccggcgtggc cgagagcgtg gccacctgcc acttcaacca cagcagcaag 180
accttcatgg tgatccacgg ctggaccgtg accggcatgt acgagagctg ggtgcccaag 240
ctggtggccg ccctgtacaa gagagagccc gacagcaacg tgatcgtggt ggactggctg 300
agcagagccc aggagcacta ccccgtgagc gccggctaca ccaagctggt gggccaggac 360
gtggccagat tcatcaactg gatggaggag gagttcaact acccccctgga caacgtgcac 420 ctgctgggct acagcctggg cgcccacgcc gccggcatcg ccggcagcct gaccaacaag 480
aaggtgaaca gaatcaccgg cctggacccc gccggcccca acttcgagta cgccgaggcc 540
cccagcagac tgagccccga cgacgccgac ttcgtggacg tgctgcacac cttcaccaga 600
ggcagccccg gcagaagcat cggcatccag aagcccgtgg gccacgtgga catctacccc 660
aacggcggca ccttccagcc cggctgcaac atcggcgagg ccatcagagt gatcgccgag 720
agaggcctgg gcgacgtgga ccagctggtg aagtgcagcc acgagagaag catccacctg 780
ttcatcgaca gcctgctgaa cgaggagaac cccagcaagg cctacagatg cagcagcaag 840
gaggccttcg agaagggcct gtgcctgagc tgcagaaaga acagatgcaa caacctgggc 900
tacgagatca acaaggtgag agccaagaga agcagcaaga tgtacctgaa gaccagaagc 960
cagatgccct acaaggtgtt ccactaccag gtgaagatcc acttcagcgg caccgagagc 1020
gagacccaca ccaaccaggc cttcgagatc agcctgtacg gcaccgtggc cgagagcgag 1080
aacatcccct tcaccctgcc cgaggtgagc accaacaaga cctacagctt cctgatctac 1140
accgaggtgg acatcggcga gctgctgatg ctgaagctga agtggaagag cgacagctac 1200
ttcagctgga gcgactggtg gagcagcccc ggcttcgcca tccagaagat cagagtgaag 1260
gccggcgaga cccagaagaa ggtgatcttc tgcagcagag agaaggtgag ccacctgcag 1320
aagggcaagg cccccgccgt gttcgtgaag tgccacgaca agagcctgaa caagaagagc 1380
ggctag 1386

<210> SEQ ID NO 125
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 125
atggagtcaa aagctctgct tgtgctgact ctggctgcag cagatcagcg cagagacttt 60
attgatattg agtccaagtt cgctcttcgt actcccgaag acactgccga agacacctgc 120
cacctgatcc cgggcgtcgc cgagtctgtg gccacctgcc atttcaatca ctcatcaaaa 180
accttcatgg taatccacgg ctggacggtc accgggatgt atgagtcctg ggtgcccaaa 240
ctggtggccg cattgtataa gagagagcca gatagcaatg tcatagtggt ggactggctt 300
tcgcgtgctc aggagcacta tccggtttcc gctgggtaca caaaactcgt cggccaggat 360
gtcgcacggt ttatcaattg gatggaagaa gaatttaatt acccactgga caatgtccat 420
ctcctagggt attcgctcgg agcccacgct gcaggtatcg ctggctcact gacgaacaaa 480
aaggtgaacc gcatcaccgg gctcgacccg gcgggtccaa actttgaata tgccgaggct 540
cccagtaggc ttagtccaga cgacgccgat ttcgtggacg tcctgcatac cttcacaagg 600
ggcagtccgg ggaggtcgat tggcattcag aagcccgtgg gccacgtgga catatatcca 660
aatggtggga cctttcagcc cggatgcaat atcggagagg cgattagggt catcgccgaa 720
cggggtcttg gcgacgttga tcagctagtt aaatgcagtc acgagcgcag tattcattta 780
tttatagatt ctctcctcaa cgaagagaat ccctcgaagg cctatcggtg tagctctaag 840
gaagcttttg agaagggact gtgccttagt tgcaggaaga accgatgcaa taatctgggc 900
tatgaaatca ataaggtgcg agcaaagaga agctcaaaaa tgtacctgaa gacccgcagc 960
cagatgccat acaaagtttt ccactaccaa gtgaagattc atttctctgg cacggagagc 1020
gagacacaca ctaaccaggc cttcgagata tcgttatatg gcacagtcgc agaatctgag 1080
aatatcccat ttacgcttcc cgaagtatct acaaacaaga catactcatt cctgatatac 1140
accgaagtgg acattggaga gctactgatg ttgaaattga agtggaagag tgactcctat 1200
ttctcttgga gcgattggtg gtcgtctccc ggcttcgcta tccagaaaat acgcgtaaag 1260
gcaggtgaaa cccagaaaaa ggtcattttc tgctcaagag aaaaggtcag ccacctacag 1320
aagggcaagg cccctgcagt tttcgtgaag tgtcatgata agtctcttaa caagaagtcg 1380
gggtag 1386

<210> SEQ ID NO 126
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 126
atggagagca aggccctgct ggtgctgacc ctggccgctg ctgaccagag gcgggacttc 60
attgatattg agagcaagtt tgccctgcgg accccagagg acacagctga ggacacctgc 120
cacctgatcc ctggggtggc cgagagcgtg gccacctgcc acttcaacca cagcagcaag 180
accttcatgg tgatccacgg ctggacagtg acaggcatgt atgagagctg ggtgcccaag 240
ctggtggccg ccctgtacaa gcgggagcca gacagcaatg tgattgtggt ggactggctg 300
agccgggccc aggagcacta ccctgtgtct gctggctaca ccaagctggt gggccaggat 360
gtggcccgct tcatcaactg gatggaggag gagttcaact accccctgga caacgtgcac 420
ctgctgggct acagcctggg cgcccacgcc gccggcattg ctggcagcct gaccaacaag 480
aaggtgaacc gcatcaccgg cctggaccct gctggcccca actttgaata tgcagaggcc 540
cccagccggc tgagcccaga tgatgctgac tttgtggatg tgctgcacac cttcacccgg 600
ggcagccctg gccgcagcat cggcatccag aagcctgtgg gccacgtgga catctaccca 660
aatggaggca ccttccagcc cggctgcaac attggagagg ccatccgggt gattgctgag 720
cggggcctgg gagatgtgga ccagctggtg aagtgcagcc atgagaggag catccacctg 780
ttcatcgaca gcctgctgaa tgaggagaac cccagcaagg cctaccgctg cagcagcaag 840
gaggcctttg agaagggcct gtgcctgagc tgcaggaaga accgctgcaa caacctgggc 900
tatgagatca acaaggtgcg ggccaagagg agcagcaaga tgtacctgaa gaccaggagc 960
cagatgccct acaaggtgtt ccactaccag gtgaagatcc acttcagcgg cacagagagc 1020
gagacccaca ccaaccaggc ctttgagatc agcctgtatg gaacagtggc cgagagcgag 1080
aacatcccct tcaccctgcc tgaggtgtcc accaacaaga cctacagctt cctgatctac 1140
acagaggtgg acattggaga gctgctgatg ctgaagctga agtggaagag tgacagctac 1200
ttctcctgga gcgactggtg gagcagccct ggctttgcca tccagaagat ccgggtgaag 1260
gccggggaga cccagaagaa ggtgatcttc tgcagccggg agaaggtgag ccacctgcag 1320
aagggcaagg ccccagctgt gtttgtgaag tgccacgaca agagcctgaa caagaagagc 1380
ggctag 1386

<210> SEQ ID NO 127
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 127
atggagagca aggccctgct ggtgctgacc ctggccgccg ccgaccagag aagagacttt 60
atagacattg aatcaaaatt cgcactccgt accccagagg ataccgcaga ggatacttgt 120
cacctgattc ctggagttgc tgaaagtgtc gcaacctgtc actttaacca ctcttccaag 180
actttcatgg tgatccatgg ctggacagtg acaggcatgt acgagtcctg ggtgcccaaa 240
ctagtggccg ccctgtataa acgcgagcct gattcgaatg tgatagtggt tgattggctc 300
agcagagctc aggagcatta cccagtgtcc gcagggtata ccaagctggt gggccaggat 360
gtggccagat ttattaattg gatggaggaa gaattcaatt atcctctgga caatgtccac 420
ttacttggtt acagcttagg cgcacacgca gctggcatcg caggctcctt gacaaataag 480
aaagtaaatc gtattaccgg actggatccg gctggcccaa acttcgaata cgcagaggcg 540
ccatcaagat tgagccctga tgatgctgac tttgttgacg ttttgcacac ctttacgaga 600
ggttctccag gaagatctat cgggatccag aaacctgttg gacacgtgga catttaccct 660
aatggcggta cctttcagcc cgggtgtaat atcggcgaag caatccgggt aatagcagag 720
cgggggctgg gcgatgtaga ccagttagtg aaatgctctc acgagcggtc tattcacctg 780
tttatcgact ccctcctgaa tgaggaaaat cccagcaagg cgtaccggtg ttcctcgaag 840
gaggcctttg agaaaggcct gtgcctgtcc tgccgaaaaa accggtgcaa taatttagga 900
tatgagatta ataaagtgcg tgccaaacgc agcagcaaaa tgtacctgaa gacccgcagt 960
cagatgccat ataaagtatt ccactatcaa gtgaaaatcc actttagcgg gaccgaaagc 1020
gagacccaca ccaaccaggc ttttgaaatc tcactgtatg gaaccgtagc tgaaagtgaa 1080
aacatcccct ttactctgcc agaggtctct actaataaga cctactcgtt cctcatatat 1140
accgaggtgg atataggcga gcttctgatg ttgaaactta agtggaagtc cgacagttat 1200
ttctcttgga gcgactggtg gtctagtcca ggcttcgcca ttcagaaaat ccgggtcaag 1260
gctggcgaga cgcaaaaaaa ggtgatcttt tgctcgaggg agaaggtgtc ccacctacaa 1320
aagggcaaag cgcccgctgt ctttgtgaag tgtcacgaca agagcctaaa caagaaatct 1380
ggctag 1386

<210> SEQ ID NO 128
<211> LENGTH: 1386
<212> TYPE: DNA
<213> ORGANISM: Artificial Sequence
<220> FEATURE:
<223> OTHER INFORMATION: Synthetic Polynucleotide

<400> SEQUENCE: 128
atggaatcca aagcactgct ggtgctgacg ctggccgctg cagatcagcg ccgtgacttt 60
atcgatatag agtccaaatt tgctctgcgc acccctgagg atactgcgga ggacacctgc 120
catctgatac caggagtggc cgagagcgtg gctacctgcc actttaacca tagctctaag 180
acttttatgg tcatccacgg atggacagtg accggcatgt atgaaagttg ggttccaaaa 240
ttggttgccg ctttgtacaa acgggaaccc gattctaacg tgatcgttgt tgactggctc 300
tcaagggctc aggaacacta ccccgtgtcc gcagggtata cgaagttggt gggacaagat 360
gttgctagat ttataaactg gatggaggag gagtttaatt acccccctgga taacgtccat 420 ttattggggt attctttagg ggcacacgct gcgggtatcg ctgggtcctt aaccaataag 480
aaggtgaacc ggatcaccgg attggatcca gccggaccga acttcgagta cgcggaagct 540
ccatccaggc tgtcacctga cgatgctgac tttgtggacg ttctccatac cttcacacgc 600
ggaagcccgg gtcggtcaat cggaattcag aagcctgtcg gccacgtgga tatctatcca 660
aacgggggaa cctttcagcc cggatgtaac atcggggagg ccatcagagt tatcgccgaa 720
cgcggactgg gggatgtgga tcagctggtg aagtgtagcc atgagcggag tatacatctg 780
tttattgact ctctgctaaa tgaagagaat ccatccaaag catatcggtg tagcagtaag 840
gaagcctttg agaagggcct gtgtttgagc tgtcgcaaaa accgttgcaa caacctcgga 900
tatgagatta acaaagtccg cgctaaaagg tctagtaaga tgtatctcaa aacgagaagt 960
cagatgcctt acaaggtgtt ccattaccaa gtgaaaatac acttcagcgg aactgagtct 1020
gagacccaca caaaccaggc gttcgaaatc agcctctacg gcacggtcgc tgaatctgag 1080
aacatcccct tcactctgcc tgaagtctca acaaacaaga catactcctt cctcatttac 1140
acggaggtgg acattggaga actgctgatg ctgaagctga aatggaaatc agacagctat 1200
ttcagctggt ctgattggtg gtcttcacca ggctttgcca ttcagaaaat tagggttaag 1260
gccggtgaga cacagaagaa agtcattttt tgctcgcgcg agaaagtttc tcacctccaa 1320
aaaggcaagg ctcctgctgt gtttgtcaaa tgccacgaca agagcttaaa taagaaatct 1380
ggctag 1386

<210> SEQ ID NO 129
<211> LENGTH: 1386
<212> TYPE: RNA
<213> ORGANISM: Artificial Sequence
<220> FEATURE:
<223> OTHER INFORMATION: Synthetic Polynucleotide

<400> SEQUENCE: 129
auggaaagua aggcacuacu cguuuugaca cuagccgccg cugaucagcg cagagacuuu 60
aucgauaucg aaucuaaauu cgcuuugcgc accccccgaag acacugcuga agauacaugc 120
caccuuaucc cuggggugge ugaauccguc gccacuugcc auuucaacca uucaagcaag 180
acuuucaugg ugauccacgg auggacgguc acaggcaugu acgaauccug ggugcccaag 240
cucgucgcug cccuguacaa gagagaacca gacuccaaug ucauuguugu cgacuggcug 300
agcagggcuc aggaacauua ucccgugucu gcuggauaca caaagcuggu cgggcaagac 360
guagccagau uuaucaacug gauggaggag gaauuuaacu acccgcugga caacguacau 420
cugcuugguu auuccuuagg ggcccacgcc gccgggauug cagggucucu gacgaacaaa 480
aaggucaauc ggauuaccgg gcucgaucca gccgguccaa auuucgaaua cgcugaagcg 540
ccuucaagac uguccccaga ugaugcagau uucguggaug uccuacacac guuuacuaga 600
ggaucaccag gacgcaguau cggaauccaa aaacccgucg gacacgugga uaucuauccc 660
aauggaggaa cuuuccaacc gggauguaau auuggugagg ccaucagggu gauugccgaa 720
cgugguuugg gagacguuga ucaacuggug aaguguagcc acgaaaggag uauucaucug 780
uuuauugacu cacuucugaa ugaggagaac cccucaaaag cuuacaggug uucaucaaag 840
gaggcauuug agaaaggccu uugucugucg ugcaggaaga aucgauguaa uaaucucgga 900
uacgaaauua acaagguuag ggcgaagcgg aguaguaaga uguauuuaaa gacccguagu 960
cagaugcccu acaaggucuu ccacuaucaa gugaaaaucc acuuuucggg caccgaaucc 1020
gaaacacaca ccaaccaggc cuucgagauu ucuuuauaug ggaccguggc cgaaagugag 1080
aauauaccuu ucacauuacc cgaggugucu acaaacaaga cguauuccuu cuuaauuuac 1140
acagaaguug acauaggcga gcugcuaaug cugaagcuaa aguggaagag cgauucguau 1200
uucaguuggu cagacuggug guccagccca ggauuugcaa uccagaaaau ucgcgucaaa 1260
gccggugaga cacaaaaaaa aguuauauuc uguucuaggg aaaaagugag ccaucuucag 1320
aaagguaagg ccccagccgu cuuuguuaag ugccacgaca agucccuaaa uaaaaaguca 1380
ggcuag 1386

<210> SEQ ID NO 130
<211> LENGTH: 1386
<212> TYPE: RNA
<213> ORGANISM: Artificial Sequence
<220> FEATURE:
<223> OTHER INFORMATION: Synthetic Polynucleotide

<400> SEQUENCE: 130
auggaaucua aggcacugcu uguguugacc uuggcugccg cugaucagag gagagacuuc 60
aucgauauug aaagcaaauu cgcccuucgc acuccugagg auacugcuga ggauacaugc 120
cauuuaaucc ccggcguagc ugagagcguu gcuacguguc acuucaacca caguucaaaa 180
acuuucaugg uaauucacgg cuggacagua accggcaugu augagagcug gguuccaaag 240
uuaguagccg cccuuuacaa acgugaaccc gacuccaaug ugauaguugu agauuggcug 300
ucccgugccc aagaacacua ccccguuuca gcuggauaca caaaacucgu aggacaggac 360
guggcccgcu uuauuaacug gauggaggag gaguucaauu acccacugga uaauguacau 420
uugcuaggau acucacuggg ggcccacgca gccggcaucg cuggcaguuu aacaaacaag 480
aaggugaaua gaauuacagg ccuggauccc gcuggcccga acuucgagua cgccgaggcc 540
ccuucacgcc ugagcccuga ugacgcggac uucgucgacg ugcugcacac cuucacacgc 600
gggucaccag gacguucuau ugguauccag aaacccgucg ggcacgucga caucuaucca 660
aaugggggaa ccuuucaacc cggaugcaau auuggcgaag caaucagagu cauagcugag 720
agaggauugg gagacgugga ccagcucgug aaauguuccc acgaacguuc aauacaccua 780
uuuaucgacu cccuacugaa ugaggagaac ccaagcaagg cauaccguug cagcucuaag 840
gaggccuucg aaaaaggauu gugccuguca ugucgaaaaa accgcuguaa uaaucucggc 900
uacgaaauua acaaaguacg cgcaaaacgg aguucuaaaa uguaccuuaa gacccggagu 960
cagaugcccu auaaaguuuu ucauuaccag guuaagaucc auuuuuccgg gacagagucu 1020
gaaacucaca ccaaccaagc cuuugaaaua agccuuuacg guacaguugc ugagucggag 1080
aacauucccu uuacccuucc agagguuagu acuaacaaga cauacagcuu ccuaauauac 1140
acugaaguag acauuggaga acuucugaug cuuaaacuca aauggaaguc ugauaguuac 1200
uuuaguuggu ccgacuggug gagcucccca ggcuucgcaa uucaaaaaau ccgcgucaaa 1260
gcaggcgaga cccaaaagaa aguuauuuuc ugcucaaggg agaaggucag ccauuuacag 1320
aaaggaaaag cccccgcggu cuucgucaag ugccaugaua aaucacugaa caaaaaguca 1380
ggguag 1386

<210> SEQ ID NO 131
<211> LENGTH: 3737
<212> TYPE: DNA
<213> ORGANISM: Artificial Sequence
<220> FEATURE:
<223> OTHER INFORMATION: Synthetic Polynucleotide

<400> SEQUENCE: 131
ccgtctgccc tttccccctc ttctcgttgg cagggttgat cctcattact gtttgctcaa 60
acgtttagaa gtgaatttag gtccctcccc ccaacttatg attttatagc caataggtga 120
tgaggtttat ttgcatattt ccagtcacat aagcagcctt ggcgtgaaaa cagtgtcaga 180
ctcgattccc cctcttcctc ctcctcaagg gaaagctgcc cacttctagc tgccctgcca 240
tcccctttaa agggcgactt gctcagcgcc aaaccgcggc tccagccctc tccagcctcc 300
ggctcagccg gctcatcagt cggtccgcgc cttgcagctc ctccagaggg acgcgccccg 360
agatggagag caaagccctg ctcgtgctga ctctggccgt gtggctccag agtctgaccg 420
cctcccgcgg aggggtggcc gccgccgacc aaagaagaga ttttatcgac atcgaaagta 480
aatttgccct aaggacccct gaagacacag ctgaggacac ttgccacctc attcccggag 540
tagcagagtc cgtggctacc tgtcatttca atcacagcag caaaaccttc atggtgatcc 600
atggctggac ggtaacagga atgtatgaga gttgggtgcc aaaacttgtg gccgccctgt 660
acaagagaga accagactcc aatgtcattg tggtggactg gctgtcacgg gctcaggagc 720
attacccagt gtccgcgggc tacaccaaac tggtgggaca ggatgtggcc cggtttatca 780
actggatgga ggaggagttt aactaccctc tggacaatgt ccatctcttg ggatacagcc 840
ttggagccca tgctgctggc attgcaggaa gtctgaccaa taagaaagtc aacagaatta 900
ctggcctcga tccagctgga cctaactttg agtatgcaga agccccgagt cgtctttctc 960
ctgatgatgc agattttgta gacgtcttac acacattcac cagagggtcc cctggtcgaa 1020
gcattggaat ccagaaacca gttgggcatg ttgacattta cccgaatgga ggtacttttc 1080
agccaggatg taacattgga gaagctatcc gcgtgattgc agagagagga cttggagatg 1140
tggaccagct agtgaagtgc tcccacgagc gctccattca tctcttcatc gactctctgt 1200
tgaatgaaga aaatccaagt aaggcctaca ggtgcagttc caaggaagcc tttgagaaag 1260
ggctctgctt gagttgtaga aagaaccgct gcaacaatct gggctatgag atcaataaag 1320

-continued

```
tcagagccaa aagaagcagc aaaatgtacg aagactcgtt ctcagatgcc ctacaaagtc   1380
ttccattacc aagtaaagat tcatttttct gggactgaga gtgaaaccca taccaatcag   1440
gcctttgaga tttctctgta tggcaccgtg gccgagagtg agaacatccc attcactctg   1500
cctgaagttt ccacaaataa gacctactcc ttcctaattt acacagaggt agatattgga   1560
gaactactca tgttgaagct caaatggaag agtgattcat actttagctg gtcagactgg   1620
tggagcagtc ccggcttcgc cattcagaag atcagagtaa aagcaggaga gactcagaaa   1680
aaggtgatct tctgttctag ggagaaagtg tctcatttgc agaaaggaaa ggcacctgcg   1740
gtatttgtga aatgccatga caagtctctg aataagaagt caggctgaaa ctgggcgaat   1800
ctacagaaca aagaacggca tgtgaattct gtgaagaatg aagtggagga agtaactttt   1860
acaaaacata cccagtgttt ggggtgtttc aaaagtggat ttcctgaat attaatccca   1920
gccctaccct tgttagttat tttaggagac agtctcaagc actaaaaagt ggctaattca   1980
atttatgggg tatagtggcc aaatagcaca tcctccaacg ttaaaagaca gtggatcatg   2040
aaaagtgctg ttttgtcctt tgagaaagaa ataattgttt gagcgcagag taaaataagg   2100
ctccttcatg tggcgtattg ggccatagcc tataattggt tagaacctcc tattttaatt   2160
ggaattctgg atctttcgga ctgaggcctt ctcaaacttt actctaagtc tccaagaata   2220
cagaaaatgc ttttccgcgg cacgaatcag actcatctac acagcagtat gaatgatgtt   2280
ttagaatgat tccctcttgc tattggaatg tggtccagac gtcaaccagg aacatgtaac   2340
ttggagaggg acgaagaaag ggtctgataa acacagaggt tttaaacagt ccctaccatt   2400
ggcctgcatc atgacaaagt tacaaattca aggagatata aaatctagat caattaattc   2460
ttaataggct ttatcgttta ttgcttaatc cctctctccc ccttcttttt tgtctcaaga   2520
ttatattata ataatgttct ctgggtaggt gttgaaaatg agcctgtaat cctcagctga   2580
cacataattt gaatggtgca gaaaaaaaaa aagaaaccgt aattttatta ttagattctc   2640
caaatgattt tcatcaattt aaaatcattc aatatctgac agttactctt cagttttagg   2700
cttaccttgg tcatgcttca gttgtacttc cagtgcgtct cttttgttcc tggctttgac   2760
atgaaaagat aggtttgagt tcaaattttg cattgtgtga gcttctacag attttagaca   2820
aggaccgttt ttactaagta aaagggtgga gaggttcctg gggtggattc ctaagcagtg   2880
cttgtaaacc atcgcgtgca atgagccaga tggagtacca tgagggttgc tatttgttgt   2940
ttttaacaac taatcaagag tgagtgaaca actatttata aactagatct cctatttttc   3000
agaatgctct tctacgtata aatatgaaat gataaagatg tcaaatatct cagaggctat   3060
agctgggaac ccgactgtga aagtatgtga tatctgaaca catactagaa agctctgcat   3120
gtgtgttgtc cttcagcata attcggaagg gaaaacagtc gatcaaggga tgtattggaa   3180
catgtcggag tagaaattgt tcctgatgtg ccagaacttc gaccctttct ctgagagaga   3240
tgatcgtgcc tataaatagt aggaccaatg ttgtgattaa catcatcagg cttggaatga   3300
attctctcta aaaataaaat gatgtatgat ttgttgttgg catccccttt attaattcat   3360
taaatttctg gatttgggtt gtgacccagg gtgcattaac ttaaaagatt cactaaagca   3420
gcacatagca ctgggaactc tggctccgaa aaactttgtt atatatatca aggatgttct   3480
ggctttacat tttatttatt agctgtaaat acatgtgtgg atgtgtaaat ggagcttgta   3540
catattggaa aggtcattgt ggctatctgc atttataaat gtgtggtgct aactgtatgt   3600
gtctttatca gtgatggtct cacagagcca actcactctt atgaaatggg ctttaacaaa   3660
acaagaaaga aacgtactta actgtgtgaa gaaatggaat cagcttttaa taaaattgac   3720
```

aacattttat taccaca 3737

<210> SEQ ID NO 132
<211> LENGTH: 828
<212> TYPE: DNA
<213> ORGANISM: Artificial Sequence
<220> FEATURE:
<223> OTHER INFORMATION: Synthetic Polynucleotide

<400> SEQUENCE: 132
atggtgatcc acggctggac cgtgaccggc atgtacgaga gctgggtgcc caagctggtg 60
gccgccctgt acaagagaga gcccgacagc aacgtgatcg tggtggactg gctgagcaga 120
gcccaggagc actaccccgt gagcgccggc tacaccaagc tggtgggcca ggacgtggcc 180
agattcatca actggatgga ggaggagttc aactaccccc tggacaacgt gcacctgctg 240
ggctacagcc tgggcgccca cgccgccggc atcgccggca gcctgaccaa caagaaggtg 300
aacagaatca ccggcctgga ccccgccggc cccaacttcg agtacgccga ggcccccagc 360
agactgagcc ccgacgacgc cgacttcgtg gacgtgctgc acaccttcac cagaggcagc 420
cccggcagaa gcatcggcat ccagaagccc gtgggccacg tggacatcta ccccaacggc 480
ggcaccttcc agcccggctg caacatcggc gaggccatca gagtgatcgc cgagagaggc 540
ctgggcgacg tggaccagct ggtgaagtgc agccacgaga gaagcatcca cctgttcatc 600
gacagcctgc tgaacgagga gaaccccagc aaggcctaca gatgcagcag caaggaggcc 660
ttcgagaagg gcctgtgcct gagctgcaga aagaacagat gcaacaacct gggctacgag 720
atcaacaagg tgagagccaa gagaagcagc aagatgtacg aggacagctt cagcgacgcc 780
ctgcagagcc tgcccctgcc cagcaaggac agcttcttct gggactag 828

<210> SEQ ID NO 133
<211> LENGTH: 828
<212> TYPE: DNA
<213> ORGANISM: Artificial Sequence
<220> FEATURE:
<223> OTHER INFORMATION: Synthetic Polynucleotide

<400> SEQUENCE: 133
atggtgatcc acgggtggac tgtcacaggc atgtacgaaa gctgggtgcc gaagctggtt 60
gctgcattgt ataaaagaga gcccgattct aatgtgatcg tggttgattg gctcagtaga 120
gcccaggaac actatcctgt atccgctgga tacacgaagc tggtcgggca agatgtagca 180
cgatttatca actggatgga agaggaattc aattatccac ttgataatgt tcacttactg 240
ggatactctc tgggcgcaca cgcagcaggt atcgctggta gcctcaccaa taagaaagtt 300
aaccgaatta caggattgga tcctgcaggg cccaattttg agtacgccga ggctcctagc 360
aggctctctc cagatgacgc tgactttgtc gatgttctgc acactttcac ccgcggttcg 420
cccggcagat ccataggcat ccaaaagcca gtgggtcacg ttgacattta ccctaacggc 480
gggacatttc aacctgggtg caacataggc gaggcgatca gagtcattgc tgagagggga 540
ctgggtgacg tcgatcagct cgttaagtgc tcacacgaga ggtccatcca tctgtttatc 600
gattcgcttc tcaacgaaga gaatcccagc aaggcgtaca gatgcagctc aaaagaggca 660
tttgaaaaag ggctatgcct gagctgtcga aagaaccggt gtaataattt gggctacgaa 720
atcaataaag tgagggctaa gaggagctcc aagatgtatg aggacagttt ttccgatgcc 780
ctacagtccc tgccgcttcc cagcaaagac agcttcttct gggattag 828

<210> SEQ ID NO 134
<211> LENGTH: 828
<212> TYPE: DNA
<213> ORGANISM: Artificial Sequence
<220> FEATURE:
<223> OTHER INFORMATION: Synthetic Polynucleotide

<400> SEQUENCE: 134
atggtgatcc acggctggac agtgacaggc atgtatgaga gctgggtgcc caagctggtg 60
gccgccctgt acaagcggga gccagacagc aatgtgattg tggtggactg gctgagccgg 120
gcccaggagc actaccctgt gtctgctggc tacaccaagc tggtgggcca ggatgtggcc 180
cgcttcatca actggatgga ggaggagttc aactaccccc tggacaacgt gcacctgctg 240
ggctacagcc tgggcgccca cgccgccggc attgctggca gcctgaccaa caagaaggtg 300
aaccgcatca ccggcctgga ccctgctggc cccaactttg aatatgcaga ggcccccagc 360
cggctgagcc cagatgatgc tgactttgtg gatgtgctgc acaccttcac ccggggcagc 420
cctggccgca gcatcggcat ccagaagcct gtgggccacg tggacatcta cccaaatgga 480
ggcaccttcc agcccggctg caacattgga gaggccatcc gggtgattgc tgagcggggc 540
ctgggagatg tggaccagct ggtgaagtgc agccatgaga ggagcatcca cctgttcatc 600
gacagcctgc tgaatgagga gaaccccagc aaggcctacc gctgcagcag caaggaggcc 660
tttgagaagg gcctgtgcct gagctgcagg aagaaccgct gcaacaacct gggctatgag 720
atcaacaagg tgcgggccaa gaggagcagc aagatgtatg aggacagctt cagtgatgcc 780
ctgcagagcc tgcccctgcc cagcaaggac agcttcttct gggactag 828

<210> SEQ ID NO 135
<211> LENGTH: 828
<212> TYPE: DNA
<213> ORGANISM: Artificial Sequence
<220> FEATURE:
<223> OTHER INFORMATION: Synthetic Polynucleotide

<400> SEQUENCE: 135
atggtgatcc acggctggac cgtgaccggc atgtacgaga gctgggttcc gaagctagta 60
gctgccctgt acaagagaga acccgactcc aacgtgatcg ttgtggactg gctttctaga 120
gcgcaggagc attatccagt ctctgcgggg tacacaaaac tggtgggcca ggacgtcgcc 180
aggttcatta actggatgga ggaggaattt aactacccgc tggacaacgt gcatctcctg 240
gggtacagcc tcggggccca cgctgcggga attgccggct cgcttactaa caagaaggtg 300
aaccggatca ctggcttaga ccccgccggt cccaactttg agtacgccga agcacccagt 360
cggctctccc cagatgatgc ggactttgtg gatgttctgc acacctttac tagaggctcc 420
cccgggcgct caatcggcat tcagaagcct gtcggccatg tggacatcta tccgaatggg 480
ggaacttttc agccaggctg caatataggt gaggccattc gggtgatcgc agaacgggga 540
ttgggggacg tagatcagtt agtgaagtgt tcacatgaga gatccatcca tctgtttata 600
gactccttgc tgaacgaaga gaacccttca aaagcttatc gctgtagttc taaggaagcc 660
ttcgagaaag ggttgtgcct ctcgtgtcga aagaaccggt gtaacaacct agggtacgag 720
attaacaagg tgagagccaa acggagctcc aagatgtatg aggacagctt cagcgatgca 780
ctgcagagct tgccattacc gtctaaggat tctttttct gggattag 828

<210> SEQ ID NO 136
<211> LENGTH: 828

<212> TYPE: DNA
<213> ORGANISM: Artificial Sequence
<220> FEATURE:
<223> OTHER INFORMATION: Synthetic Polynucleotide

<400> SEQUENCE: 136
atggttattc atgggtggac cgtcactggg atgtatgaaa gctgggtgcc gaaacttgtc 60
gcagccttat acaagagaga accggattcc aacgttatag tggtcgactg gctatctcgt 120
gcccaggaac attaccctgt gtccgcaggt tatactaagc tggttggaca ggacgtggcc 180
cgattcatca actggatgga ggaggaattc aactatccac tggacaacgt gcacctactg 240
ggatactccc tgggtgccca cgccgctgga attgcaggat ctctgacaaa taagaaagtt 300
aacagaatta ccggcctgga tccagcagga cccaacttcg agtacgcgga agcaccatct 360
cggctgagcc ccgatgacgc agatttcgtg gacgttctgc atacctttac aaggggaagt 420
ccagggcgtt ctattggcat tcagaaaccg gtcggtcatg tggacattta tccaaacggc 480
ggtacgtttc agccaggctg taacatcggc gaggctatcc gagtgattgc agaaagaggc 540
ttgggagatg tggatcagtt ggtaaagtgc tcccacgagc gctctatcca ccttttatc 600 gactctctgc tcaacgagga aaaccccagc aaagcttatc gctgctcttc taaggaagcg 660
ttcgaaaagg ggctctgctt gagttgccgc aagaatcggt gtaataattt gggttatgaa 720
atcaacaaag tgcgagccaa gaggtctagc aaaatgtatg aggattcatt ttcagatgca 780
ctgcaaagcc tgcctctgcc ttctaaggac tccttcttct gggactag 828

<210> SEQ ID NO 137
<211> LENGTH: 828
<212> TYPE: RNA
<213> ORGANISM: Artificial Sequence
<220> FEATURE:
<223> OTHER INFORMATION: Synthetic Polynucleotide

<400> SEQUENCE: 137
auggugaucc acggguggac ugucacugga auguacgagu ccugggugcc aaaguuaguu 60
gcagcgcuuu auaagagaga accugauagc aacguuauug uggucgacug gcugucccgc 120
gcccaagagc acuacccagu gucugcgggu uauacuaagc ugguagggca ggauguggca 180
cgguuuauaa auuggaugga ggaagaguuu aauuaucccc ucgacaaugu gcaucugcuc 240
ggcuauagcu ugggagcgca cgcagcaggg aucgcgggaa gucuaaccaa uaagaaggug 300
aaucgcauua cagggcuuga uccugccggc ccaaacuuug aauaugcuga agccccccuca 360 cggcugagcc cugacgacgc agauuuuguc gauguccugc acacuuucac acgcggcucu 420
ccuggcagau cuaucggcau ucaaaaaccc gugggccaug uagauauuua ucccaaugga 480
ggcacauuuc aaccuggaug caacauagga gaggcaauaa ggguaauugc cgaaaggggc 540
cugggcgacg uugaucagcu ugugaaaugc ucacacgagc guagcaucca cuuguucauc 600
gacagccugu ugaaugagga gaaccccagc aaagccuaca ggugcucaag uaaggaggcu 660
uuugaaaaag gucuuugucu uagcugccga aaaaaccgau gcaacaaucu gggcuaugaa 720
aucaauaaag uaagggccaa gcgguccuca aaaauguacg aagacucuuu uucggaugca 780
cugcagagcc ugccguugcc aucaaaagac aguuuuuucu gggacuag 828

<210> SEQ ID NO 138
<211> LENGTH: 828
<212> TYPE: RNA
<213> ORGANISM: Artificial Sequence
<220> FEATURE:

-continued

<223> OTHER INFORMATION: Synthetic Polynucleotide

<400> SEQUENCE: 138
auggugauuc auggauggac ggugacaggu auguacgaga guuggguucc aaaacuggug 60
gcggcucugu auaaacgaga accugacagc aaugugaucg ucguugauug gcugaguaga 120
gcacaggagc acuaccccgu gucagcugga uacacuaaac ucguagguca ggauguggcc 180
cguuuuauaa acuggaugga agaggaguuc aauuauccac uggauaacgu ccauuuacuu 240
ggcuacagcc ugggagccca ugccgcaggc aucgccgggu cauugacaaa uaagaaaguc 300
aaccguauua cgggcuuaga uccugccggc ccaaauuucg aauaugccga agcuccuagu 360
cgauugucac cggaugaugc ugacuucguc gaugugcugc acacuuucac cagaggcuca 420
cccgguagau ccaucgguau ccagaagcca gugggacacg uggacauuua uccaaacgga 480
gggacauuuc agccaggcug uaauauuggc gaggcuauca gggugauugc agagcgcggc 540
uuaggugacg uggaucaauu ggucaagugu ucgcacgaaa gaucaauuca ccuuuucauc 600
gauagucugc uuaacgagga aaacccauca aaggcauauc ggugcuccag uaaagaagca 660
uuugaaaagg gauugugccu gucuugcaga aagaaccgau gcaacaauuu gggguaugag 720
auuaauaaag uuagagcuaa aaggagcagu aaaauguacg aagacuccuu cucggacgcu 780
uuacaaagcc ucccucuccc auccaaggau uccuucuucu gggauuag 828

<210> SEQ ID NO 139

<400> SEQUENCE: 139

000

<210> SEQ ID NO 140

<400> SEQUENCE: 140

000

<210> SEQ ID NO 141
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 141
tgataatagg ctggagcctc ggtggccatg cttcttgccc cttgggcctc cccccagccc 60
ctcctcccct tcctgcaccc gtacccccgt ggtctttgaa taaagtctga gtgggcggc 119

<210> SEQ ID NO 142
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 142

Ala Gln Glu His
1

<210> SEQ ID NO 143
<211> LENGTH: 5
<212> TYPE: PRT
<213> ORGANISM: Artificial Sequence
<220> FEATURE:

<223> OTHER INFORMATION: Synthetic Polypeptide

<400> SEQUENCE: 143

Ala Gln Glu His Tyr
1               5

<210> SEQ ID NO 144
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 144

Ala Gln Glu His Tyr Pro Val Ser Ala Gly Tyr Thr Lys
1               5                   10

<210> SEQ ID NO 145
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 145

Pro Val Ser Ala Gly Thr Tyr Lys
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 146

Tyr Pro Val Ser Ala Gly Tyr Thr Lys
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 147

Gly Gly Gly Gly Ser
1               5

<210> SEQ ID NO 148
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 148
atggagagca aggccctgct ggtgctgacc ctggccgtgt ggctgcagag cctgaccgcc     60
agccggggag gcgtggccgc cgccgaccag cggcgggact tcatcgacat cgagtccaag    120
ttcgccctgc ggacgcccga ggacaccgcc gaagacacct gccacctgat ccccggcgtc    180
gccgagagcg tggccacatg ccacttcaac cacagcagca agaccttcat ggtgatccac    240
ggctggaccg tgaccggcat gtacgagagc tgggtgccca agctggtggc cgctctgtac    300

```
aagcgggagc ccgacagcaa cgtgatcgtg gtggactggc tgagccgggc ccaggagcac    360

taccccgtga gcgccggcta caccaagctc gtcggccagg acgtggcccg gttcatcaac    420

tggatggagg aggagttcaa ctacccgctg gacaacgtgc acctgctggg ctacagcctg    480

ggcgcccacg ccgccggcat cgccggcagc ctcaccaaca agaaggtgaa ccggatcacc    540

ggcctggacc ccgccggccc caacttcgag tacgccgagg cgcccagcag gctctcgccc    600

gacgacgccg acttcgtgga cgtgctgcac accttcaccc ggggctctcc cggacggagc    660

atcggcatcc agaagcccgt gggccacgtg gacatctacc ccaacggcgg caccttccag    720

cccggctgca acatcggcga ggccatccgg gtgatcgccg agcggggtct gggcgacgtg    780

gaccagctgg tgaagtgcag ccacgagcgg agcattcacc tgttcatcga tagcctgctg    840

aacgaggaga acccctccaa agcataccgg tgcagtagta aggaggcctt cgagaagggc    900

ctgtgcctga gctgccggaa gaacagatgc aacaaccttg ggtacgagat caacaaggtg    960

cgggccaaga gatcttccaa gatgtacctg aagacccgga gccagatgcc ctacaaggtg   1020

ttccactacc aggtgaagat ccacttcagc ggcaccgaaa gcgaaactca caccaaccag   1080

gcctttgaaa tcagcctgta cggcaccgtg gccgagtctg agaacatccc tttcacactg   1140

cccgaggtga gcactaacaa gacctacagc ttcctgatct acaccgaggt ggacattggc   1200

gagctgctga tgctgaagct gaagtggaag tcagacagct acttcagctg gagcgactgg   1260

tggtctagcc ccggattcgc catccagaag atcagggtga aggccggaga gacacagaag   1320

aaagtgatct tctgcagccg ggagaaggta agccacctgc agaagggcaa ggctcccgcc   1380

gtgttcgtca agtgccacga caagtccctg aacaagaagt ccggc                   1425
```

```
<210> SEQ ID NO 149
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 149
```

```
auggagagca aggcccugcu ggugcugacc cuggccgugu ggcugcagag ccugaccgcc     60

agccggggag gcguggccgc cgccgaccag cggcgggacu ucaucgacau cgaguccaag    120

uucgcccugc ggacgcccga ggacaccgcc gaagacaccu gccaccugau ccccggcguc    180

gccgagagcg uggccacaug ccacuucaac cacagcagca agaccuucau ggugauccac    240

ggcuggaccg ugaccggcau guacgagagc ugggugccca agcugguggc cgcucuguac    300

aagcgggagc ccgacagcaa cgugaucgug guggacuggc ugagccgggc ccaggagcac    360

uaccccguga gcgccggcua caccaagcuc gucggccagg acguggcccg guucaucaac    420

uggauggagg aggaguucaa cuacccgcug gacaacgugc accugcuggg cuacagccug    480

ggcgcccacg ccgccggcau cgccggcagc cucaccaaca agaaggugaa ccggaucacc    540

ggccuggacc ccgccggccc caacuucgag uacgccgagg cgcccagcag gcucucgccc    600

gacgacgccg acuucgugga cgugcugcac accuucaccc ggggcucucc cggacggagc    660

aucggcaucc agaagcccgu gggccacgug gacaucuacc ccaacggcgg caccuuccag    720

cccggcugca acaucggcga ggccauccgg gugaucgccg agcggggucu gggcgacgug    780

gaccagcugg ugaagugcag ccacgagcgg agcauucacc uguucaucga uagccugcug    840

aacgaggaga accccuccaa agcauaccgg ugcaguagua aggaggccuu cgagaagggc    900

cugugccuga gcugccggaa gaacagaugc aacaaccuug gguacgagau caacaaggug    960
```

cgggccaaga gaucuuccaa gauguaccug aagacccgga gccagaugcc cuacaaggug 1020
uuccacuacc aggugaagau ccacuucagc ggcaccgaaa gcgaaacuca caccaaccag 1080
gccuuugaaa ucagccugua cggcaccgug gccgagucug agaacauccc uuucacacug 1140
cccgagguga gcacuaacaa gaccuacagc uuccugaucu acaccgaggu ggacauuggc 1200
gagcugcuga ugcugaagcu gaaguggaag ucagacagcu acuucagcug gagcgacugg 1260
uggucuagcc ccggauucgc cauccagaag aucaggguga aggccggaga gacacagaag 1320
aaagugaucu ucugcagccg ggagaaggua agccaccugc agaagggcaa ggcucccgcc 1380
guguucguca agugccacga caagucccug aacaagaagu ccggc 1425

<210> SEQ ID NO 150
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 150
auggagagca aggcccugcu ggugcugacc cuggccgugu ggcugcagag ccugaccgcc 60
agccggggcg gcguggccgc cgccgaccag cgccgcgacu ucaucgacau cgaguccaag 120
uucgcccucc gcacgcccga ggacaccgcc gaggacaccu gccaccucau ccccggcguc 180
gccgaguccg ucgccaccug ccacuucaac cacuccucca agaccuucau ggucauccac 240
ggcuggaccg ucaccggcau guacgagucc ugggucccca agcucgucgc cgcccucuac 300
aagcgcgagc ccgacuccaa cgucaucguc gucgacuggc ucucccgcgc ccaggagcac 360
uaccccgucu ccgccggcua caccaagcuc gucggccagg acgucgcccg cuucaucaac 420
uggauggagg aggaguucaa cuacccacuc gacaacgucc accuccucgg cuacucccuc 480
ggcgcccacg ccgccggcau cgccggcucc cucaccaaca agaaggucaa ccgcaucacc 540
ggccucgacc ccgccggccc caacuucgag uacgccgagg cgcccucccg ccucucgccc 600
gacgacgccg acuucgucga cguccuccac accuucaccc gcggcucgcc cggccgcucc 660
aucggcaucc agaagcccgu cggccacguc gacaucuacc ccaacggcgg caccuuccag 720
cccggcugca acaucggcga ggccauccgc gucaucgccg agcgcggccu cggcgacguc 780
gaccagcucg ucaagugcuc ccacgagcgc uccauccacc ucuucaucga cucccuccuc 840
aacgaggaga accccuccaa ggccuaccgc ugcuccucca aggaggccuu cgagaagggc 900
cucugccucu ccugccgcaa gaaccgcugc aacaaccucg gcuacgagau caacaagguc 960
cgcgccaagc gcuccuccaa gauguaccuc aagacccgcu cccagaugcc cuacaagguc 1020
uuccacuacc aggucaagau ccacuucucc ggcaccgagu ccgagaccca caccaaccag 1080
gccuucgaga ucucccucua cggcaccguc gccgaguccg agaacauccc cuucacccuc 1140
cccgaggucu ccaccaacaa gaccuacucc uuccucaucu acaccgaggu cgacaucggc 1200
gagcuccuca ugcucaagcu caaguggaag uccgacuccu acuucuccug guccgacugg 1260
ugguccucgc ccggcuucgc cauccagaag auccgcguca aggccggcga gacccagaag 1320
aaggucaucu ucugcucccg cgagaagguc ucccaccucc agaagggcaa ggcgcccgcc 1380
gucuucguca agugccacga caagucccuc aacaagaagu ccggc 1425

<210> SEQ ID NO 151
<211> LENGTH: 1425
<212> TYPE: RNA

<213> ORGANISM: Artificial Sequence
<220> FEATURE:
<223> OTHER INFORMATION: Synthetic Polynucleotide

<400> SEQUENCE: 151
auggagagca aggcccugcu ggugcugacc cuggccgugu ggcugcagag ccugaccgcc 60
agccggggag gcguggccgc cgccgaccag cggcgggacu ucaucgacau cgaguccaag 120
uucgcccugc ggacccccga ggacaccgcc gaagacaccu gccaccugau ccccggcguc 180
gccgagagcg uggccacaug ccacuucaac cacagcagca agaccuucau ggugauccac 240
ggcuggaccg ugaccggcau guacgagagc ugggugccca agcugguggc cgcucuguac 300
aagcgggagc ccgacagcaa cgugaucgug guggacuggc ugagccgggc ccaggagcac 360
uaccccguga gcgccggcua caccaagcuc gucggccagg acguggcccg guucaucaac 420
uggauggagg aggaguucaa cuacccccug gacaacgugc accugcuggg cuacagccug 480
ggcgcccacg ccgccggcau cgccggcagc cucaccaaca agaaggugaa ccggaucacc 540
ggccuggacc ccgccggccc caacuucgag uacgccgagg cccccagcag gcucuccccc 600
gacgacgccg acuucgugga cgugcugcac accuucaccc ggggcucucc cggacggagc 660
aucggcaucc agaagcccgu gggccacgug gacaucuacc ccaacggcgg caccuuccag 720
cccggcugca acaucggcga ggccauccgg gugaucgccg agcggggucu gggcgacgug 780
gaccagcugg ugaagugcag ccacgagcgg agcauucacc uguucaucga uagccugcug 840
aacgaggaga accccuccaa agcauaccgg ugcaguagua aggaggccuu cgagaagggc 900
cugugccuga gcugccggaa gaacagaugc aacaaccuug gguacgagau caacaaggug 960
cgggccaaga gaucuuccaa gauguaccug aagacccgga gccagaugcc cuacaaggug 1020
uuccacuacc aggugaagau ccacuucagc ggcaccgaaa gcgaaacuca caccaaccag 1080
gccuuugaaa ucagccugua cggcaccgug gccgagucug agaacauccc uuucacacug 1140
cccgagguga gcacuaacaa gaccuacagc uuccugaucu acaccgaggu ggacauuggc 1200
gagcugcuga ugcugaagcu gaaguggaag ucagacagcu acuucagcug gagcgacugg 1260
uggucuagcc ccggauucgc cauccaaaag aucaggguga aggccggaga gacacagaag 1320
aaagugaucu ucugcagccg ggagaaggua agccaccugc agaagggcaa ggcucccgcc 1380
guguucguca agugccacga caagucccug aacaagaagu ccggc 1425

<210> SEQ ID NO 152
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 152
auggagagca aggcccugcu ggugcugacc cuggccgugu ggcugcagag ccugaccgcc 60
agccggggcg gcguggccgc cgccgaccag cgccgcgacu ucaucgacau cgaguccaag 120
uucgcccucc gcacccccga ggacaccgcc gaggacaccu gccaccucau ccccggcguc 180
gccgaguccg ucgccaccug ccacuucaac cacuccucca agaccuucau ggucauccac 240
ggcuggaccg ucaccggcau guacgagucc ugggucccca agcucgucgc cgcccucuac 300
aagcgcgagc ccgacuccaa cgucaucguc gucgacuggc ucucccgcgc ccaggagcac 360
uaccccgucu ccgccggcua caccaagcuc gucggccagg acgucgcccg cuucaucaac 420
uggauggagg aggaguucaa cuacccccuc gacaacgucc accuccucgg cuacucccuc 480

```
ggcgcccacg ccgccggcau cgccggcucc cucaccaaca agaaggucaa ccgcaucacc    540

ggccucgacc ccgccggccc caacuucgag uacgccgagg cccccucccg ccucuccccc    600

gacgacgccg acuucgucga cguccuccac accuucaccc gcggcucccc cggccgcucc    660

aucggcaucc agaagcccgu cggccacguc gacaucuacc ccaacggcgg caccuuccag    720

cccggcugca acaucggcga ggccauccgc gucaucgccg agcgcggccu cggcgacguc    780

gaccagcucg ucaagugcuc ccacgagcgc uccauccacc ucuucaucga cucccuccuc    840

aacgaggaga accccuccaa ggccuaccgc ugcuccucca aggaggccuu cgagaagggc    900

cucugccucu ccugccgcaa gaaccgcugc aacaaccucg gcuacgagau caacaagguc    960

cgcgccaagc gcuccuccaa gauguaccuc aagacccgcu cccagaugcc cuacaagguc   1020

uuccacuacc aggucaagau ccacuucucc ggcaccgagu ccgagaccca caccaaccag   1080

gccuucgaga ucucccucua cggcaccguc gccgaguccg agaacauccc cuucacccuc   1140

cccgaggucu ccaccaacaa gaccuacucc uuccucaucu acaccgaggu cgacaucggc   1200

gagcuccuca ugcucaagcu caaguggaag uccgacuccu acuucuccug guccgacugg   1260

ugguccuccc ccggcuucgc cauccagaag auccgcguca aggccggcga gacccagaag   1320

aaggucaucu ucugcucccg cgagaagguc ucccaccucc agaagggcaa ggcccccgcc   1380

gucuucguca agugccacga caagucccuc aacaagaagu ccggc                   1425
```

<210> SEQ ID NO 153
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 153

```
auggagagca aggcucugcu ggugcugacg cuggccgugu ggcugcaguc ccugaccgcc     60

agcaggggag gcguggccgc cgccgaccag cggcgcgacu ucaucgauau cgagucgaag    120

uucgcccugc gcacgcccga ggauaccgcc gaggacacgu gccaccugau ccccggggug    180

gcggagagcg ucgccaccug ucacuucaac cauagcagca agacguucau ggucauccac    240

ggcuggaccg ugacaggaau guacgaaagc ugggugccca agcucguggc cgcccucuac    300

aagagggagc ccgacagcaa ugugauagug guggacuggc ugucccgggc ccaggaacac    360

uaucccguga gcgccgggua caccaagcuc gugggccagg acguggcccg guucaucaau    420

uggauggagg aggaguucaa cuacccccug gacaacgugc aucugcucgg cuacucccug    480

ggcgcucacg ccgccggcau cgcgggcagc cugacaaaca agaaggugaa caggaucacc    540

gggcucgacc ccgccggccc caacuucgag uacgccgagg cccccagcag gcugagcccc    600

gacgaugccg acuucgugga cgugcugcac accuucaccc ggggcagccc cggcaggagc    660

aucggcaucc agaagcccgu gggccauguc gacaucuauc ccaauggcgg caccuuucag    720

cccgguugca acaucggcga ggcgaucagg gugauugccg agaggggccu gggcgacguc    780

gaucagcugg ugaaguguag ccacgagcgg uccauccauc ucuucauaga cucccuucug    840

aaugaagaga accccuccaa agccuaccga ugcagcagca aggaggcguu cgaaaagggg    900

cugugccugu ccugcaggaa gaacaggugc aacaaucugg gcuaugagau caacaaggua    960

cgcgcgaagc ggagcagcaa gauguaucug aagacccggu cgcagaugcc cuauaaagug   1020

uuccacuacc agguaaagau ccacuucucc gggaccgaga gcgagaccca cacaaaucag   1080
```

gccuucgaga ucagccugua cggcaccgug gcggagagcg agaauauccc guucacccug 1140
ccugaggugu ccaccaauaa gaccuacucc uuccugaucu acacggaggu ggacauaggc 1200
gagcugcuga ugcugaagcu gaaguggaag ucggacagcu acuucuccug gagcgacugg 1260
ugguccuccc ccggauucgc cauccagaag aucagggguga aggccggcga gacccagaaa 1320
aaggugaucu uuugcucgcg cgagaagguc ucgcaccugc agaaggggaa ggcccccgcc 1380
guguucguga agugccauga uaagagucuc aauaagaagu ccggg 1425

<210> SEQ ID NO 154
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 154
auggagagca aggcacugcu ggugcugaca cuggccgugu ggcugcagag ccugaccgcc 60
uccaggggcg gaguggccgc cgccgaccag cggcgggacu ucaucgacau cgaaucgaag 120
uucgcccugc ggaccccgga ggacaccgcc gaagacaccu gccaccucau ccccggcguc 180
gccgagagcg uggccacgug ccacuucaac cacagcagca agaccuucau ggugauccau 240
ggcuggaccg ugacaggcau guaugagagc ugggucccca aacugguggc ggcccuguac 300
aaaagggagc cggacuccaa ugugaucgua guggacuggc ucuccagggc ccaggagcac 360
uaccccguca gcgccggcua caccaagcug gugggccagg acguggccag guucaucaac 420
uggauggagg aagaguucaa uuacccccug gacaacgugc aucugcucgg guacucccug 480
ggcgcccacg ccgccgggau cgccgguagc cucaccaaca agaaggucaa ucgaaucacc 540
gggcuggacc ccgccgggcc caacuuugaa uacgccgaag cccccagccg gcucagcccc 600
gacgaugccg acuuugugga ugugcugcac accuucaccc gagguagccc cggcaggagc 660
aucggcaucc agaagcccgu gggccacgug gacaucuacc ccaacggggg uaccuuccag 720
cccgggugca acaucggaga ggccaucagg gugaucgcag agaggggccu gggcgaugug 780
gaccagcugg ucaagugcag ccacgaaagg agcauacacu uauucauaga uagccugcuc 840
aacgaagaga accccagcaa ggccuaccgu uguuccucua aggaggccuu cgagaagggg 900
cucugccuga gcugccggaa aaacaggugc aacaaccucg gcuacgagau caacaaggug 960
cgggccaaac gguccagcaa gauguaccug aagaccagga gccagaugcc cuauaagguc 1020
uuccacuacc aggucaagau ccacuucucc ggcaccgaga gcgagaccca cacuaaccag 1080
gccuucgaga ucucgcugua cgggacggug gcggaauccg agaacauccc guucacccug 1140
cccgagguga gcaccaacaa aacguacagc uuccugaucu acaccgaggu cgacaucggc 1200
gagcuccuca ugcucaagcu caaguggaag agcgauagcu acuucagcug guccgacugg 1260
uggagcagcc cgggcuucgc cauccaaaag auuaggguga aggccggcga gacccagaag 1320
aaggugaucu ucugcucgag ggagaaagug ucccaucugc agaagggcaa ggccccggcc 1380
guguucguga agugccacga uaagucgcug aacaagaagu ccggc 1425

<210> SEQ ID NO 155
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 155

```
auggagucca aggcccugcu ggugcucaca cucgccgugu ggcugcagag ccugaccgcc     60
ucccgggggg gcguggcggc cgccgaccag cggagggauu ucaucgacau cgagagcaaa    120
uucgcccuga ggacccccga ggacaccgcc gaggauaccu gccaucucau ccccggcgug    180
gcugagagcg uggccaccug ccacuucaac cacagcagca agaccuucau ggugauccac    240
ggcuggaccg ugaccggaau guacgagagc ugggugccca agcugguggc cgcccuguac    300
aagagggagc ccgauagcaa ugugauagug guggauuggc ugagcagggc ccaagagcau    360
uaccccguga gcgccggcua uaccaagcug gugggccagg acguggccag guucaucaac    420
uggauggagg aggaguucaa cuacccccug gacaacgucc accugcuggg cuacagccug    480
ggggcccacg ccgcgggcau cgccggcucc cucaccaaca agaaggugaa uaggauaacg    540
ggccuggacc ccgccggucc caacuucgag uacgccgagg ccccgucccg acugucuccc    600
gacgacgcag acuucgucga cguccugcau accuucacca gaggcagccc cgggaggucc    660
aucggcaucc agaagcccgu gggccaugug gacaucuacc cgaauggcgg caccuuccag    720
ccugguugca acauuggcga ggcgaucagg gugaucgccg agcguggccu cggggacgug    780
gaucagcugg ugaaguguuc ccacgagcgc agcauccacc ucuucaucga cagccugcuc    840
aacgaagaga accccuccaa ggccuacagg ugcaguucca aggaggcauu cgagaagggc    900
cucugccuga gcugcaggaa gaacaggugu aacaaccuag gcuacgagau caacaagguc    960
cgggccaagc ggagcucaaa gauguaccug aagacgcgga gccagaugcc cuauaaggug   1020
uuccacuacc aggugaaaau ccauuucucc ggcaccgagu ccgagaccca caccaaccaa   1080
gcauucgaga ucucccucua cggaaccgua gcagagagcg agaacauccc cuucacccuc   1140
cccgagguga gcacuaacaa gacguacucc uuccugaucu acaccgaggu ggacaucggc   1200
gagcuccuga ugcugaagcu gaaguggaag agcgacuccu acuuuuccug guccgacugg   1260
ugguccagcc ccggguuugc gauucaaaag aucaggguga aagccggcga aacccagaag   1320
aaggugaucu ucuguagccg agagaaagug agccaccugc agaaaggaaa ggcccccgcc   1380
gucuucguca agugccacga caaaagccuc aauaagaagu ccggg                   1425
```

```
<210> SEQ ID NO 156
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 156
```

```
auggagagca aggcgcugcu ggugcugaca cuggcggugu ggcugcaaag ccugaccgcg     60
agcaggggcg gcguggccgc cgccgaccag aggcgggacu ucauugacau cgaguccaag    120
uucgcccuua ggacccccga agacaccgcc gaggacaccu gccaccugau accgggggug    180
gccgaguccg uggccaccug ccacuuuaac cacuccucca agacguucau ggucauccac    240
ggcuggaccg ugaccgggau guacgaaagc ugggugccca agcugguggc cgcccucuac    300
aaaagggagc cugacuccaa cgucaucgug guggacuggc uguccagggc ccaggagcac    360
uaccccguuu ccgccggaua caccaagcug gugggccagg acguggcccg guucaucaau    420
uggauggagg aggaauucaa uuacccccug gacaacgugc aucugcucgg cuacucccug    480
ggcgcccacg ccgccggcau cgccggcagc cugacuaaca agaaggugaa ccggaucacc    540
ggccuggacc ccgccggccc caacuucgaa uacgccgagg cccccucccg acugucccca    600
```

-continued

```
gacgacgccg acuucgugga ugugcugcac accuucaccc gcggcagccc cgggcgaagc    660
aucggaaucc aaaagcccgu ggggcacgug gauaucuacc cgaacggggg aaccuuccaa    720
cccggcugca acauugggga ggccaucaga gugaucgccg agcgcgggcu gggggacguc    780
gaccagcugg ugaagugcuc ccacgagcgc agcauccacc uguucaucga cucccuacug    840
aaugaagaga accccagcaa ggcguaccgg ugcuccucca aggaggccuu cgagaagggc    900
cucugccuga gcugcaggaa gaacagaugc aacaaucugg gcuacgagau caauaagguc    960
cgcgccaaga gaagcagcaa aauguaccug aagacccgga gccagaugcc cuauaaggug   1020
uuccacuacc aggugaagau ccacuucagc gguacggagu cugagaccca uaccaaccag   1080
gcuuucgaaa ucagccugua cggaaccgug gccgagagcg agaacauccc cuuuacccug   1140
ccagaagugu ccacaaacaa gaccuacucc uuccugauau acacugaggu ggacaucggc   1200
gagcugcuga ugcugaaguu gaaguggaag agcgauagcu acuucagcug gagcgauugg   1260
uggagcagcc ccggauucgc cauccagaag auaaggguga aggccggaga gacccagaag   1320
aaggucaucu uuugcagcag ggagaaggug agccaccugc agaagggcaa ggcgcccgcc   1380
guguucguca agugucacga caagagccug aauaagaaga gcggg                    1425
```

```
<210> SEQ ID NO 157
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 157

auggaaagca aggcgcugcu cguccucacc cuggccgucu ggcugcaaag ccugaccgcc     60
agcagaggug gcguggcggc cgccgaccag cggcgagacu ucaucgauau cgaaagcaag    120
uuugcccuga ggaccccoga ggauaccgcc gaggacaccu gccaccugau ucccggagug    180
gccgagagcg uugccaccug ccacuucaac cacucgagca agaccuuuau ggugauacac    240
ggcuggaccg ucacgggcau guacgagagc ugggugccca agcugguggc cgcccuguau    300
aagagggagc cggacagcaa cgucaucguc guggacuggc ugucgagggc ccaagaacac    360
uaccccguga gcgccgggua caccaagcug gucggucaag acguggcccg cuucaucaau    420
uggauggagg aggaguucaa cuaucccuc gacaacgugc accuccuggg cuacagccug    480
ggcgcccacg ccgccggcau cgccgguucg cucaccaaua aaaaggugaa caggauuacc    540
ggucuggacc ccgcgggccc gaacuucgag uacgccgaag ccccgagcag gcuguccccg    600
gacgacgccg acuucgugga cgugcugcac accuuuaccc gcggcucccc cggccggagc    660
aucggaaucc aaaagcccgu cggcacgug gauaucuacc ccaacggcgg caccuuccag    720
cccgggugca acaucgguga ggccaucagg gucaucgccg aacggggccu gggcgacgug    780
gaccagcugg ucaaauguag ccaugagagg uccauccacc uguuuaucga cucccugcug    840
aacgaggaga accccagcaa ggccuaccgg ugcuccagca aggaggccuu cgagaaagga    900
cugugccuga gcugcaggaa gaaccguugc aacaaccugg gcuacgagau caacaaggug    960
agggcaaagc ggagcucaaa gauguaccug aagacccggu cccaaaugcc cuacaaagug   1020
uuccauuacc aggugaaaau ucauuucagc ggcaccgaga gcgaaaccca cacgaaccag   1080
gccuuugaga uaagccugua cgggaccgug gcggagagcg agaauauccc cuucacucuc   1140
cccgaggug gcacgaacaa gaccuacucc uuccugaucu acacggaggu cgauaucggu   1200
gagcugcuga ugcugaagcu gaaguggaag agcgacagcu acuucuccug gagcgacugg   1260
```

uggagcagcc cuggguucgc cauccaaaaa auccgggguga aggccggcga gacccaaaag 1320
aaggugaucu ucugcucuag ggagaaggug ucccaccugc agaagggcaa ggccccccgcc 1380 guauuuguga agugccacga caagagccug aauaagaaga gcggc 1425

<210> SEQ ID NO 158
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 158
auggagagca aggcccugcu gguccugacc cuggccgucu ggcugcagag ccugaccgcc 60
ucccgggggg gcguggccgc cgccgaccag aggcgcgacu uuauagacau cgagucgaag 120
uuugcccugc gcacccccga ggacacagcc gaagacaccu gccaccugau ccccggggug 180
gcggagagcg uggccaccug ccacuucaac cacuccucca agaccuucau ggucauucau 240
ggcuggaccg ucaccggcau guacgagagu ugggugccga agcugguggc cgcccucuac 300
aagagggagc ccgacuccaa cgugaucgug guggacuggc ugagcagggc ccaggagcac 360
uauccgguga gcgccgggua cacgaagcug gucggacagg acguggcccg cuucaucaac 420
uggauggagg aagaguuuaa cuauccgcuc gacaacgucc aucugcuggg guacagccug 480
ggcgcccaug ccgccggaau cgccggcucc cugacgaaca agaaggugaa ccggaucacc 540
gggcuagacc ccgccgggcc caauuucgag uacgccgagg cgcccagcag gcugaguccc 600
gacgacgccg acuuugugga cguccugcau accuucaccc gcggcagccc cgggcgaucc 660
aucggcaucc agaagccggu cggccacguc gacaucuacc ccaacggcgg cacauuccag 720
cccggcugca acaucggcga ggccaucagg gugaucgccg agcgugggcu gggcgacgug 780
gaucagcugg ugaagugcag ccacgagagg agcauccauc uguucaucga uagccugcug 840
aacgaggaga acccgagcaa ggccuacagg uguagcagca aggaggccuu cgagaagggc 900
cucugucugu caugcaggaa gaauaggugc aacaaccugg gcuacgagau caacaaggug 960
agggccaaaa ggagcuccaa gauguaucug aagaccaggu cccagaugcc guacaaggug 1020
uuccacuauc aggugaagau ccacuucucg ggcacagaga gcgagacgca caccaaccag 1080
gccuucgaga ucagccugua cggcaccgug gccgaguccg aaaacauccc uuuuacccug 1140
cccgaggugu ccaccaacaa gaccuacagc uuccugauau acaccgaggu ggacaucggc 1200
gaacugcuga ugcucaagcu gaaauggaag uccgacagcu acuucagcug gagcgauugg 1260
uggagcuccc cggggguucgc aauccaaaag aucaggguga aggcagggga gacccagaag 1320
aaggucaucu ucugcucccg ggaaaaagug agccaucucc agaagggcaa agcgcccgcc 1380
guguucguca agugccacga uaagagccug aacaagaaga gcggc 1425

<210> SEQ ID NO 159
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 159
auggagagca aggcgcugcu ggugcugacc cuggcggugu ggcugcagag ccucaccgcc 60
ucgcgcggug gcguggcggc cgccgaucaa cggcgggacu ucaucgauau cgagagcaag 120
uucgcccuuc ggaccccgga ggacaccgcc gaggauacuu gccaucugau ccccggcgug 180
gccgaauccg uggccaccug ccacuucaac cacuccagca agaccuucau ggugauccac 240
ggcuggaccg ugaccgggau guacgagagu ugggugccca agcugguggc cgcccuguac 300
aagcgggagc ccgacagcaa ugugaucgug guggacuggc ugagcagggc ccaggagcau 360
uauccaguga gcgccgggua uaccaaacuc gugggccagg augucgccag guucauuaac 420
uggauggagg aggaauucaa cuacccgcug gauaacgugc aucugcuggg guacucgcug 480
ggagcccaug ccgccggcau cgcgggaucc cugacgaaca agaaggucaa uaggaucacc 540
ggccuggacc cggccggccc caacuucgag uacgccgagg cgcccagccg ucugagcccc 600
gacgacgccg auuucgugga cgugcugcac accuucacca ggggcagccc cggccgcagc 660
aucggcauuc agaagcccgu gggccacguc gacauauauc ccaacggcgg aaccuuccaa 720
cccggcugua acaucgggga ggccauccgg gucaucgccg agaggggccu gggcgacgug 780
gaccagcugg ugaagugcuc ccacgagcgu agcauucauc uguucaucga cucccugcug 840
aacgaagaga accccuccaa ggccuaccgu ugcuccagca aggaggccuu cgagaagggc 900
cucugccuca gcugcaggaa gaacaggugu aacaaccugg gcuacgagau caacaaggug 960
agggccaaga ggagcuccaa gauguaucug aagacacgga gccagaugcc cuacaaggug 1020
uuccacuacc aggugaagau ccacuucucc gggacggaau cagagaccca cacgaaccag 1080
gccuuugaga ucagccugua ugggaccgug gccgaguccg agaacauccc cuucacccug 1140
cccgagguga gcaccaacaa aacuuacucc uuccugaucu acacugaagu ggacaucggg 1200
gagcugcuga ugcugaaacu caaauggaag agcgacagcu acuuuagcug gagcgacugg 1260
ugguccagcc ccggcuucgc cauccagaaa aucaggguca aagccggcga gacccagaaa 1320
aaggugaucu ucugcagcag ggaaaagguc agccaccugc agaaagggaa ggcccccgcu 1380
guguucguga aaugucacga caagagccug aacaaaaaga gcggc 1425

<210> SEQ ID NO 160
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 160
auggagagca aggcccugcu ggugcugacc cuggccgugu ggcugcaguc gcugaccgcc 60
agcaggggcg gcguggccgc ggccgaccag cgccgggacu ucaucgacau cgagagcaag 120
uuugcccuga ggacccccga ggauaccgca gaggacaccu gccaucugau ccccggcgug 180
gcagagagcg ucgccacuug ccacuucaac cauuccagca agacuuuuau ggucauccac 240
gguuggaccg ugaccggaau guacgagucc uggguccga aacugguggc cgcccuguac 300
aagcgggagc cagacuccaa cgugaucguc guggauuggc uguccagggc ccaggagcac 360
uaccccgucu ccgccggcua caccaagcug guggacaag acguggccag guucaucaac 420
uggauggaag aggaguucaa cuauccccug gacaacgugc aucuccuggg cuacagccuc 480
ggcgcccacg ccgccggcau cgcgggcagu cugacgaaca agaaggugaa caggaucacc 540
gggcuggacc ccgccggccc gaauuucgag uacgcggagg ccccgagcag gcugagcccc 600
gacgacgccg acuucgugga cgugcugcac acguucaccc gaggaagccc cggccggagc 660
aucggaaucc agaagcccgu gggccacguc gacaucuacc ccaauggcgg aaccuuccag 720
cccgggugca acauaggcga agccaucagg gugaucgccg aaagggggcu gggcgaugug 780
gaccagcugg ugaaguguuc acacgagagg uccauccacc uguuuaucga uagccugcug 840
aacgaggaga acccauccaa ggccuacagg ugcagcagca aggaggccuu ugagaagggc 900
cugugucugu cguguaggaa gaacaggugc aacaaucucg gcuacgagau caauaaggua 960
agggccaagc ggucgagcaa gauguaccuc aagaccagga gccagaugcc cuauaaggug 1020
uuccauuauc aggugaaaau ccacuuuagc ggcaccgaga gcgaaaccca caccaaccag 1080
gccuucgaaa ucucccugua cggcacugug gccgagagcg agaauauccc cuucacccug 1140
cccgagguca gcaccaacaa aaccuacagc uuccugaucu acaccgaggu cgacaucggc 1200
gaacugcuua ugcugaagcu gaaguggaaa agcgacagcu acuucagcug gagcgauugg 1260
uggagcagcc ccggcuuugc cauccagaaa auccgcguga aggcagggga gacccagaag 1320
aagguaauau ucugcagcag ggagaaggua agccaccugc agaaagguaa ggcccccgcc 1380
guguucguga aaugucacga caagucccug aauaagaagu ccggg 1425

<210> SEQ ID NO 161
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 161
auggagagca aggcccugcu ggugcugacg cuggcggugu ggcuccaguc ccugaccgcc 60
agccgggggg gcgucgccgc cgccgaccaa cgccgcgacu ucaucgacau cgaaaguaaa 120
uucgcccugc ggaccccega ggacaccgcc gaagacacgu gccaccugau cccuggaguu 180
gcggagagcg uggcgaccug ccacuucaac cacuccagca agacguucau ggugauccau 240
ggcuggaccg ucaccggcau guacgagagc ugggugccga agcucguggc cgcgcucuac 300
aagagggagc ccgacuccaa cgugaucgug gucgacuggc ugagcagggc ccaggagcac 360
uacccaguca gcgccggcua caccaagcug gugggccagg acguggcgcg guuuauaaac 420
uggauggagg aggaguucaa cuauccccug gauaacgugc accugcuggg cuacucccug 480
ggcgcccacg ccgccgggau cgccggaagc cugaccaaca agaaagugaa ccgcauuacc 540
gggcuggacc ccgccggccc caacuucgag uacgccgagg cacccagcag gcugagcccg 600
gacgacgcug acuuugugga cgugcugcac accuuuacca ggggcagccc cggucgaucc 660
aucgguauac agaagcccgu gggccacgug gacaucuauc ccaacggggg cacauuucaa 720
cccggcugca acaucggcga agccaucagg gucaucgccg agcgcggccu gggcgaugug 780
gaucagcugg ugaagugcuc ccacgagagg agcauccacc uguucaucga cagccuccuc 840
aaugaggaga aucccagcaa ggccuacagg ugcuccagca aggaggccuu cgagaagggu 900
cugugccugu ccugcagaaa aaacaggugc aacaaccugg gcuacgagau caacaaagug 960
agggccaaga ggucgagcaa aauguaccug aagaccagga gccagaugcc cuacaaggug 1020
uuccacuacc aggugaagau ccacuucagc gggacggaau ccgagacgca caccaaccag 1080
gccuucgaga ucucccucua cggcaccgug gccgagagcg agaauauccc cuucacccug 1140
ccggagguga gcacgaacaa gaccuacuca uuucugaucu auacggaggu cgauaucggc 1200
gagcugcuca ugcugaaacu gaaguggaag ucggacagcu acuucagcug gagcgauugg 1260
uggagcagcc ccggcuucgc gauccagaag aucaggguga aggccgggga gacgcagaag 1320
aaggugauuu ucuguuccag agagaaaguc ucccaccucc aaaaaggcaa ggcccccgcc 1380
guguucguga agugccauga caagucccug aacaagaaga gcggg 1425

<210> SEQ ID NO 162
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 162
auggagucaa aggcccuccu ggugcuuacc cucgccguuu ggcuccaguc ccugaccgcg 60
agccgcggcg ggguggccgc cgccgaccag aggcgagacu uuaucgacau ugaguccaag 120
uucgcccuga ggaccccega ggacaccgcc gaggacaccu gccaccugau ccccggugug 180
gccgagagcg ucgccacaug ccauuucaac cacucgagua aaaccuucau ggugauccac 240
ggcuggacug ugaccgggau guacgagucc uggguccccca agcucguggc cgcccuguac 300
aagagggagc ccgacagcaa cgugauugug guggacuggc uguccagggc ccaggaacac 360
uacccgguga gcgccggcua caccaagcug guggggccagg acguugcccg cuucaucaac 420
uggauggagg aggaguucaa cuaccccug gacaacgugc accugcuggg cuacagccug 480
ggggcccacg ccgccgggau cgcggggucc cugaccaaca aaaaggugaa caggaucacc 540
ggccuggauc cggccggacc caacuucgaa uacgccgaag ccccuagccg gcugagcccc 600
gacgacgccg acuucgugga cguccugcac accuucacaa gggggucccc uggucgcagu 660
aucgggaucc agaagccugu cggccacguc gauaucuacc ccaacggcgg gaccuuccag 720
cccggcugca acaucggcga ggccauccgg gugauugccg agaggggccu gggagacguc 780
gaccaguugg ugaaaugcag ccacgagagg agcauccacc uguucaucga cucccuccug 840
aacgaggaga accccagcaa ggccuaccgc ugcuccucca aggaggccuu cgagaaaggc 900
cugugucuga gcugccggaa gaaccggugc aauaaccucg gguacgagau caauaaggug 960
cgcgccaagc ggagcagcaa gauguaccug aagacaagga gccagaugcc cuacaaggug 1020
uuccacuacc aggugaaaau ccacuucagc ggcaccgaga gcgagaccca caccaaccag 1080
gccuucgaga ucagccugua uggcaccgug gccgaaagcg agaacauccc cuuuacacug 1140
cccgaggucu ccaccaacaa gacguacagc uuccugaucu acaccgaggu ggauaucggc 1200
gagcugcuga ugcugaagcu gaaauggaag agcgacagcu auuucucaug gagcgacugg 1260
uggagcuccc cgggcuucgc cauccagaag aucagggguga aggcgggcga gacacaaaag 1320
aaggucaucu ucugcuccag ggagaaggug agccaccugc agaagggcaa ggccccccgcc 1380 guguucguga aaugccacga caagagccug aauaagaaga gcggc 1425

<210> SEQ ID NO 163
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 163
auggagagca aggcccugcu ggugcugacc cuggccguuu ggcugcaguc ccugaccgcc 60
agccgcggug gcguggccgc cgccgaccag cggcgggauu ucaucgacau agaaucuaag 120
uuugcccuga ggaccccega ggacaccgcc gaggacaccu gccaccugau ccccggggug 180
gccgaguccg uggccacgug ucacuucaac cauagcagca agaccuuuau ggucauccac 240
ggcuggaccg ugacuggcau guacgagagc ugggugccca agcucguggc cgcccuguac 300
aagagggagc ccgacagcaa cgugaucgug guggacuggc ucagccgagc ccaggagcac 360
uaccccguca gcgccggcua caccaagcuc gugggccaag acguagccag guucaucaau 420
uggauggagg aggaguuuaa cuacccccuc gacaacgugc accuccuggg cuacucccug 480
ggcgcccaug ccgccggcau agccggaagc cugacuaaca aaaaagucaa ucggaucacc 540
ggccuagacc ccgccgggcc caacuucgaa uacgccgagg cccccuccag gcugagcccg 600
gacgacgccg acuuugugga cguccugcac accuucacga gagggucccc gggccggucg 660
aucggaaucc agaaacccgu ggggcaugug gacauuuacc ccaacggcgg caccuuccag 720
ccaggcugca acaucggcga agccaucagg gucaucgccg agaggggacu gggcgacgug 780
gaccagcugg ugaagugcag ccacgagcgg agcauccacc uguucaucga cagccugcug 840
aaugaggaga aucccagcaa ggccuacaga uguuccagca aagaggccuu cgagaaggga 900
cugugccugu ccugcagaaa gaacaggugc aauaaccugg guuacgagau aaauaaggug 960
agggccaaga gguccuccaa gauguaucug aagacccgca gccagaugcc uuacaagguc 1020
uuccacuacc aagugaaaau ccacuuuagc gggaccgaau cagagacgca cacaaaucaa 1080
gcuuucgaga ucagccugua cggcaccgug gccgaguccg agaacauccc cuucacccuc 1140
ccggaggugu ccaccaacaa gaccuacucc uuccugaucu auacagaggu ggacaucggg 1200
gagcugcuga ugcugaagcu gaaguggaaa uccgacagcu acuucagcug gagcgacugg 1260
uggagcagcc ccggcuuugc cauccagaaa aucaggguga aggccggaga aacucaaaaa 1320
aaggucaucu ucugcagccg cgagaaggug agccaccugc agaagggcaa ggcccccgcc 1380
guguucguga agugucacga caagucgcug aacaagaaga gcggu 1425

<210> SEQ ID NO 164
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 164
auggagucca aggcccuccu ggugcugacc cuggccgucu ggcugcaguc acugaccgcg 60
agcaggggcg gcguggccgc agcggaccag cgcagggacu ucaucgacau cgagagcaag 120
uucgcccuga ggacccccga ggacaccgcg gaagacaccu gccaccugau ccccggcgug 180
gccgaguccg uggccaccug ccacuucaau cacagcucca agaccuuuau ggugauccac 240
ggcuggaccg ugaccggaau guaugagagc ugggugccca agcucguggc cgcccuuuac 300
aagagggagc ccgacagcaa ugucauagug guggacuggc ugagcagggc ccaggagcac 360
uaccccguga gugccgggua caccaagcug gugggccagg acgucgcccg auucaucaac 420
uggauggagg aggaguucaa cuacccccug gacaacgugc aucugcuggg guacucccug 480
ggcgcgcacg cugccggcau cgcggggucc cuaaccaaca agaaggugaa caggaucacc 540
gggcuggacc ccgccggccc caauuucgaa uaugccgagg cccccagcag gcugagcccc 600
gacgacgccg acuucgugga cgugcugcau accuucacca ggggcagccc cggccggucg 660
auuggcauac aaaagcccgu gggccacgug gacaucuacc cgaacggggg caccuuccag 720
cccgggugca acauaggaga agccaucagg gugaucgcgg agaggggccu gggcgaugug 780
gaccagcugg ugaaaugcag ccacgaaagg uccauccacc uguuuaucga cagccugcug 840
aacgaggaga accccagcaa ggccuauagg ugcagcucaa aggaggccuu cgagaaggga 900

```
cugugccucu ccugcaggaa gaaccgcugu aacaaccugg gcuacgagau aaacaaggug     960

agggccaagc ggagcagcaa gauguaccug aagacucgcu cccagaugcc auacaaggug    1020

uuccacuacc aggugaagau ccacuucucc ggcacggaga gcgagaccca caccaaccaa    1080

gcguucgaga ucucccugua cgggacagug gccgaaucag agaacauccc cuuuacccug    1140

cccgagguga gcaccaauaa gaccuacucc uuccugaucu acacagaggu ggauaucggg    1200

gagcugcuga ugcugaagcu gaaguggaaa agcgacuccu acuucagcug gagcgauugg    1260

ugguccagcc ccggcuuugc cauccagaag aucaggguca aggccggcga gacgcagaag    1320

aaggugaucu ucugcucccg ggaaaaggug agccaccugc agaaaggcaa ggccccagcc    1380

guuuucguga agugccacga uaagucccug aacaagaaga gcggc                    1425
```

<210> SEQ ID NO 165
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 165

```
auggagagua aggcgcugcu cgugcucacg cuggcagugu ggcuccaguc ccugaccgcc      60

agccgcgggg ggguggccgc ggccgaccag aggagggacu ucaucgauau cgagagcaag     120

uucgcccugc ggacacccga ggauacagcc gaggacacau gccaccugau acccggcgug     180

gccgaaagcg uggccacgug ccacuuuaac cacuccagca agaccuucau ggucauccac     240

ggcuggaccg ucaccggcau guacgagagc ugggugccca agcuggucgc cgcccuguac     300

aagcgcgagc cugauagcaa cgugaucgug guggacuggc ugucccgggc ccaggagcac     360

uaccccguga gcgccggcua uacaaaacug gugggucagg acguggccag auucauaaac     420

uggauggaag aggaguuuaa cuacccccug gacaacgugc accugcuggg cuauagccug     480

ggcgcccacg ccgccggcau cgcgggcagc cucacuaaca agaaggugaa ucggauaacc     540

ggccuggauc ccgccgggcc caauuucgag uacgcggaag cccccagccg gcugagcccc     600

gaugacgccg auuucgugga cgugcugcac accuucacgc gcggcagccc cggccggagc     660

aucgguaucc agaaaccagu gggccaugug gacaucuacc caaauggcgg aaccuuccag     720

ccgggcugua acaucgguga agccauccgg gugaucgccg agaggggccu gggcgaugug     780

gaccagcugg ugaaauguag ccacgagcgc uccauccacc ucuucaucga cucccugcug     840

aacgaagaaa accccuccaa ggcguacagg uguagcagca aggaggccuu cgagaagggc     900

cugugccucu ccugccguaa gaacaggugu aacaaccugg gguacgagau caacaaggug     960

cgggccaaga ggagcagcaa gauguaccug aagacccgga gccagaugcc cuacaagguc    1020

uuccacuacc aggucaagau ccacuucagc ggcaccgaga gcgagaccca cacuaaccaa    1080

gccuucgaga ucagccugua cgggaccguc gccgagagcg agaacauccc cuucacccug    1140

cccgagguga gcaccaacaa aaccuacucc uuucugaucu acacggaagu ggacaucggc    1200

gagcugcuga ugcugaagcu gaaguggaaa agcgacagcu acuuuuccug guccgacugg    1260

uggagcagcc cgggcuucgc gauccagaag auccggguga aggccggcga gacccagaag    1320

aaggucaucu uuugcagcag ggagaaggug agccaccugc agaaggguaa ggcccccgcc    1380

guguucguga agugccacga caagagccug aacaagaagu ccgga                    1425
```

<210> SEQ ID NO 166
<211> LENGTH: 1425

<212> TYPE: RNA
<213> ORGANISM: Artificial Sequence
<220> FEATURE:
<223> OTHER INFORMATION: Synthetic Polynucleotide

<400> SEQUENCE: 166
auggagucca aggcccuccu ggugcugacc cuggccgugu ggcuccagag ccuaaccgcc 60
ucccggggcg gcguggccgc cgccgaucag aggcgggauu ucaucgacau agagagcaag 120
uucgcccucc gcacccccga agacaccgcc gaagacacuu gccaccugau ucccggagug 180
gccgaguccg uggccacuug ccacuucaac cacagcagca agaccuucau ggugauccac 240
ggcuggaccg uuaccggcau guacgaaagc ugggugccga agcucguggc cgcccuguac 300
aagagggagc ccgacuccaa cgugaucgug guugacuggc uguccagggc ccaggagcac 360
uaccccgugu ccgccggcua caccaagcug gucgggcagg acguggccag guucaucaac 420
uggauggaag aggaguucaa cuauccucug gacaaugugc accugcuggg cuacagccug 480
ggcgcccacg ccgcgggcau cgccggcagc cugaccaaua agaaagugaa uaggauuacc 540
ggccuggacc ccgcggggcc caacuucgag uacgccgaag cccccagcag gcugagcccc 600
gacgaugccg acuucgugga cguccugcac accuucaccc ggggcagccc cgggaggagc 660
auaggcauac agaaacccgu gggccacgug gacaucuacc ccaauggcgg cacguuccag 720
cccgggugca acaucgggga ggccaucagg gugaucgccg agaggggacu uggcgacgug 780
gaccagcugg ugaagugcag ccacgagcgc agcauacacc uguucaucga uagccugcuu 840
aacgaggaaa accccuccaa ggccuacagg ugcuccucaa aggaagcguu cgagaagggg 900
cugugucucu ccugcaggaa gaacagaugc aauaaccugg gcuacgagau caacaaggug 960
agggccaaga ggagcagcaa gauguaccug aaaacuagga gccaaaugcc cuauaaggug 1020
uuucacuacc aggugaagau ccacuucucc ggcaccgaga gcgagaccca cacaaaccag 1080
gccuucgaaa ucucgcugua cgggaccgug gccgagagcg aaaacauccc cuucacccug 1140
cccgaggugu ccaccaacaa gaccuacagc uuccugaucu acaccgaggu agacauuggu 1200
gagcugcuga ugcucaaacu caaguggaag agcgacuccu acuucagcug gagcgauugg 1260
ugguccuccc cgggcuucgc cauccagaag auacggguca aggcugggga aacccagaag 1320
aaggugaucu ucugcucccg ggagaagguc agccaccugc aaaaagggaa ggcgcccgcc 1380
gucuucguga agugccacga uaagagccug aacaagaagu caggc 1425

<210> SEQ ID NO 167
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 167
auggagagca aggcccugcu cgugcugacc cucgccgucu ggcugcagag ccugaccgcc 60
agcaggggcg gcguggccgc cgccgaucag aggcgggacu ucauagauau cgagagcaag 120
uucgcccuga ggacccccga agacaccgcg gaggacaccu gccaccugau ccccggcgug 180
gccgaguccg uggccaccug ccacuuuaac cacuccagca aaaccuuuau ggugauccau 240
ggcuggaccg ucaccgggau guacgagagc ugggugccca agcugguggc cgcccucuac 300
aagcgggaac ccgauagcaa cgugaucgug guagacuggc uguccagggc ccaagagcac 360
uaccccguga gugccggcua cacgaagcug gugggccagg acguggcccg cuucaucaau 420

-continued

```
uggauggagg aggaguucaa cuacccgcuc gauaacgugc accugcuggg cuauagccug    480

ggggcccacg ccgccgggau cgccggcagc cucaccaaca agaaggugaa caggaucacc    540

ggccucgacc ccgccggccc caacuucgaa uacgccgagg cccccagcag gcugagcccg    600

gaugacgccg acuuugugga cgugcuccac accuucacca ggggcucccc cggccggucc    660

aucgggaucc agaagcccgu cgggcacgug gacaucuacc ccaauggggg gaccuuccaa    720

cccggcugca acaucggcga ggcgaucagg gugaucgccg agcgcggccu gggggacgug    780

gaccagcugg ugaaauguuc ccaugagcgg agcauccauc uguucauuga cucccugcug    840

aacgaggaga accccuccaa ggccuaccgg ugcuccagca aggaggccuu cgagaagggu    900

cugugccuga gcugcaggaa gaaucgaugu aacaaccugg gcuacgagau caacaaggug    960

cgcgccaaga ggagcagcaa gauguaccug aagaccagga gucaaaugcc cuacaaggug   1020

uuccacuacc aggugaagau ccacuucagc ggcacggaau ccgagaccca caccaaucag   1080

gccuucgaga ucagccucua cgggaccgug gccgagagcg aaaacauccc cuucacccug   1140

cccgaggugu caaccaauaa gaccuacagc uuccugaucu acaccgaggu ggauaucggc   1200

gagcugcuga ugcugaagcu gaaguggaag agcgauagcu acuucucgug gagcgacugg   1260

uggagcagcc ccggcuucgc cauccagaag aucaggguga aggccggcga gacccaaaag   1320

aaagugaucu uuugcagcag ggagaaggug ucccaccucc agaagggaaa ggcccccgcg   1380

guguucguaa agugccauga caagucccug aacaaaaaga gcggg                   1425
```

```
<210> SEQ ID NO 168
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 168

auggaaucca aggcccuacu cgugcucacc cuggccgugu ggcugcagag ccugaccgca     60

agcagggggg gcguggccgc cgcggaccaa aggagggauu ucauugauau cgagagcaag    120

uucgcccuca ggacccccga ggacacagcc gaggacaccu gccaccugau ccccggcgua    180

gccgaguccg uggccaccug ccacuuuaau cacuccucca agaccuucau ggugauacac    240

ggguggaccg ugaccgggau guaugaaagu ugggugccaa aacugguggc cgcccuguac    300

aagagggagc ccgacuccaa cgucaucguc guggauuggc ugagccgggc ccaggagcac    360

uaucccguca gcgcuggcua uacgaagcug gugggccagg acgucgcccg guucaucaau    420

uggauggagg aggaguucaa cuacccccug gacaacgugc accugcuggg cuauagccuc    480

ggcgcccacg ccgccgguau cgcuggcagc cugaccaaca agaaggugaa ccggaucacc    540

ggccuggacc cggccggccc aaacuuugag uacgccgagg cccccuccag gcuguccccc    600

gacgacgccg acuucgugga cguccugcac accuucaccc gugggucccc cggacggagc    660

aucgggauuc agaaacccgu gggccaugug gacauuuacc ccaacggggg gaccuuccaa    720

cccgggugca acaucggaga ggcgaucagg gugaucgcug agcggggccu cggggacguc    780

gaccagcugg ugaagugcag ccacgagcgc uccauccacc uguucaucga cagccugcug    840

aacgaggaaa accccagcaa ggcguauagg ugcucgucga aggaggccuu cgaaaagggc    900

cugugccugu cgugccgaaa gaacaggugu aacaaccugg guuacgagau caacaaggug    960

agggccaaaa ggagcuccaa gauguaucug aagacccggu cccagaugcc cuauaaggug   1020

uuccacuauc aggugaagau ccacuuuagc ggaaccgaaa gcgaaaccca cacaaaccaa   1080
```

gccuucgaga ucucccugua cggcaccguc gccgaguccg agaacauccc cuucacccug 1140
cccgagguga gcacuaacaa gaccuacagc uuccucaucu acacggaggu ggacauaggc 1200
gagcugcuga ugcugaagcu gaaguggaag uccgacuccu auuucagcug gagcgacugg 1260
ugguccuccc ccgggguuugc cauccaaaag auaagggguga aggccggcga gacccaaaag 1320
aaggugaucu ucuguuccag ggaaaaggug agccaccugc agaagggcaa ggccccccgcu 1380 guguucguua agugccacga caagucccug aacaagaaga gcggc 1425

<210> SEQ ID NO 169
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 169
auggagucca aggcccugcu ggugcugacc cuugccgugu ggcugcagag ccugaccgcc 60
agcaggggcg gcgucgccgc cgcggaccag cgcagggacu uuaucgauau cgagagcaag 120
uucgcccuga ggacacccga ggacaccgcc gaggacacau gccaucugau cccaggcguu 180
gcggagagcg uggcuaccug ccacuucaau cacagcagca aaaccuuuau ggucauccac 240
ggcuggacgg ugaccggcau guacgagagc ugggugccaa agcuggugc cgcccuguac 300 aagagggaac ccgacagcaa cgugaucgug guggauuggu uauccagggc gcaggagcac 360
uaucccguca gcgccggcua caccaagcug gugggccagg acgucgccag guucaucaau 420
uggauggagg aggaauucaa uuaucccccug gauaacguac accuccuggg cuacagccuc 480
ggagcccacg ccgcgggaau agccgggagc cucacgaaua agaagguuaa caggaucacc 540
ggccuggauc ccgccggccc caacuucgag uacgcagagg caccguccag gcuguccccc 600
gacgacgccg acuucgugga cguccugcac accuucacca ggggcucccc cgggcguagc 660
aucggcaucc aaaagcccgu gggccacgug gacaucuacc ccaacggcgg caccuuccag 720
cccgggugca acaucggcga ggcgauccgg gugauagcgg aacgcgggcu gggcgacgug 780
gaucagcugg ucaaguguag ccaugagcgc agcauccacc uguucaucga cucccugcuc 840
aacgaagaaa accccagcaa ggccuaccgg ugcucgagca aggaagcguu cgagaagggc 900
cugugccuga gcugcaggaa gaauaggugc aauaaucugg gcuaugagau caacaaggug 960
cgggccaagc gaagcucuaa aauguaccug aagacucggu cccagaugcc guacaaggug 1020
uuccacuacc aggugaagau ccacuucagc gggaccgaau ccgaaacgca caccaaccaa 1080
gccuucgaga ucagccugua cgggaccguc gccgagagcg agaacauccc cuucacccug 1140
cccgaggugu ccacaaacaa gacguacagc uuccucaucu auaccgaggu cgacaucggg 1200
gagcugcuga uguuaaaacu gaaguggaag agcgacuccu auuuuagcug guccgacugg 1260
uggagcagcc ccggcuucgc cauccagaag aucaggguca aggccgguga gacgcagaag 1320
aaggugauuu ucugcagcag ggaaaaagug ucccaucucc agaaggguaa ggcgccggcc 1380
guguuuguaa aaugccacga caagagucug aacaaaaaga gcggc 1425

<210> SEQ ID NO 170
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 170
auggagucca aggccuugcu gguucugacc cuggccgugu ggcugcagag ccugacggcc 60
ucgagggggg gcgucgcggc ggccgaccag cggagggacu ucaucgacau cgagagcaaa 120
uuugcccugc ggacccccga agacaccgcg gaggauaccu gucaccugau ucccggcgug 180
gcugaaagcg uggcaaccug ccacuucaac cacucaagca agacguuuau ggucauacac 240
ggguggaccg ugaccggaau guacgagagu ugggugccca aacugguggc cgcccuguac 300
aagagggaac ccgacagcaa ugugauagug guggacuggc ugucccgggc ccaggagcac 360
uacccgguga gcgccggcua caccaagcug gugggccagg acguggcccg guucaucaac 420
uggauggagg aggaguucaa cuaucccug gauaacgugc accuccuggg guacagccug 480
ggggcccacg ccgccggaau cgccggcagc cugaccaaca agaaggugaa caggaucacu 540
ggccucgacc ccgccggccc gaacuuugag uaugccgagg ccccgagccg gcuguccccc 600
gacgacgccg acuucgucga cgugcuccac accuucacga gggggagccc cggccggagc 660
aucggcauac aaaagcccgu gggacacgug gacaucuacc ccaacggcgg caccuuucag 720
ccgggcugua auaucggcga ggccaucccgc gugaucgccg agaggggccu gggggacgug 780
gaccaacugg ugaaguguag ccacgaaagg uccauccacc ucuucaucga cagccuccug 840
aacgaggaga accccuccaa ggccuacagg ugcagcucua aagaggcguu cgagaagggg 900
cuuugccuga gcugcaggaa gaauaggugc aacaaccugg gcuacgaaau caacaaggug 960
cgggccaagc gcagcagcaa aauguaccug aagacccgua gccagaugcc cuacaaggug 1020
uuucacuacc aggugaaaau ccauuucagc ggcaccgaaa gcgaaacgca caccaaccag 1080
gccuucgaga ucucccugua cggggaccguc gcagagagcg agaacauccc cuucacgcuc 1140
ccugaggugu cgaccaacaa gaccuauucc uuccugaucu auaccgaggu ggauaucgga 1200
gagcugcuga ugcugaagcu caaauggaaa agcgacagcu auuucucaug guccgacugg 1260
uggagcagcc cgggauucgc cauccagaag aucagggguga aggccgggga gacccagaag 1320
aaggugaucu uuugcagccg cgaaaaggug agccaccugc agaagggcaa ggcccccgcg 1380
guguucguca agugucacga uaaaagucug aacaagaaga gcggc 1425

<210> SEQ ID NO 171
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 171
auggagagca aagcgcuacu ggugcugacc cucgccgugu ggcuacagag ccugaccgcc 60
ucgcggggcg gcguggccgc cgcugaccag aggcgggacu ucaucgacau cgagagcaag 120
uucgcccugc gcaccccaga ggacaccgcc gaggauaccu gucaccucau ccccggcguc 180
gccgagagcg uggcgaccug ccacuuuaac cacagcagca agaccuucau ggugauccac 240
ggcuggaccg ugacgggcau guacgagucc ugggugccca aacugguggc ggcucuguac 300
aagagggagc ccgacaguaa cgugauuguc guggacuggc ugagccgcgc ucaagaacac 360
uaucccguau ccgccgguua caccaagcug gugggccagg acguggcgcg auucauuaac 420
uggauggagg aggaguuuaa uuacccccug gauaacgugc aucugcuggg guauagccug 480
ggcgcccacg ccgccggcau agccggcucc cugaccaaca agaaggucaa ccgaaucacc 540
ggccuggacc ccgccggccc caacuuugag uacgccgagg cccccagcag gcugucccccc 600 gaugaugccg acuucgugga cgugcugcau acguucaccc gcgggagccc cgggaggagc 660
aucggcauac agaaacccgu gggccacgug gacauauacc ccaacggcgg aacguuccag 720
ccggggugca acaucggcga ggccauccgg gucaucgccg agagggggcu gggcgaugug 780
gaccaacugg ugaagugcuc ccaugaacgg uccauccauc uguucaucga cagccugcug 840
aacgaggaga accccagcaa ggccuacagg uguagcagca aggaggccuu cgagaaaggc 900
cugugucuga gcugcagaaa gaacaggugc aacaaccucg gcuacgagau caacaaggug 960
agggccaaga gguccagcaa aauguaucug aagaccagga gccagaugcc auacaagguc 1020
uuucacuacc aggucaagau ccauuucucc ggcaccgagu ccgaaaccca caccaaccag 1080
gcguucgaaa ucagccugua cggcaccgug gccgagagcg agaacauccc cuucacccuu 1140
cccgaggugu ccaccaacaa gaccuacagc uuccucaucu acaccgaggu ggauaucggc 1200
gagcugcuga ugcugaagcu gaaguggaag agcgacagcu acuucagcug gucggacugg 1260
uggagcuccc ccggcuucgc gauccagaaa auccguguga aagccgggga gacccagaag 1320
aaggugauau ucugcucccg ggagaaggua agccaccugc agaaggggaa ggcccccgcc 1380
guguucguua agugccacga caagagccua aacaaaaagu ccggc 1425

<210> SEQ ID NO 172
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 172
auggagucua aagcccugcu ggugcugacc cucgccgugu ggcugcaguc gcugaccgcc 60
ucccgcggcg ggguggccgc agccgaccag cgcccgggacu ucauugacau cgagagcaag 120
uucgcccugc gaacccccga ggauaccgcc gaggacaccu gccaccugau ccccggaguc 180
gccgagagcg uggccaccug ccacuuuaau cauagcagca agaccuucau ggugauccac 240
ggcuggacgg ugaccgggau guacgagagc ugggucccca agcugguggc cgcccuuuau 300
aaaagggagc ccgauaguaa cgugaucgug guggacuggc uguccagggc ccaagagcac 360
uaccccgugu ccgccggcua caccaagcug gugggccagg acguggccag guucaucaau 420
uggauggagg aggaauuuaa uuacccccug gacaaugugc accuccuggg cuacucgcug 480
ggcgcucacg ccgccggcau agccggcagc cugaccaaca agaaagugaa caggaucacg 540
ggccuggacc ccgccggccc caacuucgag uacgccgagg cccccagccg ucugagcccc 600
gacgacgccg acuuugugga cgugcugcac accuucacca gggggagucc ugggcggagc 660
aucggcaucc aaaagccggu gggccacgug gacaucuacc cgaacggugg uacguuucag 720
cccgggugca acaucgggga agccaucagg gugaucgccg agagggggcu gggcgacgug 780
gaccagcugg ugaagugcuc ccacgagagg uccauccacc uguucaucga cucccuucuc 840
aacgaagaaa acccgagcaa ggccuacagg uguagcagca aggaagccuu cgagaagggg 900
cugugccugu ccuguaggaa aaacaggugc aacaaccucg gcuacgagau caacaaggug 960
cgcgcuaagc gcuccagcaa gauguaccug aagacaaggu cacagaugcc cuacaaggug 1020
uuccacuacc aggugaaaau ccacuuuagc ggcaccgaaa gcgaaacgca caccaaccag 1080
gcguuugaga ucagcuuaua ugggaccgug gccgaguccg agaacauccc cuucacccug 1140
cccgaaguga gcaccaacaa gaccuauagc uuccugaucu acaccgaggu ggauaucggg 1200

-continued

```
gagcugcuga ugcucaaacu gaaauggaag agcgauagcu acuucuccug gagcgauugg   1260

uggagcagcc ccggcuucgc gauccagaag auccgcguga aggcggggga gacccagaag   1320

aaggugaucu uuugcagcag ggagaaggug agccaccugc agaaaggcaa ggcccccgcg   1380

guguuuguca agugccacga caagagccuc aacaagaaau ccggc                   1425
```

<210> SEQ ID NO 173
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 173

```
auggaaucga aggcccugcu ggugcugacg cuggcggugu ggcugcagag ccugaccgcc     60

ucccgcggcg gcgucgccgc cgccgaccag aggcgggacu ucaucgauau cgagagcaag    120

uucgcccuga ggaccccega agauaccgcc gaagacacgu gccaccugau cccgggcgug    180

gcggagucug uggccaccug ccacuucaac cacagcagca agaccuucau ggugauccac    240

ggguggaccg ugaccggcau guacgagagc ugggugccca agcuggucgc cgcgcuguac    300

aaaagggagc ccgacagcaa cgucaucguc guggacuggc ugagcagggc acaggagcau    360

uaccccgucu ccgccgguua caccaaacug guggggcagg acguggcgag guuuaucaac    420

uggauggagg aggaguucaa cuacccccug gauaacgugc accugcuggg guacagccug    480

ggggcccacg ccgcaggcau agccgggagc cugaccaaua agaaaguaaa ccggaucacg    540

gggcuggacc ccgccgggcc caauuuugag uaugccgagg cccccagccg gcuguccccc    600

gacgacgcag acuucgugga cgugcugcac accuucaccc gaggcagccc gggaagaagc    660

aucggcaucc agaagcccgu gggccacgug gacaucuacc ccaacggagg caccuuccag    720

ccaggcugua acaucggcga ggccaucagg gugaucgccg aacgcggccu gggcgacgug    780

gaccaacucg ugaagugcuc ccacgagcgc agcauccacc ucuucaucga cagccugcug    840

aaugaggaga aucccagcaa ggcauauagg ugcagcagca aggaggccuu ugagaagggc    900

cugugccugu caugccggaa gaacaggugc aacaaccugg gcuacgagau caacaagguc    960

agggccaaac gcagcuccaa gauguaccug aagacccgga gccaaaugcc cuacaaggug   1020

uuucacuacc aggugaagau ccauuuuucc ggcacggaga gugaaaccca caccaaccag   1080

gccuucgaga uaagccugua cggcaccgug gccgagagcg agaacauccc cuucacccug   1140

cccgagguga gcacgaauaa gaccuacagc uuccugaucu acacggaggu ggacaucggc   1200

gagcugcuga ugcugaagcu gaaauggaaa uccgacagcu acuucagcug guccgacugg   1260

uggagcuccc ccggcuucgc cauccagaag aucagggug a aggccgggga gacccagaaa   1320

aaggugaucu ucugcagcag ggagaaaguc agccaucugc agaaggggaa ggcccccgcg   1380

gucuucguga agugccacga caagagccug aacaagaaga gcggc                   1425
```

<210> SEQ ID NO 174
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 174

```
auggaaagca aggcccugcu gguccugacc cucgccgugu ggcuccagag ccugaccgcc     60

agccggggcg ggguggccgc cgccgaccag cgacgggacu ucauagacau cgagagcaag    120
```

```
uuugcccugc gcacgcccga ggacacggcc gaggacaccu gccaucugau ccccggcgug    180
gccgagagcg ucgccaccug ccacuuuaac cacagcagca aaaccuucau ggugauccac    240
ggauggaccg ugaccggaau guacgagagc uggguaccaa agcuggucgc cgcccuguac    300
aaaagggaac ccgauagcaa cgugaucgug guggacuggc ucuccagggc ccaagagcac    360
uaccccguca gcgccggcua caccaagcug gugggacagg acguggcccg uuucaucaau    420
uggauggagg aggaguucaa uuacccccug gacaacgugc accugcuggg cuacucccug    480
ggagcccacg ccgccgggau agccggcucc cucaccaaca agaaggucaa ccggaucacu    540
ggccucgauc ccgccggacc caacuuugag uacgccgaag cccccucgag gcugagcccc    600
gacgacgccg auuuugugga cguccuccac accuucaccc gcggguccccc cggcaggagc   660
aucggcaucc agaagcccgu gggccacgug gacaucuauc ccaacggcgg caccuuccag    720
cccggcugua acaucggcga agccauccgg gugaucgccg aacggggccu gggcgaugug    780
gaccagcugg ugaaauguag ccacgagagg agcauccacc uguuuaucga uagcuugcug    840
aacgaggaga acccauccaa agcguacagg ugcagcucca aggaggccuu cgaaaagggc    900
cugugccucu ccugcaggaa gaaccggugc aacaaccugg gguaugagau caacaaagua    960
agggcgaaga ggagcuccaa gauguaccug aagacuagga gccagaugcc cuacaaggug   1020
uuccacuauc aggugaaaau ccacuucagc ggcacagaaa gcgagaccca caccaaccag   1080
gccuucgaga ucucucugua uggcaccgug gccgagagcg agaacauacc cuucacccug   1140
cccgaaguga gcaccaacaa aaccuacagc uuccugaucu acaccgaggu ggacaucggc   1200
gagcucccuca ugcucaagcu gaaguggaag uccgacagcu acuucucgug gagcgacugg  1260
uggucgagcc ccggcuucgc cauccagaag auccggguga aagccggcga gacccagaag   1320
aaggucaucu uuugcagcag ggagaaggug agccaucucc agaagggcaa agcuccagcc   1380
guguucguca agugccacga caagucccug aacaagaaga gcggc                  1425
```

<210> SEQ ID NO 175
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 175

```
auggagucca aagcgcuucu ggugcucacc cuggcggugu ggcugcagag ccugaccgcc     60
uccagaggcg gcguggccgc cgccgaccag cggagggacu ucaucgacau cgagagcaag    120
uucgcacuca ggaccccgga ggauaccgcc gaggacaccu gccaccugau ccccggugug    180
gccgagucag uggccaccug ucauuucaac cacagcagca agaccuucau ggugauccac    240
ggcuggaccg ucaccggcau guacgagagc ugggugccca agcucgucgc ggcgcucuac    300
aagcgggagc cagacagcaa ugugaucgug guggacuggc ucagccgggc ccaggagcac    360
uacccggugu ccgccgggua cacgaagcug gugggccagg acgucgcccg cuuuauaaac    420
uggauggagg aagaguucaa cuacccccug gacaacgugc accugcucgg uuacagccuc    480
ggggcccacg ccgccggaau cgcggguucc cucaccaaca agaaggugaa uaggaucacc    540
gggcuggacc ccgccggccc caauuucgag uacgccgagg cccccucgcg gcugagcccc    600
gacgacgccg acuuugugga cgugcugcac accuucaccc ggggcagccc ugggagaucc    660
aucggcauac agaagcccgu cggccacgug gacaucuacc ccaacggggg gaccuuucag    720
```

```
cccgggugca auaucgggga agccauuagg gugaucgccg agaggggucu gggggacguc    780

gaccagcucg ugaaauguuc ccacgagagg agcauccacc uguucauaga cagccugcug    840

aaugaggaga accccuccaa agccuaccgc ugcagcagca aggaggccuu cgaaaagggg    900

cugugccuga gcugcaggaa gaauaggugu aacaaucugg gcuacgagau caacaaggug    960

cgggcgaaga gguccucuaa gauguaucuu aagacccgaa gccaaaugcc cuauaaggug   1020

uuccacuacc aagugaagau ccauuuuucc gggaccgaga gcgagaccca uaccaaccag   1080

gccuucgaga ucucccugua cgggacagug gccgaguccg aaaacauccc cuucacccug   1140

cccgaaguga gcaccaacaa gaccuacucc uuucugaucu acaccgaggu ggacaucggc   1200

gagcugcuga ugcugaagcu gaaguggaag agcgauagcu acuucagcug gucagacugg   1260

uggagcagcc ccggcuucgc aauccagaag aucagggaga aggccggcga gacgcagaag   1320

aaagugaucu ucugcagcag ggagaaggua agccaucucc agaagggcaa agcccccgcc   1380

guguucguga agugucacga caagucccug aacaaaaaaa gcggu                  1425


<210> SEQ ID NO 176
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 176

auggaaagca aagcccugcu gguacucacg cucgccgucu ggcugcaguc ccugaccgcc     60

agcagaggcg gcgucgcggc cgccgaucag agaagagacu ucaucgacau cgaaagcaag    120

uucgcgcuga ggaccccgga agacaccgcc gaggacacgu gccaccugau ccccggcgug    180

gccgagagcg uggccacgug ucacuucaac cacuccucca agaccuuuau ggugauccac    240

ggcuggacgg ugaccggaau guacgagagc ugggugccga agcugguggc cgcccuguac    300

aagcgggagc cggacagcaa cgugaucgua guggacuggc ugagcagggc ccaggagcau    360

uaucccguga gcgccggcua cacuaagcug gugggccagg acguggcccg guucauaaac    420

uggauggagg aagaguucaa cuacccacug gacaauguccc accuccuggg cuacagccug    480

ggcgcccacg ccgccggcau cgccgggucc cucaccaaca agaaggucaa ccggaucaca    540

ggccucgacc ccgccggccc caacuuugag uacgccgagg cccccucaag gcugagcccc    600

gacgacgccg acuucguaga cgugcugcac accuuuacuc gcggcagccc ggguaggucg    660

aucgggaucc agaagccugu cggccaugug gacaucuacc ccaacggcgg caccuuccaa    720

cccggaugua acaucggcga ggccauccgg gugaucgccg aacgcgggcu gggagacgug    780

gaccaacugg ugaagugcag ccacgagagg agcauccacc uguucaucga cagccugcug    840

aacgaggaga accccagcaa agccuauagg ugcagcagca aggaggccuu cgaaaaaggc    900

cucugccugu ccugcaggaa aaaccguugc aacaaccugg gcuacgaaau caacaaggug    960

cgagccaaaa ggagcagcaa gauguaccug aagaccaggu cccagaugcc guauaaggug   1020

uuccacuacc aggugaagau ccauuucucc ggaaccgagu cggaaaccca cacuaaccag   1080

gccuucgaga ucagccugua cggcacgguc gccgaguccg aaaauauccc cuucacccuc   1140

cccgaagugu ccaccaacaa gacauacagc uuccugaucu acaccgaggu ggacaucgga   1200

gagcugcuga ugcucaagcu gaaguggaag agcgacagcu acuucagcug gagcgacugg   1260

ugguccucgc cgggcuucgc cauccaaaag auccgcguca aggccgggga gacccagaag   1320

aaggucaucu ucuguuccag ggagaaggug agccaccucc agaagggcaa ggcccccgcc   1380
```

guguucguga agugccauga caagagccug aacaagaaga gcggc 1425

<210> SEQ ID NO 177
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 177
auggagagca aggcccugcu ggugcugacc cuggccgugu ggcugcaguc acucaccgca 60
uccagggggg gaguggccgc cgccgaccag aggcgggacu ucaucgauau cgagagcaag 120
uucgcccucc ggaccccga ggacacagcc gaggacaccu gccaccugau ccccggggug 180
gccgagucag uggcgaccug ccauuucaac cacuccagca agaccuuuau ggucauccac 240
ggcuggaccg ugaccggcau guacgagucc ugggucccca agcugguggc cgcgcuguau 300
aagcgggaac ccgacuccaa ugugaucguc guggauuggc ugagccgugc ccaggagcau 360
uaccccguga gcgccggcua caccaaguug gugggacagg acguggccag guucaucaac 420
uggauggagg aggaguucaa cuacccccug gauaacgugc accugcuggg cuacucccug 480
ggggcgcaug ccgcgggcau cgccgggagc cugaccaaca agaaggugaa uaggaucacc 540
ggccuggauc ccgccggccc gaacuucgag uacgccgagg cccccagcag gcugagcccg 600
gacgacgccg acuucgugga cguccuccac accuucacca gggggagccc cgggaggagc 660
auuggaaucc agaagcccgu gggccacgug gacaucuauc ccaauggcgg gacguuccaa 720
ccuggcugca acaucgguga agccauccgc gugaucgccg agcgcggccu gggcgacgug 780
gaccagcugg ugaagugcag ucacgagagg agcauccacc uguucaucga uagccugcug 840
aacgaggaga accccagcaa ggccuacagg ugcuccagca aggaggccuu cgagaagggc 900
cucugccuga gcugccgcaa gaaccggugc aacaaccucg gguacgaaau caauaaggug 960
cgggccaaga gguccagcaa gauguaucug aagacccgga gccagaugcc cuacaaggug 1020
uuccacuacc aagugaagau ccacuuuucg gguacggagu ccgagacgca caccaaccag 1080
gccuuugaaa ucagccucua cggcaccgug gccgaaagcg agaacauccc cuuuacccug 1140
cccgagguca gcaccaacaa gaccuauucc uuccugaucu acaccgaggu ggacaucggc 1200
gaacuccuga ugcugaagcu gaaguggaag uccgacagcu acuuuuccug gagcgacugg 1260
ugguccagcc ccggguucgc cauacagaag auccggguga aggcagggga gacgcagaaa 1320
aaggucaucu ucugcagccg ugaaaaggug agucaccucc aaaagggcaa ggcgcccgcc 1380
guguucguaa agugccacga uaagagccug aacaaaaaaa gcggc 1425

<210> SEQ ID NO 178
<211> LENGTH: 1425
<212> TYPE: RNA
<213> ORGANISM: Artificial Sequence
<220> FEATURE:
<223> OTHER INFORMATION: Synthetic Polynucleotide

<400> SEQUENCE: 178
auggagagca aggcccugcu ggugcugacc cuggccgugu ggcugcagag ccugaccgcc 60
agccggggag gcguggccgc cgccgaccag cggcgggacu ucaucgacau cgaguccaag 120
uucgcccugc ggacgcccga ggacaccgcc gaagacaccu gccaccugau ccccggcguc 180
gccgagagcg uggccacaug ccacuucaac cacagcagca agaccuucau ggugauccac 240
ggcuggaccg ugaccggcau guacgagagc ugggugccca agcugguggc cgcucuguac 300
aagcgggagc ccgacagcaa cgugaucgug guggacuggc ugagccgggc ccaggagcac 360
uaccccguga gcgccggcua caccaagcuc gucggccagg acguggcccg guucaucaac 420
uggauggagg aggaguucaa cuacccgcug gacaacgugc accugcuggg cuacagccug 480
ggcgcccacg ccgccggcau cgccggcagc cucaccaaca agaaggugaa ccggaucacc 540
ggccuggacc ccgccggccc caacuucgag uacgccgagg cgcccagcag gcucucgccc 600
gacgacgccg acuucgugga cgugcugcac accuucaccc ggggcucucc cggacggagc 660
aucggcaucc agaagcccgu gggccacgug gacaucuacc ccaacggcgg caccuuccag 720
cccggcugca acaucggcga ggccauccgg gugaucgccg agcggggucu gggcgacgug 780
gaccagcugg ugaagugcag ccacgagcgg agcauucacc uguucaucga uagccugcug 840
aacgaggaga accccuccaa agcauaccgg ugcaguagua aggaggccuu cgagaagggc 900
cugugccuga gcugccggaa gaacagaugc aacaaccuug gguacgagau caacaaggug 960
cgggccaaga gaucuuccaa gauguaccug aagacccgga gccagaugcc cuacaaggug 1020
uuccacuacc aggugaagau ccacuucagc ggcaccgaaa gcgaaacuca caccaaccag 1080
gccuuugaaa ucagccugua cggcaccgug gccgagucug agaacauccc uuucacacug 1140
cccgagguga gcacuaacaa gaccuacagc uuccugaucu acaccgaggu ggacauuggc 1200
gagcugcuga ugcugaagcu gaaguggaag ucagacagcu acuucagcug gagcgacugg 1260
uggucuagcc ccggauucgc cauccagaag aucaggguga aggccggaga gacacagaag 1320
aaagugaucu ucugcagccg ggagaaggua agccaccugc agaagggcaa ggcucccgcc 1380
guguucguca agugccacga caagucccug aacaagaagu ccggc 1425

<210> SEQ ID NO 179
<211> LENGTH: 1614
<212> TYPE: RNA
<213> ORGANISM: Artificial Sequence
<220> FEATURE:
<223> OTHER INFORMATION: Synthetic Polynucleotide

<400> SEQUENCE: 179
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180
cccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccccuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggccc ccagcaggcu cucccccgac gacgccgacu 660
ucguggacgu gcugcacacc uucacccggg gcucuccccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcugguga 840
agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccaaaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggccu 1500
agcuucuugc cccuugggcc uccccccagc cccuccuccc cuuccugcac ccguaccccc 1560
uccauaaagu aggaaacacu acaguggucu uugaauaaag ucugaguggg cggc 1614

<210> SEQ ID NO 180
<211> LENGTH: 1613
<212> TYPE: RNA
<213> ORGANISM: Artificial Sequence
<220> FEATURE:
<223> OTHER INFORMATION: Synthetic Polynucleotide

<400> SEQUENCE: 180
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180
cccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccccuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggccc ccagcaggcu cucccccgac gacgccgacu 660
ucguggacgu gcugcacacc uucacccggg gcucuccccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcuggug a 840 agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccaaaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggccu 1500
agcuucuugc cccuugggcc uccccccagc cccuccuccc cuuccugcac ccguaccccc 1560
cgcauuauua cucacgguac gaguggucuu ugaauaaagu cugagugggc ggc 1613

<210> SEQ ID NO 181
<211> LENGTH: 1591
<212> TYPE: RNA
<213> ORGANISM: Artificial Sequence
<220> FEATURE:
<223> OTHER INFORMATION: Synthetic Polynucleotide

<400> SEQUENCE: 181
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180
cccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccccuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggccc ccagcaggcu cucccccgac gacgccgacu 660
ucguggacgu gcugcacacc uucacccggg gcucucccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcugguga 840
agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccaaaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggccu 1500
agcuucuugc cccuugggcc uccccccagc cccuccuccc cuuccugcac ccguaccccc 1560
guggucuuug aauaaagucu gagugggcgg c 1591

<210> SEQ ID NO 182
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 182
gggaaauaag agagaaaaga agaguaagaa gaaauauaag agccaccaug gagagcaagg 60
cccugcuggu gcugacccug gccgugugc ugcagagccu gaccgccagc cggggaggcg 120
uggccgccgc cgaccagcgg cgggacuuca ucgacaucga guccaaguuc gcccugcgga 180
cccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccccuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggccc ccagcaggcu cucccccgac gacgccgacu 660
ucguggacgu gcugcacacc uucacccggg gcucucccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcugguga 840
agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccaaaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcgcuggagc cucgguggcc augcuucuug 1500
ccccuugggc cuccccccag ccccuccucc ccuuccugca cccguacccc cuccauaaag 1560
uaggaaacac uacaguggUc uuugaauaaa gucugagugg gcggc 1605

<210> SEQ ID NO 183
<211> LENGTH: 1613
<212> TYPE: RNA
<213> ORGANISM: Artificial Sequence
<220> FEATURE:
<223> OTHER INFORMATION: Synthetic Polynucleotide

<400> SEQUENCE: 183
gggaaauaag agagaaaaga agaguaagaa gaaauauaag agccaccaug gagagcaagg 60
cccugcuggu gcugacccug gccgugugc ugcagagccu gaccgccagc cggggaggcg 120
uggccgccgc cgaccagcgg cgggacuuca ucgacaucga guccaaguuc gcccugcgga 180
cccccgagga caccgccgaa gacaccugcc accugauccc cggcgucgcc gagagcgugg 240
ccacaugcca cuucaaccac agcagcaaga ccuucauggu gauccacggc uggaccguga 300

```
ccggcaugua cgagagcugg gugcccaagc ugguggccgc ucuguacaag cgggagcccg    360

acagcaacgu gaucguggug gacuggcuga gccgggccca ggagcacuac cccgugagcg    420

ccggcuacac caagcucguc ggccaggacg uggcccgguu caucaacugg auggaggagg    480

aguucaacua cccccuggac aacgugcacc ugcugggcua cagccugggc gcccacgccg    540

ccggcaucgc cggcagccuc accaacaaga aggugaaccg gaucaccggc cuggaccccg    600

ccggccccaa cuucgaguac gccgaggccc ccagcaggcu cucccccgac gacgccgacu    660

ucguggacgu gcugcacacc uucacccggg gcucucccgg acggagcauc ggcauccaga    720

agcccguggg ccacguggac aucuacccca acggcggcac cuuccagccc ggcugcaaca    780

ucggcgaggc cauccgggug aucgccgagc ggggucuggg cgacguggac cagcugguga    840

agugcagcca cgagcggagc auucaccugu ucaucgauag ccugcugaac gaggagaacc    900

ccuccaaagc auaccggugc aguaguaagg aggccuucga gaagggccug ugccugagcu    960

gccggaagaa cagaugcaac aaccuugggu acgagaucaa caaggugcgg gccaagagau   1020

cuuccaagau guaccugaag acccggagcc agaugcccua caagguguuc cacuaccagg   1080

ugaagaucca cuucagcggc accgaaagcg aaacucacac caaccaggcc uuugaaauca   1140

gccuguacgg caccguggcc gagucugaga acaucccuuu cacacugccc gaggugagca   1200

cuaacaagac cuacagcuuc cugaucuaca ccgaggugga cauuggcgag cugcugaugc   1260

ugaagcugaa guggaaguca gacagcuacu ucagcuggag cgacuggugg ucuagccccg   1320

gauucgccau ccaaaagauc agggugaagg ccggagagac acagaagaaa gugaucuucu   1380

gcagccggga gaagguaagc caccugcaga agggcaaggc ucccgccgug uucgucaagu   1440

gccacgacaa gucccugaac aagaaguccg gcugauaaua ggcuggagcc ucgguggcca   1500

ugcuucuugc cccuugggcc ucccccccagc cccuccuccc cuuccugcac ccguaccccc   1560

cgcauuauua cucacgguac gaguggucuu ugaauaaagu cugagugggc ggc          1613
```

<210> SEQ ID NO 184
<211> LENGTH: 1591
<212> TYPE: RNA
<213> ORGANISM: Artificial Sequence
<220> FEATURE:
<223> OTHER INFORMATION: Synthetic Polynucleotide

<400> SEQUENCE: 184

```
gggaaauaag agagaaaaga agaguaagaa gaaauauaag agccaccaug gagagcaagg     60

cccugcuggu gcugacccug gccgugugc ugcagagccu gaccgccagc cggggaggcg    120

uggccgccgc cgaccagcgg cgggacuuca ucgacaucga guccaaguuc gcccugcgga    180

cccccgagga caccgccgaa gacaccugcc accugauccc cggcgucgcc gagagcgugg    240

ccacaugcca cuucaaccac agcagcaaga ccuucauggu gauccacggc uggaccguga    300

ccggcaugua cgagagcugg gugcccaagc ugguggccgc ucuguacaag cgggagcccg    360

acagcaacgu gaucguggug gacuggcuga gccgggccca ggagcacuac cccgugagcg    420

ccggcuacac caagcucguc ggccaggacg uggcccgguu caucaacugg auggaggagg    480

aguucaacua cccccuggac aacgugcacc ugcugggcua cagccugggc gcccacgccg    540

ccggcaucgc cggcagccuc accaacaaga aggugaaccg gaucaccggc cuggaccccg    600

ccggccccaa cuucgaguac gccgaggccc ccagcaggcu cucccccgac gacgccgacu    660

ucguggacgu gcugcacacc uucacccggg gcucucccgg acggagcauc ggcauccaga    720

agcccguggg ccacguggac aucuacccca acggcggcac cuuccagccc ggcugcaaca    780
```

ucggcgaggc cauccgggug aucgccgagc ggggucuggg cgacguggac cagcuggua 840 agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccaaaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggcca 1500
ugcuucuugc cccuugggcc ucccccagc cccuccuccc cuuccugcac ccguaccccc 1560
guggucuuug aauaaagucu gagugggcgg c 1591

<210> SEQ ID NO 185
<211> LENGTH: 1614
<212> TYPE: RNA
<213> ORGANISM: Artificial Sequence
<220> FEATURE:
<223> OTHER INFORMATION: Synthetic Polynucleotide

<400> SEQUENCE: 185
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180 cgccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccgcuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggcgc ccagcaggcu cucgcccgac gacgccgacu 660
ucguggacgu gcugcacacc uucacccggg gcucucccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcuggua 840 agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200

```
cuaacaagac cuacagcuuc cugaucuaca ccgaggugga cauuggcgag cugcugaugc   1260

ugaagcugaa guggaaguca gacagcuacu ucagcuggag cgacuggugg ucuagccccg   1320

gauucgccau ccagaagauc agggugaagg ccggagagac acagaagaaa gugaucuucu   1380

gcagccggga gaagguaagc caccugcaga agggcaaggc ucccgccgug uucgucaagu   1440

gccacgacaa gucccugaac aagaaguccg gcugauaaua ggcuggagcc ucgguggccu   1500

agcuucuugc cccuugggcc uccccccagc cccuccuccc cuuccugcac ccguaccccc   1560

uccauaaagu aggaaacacu acaguggucu uugaauaaag ucugaguggg cggc         1614
```

<210> SEQ ID NO 186
<211> LENGTH: 1613
<212> TYPE: RNA
<213> ORGANISM: Artificial Sequence
<220> FEATURE:
<223> OTHER INFORMATION: Synthetic Polynucleotide

<400> SEQUENCE: 186

```
gggaaauaag agagaaaaga agaguaagaa gaaauauaag agccaccaug gagagcaagg     60

cccugcuggu gcugacccug gccguguggc ugcagagccu gaccgccagc cggggaggcg    120

uggccgccgc cgaccagcgg cgggacuuca ucgacaucga guccaaguuc gcccugcgga    180

cgcccgagga caccgccgaa gacaccugcc accugauccc cggcgucgcc gagagcgugg    240

ccacaugcca cuucaaccac agcagcaaga ccuucauggu gauccacggc uggaccguga    300

ccggcaugua cgagagcugg gugcccaagc ugguggccgc ucuguacaag cgggagcccg    360

acagcaacgu gaucguggug gacuggcuga gccgggccca ggagcacuac cccgugagcg    420

ccggcuacac caagcucguc ggccaggacg uggcccgguu caucaacugg auggaggagg    480

aguucaacua cccgcuggac aacgugcacc ugcugggcua cagccugggc gcccacgccg    540

ccggcaucgc cggcagccuc accaacaaga aggugaaccg gaucaccggc cuggaccccg    600

ccggccccaa cuucgaguac gccgaggcgc ccagcaggcu cucgcccgac gacgccgacu    660

ucguggacgu gcugcacacc uucacccggg gcucucccgg acggagcauc ggcauccaga    720

agcccguggg ccacguggac aucuacccca acggcggcac cuuccagccc ggcugcaaca    780

ucggcgaggc cauccgggug aucgccgagc ggggucuggg cgacguggac cagcugguga    840

agugcagcca cgagcggagc auucaccugu ucaucgauag ccugcugaac gaggagaacc    900

ccuccaaagc auaccggugc aguaguaagg aggccuucga gaagggccug ugccugagcu    960

gccggaagaa cagaugcaac aaccuugggu acgagaucaa caaggugcgg gccaagagau   1020

cuuccaagau guaccugaag acccggagcc agaugcccua caagguguuc cacuaccagg   1080

ugaagaucca cuucagcggc accgaaagcg aaacucacac caaccaggcc uuugaaauca   1140

gccuguacgg caccguggcc gagucugaga acaucccuuu cacacugccc gaggugagca   1200

cuaacaagac cuacagcuuc cugaucuaca ccgaggugga cauuggcgag cugcugaugc   1260

ugaagcugaa guggaaguca gacagcuacu ucagcuggag cgacuggugg ucuagccccg   1320

gauucgccau ccagaagauc agggugaagg ccggagagac acagaagaaa gugaucuucu   1380

gcagccggga gaagguaagc caccugcaga agggcaaggc ucccgccgug uucgucaagu   1440

gccacgacaa gucccugaac aagaaguccg gcugauaaua ggcuggagcc ucgguggccu   1500

agcuucuugc cccuugggcc uccccccagc cccuccuccc cuuccugcac ccguaccccc   1560

cgcauuauua cucacgguac gaguggucuu ugaauaaagu cugagugggc ggc          1613
```

<210> SEQ ID NO 187
<211> LENGTH: 1591
<212> TYPE: RNA
<213> ORGANISM: Artificial Sequence
<220> FEATURE:
<223> OTHER INFORMATION: Synthetic Polynucleotide

<400> SEQUENCE: 187
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180 cgccccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccgcuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggcgc ccagcaggcu cucgcccgac gacgccgacu 660
ucguggacgu gcugcacacc uucacccggg gcucucccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcugguga 840
agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccagaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggccu 1500
agcuucuugc cccuugggcc uccccccagc cccuccuccc cuuccugcac ccguacccccc 1560 guggucuuug aauaaagucu gagugggcgg c 1591

<210> SEQ ID NO 188
<211> LENGTH: 1605
<212> TYPE: RNA
<213> ORGANISM: Artificial Sequence
<220> FEATURE:
<223> OTHER INFORMATION: Synthetic Polynucleotide

<400> SEQUENCE: 188
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180
cgcccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccgcuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggcgc ccagcaggcu cucgcccgac gacgccgacu 660
ucguggacgu gcugcacacc uucacccggg gcucucccgg acggagcauc ggcauccaga 720
agcccguggg ccacguggac aucuacccca acggcggcac cuuccagccc ggcugcaaca 780
ucggcgaggc cauccgggug aucgccgagc ggggucuggg cgacguggac cagcugguga 840
agugcagcca cgagcggagc auucaccugu ucaucgauag ccugcugaac gaggagaacc 900
ccuccaaagc auaccggugc aguaguaagg aggccuucga gaagggccug ugccugagcu 960
gccggaagaa cagaugcaac aaccuugggu acgagaucaa caaggugcgg gccaagagau 1020
cuuccaagau guaccugaag acccggagcc agaugcccua caagguguuc cacuaccagg 1080
ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccagaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcgcuggagc cucgguggcc augcuucuug 1500
ccccuugggc cuccccccag ccccuccucc ccuuccugca cccguacccc cuccauaaag 1560
uaggaaacac uacagugguc uuugaauaaa gucugagugg gcggc 1605

<210> SEQ ID NO 189
<211> LENGTH: 1613
<212> TYPE: RNA
<213> ORGANISM: Artificial Sequence
<220> FEATURE:
<223> OTHER INFORMATION: Synthetic Polynucleotide

<400> SEQUENCE: 189
gggaaauaag agagaaaaga agaguaagaa gaaauauaag agccaccaug gagagcaagg 60
cccugcuggu gcugacccug gccguguggc ugcagagccu gaccgccagc cggggaggcg 120
uggccgccgc cgaccagcgg cgggacuuca ucgacaucga guccaaguuc gcccugcgga 180
cgcccgagga caccgccgaa gacaccugcc accugauccc cggcgucgcc gagagcgugg 240
ccacaugcca cuucaaccac agcagcaaga ccuucauggu gauccacggc uggaccguga 300
ccggcaugua cgagagcugg gugcccaagc ugguggccgc ucuguacaag cgggagcccg 360
acagcaacgu gaucguggug gacuggcuga gccgggccca ggagcacuac cccgugagcg 420
ccggcuacac caagcucguc ggccaggacg uggcccgguu caucaacugg auggaggagg 480
aguucaacua cccgcuggac aacgugcacc ugcugggcua cagccugggc gcccacgccg 540
ccggcaucgc cggcagccuc accaacaaga aggugaaccg gaucaccggc cuggaccccg 600
ccggccccaa cuucgaguac gccgaggcgc ccagcaggcu cucgcccgac gacgccgacu 660

```
ucguggacgu gcugcacacc uucacccggg gcucucccgg acggagcauc ggcauccaga    720
agcccguggg ccacguggac aucuacccca acggcggcac cuuccagccc ggcugcaaca    780
ucggcgaggc cauccgggug aucgccgagc ggggucuggg cgacguggac cagcugguga    840
agugcagcca cgagcggagc auucaccugu ucaucgauag ccugcugaac gaggagaacc    900
ccuccaaagc auaccggugc aguaguaagg aggccuucga gaagggccug ugccugagcu    960
gccggaagaa cagaugcaac aaccuugggu acgagaucaa caaggugcgg gccaagagau   1020
cuuccaagau guaccugaag acccggagcc agaugcccua caagguguuc cacuaccagg   1080
ugaagaucca cuucagcggc accgaaagcg aaacucacac caaccaggcc uuugaaauca   1140
gccuguacgg caccguggcc gagucugaga acaucccuuu cacacugccc gaggugagca   1200
cuaacaagac cuacagcuuc cugaucuaca ccgaggugga cauuggcgag cugcugaugc   1260
ugaagcugaa guggaaguca gacagcuacu ucagcuggag cgacuggugg ucuagccccg   1320
gauucgccau ccagaagauc agggugaagg ccggagagac acagaagaaa gugaucuucu   1380
gcagccggga gaagguaagc caccugcaga agggcaaggc ucccgccgug uucgucaagu   1440
gccacgacaa gucccugaac aagaaguccg gcugauaaua ggcuggagcc ucgguggcca   1500
ugcuucuugc cccuugggcc uccccccagc cccuccuccc cuuccugcac ccguaccccc   1560
cgcauuauua cucacgguac gaguggucuu ugaauaaagu cugagugggc ggc          1613
```

```
<210> SEQ ID NO 190
<211> LENGTH: 1591
<212> TYPE: RNA
<213> ORGANISM: Artificial Sequence
<220> FEATURE:
<223> OTHER INFORMATION: Synthetic Polynucleotide

<400> SEQUENCE: 190

gggaaauaag agagaaaaga agaguaagaa gaaauauaag agccaccaug gagagcaagg     60
cccugcuggu gcugacccug gccguguggc ugcagagccu gaccgccagc cggggaggcg    120
uggccgccgc cgaccagcgg cgggacuuca ucgacaucga guccaaguuc gcccugcgga    180
cgcccgagga caccgccgaa gacaccugcc accugauccc cggcgucgcc gagagcgugg    240
ccacaugcca cuucaaccac agcagcaaga ccuucauggu gauccacggc uggaccguga    300
ccggcaugua cgagagcugg gugcccaagc ugguggccgc ucuguacaag cgggagcccg    360
acagcaacgu gaucguggug gacuggcuga gccgggccca ggagcacuac cccgugagcg    420
ccggcuacac caagcucguc ggccaggacg uggcccgguu caucaacugg auggaggagg    480
aguucaacua cccgcuggac aacgugcacc ugcugggcua cagccugggc gcccacgccg    540
ccggcaucgc cggcagccuc accaacaaga aggugaaccg gaucaccggc cuggaccccg    600
ccggccccaa cuucgaguac gccgaggcgc ccagcaggcu cucgcccgac gacgccgacu    660
ucguggacgu gcugcacacc uucacccggg gcucucccgg acggagcauc ggcauccaga    720
agcccguggg ccacguggac aucuacccca acggcggcac cuuccagccc ggcugcaaca    780
ucggcgaggc cauccgggug aucgccgagc ggggucuggg cgacguggac cagcugguga    840
agugcagcca cgagcggagc auucaccugu ucaucgauag ccugcugaac gaggagaacc    900
ccuccaaagc auaccggugc aguaguaagg aggccuucga gaagggccug ugccugagcu    960
gccggaagaa cagaugcaac aaccuugggu acgagaucaa caaggugcgg gccaagagau   1020
cuuccaagau guaccugaag acccggagcc agaugcccua caagguguuc cacuaccagg   1080
```

ugaagaucca cuucagcggc accgaaagcg aaacucacac caaccaggcc uuugaaauca 1140
gccuguacgg caccguggcc gagucugaga acaucccuuu cacacugccc gaggugagca 1200
cuaacaagac cuacagcuuc cugaucuaca ccgaggugga cauuggcgag cugcugaugc 1260
ugaagcugaa guggaaguca gacagcuacu ucagcuggag cgacuggugg ucuagccccg 1320
gauucgccau ccagaagauc agggugaagg ccggagagac acagaagaaa gugaucuucu 1380
gcagccggga gaagguaagc caccugcaga agggcaaggc ucccgccgug uucgucaagu 1440
gccacgacaa gucccugaac aagaaguccg gcugauaaua ggcuggagcc ucgguggcca 1500
ugcuucuugc cccuugggcc uccccccagc cccuccuccc cuuccugcac ccguaccccc 1560
guggucuuug aauaaagucu gagugggcgg c 1591

<210> SEQ ID NO 191
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 191
ugauaauagg cuggagccuc gguggccuag cuucuugccc cuugggccuc cccccagccc 60
cuccuccccu uccugcaccc guacccccuc cauaaaguag gaaacacuac aguggucuuu 120
gaauaaaguc ugagugggcg gc 142

<210> SEQ ID NO 192
<211> LENGTH: 141
<212> TYPE: RNA
<213> ORGANISM: Artificial Sequence
<220> FEATURE:
<223> OTHER INFORMATION: Synthetic Polynucleotide

<400> SEQUENCE: 192
ugauaauagg cuggagccuc gguggccuag cuucuugccc cuugggccuc cccccagccc 60
cuccuccccu uccugcaccc guacccccg cauuauuacu cacgguacga guggucuuug 120
aauaaagucu gagugggcgg c 141

<210> SEQ ID NO 193
<211> LENGTH: 164
<212> TYPE: RNA
<213> ORGANISM: Artificial Sequence
<220> FEATURE:
<223> OTHER INFORMATION: Synthetic Polynucleotide

<400> SEQUENCE: 193
ugauaauagu ccauaaagua ggaaacacua cagcuggagc cucgguggcc uagcuucuug 60
ccccuugggc cuccccccag ccccuccucc ccuuccugca cccguacccc ccgcauuauu 120
acucacggua cgagugguc u uugaauaaag ucugaguggg cggc 164

<210> SEQ ID NO 194
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 194
ugauaauagu ccauaaagua ggaaacacua cagcuggagc cucgguggcc uagcuucuug 60
ccccuugggc cuccauaaag uaggaaacac uacaucccccc cagccccucc uccccuuccu 120
gcacccguac ccccuccaua aaguaggaaa cacuacagug gucuuugaau aaagucugag 180
ugggcggc 188

<210> SEQ ID NO 195
<211> LENGTH: 140
<212> TYPE: RNA
<213> ORGANISM: Artificial Sequence
<220> FEATURE:
<223> OTHER INFORMATION: Synthetic Polynucleotide

<400> SEQUENCE: 195
ugauaauagg cuggagccuc gguggccaug cuucuugccc cuugggccuc cccccagccc 60
cuccuccccu uccugcaccc guacccccag uagugcuuuc uacuuuaugg uggucuuuga 120
auaaagucug agugggcggc 140

<210> SEQ ID NO 196
<211> LENGTH: 181
<212> TYPE: RNA
<213> ORGANISM: Artificial Sequence
<220> FEATURE:
<223> OTHER INFORMATION: Synthetic Polynucleotide

<400> SEQUENCE: 196
ugauaauaga guagugcuuu cuacuuuaug gcuggagccu cgguggccau gcuucuugcc 60
ccuugggcca guagugcuuu cuacuuuaug uccccccagc cccucucccc uuccugcacc 120 cguacccccca guagugcuuu cuacuuuaug guggucuuug aauaaagucu gagugggcgg 180
c 181

<210> SEQ ID NO 197
<211> LENGTH: 184
<212> TYPE: RNA
<213> ORGANISM: Artificial Sequence
<220> FEATURE:
<223> OTHER INFORMATION: Synthetic Polynucleotide

<400> SEQUENCE: 197
ugauaauaga guagugcuuu cuacuuuaug gcuggagccu cgguggccau gcuucuugcc 60
ccuugggccu ccauaaagua ggaaacacua caucccccca gccccuccuc cccuuccugc 120
acccguaccc ccaguagugc uuucuacuuu augguggucu uugaauaaag ucugaguggg 180
cggc 184

<210> SEQ ID NO 198
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 198
ugauaauagu ccauaaagua ggaaacacua cagcuggagc cucgguggcc uagcuucuug 60
ccccuugggc cuccccccag ccccuccucc ccuuccugca cccguacccc cgguggucuuu 120 gaauaaaguc ugagugggcg gc 142

<210> SEQ ID NO 199
<211> LENGTH: 142
<212> TYPE: RNA
<213> ORGANISM: Artificial Sequence
<220> FEATURE:

<223> OTHER INFORMATION: Synthetic Polynucleotide

<400> SEQUENCE: 199
ugauaauagg cuggagccuc gguggcucca uaaaguagga aacacuacac uagcuucuug 60
ccccuugggc cuccccccag ccccuccucc ccuuccugca cccguacccc cguggucuuu 120
gaauaaaguc ugagugggcg gc 142

<210> SEQ ID NO 200
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 200
ugauaauagg cuggagccuc gguggccuag cuucuugccc cuugggccuc cauaaaguag 60
gaaacacuac auccccccag ccccuccucc ccuuccugca cccguacccc cguggucuuu 120
gaauaaaguc ugagugggcg gc 142

<210> SEQ ID NO 201
<211> LENGTH: 142
<212> TYPE: RNA
<213> ORGANISM: Artificial Sequence
<220> FEATURE:
<223> OTHER INFORMATION: Synthetic Polynucleotide

<400> SEQUENCE: 201
ugauaauagg cuggagccuc gguggccuag cuucuugccc cuugggccuc cccccagccc 60
cuccuccccu uccugcaccc guacccccac cccuaucaca auuagcauua agugggucuuu 120 gaauaaaguc ugagugggcg gc 142

<210> SEQ ID NO 202
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 202
ugauaauaga ccccuaucac aauuagcauu aagcuggagc cucgguggcc uagcuucuug 60
ccccuugggc caccccuauc acaauuagca uuaauccccc cagccccucc uccccuuccu 120
gcacccguac ccccaccccu aucacaauua gcauuaagug gucuuugaau aaagucugag 180
ugggcggc 188

<210> SEQ ID NO 203
<211> LENGTH: 188
<212> TYPE: RNA
<213> ORGANISM: Artificial Sequence
<220> FEATURE:
<223> OTHER INFORMATION: Synthetic Polynucleotide

<400> SEQUENCE: 203
ugauaauaga ccccuaucac aauuagcauu aagcuggagc cucgguggcc uagcuucuug 60
ccccuugggc cuccauaaag uaggaaacac uacaucccccc cagccccucc uccccuuccu 120
gcacccguac ccccaccccu aucacaauua gcauuaagug gucuuugaau aaagucugag 180
ugggcggc 188

POLYNUCLEOTIDES ENCODING LIPOPROTEIN LIPASE FOR THE TREATMENT OF HYPERLIPIDEMIA

RELATED APPLICATIONS

This application is the National Stage of International Application No. PCT/US2017/033403, filed on May 18, 2017, which claims the benefit under 35 U.S.C. § 119(e) of U.S. provisional applications 62/338,420, filed May 18, 2016 and 62/473,939, filed Mar. 20, 2017, the entire contents of each of which are incorporated herein by reference.

BACKGROUND

Hyperlipidemia, the elevated level of any or all lipids or lipoproteins in the blood, can be caused by several acquired or genetic disorders. Lipids, including fats, cholesterol, and triglycerides, can penetrate arterial walls, increasing the risk of atherosclerosis, and by extension, stroke, heart attack, and death.

Lipoprotein lipase (LPL; EC 3.1.1.34) is the pivotal enzyme responsible for the hydrolysis of circulating triglycerides. It is anchored to the inner walls of blood vessels, where it breaks down circulating triglycerides into non-esterified fatty acids and glycerol. A metabolic enzyme, it requires ApoC-II as a cofactor and is also expressed on endothelial cells in the heart, muscle, and adipose tissue. Mead, J. R. et al., J Mol Med. 80(12):753-769 (2002) and Ferland, A. et al. Obesity 20(5):1006-1011 (2012). LPL has the dual function of (1) hydrolyzing triglycerides in lipoproteins, such as those found in chylomicrons and very low-density lipoproteins (VLDL), into three free fatty acids and one glycerol molecule and (2) serving as a ligand/bridging factor for receptor-mediated cellular uptake of chylomicron remnants, cholesterol-rich lipoproteins, and free fatty acids. Id. LPL's biological function is to aid in the creation of cholesterol and in the storage and metabolism of fatty acids. Lo, J. Y. et al., *Biochem. Biophys. Res. Commun.* 206: 266-271 (1995). A complete or partial loss of LPL function leads to buildup of triglycerides and chylomicrons in the plasma. For example, loss of LPL function has been reported to lead to triglyceride levels that are greater than 2,000 mg/dL as compared to 150 mg/dL or less in normal individuals.

Primary hypertriglyceridemia (HTG) occurs when there are defects in LPL or genes relating to LPL or lipoprotein clearance/uptake, such as apoCII, apoCIII, apoAV, GPIHBP1, and LMF1, among others. Secondary HTG is associated with obesity, metabolic syndrome, diabetes, alcohol abuse, renal disease, and certain medications, including anti-psychotics and anti-retrovirals. At triglyceride levels above 1,000 mg/dL, acute pancreatitis (AP) may result.

Individuals rarely exhibit any signs or symptoms of hyperlipidemia; diagnosis usually comes from a simple bood test. According to the CDC, approximately one in six adult Americans has hyperlipidemia, yet only about one in three adults has the condition under control.

The standard-of-care for hyperlipidemia includes dietary restrictions, exercise, fibrates, omega-3, and niacin. Existing hyperlipidemia treatments focus on reducing the risk of coronary heart disease, as the two have been shown to be associated with one another. Changes in triglyceride concentrations have been shown to change the risk of coronary heart disease, but a causal link has not been established. For mild to moderate hyperlipidemia, statins are usually recommended. For those with triglycerides above 1000 mg/dL, other triglyceride-lowering treatments are administered. Fibrates have shown a 20-50% reduction in triglycerides, with the greatest benefit being realized in more severely affected patients. However, in cases of non-severe hyperlipidemia, treatment elevates the risk of pancreatitis. Nicotinic acid can decrease TG by 15-25%, but may worsen glucose tolerance in diabetic patients and may be harmful when combined with statins. Omega-3 (fish oil) yields a 50% reduction in TG, but the first generation preparations may raise LDL. GLYBERA®, which was approved in Europe after multiple attempts and is not currently approved in the US, is only focused on LPLD patients, and not hyperlipidemia broadly. It has shown limited (if any) short term efficacy and no longer term efficacy when used alone.

SUMMARY OF THE INVENTION

The present invention provides mRNA therapeutics for the treatment of hyperlipidemia. The mRNA therapeutics of the invention are particularly well-suited for the treatment of hyperlipidemia, as the technology provides for the intracellular delivery of mRNA encoding lipoprotein lipase (LPL) followed by de novo synthesis of functional LPL protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modification to reduce the innate immune response and sequence optimization, in particular, within the open reading frame (ORF) of therapeutic mRNAs encoding LPL to enhance protein expression.

The mRNA therapeutic technology of the instant invention also features delivery of mRNA encoding LPL via a lipid nanoparticle (LNP) delivery system. The instant invention features novel ionizable lipid-based LNPs which have improved properties when administered in vivo, for example, cellular uptake, intracellular transport, and/or endosomal release or endosomal escape. The LNPs of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a messenger RNA (mRNA), encoding lipoprotein lipase and methods for treating hyperlipidemia in a subject in need thereof by administering the same.

Aspects of the invention relate to an RNA polynucleotide comprising an open reading frame (ORF) encoding lipoprotein lipase (LPL) polypeptide formulated in a ionizable lipid nanoparticle, wherein the ionizable lipid nanoparticle has a molar ratio of about 20-60% ionizablelipid:about 5-25% non-cationic lipid:about 25-55% sterol; and about 0.5-15% PEG-modified lipid. Some aspects of the invention relate to an RNA polynucleotide comprising an open reading frame (ORF) encoding a lipoprotein lipase (LPL) variant polypeptide formulated in a ionizablelipid nanoparticle.

Other aspects of the invention relate to an RNA polynucleotide comprising an open reading frame (ORF) encoding lipoprotein lipase (LPL) polypeptide formulated in a ionizable lipid nanoparticle, wherein the RNA polynucleotide in the ionizable lipid nanoparticle has a therapeutic index of greater than 10% of the therapeutic index of the RNA polynucleotide alone.

In some embodiments, the LPL polypeptide is a LPL variant polypeptide. In some embodiments, at least 30%-50% of the mRNA is on the surface of the ionizable lipid nanoparticle. In other embodiments, the ionizable lipid nanoparticle has a mean diameter of 50-200 nm.

In some embodiments, the ionizable lipid nanoparticle has a 5:1 to 18:1 weight ratio of total lipid to RNA polynucleotide. In some embodiments, the composition is a unit dosage form having a dosage of 25-200 micrograms of the RNA polynucleotide. In some embodiments, the ionizable lipid is a lipid selected from compound 1-20. In some embodiments, the open reading frame is codon optimized.

In other embodiments, the RNA comprises at least one chemical modification. In some embodiments, the chemical modification is selected from pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine and 2'-O-methyl uridine.

In some embodiments, the RNA polynucleotide formulated in the ionizable lipid nanoparticle has a therapeutic index of greater than 60% of the therapeutic index of the RNA polynucleotide alone. In some embodiments, the RNA polynucleotide formulated in the cationic lipid nanoparticle has a therapeutic index of greater than 10% of the therapeutic index of the RNA polynucleotide alone.

In some embodiments, the RNA polynucleotide does not have an open reading frame nucleic acid sequence selected from sequences of Table 3. In some embodiments, the LPL variant is $LPL^{S447X}$ variant polypeptide.

In other embodiments, the ionizable amino lipid is a lipid of Formula (I):

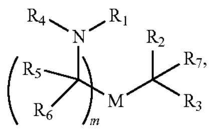

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_2$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{13}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2. In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=N$R_9$)N$(R)_2$, —N(R)C(=CH$R_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(=N$R_9$)N$(R)_2$, —N(OR)C(=CH$R_9$)N$(R)_2$, —C(=N$R_9$)N$(R)_2$, —C(=N$R_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In other embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —C(O)N(R)OR, and —$C(=NR_9)N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —C(O)N(R)OR, and —$C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5;

each $R_5$ is independently selected from the group consisting of $C_{13}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In other embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

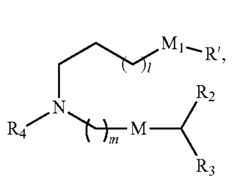

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)$N(R)_2$, —NHC(O)$N(R)_2$, —N(R)C(O)R, —N(R)$S(O)_2$R, —N(R)$R_8$, —NHC(=$NR_9$)$N(R)_2$, —NHC(=$CHR_9$)N$(R)_2$, —OC(O)$N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the nanoparticle has a polydispersity value of less than 0.4. In some embodiments, the nanoparticle has a net neutral charge at a neutral pH. In some embodiments, the ORF is at least 90% identical to CO-01. In some embodiments, the ORF is at least 90% identical to CO-02. In other embodiments, the ORF is at least 90% identical to CO-03. In some embodiments, the ORF is at least 90% identical to CO-04. In further embodiments, the ORF is at least 90% identical to CO-30.

In some embodiments, 80% of the uracil in the open reading frame have a chemical modification. In some embodiments, 100% of the uracil in the open reading frame have a chemical modification. In some embodiments, the chemical modification is in the 5-position of the uracil. In some embodiments, the chemical modification is N1-methylpseudouridine. In other embodiments, the uracil and thymine content of the RNA polynucleotide is 100-150% greater than that of wild-type LPL polynucleotide.

Aspects of the invention relate to a method of increasing the therapeutic index of an RNA polynucleotide comprising an open reading frame (ORF) encoding lipoprotein lipase (LPL) polypeptide, the method comprising associating the RNA polynucleotide with a ionizable amino lipid to produce a composition, thereby increasing the therapeutic index of the RNA polynucleotide in the composition relative to the therapeutic index of the RNA polynucleotide alone.

In some embodiments, the therapeutic index of the RNA polynucleotide in the composition is greater than 10:1. In other embodiments, the therapeutic index of the RNA polynucleotide in the composition is greater than 50:1.

Further aspects of the invention relate to a method for treating a subject comprising administering to a subject in need thereof the composition produced according to any one of the above methods in an effective amount to treat the subject.

Aspects of the invention relate to a method of treating hyperlipidemia in a subject in need thereof, comprising administering to the subject a therapeutically effective amount of an RNA polynucleotide comprising an open reading frame (ORF) encoding lipoprotein lipase (LPL) polypeptide wherein administration of the RNA polynucleotide results in a decrease in the subject's plasma lipids to a physiological level.

In some embodiments, the method of treating hyperlipidemia involves a single administration of the RNA polynucleotide. In some embodiments, the method of treating hyperlipidemia further comprises administering a weekly dose. In other embodiments, the RNA polynucleotide is formulated in a ionizable amino lipid nanoparticle.

In some embodiments, the RNA polynucleotide is in a composition as described above. In some embodiments, upon administration to the subject the dosage form exhibits a pharmacokinetic (PK) profile comprising: a) a $T_{max}$ at about 30 to about 240 minutes after administration; and b) a plasma drug (LPL polypeptide produced by RNA polynucleotide) concentration plateau of at least 50% $C_{max}$ for a duration of about 90 to about 240 minutes.

In some embodiments, upon administration to the subject at least a 25% reduction in triglyceride level relative to baseline levels is achieved. In other embodiments, upon administration to the subject at least a 50% reduction in triglyceride level relative to baseline levels is achieved.

In some embodiments, upon administration to the subject at least a 60% reduction in triglyceride level relative to baseline levels is achieved. In other embodiments, triglyceride level reduction is achieved for up to 3 days. In other embodiments, triglyceride level reduction is achieved for up to 5 days.

In some embodiments, triglyceride level reduction is achieved for up to 7 days. In some embodiments, triglyceride level reduction is achieved within 1 hour of dosing the subject. In other embodiments, triglyceride level reduction is achieved within 3 hours of dosing the subject.

In some embodiments, the RNA polynucleotide is administered 1 per week for 3 weeks to 1 year. In some embodiments, the RNA polynucleotide is administered to the subject by intravenous administration. In some embodiments, the RNA polynucleotide is administered to the subject by subcutaneous administration. In some embodiments, further comprising administering to the subject a standard of care therapy for hyperlipidemia.

In other embodiments, the standard of care therapy is selected from the group consisting of fibrates, omega-3, niacin, ANGPTL3, antibodies/antisense (Evinacumab, ALN-ANG), apoCIII inhibitors (ALN-AC3, volanesorsen), and CAT-2003 (niacin/omega-3 FA linker). In some embodiments, upon administration to the subject the dosage form exhibits a PK profile wherein at least about 90% of drug is cleared from plasma within about 5 to 7 days of the plasma drug concentration plateau.

In some embodiments, the RNA polynucleotide is present in a dosage of between 25 and 100 micrograms. In other embodiments, the method comprises administering to the subject a single dosage of between 0.001 mg/kg and 0.005 mg/kg of the RNA polynucleotide.

Aspects of the invention relate to a method of treating hyperlipidemia in a subject in need thereof, comprising administering to the subject an RNA polynucleotide comprising an open reading frame (ORF) encoding lipoprotein lipase (LPL) polypeptide and a standard of care therapy for hyperlipidemia wherein the combined administration of the RNA polynucleotide and standard of care therapy results in a decrease in the subject's plasma lipids to a physiological level.

In some embodiments, the standard of care therapy is selected from the group consisting of fibrates, omega-3, niacin, ANGPTL3, antibodies/antisense (Evinacumab, ALN-ANG), apoCIII inhibitors (ALN-AC3, volanesorsen), and CAT-2003 (niacin/omega-3 FA linker). In some embodiments, the RNA polynucleotide and the standard of care therapy provide a synergistic response. In other embodiments, the administration involves a sub therapeutic dose of the RNA polynucleotide. In some embodiments, the administration involves a sub therapeutic dose of the standard of care therapy.

The present disclosure provides a polynucleotide comprising an open reading frame (ORF) encoding a lipoprotein lipase (LPL) polypeptide, wherein the uracil or thymine content of the ORF is between 100% and about 150% of the theoretical minimum uracil or thymine content of a nucleotide sequence encoding the LPL polypeptide (% $U_{TM}$ or % $T_{TM}$, respectively). In some embodiments, the uracil or thymine content in the ORF is between about 105% and about 145%, about 105% and about 140%, about 110% and about 145%, about 110% and about 140%, about 115% and about 145%, about 115% and about 140%, about 120% and about 145%, about 120% and about 140%, about 125% and about 145%, or about 125% and about 140% of the % $U_{TM}$ or % $T_{TM}$. In some embodiments, the uracil or thymine content in the ORF is between (i) 115%, 116%, 117%, 118%, 119%, 120%, 121%, 122%, 123%, 124%, or 125% and (ii) 139%, 140%, 141%, 142%, 143%, 144%, or 145% of the % $U_{TM}$ or % $T_{TM}$.

In some embodiments, the ORF further comprises at least one low-frequency codon. In some embodiments of the polynucleotides disclosed herein, (i) the ORF is at least 89%, at least 90%, at least 91%, at least 92%, at least 93%, at least 94%, at least 95%, at least 96%, at least 97%, at least 98%, at least 99%, or 100% identical to LPL-CO1, (ii) the ORF is at least 89%, at least 90%, at least 91%, at least 92%, at least 93%, at least 94%, at least 95%, at least 96%, at least 97%, at least 98%, at least 99%, or 100% identical to LPL-CO2, (iii) the ORF is at least 89%, at least 90%, at least 91%, at least 92%, at least 93%, at least 94%, at least 95%, at least 96%, at least 97%, at least 98%, at least 99%, or 100% identical to LPL-CO3, (iv) the ORF is at least 89%, at least 90%, at least 91%, at least 92%, at least 93%, at least 94%, at least 95%, at least 96%, at least 97%, at least 98%, at least 99%, or 100% identical to LPL-CO4, (vi) the ORF is at least 90%, at least 91%, at least 92%, at least 93%, at least 94%, at least 95%, at least 96%, at least 97%, at least 98%, at least 99%, or 100% identical to LPL-CO5, LPL-CO6, LPL-CO7, LPL-CO8, LPL-CO9, LPL-CO10, LPL-CO11, LPL-CO12, LPL-CO13, LPL-CO14, LPL-CO15, LPL-CO16, LPL-CO17, LPL-CO18, LPL-CO19, LPL- CO20, LPL-CO-21, LPL-CO22, LPL-CO23, LPL-CO24, LPL-CO25, LPL-CO26, LPL-CO27, LPL-CO28, LPL-CO29, or LPL-CO30.

In some embodiments, the ORF has at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 5 to 29, 80-83, 148. In some embodiments, the LPL polypeptide comprises an amino acid sequence at least about 95%, at least about 96%, at least about 97%, at least about 98%, at least about 99%, or about 100% identical to the polypeptide sequence of wild type LPL (SEQ ID NO: 1; FIG. 1A), and wherein the LPL polypeptide has triglyceride hydrolase activity. In some embodiments, the LPL polypeptide is a variant, derivative, or mutant having a triglyceride hydrolase activity. In some embodiments, the LPL polypeptide comprises an amino acid sequence at least about 95%, at least about 96%, at least about 97%, at least about 98%, at least about 99%, or about 100% identical to the polypeptide sequence of the $LPL^{S447X}$ variant (SEQ ID NO: 3; FIG. 3A), and wherein the LPL polypeptide has triglyceride hydrolase activity. In some embodiments, the polynucleotide sequence further comprises a nucleotide sequence encoding a transit peptide.

In some embodiments, the polynucleotide further comprises a miRNA binding site. In some embodiments, the miRNA binding site comprises one or more nucleotide sequences selected from TABLE 4. In some embodiments, the miRNA binding site binds to miR-142. In some embodiments, the miRNA binding site binds to miR-142-3p or miR-142-5p. In some embodiments, the miR142 comprises SEQ ID NO: 30.

In some embodiments, the polynucleotide further comprises a 5' UTR. In some embodiments, the 5' UTR comprises a nucleic acid sequence at least 90%, at least about 95%, at least about 96%, at least about 97%, at least about 98%, at least about 99%, or about 100% identical to a sequence selected from the group consisting of SEQ ID NO: 35-59, or any combination thereof. In some embodiments, the polynucleotide further comprises a 3' UTR. In some embodiments, the 3' UTR comprises a nucleic acid sequence at least about 90%, at least about 95%, at least about 96%, at least about 97%, at least about 98%, at least about 99%, or about 100% identical to a sequence selected from the group consisting of SEQ ID NO: 60-77 and 191-203, or any combination thereof. In some embodiments, the miRNA binding site is located within the 3' UTR.

In some embodiments, the polynucleotide further comprises a 5' terminal cap. In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the polynucleotide further comprises a poly-A region. In some embodiments, the poly-A region is at least about 10, at least about 20, at least about 30, at least about 40, at least about 50, at least about 60, at least about 70, at least about 80, or at least about 90 nucleotides in length. In some embodiments, the poly-A region has about 10 to about 200, about 20 to about 180, about 50 to about 160, about 70 to about 140, about 80 to about 120 nucleotides in length.

In some embodiments, upon administration to a subject, the polynucleotide has: (i) a longer plasma half-life; (ii) increased expression of a LPL polypeptide encoded by the ORF; (iii) a lower frequency of arrested translation resulting in an expression fragment; (iv) greater structural stability; or (v) any combination thereof, relative to a corresponding polynucleotide comprising SEQ ID NO: 2 (FIG. 1, panel D) or SEQ ID NO: 4 (FIG. 2, panel D).

In some embodiments, the polynucleotide comprises: (i) a 5'-terminal cap; (ii) a 5'-UTR; (iii) an ORF encoding a LPL polypeptide; (iv) a 3'-UTR; and (v) a poly-A region. In some embodiments, the 3'-UTR comprises a miRNA binding site.

The present disclosure also provides a method of producing the polynucleotide described herein, the method comprising modifying an ORF encoding a LPL polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions. In some embodiments, the method further comprises replacing at least about 90%, at least about 95%, at least about 99%, or about 100% of uracils with 5-methoxyuracils.

In certain embodiments, a subset of compounds of Formula (I) includes those of Formula (IIa), (IIb), (IIc), or (IIe):

(IIa)

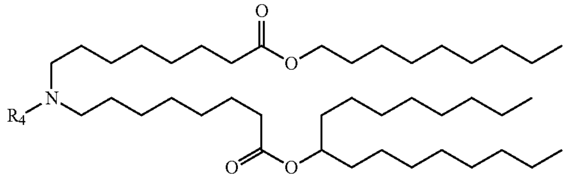

, (IIb)

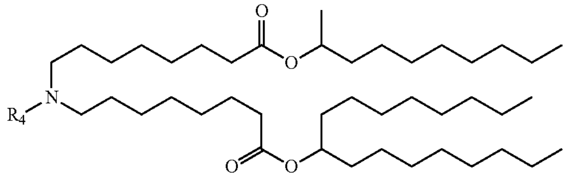

, (IIc)

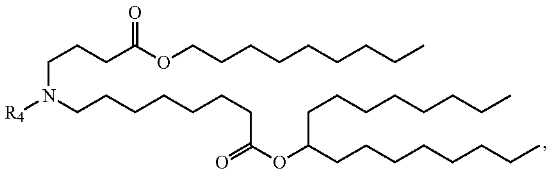

, or (IIe)

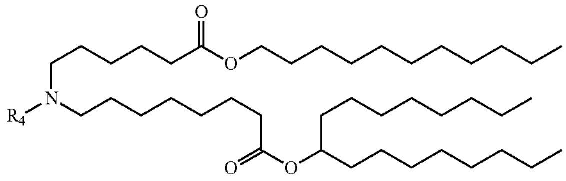

, or a salt or isomer thereof, wherein $R_4$ is as described herein.

In some embodiments, $R_4$ is as described herein.

In some embodiments, the compound is of the Formula (IId), (IId)

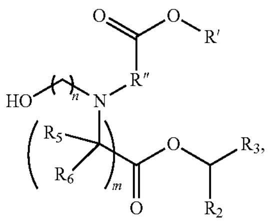

or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined above.

In some embodiments, $R_2$ is $C_8$ alkyl. In some embodiments, $R_3$ is $C_5$ alkyl, $C_6$ alkyl, $C_7$ alkyl, $C_8$ alkyl, or $C_9$ alkyl. In some embodiments, m is 5, 7, or 9. In some embodiments, each $R_5$ is H. In some embodiments, each $R_6$ is H.

In another aspect, the disclosure features a nanoparticle composition including a lipid component comprising a compound as described herein (e.g., a compound according to Formula (I), (IA), (II), (IIa), (IIb), (IIe), (IId) or (IIe)).

In yet another aspect, the disclosure features a pharmaceutical composition comprising a nanoparticle composition according to the preceding aspects and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In another aspect, the disclosure provides a method of delivering a therapeutic and/or prophylactic (e.g., an mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In another aspect, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) an mRNA encoding the polypeptide of interest, whereby the mRNA is capable of being translated in the cell to produce the polypeptide.

In another aspect, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In another aspect, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In another aspect, the disclosure features a method for the enhanced delivery of a therapeutic and/or prophylactic (e.g., an mRNA) to a target tissue (e.g., a liver, spleen, lung, muscle, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue In some embodiments, the composition disclosed herein is a nanoparticle composition. In some embodiments, the delivery agent further comprises a phospholipid. In some embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16:0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and any mixtures thereof.

In some embodiments, the delivery agent further comprises a structural lipid. In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In some embodiments, the delivery agent further comprises a PEG lipid. In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

In some embodiments, the delivery agent further comprises an ionizable lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In some embodiments the LPL protein is a LPL fusion protein. The LPL fusion protein may be an immunoglobulin (Ig) fragment. In some embodiments the Ig fragment is a variable chain fragment. In other embodiments the Ig fragment is a constant chain fragment. In some embodiments the Ig fragment is a variable light chain fragment. In some embodiments the LPL is linked to the light chain or heavy chain region through a linker.

In some embodiments, the delivery agent further comprises a phospholipid, a structural lipid, a PEG lipid, or any combination thereof.

In some embodiments, the composition is formulated for in vivo delivery. In some embodiments, the composition is formulated for intramuscular, subcutaneous, or intradermal delivery.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS/FIGURES

FIG. 3 shows a multiple sequence alignment wild type LPL and 25 sequence optimized LPL polynucleotides. Asterisks below the alignment indicate the location of conserved nucleobases that are identical between the wild type polynucleotide sequence and the sequence optimized LPL polynucleotides. Non-conserved nucleobases are indicated by spaces and periods below the alignment.

Figure 4:
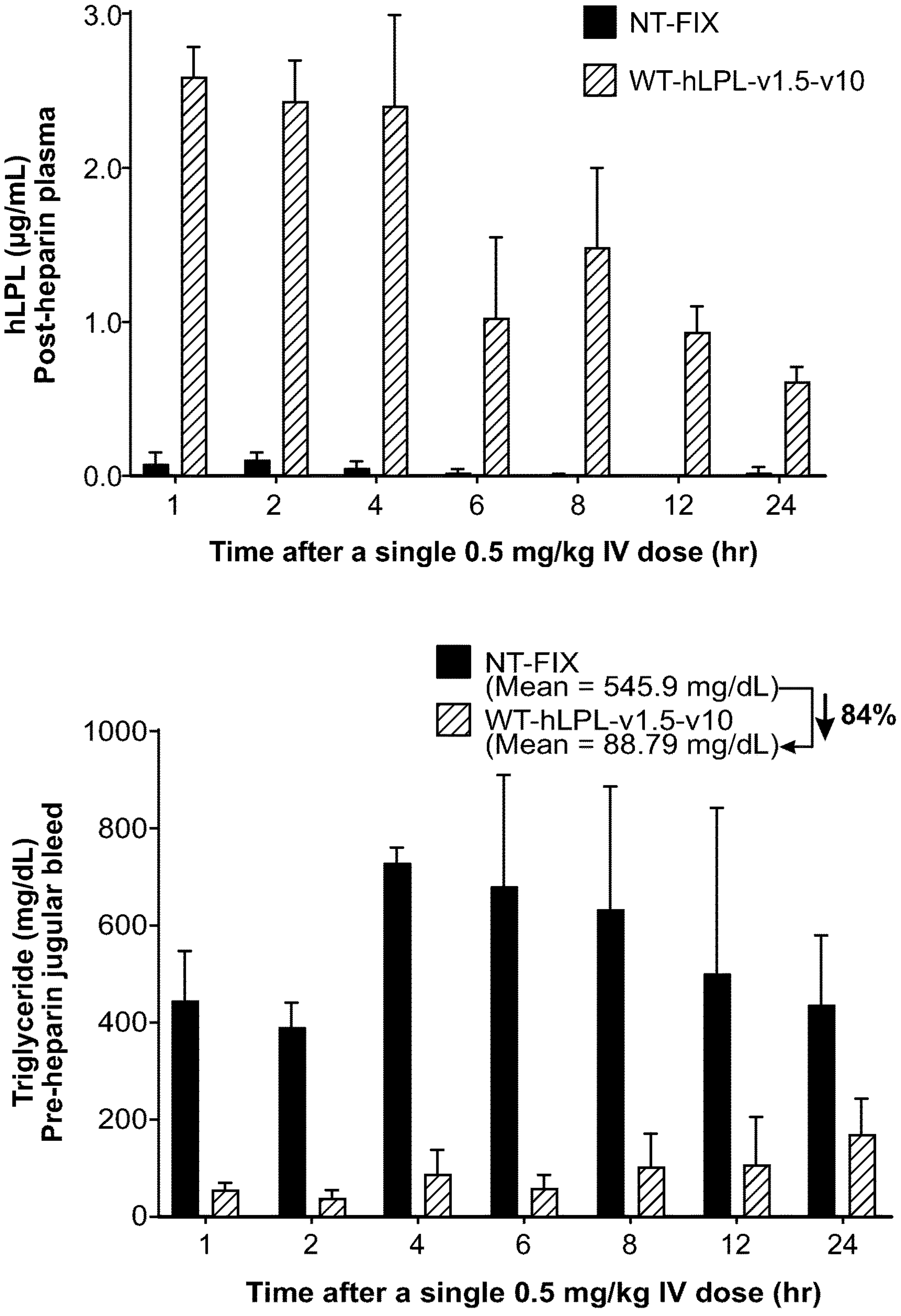
Figure 4:
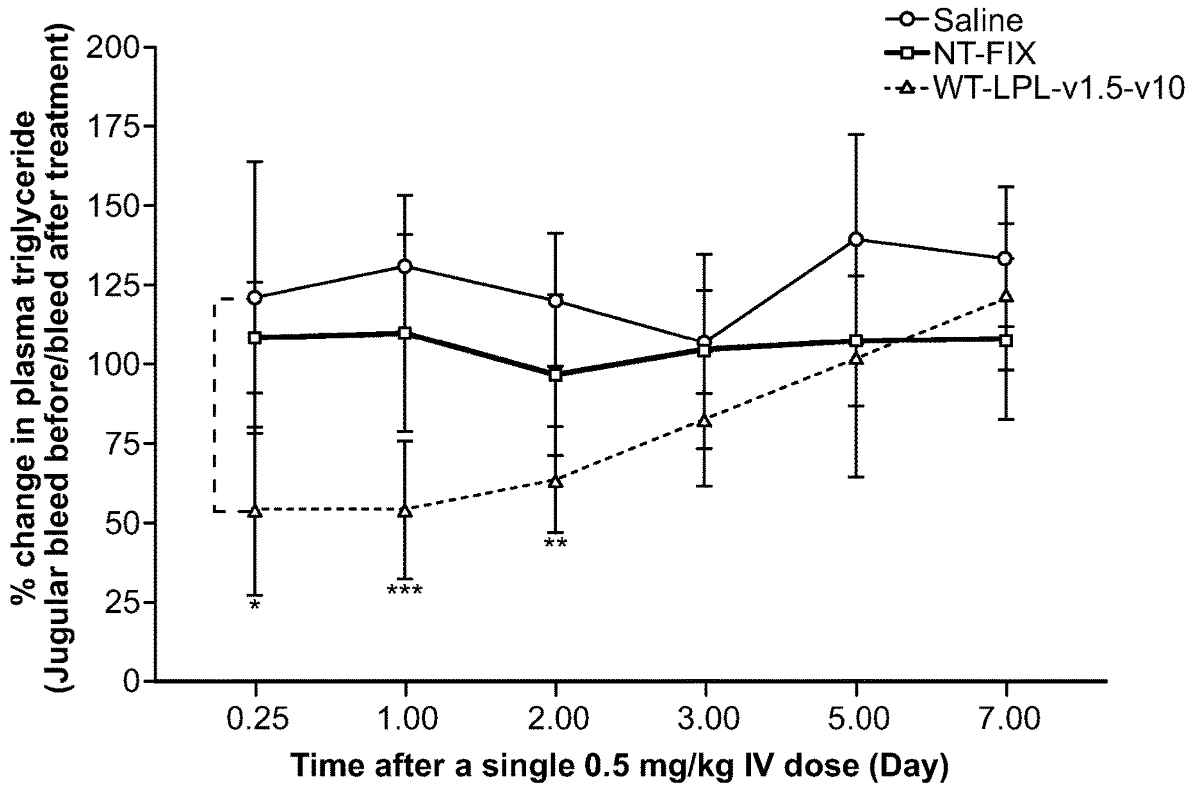

FIG. 4 shows that modified RNA results in hLPL expression and a significant decrease in plasma triglycerides in Zucker fa/fa rats.

Figure 5:
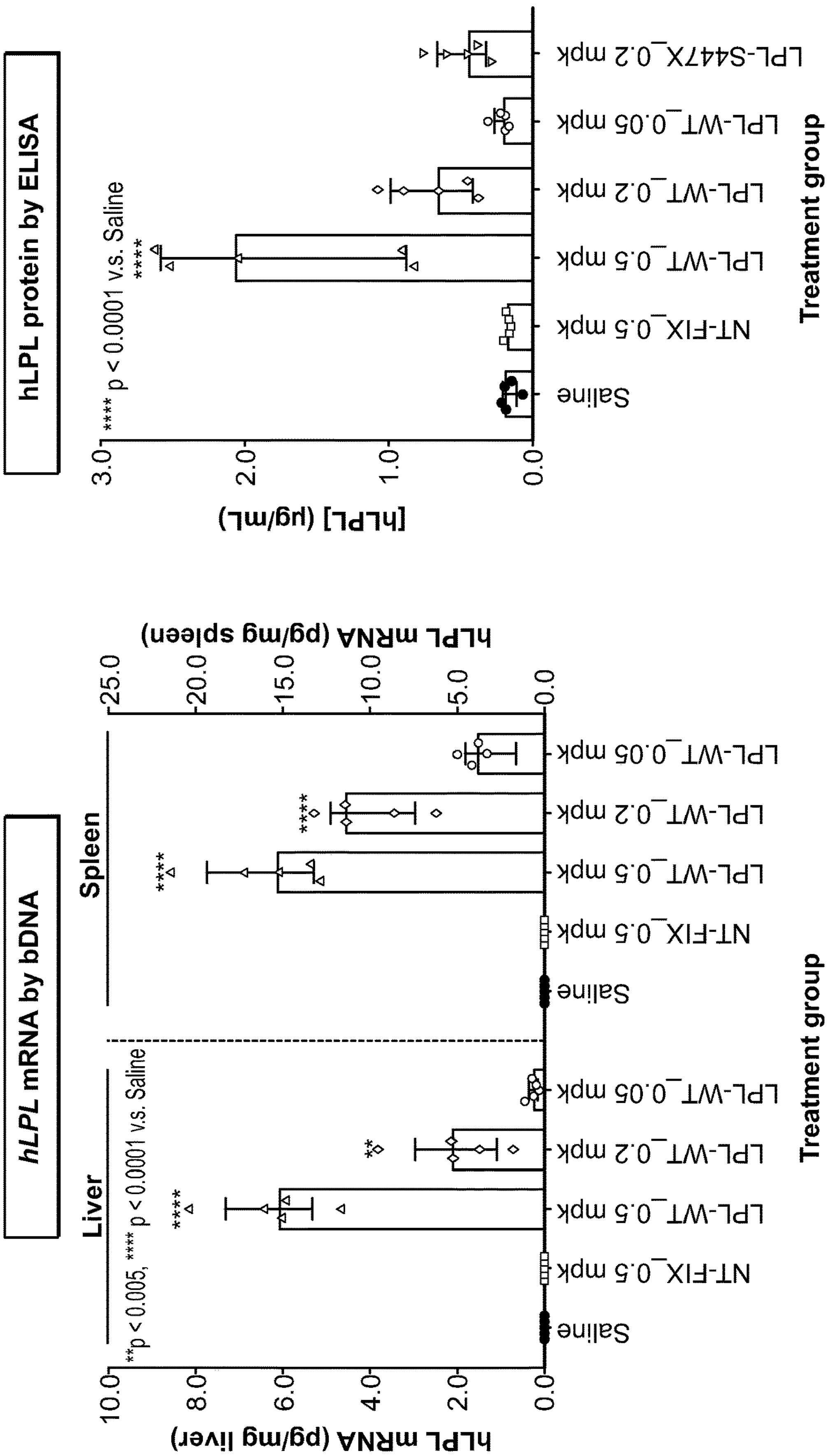

FIG. 5 shows the pharmacokinetic results of the three week administration study (two doses per week). The concentration of hLPL mRNA in liver (left) and the concentration of hLPL protein in post-heparin plasma (right) are shown.

Figure 6:
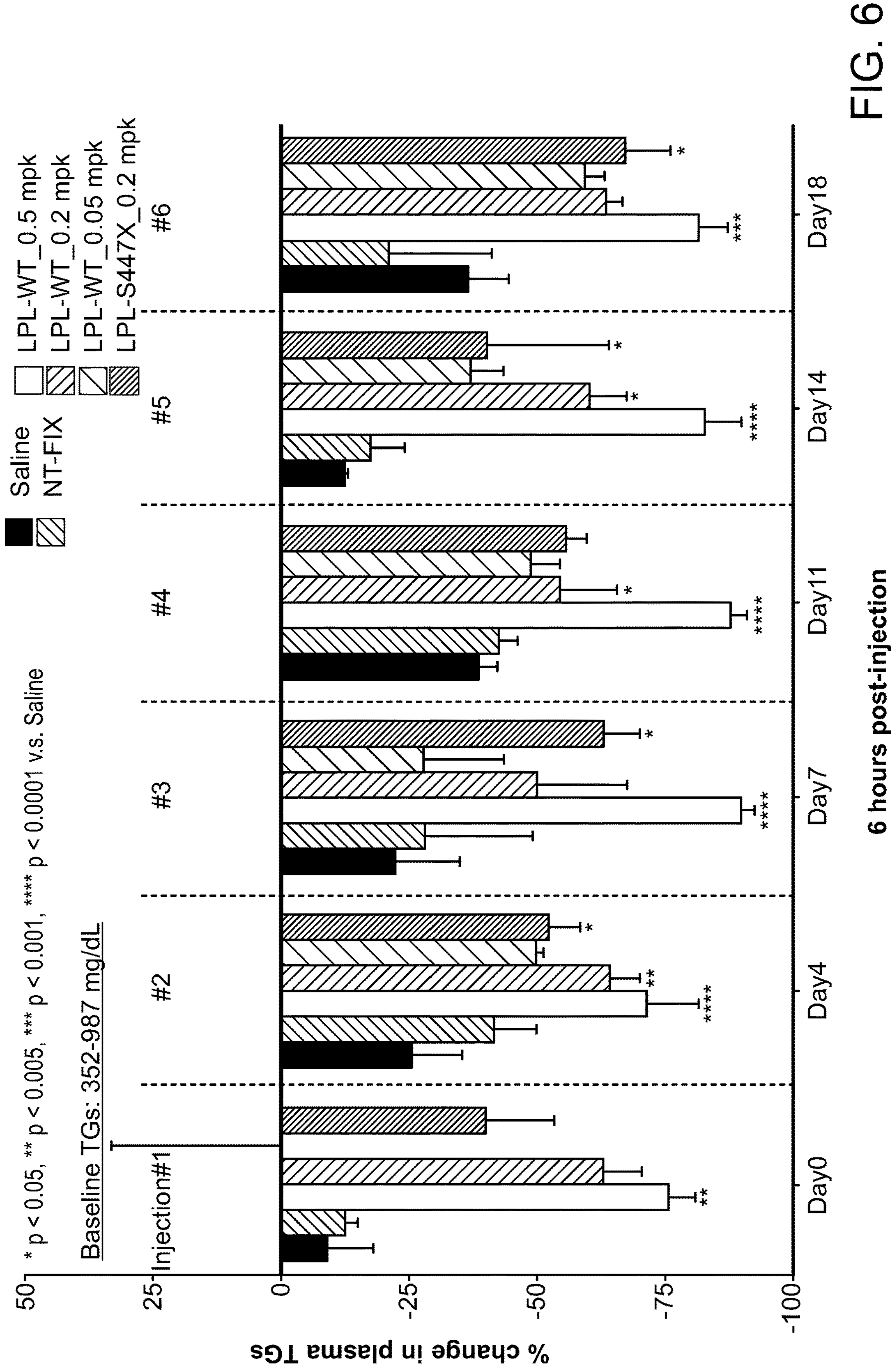

FIG. 6 shows the pharmacodynamics results of the three week administration study (2 doses per week). The percent change in plasma triglycerides six hours after an injection of the indicated formulation is given.

Figure 7:
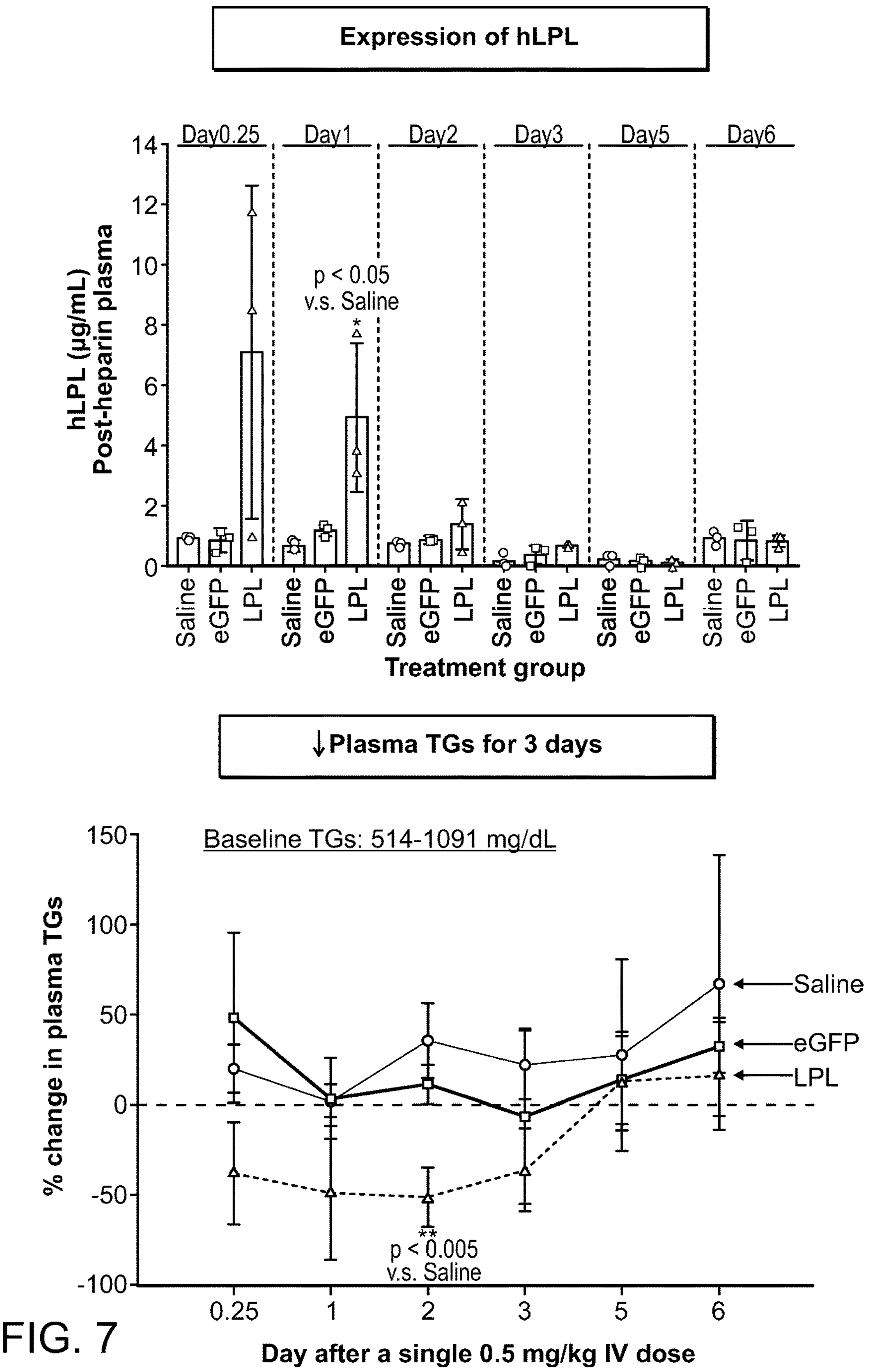

FIG. 7 shows the expression of hLPL in post-heparin plasma (left) and the percent change in plasma triglycerides in the single IV dose fa/fa rat study.

Figure 8:
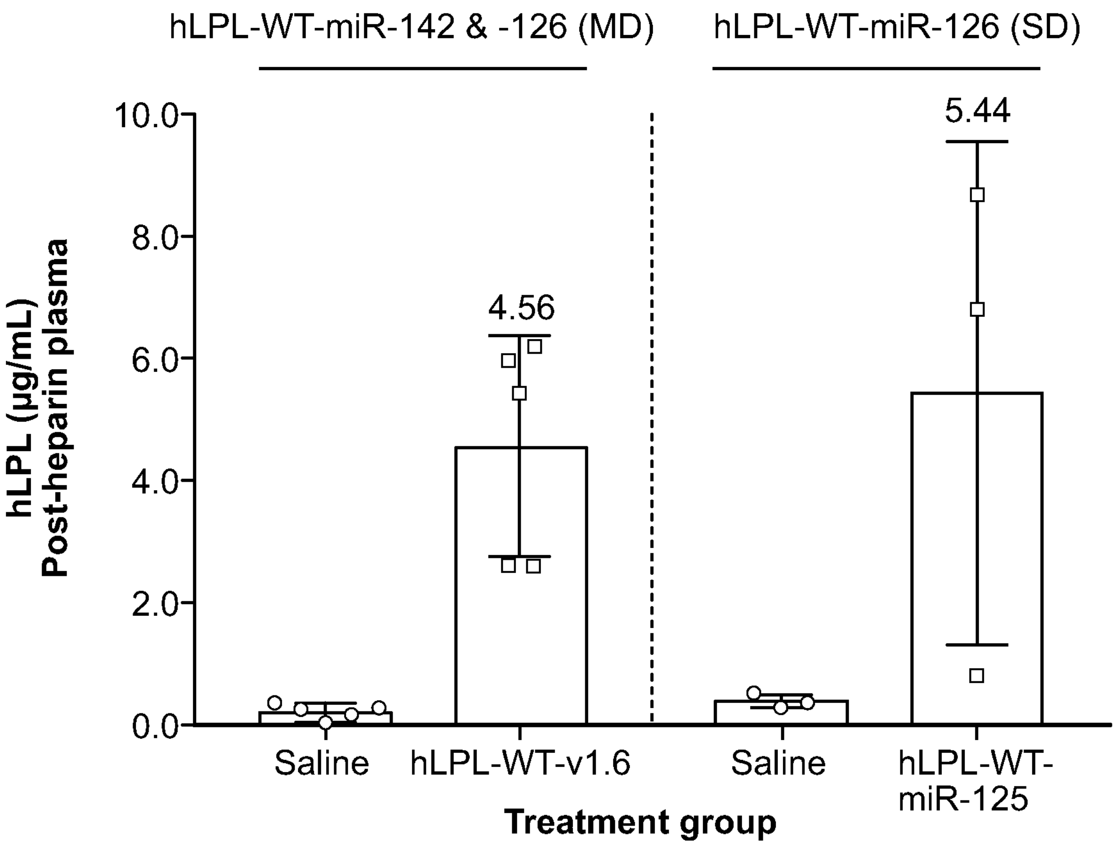

FIG. 8 shows the expression of hLPL following heparin administration in the single IV dose fa/fa rat study for the indicated constructs. Data is presented as mean±standard deviation.

Figure 9:
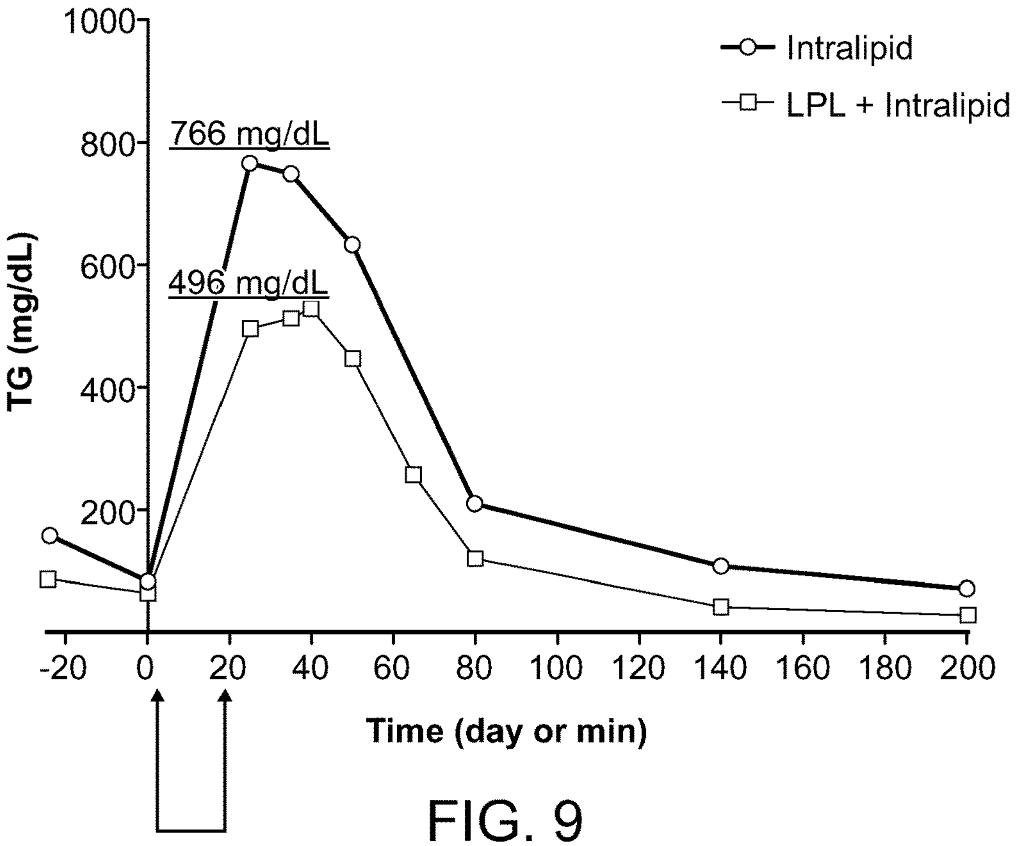

FIG. 9 shows data from an intralipid challenge (prior to hLPL-WT-miR-126 mRNA injection) in Sprague Dawley rats.

Figure 10:
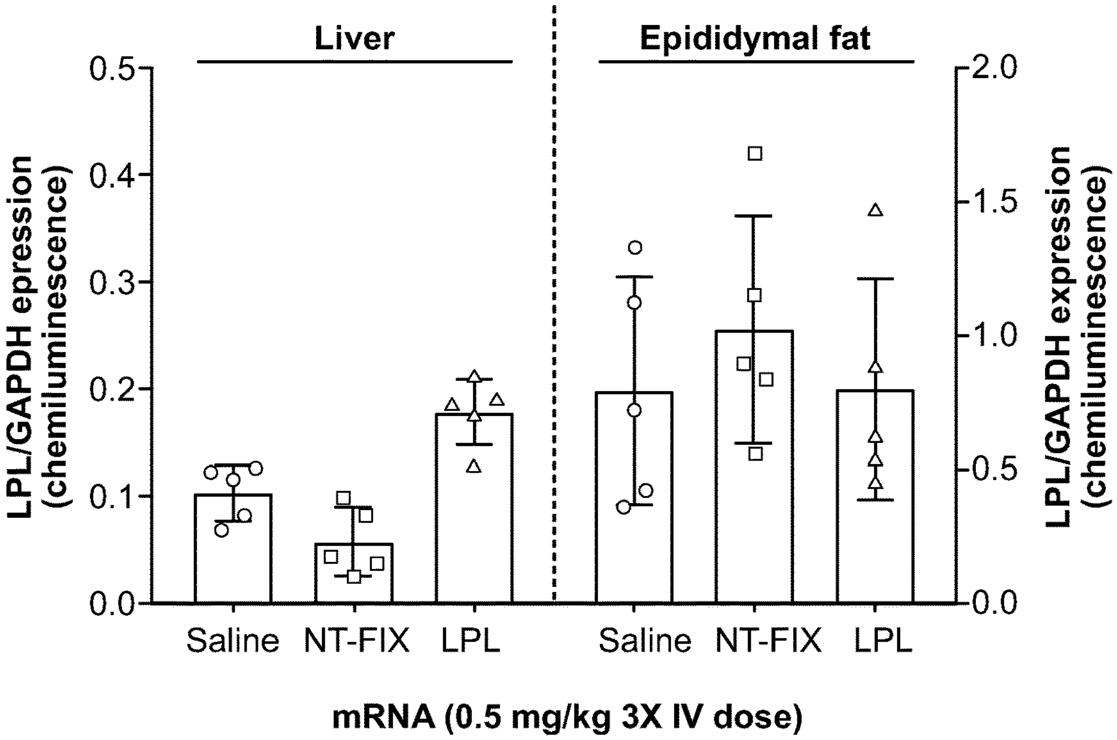

FIG. 10 shows the expression of hLPL in different tissues following the protocol described in Example 26.

Figure 11:
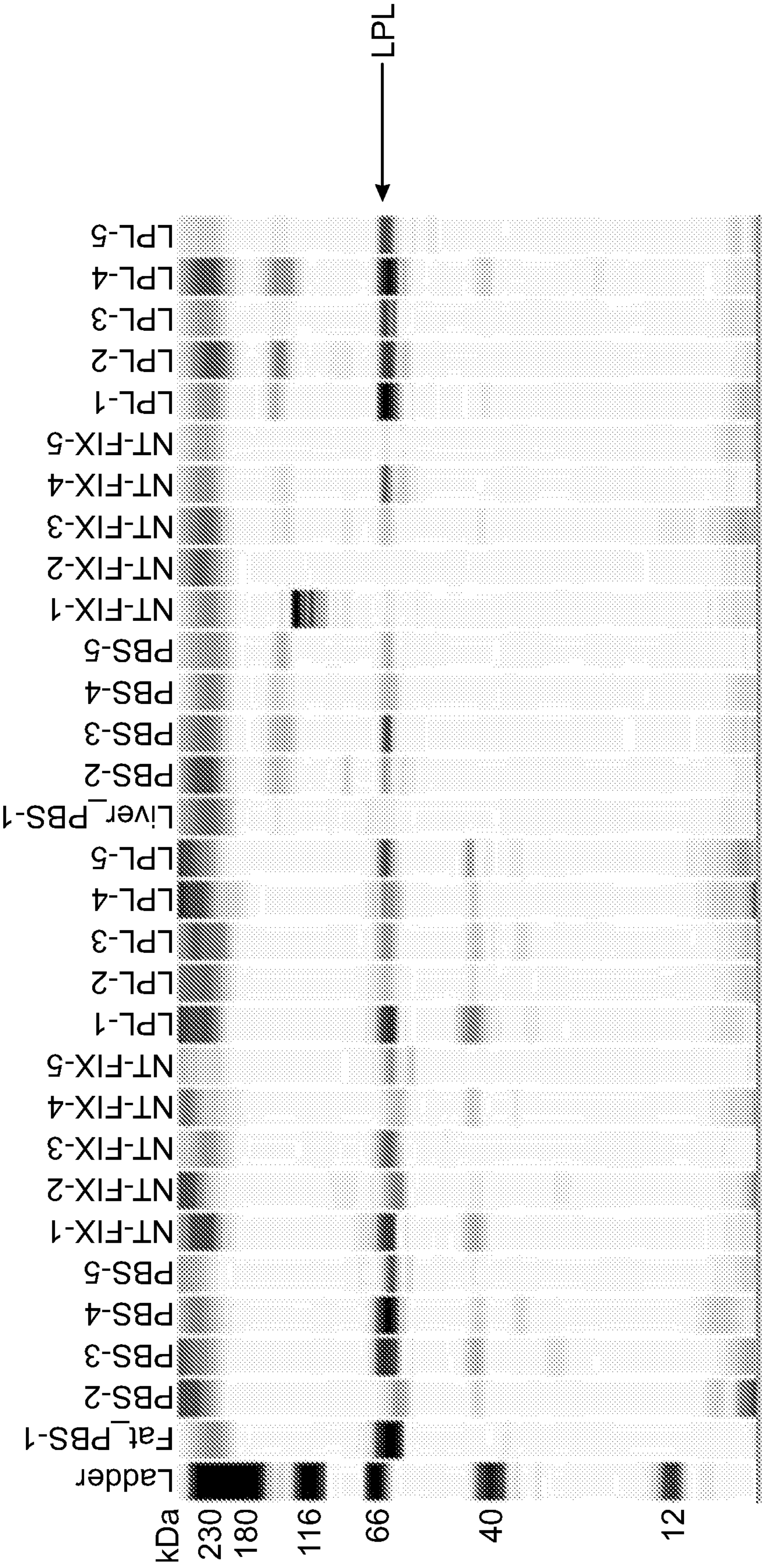
Figure 11:
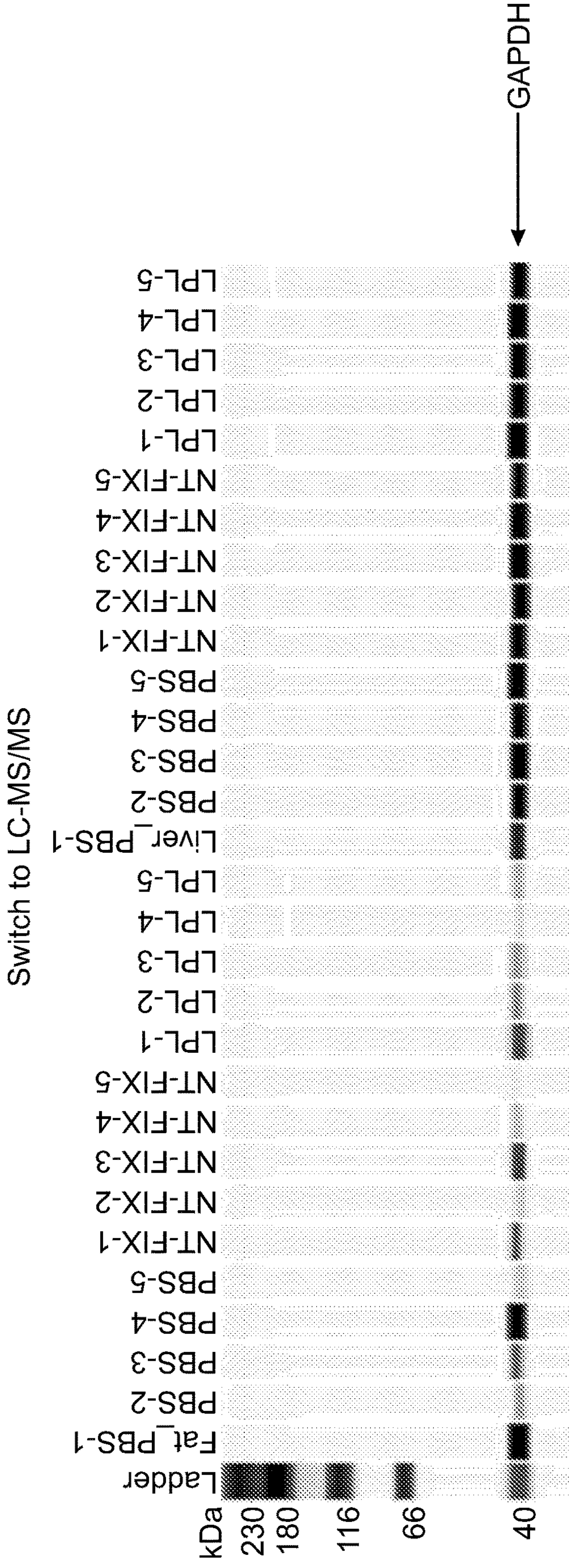

FIG. 11 is a Western blot showing the results from the experiment described in Example 26.

Figure 12:
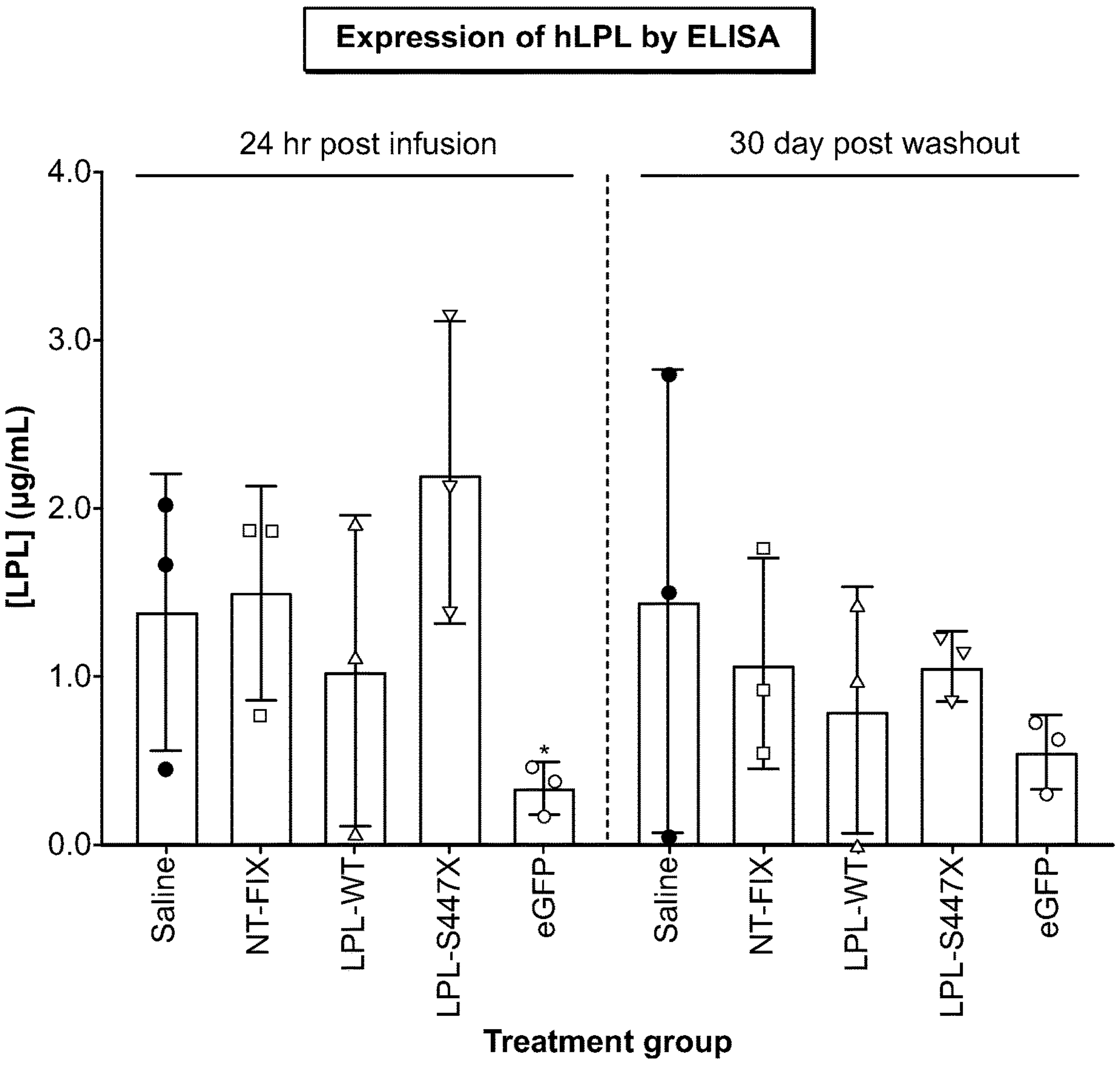

FIG. 12 is a graph showing the expression of hLPL of the groups described in Example 27.

Figure 13A:
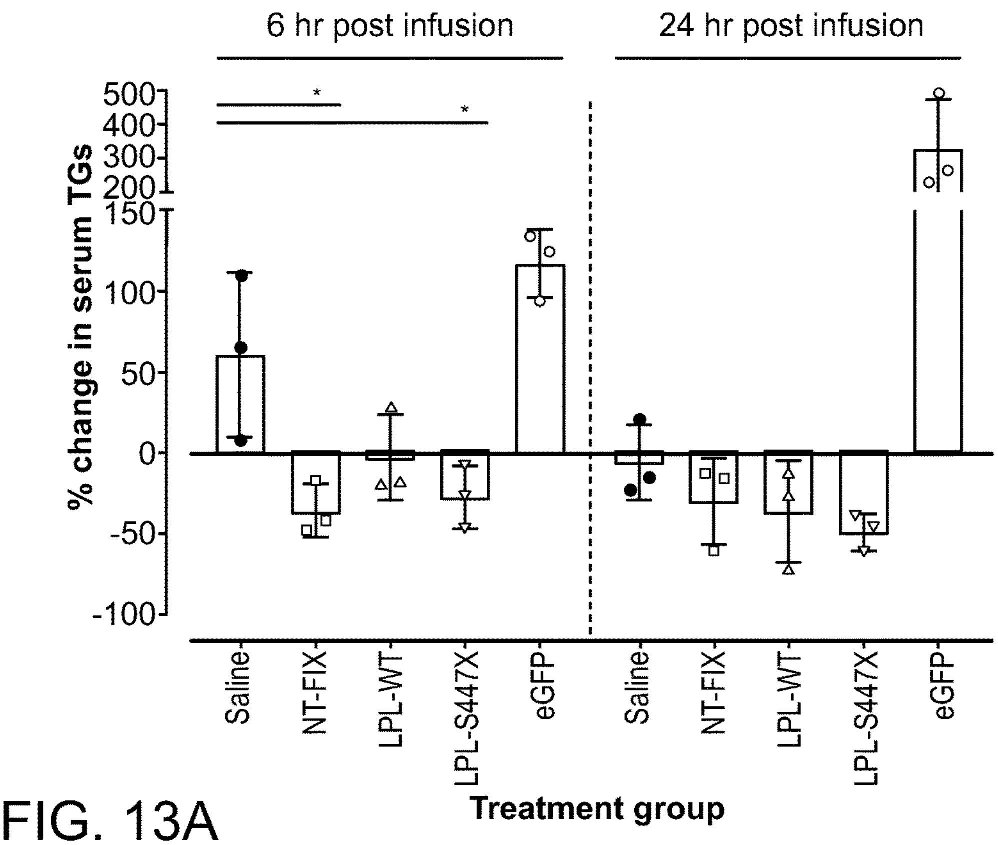
Figure 13B:
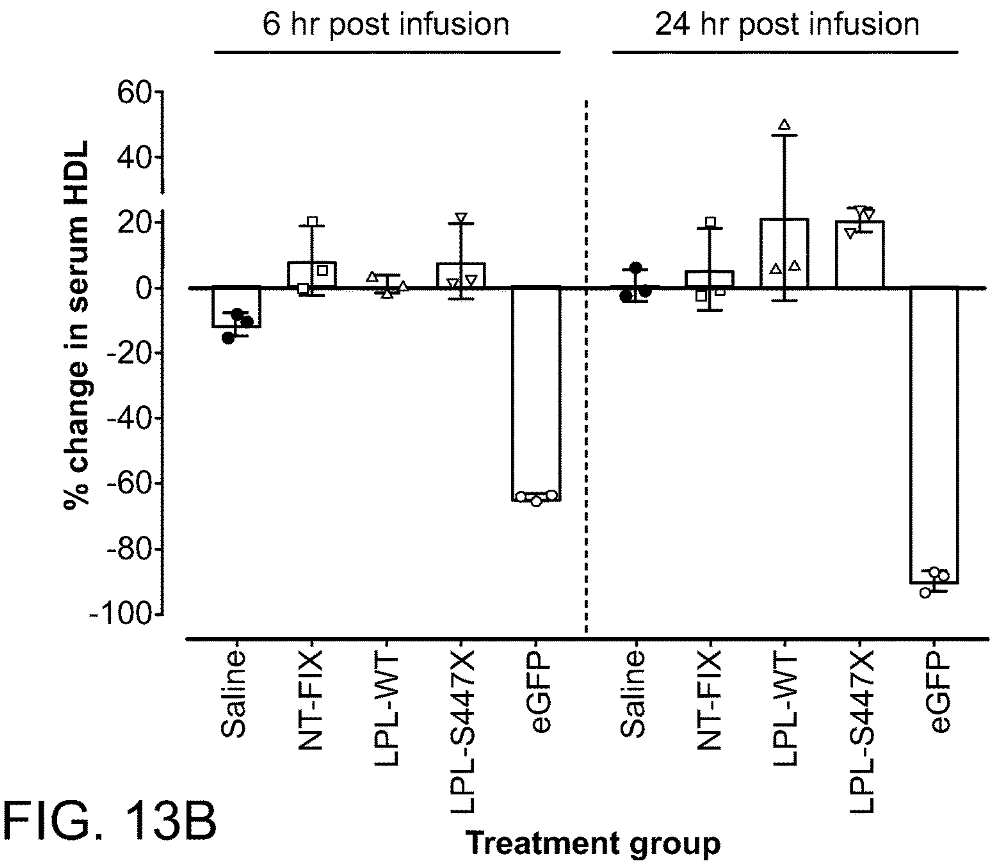
Figure 13C:
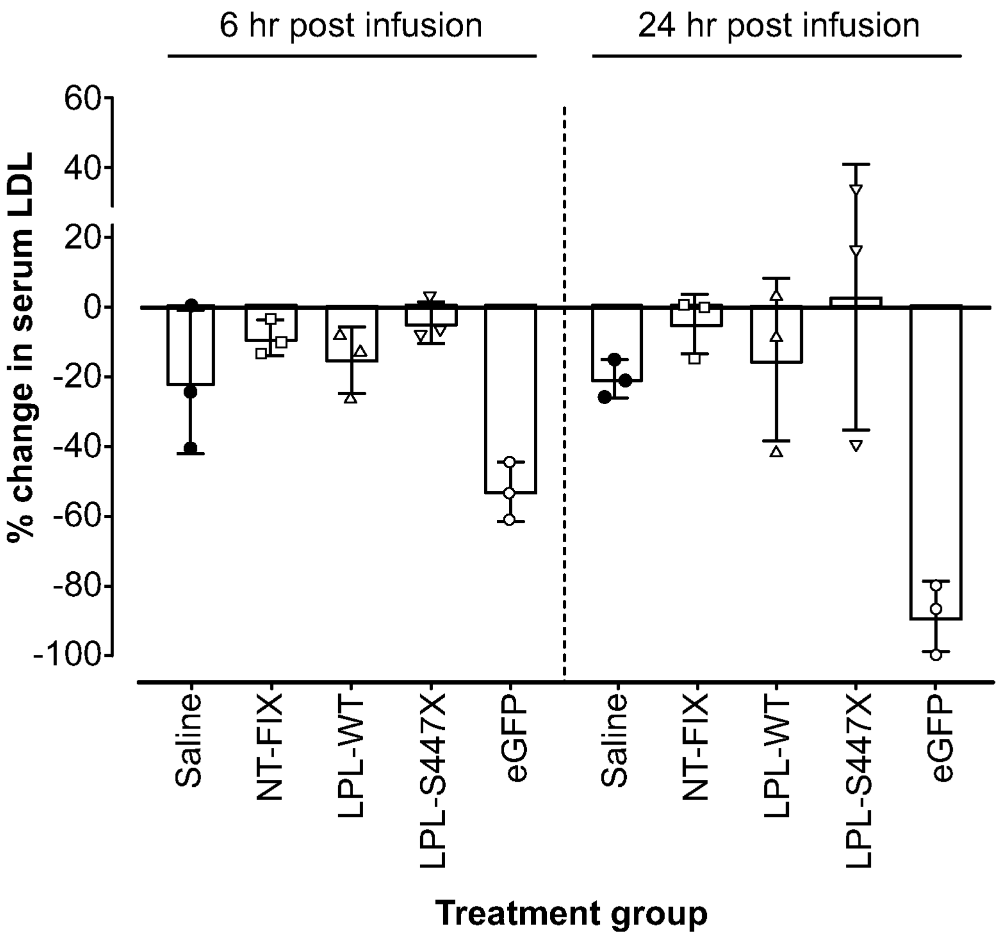

FIGS. 13A-13C show the triglyceride (FIG. 13A), HDL (FIG. 13B), and LDL (FIG. 13C) levels in each group 24 hours after the treatment described in Example 27.

Figure 14:
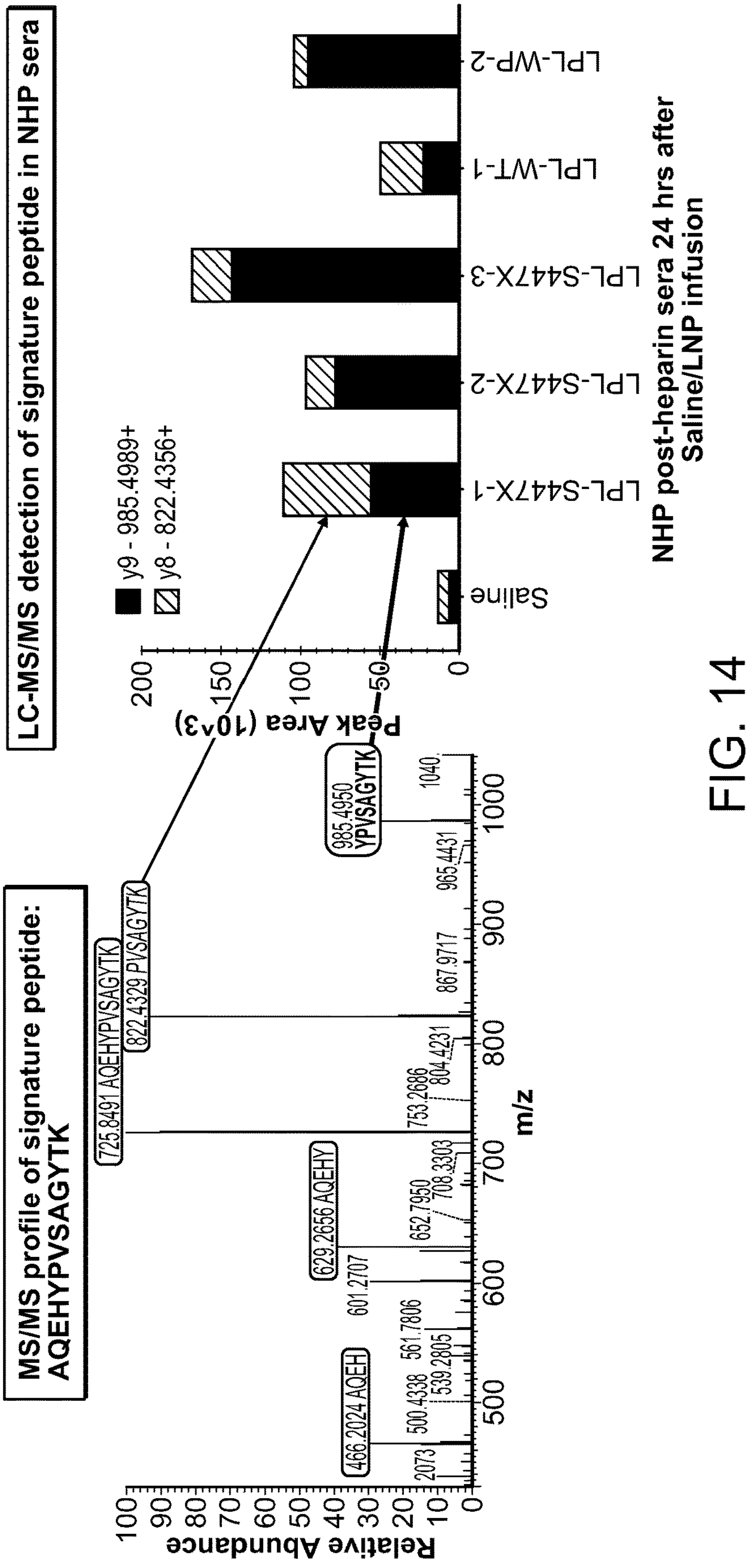

FIG. 14 shows MS/MS profile of the signature peptide (left) and the LC-MS/MS detection of the signature peptide in NHP sera (right). The peptides, from top to bottom and then left to right, correspond to SEQ ID NOs: 144, 144 and 142-146.

Figure 15:
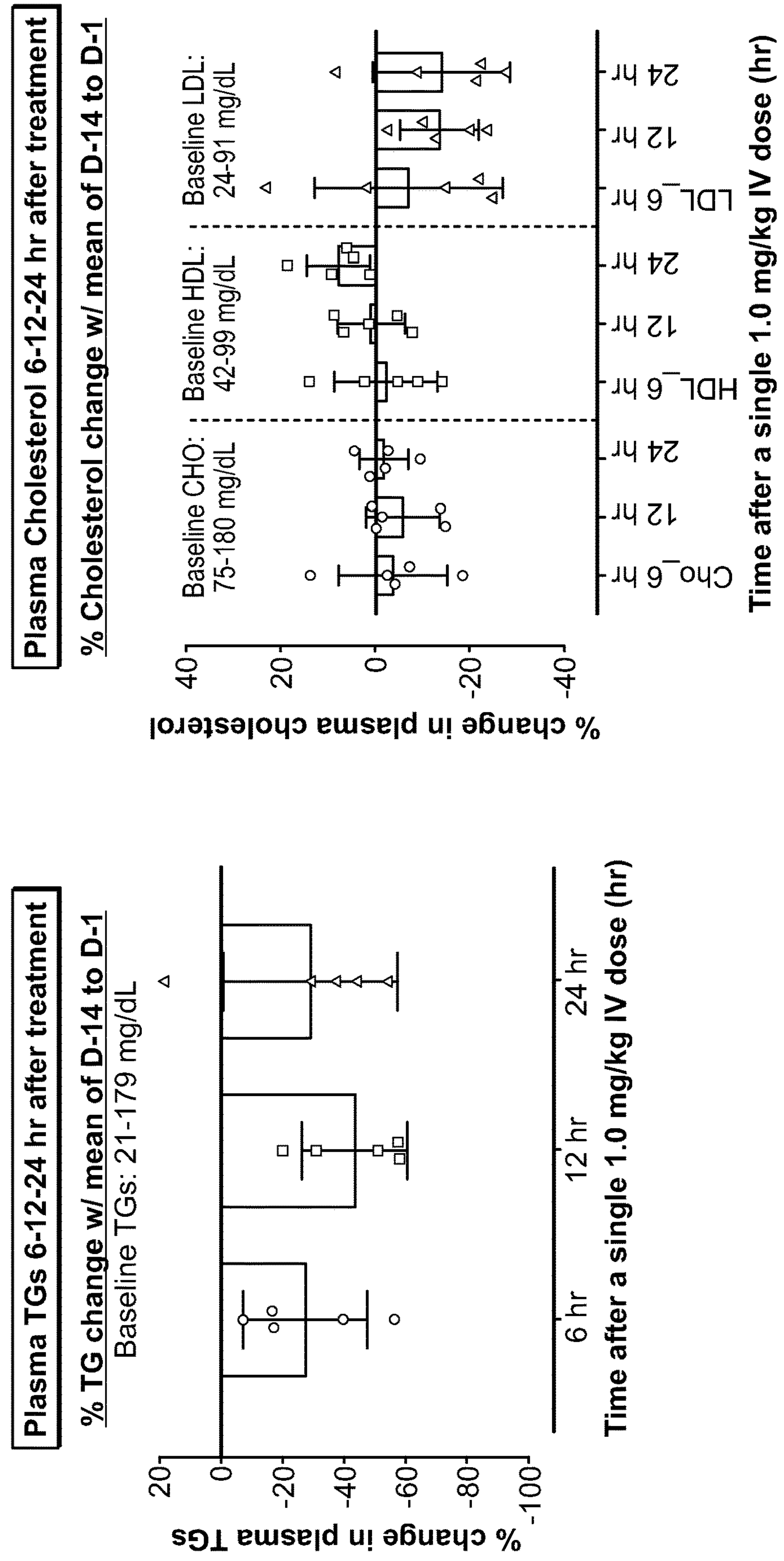

FIG. 15 shows the plasma triglycerides (left) and plasma cholesterol (right) levels six, 12, and 24 hours after treatment, as described in Example 17.

Figure 16:
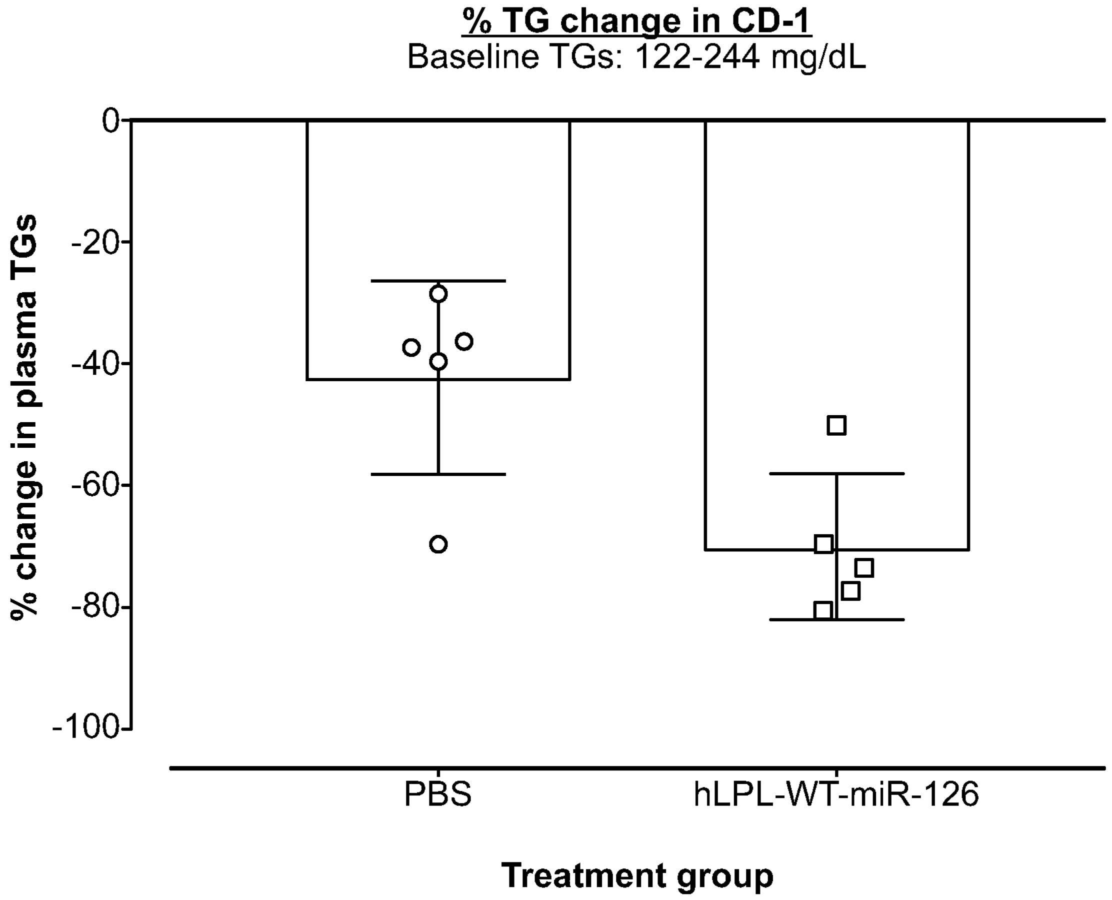

FIG. 16 shows the percent change in plasma triglycerides (TGs) in CD-1 mice six hours after 0.5 mg/kg injections of either hLPL-WT-miR-126 or saline.

DETAILED DESCRIPTION

The present invention provides mRNA therapeutics for the treatment of hyperlipidemia. Hyperlipidemia, the elevated level of any or all lipids or lipoproteins in the blood, can be caused by several acquired or genetic disorders. It is generally results from non-functional or low levels of lipoprotein lipase (LPL). A complete or partial loss of LPL function leads to buildup of triglycerides and chylomicrons in the plasma and results in a host of problems. mRNA therapeutics are particularly well-suited for the treatment of hyperlipidemia, as the technology provides for the intracellular delivery of mRNA encoding LPL followed by de novo synthesis of functional LPL protein within target cells. After delivery of mRNA to the target cells, the desired LPL protein is expressed by the cells' own translational machinery, leading to the producing of fully functional LPL, which replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution, and a strong type I interferon (type I IFN) response. The instant invention features the incorporation of different modified nucleotides within therapeutic mRNAs to minimize the immune activation and optimize the translation efficiency of mRNA to protein. Particular aspects of the invention feature a combination of nucleotide modification to reduce the innate immune response and sequence optimization, in particular, within the open reading frame (ORF) of therapeutic mRNAs encoding LPL to enhance protein expression.

The mRNA therapeutic technology of the instant invention also features delivery of mRNA encoding LPL via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features novel ionizable amino lipid-based LNPs which have improved properties when administered in vivo. Without being bound in theory, it is believed that the novel ionizable amino lipid-based LNPs of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., LPL) in a therapeutic context. This is because repeat administration of mRNA therapeutics is in most instances essential to maintain necessary levels of enzyme in target tissues in subjects (e.g., subjects suffering from hyperlipidemia). Repeat dosing challenges can be addressed on multiple levels. mRNA engineering and/or efficient delivery by LNPs can result in increased levels and or enhanced duration of protein (e.g., LPL) being expressed following a first dose of administration, which in turn, can lengthen the time between first dose and subsequent dosing. It is known that the accelerated blood clearance (ABC) phenomenon is, at least in part, transient in nature, with the immune responses underlying ABC resolving after sufficient time following systemic administration. As such, increasing the duration of protein expression and/or activity following systemic delivery of an mRNA therapeutic of the invention in one aspect, combats the ABC phenomenon. Moreover, LNPs can be engineered to avoid immune sensing and/or recognition and can thus further avoid ABC upon subsequent or repeat dosing. Exemplary aspect of the invention feature novel LNPs which have been engineered to have reduced ABC.

Lipoprotein Lipase (LPL)

Lipoprotein lipase (LPL, NM_000237; NP_000228), is a metabolic enzyme (E.C. 3.1.1.34) that plays a critical role in the hydrolysis of free triglycerides into free fatty acids and catabolism of chylomicrons and very low density lipoproteins. LPL's biological function is to aid in the creation of cholesterol and storage and metabolism of fatty acids. Lo, J. Y. et al., *Biochem. Biophys. Res. Commun.* 206: 266-271 (1995). LPL is expressed in a variety of tissues, primarily adipocytes and skeletal muscle cells, and localizes to the capillary lumen and functions as a homodimer. J. R. et al., J Mol Med. 80(12):753-769 (2002) and Ferland, A. et al. Obesity 20(5):1006-1011 (2012). The precursor form of human LPL is 475 amino acids, while its mature form is 448 amino acids—a 27 amino acid leader sequence is cleaved off once LPL reaches the capillary lumen. This leader sequence is referred to as LPL's signal peptide. Mutations at amino acid 159 from a serine to either a glycine or threonine and mutations at amino acid 268 from a histidine to either a glycine or glutamine lead to dysfunctional LPL.

The LPL S447Stop protein is a polymorphic LPL variant resulting from a single nucleotide polymorphism (a C to G mutation in exon 9 at position 1595), which introduces a premature stop codon at position 447. Rip, J. et al., Arterioscler Thromb Vase Biol. 26(6):1236-1245 (2006). This mutation is associated with beneficial effects on lipid homeostasis and atheroprotection. Id. For example, the X447 allele of the LPL gene is associated with an increase in high density lipoprotein cholesterol (HDL-C) and a decrease in triglycerides in adults and a lower family history of coronary artery disease. Chen, W. et al., Atherosclerosis 159(2):367-373 (2001).

The invention in aspects is a composition of an RNA polynucleotide comprising an open reading frame (ORF) encoding lipoprotein lipase (LPL) polypeptide which may be formulated in a ionizable amino lipid nanoparticle. The LPL may be a wild type LPL or a variant polypeptide. The compositions of the invention have several advantages over prior art methods for treating hyperlipidemia, including prior art LPL formulations such as protein or nucleic acid LPL formulations.

It has been discovered according to aspects of the invention that the mRNA formulations encoding LPL described herein have dramatic therapeutic effects in vivo in animal models of hyperlipidemia. A single intravenous (IV) dose of 0.5 mg/kg 5-methoxy uridine (mo5U)-modified WT-hLPL modRNA/Compound 18 formulation in Zucker fa/fa rats showed hLPL expression as early as one hour after administration, which was sustained after LNP administration, a significant reduction in plasma triglycerides levels (over 65%).

In some embodiments the RNA polynucleotide formulated in a ionizable amino lipid nanoparticle has a therapeutic index of greater than 10% of the therapeutic index of the RNA polynucleotide alone. In other embodiments the RNA polynucleotide formulated in the ionizable amino lipid nanoparticle has a therapeutic index of greater than 20%, 30%, 40%, 50%, 60%, 70%, 80%, or 90% of the therapeutic index of the RNA polynucleotide alone. The therapeutic index (TI) (also referred to as therapeutic ratio) is a comparison of the amount of a therapeutic agent that causes the therapeutic effect to the amount that causes toxicity.

The invention involves methods for reducing lipids such as triglycerides. In some embodiments the composition is in a dosage form that exhibits a pharmacokinetic (PK) profile comprising: a) a Tmax at about 30 to about 240 minutes after administration; and b) a plasma drug (LPL polypeptide produced by RNA polynucleotide) concentration plateau of at least 50% Cmax for a duration of about 90 to about 240 minutes. In other embodiments at least a 25%, 30%, 35%, 40%, 45%, 50%, 55%, 60%, 65%, 70%, 75%, 80%, 85%, 90, 95%, or 99% reduction in triglyceride level relative to baseline levels is achieved.

Another advantage of the methods of the invention is that the triglyceride level reduction is achieved rapidly following dosing of the subject. For instance therapeutic or maximal therapeutic levels may be achieved within 1, 2, 3, or 4 hours of dosing the subject. The term Cmax refers to the maximum (or peak) serum concentration that a drug achieves in a specified compartment or test area of the body after the drug has been administrated and before the administration of a second dose. Tmax refers to the time after administration of a drug when the maximum plasma concentration is reached; when the rate of absorption equals the rate of elimination.

It has also been discovered that certain therapeutic advantages can be achieved by combining the therapies of the invention with a standard of care therapy for hyperlipidemia. The standard-of-care for hyperlipidemia includes dietary restrictions, exercise, fibrates, omega-3, and niacin. Existing hyperlipidemia treatments focus on reducing the risk of coronary heart disease, as the two have been shown to be associated with one another. Changes in triglyceride concentrations have been shown to change the risk of coronary heart disease, but a causal link has not been established. For mild to moderate hyperlipidemia, statins are usually recommended. For those with triglycerides above 1000 mg/dL, other triglyceride-lowering treatments are administered. Fibrates have shown a 20-50% reduction in triglycerides, with the greatest benefit being realized in more severely affected patients. However, in cases of non-severe hyperlipidemia, treatment elevates the risk of pancreatitis. Nicotinic acid can decrease TG by 15-25%, but may worsen glucose tolerance in diabetic patients and may be harmful when combined with statins. Omega-3 (fish oil) yields a 50% reduction in TG, but the first generation preparations may raise LDL. GLYBERA®, which was approved in Europe after multiple attempts and is not currently approved in the US, is only focused on LPLD patients, and not hyperlipidemia broadly. It has shown limited (if any) short term efficacy and no longer term efficacy when used alone. In contrast, the compositions of the invention show a 50% improvement when combined with standard-of-care recommendations (diet, exercise, etc.) compared to omega-3/fibrate treatment.

Hyperlipidemia, the elevated level of any or all lipids or lipoproteins in the blood, can be caused by several acquired or genetic disorders. Lipids, including fats, cholesterol, and triglycerides, can penetrate arterial walls, increasing the risk of atherosclerosis, and by extension, stroke, heart attack, and death. Primary hyperlipidemias are divided into five types. Type I hyperlipoproteinemias include liprotein lipase deficiency (type Ia) is caused by a lack of LPL, which elevates the level of chylomicrons. Further complications of the disease include retinal vein occlusion, acute pancreatitis, steatosis and organomegaly, and lipaemia retinalis. Type II, the most common form, includes familial hypercholesterolemia, which can result from a mutation either in the LDL receptor gene on chromosome 19 or the ApoB gene. Subjects may experience tendon xanthoma, xanthelasma, and premature cardiovascular disease. The prevalence of the disease is about one in 500 for heterozygotes and one in 1,000,000 for homozygotes. Other Type II hyperlipidemias include familial combined hyperlipoproteinemia (FCH), lysosomal acid lipase deficiency (cholesteryl ester storage disease), and secondary combined hyperlipoproteinemia. Type III hyperlipidemias result from high chylomicrons and intermediate density lipoprotein, most commonly caused by ApoE E2/E2 genotype and is associated with hypercholesterolaemia, hypertrigyceridaemia, and a normal ApoB concentration. Type IV hyperlipidemia includes familial hypertriglyceridemia, an autosomal dominant condition that occurs in about 1% of the population. There are also secondary (acquired) forms of hyperlipidemia, which also result in an increased risk of premature atherosclerosis, pancreatitis, hypothyroidism, renal failure, nephrotic syndrome, and several rare endocrine disorders and metabolic disorders.

In some embodiments the hyperlipidemia is not familial lipoprotein lipase deficiency (FLLD).

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

LPL Protein Expression Levels

Certain aspects of the invention feature measurement, determination and/or monitoring of the expression level or levels of LPL protein in a subject, for example, in an animal (e.g., rodents, primates, and the like) or in a human subject. Animals include normal, healthy or wildtype animals, as well as animal models for use in understanding hyperlipidemia and treatments thereof. Exemplary animal models include rodent models, for example, LPL deficient mice also referred to as hyperlipidemic mice. LPL protein expression levels can be measured or determined by any art-recognized method for determining protein levels in biological samples, e.g., in a serum or plasma sample. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased LPL protein expression levels in the liver tissue of the subject (e.g., 2-fold, 3-fold, 4-fold, 5-fold, 6-fold, 7-fold, 8-fold, 9-fold, or 10-fold increase and/or increased to at least 50%, at least 60%, at least 70%, at least 75%, 80%, at least 85%, at least 90%, at least 95%, or at least 100% normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy.

LPL Protein Activity

In hyperlipidemia patients, LPL enzymatic activity is reduced, e.g., to about 50% of normal. Further aspects of the invention feature measurement, determination and/or monitoring of the activity level(s) (i.e., enzymatic activity level(s)) of LPL protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. Exemplary embodiments of the invention feature LPL activity described in terms of U/ml plasma or U/mg protein (tissue), where units ("U") are described in terms of nmol substrate hydrolyzed per hour (or nmol/hr). An exemplary enzymatic assay features that triglyceride hydrolysis. LPL activity in tissue (e.g., plasma or serum) can be quantitated, e.g., as level of triglycerides produced per mg of protein per hour.

In exemplary embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of LPL activity in tissue between 6 and 12 hours, or between 12 and 24, between 24 and 48, or between 48 and 72 hours post administration (e.g., at 48 or at 72 hours post administration). In exemplary embodiments, an mRNA therapy of the invention features a pharmaceutical composition comprising a dose of mRNA effective to result in at least 50 U/mg, at least 100 U/mg, at least 200 U/mg, at least 300 U/mg, at least 400 U/mg, at least 500 U/mg, at least 600 U/mg, at least 700 U/mg, at least 800 U/mg, at least 900 U/mg, at least 1,000 U/mg, or at least 1,500 U/mg of LPL activity between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

The LPL polypeptide may exhibit a $V_{max}$ of about 0.01-50 mmoles FA/hr/mg in for example a $[^{3H}]$-triolein liposome activity assay and/or a $K_m$ value of about 0.01-1 μM.

LPL Biomarkers

Further aspects of the invention feature determining the level (or levels) of a biomarker, e.g., ApoB, high-density lipoprotein cholesterol (HDLc), triglycerides, chylomicrons, and/or VLDL, determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase "elevated level" means amounts greater than normally found in a normal or wildtype preclinical animal or in a normal or healthy subject, e.g. a human subject. As used herein, the term "supraphysiologic" means amounts greater than normally found in a normal or wildtype preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference serum ApoB, high-density lipoprotein cholesterol (HDLc), triglycerides, chylomicrons, and/or VLDL level in said subject prior to administration (e.g., in a person suffering from hyperlipidemia) or in a normal or healthy subject.

As used herein, a "control" is preferably a sample from a subject wherein the hyperlipidemia status of said subject is known. In one embodiment, a control is a sample of a healthy patient. In another embodiment, the control is a sample from at least one subject having a known hyperlipidemia status, for example, a severe, mild, or healthy lipid status, e.g. a control patient. In another embodiment, the control is a sample from a subject not being treated for hyperlipidemia. In a still further embodiment, the control is a sample from a single subject or a pool of samples from different subjects and/or samples taken from the subject(s) at different time points.

The term "level" or "level of a biomarker" as used herein, preferably means the mass, weight or concentration of a biomarker of the invention within a sample or a subject. Biomarkers of the invention include, for example, ApoB, high-density lipoprotein cholesterol (HDLc), triglycerides, chylomicrons, and/or VLDL. It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In exemplary embodiments, LC-MS can be used as a means for determining the level of a biomarker according to the invention.

The term "determining the level" of a biomarker as used herein can mean methods which include quantifying an amount of at least one substance in a sample from a subject, for example, in a bodily fluid from the subject (e.g., serum, plasma, urine, blood, lymph, fecal, etc.) or in a tissue of the subject (e.g., liver, heart, spleen kidney, etc.).

The term "reference level" as used herein can refer to levels (e.g., of a biomarker) in a subject prior to administration of an mRNA therapy of the invention (e.g., in a person suffering from hyperlipidemia) or in a normal or healthy subject.

As used herein, the term "normal subject" or "healthy subject" refers to a subject not suffering from symptoms associated with hyperlipidemia. Moreover, a subject will be considered to be normal (or healthy) if it has no mutation of the functional portions or domains of the gene and/or no mutation of the LPL gene resulting in a reduction of or deficiency of the enzyme LPL or the activity thereof, resulting in symptoms associated with hyperlipidemia. Said mutations will be detected if a sample from the subject is subjected to a genetic testing for such LPL mutations. In exemplary embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for hyperlipidemia or in a subject being treated for hyperlipidemia to a control level of the biomarker comprises comparing the level of the biomarker in the sample from the subject (in need of treatment or being treated for hyperlipidemia) to a baseline or reference level, wherein if a level of the biomarker in the sample from the subject (in need of treatment or being treated for hyperlipidemia) is elevated, increased or higher compared to the baseline or reference level, this is indicative that the subject is suffering from hyperlipidemia and/or is in need of treatment; and/or wherein if a level of the biomarker in the sample from the subject (in need of treatment or being treated for hyperlipidemia) is decreased or lower compared to the baseline level this is indicative that the subject is not suffering from, is successfully being treated for hyperlipidemia, or is not in need of treatment for hyperlipidemia. The stronger the reduction (e.g., at least 2-fold, at least 3-fold, at least 4-fold, at least 5-fold, at least 6-fold, at least 7-fold, at least 8-fold, at least 10-fold reduction and/or at least 10%, at least 20%, at least 30% at least 40%, at least 50%, at least 60%, at least 70%, at least 80%, at least 90%, or at least 100% reduction) of the level of a biomarker, e.g., ApoB, high-density lipoprotein cholesterol (HDLc), triglycerides, chylomicrons, and/or VLDL, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., plasma, urine, e.g., urinary sediment) or in tissue(s) in a subject (e.g., liver, heart, spleen, kidney, brain or lung), for example an ApoB, high-density lipoprotein cholesterol (HDLc), triglycerides, chylomicrons, and/or VLDL, within 1, 2, 3, 4, 5, 6 or more days following administration is indicative of a dose suitable for successful treatment hyperlipidemia, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours post administration, in particular 24, 48, 72 or 96 hours post administration.

A sustained reduction in substrate levels (e.g., biomarkers such as ApoB, high-density lipoprotein cholesterol (HDLc), triglycerides, chylomicrons, and/or VLDL) is particularly indicative of mRNA therapeutic dosing and/or administration regimens successful for treatment of hyperlipidemia. Such sustained reduction can be referred to herein as "duration" of effect. In exemplary embodiments, a reduction of at least about 40%, at least about 50%, at least about 60%, at least about 65%, at least about 70%, at least about 75%, at least about 80%, at least about 85%, at least about 90%, or at least about 95% or more of the level of biomarker, in particular, in a bodily fluid (e.g., plasma, urine, e.g., urinary sediment) or in tissue(s) in a subject (e.g., liver, heart, spleen, kidney, brain or lung), for example ApoB, high-density lipoprotein cholesterol (HDLc), triglycerides, chylomicrons, and/or VLDL, within 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in ApoB, high-density lipoprotein cholesterol (HDLc), triglycerides, chylomicrons, and/or VLDL (as defined herein), optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk. about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk.

LPL is secreted from cells as a homodimer and is carried across endothelial cells for presentation on the luminal surface of vascular endothelium. Ong, J. M. et al. J Biol Chem. 264(6):3177-3182 (1989). The precursor form of wild-type human LPL is 475 amino acids, while its mature form is 448 amino acids due to the cleavage of a 27 amino acid leader sequence once LPL reaches the capillary lumen. This leader sequence is referred to as LPL's signal peptide.

The coding sequence (CDS) for wild type LPL canonical mRNA sequence is described at the NCBI Reference Sequence database (RefSeq) under accession number NM_000237.2 ("*Homo sapiens* lipoprotein lipase (LPL), mRNA"). The wild type LPL canonical protein sequence is described at the RefSeq database under accession number NP_0002228.1 ("lipoprotein lipase precursor [*Homo sapiens*]"). It is noted that the specific nucleic acid sequences encoding the reference protein sequence in the Ref Seq sequences are the coding sequence (CDS) as indicated in the respective RefSeq database entry.

The LPL-S447Stop protein is a polymorphic LPL variant resulting from a single nucleotide polymorphism (a C to G mutation in exon 9 at position 1595), which introduces a premature stop codon at position 447. Rip, J. et al., Arterioscler Thromb Vase Biol. 26(6):1236-1245 (2006). This mutation is associated with beneficial effects on lipid homeostasis and atheroprotection. Id. For example, the X447 allele of the LPL gene is associated with an increase in high density lipoprotein cholesterol (HDL-C) and a decrease in triglycerides in adults and a lower family history of coronary artery disease. Chen, W. et al., Atherosclerosis 159(2):367-373 (2001).

In certain aspects, the invention provides a polynucleotide (e.g., a ribonucleic acid (RNA), e.g., a messenger RNA (mRNA)) comprising a nucleotide sequence (e.g., an open reading frame (ORF)) encoding a LPL polypeptide. In some embodiments, the LPL polypeptide of the invention is a wild type LPL or variant LPL protein such as LPL-S447Stop protein. In some embodiments, the LPL polypeptide of the invention is a variant, a peptide or a polypeptide containing a substitution, and insertion and/or an addition, a deletion and/or a covalent modification with respect to a wild-type LPL or LPL-S447Stop sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a wild type LPL or LPL-S447Stop sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

Figure 1:
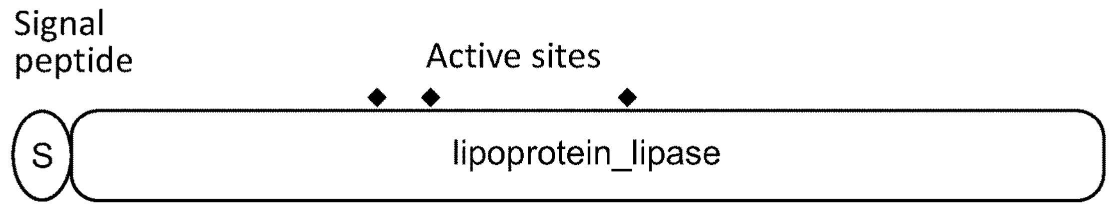
FIG. 1 shows the protein sequence (panel A), table with domain features (panel B), graphic representation of domain structure (panel C), and nucleic acid sequence (panel D) of wild type LPL.
Figure 2:
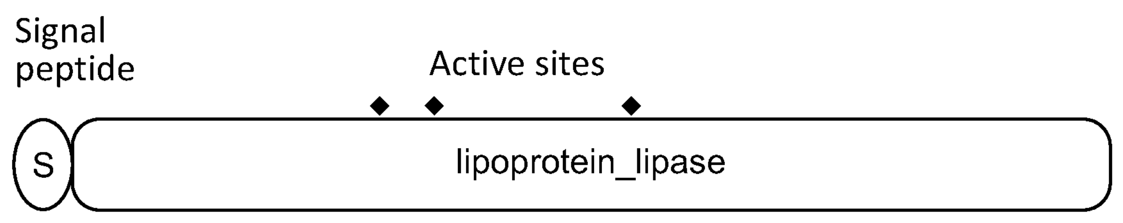
FIG. 2 shows the protein sequence (panel A), table with domain features (panel B), graphic representation of domain structure (panel C), and nucleic acid sequence (panel D) of LPL-S447Stop.

As recognized by those skilled in the art, wild type or LPL-S447Stop protein fragments, functional protein domains, variants, and homologous proteins (orthologs) are also considered to be within the scope of the LPL polypeptides of the invention. Nonlimiting examples of polypeptides encoded by the polynucleotides of the invention are shown in FIGS. 1 and 2. For example, FIG. 1 shows the amino acid sequence of wild type human LPL.

Certain compositions and methods presented in this disclosure refer to the protein or polynucleotide sequences of wild type LPL or LPL-S447Stop. A person skilled in the art will understand that such disclosures are equally applicable to any other isoforms of LPL known in the art.

In certain aspects, the invention provides polynucleotides (e.g., a RNA, e.g., an mRNA) that comprise a nucleotide sequence (e.g., an ORF) encoding one or more LPL polypeptides. In some embodiments, the encoded LPL polypeptide of the invention can be selected from:

a full length LPL polypeptide (e.g., having the same or essentially the same length as wild type LPL or LPL-S447Stop);

a variant such as a functional fragment of any of wild type LPL or LPL-S447Stop described herein (e.g., a truncated (e.g., deletion of carboxy, amino terminal, or internal regions) sequence shorter than one of wild type LPL or LPL-S447Stop; but still retaining LPL enzymatic activity);

a variant such as a full length or truncated wild type LPL or LPL-S447Stop proteins in which one or more amino acids have been replaced, e.g., variants that retain all or most of the LPL activity of the polypeptide with respect to a reference isoform (e.g., any natural or artificial variant known in the art); or a fusion protein comprising (i) a full length wild type LPL, variant LPL, or LPL-S447Stop isoform protein, a functional fragment or a variant thereof, and (ii) a heterologous protein.

In certain embodiments, the encoded LPL polypeptide is a mammalian LPL polypeptide, such as a human LPL polypeptide, a functional fragment or a variant thereof.

In some embodiments, the polynucleotide (e.g., a RNA, e.g., an mRNA) of the invention increases LPL protein expression levels and/or detectable LPL enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to LPL protein expression levels and/or detectable LPL enzymatic activity levels in the cells prior to the administration of the polynucleotide of the invention. LPL protein expression levels and/or LPL enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human LPL or a human LPL-S447Stop, e.g., wild-type human LPL (SEQ ID NO: 1, see FIG. 1) or human LPL-S447Stop (SEQ ID NO: 3, see FIG. 2).

In some embodiments, the polynucleotide (e.g., a RNA, e.g., an mRNA) of the invention comprises a codon optimized nucleic acid sequence, wherein the open reading frame (ORF) of the codon optimized nucleic sequence is derived from a wild-type LPL or LPL-S447Stop sequence. For example, for polynucleotides of invention comprising a sequence optimized ORF encoding LPL-S447Stop, the corresponding wild type sequence is the native LPL-S447Stop. Similarly, for a sequence optimized mRNA encoding a functional fragment of wild type LPL, the corresponding wild type sequence is the corresponding fragment from wild-type LPL.

In some embodiments, the polynucleotides (e.g., a RNA, e.g., an mRNA) of the invention comprise a nucleotide sequence encoding wild type LPL having the full length sequence of wild type human LPL (i.e., including the initiator methionine). In mature wild type human LPL, the initiator methionine can be removed to yield a "mature LPL" comprising amino acid residues of 2-475 of the translated product. The teachings of the present disclosure directed to the full sequence of human LPL (amino acids 1-475) are also applicable to the mature form of human LPL lacking the initiator methionine (amino acids 2-475). Thus, in some embodiments, the polynucleotides (e.g., a RNA, e.g., an mRNA) of the invention comprise a nucleotide sequence encoding wild type LPL having the mature sequence of wild type human LPL (i.e., lacking the initiator methionine). In some embodiments, the polynucleotide (e.g., a RNA, e.g., an mRNA) of the invention comprising a nucleotide sequence encoding wild type LPL having the full length or mature sequence of human wild type LPL is sequence optimized.

In some embodiments, the polynucleotides (e.g., a RNA, e.g., an mRNA) of the invention comprise a nucleotide sequence (e.g., an ORF) encoding a mutant LPL polypeptide. In some embodiments, the polynucleotides of the invention comprise an ORF encoding a LPL polypeptide that comprises at least one point mutation in the LPL sequence and retains LPL enzymatic activity. In some embodiments, the mutant LPL polypeptide has a LPL activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the LPL activity of the corresponding wild-type LPL (i.e., the same wild type LPL but without the mutation(s)). In some embodiments, the polynucleotide (e.g., a RNA, e.g., an mRNA) of the invention comprising an ORF encoding a mutant LPL polypeptide is sequence optimized.

In some embodiments, the polynucleotide (e.g., a RNA, e.g., an mRNA) of the invention comprises a nucleotide sequence (e.g., an ORF) that encodes a LPL polypeptide with mutations that do not alter LPL enzymatic activity. Such mutant LPL polypeptides can be referred to as function-neutral. In some embodiments, the polynucleotide comprises an ORF that encodes a mutant LPL polypeptide comprising one or more function-neutral point mutations.

In some embodiments, the mutant LPL polypeptide has higher LPL enzymatic activity than the corresponding wild-type LPL. In some embodiments, the mutant LPL polypeptide has a LPL activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type LPL (i.e., the same wild type LPL but without the mutation(s)).

In some embodiments, the polynucleotides (e.g., a RNA, e.g., an mRNA) of the invention comprise a nucleotide sequence (e.g., an ORF) encoding a functional LPL fragment, e.g., where one or more fragments correspond to a polypeptide subsequence of a wild type LPL polypeptide and retain LPL enzymatic activity. In some embodiments, the LPL fragment has a LPL activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the LPL activity of the corresponding full length LPL. In some embodiments, the polynucleotides (e.g., a RNA, e.g., an mRNA) of the invention comprising an ORF encoding a functional LPL fragment is sequence optimized.

In some embodiments, the polynucleotide (e.g., a RNA, e.g., an mRNA) of the invention comprises a nucleotide sequence (e.g., an ORF) encoding a LPL fragment that has higher LPL enzymatic activity than the corresponding full length LPL. Thus, in some embodiments the LPL fragment has a LPL activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the LPL activity of the corresponding full length LPL.

In some embodiments, the polynucleotide (e.g., a RNA, e.g., an mRNA) of the invention comprises a nucleotide sequence (e.g., an ORF) encoding a LPL fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type LPL or LPL-S447Stop.

In some embodiments, the polynucleotide (e.g., a RNA, e.g., an mRNA) of the invention comprises a nucleotide sequence (e.g., an ORF) encoding a LPL polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises a nucleotide sequence (e.g., an ORF) encoding a LPL polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 5 to 29, 80 to 83, and 148. See TABLE 2.

In some embodiments, the polynucleotide (e.g., a RNA, e.g., an mRNA) of the invention comprises a nucleotide sequence (e.g., an ORF) encoding a LPL polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 5 to 29, 80 to 83, 148. See TABLE 2.

In some embodiments, the polynucleotide (e.g., a RNA, e.g., an mRNA) of the invention comprises a nucleotide sequence (e.g., an ORF) encoding a LPL polypeptide (e.g., the wild-type sequence, functional fragment, or variant thereof), wherein the nucleotide sequence is at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2 or 4 (see, e.g, panel D in FIGS. 1 and 2, respectively).

In some embodiments the polynucleotide (e.g., a RNA, e.g., an mRNA) of the invention comprises a nucleotide sequence (e.g., an ORF) encoding a LPL polypeptide (e.g., the wild-type sequence, functional fragment, or variant thereof), wherein the nucleotide sequence is between 70% and 92% identical; 70% and 91% identical, 70% and 90% identical; between 75% and 85% identical; between 74% and 84% identical; between 73% and 83% identical; between 74% and 82% identical, between 75% and 81% identical, or between 76% and 80% identical to the sequence of SEQ ID NO:2 or 4 (see, e.g., panel D in FIGS. 1 and 2, respectively).

In some embodiments, the polynucleotide (e.g., a RNA, e.g., an mRNA) of the invention comprises from about 1,200 to about 100,000 nucleotides (e.g., from 1,200 to 1,500, from 1,200 to 1,600, from 1,200 to 1,700, from 1,200 to 1,800, from 1,200 to 1,900, from 1,200 to 2,000, from 1,300 to 1,500, from 1,300 to 1,600, from 1,300 to 1,700, from 1,300 to 1,800, from 1,300 to 1,900, from 1,300 to 2,000, from 1,425 to 1,500, from 1,425 to 1,600, from 1,425 to 1,700, from 1,425 to 1,800, from 1,425 to 1,900, from 1,425 to 2,000, from 1,425 to 3,000, from 1,425 to 5,000, from 1,425 to 7,000, from 1,425 to 10,000, from 1,425 to 25,000, from 1,425 to 50,000, from 1,425 to 70,000, or from 1,425 to 100,000).

In some embodiments, the polynucleotide of the invention (e.g., a RNA, e.g., an mRNA) comprises a nucleotide sequence (e.g., an ORF) encoding a LPL polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,100, 1,200, 1,300, 1,400, 1,425, 1450, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a LPL polypeptide (e.g., the wild-type sequence, functional fragment, or variant thereof) further comprises at least one nucleic acid sequence that is noncoding, e.g., a miRNA binding site.

In some embodiments, the polynucleotide of the invention comprising a nucleotide sequence (e.g., an ORF) encoding a LPL polypeptide (e.g., the wild-type sequence, functional fragment, or variant thereof) is RNA. In some embodiments, the polynucleotide of the invention is, or functions as, a messenger RNA (mRNA). In some embodiments, the mRNA comprises a nucleotide sequence (e.g., an ORF) that encodes at least one LPL polypeptide, and is capable of being translated to produce the encoded LPL polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a LPL polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142. In some embodiments, the polynucleotide disclosed herein is formulated with a delivery agent, e.g., a ionizable amino lipid nanoparticle such as a compound having Formula (I), (IA), (II), (IIa), (IIb), (IIc), (IId) or (IIe), e.g., any of Compounds 1-232.

Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked a nucleotide sequence that encodes a LPL polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a wild type LPL or LPL-S447Stop polypeptide, wherein the nucleotide sequence further comprises a 5' nucleic acid sequence encoding a native signal peptide. In another embodiment, the polynucleotide of the invention comprises a nucleotide sequence encoding a wild type LPL or LPL-S447Stop polypeptide, wherein the nucleotide sequence lacks the nucleic acid sequence encoding a native signal peptide.

In some embodiments, the polynucleotide of the invention comprises a nucleotide sequence encoding a LPL polypeptide, wherein the nucleotide sequence further comprises a 5' nucleic acid sequence encoding a heterologous signal peptide.

Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a LPL polypeptide, a functional fragment, or a variant thereof. However, in some embodiments, the polynucleotide of the invention can comprise more than one ORF, for example, a first ORF encoding a LPL polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a $G_4S$ peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide.

In some embodiments, the polynucleotide of the invention (e.g., a RNA, e.g., an mRNA) can comprise a first nucleic acid sequence (e.g., a first ORF) encoding a LPL polypeptide and a second nucleic acid sequence (e.g., a second ORF) encoding a second polypeptide such as a stabilizing sequence.

A stabilizing sequence, as used herein, is a peptide sequence which confers stability on a fused protein. The stabilizing sequence may in some embodiments be an immunoglobulin (Ig) or fragment thereof. Immunoglobulins include four IgG subclasses (IgG1, 2, 3, and 4) in humans, named in order of their abundance in serum. The IgG isotype, is composed of two light chains and two heavy chains, where each heavy chain contains three constant heavy domains (CH1, CH2, CH3). The two heavy chains of IgG are linked to each other and to a light chain each by disulfide bonds. The antigen binding site of IgG is located in the Fragment antigen binding region (Fab region), which contains variable light (VL) and variable heavy (VH) chain domains as well as constant light (CL) and constant heavy (CH1) chain domains. The fragment crystallizable region (Fc region) of IgG is a portion of the heavy chain containing the CH2 and CH3 domains that binds to an Fc receptor found on the surface of certain cells, including the neonatal Fe receptor (FcRn). The heavy chain of IgG also has a hinge region (hinge) between the CH1 and CH2 domains that separates the Fab region from the Fc region and participates in linking the two heavy chains together via disulfide bonds.

In some embodiments the Ig fragment is a portion of a constant heavy region ($C_H$) or variable heavy region ($V_H$) derived from an Ig molecule. The Ig fragment can include any portion of the constant or variable heavy region, including one or more constant or variable heavy domains, a hinge region, an Fc region, and/or combinations thereof.

In some embodiments the Ig fragment is a portion of a constant light region ($C_L$) or variable light region ($V_L$) derived from an Ig molecule. The Ig fragment can include any portion of the constant or variable light region, including one or more constant or variable light domains, a hinge region, an Fc region, and/or combinations thereof.

In certain embodiments, the Ig fragment of the fusion protein comprises a single chain Fe (sFc or scFc), a monomer, that is incapable of forming a dimer. In some embodiments, the fusion protein includes a sequence corresponding to an immunoglobulin hinge region. In various embodiments, the hinge region contains a modification that prevents the fusion protein from forming a disulfide bond with another fusion protein or another immunoglobulin molecule. In some embodiments, the hinge region is modified by mutating and/or deleting one or more cysteine amino acids to prevent the formation of a disulfide bond.

The fusion protein may have the LPL linked to the N-terminus of the Ig fragment. Alternatively, the fusion protein may have the LPL linked to the C-terminus of the Ig fragment. In specific embodiments, the fusion protein comprises the LPL at its N-terminus that is linked to a light or heavy chain sequence. In other embodiments, the fusion protein comprises the LPL at its C-terminus that is linked to a Ig fragment.

The linkage may be a covalent bond, and preferably a peptide bond. The fusion protein may optionally comprise at least one linker. Thus, the LPL may not be directly linked to the Ig fragment. The linker may intervene between the LPL and the Ig fragment. The linker can be linked to the N-terminus of the Ig fragment or the C-terminus of the Ig fragment. In one embodiment, the linker includes amino acids. The linker may include 1-5 amino acids.

Sequence Optimization of Nucleotide Sequence Encoding a LPL Polypeptide

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a LPL polypeptide, a nucleotide sequence (e.g, an ORF) encoding another polypeptide of interest, a 5'-UTR, a 3'-UTR, a miRNA, a nucleotide sequence encoding a linker, or any combination thereof) that is sequence optimized.

A sequence-optimized nucleotide sequence, e.g., a codon-optimized mRNA sequence encoding a LPL polypeptide, is a sequence comprising at least one synonymous nucleobase substitution with respect to a reference sequence (e.g., a wild type nucleotide sequence encoding a LPL polypeptide).

A sequence-optimized nucleotide sequence can be partially or completely different in sequence from the reference sequence. For example, a reference sequence encoding polyserine uniformly encoded by TCT codons can be sequence-optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

In some embodiments, a polynucleotide (e.g., a RNA, e.g., an mRNA) of the invention comprises a sequence-optimized nucleotide sequence (e.g., an ORF) encoding a LPL polypeptide, a functional fragment, or a variant thereof, wherein the LPL polypeptide, functional fragment, or a variant thereof encoded by the sequence-optimized nucleotide sequence has improved properties (e.g., compared to a LPL polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g, an ORF) encoding a LPL polypeptide, a nucleotide sequence (e.g, an ORF) encoding another polypeptide of interest, a 5'-UTR, a 3'-UTR, a microRNA, a nucleic acid sequence encoding a linker, or any combination thereof) that is sequence-optimized according to a method comprising: (i) substituting at least one codon in a reference nucleotide sequence (e.g., an ORF encoding a LPL polypeptide) with an alternative codon to increase or decrease uridine content to generate a uridine-modified sequence; (ii) substituting at least one codon in a reference nucleotide sequence (e.g., an ORF encoding a LPL polypeptide) with an alternative codon having a higher codon frequency in the synonymous codon set; (iii) substituting at least one codon in a reference nucleotide sequence (e.g., an ORF encoding a LPL polypeptide) with an alternative codon to increase G/C content; or (iv) a combination thereof.

In some embodiments, the sequence-optimized nucleotide sequence (e.g., an ORF encoding a LPL polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the LPL polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR. a 3' UTR and/or a miRNA. In some embodiments, the polynucleotide comprises two or more 5' UTRs and/or 3' UTRs, which can be the same or different sequences. In some embodiments, the polynucleotide comprises two or more miRNA, which can be the same or different sequences. Any portion of the 5' UTR, 3' UTR, and/or miRNA, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

Sequence-Optimized Nucleotide Sequences Encoding LPL Polypeptides

In some embodiments, the polynucleotide of the invention comprises a sequence-optimized nucleotide sequence encoding a LPL polypeptide disclosed herein. In some embodiments, the polynucleotide of the invention comprises an open reading frame (ORF) encoding a LPL polypeptide, wherein the ORF has been sequence optimized.

Exemplary sequence-optimized nucleotide sequences encoding wild type human LPL are shown in TABLE 2. In some embodiments, the sequence optimized LPL sequences in TABLE 2, fragments, and variants thereof are used to practice the methods disclosed herein. In some embodiments, the sequence optimized LPL sequences in TABLE 2, fragments and variants thereof are combined with or alternatives to the wild-type LPL and LPL-S447Stop sequences disclosed in FIGS. 1 and 2.

TABLE 2

Sequence optimized sequences for wild type human LPL

| SEQ ID NO | Name | Sequence |
|---|---|---|
| 5 | LPL-CO01 | ATGGAGAGCAAGGCCCTGCTGGTGCTGACCCTGGCCGTGTGGCTGCAGAGCCTG ACCGCCAGCCGGGGAGGCGTGGCCGCCGCCGACCAGCGGCGGGACTTCATCGA CATCGAGTCCAAGTTCGCCCTGCGGACGCCCGAGGACACCGCCGAAGACACCT GCCACCTGATCCCCGGCGTCGCCGAGAGCGTGGCCACATGCCACTTCAACCACA GCAGCAAGACCTTCATGGTGATCCACGGCTGGACCGTGACCGGCATGTACGAG AGCTGGGTGCCCAAGCTGGTGGCCGCTCTGTACAAGCGGGAGCCCGACAGCAA CGTGATCGTGGTGGACTGGCTGAGCCGGGCCCAGGAGCACTACCCCGTGAGCG CCGGCTACACCAAGCTCGTCGGCCAGGACGTGGCCCGGTTCATCAACTGGATGG AGGAGGAGTTCAACTACCCGCTGGACAACGTGCACCTGCTGGGCTACAGCCTG GGCGCCCACGCCGCCGGCATCGCCGGCAGCCTCACCAACAAGAAGGTGAACCG GATCACCGGCCTGGACCCCGCCGGCCCCAACTTCGAGTACGCCGAGGCGCCCA GCAGGCTCTCGCCCGACGACGCCGACTTCGTGGACGTGCTGCACACCTTCACCC GGGGCTCTCCCGGACGGAGCATCGGCATCCAGAAGCCCGTGGGCCACGTGGAC ATCTACCCCAACGGCGGCACCTTCCAGCCCGGCTGCAACATCGGCGAGGCCATC CGGGTGATCGCCGAGCGGGGTCTGGGCGACGTGGACCAGCTGGTGAAGTGCAG CCACGAGCGGAGCATTCACCTGTTCATCGATGCCTGCTGAACGAGGAGAACCC CTCCAAAGCATACCGGTGCAGTAGTAAGGAGGCCTTCGAGAAGGGCCTGTGCC TGAGCTGCCGGAAGAACAGATGCAACAACCTTGGGTACGAGATCAACAAGGTG CGGGCCAAGAGATCTTCCAAGATGTACCTGAAGACCCGGAGCCAGATGCCCTA CAAGGTGTTCCACTACCAGGTGAAGATCCACTTCAGCGGCACCGAAAGCGAAA CTCACACCAACCAGGCCTTTGAAATCAGCCTGTACGGCACCGTGGCCGAGTCTG AGAACATCCCTTTCACACTGCCCGAGGTGAGCACTAACAAGACCTACAGCTTCC TGATCTACACCGAGGTGGACATTGGCGAGCTGCTGATGCTGAAGCTGAAGTGG AAGTCAGACAGCTACTTCAGCTGGAGCGACTGGTGGTCTAGCCCCGGATTCGCC ATCCAGAAGATCAGGGTGAAGGCCGGAGAGACACAGAAGAAAGTGATCTTCTG |

TABLE 2-continued

| Sequence optimized sequences for wild type human LPL | | |
|---|---|---|
| SEQ ID NO | Name | Sequence |
| | | CAGCCGGGAGAAGGTAAGCCACCTGCAGAAGGGCAAGGCTCCCGCCGTGTTCG<br>TCAAGTGCCACGACAAGTCCCTGAACAAGAAGTCCGGC |
| 6 | LPL-CO02 | ATGGAGAGCAAGGCCCTGCTGGTGCTGACCCTGGCCGTGTGGCTGCAGAGCCTG<br>ACCGCCAGCCGGGGCGGCGTGGCCGCCGCCGACCAGCGCCGCGACTTCATCGA<br>CATCGAGTCCAAGTTCGCCCTCCGCACGCCCGAGGACACCGCCGAGGACACCTG<br>CCACCTCATCCCCGGCGTCGCCGAGTCCGTCGCCACCTGCCACTTCAACCACTC<br>CTCCAAGACCTTCATGGTCATCCACGGCTGGACCGTCACCGGCATGTACGAGTC<br>CTGGGTCCCCAAGCTCGTCGCCGCCCTCTACAAGCGCGAGCCCGACTCCAACGT<br>CATCGTCGTCGACTGGCTCTCCCGCGCCCAGGAGCACTACCCCGTCTCCGCCGG<br>CTACACCAAGCTCGTCGGCCAGGACGTCGCCCGCTTCATCAACTGGATGGAGGA<br>GGAGTTCAACTACCCACTCGACAACGTCCACCTCCTCGGCTACTCCCTCGGCGC<br>CCACGCCGCCGGCATCGCCGGCTCCCTCACCAACAAGAAGGTCAACCGCATCAC<br>CGGCCTCGACCCCGCCGGCCCCAACTTCGAGTACGCCGAGGCGCCCTCCCGCCT<br>CTCGCCCGACGACGCCGACTTCGTCGACGTCCTCCACACCTTCACCCGCGGCTC<br>GCCCGGCCGCTCCATCGGCATCCAGAAGCCCGTCGGCCACGTCGACATCTACCC<br>CAACGGCGGCACCTTCCAGCCCGGCTGCAACATCGGCGAGGCCATCCGCGTCAT<br>CGCCGAGCGCGGCCTCGGCGACGTCGACCAGCTCGTCAAGTGCTCCCACGAGC<br>GCTCCATCCACCTCTTCATCGACTCCCTCCTCAACGAGGAGAACCCCTCCAAGG<br>CCTACCGCTGCTCCTCCAAGGAGGCCTTCGAGAAGGGCCTCTGCCTCTCCTGCC<br>GCAAGAACCGCTGCAACAACCTCGGCTACGAGATCAACAAGGTCCGCGCCAAG<br>CGCTCCTCCAAGATGTACCTCAAGACCCGCTCCCAGATGCCCTACAAGGTCTTC<br>CACTACCAGGTCAAGATCCACTTCTCCGGCACCGAGTCCGAGACCCACACCAAC<br>CAGGCCTTCGAGATCTCCCTCTACGGCACCGTCGCCGAGTCCGAGAACATCCCC<br>TTCACCCTCCCCGAGGTCTCCACCAACAAGACCTACTCCTTCCTCATCTACACCG<br>AGGTCGACATCGGCGAGCTCCTCATGCTCAAGCTCAAGTGGAAGTCCGACTCCT<br>ACTTCTGCTGGTCCGACTGGTGGTCCTCGCCCGGCTTCGCCATCCAGAAGATCC<br>GCGTCAAGGCCGGCGAGACCCAGAAGAAGGTCATCTYCTGCTCCCGCGAGAAG<br>GTCTCCCACCTCCAGAAGGGCAAGGCGCCCGCCGTCTTCGTCAAGTGCCACGAC<br>AAGTCCCTCAACAAGAAGTCCGGC |
| 7 | LPL-CO03 | ATGGAGAGCAAGGCCCTGCTGGTGCTGACCCTGGCCGTGTGGCTGCAGAGCCTG<br>ACCGCCAGCCGGGGAGGCGTGGCCGCCGCCGACCAGCGGCGGGACTTCATCGA<br>CATCGAGTCCAAGTTCGCCCTGCGGACCCCCGAGGACACCGCCGAAGACACCT<br>GCCACCTGATCCCCGGCGTCGCCGAGAGCGTGGCCACATGCCACTTCAACCACA<br>GCAGCAAGACCTTCATGGTGATCCACGGCTGGACTTCATCGACATCGAGTCCAA<br>GTTCGCCCTGCGGACCCCCGAGGACACCGCCGAAGACACCTGCCACCTGATCCC<br>CGGCGTCGCCGAGAGCGTGGCCACATGCCACTTCAACCACAGCAGCAAGACCT<br>TCATGGTGATCCACGGCTGGACCGTGACCGGCATGTACGAGAGCTGGGTGCCCA<br>AGCTGGTGGCCGCTCTGTACAAGCGGGAGCCCGACAGCAACGTGATCGTGGTG<br>GACTGGCTGAGCCGGGCCCAGGAGCACTACCCCGTGAGCGCCGGCTACACCAA<br>GCTCGTCGGCCAGGACGTGGCCCGGTTCATCAACTGGATGGAGGAGGAGTTCA<br>ACTACCCCCTGGACAACGTGCACCTGCTGGGCTACAGCCTGGGCGCCCACGCCG<br>CCGGCATCGCCGGCAGCCTCACCAACAAGAAGGTGAACCGGATCACCGGCCTG<br>GACCCCGCCGGCCCCAACTTCGAGTACGCCGAGGCCCCCAGCAGGCTCTCCCCC<br>GACGACGCCGACTTCGTGGACGTGCTGCACACCTTCACCCGGGGCTCTCCCGGA<br>CGGAGCATCGGCATCCAGAAGCCCGTGGGCCACGTGGACATCTACCCCAACGG<br>CGGCACCTTCCAGCCCGGCTGCAACATCGGCGAGGCCATCCGGGTGATCGCCGA<br>GCGGGGTCTGGGCGACGTGGACCAGCTGGTGAAGTGCAGCCACGAGCGGAGCA<br>TTCACCTGTTCATCGATAGCCTGCTGAACGAGGAGAACCCCTCCAAAGCATACC<br>GGTGCAGTAGTAAGGAGGCCTTCGAGAAGGGCCTGTGCCTGAGCTGCCGGAAG<br>AACAGATGCAACAACCTTGGGTACGAGATCAACAAGGTGCGGGCCAAGAGATC<br>TTCCAAGATGTACCTGAAGACCCGGAGCCAGATGCCCTACAAGGTGTTCCACTA<br>CCAGGTGAAGATCCACTTCAGCGGCACCGAAAGCGAAACTCACACCAACCAGG<br>CCTTTGAAATCAGCCTGTACGGCACCGTGGCCGAGTCTGAGAACATCCCTTTCA<br>CACTGCCCGAGGTGAGCACTAACAAGACCTACAGCTTCCTGATCTACACCGAGG<br>TGGACATTGGCGAGCTGCTGATGCTGAAGCTGAAGTGGAAGTCAGACAGCTAC<br>TTCAGCTGGAGCGACTGGTGGTCTAGCCCCGGATTCGCCATCCAAAAGATCAGG<br>GTGAAGGCCGGAGAGACACAGAAGAAAGTGATCTTCTGCAGCCGGGAGAAGGT<br>AAGCCACCTGCAGAAGGGCAAGGCTCCCGCCGTGTTCGTCAAGTGCCACGACA<br>AGTCCCTGAACAAGAAGTCCGGC |
| 8 | LPL-CO04 | ATGGAGAGCAAGGCCCTGCTGGTGCTGACCCTGGCCGTGTGGCTGCAGAGCCTG<br>ACCGCCAGCCGGGGCGGCGTGGCCGCCGCCGACCAGCGCCGCGACTTCATCGA<br>CATCGAGTCCAAGTTCGCCCTCCGCACCCCCGAGGACACCGCCGAGGACACCTG<br>CCACCTCATCCCCGGCGTCGCCGAGTCCGTCGCCACCTGCCACTTCAACCACTC<br>CTCCAAGACCTTCATGGTCATCCACGGCTGGACCGTCACCGGCATGTACGAGTC<br>CTGGGTCCCCAAGCTCGTCGCCGCCCTCTACAAGCGCGAGCCCGACTCCAACGT<br>CATCGTCGTCGACTGGCTCTCCCGCGCCCAGGAGCACTACCCCGTCTCCGCCGG<br>CTACACCAAGCTCGTCGGCCAGGACGTCGCCCGCTTCATCAACTGGATGGAGGA<br>GGAGTTCAACTACCCCCTCGACAACGTCCACCTCCTCGGCTACTCCCTCGGCGC<br>CCACGCCGCCGGCATCGCCGGCTCCCTCACCAACAAGAAGGTCAACCGCATCAC<br>CGGCCTCGACCCCGCCGGCCCCAACTTCGAGTACGCCGAGGCCCCCTCCCGCCT<br>CTCCCCCGACGACGCCGACTTCGTCGACGTCCTCCACACCTTCACCCGCGGCTC |

TABLE 2-continued

Sequence optimized sequences for wild type human LPL

| SEQ ID NO | Name | Sequence |
|---|---|---|
| | | CCCCGGCCGCTCCATCGGCATCCAGAAGCCCGTCGGCCACGTCGACATCTACCC<br>CAACGGCGGCACCTTCCAGCCCGGCTGCAACATCGGCGAGGCCATCCGCGTCAT<br>CGCCGAGCGCGGCCTCGGCGACGTCGACCAGCTCGTCAAGTGCTCCCACGAGC<br>GCTCCATCCACCTCTTCATCGACTCCCTCCTCAACGAGGAGAACCCCTCCAAGG<br>CCTACCGCTGCTCCTCCAAGGAGGCCTTCGAGAAGGGCCTCTGCCTCTCCTGCC<br>GCAAGAACCGCTGCAACAACCTCGGCTACGAGATCAACAAGGTCCGCGCCAAG<br>CGCTCCTCCAAGATGTACCTCAAGACCCGCTCCCAGATGCCCTACAAGGTCTTC<br>CACTACCAGGTCAAGATCCACTTCTCCGGCACCGAGTCCGAGACCCACACCAAC<br>CAGGCCTTCGAGATCTCCCTCTACGGCACCGTCGCCGAGTCCGAGAACATCCCC<br>TTCACCCTCCCCGAGGTCTCCACCAACAAGACCTACTCCTTCCTCATCTACACCG<br>AGGTCGACATCGGCGAGCTCCTCATGCTCAAGCTCAAGTGGAAGTCCGACTCCT<br>ACTTCTCCTGGTCCGACTGGTGGTCCTCCCCCGGCTTCGCCATCCAGAAGATCCG<br>CGTCAAGGCCGGCGAGACCCAGAAGAAGGTCATCTTCTGCTCCCGCGAGAAGG<br>TCTCCCACCTCCAGAAGGGCAAGGCCCCCGCCGTCTTCGTCAAGTGCCACGACA<br>AGTCCCTCAACAAGAAGTCCGGC |
| 9 | LPL-CO05 | ATGGAGAGCAAGGCTCTGCTGGTGCTGACGCTGGCCGTGTGGCTGCAGTCCCTG<br>ACCGCCAGCAGGGGAGGCGTGGCCGCCGCCGACCAGCGGCGCGACTTCATCGA<br>TATCGAGTCGAAGTTCGCCCTGCGCACGCCCGAGGATACCGCCGAGGACACGT<br>GCCACCTGATCCCCGGGGTGGCGGAGAGCGTCGCCACCTGTCACTTCAACCATA<br>GCAGCAAGACGTTCATGGTCATCCACGGCTGGACCGTGACAGGAATGTACGAA<br>AGCTGGGTGCCCAAGCTCGTGGCCGCCCTCTACAAGAGGGAGCCCGACAGCAA<br>TGTGATAGTGGTGGACTGGCTGTCCCGGGCCCAGGAACACTATCCCGTGAGCGC<br>CGGGTACACCAAGCTCGTGGGCCAGGACGTGGCCCGGTTCATCAATTGGATGG<br>AGGAGGAGTTCAACTACCCCCTGGACAACGTGCATCTGCTCGGCTACTCCCTGG<br>GCGCTCACGCCGCCGGCATCGCGGGCAGCCTGACAAACAAGAAGGTGAACAGG<br>ATCACCGGGCTCGACCCCGCCGGCCCCAACTTCGAGTACGCCGAGGCCCCCAGC<br>AGGCTGAGCCCCGACGATGCCGACTTCGTGGACGTGCTGCACACCTTCACCCGG<br>GGCAGCCCCGGCAGGAGCATCGGCATCCAGAAGCCCGTGGGCCATGTCGACAT<br>CTATCCCAATGGCGGCACCTTTCAGCCCGGTTGCAACATCGGCGAGGCGATCAG<br>GGTGATTGCCGAGAGGGGCCTGGGCGACGTCGATCAGCTGGTGAAGTGTAGCC<br>ACGAGCGGTCCATCCATCTCTTCATAGACTCCCTTCTGAATGAAGAGAACCCCT<br>CCAAAGCCTACCGATGCAGCAGCAAGGAGGCGTTCGAAAAGGGGCTGTGCCTG<br>TCCTGCAGGAAGAACAGGTGCAACAATCTGGGCTATGAGATCAACAAGGTACG<br>CGCGAAGCGGAGCAGCAAGATGTATCTGAAGACCCGGTCGCAGATGCCCTATA<br>AAGTGTTCCACTACCAGGTAAAGATCCACTTCTCCGGGACCGAGAGCGAGACCC<br>ACACAAATCAGGCCTTCGAGATCAGCCTGTACGGCACCGTGGCGGAGAGCGAG<br>AATATCCCGTTCACCCTGCCTGAGGTGTCCACCAATAAGACCTACTCCTTCCTGA<br>TCTACACGGAGGTGGACATAGGCGAGCTGCTGATGCTGAAGCTGAAGTGGAAG<br>TCGGACAGCTACTTCTCCTGGAGCGACTGGTGGTCCTCCCCCGGATTCGCCATC<br>CAGAAGATCAGGGTGAAGGCCGGCGAGACCCAGAAAAAGGTGATCTTTTGCTC<br>GCGCGAGAAGGTCTCGCACCTGCAGAAGGGGAAGGCCCCCGCCGTGTTCGTGA<br>AGTGCCATGATAAGAGTCTCAATAAGAAGTCCGGG |
| 10 | LPL-CO06 | ATGGAGAGCAAGGCACTGCTGGTGCTGACACTGGCCGTGTGGCTGCAGAGCCT<br>GACCGCCTCCAGGGGCGGAGTGGCCGCCGCCGACCAGCGGCGGGACTTCATCG<br>ACATCGAATCGAAGTTCGCCCTGCGGACCCCGGAGGACACCGCCGAAGACACC<br>TGCCACCTCATCCCCGGCGTCGCCGAGAGCGTGGCCACGTGCCACTTCAACCAC<br>AGCAGCAAGACCTTCATGGTGATCCATGGCTGGACCGTGACAGGCATGTATGA<br>GAGCTGGGTCCCCAAACTGGTGGCGGCCCTGTACAAAAGGGAGCCGGACTCCA<br>ATGTGATCGTAGTGGACTGGCTCTCCAGGGCCCAGGAGCACTACCCCGTCAGCG<br>CCGGCTACACCAAGCTGGTGGGCCAGGACGTGGCCAGGTTCATCAACTGGATG<br>GAGGAAGAGTTCAATTACCCCCTGGACAACGTGCATCTGCTCGGGTACTCCCTG<br>GGCGCCCACGCCGCCGGGATCGCCGGTAGCCTCACCAACAAGAAGGTCAATCG<br>AATCACCGGGCTGGACCCCGCCGGGCCCAACTTTGAATACGCCGAAGCCCCCA<br>GCCGGCTCAGCCCCGACGATGCCGACTTTGTGGATGTGCTGCACACCTTCACCC<br>GAGGTAGCCCCGGCAGGAGCATCGGCATCCAGAAGCCCGTGGGCCACGTGGAC<br>ATCTACCCCAACGGGGGTACCTTCCAGCCCGGGTGCAACATCGGAGAGGCCATC<br>AGGGTGATCGCAGAGAGGGGCCTGGGCGATGTGGACCAGCTGGTCAAGTGCAG<br>CCACGAAAGGAGCATACACTTATTCATAGATAGCCTGCTCAACGAAGAGAACC<br>CCAGCAAGGCCTACCGTTGTTCCTCTAAGGAGGCCTTCGAGAAGGGGCTCTGCC<br>TGAGCTGCCGGAAAAACAGGTGCAACAACCTCGGCTACGAGATCAACAAGGTG<br>CGGGCCAAACGGTCCAGCAAGATGTACCTGAAGACCAGGAGCCAGATGCCCTA<br>TAAGGTCTTCCACTACCAGGTCAAGATCCACTTCTCCGGCACCGAGAGCGAGAC<br>CCACACTAACCAGGCCTTCGAGATCTCGCTGTACGGGACGGTGGCGGAATCCGA<br>GAACATCCCGTTCACCCTGCCCGAGGTGAGCACCAACAAAACGTACAGCTTCCT<br>GATCTACACCGAGGTCGACATCGGCGAGCTCCTCATGCTCAAGCTCAAGTGGAA<br>GAGCGATAGCTACTTCAGCTGGTCCGACTGGTGGAGCAGCCCGGGCTTCGCCAT<br>CCAAAAGATTAGGGTGAAGGCCGGCGAGACCCAGAAGAAGGTGATCTTCTGCT<br>CGAGGGAGAAAGTGTCCCATCTGCAGAAGGGCAAGGCCCCGGCCGTGTTCGTG<br>AAGTGCCACGATAAGTCGCTGAACAAGAAGTCCGGC |
| 11 | LPL-CO07 | ATGGAGTCCAAGGCCCTGCTGGTGCTCACACTCGCCGTGTGGCTGCAGACCCTG<br>ACCGCCTCCCGGGGGGGCGTGGCGGCCGCCGACCAGCGGAGGGATTTCATCGA |

TABLE 2-continued

| SEQ ID NO | Name | Sequence |
|---|---|---|
| | | CATCGAGAGCAAATTCGCCCTGAGGACCCCCGAGGACACCGCCGAGGATACCT<br>GCCATCTCATCCCCGGCGTGGCTGAGAGCGTGGCCACCTGCCACTTCAACCACA<br>GCAGCAAGACCTTCATGGTGATCCACGGCTGGACCGTGACCGGAATGTACGAG<br>AGCTGGGTGCCCAAGCTGGTGGCCGCCCTGTACAAGAGGGAGCCCGATAGCAA<br>TGTGATAGTGGTGGATTGGCTGAGCAGGGCCCAAGAGCATTACCCCGTGAGCG<br>CCGGCTATACCAAGCTGGTGGGCCAGGACGTGGCCAGGTTCATCAACTGGATG<br>GAGGAGGAGTTCAACTACCCCCTGGACAACGTCCACCTGCTGGGCTACAGCCTG<br>GGGGCCCACGCCGCGGGCATCGCCGGCTCCCTCACCAACAAGAAGGTGAATAG<br>GATAACGGGCCTGGACCCCGCCGGTCCCAACTTCGAGTACGCCGAGGCCCCGTC<br>CCGACTGTCTCCCGACGACGCAGACTTCGTCGACGTCCTGCATACCTTCACCAG<br>AGGCAGCCCCGGGAGGTCCATCGGCATCCAGAAGCCCGTGGGCCATGTGGACA<br>TCTACCCGAATGGCGGCACCTTCCAGCCTGGTTGCAACATTGGCGAGGCGATCA<br>GGGTGATCGCCGAGCGTGGCCTCGGGGACGTGGATCAGCTGGTGAAGTGTTCCC<br>ACGAGCGCAGCATCCACCTCTTCATCGACAGCCTGCTCAACGAAGAGAACCCCT<br>CCAAGGCCTACAGGTGCAGTTCCAAGGAGGCATTCGAGAAGGGCCTCTGCCTG<br>AGCTGCAGGAAGAACAGGTGTAACAACCTAGGCTACGAGATCAACAAGGTCCG<br>GGCCAAGCGGAGCTCAAAGATGTACCTGAAGACGCGGAGCCAGATGCCCTATA<br>AGGTGTTCCACTACCAGGTGAAAATCCATTTCTCCGGCACCGAGTCCGAGACCC<br>ACACCAACCAAGCATTCGAGATCTCCCTCTACGGAACCGTAGCAGAGAGCGAG<br>AACATCCCCTTCACCCTCCCCGAGGTGAGCACTAACAAGACGTACTCCTTCCTG<br>ATCTACACCGAGGTGGACATCGGCGAGCTCCTGATGCTGAAGCTGAAGTGGAA<br>GAGCGACTCCTACTTTTCCTGGTCCGACTGGTGGTCCAGCCCCGGGTTTGCGATT<br>CAAAAGATCAGGGTGAAAGCCGGCGAAACCCAGAAGAAGGTGATCTTCTGTAG<br>CCGAGAGAAAGTGAGCCACCTGCAGAAAGGAAAGGCCCCCGCCGTCTTCGTCA<br>AGTGCCACGACAAAAGCCTCAATAAGAAGTCCGGG |
| 12 | LPL-CO08 | ATGGAGAGCAAGGCGCTGCTGGTGCTGACACTGGCGGTGTGGCTGCAAAGCCT<br>GACCGCGAGCAGGGGCGGCGTGGCCGCCGCCGACCAGAGGCGGGACTTCATTG<br>ACATCGAGTCCAAGTTCGCCCTTAGGACCCCCGAAGACACCGCCGAGGACACCT<br>GCCACCTGATACCGGGGGTGGCCGAGTCCGTGGCCACCTGCCACTTTAACCACT<br>CCTCCAAGACGTTCATGGTCATCCACGGCTGGACCGTGACCGGGATGTACGAAA<br>GCTGGGTGCCCAAGCTGGTGGCCGCCCTCTACAAAAGGGAGCCTGACTCCAAC<br>GTCATCGTGGTGGACTGGCTGTCCAGGGCCCAGGAGCACTACCCCGTTTCCGCC<br>GGATACACCAAGCTGGTGGGCCAGGACGTGGCCCGGTTCATCAATTGGATGGA<br>GGAGGAATTCAATTACCCCCTGGACAACGTGCATCTGCTCGGCTACTCCCTGGG<br>CGCCCACGCCGCCGGCATCGCCGGCAGCCTGACTAACAAGAAGGTGAACCGGA<br>TCACCGGCCTGGACCCCGCCGGCCCCAACTTCGAATACGCCGAGGCCCCCTCCC<br>GACTGTCCCCAGACGACGCCGACTTCGTGGATGTGCTGCACACCTTCACCCGCG<br>GCAGCCCCGGGCGAAGCATCGGAATCCAAAAGCCCGTGGGGCACGTGGATATC<br>TACCCGAACGGGGGAACCTTCCAACCCGGCTGCAACATTGGGGAGGCCATCAG<br>AGTGATCGCCGAGCGCGGGCTGGGGGACGTCGACCAGCTGGTGAAGTGCTCCC<br>ACGAGCGCAGCATCCACCTGTTCATCGACTCCCTACTGAATGAAGAGAACCCCA<br>GCAAGGCGTACCGGTGGTCCTCCAAGGAGGCCTTCGAGAAGGGCCTCTGCCTGA<br>GCTGCAGGAAGAACAGATGCAACAATCTGGGCTACGAGATCAATAAGGTCCGC<br>GCCAAGAGAAGCAGCAAAATGTACCTGAAGACCCGGAGCCAGATGCCCTATAA<br>GGTGTTCCACTACCAGGTGAAGATCCACTTCAGCGGTACGGAGTCTGAGACCCA<br>TACCAACCAGGCTTTCGAAATCAGCCTGTACGGAACCGTGGCCGAGAGCGAGA<br>ACATCCCCTTTACCCTGCCAGAAGTGTCCACAAACAAGACCTACTCCTTCCTGA<br>TATACACTGAGGTGGACATCGGCGAGCTGCTGATGCTGAAGTTGAAGTGGAAG<br>AGCGATAGCTACTTCAGCTGGAGCGATTGGTGGAGCAGCCCCGGATTCGCCATC<br>CAGAAGATAAGGGTGAAGGCCGGAGAGACCCAGAAGAAGGTCATCTTTTGCAG<br>CAGGGAGAAGGTGAGCCACCTGCAGAAGGGCAAGGCGCCCGCCGTGTTCGTCA<br>AGTGTCACGACAAGAGCCTGAATAAGAAGAGCGGG |
| 13 | LPL-CO09 | ATGGAAAGCAAGGCGCTGCTCGTCCTCACCCTGGCCGTCTGGCTGCAAAGCCTG<br>ACCGCCAGCAGAGGTGGGGTGGCGGCCGCCGACCAGCGGCGAGACTTCATCGA<br>TATCGAAAGCAAGTTTGCCCTGAGGACCCCCGAGGATACCGCCGaGGACACCT<br>GCCACCTGATTCCCGGAGTGGCCGAGAGCGTTGCCACCTGCCACTTCAACCACT<br>CGAGCAAGACCTTTATGGTGATACACGGCTGGACCGTCACGGGCATGTACGAG<br>AGCTGGGTGCCCAAGCTGGTGGCCGCCCTGTATAAGAGGGAGCCGGACAGCAA<br>CGTCATCGTCGTGGACTGGCTGTCGAGGGCCCAAGAACACTACCCCGTGAGCGC<br>CGGGTACACCAAGCTGGTCGGTCAAGACGTGGCCCGCTTCATCAATTGGATGGA<br>GGAGGAGTTCAACTATCCCCTCGACAACGTGCACCTCCTGGGCTACAGCCTGGG<br>CGCCCACGCCGCCGGCATCGCCGGTTCGCTCACCAATAAAAAGGTGAACAGGA<br>TTACCGGTCTGGACCCCGCGGGCCCGAACTTCGAGTACGCCGAAGCCCCGAGCA<br>GGCTGTCCCCGGACGACGCCGACTTCGTGGACGTGCTGCACACCTTTACCCGCG<br>GCTCCCCCGGCCGGAGCATCGGAATCCAAAAGCCCGTCGGGCACGTGGATATCT<br>ACCCCAACGGCGGCACCTTCCAGCCCGGGTGCAACATCGGTGAGGCCATCAGG<br>GTCATCGCCGAACGGGGCCTGGGCGACGTGGACCAGCTGGTCAAATGTAGCCA<br>TGAGAGGTCCATCCACCTGTTTATCGACTCCCTGCTGAACGAGGAGAACCCCAG<br>CAAGGCCTACCGGTGCTCCAGCAAGGAGGCCTTCGAGAAAGGACTGTGCCTGA<br>GCTGCAGGAAGAACCGTTGCAACAACCTGGGCTACGAGATCAACAAGGTGAGG<br>GCAAAGCGGAGCTCAAAGATGTACCTGAAGACCCGGTCCCAAATGCCCTACAA<br>AGTGTTCCATTACCAGGTGAAAATTCATTTCAGCGGCACCGAGAGCGAAACCCA |

TABLE 2-continued

Sequence optimized sequences for wild type human LPL

| SEQ ID NO | Name | Sequence |
|---|---|---|
| | | CACGAACCAGGCCTTTGAGATAAGCCTGTACGGGACCGTGGCGGAGAGCGAGA<br>ATATCCCCTTCACTCTCCCCGAGGTGAGCACGAACAAGACCTACTCCTTCCTGA<br>TCTACACGGAGGTCGATATCGGTGAGCTGCTGATGCTGAAGCTGAAGTGGAAG<br>AGCGACAGCTACTTCTCCTGGAGCGACTGGTGGAGCAGCCCTGGGTTCCTCCATC<br>CAAAAAATCCGGGTGAAGGCCGGCGAGACCCAAAAGAAGGTGATCTTCTGCTC<br>TAGGGAGAAGGTGTCCCACCTGCAGAAGGGCAAGGCCCCCGCCGTATTTGTGA<br>AGTGCCACGACAAGAGCCTGAATAAGAAGAGCGGC |
| 14 | LPL-CO10 | ATGGAGAGCAAGGCCCTGCTGGTCCTGACCCTGGCCGTCTGGCTGCAGAGCCTG<br>ACCGCCTCCCGGGGGGGCGTGGCCGCCGCCGACCAGAGGCGCGACTTTATAGA<br>CATCGAGTCGAAGTTTGCCCTGCGCACCCCCGAGGACACAGCCGAAGACACCT<br>GCCACCTGATCCCCGGGGTGGCGGAGAGCGTGGCCACCTGCCACTTCAACCACT<br>CCTCCAAGACCTTCATGGTCATTCATGGCTGGACCGTCACCGGCATGTACGAGA<br>GTTGGGTGCCGAAGCTGGTGGCCGCCCTCTACAAGAGGGAGCCCGACTCCAAC<br>GTGATCGTGGTGGACTGGCTGAGCAGGGCCCAGGAGCACTATCCGGTGAGCGC<br>CGGGTACACGAAGCTGGTCGGACAGGACGTGGCCCGCTTCATCAACTGGATGG<br>AGGAAGAGTTTAACTATCCGCTCGACAACGTCCATCTGCTGGGGTACAGCCTGG<br>GCGCCCATGCCGCCGGAATCGCCGGCTCCCTGACGAACAAGAAGGTGAACCGG<br>ATCACCGGGCTAGACCCCGCCGGGCCCAATTTCGAGTACGCCGAGGCGCCCAG<br>CAGGCTGAGTCCCGACGACGCCGACTTTGTGGACGTCCTGCATACCTTCACCCG<br>CGGCAGCCCCGGGCGATCCATCGGCATCCAGAAGCCGGTCGGCCACGTCGACA<br>TCTACCCCAACGGCGGCACATTCCAGCCCGGCTGCAACATCGGCGAGGCCATCA<br>GGGTGATCGCCGAGCGTGGGCTGGGCGACGTGGATCAGCTGGTGAAGTGCAGC<br>CACGAGAGGAGCATCCATCTGTTCATCGATAGCCTGCTGAACGAGGAGAACCC<br>GAGCAAGGCCTACAGGTGTAGCAGCAAGGAGGCCTTCGAGAAGGGCCTCTGTC<br>TGTCATGCAGGAAGAATAGGTGCAACAACCTGGGCTACGAGATCAACAAGGTG<br>AGGGCCAAAAGGAGCTCCAAGATGTATCTGAAGACCAGGTCCCAGATGCCGTA<br>CAAGGTGTTCCACTATCAGGTGAAGATCCACTTCTCGGGCACAGAGAGCGAGA<br>CGCACACCAACCAGGCCTTCGAGATCAGCCTGTACGGCACCGTGGCCGAGTCCG<br>AAAACATCCCTTTTACCCTGCCCGAGGTGTCCACCAACAAGACCTACAGCTTCC<br>TGATATACACCGAGGTGGACATCGGCGAAGTGCTGATGCTCAAGCTGAAATGG<br>AAGTCCGACAGCTACTTCAGCTGGAGCGATTGGTGGAGCTCCCCGGGGTTCGCA<br>ATCCAAAAGATCAGGGTGAAGGCAGGGGAGACCCAGAAGAAGGTCATCTTCTG<br>CTCCCGGGAAAAAGTGAGCCATCTCCAGAAGGGCAAAGCGCCCGCCGTGTTCG<br>TCAAGTGCCACGATAAGAGCCTGAACAAGAAGAGCGGC |
| 15 | LPL-CO11 | ATGGAGAGCAAGGCGCTGCTGGTGCTGACCCTGGCGGTGTGGCTGCAGAGCCT<br>CACCGCCTCGCGCGGTGGCGTGGCGGCCGCCGATCAACGGCGGGACTTCATCG<br>ATATCGAGAGCAAGTTCGCCCTTCGGACCCCGGAGGACACCGCCGAGGATACTT<br>GCCATCTGATCCCCGGCGTGGCCGAATCCGTGGCCACCTGCCACTTCAACCACT<br>CCAGCAAGACCTTCATGGTGATCCACGGCTGGACCGTGACCGGGATGTACGAG<br>AGTTGGGTGCCCAAGCTGGTGGCCGCCCTGTACAAGCGGGAGCCCGACAGCAA<br>TGTGATCGTGGTGGACTGGCTGAGCAGGGCCCAGGAGCATTATCCAGTGAGCG<br>CCGGGTATACCAAACTCGTGGGCCAGGATGTCGCCAGGTTCATTAACTGGATGG<br>AGGAGGAATTCAACTACCCGCTGGATAACGTGCATCTGCTGGGGTACTCGCTGG<br>GAGCCCATGCCGCCGGCATCGCGGGATCCCTGACGAACAAGAAGGTCAATAGG<br>ATCACCGGCCTGGACCCGGCCGGCCCCAACTTCGAGTACGCCGAGGCGCCCAG<br>CCGTCTGAGCCCCGACGACGCCGATTTCGTGGACGTGCTGCACACCTTCACCAG<br>GGGCAGCCCCGGCCGCAGCATCGGCATTCAGAAGCCCGTGGGCCACGTCGACA<br>TATATCCCAACGGCGGAACCTTCCAACCCGGCTGTAACATCGGGGAGGCCATCC<br>GGGTCATCGCCGAGAGGGGCCTGGGCGACGTGGACCAGCTGGTGAAGTGCTCC<br>CACGAGCGTAGCATTCATCTGTTCATCGACTCCCTGCTGAACGAAGAGAACCCC<br>TCCAAGGCCTACCGTTGCTCCAGCAAGGAGGCCTTCGAGAAGGGCCTCTGCCTC<br>AGCTGCAGGAAGAACAGGTGTAACAACCTGGGCTACGAGATCAACAAGGTGAG<br>GGCCAAGAGGAGCTCCAAGATGTATCTGAAGACACGGAGCCAGATGCCCTACA<br>AGGTGTTCCACTACCAGGTGAAGATCCACTTCTCCGGGACGGAATCAGAGACCC<br>ACACGAACCAGGCCTTTGAGATCAGCCTGTATGGGACCGTGGCCGAGTCCGAG<br>AACATCCCCTTCACCCTGCCCGAGGTGAGCACCAACAAAACTTACTCCTTCCTG<br>ATCTACACTGAAGTGGACATCGGGGAGCTGCTGATGCTGAAACTCAAATGGAA<br>GAGCGACAGCTACTTTAGCTGGAGCGACTGGTGGTCCAGCCCCGGCTTCGCCAT<br>CCAGAAAATCAGGGTCAAAGCCGGCGAGACCCAGAAAAAGGTGATCTTCTGCA<br>GCAGGGAAAAGGTCAGCCACCTGCAGAAAGGGAAGGCCCCCGCTGTGTTCGTG<br>AAATGTCACGACAAGAGCCTGAACAAAAAGAGCGGC |
| 16 | LPL-CO12 | ATGGAGAGCAAGGCCCTGCTGGTGCTGACCCTGGCCGTGTGGCTGCAGTCGCTG<br>ACCGCCAGCAGGGGCGGCGTGGCCGCGGCCGACCAGCGCCGGGACTTCATCGA<br>CATCGAGAGCAAGTTTGCCCTGAGGACCCCCGAGGATACCGCAGAGGACACCT<br>GCCATCTGATCCCCGGCGTGGCAGAGAGCGTCGCCACTTGCCACTTCAACCATT<br>CCAGCAAGACTTTTATGGTCATCCACGGTTGGACCGTGACCGGAATGTACGAGT<br>CCTGGGTCCCGAAACTGGTGGCCGCCCTGTACAAGCGGGAGCCAGACTCCAAC<br>GTGATCGTCGTGGATTGGCTGTCCAGGGCCCAGGAGCACTACCCCGTCTCCGCC<br>GGCTACACCAAGCTGGTGGGACAAGACGTGGCCAGGTTCATCAACTGGATGGA<br>AGAGGAGTTCAACTATCCCCTGGACAACGTGCATCTCCTGGGCTACAGCCTCGG<br>CGCCCACGCCGCCGGCATCGCGGGCAGTCTGACGAACAAGAAGGTGAACAGGA |

TABLE 2-continued

Sequence optimized sequences for wild type human LPL

| SEQ ID NO | Name | Sequence |
|---|---|---|
| | | TCACCGGGCTGGACCCCGCCGGCCCGAATTTCGAGTACGCGGAGGCCCCGAGC<br>AGGCTGAGCCCCGACGACGCCGACTTCGTGGACGTGCTGCACACGTTCACCCGA<br>GGAAGCCCCGGCCGGAGCATCGGAATCCAGAAGCCCGTGGGCCACGTCGACAT<br>CTACCCCAATGGCGGAACCTTCCAGCCCGGGTGCAACATAGGCGAAGCCATCA<br>GGGTGATCGCCGAAAGGGGGCTGGGCGATGTGGACCAGCTGGTGAAGTGTTCA<br>CACGAGAGGTCCATCCACCTGTTTATCGATAGCCTGCTGAACGAGGAGAACCCA<br>TCCAAGGCCTACAGGTGCAGCAGCAAGGAGGCCTTTGAGAAGGGCCTGTGTCT<br>GTCGTGTAGGAAGAACAGGTGCAACAATCTCGGCTACGAGATCAATAAGGTAA<br>GGGCCAAGCGGTCGAGCAAGATGTACCTCAAGACCAGGAGCCAGATGCCCTAT<br>AAGGTGTTCCATTATCAGGTGAAAATCCACTTTAGCGGCACCGAGAGCGAAACC<br>CACACCAACCAGGCCTTCGAAATCTCCCTGTACGGCACTGTGGCCGAGAGCGAG<br>AATATCCCCTTCACCCTGCCCGAGGTCAGCACCAACAAAACCTACAGCTTCCTG<br>ATCTACACCGAGGTCGACATCGGCGAACTGCTTATGCTGAAGCTGAAGTGGAA<br>AAGCGACAGCTACTTCAGCTGGAGCGATTGGTGGAGCAGCCCCGGCTTTGCCAT<br>CCAGAAAATCCGCGTGAAGGCAGGGGAGACCCAGAAGAAGGTAATATTCTGCA<br>GCAGGGAGAAGGTAAGCCACCTGCAGAAAGGTAAGGCCCCCGCCGTGTTCGTG<br>AAATGTCACGACAAGTCCCTGAATAAGAAGTCCGGG |
| 17 | LPL-<br>CO13 | ATGGAGAGCAAGGCCCTGCTGGTGCTCACGCTGGCGGTGTGGCTCCACTCCCTG<br>ACCGCCAGCCGGGGGGGCGTCGCCGCCGCCGACCAACGCCGCGACTTCATCGA<br>CATCGAAAGTAAATTCGCCCTGCGGACCCCCGAGGACACCGCCGAAGACACGT<br>GCCACCTGATCCCTGGAGTTGCGGAGAGCGTGGCGACCTGCCACTTCAACCACT<br>CCAGCAAGACGTTCATGGTGATCCATGGCTGGACCGTCACCGGCATGTACGAGA<br>GCTGGGTGCCGAAGCTCGTGGCCGCGCTCTACAAGAGGGAGCCCGACTCCAAC<br>GTGATCGTGGTCGACTGGCTGAGCAGGGCCCAGGAGCACTACCCAGTCAGCGC<br>CGGCTACACCAAGCTGGTGGGCCAGGACGTGGCGCGGTTTATAAACTGGATGG<br>AGGAGGAGTTCAACTATCCCCTGGATAACGTGCACCTGCTGGGCTACTCCCTGG<br>GCGCCCACGCCGCCGGGATCGCCGGAAGCCTGACCAACAAGAAAGTGAACCGC<br>ATTACCGGGCTGGACCCCGCCGGCCCCAACTTCGAGTACGCCGAGGCACCCAGC<br>AGGCTGAGCCCGGACGACGCTGACTTTGTGGACGTGCTGCACACCTTTACCAGG<br>GGCAGCCCCGGTCGATCCATCGGTATACAGAAGCCCGTGGGCCACGTGGACAT<br>CTATCCCAACGGGGGCACATTTCAACCCGGCTGCAACATCGGCGAAGCCATCAG<br>GGTCATCGCCGAGCGCGGCCTGGGCGATGTGGATCAGCTGGTGAAGTGCTCCCA<br>CGAGAGGAGCATCCACCTGTTCATCGACAGCCTCCTCAATGAGGAGAATCCCAG<br>CAAGGCCTACAGGTGCTCCAGCAAGGAGGCCTTCGAGAAGGGTCTGTGCCTGTC<br>CTGCAGAAAAAACAGGTGCAACAACCTGGGCTACGAGATCAACAAAGTGAGGG<br>CCAAGAGGTCGAGCAAAATGTACCTGAAGACCAGGAGCCAGATGCCCTACAAG<br>GTGTTCCACTACCAGGTGAAGATCCACTTCAGCGGGACGGAATCCGAGACGCA<br>CACCAACCAGGCCTTCGAGATCTCCCTCTACGGCACCGTGGCCGAGAGCGAGA<br>ATATCCCCTTCACCCTGCCGGAGGTGAGCACGAACAAGACCTACTCATTTCTGA<br>TCTATACGGAGGTCGATATCGGCGAGCTGCTCATGCTGAAACTGAAGTGGAAGT<br>CGGACAGCTACTTCAGCTGGAGCGATTGGTGGAGCAGCCCCGGCTTCGCGATCC<br>AGAAGATCAGGGTGAAGGCCGGGGAGACGCAGAAGAAGGTGATTTTCTGTTCC<br>AGAGAGAAAGTCTCCCACCTCCAAAAAGGCAAGGCCCCCGCCGTGTTCGTGAA<br>GTGCCATGACAAGTCCCTGAACAAGAAGAGCGGG |
| 18 | LPL-<br>CO14 | ATGGAGTCAAAGGCCCTCCTGGTGCTTACCCTCGCCGTTTGGCTCCAGTCCCTG<br>ACCGCGAGCCGCGGCGGGGTGGCCGCCGCCGACCAGAGGCGAGACTTTATCGA<br>CATTGAGTCCAAGTTCGCCCTGAGGACCCCCGAGGACACCGCCGAGGACACCT<br>GCCACCTGATCCCCGGTGTGGCCGAGAGCGTCGCCACATGCCATTTCAACCACT<br>CGAGTAAAACCTTCATGGTGATCCACGGCTGGACTGTGACCGGGATGTACGAGT<br>CCTGGGTCCCCAAGCTCGTGGCCGCCCTGTACAAGAGGGAGCCCGACAGCAAC<br>GTGATTGTGGTGGACTGGCTGTCCAGGGCCCAGGAACACTACCCGGTGAGCGCC<br>GGCTACACCAAGCTGGTGGGCCAGGACGTTGCCCGCTTCATCAACTGGATGGAG<br>GAGGAGTTCAACTACCCCCTGGACAACGTGCACCTGCTGGGCTACAGCCTGGGG<br>GCCCACGCCGCCGGGATCGCGGGGTCCCTGACCAACAAAAAGGTGAACAGGAT<br>CACCGGCCTGGATCCGGCCGGACCCAACTTCGAATACGCCGAAGCCCCTAGCCG<br>GCTGAGCCCCGACGACGCCGACTTCGTGGACGTCCTGCACACCTTCACAAGGGG<br>GTCCCCTGGTCGCAGTATCGGGATCCAGAAGCCTGTCGGCCACGTCGATATCTA<br>CCCCAACGGCGGGACCTTCCAGCCCGGCTGCAACATCGGCGAGGCCATCCGGG<br>TGATTGCCGAGAGGGGCCTGGGAGACGTCGACCAGTTGGTGAAATGCAGCCAC<br>GAGAGGAGCATCCACCTGTTCATCGACTCCCTCCTGAACGAGGAGAACCCCAGC<br>AAGGCCTACCGCTGCTCCTCCAAGGAGGCCTTCGAGAAAGGCCTGTGTCTGAGC<br>TGCCGGAAGAACCGGTGCAATAACCTCGGGTACGAGATCAATAAGGTGCGCGC<br>CAAGCGGAGCAGCAAGATGTACCTGAAGACAAGGAGCCAGATGCCCTACAAGG<br>TGTTCCACTACCAGGTGAAAATCCACTTCAGCGGCACCGAGAGCGAGACCCAC<br>ACCAACCAGGCCTTCGAGATCAGCCTGTATGGCACCGTGGCCGAAAGCGAGAA<br>CATCCCCTTTACACTGCCCGAGGTCTCCACCAACAAGACGTACAGCTTCCTGAT<br>CTACACCGAGGTGGATATCGGCGAGCTGCTGATGCTGAAGCTGAAATGGAAGA<br>GCGACAGCTATTTCTCATGGAGCGACTGGTGGAGCTCCCCGGGCTTCGCCATCC<br>AGAAGATCAGGGTGAAGGCGGGCGAGACACAAAAGAAGGTCATCTTCTGCTCC<br>AGGGAGAAGGTGAGCCACCTGCAGAAGGGCAAGGCCCCCGCCGTGTTCGTGAA<br>ATGCCACGACAAGAGCCTGAATAAGAAGAGCGGC |

TABLE 2-continued

Sequence optimized sequences for wild type human LPL

| SEQ ID NO | Name | Sequence |
|---|---|---|
| 19 | LPL-CO15 | ATGGAGAGCAAGGCCCTGCTGGTGCTGACCCTGGCCGTTTGGCTGCAGTCCCTGACCGCCAGCCGCGGTGGCGTGGCCGCCGCCGACCAGCGGCGGGATTTCATCGACATAGAATCTAAGTTTGCCCTGAGGACCCCCGAGGACACCGCCGAGGACACCTGCCACCTGATCCCCGGGGTGGCCGAGTCCGTGGCCACGTGTCACTTCAACCATAGCAGCAAGACCTTTATGGTCATCCACGGCTGGACCGTGACTGGCATGTACGAGAGCTGGGTGCCCAAGCTCGTGGCCGCCCTGTACAAGAGGGAGCCCGACAGCAACGTGATCGTGGTGGACTGGCTCAGCCGAGCCCAGGAGCACTACCCCGTCAGCGCCGGCTACACCAAGCTCGTGGGCCAAGACGTAGCCAGGTTCATCAATTGGATGGAGGAGGAGTTTAACTACCCCCTCGACAACGTGCACCTCCTGGGCTACTCCCTGGGCGCCCATGCCGCCGGCATAGCCGGAAGCCTGACTAACAAAAAAGTCAATCGGATCACCGGCCTAGACCCCGCCGGGCCCAACTTCGAATACGCCGAGGCCCCCTCCAGGCTGAGCCCGGACGACGCCGACTTTGTGGACGTCCTGCACACCTTCACGAGAGGGTCCCCGGGCCGGTCGATCGGAATCCAGAAACCCGTGGGGCATGTGGACATTTACCCCAACGGCGGCACCTTCCAGCCAGGCTGCAACATCGGCGAAGCCATCAGGGTCATCGCCGAGAGGGGACTGGGCGACGTGGACCAGCTGGTGAAGTGCAGCCACGAGCGGAGCATCCACCTGTTCATCGACAGCCTGCTGAATGAGGAGAATCCCAGCAAGGCCTACAGATGTTCCAGCAAAGAGGCCTTCGAGAAGGGACTGTGCCTGTCCTGCAGAAAGAACAGGTGCAATAACCTGGGTTACGAGATAAATAAGGTGAGGGCCAAGAGGTCCTCCAAGATGTATCTGAAGACCCGCAGCCAGATGCCTTACAAGGTCTTCCACTACCAAGTGAAAATCCACTTTAGCGGGACCGAATCAGAGACGCACACAAATCAAGCTTTCGAGATCAGCCTGTACGGCACCGTGGCCGAGTCCGAGAACATCCCCTTCACCCTCCCGGAGGTGTCCACCAACAAGACCTACTCCTTCCTGATCTATACAGAGGTGGACATCGGGGAGCTGCTGATGCTGAAGCTGAAGTGGAAATCCGACAGCTACTTCAGCTGGAGCGACTGGTGGAGCAGCCCCGGCTTTGCCATCCAGAAAATCAGGGTGAAGGCCGGAGAAACTCAAAAAAAGGTCATCTTCTGCAGCCGCGAGAAGGTGAGCCACCTGCAGAAGGGCAAGGCCCCCGCCGTGTTCGTGAAGTGTCACGACAAGTCGCTGAACAAGAAGAGCGGT |
| 20 | LPL-CO16 | ATGGAGTCCAAGGCCCTCCTGGTGCTGACCCTGGCCGTCTGGCTGCAGTCACTGACCGCGAGCAGGGGCGGCGTGGCCGCAGCGGACCAGCGCAGGGACTTCATCGACATCGAGAGCAAGTTCGCCCTGAGGACCCCCGAGGACACCGCGGAAGACACCTGCCACCTGATCCCCGGCGTGGCCGAGTCCGTGGCCACCTGCCACTTCAATCACAGCTCCAAGACCTTTATGGTGATCCACGGCTGGACCGTGACCGGAATGTATGAGAGCTGGGTGCCCAAGCTCGTGGCCGCCCTTTACAAGAGGGAGCCCGACAGCAATGTCATAGTGGTGGACTGGCTGAGCAGGGCCCAGGAGCACTACCCCGTGAGTGCCGGGTACACCAAGCTGGTGGGCCAGGACGTCGCCCGATTCATCAACTGGATGGAGGAGGAGTTCAACTACCCCCTGGACAACGTGCATCTGCTGGGGTACTCCCTGGGCGCGCACGCTGCCGGCATCGCGGGGTCCCTAACCAACAAGAAGGTGAACAGGATCACCGGGCTGGACCCCGCCGGCCCCAATTTCGAATATGCCGAGGCCCCCAGCAGGCTGAGCCCCGACGACGCCGACTTCGTGGACGTGCTGCATACCTTCACCAGGGGCAGCCCCGGCCGGTCGATTGGCATACAAAAGCCCGTGGGCCACGTGGACATCTACCCGAACGGGGGCACCTTCCAGCCCGGGTGCAACATAGGAGAAGCCATCAGGGTGATCGCGGAGAGGGGCCTGGGCGATGTGGACCAGCTGGTGAAATGCAGCCACGAAAGGTCCATCCACCTGTTTATCGACAGCCTGCTGAACGAGGAGAACCCCAGCAAGGCCTATAGGTGCAGCTCAAAGGAGGCCTTCGAGAAGGGACTGTGCCTCTCCTGCAGGAAGAACCGCTGTAACAACCTGGGCTACGAGATAAACAAGGTGAGGGCCAAGCGGAGCAGCAAGATGTACCTGAAGACTCGCTCCCAGATGCCATACAAGGTGTTCCACTACCAGGTGAAGATCCACTTCTCCGGCACGGAGAGCGAGACCCACACCAACCAAGCGTTCGAGATCTCCCTGTACGGGACAGTGGCCGAATCAGAGAACATCCCCTTTACCCTGCCCGAGGTGAGCACCAATAAGACCTACTCCTTCCTGATCTACACAGAGGTGGATATCGGGGAGCTGCTGATGCTGAAGCTGAAGTGGAAAAGCGACTCCTACTTCAGCTGGAGCGATTGGTGGTCCAGCCCCGGCTTTGCCATCCAGAAGATCAGGGTCAAGGCCGGCGAGACGCAGAAGAAGGTGATCTTCTGCTCCCGGGAAAAGGTGAGCCACCTGCAGAAAGGCAAGGCCCCAGCCGTTTTCGTGAAGTGCCACGATAAGTCCCTGAACAAGAAGAGCGGC |
| 21 | LPL-CO17 | ATGGAGAGTAAGGCGCTGCTCGTGCTCACGCTGGCAGTGTGGCTCCAGTCCCTGACCGCCAGCCGCGGGGGGGTGGCCGCGGCCGACCAGAGGAGGGACTTCATCGATATCGAGAGCAAGTTCGCCCTGCGGACACCCGAGGATACAGCCGAGGACACATGCCACCTGATACCCGGCGTGGCCGAAAGCGTGGCCACGTGCCACTTTAACCACTCCAGCAAGACCTTCATGGTCATCCACGGCTGGACCGTCACCGGCATGTACGAGAGCTGGGTGCCCAAGCTGGTCGCCGCCCTGTACAAGCGCGAGCCTGATAGCAACGTGATCGTGGTGGACTGGCTGTCCCGGGCCCAGGAGCACTACCCCGTGAGCGCCGGCTATACAAAACTGGTGGGTCAGGACGTGGCCAGATTCATAAACTGGATGGAAGAGGAGTTTAACTACCCCCTGGACAACGTGCACCTGCTGGGCTATAGCCTGGGCGCCCACGCCGCCGGCATGGCGGGCAGCCTCACTAACAAGAAGGTGAATCGGATAACCGGCCTGGATCCCGCCGGGCCCAATTTCGAGTACGCGGAAGCCCCCAGCCGGCTGAGCCCCGATGACGCCGATTTCGTGGACGTGCTGCACACCTTCACGCGCGGCAGCCCCGGCCGGAGCATCGGTATCCAGAAACCAGTGGGCCATGTGGACATCTACCCAAATGGCGGAACCTTCCAGCCGGGCTGTAACATCGGTGAAGCCATCCGGGTGATCGCCGAGAGGGGCCTGGGCGATGTGGACCAGCTGGTGAAATGTAGCCACGAGCGCTCCATCCACCTCTTCATCGACTCCCTGCTGAACGAAGAAAACCCCTCCAAGGCGTACAGGTGTAGCAGCAAGGAGGCCTTCGAGAAGGGCCTGTGCCTCTCCTGCCGTAAGAACAGGTGTAACAACCTGGGGTACGAGATCAACAAGGTGCGG |

TABLE 2-continued

Sequence optimized sequences for wild type human LPL

| SEQ ID NO | Name | Sequence |
|---|---|---|
| | | GCCAAGAGGAGCAGCAAGATGTACCTGAAGACCCGGAGCCAGATGCCCTACAA<br>GGTCTTCCACTACCAGGTCAAGATCCACTTCAGCGGCACCGAGAGCGAGACCCA<br>CACTAACCAAGCCTTCGAGATCAGCCTGTACGGGACCGTCGCCGAGAGCGAGA<br>ACATCCCCTTCACCCTGCCCGAGGTGAGCACCAACAAAACCTACTCCTTTCTGA<br>TCTACACGGAAGTGGACATCGGCGAGCTGCTGATGCTGAAGCTGAAGTGGAAA<br>AGCGACAGCTACTTTTCCTGGTCCGACTGGTGGAGCAGCCCGGGCTTCGCGATC<br>CAGAAGATCCGGGTGAAGGCCGGCGAGACCCAGAAGAAGGTCATCTTTTGCAG<br>CAGGGAGAAGGTGAGCCACCTGCAGAAGGGTAAGGCCCCCGCCGTGTTCGTGA<br>AGTGCCACGACAAGAGCCTGAACAAGAAGTCCGGA |
| 22 | LPL-CO18 | ATGGAGTCCAAGGCCCTCCTGGTGCTGACCCTGGCCGTGTGGCTCCAGAGCCTA<br>ACCGCCTCCCGGGGCGGCGTGGCCGCCGCCGATCAGAGGCGGGATTTCATCGA<br>CATAGAGAGCAAGTTCGCCCTCCGCACCCCCGAAGACACCGCCGAAGACACTT<br>GCCACCTGATTCCCGGAGTGGCCGAGTCCGTGGCCACTTGCCACTTCAACCACA<br>GCAGCAAGACCTTCATGGTGATCCACGGCTGGACCGTTACCGGCATGTACGAAA<br>GCTGGGTGCCGAAGCTCGTGGCCGCCCTGTACAAGAGGGAGCCCGACTCCAAC<br>GTGATCGTGGTTGACTGGCTGTCCAGGGCCCAGGAGCACTACCCCGTGTCCGCC<br>GGCTACACCAAGCTGGTCGGGCAGGACGTGGCCAGGTTCATCAACTGGATGGA<br>AGAGGAGTTCAACTATCCTCTGGACAATGTGCACCTGCTGGGCTACAGCCTGGG<br>CGCCCACGCCGCGGGCATCGCCGGCAGCCTGACCAATAAGAAAGTGAATAGGA<br>TTACCGGCCTGGACCCCGCGGGGCCCAACTTCGACTACGCCGAAGCCCCCAGCA<br>GGCTGAGCCCCGACGATGCCGACTTCGTGGACGTCCTGCACACCTTCACCCGGG<br>GCAGCCCCGGGAGGAGCATAGGCATACAGAAACCCGTGGGCCACGTGGACATC<br>TACCCCAATGGCGGCACGTTCCAGCCCGGGTGCAACATCGGGGAGGCCATCAG<br>GGTGATCGCCGAGAGGGGACTTGGCGACGTGGACCAGCTGGTGAAGTGCAGCC<br>ACGAGCGCAGCATACACCTGTTCATCGATAGCCTGCTTAACGAGGAAAACCCCT<br>CCAAGGCCTACAGGTGCTCCTCAAAGGAAGCGTTCGAGAAGGGGCTGTGTCTCT<br>CCTGCAGGAAGAACAGATGCAATAACCTGGGCTACGAGATCAACAAGGTGAGG<br>GCCAAGAGGAGCAGCAAGATGTACCTGAAAACTAGGAGCCAAATGCCCTATAA<br>GGTGTTTCACTACCAGGTGAAGATCCACTTCTCCGGCACCGAGAGCGAGACCCA<br>CACAAACCAGGCCTTCGAAATCTCGCTGTACGGGACCGTGGCCGAGAGCGAAA<br>ACATCCCGTTCACCCTGCCCGAGGTGTCCACCAACAAGACCTACAGCTTCCTGA<br>TCTACACCGAGGTAGACATTGGTGAGCTGCTGATGCTCAAACTCAAGTGGAAGA<br>GCGACTCCTACTTCAGCTGGAGCGATTGGTGGTCCTCCCCGGGCTTCGCCATCC<br>AGAAGATACGGGTCAAGGCTGGGGAAACCCAGAAGAAGGTGATCTTCTGCTCC<br>CGGGAGAAGGTCAGCCACCTGCAAAAAGGGAAGGCGCCCGCCGTCTTCGTGAA<br>GTGCCACGATAAGAGCCTGAACAAGAAGTCAGGC |
| 23 | LPL-CO19 | ATGGAGAGCAAGGCCCTGCTCGTGCTGACCCTCGCCGTCTGGCTGCAGAGCCTG<br>ACCGCCAGCAGGGGCGGCGTGGCCGCCGCCGATCAGAGGCGGGACTTCATAGA<br>TATCGAGAGCAAGTTCGCCCTGAGGACCCCCGAAGACACCGCGGAGGACACCT<br>GCCACCTGATCCCCGGCGTGGCCGAGTCCGTGGCCACCTGCCACTTTAACCACT<br>CCAGCAAAACCTTTATGGTGATCCATGGCTGGACCGTCACCGGGATGTACGAGA<br>GCTGGGTGCCCAAGCTGGTGGCCGCCCTCTACAAGCGGGAACCCGATAGCAAC<br>GTGATCGTGGTAGACTGGCTGTCCAGGGCCCAAGAGCACTACCCCGTGAGTGCC<br>GGCTACACGAAGCTGGTGGGCCAGGACGTGGCCCGCTTCATCAATTGGATGGA<br>GGAGGAGTTCAACTACCCGCTCGATAACGTGCACCTGCTGGGCTATAGCCTGGG<br>GGCCCACGCCGCCGGGATCGCCGGCAGCCTCACCAACAAGAAGGTGAACAGGA<br>TCACCGGCCTCGACCCCGCCGGCCCCAACTTCGAATACGCCGAGGCCCCCAGCA<br>GGCTGAGCCCGGATGACGCCGACTTTGTGGACGTGCTCCACACCTTCACCAGGG<br>GCTCCCCCGGCCGGTCCATCGGGATCCAGAAGCCCGTCGGGCACGTGGACATCT<br>ACCCCAATGGGGGGACCTTCCAACCCGGCTGCAACATCGGCGAGGCGATCAGG<br>GTGATCGCCGAGCGCGGCCTGGGGGACGTGGACCAGCTGGTGAAATGTTCCCA<br>TGAGCGGAGCATCCATCTGTTCATTGACTCCCTGCTGAACGAGGAGAACCCCTC<br>CAAGGCCTACCGGTGCTCCAGCAAGGAGGCCTTCGAGAAGGGTCTGTGCCTGA<br>GCTGCAGGAAGAATCGATGTAACAACCTGGGCTACGAGATCAACAAGGTGCGC<br>GCCAAGAGGAGCAGCAAGATGTACCTGAAGACCAGGAGTCAAATGCCCTACAA<br>GGTGTTCCACTACCAGGTGAAGATCCACTTCAGCGGCACGGAATCCGAGACCCA<br>CACCAATCAGGCCTTCGAGATCAGCCTCTACGGGACCGTGGCCGAGAGCGAAA<br>ACATCCCCTTCACCCTGCCCGAGGTGTCAACCAATAAGACCTACAGCTTCCTGA<br>TCTACACCGAGGTGGATATCGGCGAGCTGCTGATGCTGAAGCTGAAGTGGAAG<br>AGCGATAGCTACTTCTCGTGGAGCGACTGGTGGAGCAGCCCCGGCTTCGCCATC<br>CAGAAGATCAGGGTGAAGGCCGGCGAGACCCAAAAGAAAGTGATCTTTTGCAG<br>CAGGGAGAAGGTGTCCCACCTCCAGAAGGGAAAGGCCCCCGCGGTGTTCGTAA<br>AGTGCCATGACAAGTCCCTGAACAAAAAGAGCGGG |
| 24 | LPL-CO20 | ATGGAATCCAAGGCCCTACTCGTGCTCACCCTGGCCGTGTGGCTGCAGAGCCTG<br>ACCGCAAGCAGGGGGGGCGTGGCCGCCGCGGACCAAAGGAGGGATTTCATTGA<br>TATCGAGAGCAAGTTCGCCCTCAGGACCCCCGAGGACACAGCCGAGGACACCT<br>GCCACCTGATCCCCGGCGTAGCCGAGTCCGTGGCCACCTGCCACTTTAATCACT<br>CCTCCAAGACCTTCATGGTGATACACGGGTGGACCGTGACCGGGATGTATGAAA<br>GTTGGGTGCCAAAACTGGTGGCCGCCCTGTACAAGAGGGAGCCCGACTCCAAC<br>GTCATCGTCGTGGATTGGCTGAGCCGGGCCCAGGAGCACTATCCCGTCAGCGCT<br>GGCTATACGAAGCTGGTGGGCCAGGACGTCGCCCGGTTCATCAATTGGATGGA |

TABLE 2-continued

Sequence optimized sequences for wild type human LPL

| SEQ ID NO | Name | Sequence |
|---|---|---|
| | | GGAGGAGTTCAACTACCCCCTGGACAACGTGCACCTGCTGGGCTATAGCCTCGG<br>CGCCCACGCCGCCGGTATCGCTGGCAGCCTGACCAACAAGAAGGTGAACCGGA<br>TCACCGGCCTGGACCCGGCCGGCCCAAACTTTGAGTAGGCCGAGGCCCCCTCCA<br>GGCTGTCCCCCGACGACGCCGACTTCGTGGACGTCCTGCACACCTTCACCCGTG<br>GGTCCCCCGGACGGAGCATCGGGATTCAGAAACCCGTGGGCCATGTGGACATTT<br>ACCCCAACGGGGGGACCTTCCAACCCGGGTGCAACATCGGAGAGGCGATCAGG<br>GTGATCGCTGAGCGGGGCCTCGGGGACGTCGACCAGCTGGTGAAGTGCAGCCA<br>CGAGCGCTCCATCCACCTGTTCATCGACAGCCTGCTGAACGAGGAAAACCCCAG<br>CAAGGCGTATAGGTGCTCGTCGAAGGAGGCCTTCGAAAAGGGCCTGTGCCTGTC<br>GTGCCGAAAGAACAGGTGTAACAACCTGGGTTACGAGATCAACAAGGTGAGGG<br>CCAAAAGGAGCTCCAAGATGTATCTGAAGACCCGGTCCCAGATGCCCTATAAG<br>GTGTTCCACTATCAGGTGAAGATCCACTTTAGCGGAACCGAAAGCGAAACCCAC<br>ACAAACCAAGCCTTCGAGATCTCCCTGTACGGCACCGTCGCCGAGTCCGAGAAC<br>ATCCCCTTCACCCTGCCCGAGGTGAGCACTAACAAGACCTACAGCTTCCTCATC<br>TACACGGAGGTGGACATAGGCGAGCTGCTGATGCTGAAGCTGAAGTGGAAGTC<br>CGACTCCTATTTCAGCTGGAGCGACTGGTGGTCCTCCCCCGGGTTTGCCATCCA<br>AAAGATAAGGGTGAAGGCCGGCGAGACCCAAAAGAAGGTGATCTTCTGTTCCA<br>GGGAAAAGGTGAGCCACCTGCAGAAGGGCAAGGCCCCCGCTGTGTTCGTTAAG<br>TGCCACGACAAGTCCCTGAACAAGAAGAGCGGC |
| 25 | LPL-CO21 | ATGGAGTCCAAGGCCCTGCTGGTGCTGACCCTTGCCGTGTGGCTGCAGAGCCTG<br>ACCGCCAGCAGGGGCGGCGTCGCCGCCGCGGACCAGCGCAGGGACnTATCGA<br>TATCGAGAGCAAGTTCGCCCTGAGGACACCCGAGGACACCGCCGAGGACACAT<br>GCCATCTGATCCCAGGCGTTGCGGAGAGCGTGGCTACCTGCCACTTCAATCACA<br>GCAGCAAAACCTTTATGGTCATCCACGGCTGGACGGTGACCGGCATGTACGAG<br>AGCTGGGTGCCAAAGCTGGTGGCCGCCCTGTACAAGAGGGAACCCGACAGCAA<br>CGTGATCGTGGTGGATTGGTTATCCAGGGCGCAGGAGCACTATCCCGTCAGCGC<br>CGGCTACACCAAGCTGGTGGGCCAGGACGTCGCCAGGTTCATCAATTGGATGG<br>AGGAGGAATTCAATTATCCCCTGGATAACGTACACCTCCTGGGCTACAGCCTCG<br>GAGCCCACGCCGCGGGAATAGCCGGGAGCCTCACGAATAAGAAGGTTAACAGG<br>ATCACCGGCCTGGATCCCGCCGGCCCCAACTTCGAGTACGCAGAGGCACCGTCC<br>AGGCTGTCCCCCGACGACGCCGACTTCGTGGACGTCCTGCACACCTTCACCAGG<br>GGCTCCCCCGGGCGTAGCATCGGCATCCAAAAGCCCGTGGGCCACGTGGACAT<br>CTACCCCAACGGCGGCACCTTCCAGCCCGGGTGCAACATCGGCGAGGCGATCC<br>GGGTGATAGCGGAACGCGGGCTGGGCGACGTGGATCAGCTGGTCAAGTGTAGC<br>CATGAGCGCAGCATCCACCTGTTCATCGACTCCCTGCTCAACGAAGAAAACCCC<br>AGCAAGGCCTACCGGTGCTCGAGCAAGGAAGCGTTCGAGAAGGGCCTGTGCCT<br>GAGCTGCAGGAAGAATAGGTGCAATAATCTGGGCTATGAGATCAACAAGGTGC<br>GGGCCAAGCGAAGCTCTAAAATGTACCTGAAGACTCGGTCCCAGATGCCGTAC<br>AAGGTGTTCCACTACCAGGTGAAGATCCACTTCAGCGGGACCGAATCCGAAAC<br>GCACACCAACCAAGCCTTCGAGATCAGCCTGTACGGGACCGTCGCCGAGAGCG<br>AGAACATCCCCTTCACCCTGCCCGAGGTGTCCACAAACAAGACGTACAGCTTCC<br>TCATCTATACCGAGGTCGACATCGGGGAGCTGCTGATGTTAAAACTGAAGTGGA<br>AGAGCGACTCCTATTTTAGCTGGTCCGACTGGTGGAGCAGCCCCGGCTTCGCCA<br>TCCAGAAGATCAGGGTCAAGGCCGGTGAGACGCAGAAGAAGGTGATTTTCTGC<br>AGCAGGGAAAAAGTGTCCCATCTCCAGAAGGGTAAGGCGCCGGCCGTGTTTGT<br>AAAATGCCACGACAAGAGTCTGAACAAAAAGAGCGGC |
| 26 | LPL-CO22 | ATGGAGTCCAAGGCCTTGCTGGTTCTGACCCTGGCCGTGTGGCTGCAGAGCCTG<br>ACGGCCTCGAGGGGGGGCGTCGCGGCGGCCGACCAGCGGAGGGACTTCATCGA<br>CATCGAGAGCAAATTTGCCCTGCGGACCCCCGAAGACACCGCGGAGGATACCT<br>GTCACCTGATTCCCGGCGTGGCTGAAAGCGTGGCAACCTGCCACTTCAACCACT<br>CAAGCAAGACGTTTATGGTCATACACGGGTGGACCGTGACCGGAATGTACGAG<br>AGTTGGGTGCCCAAACTGGTGGCCGCCCTGTACAAGAGGGAACCCGACAGCAA<br>TGTGATAGTGGTGGACTGGCTGTCCCGGGCCCAGGAGCACTACCCGGTGAGCGC<br>CGGCTACACCAAGCTGGTGGGCCAGGACGTGGCCCGGTTCATCAACTGGATGG<br>AGGAGGAGTTCAACTATCCCCTGGATAACGTGCACCTCCTGGGGTACAGCCTGG<br>GGGCCCACGCCGCCGGAATCGCCGGCAGCCTGACCAACAAGAAGGTGAACAGG<br>ATCACTGGCCTCGACCCCGCCGGCCCGAACTTTGAGTATGCCGAGGCCCCGAGC<br>CGGCTGTCCCCCGACGACGCCGACTTCGTCGACGTGCTCCACACCTTCACGAGG<br>GGGAGCCCCGGCCGGAGCATCGGCATACAAAAGCCCGTGGGACACGTGGACAT<br>CTACCCCAACGGCGGCACCTTTCAGCCGGGCTGTAATATCGGCGAGGCCATCCG<br>CGTGATCGCCGAGAGGGGCCTGGGGGACGTGGACCAACTGGTGAAGTGTAGCC<br>ACGAAAGGTCCATCCACCTCTTCATCGACAGCCTCCTGAACGAGGAGAACCCCT<br>CCAAGGCCTACAGGTGCAGCTCTAAAGAGGCGTTCGAGAAGGGGCTTTGCCTG<br>AGCTGCAGGAAGAATAGGTGCAACAACCTGGGCTACGAAATCAACAAGGTGCG<br>GGCCAAGCGCAGCAGCAAAATGTACCTGAAGACCCGTAGCCAGATGCCCTACA<br>AGGTGTTTCACTACCAGGTGAAAATCCATTTCAGCGGCACCGAAAGCGAAACG<br>CACACCAACCAGGCCTTCGAGATCTCCCTGTACGGGACCGTCGCAGAGAGCGA<br>GAACATCCCCTTCACGCTCCCTGAGGTGTCGACCAACAAGACCTATTCCTTCCT |

TABLE 2-continued

Sequence optimized sequences for wild type human LPL

| SEQ ID NO | Name | Sequence |
|---|---|---|
| | | GATCTATACCGAGGTGGATATCGGAGAGCTGCTGATGCTGAAGCTCAAATGGA<br>AAAGCGACAGCTATTTCTCATGGTCCGACTGGTGGAGCAGCCCGGGATTCGCCA<br>TCCAGAAGATCAGGGTGAAGGCCGGGGAGACCCAGAAGAAGGTGATCTTTTGC<br>AGCCGCGAAAAGGTGAGCCACCTGCAGAAGGGCAAGGCCCCCGCGGTGTTCGT<br>CAAGTGTCACGATAAAAGTCTGAACAAGAAGAGCGGC |
| 27 | LPL-CO23 | ATGCAGAGCAAAGCGCTACTGGTGCTGACCCTCGCCGTGTGGCTACAGAGCCTG<br>ACCGCCTCGCGGGGCGGCGTGGCCGCCGCTGACCAGAGGCGGGACTTCATCGA<br>CATCGAGAGCAAGTTCGCCCTGCGCACCCCAGAGGACACCGCCGAGGATACCT<br>GTCACCTCATCCCCGGCGTCGCCGAGAGCGTGGCGACCTGCCACTTTAACCACA<br>GCAGCAAGACCTTCATGGTGATCCACGGCTGGACCGTGACGGGCATGTACGAG<br>TCCTGGGTGCCCAAACTGGTGGCGGCTCTGTACAAGAGGGAGCCCGACAGTAA<br>CGTGATTGTCGTGGACTGGCTGAGCCGCGCTCAAGAACACTATCCCGTATCCGC<br>CGGTTACACCAAGCTGGTGGGCCAGGACGTGGCGCGATTCATTAACTGGATGG<br>AGGAGGAGTTTAATTACCCCCTGGATAACGTGCATCTGCTGGGGTATAGCCTGG<br>GCGCCCACGCCGCCGGCATAGCCGGCTCCCTGACCAACAAGAAGGTCAACCGA<br>ATCACCGGCCTGGACCCCGCCGGCCCCAACTTTGAGTACGCCGAGGCCCCCAGC<br>AGGCTGTCCCCCGATGATGCCGACTTCGTGGACGTGCTGCATACGTTCACCCGC<br>GGGAGCCCCGGGAGGAGCATCGGCATACAGAAACCCGTGGGCCACGTGGACAT<br>ATACCCCAACGGCGGAACGTTCCAGCCGGGGTGCAACATCGGCGAGGCCATCC<br>GGGTCATCGCCGAGAGGGGGCTGGGCGATGTGGACCAACTGGTGAAGTGCTCC<br>CATGAACGGTCCATCCATCTGTTCATCGACAGCCTGCTGAACGAGGAGAACCCC<br>AGCAAGGCCTACAGGTGTAGCAGCAAGGAGGCCTTCGAGAAAGGCCTGTGTCT<br>GAGCTGCAGAAAGAACAGGTGCAACAACCTCGGCTACGAGATCAACAAGGTGA<br>GGGCCAAGAGGTCCAGCAAAATGTATCTGAAGACCAGGAGCCAGATGCCATAC<br>AAGGTCTTTCACTACCAGGTCAAGATCCATTTCTCCGGCACCGAGTCCGAAACC<br>CACACCAACCAGGCGTTCGAAATCAGCCTGTACGGCACCGTGGCCGAGAGCGA<br>GAACATCCCCTTCACCCTTCCCGAGGTGTCCACCAACAAGACCTACAGCTTCCT<br>CATCTACACCGAGGTGGATATCGGCGAGCTGCTGATGCTGAAGCTGAAGTGGA<br>AGAGCGACAGCTACTTCAGCTGGTCGGACTGGTGGAGCTCCCCCGGCTTCGCGA<br>TCCAGAAAATCCGTGTGAAAGCCGGGGAGACCCAGAAGAAGGTGATATTCTGC<br>TCCCGGGAGAAGGTAAGCCACCTGCAGAAGGGGAAGGCCCCCGCCGTGTTCGT<br>TAAGTGCCACGACAAGAGCCTAAACAAAAAGTCCGGC |
| 28 | LPL-CO24 | ATGGAGTCTAAAGCCCTGCTGGTGCTGACCCTCGCCGTGTGGCTGCAGTCGCTG<br>ACCGCCTCCCGCGGCGGGGTGGCCGCAGCCGACCAGCGCCGGGACTTCATTGA<br>CATCGAGAGCAAGTTCGCCCTGCGAACCCCCGAGGATACCGCCGAGGACACCT<br>GCCACCTGATCCCCGGAGTCGCCGAGAGCGTGGCCACCTGCCACTTTAATCATA<br>GCAGCAAGACCTTCATGGTGATCCACGGCTGGACGGTGACCGGGATGTACGAG<br>AGCTGGGTCCCCAAGCTGGTGGCCGCCCTTTATAAAAGGGAGCCCGATAGTAAC<br>GTGATCGTGGTGGACTGGCTGTCCAGGGCCCAAGAGCACTACCCCGTGTCCGCC<br>GGCTACACCAAGCTGGTGGGCCAGGACGTGGCCAGGTTCATCAATTGGATGGA<br>GGAGGAATTTAATTACCCCCTGGACAATGTGCACCTCCTGGGCTACTCGCTGGG<br>CGCTCACGCCGCCGGCATAGCCGGCAGCCTGACCAACAAGAAAGTGAACAGGA<br>TCACGGGCCTGGACCCCGCCGGCCCCAACTTCGAGTACGCCGAGGCCCCCAGCC<br>GTCTGAGCCCCGACGACGCCGACTTTGTGGACGTGCTGCACACCTTCACCAGGG<br>GGAGTCCTGGGCGGAGCATCGGCATCCAAAAGCCGGTGGGCCACGTGGACATC<br>TACCCGAACGGTGGTACGTTTCAGCCCGGGTGCAACATCGGGGAAGCCATCAG<br>GGTGATCGCCGAGAGGGGGCTGGGCGACGTGGACCAGCTGGTGAAGTGCTCCC<br>ACGAGAGGTCCATCCACCTGTTCATCGACTCCCTTCTCAACGAAGAAAACCCGA<br>GCAAGGCCTACAGGTGTAGCAGCAAGGAAGCCTTCGAGAAGGGGCTGTGCCTG<br>TCCTGTAGGAAAAACAGGTGCAACAACCTCGGCTACGAGATCAACAAGGTGCG<br>CGCTAAGCGCTCCAGCAAGATGTACCTGAAGACAAGGTCACAGATGCCCTACA<br>AGGTGTTCCACTACCAGGTGAAAATCCACTTTAGCGGCACCGAAAGCGAAACG<br>CACACCAACCAGGCGTTTGAGATCAGCTTATATGGGACCGTGGCCGAGTCCGAG<br>AACATCCCCTTCACCCTGCCCGAAGTGAGCACCAACAAGACCTATAGCTTCCTG<br>ATCTACACCGAGGTGGATATCGGGGAGCTGCTGATGCTCAAACTGAAATGGAA<br>GAGCGATAGCTACTTCTCCTGGAGCGATTGGTGGAGCAGCCCCGGCTTCGCGAT<br>CCAGAAGATCCGCGTGAAGGCGGGGGAGACCCAGAAGAAGGTGATCTTTTGCA<br>GCAGGGAGAAGGTGAGCCACCTGCAGAAAGGCAAGGCCCCCGCGGTGTTTGTC<br>AAGTGCCACGACAAGAGCCTCAACAAGAAATCCGGC |
| 29 | LPL-CO25 | ATGGAATCGAAGGCCCTGCTGGTGCTGACGCTGGCGGTGTGGCTGCAGAGCCTG<br>ACCGCCTCCCGCGGCGGCGTCGCCGCCGCCGACCAGAGGCGGGACTTCATCGAT<br>ATCGAGAGCAAGTTCGCCCTGAGGACCCCCGAAGATACCGCCGAAGACACGTG<br>CCACCTGATCCCGGGCGTGGCGGAGTCTGTGGCCACCTGCCACTTCAACCACAG<br>CAGCAAGACCTTCATGGTGATCCACGGGTGGACCGTGACCGGCATGTACGAGA<br>GCTGGGTGCCCAAGCTGGTCGCCGCGCTGTACAAAAGGGAGCCCGACAGCAAC<br>GTCATCGTCGTGGACTGGCTGAGCAGGGCACAGGAGCATTACCCCGTCTCCGCC<br>GGTTACACCAAACTGGTGGGGCAGGACGTGGCGAGGTTTATCAACTGGATGGA<br>GGAGGAGTTCAACTACCCCCTGGATAACGTGCACCTGCTGGGGTACAGCCTGGG<br>GGCCCACGCCGCAGGCATAGCCGGGAGCCTGACCAATAAGAAAGTAAACCGGA<br>TCACGGGGCTGGACCCCGCCGGGCCCAATTTTGAGTATGCCGAGGCCCCCAGCC<br>GGCTGTCCCCCGACGACGCAGACTTCGTGGACGTGCTGCACACCTTCACCCGAG |

TABLE 2-continued

Sequence optimized sequences for wild type human LPL

| SEQ ID NO | Name | Sequence |
|---|---|---|
| | | GCAGCCCGGGAAGAAGCATCGGCATCCAGAAGCCCGTGGGCCACGTGGACATC TACCCCAACGGAGGCACCTTCCAGCCAGGCTGTAACATCGGCGAGGCCATCAG GGTGATCGCCGAACGCGGCCTGGGCGACGTGGACCAACTCGTGAAGTGCTCCC ACGAGCGCAGCATCCACCTCTTCATCGACAGCCTGCTGAATGAGGAGAATCCCA GCAAGGCATATAGGTGCAGCAGCAAGGAGGCCTTTGAGAAGGGCCTGTGCCTG TCATGCCGGAAGAACAGGTGCAACAACCTGGGCTACGAGATCAACAAGGTCAG GGCCAAACGCAGCTCCAAGATGTACCTGAAGACCCGGAGCCAAATGCCCTACA AGGTGTTTCACTACCAGGTGAAGATCCATTTTTCCGGCACGGAGAGTGAAACCC ACACCAACCAGGCCTTCGAGATAAGCCTGTACGGCACCGTGGCCGAGAGCGAG AACATCCCCTTCACCCTGCCCGAGGTGAGCACGAATAAGACCTACAGCTTCCTG ATCTACACGGAGGTGGACATCGGCGAGCTGCTGATGCTGAAGCTGAAATGGAA ATCCGACAGCTACTTCAGCTGGTCCGACTGGTGGAGCTCCCCCGGCTTCGCCAT CCAGAAGATCAGGGTGAAGGCCGGGGAGACCCAGAAAAAGGTGATCTTCTGCA GCAGGGAGAAAGTCAGCCATCTGCAGAAGGGGAAGGCCCCCGCGGTCTTCGTG AAGTGCCACGACAAGAGCCTGAACAAGAAGAGCGGC |
| 80 | LPL-CO26 | ATGGAAAGCAAGGCCCTGCTGGTCCTGACCCTCGCCGTGTGGCTCCAGAGCCTG ACCGCCAGCCGGGGCGGGGTGGCCGCCGCCGACCAGCGACGGGACTTCATAGA CATCGAGAGCAAGTTTGCCCTGCGCACGCCCGAGGACACGGCCGAGGACACCT GCCATCTGATCCCCGGCGTGGCCGAGAGCGTCGCCACCTGCCACTTTAACCACA GCAGCAAAACCTTCATGGTGATCCACGGATGGACCGTGACCGGAATGTACGAG AGCTGGGTACCAAAGCTGGTCGCCGCCCTGTACAAAAGGGAACCCGATAGCAA CGTGATCGTGGTGGACTGGCTCTCCAGGGCCCAAGAGCACTACCCCGTCAGCGC CGGCTACACCAAGCTGGTGGGACAGGACGTGGCCCGTTTCATCAATTGGATGGA GGAGGAGTTCAATTACCCCCTGGACAACGTGCACCTGCTGGGCTACTCCCTGGG AGCCCACGCCGCCGGGATAGCCGGCTCCCTCACCAACAAGAAGGTCAACCGGA TCACTGGCCTCGATCCCGCCGGACCCAACTTTGAGTACGCCGAAGCCCCCTCGA GGCTGAGCCCCGACGACGCCGATTTTGTGGACGTCCTCCACACCTTCACCCGCG GGTCCCCCGGCAGGAGCATCGGCATCCAGAAGCCCGTGGGCCACGTGGACATC TATCCCAACGGCGGCACCTTCCAGCCCGGCTGTAACATCGGCGAAGCCATCCGG GTGATCGCCGAACGGGGCCTGGGCGATGTGGACCAGCTGGTGAAATGTAGCCA CGAGAGGAGCATCCACCTGTTTATCGATAGCTTGCTGAACGAGGAGAACCCATC CAAAGCGTACAGGTGCAGCTCCAAGGAGGCCTTCGAAAAGGGCCTGTGCCTCT CCTGCAGGAAGAACCGGTGCAACAACCTGGGGTATGAGATCAACAAAGTAAGG GCGAAGAGGAGCTCCAAGATGTACCTGAAGACTAGGAGCCAGATGCCCTACAA GGTGTTCCACTATCAGGTGAAAATCCACTTCAGCGGCACAGAAAGCGAGACCC ACACCAACCAGGCCTTCGAGATCTCTCTGTATGGCACCGTGGCCGAGAGCGAGA ACATACCCTTCACCCTGCCCGAAGTGAGCACCAACAAAACCTACAGCTTCCTGA TCTACACCGAGGTGGACATCGGCGAGCTCCTCATGCTCAAGCTGAAGTGGAAGT CCGACAGCTACTTCTCGTGGAGCGACTGGTGGTCGAGCCCCGGCTTCGCCATCC AGAAGATCCGGGTGAAAGCCGGCGAGACCCAGAAGAAGGTCATCTTTTGCAGC AGGGAGAAGGTGAGCCATCTCCAGAAGGGCAAAGCTCCAGCCGTGTTCGTCAA GTGCCACGACAAGTCCCTGAACAAGAAGAGCGGC |
| 81 | LPL-CO27 | ATGGAGTCCAAAGCGCTTCTGGTGCTCACCCTGGCGGTGTGGCTGCAGAGCCTG ACCGCCTCCAGAGGCGGCGTGGCCGCCGCCGACCAGCGGAGGGACTTCATCGA CATCGAGAGCAAGTTCGCACTCAGGACCCCGGAGGATACCGCCGAGGACACCT GCCACCTGATCCCCGGTGTGGCCGAGTCAGTGGCCACCTGTCATTTCAACCACA GCAGCAAGACCTTCATGGTGATCCACGGCTGGACCGTCACCGGCATGTACGAG AGCTGGGTGCCCAAGCTCGTCGCGGCGCTCTACAAGCGGGAGCCAGACAGCAA TGTGATCGTGGTGGACTGGCTCAGCCGGGCCCAGGAGCACTACCCGGTGTCCGC CGGGTACACGAAGCTGGTGGGCCAGGACGTCGCCCGCTTTATAAACTGGATGG AGGAAGAGTTCAACTACCCCCTGGACAACGTGCACCTGCTCGGTTACAGCCTCG GGGCCCACGCCGCCGGAATCGCGGGTTCCCTCACCAACAAGAAGGTGAATAGG ATCACCGGGCTGGACCCCGCCGGCCCCAATTTCGAGTACGCCGAGGCCCCCTCG CGGCTGAGCCCCGACGACGCCGACTTTGTGGACGTGCTGCACACCTTCACCCGG GGCAGCCCTGGGAGATCCATCGGCATACAGAAGCCCGTCGGCCACGTGGACAT CTACCCCAACGGGGGGACCTTTCAGCCCGGGTGCAATATCGGGGAAGCCATTA GGGTGATCGCCGAGAGGGGTCTGGGGGACGTCGACCAGCTCGTGAAATGTTCC CACGAGAGGAGCATCCACCTGTTCATAGACAGCCTGCTGAATGAGGAGAACCC CTCCAAAGCCTACCGCTGCAGCAGCAAGGAGGCCTTCGAAAAGGGGCTGTGCC TGAGCTGCAGGAAGAATAGGTGTAACAATCTGGGCTACGAGATCAACAAGGTG CGGGCGAAGAGGTCCTCTAAGATGTATCTTAAGACCCGAAGCCAAATGCCCTAT AAGGTGTTCCACTACCAAGTGAAGATCCATTTTTCCGGGACCGAGAGCGAGACC CATACCAACCAGGCCTTCGAGATCTCCCTGTACGGGACAGTGGCCGAGTCCGAA AACATCCCCTTCACCCTGCCCGAAGTGAGCACCAACAAGACCTACTCCTTTCTG ATCTACACCGAGGTGGACATCGGCGAGCTGCTGATGCTGAAGCTGAAGTGGAA GAGCGATAGCTACTTCAGCTGGTCAGACTGGTGGAGCAGCCCCGGCTTCGCAAT CCAGAAGATCAGGGTGAAGGCCGGCGAGACGCAGAAGAAAGTGATCTTCTGCA GCAGGGAGAAGGTAAGCCATCTCCAGAAGGGCAAAGCCCCCGCCGTGTTCGTG AAGTGTCACGACAAGTCCCTGAACAAAAAAAGCGGT |
| 82 | LPL-CO28 | ATGGAAAGCAAAGCCCTGCTGGTACTCACGCTCGCCGTCTGGCTGCAGTCCCTG ACCGCCAGCAGAGGCGGCGTCGCGGCCGCCGATCAGAGAAGAGACTTCATCGA |

TABLE 2-continued

Sequence optimized sequences for wild type human LPL

| SEQ ID NO | Name | Sequence |
|---|---|---|
| | | CATCGAAAGCAAGTTCGCGCTGAGGACCCCGGAAGACACCGCCGAGGACACGT GCCACCTGATCCCCGGCGTGGCCGAGAGCGTGGCCACGTGTCACTTCAACCACT CCTCCAAGACCTTTATGGTGATCCACGGCTGGACGGTGACCGGAATGTACGAGA GCTGGGTGCCGAAGCTGGTGGCCGCCCTGTACAAGCGGGAGCCGGACAGCAAC GTGATCGTAGTGGACTGGCTGAGCAGGGCCCAGGAGCATTATCCCGTGAGCGC CGGCTACACTAAGCTGGTGGGCCAGGACGTGGCCCGGTTCATAAACTGGATGG AGGAAGAGTTCAACTACCCACTGGACAATGTCCACCTCCTGGGCTACAGCCTGG GCGCCCACGCCGCCGGCATCGCCGGGTCCCTCACCAACAAGAAGGTCAACCGG ATCACAGGCCTCGACCCCGCCGGCCCCAACTTTGAGTACGCCGAGGCCCCCTCA AGGCTGAGCCCCGACGACGCCGACTTCGTAGACGTGCTGCACACCTTTACTCGC GGCAGCCCGGGTAGGTCGATCGGGATCCAGAAGCCTGTCGGCCATGTGGACAT CTACCCCAACGGCGGCACCTTCCAACCCGGATGTAACATCGGCGAGGCCATCCG GGTGATCGCCGAACGCGGGCTGGGAGACGTGGACCAACTGGTGAAGTGCAGCC ACGAGAGGAGCATCCACCTGTTCATCGACAGCCTGCTGAACGAGGAGAACCCC AGCAAAGCCTATAGGTGCAGCAGCAAGGAGGCCTTCGAAAAAGGCCTCTGCCT GTCCTGCAGGAAAAACCGTTGCAACAACCTGGGCTACGAAATCAACAAGGTGC GAGCCAAAAGGAGCAGCAAGATGTACCTGAAGACCAGGTCCCAGATGCCGTAT AAGGTGTTCCACTACCAGGTGAAGATCCATTTCTCCGGAACCGAGTCGGAAACC CACACTAACCAGGCCTTCGAGATCAGCCTGTACGGCACGGTCGCCGAGTCCGAA AATATCCCCTTCACCCTCCCCGAAGTGTCCACCAACAAGACATACAGCTTCCTG ATCTACACCGAGGTGGACATCGGAGAGCTGCTGATGCTCAAGCTGAAGTGGAA GAGCGACAGCTACTTCAGCTGGAGCGACTGGTGGTCCTCGCCGGGCTTCGCCAT CCAAAAGATCCGCGTCAAGGCCGGGGAGACCCAGAAGAAGGTCATCTTCTGTT CCAGGGAGAAGGTGAGCCACCTCCAGAAGGGCAAGGCCCCCGCCGTGTTCGTG AAGTGCCATGACAAGAGCCTGAACAAGAAGAGCGGC |
| 83 | LPL-CO29 | ATGGAGAGCAAGGCCCTGCTGGTGCTGACCCTGGCCGTGTGGCTGCAGTCACTC ACCGCATCCAGGGGGGGAGTGGCCGCCGCCGACCAGAGGCGGGACTTCATCGA TATCGAGAGCAAGTTCGCCCTCCGGACCCCCGAGGACACAGCCGAGGACACCT GCCACCTGATCCCCGGGGTGGCCGAGTCAGTGGCGACCTGCCATTTCAACCACT CCAGCAAGACCTTTATGGTCATCCACGGCTGGACCGTGACCGGCATGTACGAGT CCTGGGTCCCCAAGCTGGTGGCCGCGCTGTATAAGCGGGAACCCGACTCCAATG TGATCGTCGTGGATTGGCTGAGCCGTGCCCAGGAGCATTACCCCGTGAGCGCCG GCTACACCAAGTTGGTGGGACAGGACGTGGCCAGGTTCATCAACTGGATGGAG GAGGAGTTCAACTACCCCCTGGATAACGTGCACCTGCTGGGCTACTCCCTGGGG GCGCATGCCGCGGGCATCGCCGGGAGCCTGACCAACAAGAAGGTGAATAGGAT CACCGGCCTGGATCCCGCCGGCCCGAACTTTCGAGTACGCCGAGGCCCCCAGCA GGCTGAGCCCGGACGACGCCGACTTCGTGGACGTCCTCCACACCTTCACCAGGG GGAGCCCCGGGAGGAGCATTGGAATCCAGAAGCCCGTGGGCCACGTGGACATC TATCCCAATGGCGGGACGTTCCAACCTGGCTGCAACATCGGTGAAGCCATCCGC GTGATCGCCGAGCGCGGCCTGGGCGACGTGGACCAGCTGGTGTTAGTGCAGTCA CGAGAGGAGCATCCACCTGTTCATCGATAGCCTGCTGAACGAGGAGAACCCCA GCAAGGCCTACAGGTGCTCCAGCAAGGAGGCCTTCGAGAAGGGCCTCTGCCTTG AGCTGCCGCAAGAACCGGTGCAACAACCTCGGGTACGAAATCAATAAGGTGCG GGCCAAGAGGTCCAGCAAGATGTATCTGAAGACCCGGAGCCAGATGCCCTACA AGGTGTTCCACTACCAAGTGAAGATCCACTTTTCGGGTACGGAGTCCGAGACGC ACACCAACCAGGCCTTTGAAATCAGCCTCTACGCCACCGTGGCCGAAAGCGAG AACATCCCCTTTACCCTGCCCGAGGTCAGCACCAACAAGACCTATTCCTTCCTG ATCTACACCGAGGTGGACATCGGCGAACTCCTGATGCTGAAGCTGAAGTGGAA GTCCGACAGCTACTTTTCCTGGAGCGACTGGTGGTCCAGCCCCGGGTTCGCCAT ACAGAAGATCCGGGTGAAGGCAGGGGAGACGCAGAAAAAGGTCATCTTCTGCA GCCGTGAAAAGGTGAGTCACCTCCAAAAGGGCAAGGCGCCCGCCGTGTTCGTA AAGTGCCACGATAAGAGCCTGAACAAAAAAAGCGGC |
| 148 | LPL-CO30 | ATGGAGAGCAAGGCCCTGCTGGTGCTGACCCTGGCCGTGTGGCTGCAGAGCCTG ACCGCCAGCCGGGGAGGCGTGGCCGCCGCCGACCAGCGGCGGGACTTCATCGA CATCGAGTCCAAGTTCGCCCTGCGGACGCCCGAGGACACCGCCGAAGACACCT GCCACCTGATCCCCGGCGTCGCCGAGAGCGTGGCCACATGCCACTTCAACCACA GCAGCAAGACCTTCATGGTGATCCACGGCTGGACCGTGACCGGCATGTACGAG AGCTGGGTGCCCAAGCTGGTGGCCGCTCTGTACAACCGGGAGCCCGACAGCAA CGTGATCGTGGTGGACTGGCTGAGCCGGGCCCAGGAGCACTACCCCGTGAGCG CCGGCTACACCAAGCTCGTCGGCCAGGACGTGGCCCGGTTTCATCAACTGGATGG AGGAGGAGTTCAACTACCCGCTGGACAACGTGCACCTGCTGGGCTACAGCCTG GGCGCCCACGCCGCCGGCATCGCCGGCAGCCTCACCAACAAGAAGGTGAACCG GATCACCGGCCTGGACCCCGCCGGCCCCAACTTCGAGTACGCCGAGGCGCCCA GCAGGCTCTCGCCCGACGACGCCGACTTTCGTGGACGTGCTGCACACCTTCACCC GGGGCTCTCCCGGACGGAGCATCGGCATCCAGAAGCCCGTGGGCCACGTGGAC ATCTACCCCAACGGCGGCACCTTCCAGCCCGGCTGCAACATCGGCGAGGCCATC CGGGTGATCGCCGAGCGGGGTCTGGGCGACGTGGACCAGCTGGTGAAGTGCAG CCACGAGCGGAGCATTCACCTGTTCATCGATAGCCTGCTGAACGAGGAGAACCC CTCCAAAGCATACCGGTGCAGTAGTAAGGAGGCCTTCGAGAAGGGCCTGTGCC TGAGCTGCCGGAAGAACAGATGCAACAACCTTGGGTACGAGATCAACAAGGTG CGGGCCAAGAGATCTTCCAAGATGTACCTGAAGACCCGGAGCCAGATGCCCTA CAAGGTGTTCCACTACCAGGTGAAGATCCACTTCAGCGGCACCGAAAGCGAAA |

TABLE 2-continued

Sequence optimized sequences for wild type human LPL

| SEQ ID NO | Name | Sequence |
|---|---|---|
| | | CTCACACCAACCAGGCCTTTGAAATCAGCCTGTACGGCACCGTGGCCGAGTCTG<br>AGAACATCCCTTTCACACTGCCCGAGGTGAGCACTAACAAGACCTACAGCTTCC<br>TGATCTACACCGAGGTGGACATTGGCGAGCTGCTGATGCTGAAGCTGAAGTGG<br>AAGTCAGACAGCTACTTCAGCTGGAGCGACTGGTGGTCTAGCCCCGGATTCGCC<br>ATCCAGAAGATCAGGGTGAAGGCCGGAGAGACACAGAAGAAAGTGATCTTCTG<br>CAGCCGGGAGAAGGTAAGCCACCTGCAGAAGGGCAAGGCTCCCGCCGTGTTCG<br>TCAAGTGCCACGACAAGTCCCTGAACAAGAAGTCCGGC |
| 149 | LPL-CO01 | AUGGAGAGCAAGGCCCUGCUGGUGCUGACCCUGGCCGUGUGGCUGCAGAGCC<br>UGACCGCCAGCCGGGGAGGCGUGGCCGCCGCCGACCAGCGGCGGGACUUCAU<br>CGACAUCGAGUCCAAGUUCGCCCUGCGGACGCCCGAGGACACCGCCGAAGAC<br>ACCUGCCACCUGAUCCCCGGCGUCGCCGAGAGCGUGGCCACAUGCCACUUCAA<br>CCACAGCAGCAAGACCUUCAUGGUGAUCCACGGCUGGACCGUGACCGGCAUG<br>UACGAGAGCUGGGUGCCCAAGCUGGUGGCCGCUCUGUACAAGCGGGAGCCCG<br>ACAGCAACGUGAUCGUGGUGGACUGGCUGAGCCGGGCCCAGGAGCACUACCC<br>CGUGAGCGCCGGCUACACCAAGCUCGUCGGCCAGGACGUGGCCCGGUUCAUC<br>AACUGGAUGGAGGAGGAGUUCAACUACCCGCUGGACAACGUGCACCUGCUGG<br>GCUACAGCCUGGGCGCCCACGCCGCCGGCAUCGCCGGCAGCCUCACCAACAAG<br>AAGGUGAACCGGAUCACCGGCCUGGACCCCGCCGGCCCCAACUUCGAGUACG<br>CCGAGGCGCCCAGCAGGCUCUCGCCCGACGACGCCGACUUCGUGGACGUGCU<br>GCACACCUUCACCCGGGGCUCUCCCGGACGGAGCAUCGGCAUCCAGAAGCCCG<br>UGGGCCACGUGGACAUCUACCCCAACGGCGGCACCUUCCAGCCCGGCUGCAAC<br>AUCGGCGAGGCCAUCCGGGUGAUCGCCGAGCGGGGUCUGGGCGACGUGGACC<br>AGCUGGUGAAGUGCAGCCACGAGCGGAGCAUUCACCUGUUCAUCGAUAGCCU<br>GCUGAACGAGGACAACCCCUCCAAAGCAUACCGGUGCAGUAGUAAGGAGGCC<br>UUCGAGAAGGGCCUGUGCCUGAGCUGCCGGAAGAACAGAUGCAACAACCUUG<br>GGUACGAGAUCAACAAGGUGCGGGCCAAGAGAUCUUCCAAGAUGUACCUGAA<br>GACCCGGAGCCAGAUGCCCUACAAGGUGUUCCACUACCAGGUGAAGAUCCAC<br>UUCAGCGGCACCGAAAGCGAAACUCACACCAACCAGGCCUUUGAAAUCAGCC<br>UGUACGGCACCGUGGCCGAGUCUGAGAACAUCCCUUUCACACUGCCCGAGGU<br>GAGCACUAACAAGACCUACAGCUUCCUGAUCUACACCGAGGUGGACAUUGGC<br>GAGCUGCUGAUGCUGAAGCUGAAGUGGAAGUCAGACAGCUACUUCAGCUGGA<br>GCGACUGGUGGUCUAGCCCCGGAUUCGCCAUCCAGNAGAUCAGGGUGAAGGC<br>CGGAGAGACACAGAAGAAAGUGAUCUUCUGCAGCCGGGAGAAGGUAAGCCAC<br>CUGCAGAAGGGCAAGGCUCCCGCCGUGUUCGUCAAGUGCCACGACAAGUCCC<br>UGAACAAGAAGUCCGGC |
| 150 | LPL-CO02 | AUGGAGAGCAAGGCCCUGCUGGUGCUGACCCUGGCCGUGUGGCUGCAGAGCC<br>UGACCGCCAGCCGGGGCGGCGUGGCCGCCGCCGACCAGCGCCGCGACUUCAUC<br>GACAUCGAGUCCAAGUUCGCCCUCCGCACGCCCGAGGACACCGCCGAGGACAC<br>CUGCCACCUCAUCCCCGGCGUCGCCGAGUCCGUCGCCACCUGCCACUUCAACC<br>ACUCCUCCAAGACCUUCAUGGUCAUCCACGGCUGGACCGUCACCGGCAUGUA<br>CGAGUCCUGGGUCCCCAAGCUCGUCGCCGCCCUCUACAAGCGCGAGCCCGACU<br>CCAACGUCAUCGUCGUCGACUGGCUCUCCCGCGCCCAGGAGCACUACCCCGUC<br>UCCGCCGGCUACACCAAGCUCGUCGGCCAGGACGUCGCCCGCUUCAUCAACUG<br>GAUGGAGGAGGAGUUCAACUACCCACUCGACAACGUCCACCUCCUCGGCUAC<br>UCCCUCGGCGCCCACGCCGCCGGCAUCGCCGGCUCCCUCACCAACAAGAAGGU<br>CAACCGCAUCACCGGCCUCGACCCCGCCGGCCCCAACUUCGAGUACGCCGAGG<br>CGCCCUCCCGCCUCUCGCCCGACGACGCCGACUUCGUCGACGUCCUCCACACC<br>UUCACCCGCGGCUCGCCCGGCCGCUCCAUCGGCAUCCAGAAGCCCGUCGGCCA<br>CGUCGACAUCUACCCCAACGGCGGCACCUUCCAGCCCGGCUGCAACAUCGGCG<br>AGGCCAUCCGCGUCAUCGCCGAGCGCGGCCUCGGCGACGUCGACCAGCUCGUC<br>AAGUGCUCCCACGAGCGCUCCAUCCACCUCUUCAUCGACUCCCUCCUCAACGA<br>GGAGAACCCCUCCAAGGCCUACCGCUGCUCCUCCAAGGAGGCCUUCGAGAAG<br>GGCCUCUGCCUCUCCUGCCGCAAGAACCGCUGCAACAACCUCGGCUACGAGA<br>UCAACAAGGUCCGCGCCAAGCGCUCCUCCAAGAUGUACCUCAAGACCCGCUCC<br>CAGAUGCCCUACAAGGUCUUCCACUACCAGGUCAAGAUCCACUUCUCCGGCA<br>CCGAGUCCGAGACCCACACCAACCAGGCCUUCGAGAUCUCCCUCUACGGCACC<br>GUCGCCGAGUCCGAGAACAUCCCCUUCACCCUCCCCGAGGUCUCCACCAACAA<br>GACCUACUCCUUCCUCAUCUACACCGAGGUCGACAUCGGCGAGCUCCUCAUG<br>CUCAAGCUCAAGUGGAAGUCCGACUCCUACUUCUCCUGGUCCGACUGGUGGU<br>CCUCGCCCGGCUUCGCCAUCCAGAAGAUCCGCGUCAAGGCCGGCGAGACCCAG<br>AAGAAGGUCAUCUUCUGCUCCCGCGAGAAGGUCUCCCACCUCCAGAAGGGCA<br>AGGCGCCCGCCGUCUUCGUCAAGUGCCACGACAAGUCCCUCAACAAGAAGUC<br>CGGC |
| 151 | LPL-CO03 | AUGGAGAGCAAGGCCCUGCUGGUGCUGACCCUGGCCGUGUGGCUGCAGAGCC<br>UGACCGCCAGCCGGGGAGGCGUGGCCGCCGCCGACCAGCGGCGGGACUUCAU<br>CGACAUCGAGUCCAAGUUCGCCCUGCGGACCCCCGAGGACACCGCCGAAGAC<br>ACCUGCCACCUGAUCCCCGGCGUCGCCGAGAGCGUGGCCACAUGCCACUUCAA<br>CCACAGCAGCAAGACCUUCAUGGUGAUCCACGGCUGGACCGUGACCGGCAUG<br>UACGAGAGCUGGGUGCCCAACCUGGUGGCCGCUCUGUACAAGCGGGAGCCCG<br>ACAGCAACGUGAUCGUGGUGGACUGGCUGAGCCGGGCCCAGGAGCACUACCC<br>CGUGAGCGCCGGCUACACCAAGCUCGUCGGCCAGGACGUGGCCCGGUUCAUC |

TABLE 2-continued

Sequence optimized sequences for wild type human LPL

| SEQ ID NO | Name | Sequence |
|---|---|---|
| | | AACUGGAUGGAGGAGGAGUUCAACUACCCCCUGGACAACGUGCACCUGCUGG<br>GCUACAGCCUGGGCGCCCACGCCGCCGGCAUCGCCGGCAGCCUCACCAACAAG<br>AAGGUGAACCGGAUCACCGGCCUGGACCCCGCCGGCCCCAACUUCGAGUACG<br>CCGAGGCCCCCAGCAGGCUCUCCCCCGACGACGCCGACUUCGUGGACGUGCUG<br>CACACCUUCACCCGGGGCUCUCCCGGACGGAGCAUCGGCAUCCAGAAGCCCGU<br>GGGCCACGUGGACAUCUACCCCAACGGCGGCACCUUCCAGCCCGGCUGCAACA<br>UCGGCGAGGCCAUCCGGGUGAUCGCCGAGCGGGGUCUGGGCGACGUGGACCA<br>GCUGCTUGAAGUGCAGCCACGAGCGGAGCAUUCACCUGUUCAUCGAUAGCCUG<br>CUGAACGAGGAGAACCCCUCCAAAGCAUACCGGUGCAGUAGUAAGGAGGCCU<br>UCGAGAAGGGCCUGUGCCUGAGCUGCCGGAAGAACAGAUGCAACAACCUUGG<br>GUACGAGAUCAACAAGGUGCGGGCCAAGAGAUCUUCCAAGAUGUACCUGAAG<br>ACCCGGAGCCAGAUGCCCUACAAGGUUTUCCACUACCAGGUGAAGAUCCACU<br>UCAGCGGCACCGAAAGCGAAACUCACACCAACCAGGCCUUUGAAAUCAGCCU<br>GUACGGCACCGUGGCCGAGUCUGAGAACAUCCCUUUCACACUGCCCGAGGUG<br>AGCACUAACAAGACCUACAGCUUCCUGAUCUACACCGAGGUGGACAUUGGCG<br>AGCUGCUGAUGCUGAAGCUGAAGUGGAAGUCAGACAGCUACUUCAGCUGGAG<br>CGACUGGUGGUCUAGCCCCGGAUUCGCCAUCCAAAAGAUCAGGGUGAAGGCC<br>GGAGAGACACAGAAGAAAGUGAUCUUCUGCAGCCGGGAGAAGGUAAGCCACC<br>UGCAGAAGGGCAAGGCUCCCGCCGUGUUCGUCAAGUGCCACGACAAGUCCCU<br>GAACAAGAAGUCCGGC |
| 152 | LPL-CO04 | AUGGAGAGCAAGGCCCUGCUGGUGCUGACCCUGGCCGUGUGGCUGCAGAGCC<br>UGACCGCCAGCCGGGGCGGCGUGGCCGCCGCCGACCAGCGCCGCGACUUCAUC<br>GACAUCGAGUCCAAGUUCGCCCUCCGCACCCCCGAGGACACCGCCGAGGACAC<br>CUGCCACCUCAUCCCCGGCGUCGCCGAGUCCGUCGCCACCUGCCACUUCAACC<br>ACUCCUCCAAGACCUUCAUGGUCAUCCACGGCUGGACCGUCACCGGCAUGUA<br>CGAGUCCUGGGUCCCCAAGCUCGUCGCCGCCCUCUACAAGCGCGAGCCCGACU<br>CCAACGUCAUCGUCGUCGACUGGCUCUCCCGCGCCCAGGAGCACUACCCCGUC<br>UCCGCCGGCUACACCAAGCUCGUCGGCCAGGACGUCGCCCGCUUCAUCAACUG<br>GAUGGAGGAGGAGUUCAACUACCCCCUCGACAACGUCCACCUCCUCGGCUAC<br>UCCCUCGGCGCCCACGCCGCCGGCAUCGCCGGCUCCCUCACCAACAAGAAGGU<br>CAACCGCAUCACCGGCCUCGACCCCGCCGGCCCCAACUUCGAGUACGCCGAGG<br>CCCCCUCCCGCCUCUCCCCCGACGACGCCGACUUCGUCGACGUCCUCCACACC<br>UUCACCCGCGGCUCCCCCGGCCGCUCCAUCGGCAUCCAGAAGCCCGUCGGCCA<br>CGUCGACAUCUACCCCAACGGCGGCACCUUCCAGCCCGGCUGCAACAUCGGCG<br>AGGCCAUCCGCGUCAUCGCCGAGCGCGGCCUCGGCGACGUCGACCAGCUCGUC<br>AAGUGCUCCCACGAGCGCUCCAUCCACCUCUUCAUCGACUCCCUCCUCAACGA<br>GGAGAACCCCUCCAAGGCCUACCGCUGCUCCUCCAAGGAGGCCUUCGAGAAG<br>GGCCUCUGCCUCUCCUGCCGCAAGAACCGCUGCAACAACCUCGGCUACGAGA<br>UCAACAAGGUCCGCGCCAAGCGCUCCUCCAAGAUGUACCUCAAGACCCGCUCC<br>CAGAUGCCCUACAAGGUCUUCCACUACCAGGUCAAGAUCCACUUCUCCGGCA<br>CCGAGUCCGAGACCCACACCAACCAGGCCUUCGAGAUCUCCCUCUACGGCACC<br>GUCGCCGAGUCCGAGAACAUCCCCUUCACCCUCCCCGAGGUCUCCACCAACAA<br>GACCUACUCCUUCCUCAUCUACACCGAGGUCGACAUCGGCGAGCUCCUCAUG<br>CUCAAGCUCAAGUGGAAGUCCGACUCCUACUUCUCCUGGUCCGACUGGUGGU<br>CCUCCCCCGGCUUCGCCAUCCAGAAGAUCCGCGUCAAGGCCGGCGAGACCCAG<br>AAGAAGGUCAUCUUCUGCUCCCGCGAGAAGGUCUCCCACCUCCAGAAGGGCA<br>AGGCCCCCGCCGUCUUCGUCAAGUGCCACGACAAGUCCCUCAACAAGAAGUC<br>CGGC |
| 153 | LPL-CO05 | AUGGAGAGCAAGGCUCUGCUGGUGCUGACGCUGGCCGUGUGGCUGCAGUCCC<br>UGACCGCCAGCAGGGGAGGCGUGGCCGCCGCCGACCAGCGGCGCGACUUCAU<br>CGAUAUCGAGUCGAAGUUCGCCCUGCGCACGCCCGAGGAUACCGCCGAGGAC<br>ACGUGCCACCUGAUCCCCGGGGUGGCGGAGAGCGUCGCCACCUGUCACUUCA<br>ACCAUAGCAGCAAGACGUUCAUGGUCAUCCACGGCUGGACCGUGACAGGAAU<br>GUACGAAAGCUGGGUGCCCAAGCUCGUGGCCGCCCUCUACAAGAGGGAGCCC<br>GACAGCAAUGUGAUAGUGGUGGACUGGCUGUCCCGGGCCCAGGAACACUAUC<br>CCGUGAGCGCCGGGUACACCAAGCUCGUGGGCCAGGACGUGGCCCGGUUCAU<br>CAAUUGGAUGGAGGAGGAGUUCAACUACCCCCUGGACAACGUGCAUCUGCUC<br>GGCUACUCCCUGGGCGCUCACGCCGCCGGCAUCGCGGGCAGCCUGACAAACA<br>AGAAGGUGAACAGGAUCACCGGGCUCGACCCCGCCGGCCCCAACUUCGAGUA<br>CGCCGAGGCCCCCAGCAGGCUGAGCCCCGACGAUGCCGACUUCGUGGACGUG<br>CUGCACACCUUCACCCGGGGCAGCCCCGGCAGGAGCAUCGGCAUCCAGAAGCC<br>CGUGGGCCAUGUCGACAUCUAUCCCAAUGGCGGCACCUUUCAGCCCGGUUGC<br>AACAUCGGCGAGGCGAUCAGGGUGAUUGCCGAGAGGGGCCUGGGCGACGUCG<br>AUCAGCUGGUGAAGUGUAGCCACGAGCGGUCCAUCCAUCUCUUCAUAGACUC<br>CCUUCUGAAUGAAGAGAACCCCUCCAAAGCCUACCGAUGCAGCAGCAAGGAG<br>GCGUUCGAAAAGGGGCUGUGCCUGUCCUGCAGGAAGAACAGGUGCAACAAUC<br>UGGGCUAUGAGAUCAACAAGGUACGCGCGAAGCGGAGCAGCAAGAUGUAUCU<br>GAAGACCCGGUCGCAGAUGCCCUAUAAAGUGUUCCACUACCAGGUAAAGAUC<br>CACUUCUCCGGGACCGAGAGCGAGACCCACACAAAUCAGGCCUUCGAGAUCA<br>GCCUGUACGGCACCGUGGCGGAGAGCGAGAAUAUCCCGUUCACCCUGCCUGA<br>GGUGUCCACCAAUAAGACCUACUCCUUCCUGAUCUACACGGAGGUGGACAUA<br>GGCGAGCUGCUGAUGCUGAAGCUGAAGUGGAAGUCGGACAGCUACUUCUCCU |

TABLE 2-continued

Sequence optimized sequences for wild type human LPL

| SEQ ID NO | Name | Sequence |
|---|---|---|
| | | GGAGCGACUGGUGGUCCUCCCCCGGAUUCGCCAUCCAGAAGAUCAGGGUGAAGGCCGGCGAGACCCAGAAAAAGGUGAUCUUUUGCUCGCGCGAGAAGGUCUCGCACCUGCAGAAGGGGAAGGCCCCCGCCGUGUUCGUGAAGUGCCAUGAUAAGAGUCUCAAUAAGAAGUCCGGG |
| 154 | LPL-CO06 | AUGGAGAGCAAGGCACUGCUGGUGCUGACACUGGCCGUGUGGCUGCAGAGCCUGACCGCCUCCAGGGGCGGAGUGGCCGCCGCCGACCAGCGGCGGGACUUCAUCGACAUCGAAUCGAAGUUCGCCCUGCGGACCCCGGAGGACACCGCCGAAGACACCUGCCACCUCAUCCCCGGCGUCGCCGAGAGCGUGGCCACGUGCCACUUCAACCACAGCAGCAAGACCUUCAUGGUGAUCCAUGGCUGGACCGUGACAGGCAUGUAUGAGAGCUGGGUCCCCAAACUGGUGGCGGCCCUGUACAAAAGGGAGCCGGACUCCAAUGUGAUCGUAGUGGACUGGCUCUCCAGGGCCCAGGAGCACUACCCCGUCAGCGCCGGCUACACCAAGCUGGUGGGCCAGGACGUGGCCAGGUUCAUCAACUGGAUGGAGGAAGAGUUCAAUUACCCCCUGGACAACGUGCAUCUGCUCGGGUACUCCCUGGGCGCCCACGCCGCCGGGAUCGCCGGUAGCCUCACCAACAAGAAGGUCAAUCGAAUCACCGGGCUGGACCCCGCCGGGCCCAACUUUGAAUACGCCGAAGCCCCCAGCCGGCUCAGCCCCGACGAUGCCGACUUUGUGGAUGUGCUGCACACCUUCACCCGAGGUAGCCCCGGCAGGAGCAUCGGCAUCCAGAAGCCCGUGGGCCACGUGGACAUCUACCCCAACGGGGGUACCUUCCAGCCCGGGUGCAACAUCGGAGAGGCCAUCAGGGUGAUCGCAGAGAGGGGCCUGGGCGAUGUGGACCAGCUGGUCAAGUGCAGCCACGAAAGGAGCAUACACUUAUUCAUAGAUAGCCUGCUCAACGAAGAGAACCCCAGCAAGGCCUACCGUUGUUCCUCUAAGGAGGCCUUCGAGAAGGGGCUCUGCCUGAGCUGCCGGAAAAACAGGUGCAACAACCUCGGCUACGAGAUCAACAAGGUGCGGGCCAAACGGUCCAGCAAGAUGUACCUGAAGACCAGGAGCCAGAUGCCCUAUAAGGUCUUCCACUACCAGGUCAAGAUCCACUUCUCCGGCACCGAGAGCGAGACCCACACUAACCAGGCCUUCGAGAUCUCGCUGUACGGGACGGUGGCGGAAUCCGAGAACAUCCCGUUCACCCUGCCCGAGGUGAGCACCAACAAAACGUACAGCUUCCUGAUCUACACCGAGGUCGACAUCGGCGAGCUCCUCAUGCUCAAGCUCAAGUGGAAGAGCGAUAGCUACUUCAGCUGGUCCGACUGGUGGAGCAGCCCGGGCUUCGCCAUCCAAAAGAUUAGGGUGAAGGCCGGCGAGACCCAGAAGAAGGUGAUCUUCUGCUCGAGGGAGAAAGUGUCCCAUCUGCAGAAGGGCAAGGCCCCGGCCGUGUUCGUGAAGUGCCACGAUAAGUCGCUGAACAAGAAGUCCGGC |
| 155 | LPL-CO07 | AUGGAGUCCAAGGCCCUGCUGGUGCUCACACUCGCCGUGUGGCUGCAGAGCCUGACCGCCUCCCGGGGGGGCGUGGCGGCCGCCGACCAGCGGAGGGAUUUCAUCGACAUCGAGAGCAAAUUCGCCCUGAGGACCCCCGAGGACACCGCCGAGGAUACCUGCCAUCUCAUCCCCGGCGUGGCUGAGAGCGUGGCCACCUGCCACUUCAACCACAGCAGCAAGACCUUCAUGGUGAUCCACGGCUGGACCGUGACCGGAAUGUACGAGAGCUGGGUGCCCAAGCUGGUGGCCGCCCUGUACAAGAGGGAGCCCGAUAGCAAUGUGAUAGUGGUGGAUUGGCUGAGCAGGGCCCAAGAGCAUUACCCCGUGAGCGCCGGCUAUACCAAGCUGGUGGGCCAGGACGUGGCCAGGUUCAUCAACUGGAUGGAGGAGGAGUUCAACUACCCCCUGGACAACGUCCACCUGCUGGGCUACAGCCUGGGGGCCCACGCCGCGGGCAUCGCCGGCUCCCUCACCAACAAGAAGGUGAAUAGGAUAACGGGCCUGGACCCCGCCGGUCCCAACUUCGAGUACGCCGAGGCCCCGUCCCGACUGUCUCCCGACGACGCAGACUUCGUCGACGUCCUGCAUACCUUCACCAGAGGCAGCCCCGGGAGGUCCAUCGGCAUCCAGAAGCCCGUGGGCCAUGUGGACAUCUACCCGAAUGGCGGCACCUUCCAGCCUGGUUGCAACAUUGGCGAGGCGAUCAGGGUGAUCGCCGAGCGUGGCCUCGGGGACGUGGAUCAGCUGGUGAAGUGUUCCCACGAGCGCAGCAUCCACCUCUUCAUCGACAGCCUGCUCAACGAAGAGAACCCCUCCAAGGCCUACAGGUGCAGUUCCAAGGAGGCAUUCGAGAAGGGCCUCUGCCUGAGCUGCAGGAAGAACAGGUGUAACAACCUAGGCUACGAGAUCAACAAGGUCCGGGCCAAGCGGAGCUCAAAGAUGUACCUGAAGACGCGGAGCCAGAUGCCCUAUAAGGUGUUCCACUACCAGGUGAAAAUCCAUUUCUCCGGCACCGAGUCCGAGACCCACACCAACCAAGCAUUCGAGAUCUCCCUCUACGGAACCGUAGCAGAGAGCGAGAACAUCCCCUUCACCCUCCCCGAGGUGAGCACUAACAAGACGUACUCCUUCCUGAUCUACACCGAGGUGGACAUCGGCGAGCUCCUGAUGCUGAAGCUGAAGUGGAAGAGCGACUCCUACUUUUCCUGGUCCGACUGGUGGUCCAGCCCCGGGUUUGCGAUUCAAAAGAUCAGGGUGAAAGCCGGCGAAACCCAGAAGAAGGUGAUCUUCUGUAGCCGAGAGAAAGUGAGCCACCUGCAGAAAGGAAAGGCCCCCGCCGUCUUCGUCAAGUGCCACGACAAAAGCCUCAAUAAGAAGUCCGGG |
| 156 | LPL-CO08 | AUGGAGAGCAAGGCGCUGCUGGUGCUGACACUGGCGGUGUGGCUGCAAAGCCUGACCGCGAGCAGGGGCGGCGUGGCCGCCGCCGACCAGAGGCGGGACUUCAUUGACAUCGAGUCCAAGUUCGCCCUUAGGACCCCCGAAGACACCGCCGAGGACACCUGCCACCUGAUACCGGGGGUGGCCGAGUCCGUGGCCACCUGCCACUUUAACCACUCCUCCAAGACGUUCAUGGUCAUCCACGGCUGGACCGUGACCGGGAUGUACGAAAGCUGGGUGCCCAAGCUGGUGGCCGCCCUCUACAAAAGGGAGCCUGACUCCAACGUCAUCGUGGUGGACUGGCUGUCCAGGGCCCAGGAGCACUACCCCGUUUCCGCCGGAUACACCAAGCUGGUGGGCCAGGACGUGGCCCGGUUCAUCAAUUGGAUGGAGGAGGAAUUCAAUUACCCCCUGGACAACGUGCAUCUGCUCGGCUACUCCCUGGGCGCCCACGCCGCCGGCAUCGCCGGCAGCCUGACUAACAAGAAGGUGAACCGGAUCACCGGCCUGGACCCCGCCGGCCCCAACUUCGAAUAC |

TABLE 2-continued

Sequence optimized sequences for wild type human LPL

| SEQ ID NO | Name | Sequence |
|---|---|---|
| | | GCCGAGGCCCCCUCCCGACUGUCCCCAGACGACGCCGACUUCGUGGAUGUGCU<br>GCACACCUUCACCCGCGGCAGCCCCGGGCGAAGCAUCGGAAUCCAAAAGCCCG<br>UGGGGCACGUGGAUAUCUACCCGAACGGGGGAACCUUCCAACCCGGCUGCAA<br>CAUUGGGGAGGCCAUCAGAGUGAUCGCCGAGCGCGGGCUGGGGGACGUCGAC<br>CAGCUGGUGAAGUGCUCCCACGAGCGCAGCAUCCACCUGUUCAUCGACUCCC<br>UACUGAAUGAAGAGAACCCCAGCAAGGCGUACCGGUGCUCCUCCAAGGAGGC<br>CUUCGAGAAGGGCCUCUGCCUGAGCUGCAGGAAGAACAGAUGCAACAAUCUG<br>GGCUACGAGAUCAAUAAGGUCCGCGCCAAGAGAAGCAGCAAAAUGUACCUGA<br>AGACCCGGAGCCAGAUGCCCUAUAAGGUGUUCCACUACCAGGUGAAGAUCCA<br>CUUCAGCGGUACGGAGUCUGAGACCCAUACCAACCAGGCUUUCGAAAUCAGC<br>CUGUACGGAACCGUGGCCGAGAGCGAGAACAUCCCCUUUACCCUGCCAGAAG<br>UGUCCACAAACAAGACCUACUCCUUCCUGAUAUACACUGAGGUGGACAUCGG<br>CGAGCUGCUGAUGCUGAAGUUGAAGUGGAAGAGCGAUAGCUACUUCAGCUGG<br>AGCGAUUGGUGGAGCAGCCCCGGAUUCGCCAUCCAGAAGAUAAGGGUGAAGG<br>CCGGAGAGACCCAGAAGAAGGUCAUCUUUUGCAGCAGGGAGAAGGUGAGCCA<br>CCUGCAGAAGGGCAAGGCGCCCGCCGUGUUCGUCAAGUGUCACGACAAGAGC<br>CUGAAUAAGAAGAGCGGG |
| 157 | LPL-CO09 | AUGGAAAGCAAGGCGCUGCUCGUCCUCACCCUGGCCGUCUGGCUGCANAGCC<br>UGACCGCCAGCAGAGGUGGCGUGGCGGCCGCCGACCAGCGGCGAGACUUCAU<br>CGAUAUCGAAAGCAAGUUUGCCCUGAGGACCCCCGAGGAUACCGCCGAGGAC<br>ACCUGCCACCUGAUUCCCGGAGUGGCCGAGAGCGUUGCCACCUGCCACUUCA<br>ACCACUCGAGCAAGACCUUUAUGGUGAUACACGGCUGGACCGUCACGGGCAU<br>GUACGAGAGCUGGGUGCCCAAGCUGGUGGCCGCCCUGUAUAAGAGGGAGCCG<br>GACAGCAACGUCAUCGUCGUGGACUGGCUGUCGAGGGCCCAAGAACACUACC<br>CCGUGAGCGCCGGGUACACCAAGCUGGUCGGUCAAGACGUGGCCCGCUUCAU<br>CAAUUGGAUGGAGGAGGAGUUCAACUAUCCCCUCGACAACGUGCACCUCCUG<br>GGCUACAGCCUGGGCGCCCACGCCGCCGGCAUCGCCGGUUCGCUCACCAAUAA<br>AAAGGUGAACAGGAUUACCGGUCUGGACCCCGCGGGCCCGAACUUCGAGUAC<br>GCCGAAGCCCCGAGCAGGCUGUCCCCGGACGACGCCGACUUCGUGGACGUGC<br>UGCACACCUUUACCCGCGGCUCCCCCGGCCGGAGCAUCGGAAUCCAAAAGCCC<br>GUCGGGCACGUGGAUAUCUACCCCAACGGCGGCACCUUCCAGCCCGGGUGCA<br>ACAUCGGUGAGGCCAUCAGGGUCAUCGCCGAACGGGGCCUGGGCGACGUGGA<br>CCAGCUGGUCAAAUGUAGCCAUGAGAGGUCCAUCCACCUGUUUAUCGACUCC<br>CUGCUGAACGAGGAGAACCCCAGCAAGGCCUACCGGUGCUCCAGCAAGGAGG<br>CCUUCGAGAAAGGACUGUGCCUGAGCUGCAGGAAGAACCGUUGCAACAACCU<br>GGGCUACGAGAUCAACAAGGUGAGGGCAAAGCGGAGCUCAAAGAUGUACCUG<br>AAGACCCGGUCCCAAAUGCCCUACAAAGUGUUCCAUUACCAGGUGAAAAUUC<br>AUUUCAGCGGCACCGAGAGCGAAACCCACACGAACCAGGCCUUUGAGAUAAG<br>CCUGUACGGGACCGUGGCGGAGAGCGAGAAUAUCCCCUUCACUCUCCCCGAG<br>GUGAGCACGAACAAGACCUACUCCUUCCUGAUCUACACGGAGGUCGAUAUCG<br>GUGAGCUGCUGAUGCUGAAGCUGAAGUGGAAGAGCGACAGCUACUUCUCCUG<br>GAGCGACUGGUGGAGCAGCCCUGGGUUCGCCAUCCAAAAAAUCCGGGUGAAG<br>GCCGGCGAGACCCAAAAGAAGGUGAUCUUCUGCUCUAGGGAGAAGGUGUCCC<br>ACCUGCAGAAGGGCAAGGCCCCCGCCGUAUUUGUGAAGUGCCACGACAAGAG<br>CCUGAAUAAGAAGAGCGGC |
| 158 | LPL-CO10 | AUGGAGAGCAAGGCCCUGCUGGUCCUGACCCUGGCCGUCUGGCUGCAGAGCC<br>UGACCGCCUCCCGGGGGGGCGUGGCCGCCGCCGACCAGAGGCGCGACUUUAU<br>AGACAUCGAGUCGAAGUUUGCCCUGCGCACCCCCGAGGACACAGCCGAAGAC<br>ACCUGCCACCUGAUCCCCGGGGUGGCGGAGAGCGUGGCCACCUGCCACUUCA<br>ACCACUCCUCCAAGACCUUCAUGGUCAUUCAUGGCUGGACCGUCACCGGCAU<br>GUACGAGAGUUGGGUGCCGAAGCUGGUGGCCGCCCUCUACAAGAGGGAGCCC<br>GACUCCAACGUGAUCGUGGUGGACUGGCUGAGCAGGGCCCAGGAGCACUAUC<br>CGGUGAGCGCCGGGUACACGAAGCUGGUCGGACAGGACGUGGCCCGCUUCAU<br>CAACUGGAUGGAGGAAGAGUUUAACUAUCCGCUCGACAACGUCCAUCUGCUG<br>GGGUACAGCCUGGGCGCCCAUGCCGCCGGAAUCGCCGGCUCCCUGACGAACA<br>AGAAGGUGAACCGGAUCACCGGGCUAGACCCCGCCGGGCCCAAUUUCGAGUA<br>CGCCGAGGCGCCCAGCAGGCUGAGUCCCGACGACGCCGACUUUGUGGACGUC<br>CUGCAUACCUUCACCCGCGGCAGCCCCGGGCGAUCCAUCGGCAUCCAGAAGCC<br>GGUCGGCCACGUCGACAUCUACCCCAACGGCGGCACAUUCCAGCCCGGCUGCA<br>ACAUCGGCGAGGCCAUCAGGGUGAUCGCCGAGCGUGGGCUGGGCGACGUGGA<br>UCAGCUGGUGAAGUGCAGCCACGAGAGGAGCAUCCAUCUGUUCAUCGAUAGC<br>CUGCUGAACGAGGAGAACCCGAGCAAGGCCUACAGGUGUAGCAGCAAGGAGG<br>CCUUCGAGAAGGGCCUCUGUCUGUCAUGCAGGAAGAAUAGGUGCAACAACCU<br>GGGCUACGAGAUCAACAAGGUGAGGGCCAAAAGGAGCUCCAAGAUGUAUCUG<br>AAGACCAGGUCCCAGAUGCCGUACAAGGUGUUCCACUAUCAGGUGAAGAUCC<br>ACUUCUCGGGCACAGAGAGCGAGACGCACACCAACCAGGCCUUCGAGAUCAG |

TABLE 2-continued

Sequence optimized sequences for wild type human LPL

| SEQ ID NO | Name | Sequence |
|---|---|---|
| | | CCUGUACGGCACCGUGGCCGAGUCCGAAAACAUCCCUUUUACCCUGCCCGAG<br>GUGUCCACCAACAAGACCUACAGCUUCCUGAUAUACACCGAGGUGGACAUCG<br>GCGAACUGCUGAUGCUCAAGCUGAAAUGGAAGUCCGACAGCUACUUCAGCUG<br>GAGCGAUUGGUGGAGCUCCCCGGGGUUCGCAAUCCAAAAGAUCAGGGUGAAG<br>GCAGGGGAGACCCAGAAGAAGGUCAUCUUCUGCUCCCGGGAAAAAGUGAGCC<br>AUCUCCAGAAGGGCAAAGCGCCCGCCGUGUUCGUCAAGUGCCACGAUAAGAG<br>CCUGAACAAGAAGAGCGGC |
| 159 | LPL-CO11 | AUGGAGAGCAAGGCGCUGCUGGUGCUGACCCUGGCGGUGUGGCUGCAGAGCC<br>UCACCGCCUCGCGCGGUGGCGUGGCGGCCGCCGAUCAACGGCGGGACUUCAU<br>CGAUAUCGAGACCAAGUUCGCCCUUCGGACCCCGGAGGACACCGCCGAGGAU<br>ACUUGCCAUCUGAUCCCCGGCGUGGCCGAAUCCGUGGCCACCUGCCACUUCA<br>ACCACUCCAGCAAGACCUUCAUGGUGAUCCACGGCUGGACCGUGACCGGGAU<br>GUACGAGAGUUGGGUGCCCAAGCUGGUGGCCGCCCUGUACAAGCGGGAGCCC<br>GACAGCAAUGUGAUCGUGGUGGACUGGCUGAGCAGGGCCCAGGAGCAUUAUC<br>CAGUGAGCGCCGGGUAUACCAAACUCGUGGGCCAGGAUGUCGCCAGGUUCAU<br>UAACUGGAUGGAGGAGGAAUUCAACUACCCGCUGGAUAACGUGCAUCUGCUG<br>GGGUACUCGCUGGGAGCCCAUGCCGCCGGCAUCGCGGGAUCCCUGACGAACA<br>AGAAGGUCAAUAGGAUCACCGGCCUGGACCCGGCCGGCCCCAACUUCGAGUA<br>CGCCGAGGCGCCCAGCCGUCUGAGCCCCGACGACGCCGAUUUCGUGGACGUG<br>CUGCACACCUUCACCAGGGGCAGCCCCGGCCGCAGCAUCGGCAUUCAGAAGCC<br>CGUGGGCCACGUCGACAUAUAUCCCAACGGCGGAACCUUCCAACCCGGCUGU<br>AACAUCGGGGAGGCCAUCCGGGUCAUCGCCGAGAGGGGCCUGGGCGACGUGG<br>ACCAGCUGGUGAAGUGCUCCCACGAGCGUAGCAUUCAUCUGUUCAUCGACUC<br>CCUGCUGAACGAAGAGAACCCCUCCAAGGCCUACCGUUGCUCCAGCAAGGAG<br>GCCUUCGAGAAGGGCCUCUGCCUCAGCUGCAGGAAGAACAGGUGUAACAACC<br>UGGGCUACGAGAUCAACAAGGUGAGGGCCAAGAGGAGCUCCAAGAUGUAUCU<br>GAAGACACGGAGCCAGAUGCCCUACAAGGUGUUCCACUACCAGGUGAAGAUC<br>CACUUCUCCGGGACGGAAUCAGAGACCCACACGAACCAGGCCUUUGAGAUCA<br>GCCUGUAUGGGACCGUGGCCGAGUCCGAGAACAUCCCCUUCACCCUGCCCGA<br>GGUGAGCACCAACAAAACUUACUCCUUCCUGAUCUACACCTGAAGUGGACAUC<br>GGGGAGCUGCUGAUGCUGAAACUCAAAUGGAAGAGCGACAGCUACUUUAGCU<br>GGAGCGACUGGUGGUCCAGCCCCGGCUUCGCCAUCCAGAAAAUCAGGGUCAA<br>AGCCGGCGAGACCCAGAAAAAGGUGAUCUUCUGCAGCAGGGAAAAGGUCAGC<br>CACCUGCAGAAAGGGAAGGCCCCCGCUGUGUUCGUGAAAUGUCACGACAAGA<br>GCCUGAACAAAAAGAGCGGC |
| 160 | LPL-CO12 | AUGGAGAGCAAGGCCCUGCUGGUGCUGACCCUGGCCGUGUGGCUGCAGUCGC<br>UGACCGCCAGCAGGGGCGGCGUGGCCGCGGCCGACCAGCGCCGGGACUUCAU<br>CGACAUCGAGAGCAAGUUUGCCCUGAGGACCCCCGAGGAUACCGCAGAGGAC<br>ACCUGCCAUCUGAUCCCCGGCGUGGCAGAGAGCGUCGCCACUUGCCACUUCA<br>ACCAUUCCAGCAAGACUUCTUAUGGUCAUCCACGGUUGGACCGUGACCGGAAU<br>GUACGAGUCCUGGGUCCCGAAACUGGUGGCCGCCCUGUACAAGCGGGAGCCA<br>GACUCCAACGUGAUCGUCGUGGAUUGGCUGUCCAGGGCCCAGGAGCACUACC<br>CCGUCUCCGCCGGCUACACCAAGCUGGUGGGACAAGACGUGGCCAGGUUCAU<br>CAACUGGAUGGAAGAGGAGUUCAACUAUCCCCUGGACAACGUGCAUCUCCUG<br>GGCUACAGCCUCGGCGCCCACGCCGCCGGCAUCGCGGGCAGUCUGACGAACA<br>AGAAGGUGAACAGGAUCACCGGGCUGGACCCCGCCGGCCCGAAUUUCGAGUA<br>CGCGGAGGCCCCGAGCAGGCUGAGCCCCGACGACGCCGACUUCGUGGACGUG<br>CUGCACACGUUCACCCGAGGAAGCCCCGGCCGGAGCAUCGGAAUCCAGAAGC<br>CCGUGGGCCACGUCGACAUCUACCCCAAUGGCGGAACCUUCCAGCCCGGGUG<br>CAACAUAGGCGAAGCCAUCAGGGUGAUCGCCGAAAGGGGGCUGGGCGAUGUG<br>GACCAGCUGGUGAAGUGUCTCACACGAGAGGUCCAUCCACCUGUUUAUCGAUA<br>GCCUGCUGAACGAGGAGAACCCAUCCAAGGCCUACAGGUGCAGCAGCAAGGA<br>GGCCUUUGAGAAGGGCCUGUGUCUGUCGUGUAGGAAGAACAGGUGCAACAAU<br>CUCGGCUACGAGAUCAAUAAGGUAAGGGCCAAGCGGUCGAGCAAGAUGUACC<br>UCAAGACCAGGAGCCAGAUGCCCUAUAAGGUGUUCCAUUAUCAGGUGAAAAU<br>CCACUUUAGCGGCACCGAGAGCGAAACCCACACCAACCAGGCCUUCGAAAUC<br>UCCCUGUACGGCACUGUGGCCGAGAGCGAGAAUAUCCCCUUCACCCUGCCCG<br>AGGUCAGCACCAACAAAACCUACAGCUUCCUGAUCUACACCGAGGUCGACAU<br>CGGCGAACUGCUUAUGCUGAAGCUGAAGUGGAAAAGCGACAGCUACUUCAGC<br>UGGAGCGAUUGGUGGAGCAGCCCCGGCUUUGCCAUCCAGAAAAUCCGCGUGA<br>AGGCAGGGGAGACCCAGAAGAAGGUAAUAUUCUGCAGCAGGGAGAAGGUAA<br>GCCACCUGCAGAAAGGUAAGGCCCCCGCCGUGUUCGUGAAAUGUCACGACAA<br>GUCCCUGAAUAAGAAGUCCGGG |
| 161 | LPL-CO13 | AUGGAGAGCAAGGCCCUGCUGGUGCUGACGCUGGCGGUGUGGCUCCAGUCCC<br>UGACCGCCAGCCGGGGGGGCGUCGCCGCCGCCGACCAACGCCGCGACUUCAUC<br>GACAUCGAAAGUAAAUUCGCCCUGCGGACCCCCGAGGACACCGCCGAAGACA<br>CGUGCCACCUGAUCCCUGGAGUUGCGGAGAGCGUGGCGACCUGCCACUUAA<br>CCACUCCAGCAAGACGUUCAUGGUGAUCCAUGGCUGGACCGUCACCGGCAUG<br>UACGAGAGCUGGGUGCCGAAGCUCGUGGCCGCGCUCUACAAGAGGGAGCCCG<br>ACUCCAACGUGAUCGUGGUCGACUGGCUGAGCAGGGCCCAGGAGCACUACCC<br>AGUCAGCGCCGGCUACACCAAGCUGGUGGGCCAGGACGUGGCGCGGUUUAUA |

TABLE 2-continued

| SEQ ID NO | Name | Sequence |
|---|---|---|
| | | AACUGGAUGGAGGAGGAGUUCAACUAUCCCCUGGAUAACGUGCACCUGCUGG GCUACUCCCUGGGCGCCCACGCCGCCGGGAUCGCCGGAAGCCUGACCAACAAG AAAGUGAACCGCAUUACCGGGCUGGACCCCGCCGGCCCCAACUUCGAGUACG CCGAGGCACCCAGCAGGCUGAGCCCGGACGACGCUGACUUUGUGGACGUGCU GCACACGAUUACCAGGGGCAGCCCCGGUCGAUCCAUCGGUAUACAGAAGCCC GUGGGCCACGUGGACAUCUAUCCCAACGGGGGCACAUUUCAACCCGGCUGCA ACAUCGGCGAAGCCAUCAGGGUCAUCGCCGAGCGCGGCCUGGGCGAUGUGGA UCAGCUGGUGAAGUGCUCCCACGAGAGGAGCAUCCACCUGUUCAUCGACAGC CUCCUCAAUGAGGAGAAUCCCAGCAAGGCCUACAGGUGCUCCAGCAAGGAGG CCUUCGAGAAGGGUCUGUGCCUGUCCUGCAGAAAAAACAGGUGCAACAACCU GGGCUACGAGAUCAACAAAGUGAGGGCCAAGAGGUCGAGCAAAAUGUACCUG AAGACCAGGAGCCAGAUGCCCUACAAGGUGUUCCACUACCAGGUGAAGAUCC ACCUCAGCGGGACGGAAUCCGAGACGCACACCAACCAGGCCUUCGAGAUCUC CCUCUACGGCACCGUGGCCGAGAGCGAGAAUAUCCCCUUCACCCUGCCGGAG GUGAGCACGAACAAGACCUACUCAUUUCUGAUCUAUACGGAGGUCGAUAUCG GCGAGCUGCUCAUGCUGAAACUGAAGUGGAAGUCGGACAGCUACUUCAGCUG GAGCGAUUGGUGGAGCAGCCCCGGCUUCGCGAUCCAGAAGAUCAGGGUGAAG GCCGGGGAGACGCAGAAGAAGGUGAUUUUCUGUUCCAGAGAGAAAGUCUCCC ACCUCCAAAAAGGCAAGGCCCCCGCCGUGUUCGUGAAGUGCCAUGACAAGUC CCUGAACAAGAAGAGCGGG |
| 162 | LPL-CO14 | AUGGAGUCAAAGGCCCUCCUGGUGCUUACCCUCGCCGUUUGGCUCCAGUCCC UGACCGCGAGCCGCGGCGGGGUGGCCGCCGCCGACCAGAGGCGAGACUUUAU CGACAUUGAGUCCAAGUUCGCCCUGAGGACCCCCGAGGACACCGCCGAGGAC ACCUGCCACCUGAUCCCCGGUGUGGCCGAGAGCGUCGCCACAUGCCAUUUCA ACCACUCGAGUAAAACCUUCAUGGUGAUCCACGGCUGGACUGUGACCGGGAU GUACGAGUCCUGGGUCCCCAAGCUCGUGGCCGCCCUGUACAAGAGGGAGCCC GACAGCAACGUGAUUGUGGUGGACUGGCUGUCCAGGGCCCAGGAACACUACC CGGUGAGCGCCGGCUACACCAAGCUGGUGGGCCAGGACGUUCCCCGCUUCAU CAACUGGAUGGAGGAGGAGUUCAACUACCCCCUGGACAACGUGCACCUGCUG GGCUACAGCCUGGGGGCCCACGCCGCCGGGAUCGCGGGGUCCCUGACCAACA AAAAGGUGAACAGGAUCACCGGCCUGGAUCCGGCCGGACCCAACUUCGAAUA CGCCGAAGCCCCUAGCCGGCUGAGCCCCGACGACGCCGACUUCGUGGACGUCC UGCACACCUUCACAAGGGGGUCCCCUGGUCGCAGUAUCGGGAUCCAGAAGCC UGUCGGCCACGUCGAUAUCUACCCCAACGGCGGGACCUUCCAGCCCGGCUGC AACAUCGGCGAGGCCAUCCGGGUGAUUGCCGAGAGGGGCCUGGGAGACGUCG ACCAGUUGGUGAAAUGCAGCCACGAGAGGAGCAUCCACCUGUUCAUCGACUC CCUCCUGAACGAGGAGAACCCCAGCAAGGCCUACCGCUGCUCCUCCAAGGAG GCCUUCGAGAAAGGCCUGUGUCUGAGCUGCCGGAAGAACCGGUGCAAUAACC UCGGGUACGAGAUCAAUAAGGUGCGCGCCAAGCGGAGCAGCAAGAUGUACCU GAAGACAAGGAGCCAGAUGCCCUACAAGGUGUUCCACUACCAGGUGAAAAUC CACUUCAGCGGCACCGAGAGCGAGACCCACACCAACCAGGCCUUCGAGAUCA GCCUGUAUGGCACCGUGGCCGAAAGCGAGAACAUCCCCUUUACACUGCCCGA GGUCUCCACCAACAAGACGUACAGCUUCCUGAUCUACACCGAGGUGGAUAUC GGCGAGCUGCUGAUGCUGAAGCUGAAAUGGAAGAGCGACAGCUAUCUUCUCAU GGAGCGACUGGUGGAGCUCCCCGGGCUUCGCCAUCCAGAAGAUCAGGGUGAA GGCGGGCGAGACACAAAAGAAGGUCAUCUUCUGCUCCAGGGAGAAGGUGAGC CACCUGCAGAAGGGCAAGGCCCCCGCCGUGUUCGUGAAAUGCCACGACAAGA GCCUGAAUAAGAAGAGCGGC |
| 163 | LPL-CO15 | AUGGAGAGCAAGGCCCUGCUGGUGCUGACCCUGGCCGUUGGCUGCAGUCCC UGACCGCCAGCCGCGGUGGCGUGGCCGCCGCCGACCAGCGGCGGGAUUUCAU CGACAUAGAAUCUAAGUUUGCCCUGAGGACCCCCGAGGACACCGCCGAGGAC ACCUGCCACCUGAUCCCCGGGGUGGCCGAGUCCGUGGCCACGUGUCACUUCA ACCAUAGCAGCAAGACCUUUAUGGUCAUCCACGGCUGGACCGUGACUGGCAU GUACGAGAGCUGGGUGCCCAAGCUCGUGGCCGCCCUGUACAAGAGGGAGCCC GACAGCAACGUGAUCGUGGUGGACUGGCUCAGCCGAGCCCACGAGCACUACC CCGUCAGCGCCGGCUACACCAAGCUCGUGGGCCAAGACGUAGCCAGGUUCAU CAAUUGGAUGGAGGAGGAGUUAACUACCCCCUCGACAACGUGCACCUCCUG GGCUACUCCCUGGGCGCCCAUGCCGCCGGCAUAGCCGGAAGCCUGACUAACA AAAAAGUCAAUCGGAUCACCGGCCUAGACCCCGCCGGGCCCAACUUCGAAUA CGCCGAGGCCCCCUCCAGGCUGAGCCCGGACGACGCCGACUUUGUGGACGUCC UGCACACCUUCACGAGAGGGUCCCCGGGCCGGUCGAUCGGAAUCCAGAAACC CGUGGGGCAUGUGGACAUCTUACCCCAACGGCGGCACCUUCCAGCCAGGCUGC AACAUCGGCGAAGCCAUCAGGGUCAUCGCCGAGAGGGGACUGGGCGACGUGG ACCAGCUGGUGAAGUGCAGCCACGAGCGGAGCAUCCACCUGUUCAUCGACAG CCUGCUGAAUGAGGAGAAUCCCAGCAAGGCCUACAGAUGUUCCAGCAAAGAG GCCUUCGAGAAGGGACUGUGCCUGUCCUGCAGAAAGAACAGGUGCAAUAACC UGGGUUACGAGAUAAAUAAGGUGAGGGCCAAGAGGUCCUCCAAGAUGUAUC UGAAGACCCGCAGCCAGAUGCCUUACAAGGUCUUCCACUACCAAGUGAAAAU CCACUUUAGCGGGACCGAAUCAGAGACGCACACAAAUCAAGCUUUCGAGAUC AGCCUGUACGGCACCGUGGCCGAGUCCGAGAACAUCCCCUUCACCCUCCCGGA GGUGUCCACCAACAAGACCUACUCCUUCCUGAUCUAUACAGAGGUGGACAUC GGGGAGCUGCUGAUGCUGAAGCUGAAGUGGAAAUCCGACAGCUACUUCAGCU |

Sequence optimized sequences for wild type human LPL

TABLE 2-continued

Sequence optimized sequences for wild type human LPL

| SEQ ID NO | Name | Sequence |
|---|---|---|
| | | GGAGCGACUGGUGGAGCAGCCCCGGCUUUGCCAUCCAGAAAAUCAGGGUGAA GGCCGGAGAAACUCAAAAAAAGGUCAUCUUCUGCAGCCGCGAGAAGGUGAGC CACCUGCAGAAGGGCAAGGCCCCCGCCGUGUUCGUGAAGUGUCACGACAAGU CGCUGAACAAGAAGAGCGGU |
| 164 | LPL-CO16 | AUGGAGUCCAAGGCCCUCCUGGUGCUGACCCUGGCCGUCUGGCUGCAGUCAC UGACCGCGAGCAGGGGCGGCGUGGCCGCAGCGGACCAGCGCAGGGACUUCAU CGACAUCGAGAGCAAGUUCGCCCUGAGGACCCCCGAGGACACCGCGGAAGAC ACCUGCCACCUGAUCCCCGGCGUGGCCGAGUCCGUGGCCACCUGCCACUUCAA UCACAGCUCCAAGACCUUUAUGGUGAUCCACGGCUGGACCGUGACCGGAAUG UAUGAGAGCUGGUGCCCAAGCUCGUGGCCGCCCUUUACAAGAGGGAGCCCG ACAGCAAUGUCAUAGUGGUGGACUGGCUGAGCAGGGCCCAGGAGCACUACCC CGUGAGUGCCGGGUACACCAAGCUGGUGGGCCAGGACGUCGCCCGAUUCAUC AACUGGAUGGAGGAGGAGUUCAACUACCCCCUGGACAACGUGCAUCUGCUGG GGUACUCCCUGGGCGCGCACGCUGCCGGCAUCGCGGGGUCCCUAACCAACAA GAAGGUGAACAGGAUCACCGGGCUGGACCCCGCCGGCCCCAAUUUCGAAUAU GCCGAGGCCCCCAGCAGGCUGAGCCCCGACGACGCCGACUUCGUGGACGUGC UGCAUACCUUCACCAGGGGCAGCCCCGGCCGGUCGAUUGGCAUACAAAAGCC CGUGGGCCACGUGGACAUCUACCCGAACGGGGGCACCUUCCAGCCCGGGUGC AACAUAGGAGAAGCCAUCAGGGUGAUCGCGGAGAGGGGCCUGGGCGAUGUGG ACCAGCUGGUGAAAUGCAGCCACGAAAGGUCCAUCCACCUGUUUAUCGACAG CCUGCUGAACGAGGAGAACCCCAGCAAGGCCUAUAGGUGCAGCUCAAAGGAG GCCUUCGAGAAGGGACUGUGCCUCUCCUGCAGGAAGAACCGCUGUAACAACC UGGGCUACGAGAUAAACAAGGUGAGGGCCAAGCGGAGCAGCAAGAUGUACCU GAAGACUCGCUCCCAGAUGCCAUACAAGGUGUUCCACUACCAGGUGAAGAUC CACUUCUCCGGCACGGAGAGCGAGACCCACACCAACCAAGCGUUCGAGAUCU CCCUGUACGGGACAGUGGCCGAAUCAGAGAACAUCCCCUUUACCCUGCCCGA GGUGAGCACCAAUAAGACCUACUCCUUCCUGAUCUACACAGAGGUGGAUAUC GGGGAGCUGCUGAUGCUGAAGCUGNAGUGGAAAAGCGACUCCUACUUCAGCU GGAGCGAUUGGUGGUCCAGCCCCGGCUUUGCCAUCCAGAAGAUCAGGGUCAA GGCCGGCGAGACGCAGAAGAAGGUGAUCUUCUGCUCCCGGGAAAAGGUGAGC CACCUGCAGAAAGGCAAGGCCCCAGCCGUUUUCGUGAAGUGCCACGAUAAGU CCCUGAACAAGAAGAGCGGC |
| 165 | LPL-CO17 | AUGGAGAGUAAGGCGCUGCUCGUGCUCACGCUGGCAGUGUGGCUCCAGUCCC UGACCGCCAGCCGCGGGGGGGUGGCCGCGGCCGACCAGAGGAGGGACUUCAU CGAUAUCGAGAGCAAGUUCGCCCUGCGGACACCCGAGGAUACAGCCGAGGAC ACAUGCCACCUGAUACCCGGCGUGGCCGAAAGCGUGGCCACGUGCCACUUUA ACCACUCCAGCAAGACCUUCAUGGUCAUCCACGGCUGGACCUGUCACCGGCAU GUACGAGAGCUGGGUGCCCAAGCUGGUCGCCGCCCUGUACAAGCGCGAGCCU GAUAGCAACGUGAUCGUGGUGGACUGGCUGUCCCGGGCCCAGGAGCACUACC CCGUGAGCGCCGGCUAUACAAAACUGGUGGGUCAGGACGUGGCCAGAUUCAU AAACUGGAUGGAAGAGGAGUUUAACUACCCCCUGGACAACGUGCACCUGCUG GGCUAUAGCCUGGGCGCCCACGCCGCCGGCAUCGCGGGCAGCCUCACUAACA AGAAGGUGAAUCGGAUAACCGGCCUGGAUCCCGCCGGGCCCAAUUUCGAGUA CGCGGAAGCCCCCAGCCGGCUGAGCCCCGAUGACGCCGAUUUCGUGGACGUG CUGCACACCUUCACGCGCGGCAGCCCCGGCCGGAGCAUCGGUAUCCAGAAACC AGUGGGCCAUGUGGACAUCUACCCAAAUGGCGGAACCUUCCAGCCGGGCUGU AACAUCGGUGAAGCCAUCCGGGUGAUCGCCGAGAGGGGCCUGGGCGAUGUGG ACCAGCUGGUGAAAUGUAGCCACGAGCGCUCCAUCCACCUCUUCAUCGACUC CCUGCUGAACGAAGAAAACCCCUCCAAGGCGUACAGGUGUAGCAGCAAGGAG GCCUUCGAGAAGGGCCUGUGCCUCUCCUGCCGUAAGAACAGGUGUAACAACC UGGGGUACGAGAUCAACAAGGUGCGGGCCAAGAGGAGCAGCAAGAUGUACCU GAAGACCCGGAGCCAGAUGCCCUACAAGGUCUUCCACUACCAGGUCAAGAUC CACUUCAGCGGCACCGAGAGCGAGACCCACACUAACCAAGCCUUCGAGAUCA GCCUGUACGGGACCGUCGCCGAGAGCGAGAACAUCCCCUUCACCCUGCCCGA GGUGAGCACCAACAAAACCUACUCCUUUCUGAUCUACACGGAAGUGGACAUC GGCGAGCUGCUGAUGCUGAAGCUGAAGUGGAAAAGCGACAGCUACUUUUCCU GGUCCGACUGGUGGAGCAGCCCGGGCUUCGCGAUCCAGAAGAUCCGGGUGAA GGCCGGCGAGACCCAGAAGAAGGUCAUCUUUUGCAGCAGGGAGAAGGUGAGC CACCUGCAGAAGGGUAAGGCCCCGCCGUGUUCGUGAAGUGCCACGACAAGA GCCUGAACAAGAAGUCCGGAGGG |
| 166 | LPL-CO18 | AUGGAGUCCAAGGCCCUCCUGGUGCUGACCCUGGCCGUGUGGCUCCAGAGCC UAACCGCCUCCCGGGGCGGCGUGGCCGCCGCCGAUCAGAGGCGGGAUUUCAU CGACAUAGAGAGCAAGUUCGCCCUCCGCACCCCCGAAGACACCGCCGAAGAC ACUUGCCACCUGAUUCCCGGAGUGGCCGAGUCCCGUGGCCACUUGCCACUUCA ACCACAGCAGCAAGACCUUCAUGGUGAUCCACGGCUGGACCUUUACCGGCAU GUACGAAAGCUGGGUGCCGAAGCUCGUGGCCGCCCUGUACAAGAGGGAGCCC GACUCCAACGUGAUCGUGGUUGACUGGCUGUCCAGGGCCCAGGAGCACUACC CCGUGUCCGCCGGCUACACCAAGCUGGUCGGGCAGGACGUGGCCAGGUUCAU CAACUGGAUGGAAGAGGAGUUCAACUAUCCUCUGGACAAUGUGCACCUGCUG GGCUACAGCCUGGGCGCCCACGCCGCGGGCAUCGCCGGCAGCCUGACCAAUA AGAAAGUGAAUAGGAUUACCGGCCUGGACCCCGCGGGGCCCAACUUCGAGUA |

TABLE 2-continued

Sequence optimized sequences for wild type human LPL

| SEQ ID NO | Name | Sequence |
| --- | --- | --- |
| | | CGCCGAAGCCCCCAGCAGGCUGAGCCCCGACGAUGCCGACUUCGUGGACGUCC<br>UGCACACCUUCACCCGGGGCAGCCCCGGGAGGAGCAUAGGCAUACAGAAACC<br>CGUGGGCCACGUGGACAUCUACCCCAAUGGCGGCACGUUCCAGCCCGGGUGC<br>AACAUCGGGGAGGCCAUCAGGGUGAUCGCCGAGAGGGGACUUGGCGACGUGG<br>ACCAGCUGGUGAAGUGCAGCCACGAGCGCAGCAUACACCUGUUCAUCGAUAG<br>CCUGCUUAACGAGGAAAACCCCUCCAAGGCCUACAGGUGCUCCUCAAAGGAA<br>GCGUUCGAGAAGGGGCUGUGUCUCUCCUGCAGGAAGAACAGAUGCAAUAACC<br>UGGGCUACGAGAUCAACAAGGUGAGGGCCAAGAGGAGCAGCAAGAUGUACCU<br>GAAAACUAGGAGCCAAAUGCCCUAUAAGGUGUUUCACUACCAGGUGAAGAUC<br>CACUUCUCCGGCACCGAGAGCGAGACCCACACAAACCAGGCCUUCGAAAUCU<br>CGCUGUACGGGACCGUGGCCGAGAGCGAAAACAUCCCCUUCACCCUGCCCGA<br>GGUGUCCACCAACAAGACCUACAGCUUCCUGAUCUACACCGAGGUAGACAUU<br>GGUGAGCUGCUGAUGCUCAAACUCAAGUGGAAGAGCGACUCCUACUUCAGCU<br>GGAGCGAUUGGUGGUCCUCCCCGGGCUUCGCCAUCCAGAAGAUACGGGUCAA<br>GGCUGGGGAAACCCAGAAGAAGGUGAUCUUCUGCUCCCGGGAGAAGGUCAGC<br>CACCUGCAAAAAGGGAAGGCGCCCGCCGUCUUCGUGAAGUGCCACGAUAAGA<br>GCCUGAACAAGAAGUCAGGC |
| 167 | LPL-CO19 | AUGGAGAGCAAGGCCCUGCUCGUGCUGACCCUCGCCGUCUGGCUGCAGAGCC<br>UGACCGCCAGCAGGGGCGGCGUGGCCGCCGCCGAUCAGAGGCGGGACUUCAU<br>AGAUAUCGAGAGCAAGUUCGCCCUGAGGACCCCCGAAGACACCGCGGAGGAC<br>ACCUGCCACCUGAUCCCCGGCGUGGCCGAGUCCGUGGCCACCUGCCACUUUAA<br>CCACUCCAGCAAAACCUUUAUGGUGAUCCAUGGCUGGACCGUCACCGGGAUG<br>UACGAGAGCUGGGUGCCCAAGCUGGUGGCCGCCCUCUACAAGCGGGAACCCG<br>AUAGCAACGUGAUCGUGGUAGACUGGCUGUCCAGGGCCCAAGAGCACUACCC<br>CGUGAGUGCCGGCUACACGAAGCUGGUGGGCCAGGACGUGGCCCGCUUCAUC<br>AAUUGGAUGGAGGAGGAGUUCAACUACCCGCUCGAUAACGUGCACCUGCUGG<br>GCUAUAGCCUGGGGGCCCACGCCGCCGGGAUCGCCGGCAGCCUCACCAACAA<br>GAAGGUGAACAGGAUCACCGGCCUCGACCCCGCCGGCCCCAACUUCGAAUAC<br>GCCGAGGCCCCCAGCAGGCUGAGCCCGGAUGACGCCGACUUUGUGGACGUGC<br>UCCACACCUUCACCAGGGGCUCCCCCGGCCGGUCCAUCGGGAUCCAGAAGCCC<br>GUCGGGCACGUGGACAUCUACCCCAAUGGGGGGACCUUCCAACCCGGCUGCA<br>ACAUCGGCGAGGCGAUCAGGGUGAUCGCCGAGCGCGGCCUGGGGGACGUGGA<br>CCAGCUGGUGAAAUGUUCCCAUGAGCGGAGCAUCCAUCUGUUCAUUGACUCC<br>CUGCUGAACGAGGAGAACCCCUCCAAGGCCUACCGGUGCUCCAGCAAGGAGG<br>CCUUCGAGAAGGGUCUGUGCCUGAGCUGCAGGAAGAAUCGAUGUAACAACCU<br>GGGCUACGAGAUCAACAAGGUGCGCGCCAAGAGGAGCAGCAAGAUGUACCUG<br>AAGACCAGGAGUCAAAUGCCCUACAAGGUGUUCCACUACCAGGUGAAGAUCC<br>ACUUCAGCGGCACGGAAUCCGAGACCCACACCAAUCAGGCCUUCGAGAUCAG<br>CCUCUACGGGACCGUGGCCGAGAGCGAAAACAUCCCCUUCACCCUGCCCGAG<br>GUGUCAACCAAUAAGACCUACAGCUUCCUGAUCUACACCGAGGUGGAUAUCG<br>GCGAGCUGCUGAUGCUGAAGCUGAAGUGGAAGAGCGAUAGCUACUUCUCGUG<br>GAGCGACUGGUGGAGCAGCCCCGGCUUCGCCAUCCAGAAGAUCAGGGUGAAG<br>GCCGGCGAGACCCAAAAGAAAGUGAUCUUUUGCAGCAGGGAGAAGGUGUCCC<br>ACCUCCAGAAGGGAAAGGCCCCCGCGGUGUUCGUAAAGUGCCAUGACAAGUC<br>CCUGAACAAAAAGAGCGGG |
| 168 | LPL-CO20 | AUGGAAUCCAAGGCCCUACUCGUGCUCACCCUGGCCGUGUGGCUGCAGAGCC<br>UGACCGCAAGCAGGGGGGGCGUGGCCGCCGCGGACCAAAGGAGGGAUUUCAU<br>UGAUAUCGAGAGCAAGUUCGCCCUCAGGACCCCCGAGGACACAGCCGAGGAC<br>ACCUGCCACCUGAUCCCCGGCGUAGCCGAGUCCGUCCCCACGCCACUUUAA<br>UCACUCCUCCAAGACCUUCAUGGUGAUACACGGGUGGACCGUGACCGGGAUG<br>UAUGAAAGUUGGGUGCCAAAACUGGUGGCCGCCCUGUACAAGAGGGAGCCCG<br>ACUCCAACGUCAUCGUCGUGGAUUGGCUGAGCCGGGCCGAGGAGCACUAUCC<br>CGUCAGCGCUGGCUAUACGAAGCUGGUGGGCCAGGACGUCGCCCGGUUCAUC<br>AAUUGGAUGGAGGAGGAGUUCAACUACCCCCUGGACAACGUGCACCUGCUGG<br>GCUAUAGCCUCGGCGCCCACGCCGCCGGUAUCGCUGGCAGCCUGACCAACAA<br>GAAGGUGAACCGGAUCACCGGCCUGGACCCGGCCGGCCCAAACUUUGAGUAC<br>GCCGAGGCCCCCUCCAGGCUGUCCCCCGACGACGCCGACUUCGUGGACGUCCU<br>GCACACCUUCACCCGUGGGUCCCCCGGACGGAGCAUCGGGAUUCAGAAACCC<br>GUGGGCCAUGUGGACAUUUACCCCAACGGGGGGACCUUCCAACCCGGGUGCA<br>ACAUCGGAGAGGCGAUCAGGGUGAUCGCUGAGCGGGGCCUCGGGGACGUCGA<br>CCAGCUGGUGAAGUGCAGCCACGAGCGCUCCAUCCACCUGUUCAUCGACAGC<br>CUGCUGAACGAGGAAAACCCCAGCAAGGCGUAUAGGUGCUCGUCGAAGGAGG<br>CCUUCGAAAAGGGCCUGUGCCUGUCGUGCCGAAAGAACAGGUGUAACAACCU<br>GGGUUACGAGAUCAACAAGGUGAGGGCCAAAAGGAGCUCCAAGAUGUAUCUG<br>AAGACCCGGUCCCAGAUGCCCUAUAAGGUGUUCCACUAUCAGGUGAAGAUCC<br>ACUUUAGCGGAACCGAAAGCGAAACCCACACAAACCAAGCCUUCGAGAUCUC<br>CCUGUACGGCACCGUCGCCGAGUCCGAGAACAUCCCCUUCACCCUGCCCGAGG<br>UGAGCACUAACAAGACCUACAGCUUCCUCAUCUACACGGAGGUGGACAUAGG<br>CGAGCUGCUGAUGCUGAAGCUGAACTUGGAAGUCCGACUCCUAUUUCAGCUGG |

TABLE 2-continued

Sequence optimized sequences for wild type human LPL

| SEQ ID NO | Name | Sequence |
|---|---|---|
| | | AGCGACUGGUGGUCCUCCCCCGGGUUUGCCAUCCAAAAGAUAAGGGUGAAGG<br>CCGGCGAGACCCAAAAGAAGGUGAUCUUCUGUUCCAGGGAAAAGGUGAGCCA<br>CCUGCAGAAGGGCAAGGCCCCCGCUGUGUUCGUUAAGUGCCACGACAAGUCC<br>CUGAACAAGAAGAGCGGC |
| 169 | LPL-CO21 | AUGGAGUCCAAGGCCCUGCUGGUGCUGACCCUUGCCGUGUGGCUGGAGAGCC<br>UGACCGCCAGCAGGGGCGGCGUCGCCGCCGCGGACCAGCGCAGGGACUUUAU<br>CGAUAUCGAGAGCAAGUUCGCCCUGAGGACACCCGAGGAGACCGCCGAGGAC<br>ACAUGCCAUCUGAUCCCAGGCGUUGCGGAGAGCGUGGCUACCUGCCACUUCA<br>AUCACAGCAGCAAAACCUUUAUGGUCAUCCACGGCUGGACGGUGACCGGCAU<br>GUACGAGAGCUGGGUGCCAAAGCUGGUGGCCGCCCUGUACAAGAGGGAACCC<br>GACAGCAACGUGAUCGUGGUGGAUUGCAUUAUCCAGGGCGCAGGAGCACUAUC<br>CCGUCAGCGCCGGCUACACCAAGCUGGUGGGCCAGGACGUCGCCAGGUUCAU<br>CAAUUGGAUGGAGGAGGAAUUCAAUUAUCCCCUGGAUAACGUACACCUCCUG<br>GGCUACAGCCUCGGAGCCCACGCCGCGGGAAUAGCCGGGAGCCUCACGAAUA<br>AGAAGGUUAACAGGAUCACCGGCCUGGAUCCCGCCGGCCCCAACUUCGAGUA<br>CGCAGAGGCACCGUCCAGGCUGUCCCCCGACGACGCCGACUUCGUGGACGUCC<br>UGCACACCUUCACCAGGGGCUCCCCCGGGCGUAGCAUCGGCAUCCAAAAGCCC<br>GUGGGCCACGUGGACAUCUACCCCAACGGCGGCACCUUCCAGCCCGGGUGCA<br>ACAUCGGCGAGGCGAUCCGGGUGAUAGCGGAACGCGGGCUGGGCGACGUGGA<br>UCAGCUGGUCAAGUGUAGCCAUGAGCGCAGCAUCCACCUGUUCAUCGACUCC<br>CUGCUCAACGAAGAAAACCCCAGCAAGGCCUACCGGUGCUCGAGCAAGGAAG<br>CGUUCGAGAAGGGCCUGUGCCUGAGCUGCAGGAAGAAUAGGUGCAAUAAUCU<br>GGGCUAUGAGAUCAACAAGGUGCGGGCCAAGCGAAGCUCUAAAAUGUACCUG<br>AAGACUCGGUCCCAGAUGCCGUACAAGGUGUUCCACUACCAGGUGAAGAUCC<br>ACUUCAGCGGGACCGAAUCCGAAACGCACACCAACCAAGCCUUCGAGAUCAG<br>CCUGUACGGGACCGUCGCCGAGAGCGAGAACAUCCCCUUCACCCUGCCCGAG<br>GUGUCCACAAACAAGACGUACAGCUUCCUCAUCUAUACCGAGGUCGACAUCG<br>GGGAGCUGCUGAUGUUAAAACUGAAGUGGAAGAGCGACUCCUAUUUUAGCU<br>GGUCCGACUGGUGGAGCAGCCCCGGCUUCGCCAUCCAGAAGAUCAGGGUCAA<br>GGCCGGUGAGACGCAGAAGAAGGUGAUUUUCUGCAGCAGGGAAAAAGUGUCC<br>CAUCUCCAGAAGGGUAAGGCGCCGGCCGUGUUUGUAAAAUGCCACGACAAGA<br>GUCUGAACAAAAAGAGCGGC |
| 170 | LPL-CO22 | AUGGAGUCCAAGGCCUUGCUGGUUCUGACCCUGGCCGUGUGGCUGCAGAGCC<br>UGACGGCCUCGAGGGGGGGCGUCGCGGCGGCCGACCAGCGGAGGGACUUCAU<br>CGACAUCGAGAGCAAAUUUGCCCUGCGGACCCCCGAAGACACCGCGGAGGAU<br>ACCUGUCACCUGAUUCCCGGCGUGGCUGAAAGCGUGGCAACCUGCCACUUCA<br>ACCACUCAAGCAAGACGUUUAUGGUCAUACACGGGUGGACCGUGACCGGAAU<br>GUACGAGAGUUGGGUGCCCAAACUGGUGGCCGCCCUGUACAAGAGGGAACCC<br>GACAGCAAUGUGAUAGUGGUGGACUGGCUGUCCCGGGCCCAGGAGCACUACC<br>CGGUGAGCGCCGGCUACACCAAGCUGGUGGGCCAGGACGUGGCCCGGUUCAU<br>CAACUGGAUGGAGGAGGAGUUCAACUAUCCCCUGGAUAACGUGCACCUCCUG<br>CGGUACAGCCUGGGGGCCCACGCCGCCGGAAUCCCCGGCAGCCUGACCAACA<br>AGAAGGUGAACAGGAUCACUGGCCUCGACCCCGCCGGCCCGAACUUUGAGUA<br>UGCCGAGGCCCCGAGCCGGCUGUCCCCCGACGACGCCGACUUCGUCGACGUGC<br>UCCACACCUUCACGAGGGGGAGCCCCGGCCGGAGCAUCGGCAUACAAAAGCC<br>CGUGGGACACGUGGACAUCUACCCCAACGGCGGCACCUUUCAGCCGGGCUGU<br>AAUAUCGGCGAGGCCAUCCGCGUGAUCGCCGAGAGGGGCCUGGGGGACGUGG<br>ACCAACUGGUGAAGUGUAGCCACGAAAGGUCCAUCCACCUCUUCAUCGACAG<br>CCUCCUGAACGAGGAGAACCCCUCCAAGGCCUACAGGUGCAGCUCUAAAGAG<br>GCGUUCGAGAAGGGGCUUUGCCUGAGCUGCAGGAAGAAUAGGUGCAACAACC<br>UGGGCUACGAAAUCAACAAGGUGCGGGCCAAGCGCAGCAGCAAAAUGUACCU<br>GAAGACCCGUAGCCAGAUGCCCUACAAGGUGUUUCACUACCAGGUGAAAAUC<br>CAUUUCAGCGGCACCGAAAGCGAAACGCACACCAACCAGGCCUUCGAGAUCU<br>CCCUGUACGGGACCGUCGCAGAGAGCGAGAACAUCCCCUUCACGCUCCCUGA<br>GGUGUCGACCAACAAGACCUAUUCCUUCCUGAUGUAUACCGAGCUGGAUAUC<br>GGAGAGCUGCUGAUGCUGAAGGUCAAAUGGAAAAGCGACAGCUAUUUCUCAU<br>GGUCCGACUGGUGGAGCAGCCCGGGAUUCGCCAUCCAGAAGAUCAGGGUGAA<br>GGCCGGGGAGACCCAGAAGAAGGUGAUCUUUUGCAGCCGCGAAAAGGUGAGC<br>CACCUGCAGAAGGGCAAGGCCCCCGCGGUGUUCGUCAAGUGUCACGAUAAAA<br>GUCUGAACAAGAAGAGCGGC |
| 171 | LPL-CO23 | AUGGAGAGCAAAGCGCUACUGGUGCUGACCCUCGCCGUGUGGCUACAGAGCC<br>UGACCGCCUCGCGGGGCGGCGUGGCCGCCGCUGACCAGAGGCGGGACUUCAU<br>CGACAUCGAGAGCAAGUUCGCCCUGCGCACCCCAGAGGACACCGCCGAGGAU<br>ACCUGUCACCUCAUCCCCGGCGUCGCCGAGAGCGUGGCGACCUGCCACUUUA<br>ACCACAGCAGCAAGACCUUCAUGGUGAUCCACGGCUGGACCGUGACGGGCAU<br>GUACGAGUCCUGGGUGCCCAAACUGGUGGCGGCUCUGUACAAGAGGGAGCCC<br>GACAGUAACGUGAUUGUCGUGGACUGGCUGAGCCGCGCUCAAGAACACUAUC<br>CCGUAUCCGCCGGUUAACCAAGCUGGUGGGCCAGGACGUGGCGCGAUUCAU<br>UAACUGGAUGGAGGAGGAGUUUAAUUACCCCCUGGAUAACGUGCAUCUGCUG<br>GGGUAUAGCCUGGGCGCCCACGCCGCCGGCAUAGCCGGCUCCCUGACCAACA<br>AGAAGGUCAACCGAAUCACCGGCCUGGACCCCGCCGGCCCCAACUUUGAGUA |

TABLE 2-continued

Sequence optimized sequences for wild type human LPL

| SEQ ID NO | Name | Sequence |
|---|---|---|
| | | CGCCGAGGCCCCCAGCAGGCUGUCCCCCGAUGAUGCCGACUUCGUGGACGUG<br>CUGCAUACGUUCACCCGCGGGAGCCCCGGGAGGAGCAUCGGCAUACAGAAAC<br>CCGUGGGCCACGUGGACAUAUACCCCAACGGCGGAACGUUCCAGCCGGGGUG<br>CAACAUCGGCGAGGCCAUCCGGGUCAUCGCCGAGAGGGGGCUGGGCGAUGUG<br>GACCAACUGGUGAAGUGCUCCCAUGAACGGUCCAUCCAUGUGUUCAUCGACA<br>GCCUGCUGAACGAGGAGAACCCCAGCAAGGCCUACAGGUGUAGCAGCAAGGA<br>GGCCUUCGAGAAAGGCCUGUGUCUGAGCUGCAGAAAGAACAGGUGCAACAAC<br>CUCGGCUACGAGAUCAACAAGGUGAGGGCCAAGAGGUCCAGCAAAAUGUAUC<br>UGAAGACCAGGAGCCAGAUGCCAUACAAGGUCUUUCACUACCAGGUCAAGAU<br>CCAUUUCUCCGGCACCGAGUCCGAAACCCACACCAACCAGGCCUUCGAAAUC<br>AGCCUGUACGGCACCGUGGCCGAGAGCGAGAACAUCCCCUUCACCCUUCCCG<br>AGGUGUCCACCAACAAGACCUACAGCUUCCUCAUCUACACCGAGGUGGAUAU<br>CGGCGAGCUGCUGAUGCUGAAGCUGAAGUGGAAGAGCGACAGCUACUUCAGC<br>UGGUCGGACUGGUGGAGCUCCCCCGGCUUCGCGAUCCAGAAAAUCCGUGUGA<br>AAGCCGGGGAGACCCAGAAGAAGGUGAUAUUCUGCUCCCGGGAGAAGGUAAG<br>CCACCUGCAGAAGGGGAAGGCCCCCGCCGUGUUCGUUAAGUGCCACGACAAG<br>AGCCUAAACAAAAAGUCCGGC |
| 172 | LPL-CO24 | AUGGAGUCUAAAGCCCUGCUGGUGCUGACCCUCGCCGUGUGGCUGCAGUCGC<br>UGACCGCCUCCCGCGGCGGGGUGGCCGCAGCCGACCAGCGCCGGGACUUCAU<br>UGACAUCGAGAGCAAGUUCGCCCUGCGAACCCCCGAGGAUACCGCCGAGGAC<br>ACCUGCCACCUGAUCCCCGGAGUCGCCGAGAGCGUGGCCACCUGCCACUUUA<br>AUCAUAGCAGCAAGACCUUCAUGGUGAUCCACGGCUGGACGGUGACCGGGAU<br>GUACGAGAGCUGGGUCCCCAAGCUGGUGGCCGCCCUUUAUAAAAGGGAGCCC<br>GAUAGUAACGUGAUCGUGGUGGACUGGCUGUCCAGGGCCCAAGAGCACUACC<br>CCGUGUCCGCCGGCUACACCAAGCUGGUGGGCCAGGACGUGGCCAGGUUCAU<br>CAAUUGGAUGGAGGAGGAAUUUAAUUACCCCCUGGACAAUGUGCACCUCCUG<br>GGCUACUCGCUGGGCGCUCACGCCGCCGGCAUAGCCGGCAGCCUGACCAACA<br>AGAAAGUGAACAGGAUCACGGGCCUGGACCCCGCCGGCCCCAACUUCGAGUA<br>CGCCGAGGCCCCCAGCCGUCUGAGCCCCGACGACGCCGACUUUGUGGACGUGC<br>UGCACACCUUCACCAGGGGGAGUCCUGGGCGGAGCAUCGGCAUCCAAAAGCC<br>GGUGGGCCACGUGGACAUCUACCCGAACGGUGGUACGUUUCAGCCCGGGUGC<br>AACAUCGGGGAAGCCAUCAGGGUGAUCGCCGAGAGGGGGCUGGGCGACGUGG<br>ACCAGCUGGUGAAGUGCUCCCACGAGAGGUCCAUCCACCUGUUCAUCGACUC<br>CCUUCUCAACGAAGAAAACCCGAGCAAGGCCUACAGGUGUAGCAGCAAGGAA<br>GCCUUCGAGAAGGGGCUGUGCCUGUCCUGUAGGAAAAACAGGUGCAACAACC<br>UCGGCUACGAGAUCAACAAGGUGCGCGCUAAGCGCUCCAGCAAGAUGUACCU<br>GAAGACAAGGUCACAGAUGCCCUACAAGGUGUUCCACUACCAGGUGAAAAUC<br>CACUUUAGCGGCACCGAAAGCGAAACGCACACCAACCAGGCGUUUGAGAUCA<br>GCUUAUAUGGGACCGUGGCCGAGUCCGAGAACAUCCCCUUCACCCUGCCCGA<br>AGUGAGCACCAACAAGACCUAUACCUUCCUGAUCUAGACCGAGGUGGAUAUC<br>GGGGAGCUGCUGAUGCUCAAACUGAAAUGGAAGAGCGAUAGCUACUUCUCCU<br>GGAGCGAUUGGUGGAGCAGCCCCGGCUUCGCGAUCCAGAAGAUCCGCGUGAA<br>GGCGGGGGAGACCCAGAAGAAGGUGAUCUUUUGCAGCAGGGAGAAGGUGAG<br>CCACCUGCAGAAAGGCAAGGCCCCCGCGGUGUUUGUCAAGUGCCACGACAAG<br>AGCCUCAACAAGAAAUCCGGC |
| 173 | LPL-CO25 | AUGGAAUCGAAGGCCCUGCUGGUGCUGACGCUGGCGGUGUGGCUGCAGAGCC<br>UGACCGCCUCCCGCGGCGGCGUCGCCGCCGCCGACCAGAGGCGGGACUUCAUC<br>GAUAUCGAGAGCAAGUUCGCCCUGAGGACCCCCGAAGAUACCGCCGAAGACA<br>CGUGCCACCUGAUCCCGGGCGUGGCGGAGUCUGUGGCCACCUGCCACUUCAA<br>CCACAGCAGCAAGACCUUCAUGGUGAUCCACGGGUGGACCGUGACCGGCAUG<br>UACGAGAGCUGGGUGCCCAAGCUGGUCGCCGCGCUGUACAAAAGGGAGCCCG<br>ACAGCAACGUCAUCGUCGUGGACUGGCUGAGCAGGGCACAGGAGCAUUACCC<br>CGUCUCCGCCGGUTACACCAAACUGGUGGGGCAGGACGUGGCGAGGUUUAUC<br>AACUGGAUGGAGGAGGAGUUCAACUACCCCCUGGAUAACGUGGACCUGCUGG<br>GGUACAGCCUGGGGGCCCACGCCGCAGGCAUAGCCGGGAGCCUGACCAAUAA<br>GAAAGUAAACCGGAUCACGGGGCUGGACCCCGCCGGGCCCAAUUUUGAGUAU<br>GCCGAGGCCCCCAGCCGGCUGUCCCCCGACGACGCAGACUUCGUGGACGUGCU<br>GCACACCUUCACCCGAGGCAGCCCGGGAAGAAGCAUCGGCAUCCAGAAGCCC<br>GUGGGCCACGUGGACAUCUACCCCAACGGAGGCACCUUCCAGCCAGGCUGUA<br>ACAUCGGCGAGGCCAUCAGGGUGAUCGCCGAACGCGGCCUGGGCGACGUGGA<br>CCAACUCGUGAAGUGCUCCCACGAGCGCAGCAUCCACCUCUUCAUCGACAGCC<br>UGCUGAAUGAGGAGAAUCCCAGCAAGGCAUAUAGGUGCAGCAGCAAGGAGGC<br>CUUUGAGAAGGGCCUGUGCCUGUCAUGCCGGAAGAACAGGUGCAACAACCUG<br>GGCUACGAGAUCAACAAGGUCAGGGCCAAACGCAGCUCCAAGAUGUACCUGA<br>AGACCCGGAGCCAAAUGCCCUACAAGGUGUUUCACUACCAGGUGAAGAUCCA<br>UUUUUCCGGCACGGAGAGUGAAACCCACACCAACCAGGCCUUCGAGAUAAGC<br>CUGUACGGCACCGUGGCCGAGAGCGAGAACAUCCCCUUCACCCUGCCCGAGG<br>UGAGCACGAAUAAGACCUACAGCUUCCUGAUCUACACGGAGGUGGACAUCGG<br>CGAGCUGCUGAUGCUGAAGCUGAAAUGGAAAUCCGACAGCUACUUCAGCUGG |

TABLE 2-continued

Sequence optimized sequences for wild type human LPL

| SEQ ID NO | Name | Sequence |
|---|---|---|
| | | UCCGACUGGUGGAGCUCCCCCGGCUUCGCCAUCCAGAAGAUCAGGGUGAAGG<br>CCGGGGAGACCCAGAAAAAGGUGAUCUUCUGCAGCAGGGAGAAAGUCAGCCA<br>UCUGCAGAAGGGGAAGGCCCCCGCGGUCUUCGUGAAGUGCCACGACAAGAGC<br>CUGAACAAGAAGAGCGGC |
| 174 | LPL-CO26 | AUGGAAAGCAAGGCCCUGCUGGUCCUGACCCUCGCCGUGUGGCUCCAGAGCC<br>UGACCGCCAGCCGGGGCGGGGUGGCCGCCGCCGACCAGCGACGGGACUUCAU<br>AGACAUCGAGAGCAAGUUUGCCCUGCGCACGCCCGAGGACACGGCCGAGGAC<br>ACCUGCCAUCUGAUCCCCGGCGUGGCCGAGAGCGUCGCCACCUGCCACUUUA<br>ACCACAGCAGCAAAACCUUCAUGGUGAUCCACGGAUGGACCGUGACCGGAAU<br>GUACGAGAGCUGGGUACCAAAGCUGGUCGCCGCCCUGUACAAAAGGGAACCC<br>GAUAGCAACGUGAUCGUGGUGGACUGGCUCUCCAGGGCCCAAGAGCACUACC<br>CCGUCAGCGCCGGCUACACCAAGCUGGUGGGACAGGACGUGGCCCGUUUCAU<br>CAAUUGGAUGGAGGAGGAGUUCAAUUACCCCCUGGACAACGUGCACCUGCUG<br>GGCUACUCCCUGGGAGCCCACGCCGCCGGGAUAGCCGGCUCCCUCACCAACAA<br>GAAGGUCAACCGGAUCACUGGCCUCGAUCCCGCCGGACCCAACUUUGAGUAC<br>GCCGAAGCCCCCUCGAGGCUGAGCCCCGACGACGCCGAUUUUGUGGACGUCC<br>UCCACACCUUCACCCGCGGGUCCCCCGGCAGGAGCAUCGGCAUCCAGAAGCCC<br>GUGGGCCACGUGGACAUCUAUCCCAACGGCGGCACCUUCCAGCCCGGCUGUA<br>ACAUCGGCGAAGCCAUCCGGGUGAUCGCCGAACGGGGCCUGGGCGAUGUGGA<br>CCAGCUGGUGAAAUGUAGCCACGAGAGGAGCAUCCACCUGUUUAUCGAUAGC<br>UUGCUGAACGAGGAGAACCCAUCCAAAGCGUACAGGUGCAGCUCCAAGGAGG<br>CCUUCGAAAAGGGCCUGUGCCUCUCCUGCAGGAAGAACCGGUGCAACAACCU<br>GGGGUAUGAGAUCAACAAAGUAAGGGCGAAGAGGAGCUCCAAGAUGUACCU<br>GAAGACUAGGAGCCAGAUGCCCUACAAGGUGUUCCACUAUCAGGUGAAAAUC<br>CACUUCAGCGGCACAGAAAGCGAGACCCACACCAACCAGGCCUUCGAGAUCU<br>CUCUGUAUGGCACCGUGGCCGAGAGCGAGAACAUACCCUUCACCCUGCCCGA<br>AGUGAGCACCAACAAAACCUACAGCUUCCUGAUCUACACCGAGGUGGACAUC<br>GGCGAGCUCCUCAUGCUCAAGCUGAAGUGGAAGUCCGACAGCUACUUCUCGU<br>GGAGCGACUGGUGGUCGAGCCCCGGCUUCGCCAUCCAGAAGAUCCGGGUGAA<br>AGCCGGCGAGACCCAGAAGAAGGUCAUCUUUUGCAGCAGGGAGAAGGUGAGC<br>CAUCUCCAGAAGGGCAAAGCUCCAGCCGUGUUCGUCAAGUGCCACGACAAGU<br>CCCUGAACAAGAAGAGCGGC |
| 175 | LPL-CO27 | AUGGAGUCCAAAGCGCUUCUGGUGCUCACCCUGGCGGUGUGGCUGCAGAGCC<br>UGACCGCCUCCAGAGGCGGCGUGGCCGCCGCCGACCAGCGGAGGGACUUCAU<br>CGACAUCGAGAGCAAGUUCGCACUCAGGACCCCGGAGGAUACCGCCGAGGAC<br>ACCUGCCACCUGAUCCCCGGUGUGGCCGAGUCAGUGGCCACCUGUCAUUUCA<br>ACCACAGCAGCAAGACCUUCAUGGUGAUCCACGGCUGGACCGUCACCGGCAU<br>GUACGAGAGCUGGGUGCCCAAGCUCGUCGCGGCGCUCUACAAGCGGGAGCCA<br>GACAGCAAUGUGAUCGUGGUGGACUGGCUCAGCCGGGCCCAGGAGCACUACC<br>CGGUGUCCGCCGGGUACACGAAGCUGGUGGGCCAGGACGUCGCCCGCUUUAU<br>AAACUGGAUGGAGGAAGAGUUCAACUACCCCCUGGACAACGUGCACCUGCUC<br>GGUUACAGCCUCGGGGCCCACGCCGCCGGAAUCGCGGGUUCCCUCACCAACA<br>AGAAGGUGAAUAGGAUCACCGGGCUGGACCCCGCCGGCCCCAAUUUCGAGUA<br>CGCCGAGGCCCCCUCGCGGCUGAGCCCCGACGACGCCGACUUUGUGGACGUGC<br>UGCACACCUUCACCCGGGGCAGCCCUGGGAGAUCCAUCGGCAUACAGAAGCC<br>CGUCGGCCACGUGGACAUCUACCCCAACGGGGGACCUUUCAGCCCGGGUGC<br>AAUAUCGGGGAAGCCAUUAGGGUGAUCGCCGAGAGGGGUCUGGGGGACGUCG<br>ACCAGCUCGUGAAAUGUUCCCACGAGAGGAGCAUCCACCUGUUCAUAGACAG<br>CCUGCUGAAUGAGGAGAACCCCUCCAAAGCCUACCGCUGCAGCAGCAAGGAG<br>GCCUUCGAAAAGGGGCUGUGCCUGAGCUGCAGGAAGAAUAGGUGUAACAAUC<br>UGGGCUACGAGAUCAACAAGGUGCGGGCGAAGAGGUCCUCUAAGAUGUAUCU<br>UAAGACCCGAAGCCAAAUGCCCUAUAAGGUGUUCCACUACCAAGUGAAGAUC<br>CAUUUUUCCGGGACCGAGAGCGAGACCCAUACCAACCAGGCCUUCGAGAUCU<br>CCCUGUACGGGACAGUGGCCGAGUCCGAAAACAUCCCCUUCACCCUGCCCGA<br>AGUGAGCACCAACAAGACCUACUCCUUUCUGAUCUACACCGAGGUGGACAUC<br>GGCGAGCUGCUGAUGCUGAAGCUGAAGUGGAAGAGCGAUAGCUACUUCAGCU<br>GGUCAGACUGGUGGAGCAGCCCCGGCUUCGCAAUCCAGAAGAUCAGGGUGAA<br>GGCCGGCGAGACGCAGAAGAAAGUGAUCUUCUGCAGCAGGGAGAAGGUAAGC<br>CAUCUCCAGAAGGGCAAAGCCCCCGCCGUGUUCGUGAAGUGUCACGACAAGC<br>CCCUGAACAAAAAAAGCGGU |
| 176 | LPL-CO28 | AUGGAAAGCAAAGCCCUGCUGGUACUCACGCUCGCCGUCUGGCUGCAGUCCC<br>UGACCGCCAGCAGAGGCGGCGUCGCGGCCGCCGAUCAGAGAAGAGACUUCAU<br>CGACAUCGAAAGCAAGUUCGCGCUGAGGACCCCGGAAGACACCGCCGAGGAC<br>ACGUGCCACCUGAUCCCCGGCGUGGCCGAGAGCGUGGCCACGUGUCACUUCA<br>ACCACUCCUCCAAGACCUUCTAUGGUGAUCCACGGCUGGACGUTGACCGGAAU<br>GUACGAGAGCUGGGUGCCGAAGCUGGUGGCCGCCCUGUACAAGCGGGAGCCG<br>GACAGCAACGUGAUCGUAGUGGACUGGCUGAGCAGGGCCCAGGAGCAUUAUC<br>CCGUGAGCGCCGGCUACACUAAGCUGGUGGGCCAGGACGUGGCCCGGUUCAU<br>AAACUGGAUGGAGGAAGAGUUCAACUACCCACUGGACAAUGUCCACCUCCUG<br>GGCUACAGCCUGGGCGCCCACGCCGCCGGCAUCGCCGGGUCCCUCACCAACAA<br>GAAGGUCAACCGGAUCACAGGCCUCGACCCCGCCGGCCCCAACUUUGAGUAC |

TABLE 2-continued

| Sequence optimized sequences for wild type human LPL | | |
|---|---|---|
| SEQ ID NO | Name | Sequence |
| | | GCCGAGGCCCCCUCAAGGCUGAGCCCCGACGACGCCGACUUCGUAGACGUGC<br>UGCACACCUUUACUCGCGGCAGCCCGGGUAGGUCGAUCGGGAUCCAGAAGCC<br>UGUCGGCCAUGUGGACAUCUACCCCAACGGCGGCACCUUCCAACCCGGAUGU<br>AACAUCGGCGAGGCCAUCCGGGUGAUCGCCGAACGCGGGCUGGGAGACGUGG<br>ACCAACUGGUGAAGUGCAGCCACGAGAGGAGCAUCCACCUGUUCAUCGACAG<br>CCUGCUGAACGAGGAGAACCCCAGCAAAGCCUAUAGGUGCAGCAGCAAGGAG<br>GCCUUCGAAAAAGGCCUCUGCCUGUCCUGCAGGAAAAACCGUUGCAACAACC<br>UGGGCUACGAAAUCAACAAGGUGCGAGCCAAAAGGAGCAGCAAGAUGUACCU<br>GAAGACCAGGUCCCAGAUGCCGUAUAAGGUGUUCCACUACCAGGUGAAGAUC<br>CAUUUCUCCGGAACCGAGUCGGAAACCCACACUAACCAGGCCUUCGAGAUCA<br>GCCUGUACGGCACGGUCGCCGAGUCCGAAAAUAUCCCCUUCACCCUCCCCGAA<br>GUGUCCACCAACAAGACAUACAGCUUCCUGAUCUACACCGAGGUGGACAUCG<br>GAGAGCUGCUGAUGCUCAAGCUGAAGUGGAAGAGCGACAGCUACUUCAGCUG<br>GAGCGACUGGUGGUCCUCGCCGGGCUUCGCCAUCCAAAAGAUCCGCGUCAAG<br>GCCGGGGAGACCCAGAAGAAGGUCAUCUUCUGUUCCAGGGAGAAGGUGAGCC<br>ACCUCCAGAAGGGCAAGGCCCCCGCCGUGUUCGUGAAGUGCCAUGACAAGAG<br>CCUGAACAAGAAGAGCGGC |
| 177 | LPL-CO29 | AUGGAGAGCAAGGCCCUGCUGGUGCUGACCCUGGCCGUGUGGCUGCAGUCAC<br>UCACCGCAUCCAGGGGGGGAGUGGCCGCCGCCGACCAGAGGCGGGACUUCAU<br>CGAUAUCGAGAGCAAGUUCGCCCUCCGGACCCCCGAGGACACAGCCGAGGAC<br>ACCUGCCACCUGAUCCCCGGGGUGGCCGAGUCAGUGGCGACCUGCCAUUUCA<br>ACCACUCCAGCAAGACCUUUAUGGUCAUCCACGGCUGGACCGUGACCGGCAU<br>GUACGAGUCCUGGGUCCCCAAGCUGGUGGCCGCGCUGUAUAAGCGGGAACCC<br>GACUCCAAUGUGAUCGUCGUGGAUUGGCUGAGCCGUGCCCAGGAGCAUUACC<br>CCGUGAGCGCCGGCUACACCAAGUUGGUGGGACAGGACGUGGCCAGGUUCAU<br>CAACUGGAUGGAGGAGGAGUUCAACUACCCCCUGGAUAACGUGCACCUCCUG<br>GGCUACUCCCUGGGGGCGCAUGCCGCGGGCAUCGCCGGGAGCCUGACCAACA<br>AGAAGGUGAAUAGGAUCACCGGCCUGGAUCCCGCCGGCCCGAACUUCGAGUA<br>CGCCGAGGCCCCCAGCAGGCUGAGCCCGGACGACGCCGACUUCGUGGACGUCC<br>UCCACACCUUCACCAGGGGGAGCCCCGGGAGGAGCAUUGGAAUCCAGAAGCC<br>CGUGGGCCACGUGGACAUCUAUCCCAAUGGCGGGACGUUCCAACCUGGCUGC<br>AACAUCGGUGAAGCCAUCCGCGUGAUCGCCGAGCGCGGCCUGGGCGACGUGG<br>ACCAGCUGGUGAAGUGCAGUCACGAGAGGAGCAUCCACCUGUUCAUCGAUAG<br>CCUGCUGAACGAGGAGAACCCCAGCAAGGCCUACAGGUGCUCCAGCAAGGAG<br>GCCUUCGAGAAGGGCCUCUGCCUGAGCUGCCGCAAGAACCGGUGCAACAACC<br>UCGGGUACGAAAUCAAUAAGGUGCGGGCCAAGAGGUCCAGCAAGAUGUAUCU<br>GAAGACCCGGAGCCAGAUGCCCUACAAGGUGUUCCACUACCAAGUGAAGAUC<br>CACUUUUCGGGUACGGAGUCCGAGACGCACACCAACCAGGCCUUUGAAAUCA<br>GCCUCUACGGCACCGUGGCCGAAAGCGAGAACAUCCCCUUUACCCUGCCCGA<br>GGUCAGCACCAACAAGACCUAUUCCUUCCUGAUCUACACCGAGGUGGACAUC<br>GGCGAACUCCUGAUGCUGAAGCUGAAGUGGAAGUCCGACAGCUACUUUUCCU<br>GGAGCGACUGGUGGUCCAGCCCCGGGUUCGCCAUACAGAAGAUCCGGGUGAA<br>GGCAGGGGAGACGCAGAAAAAGGUCAUCUUCUGCAGCCGUGAAAAGGUGAGU<br>CACCUCCAAAAGGGCAAGGCGCCCGCCGUGUUCGUAAAGUGCCACGAUAAGA<br>GCCUGAACAAAAAAAGCGGC |
| 178 | LPL-CO30 | AUGGAGAGCAAGGCCCUGCUGGUGCUGACCCUGGCCGUGUGGCUGCAGAGCC<br>UGACCGCCAGCCGGGGAGGCGUGGCCGCCGCCGACCAGCGGCGGGACUUCAU<br>CGACAUCGAGUCCAAGUUCGCCCUGCGGACGCCCGAGGACACCGCCGAAGAC<br>ACCUGCCACCUGAUCCCCGGCGUCGCCGAGAGCGUGGCCACAUGCCACUUCAA<br>CCACAGCAGCAAGACCUUCAUGGUGAUCCACGGCUGGACCGUGACCGGCAUG<br>UACGAGAGCUGGGUGCCCAACCUGGUGGCCGCUCUGUACAAGCGGGAGCCCG<br>ACAGCAACGUGAUCGUGGUGGACUGGCUGAGCCGGGCCCAGGAGCACUACCC<br>CGUGAGCGCCGGCUACACCAAGCUCGUCGGCCAGGACGUGGCCCGGUUCAUC<br>AACUGGAUGGAGGAGGAGUUCAACUACCCGCUGGACAACGUGCACCUGCUGG<br>GCUACAGCCUGGGCGCCCACGCCGCCGGCAUCGCCGGCAGCCUCACCAACAAG<br>AAGGUGAACCGGAUCACCGGCCUGGACCCCGCCGGCCCCAACUUCGAGUACG<br>CCGAGGCGCCCAGCAGGCUCUCCUCCCGACGACGCCGACUUCGUGGACGUGCU<br>GCACACCUUCACCCGGGGCUCUCCCGGACGGAGCAUCGGCAUCCAGAAGCCCG<br>UGGGCCACGUGGACAUCUACCCCAACGGCGGCACCUUCCAGCCCGGCUGCAAC<br>AUCGGCGAGGCCAUCCGGGUGAUCGCCGAGCGGGGUCUGGGCGACGUGGACC<br>AGCUGGUGAAGUGCAGCCACGAGCGGAGCAUUCACCUGUUCAUCGAUAGCCU<br>GCUGAACGAGGAGAACCCCUCCAAAGCAUACCGGUGCAGUAGUAAGGAGGCC<br>UUCGAGAAGGGCCUGUGCCUGAGCUGCCGGAAGAACAGAUGCAACAACCUUG<br>GGUACGAGAUCAACAAGGUGCGGGCCAAGAGAUCUUCCAAGAUGUACCUGAA<br>GACCCGGAGCCAGAUGCCCUACAAGGUGUUCCACUACCAGGUGAAGAUCCAC<br>UUCAGCGGCACCGAAAGCGAAACUCACACCAACCAGGCCUUUGAAAUCAGCC<br>UGUACGGCACCGUGGCCGAGUCUGAGAACAUCCCUUUCACACUGCCCGAGGU<br>GAGCACUAACAAGACCUACAGCUUCCUGAUCUACACCGAGGUGGACAUUGGC |

TABLE 2-continued

Sequence optimized sequences for wild type human LPL

| SEQ ID NO | Name | Sequence |
|---|---|---|
| | | GAGCUGCUGAUGCUGAAGCUGAAGUGGAAGUCAGACAGCUACUUCAGCUGGA<br>GCGACUGGUGGUCUAGCCCCGGAUUCGCCAUCCAGAAGAUCAGGGUGAAGGC<br>CGGAGAGACACAGAAGAAAGUGAUCUUCUGCAGCCGGGAGAAGGUAAGCCAC<br>CUGCAGAAGGGCAAGGCUCCCGCCGUGUUCGUCAAGUGCCACGACAAGUCCC<br>UGAACAAGAAGUCCGGC |
| 179 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACCCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCVCCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCCCCCAGCAGGCUCUCCCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAAAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCUAGCUUCUUGCCC<br>CUUGGGCCUCCCCCCAGCCCCUCCUCCCCUUCCUGCACCCGUACCCCCUCCAU<br>AAAGUAGGAAACACUACAGUGGUCUUUGAAUAAAGUCUGAGUGGGCGGC |
| 180 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACCCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCCCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCCCCCAGCAGGCUCUCCCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAAAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCUAGCUUCUUGCCC<br>CUUGGGCCUCCCCCCAGCCCCUCCUCCCCUUCCUGCACCCGUACCCCCCGCAU<br>UAUUACUCACGGUACGAGUGGUCUUUGAAUAAAGUCUGAGUGGGCGGC |
| 181 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACCCCCGAGGACACCGCCGAAGACACCU |

TABLE 2-continued

Sequence optimized sequences for wild type human LPL

| SEQ ID NO | Name | Sequence |
|---|---|---|
| | | GCCACCUGAUCCCCGGCGUCGCCGAGAGCGUGGCCACAUGCCACUUCAACCAC AGCAGCAAGACCUUCAUGGUGAUCCACGGCUGGACCGUGACCGGCAUGUACG AGAGCUGGGUGCCCAAGCUGGUGGCCGCUCUGUACAAGCGGGAGCCCGACAG CAACGUGAUCGUGGUGGACUGGCUGAGCCGGGCCCAGGAGCACUACCCCGUG AGCGCCGGCUACACCAAGCUCGUCGGCCAGGACGUGGCCCGGUUCAUCAACU GGAUGGAGGAGGAGUUCAACUACCCCCUGGACAACGUGCACCUGCUGGGCUA CAGCCUGGGCGCCCACGCCGCCGGCAUCGCCGGCAGCCUCACCAACAAGAAGG UGAACCGGAUCACCGGCCUGGACCCCGCCGGCCCCAACUUCGAGUACGCCGAG GCCCCCAGCAGGCUCUCCCCCGACGACGCCGACUUCGUGGACGUGCUGCACAC CUUCACCCGGGGCUCUCCCGGACGGAGCAUCGGCAUCCAGAAGCCCGUGGGC CACGUGGACAUCUACCCCAACGGCGGCACCUUCCAGCCCGGCUGCAACAUCGG CGAGGCCAUCCGGGUGAUCGCCGAGCGGGGUCUGGGCGACGUGGACCAGCUG GUGAAGUGCAGCCACGAGCGGAGCAUUCACCUGUUCAUCGAUAGCCUGCUGA ACGAGGAGAACCCCUCCAAAGCAUACCGGUGCAGUAGUAAGGAGGCCUUCGA GAAGGGCCUGUGCCUGACCUGCCGGAAGAACAGAUGCAACAACCUUGGGUAC GAGAUCAACAAGGUGCGGGCCAAGAGAUCUUCCAAGAUGUACCUGAAGACCC GGAGCCAGAUGCCCUACAAGGUGUUCCACUACCAGGUGAAGAUCCACUUCAG CGGCACCGAAAGCGAAACUCACACCAACCAGGCCUUUGAAAUCAGCCUGUAC GGCACCGUGGCCGAGUCUGAGAACAUCCCUUUCACACUGCCCGAGGUGAGCA CUAACAAGACCUACAGCUUCCUGAUCUACACCGAGGUGGACAUUGGCGAGCU GCUGAUGCUGAAGCUGAAGUGGAAGUCAGACAGCUACUUCAGCUGGAGCGAC UGGUGGUCUAGCCCCGGAUUCGCCAUCCAAAAGAUCAGGGUGAAGGCCGGAG AGACACAGAAGAAAGUGAUCUUCUGCAGCCGGGAGAAGGUAAGCCACCUGCA GAAGGGCAAGGCUCCCGCCGUGUUCGUCAAGUGCCACGACAAGUCCCUGAAC AAGAAGUCCGGCUGAUAAUAGGCUGGAGCCUCGGUGGCCUAGCUUCUUGCCC CUUGGGCCUCCCCCCAGCCCCUCCUCCCCUUCCUGCACCCGUACCCCCGUGGU CUUUGAAUAAAGUCUGAGUGGGCGGC |
| 182 | | GGGAAAUAAGAGAGAAAAGAAGAGUAAGAAGAAAUAUAAGAGCCACCAUGG AGAGCAAGGCCCUGCUGGUGCUGACCCUGGCCGUGUGGCUGCAGAGCCUGAC CGCCAGCCGGGGAGGCGUGGCCGCCGCCGACCAGCGGCGGGACUUCAUCGAC AUCGAGUCCAAGUUCGCCCUGCGGACCCCCGAGGACACCGCCGAAGACACCU GCCACCUGAUCCCCGGCGUCGCCGAGAGCGUGGCCACAUGCCACUUCAACCAC AGCAGCAAGACCUUCAUGGUGAUCCACGGCUGGACCGUGACCGGCAUGUACG AGAGCUGGGUGCCCAAGCUGGUGGCCGCUCUGUACAAGCGGGAGCCCGACAG CAACGUGAUCGUGGUGGACUGGCUGAGCCGGGCCCAGGAGCACUACCCCGUG AGCGCCGGCUACACCAAGCUCGUCGGCCAGGACGUGGCCCGGUUCAUCAACU GGAUGGAGGAGGAGUUCAACUACCCCCUGGACAACGUGCACCUGCUGGGCUA CAGCCUGGGCGCCCACGCCGCCGGCAUCGCCGGCAGCCUCACCAACAAGAAGG UGAACCGGAUCACCGGCCUGGACCCCGCCGGCCCCAACUUCGAGUACGCCGAG GCCCCCAGCAGGCUCUCCCCCGACGACGCCGACUUCGUGGACGUGCUGCACAC CUUCACCCGGGGCUCUCCCGGACGGAGCAUCGGCAUCCAGAAGCCCGUGGGC CACGUGGACAUCUACCCCAACGGCGGCACCUUCCAGCCCGGCUGCAACAUCGG CGAGGCCAUCCGGGUGAUCGCCGAGCGGGGUCUGGGCGACGUGGACCAGCUG GUGAAGUGCAGCCACGAGCGGAGCAUUCACCUGUUCAUCGAUAGCCUGCUGA ACGAGGAGAACCCCUCCAAAGCAUACCGGUGCAGUAGUAAGGAGGCCUUCGA GAAGGGCCUGUGCCUGAGCUGCCGGAAGAACAGAUGCAACAACCUUGGGUAC GAGAUCAACAAGGUGCGGGCCAAGAGAUCUUCCAAGAUGUACCUGAAGACCC GGAGCCAGAUGCCCUACAAGGUGUUCCACUACCAGGUGAAGAUCCACUUCAG CGGCACCGAAAGCGAAACUCACACCAACCAGGCCUUUGAAAUCAGCCUCUAC GGCACCGUGGCCGAGUCUGAGAACAUCCCUUUCACACUGCCCGAGGUGAGCA CUAACAAGACCUAUAGCUUCCUGAUCUACACCGAGGUGGACAUUGGCGAGCU GCUGAUGCUGAAGCUGAAGUGGAAGUCAGACAGCUACUUCAGCUGGAGCGAC UGGUGGUCUAGCCCCGGAUUCGCCAUCCAAAAGAUCAGGGUGAAGGCCGGAG AGACACAGAAGAAAGUGAUCUUCUGCAGCCGGGAGAAGGUAAGCCACCUGCA GAAGGGCAAGGCUCCCGCCGUGUUCGUCAAGUGCCACGACAAGUCCCUGAAC AAGAAGUCCGGCGCUGGAGCCUCGGUGGCCAUGCUUCUUGCCCCUUGGGCCU CCCCCGAGCCCCUCCUCCCCUUCCUGCACCCGUACCCCCUCCAUAAAGUAGGA AACACUACAGUGGUCUUUGAAUAAAGUCUGAGUGGGCGGC |
| 183 | | GGGAAAUAAGAGAGAAAAGAAGAGUAAGAAGAAAUAUAAGAGCCACCAUGG AGAGCAAGGCCCUGCUGGUGCUGACCCUGGCCGUGUGGCUGCAGAGCCUGAC CGCCAGCCGGGGAGGCGUGGCCGCCGCCGACCAGCGGCGGGACUUCAUCGAC AUCGAGUCCAAGUUCGCCCUGCGGACCCCCGAGGACACCGCCGAAGACACCU GCCACCUGAUCCCCGGCGUCGCCGAGAGCGUGGCCACAUGCCACUUCAACCAC AGCAGCAAGACCUUCAUGGUGAUCCACGGCUGGACCGUGACCGGCAUGUACG AGAGCUGGGUGCCCAAGCUGGUGGCCGCUCUGUACAAGCGGGAGCCCGACAG CAACGUGAUCGUGGUGGACUGGCUGAGCCGGGCCCAGGAGCACUACCCCGUG AGCGCCGGCUACACCAAGCUCGUCGGCCAGGACGUGGCCCGGUUCAUCAACU GGAUGGAGGAGGAGUUCAACUACCCCCUGGACAACGUGCACCUGCUGGGCUA CAGCCUGGGCGCCCACGCCGCCGGCAUCGCCGGCAGCCUCACCAACAAGAAGG UGAACCGGAUCACCGGCCUGGACCCCGCCGGCCCCAACUUCGAGUACGCCGAG GCCCCCAGCAGGCUCUCCCCCGACGACGCCGACUUCGUGGACGUGCUGCACAC CUUCACCCGGGGCUCUCCCGGACGGAGCAUCGGCAUCCAGAAGCCCGUGGGC |

TABLE 2-continued

Sequence optimized sequences for wild type human LPL

| SEQ ID NO | Name | Sequence |
|---|---|---|
| | | CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGACCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAAAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCAUGCUUCUUGCCC<br>CUUGGGCCUCCCCCCAGCCCCUCCUCCCCUUCCUGCACCCGUACCCCCGCAU<br>UAUUACUCACGGUACGAGUGGUCUUUGAAUAAAGUCUGAGUGGGCGGC |
| 184 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACCCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAAGUACCCCCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCCCCCAGCAGGCUCUCCCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUCUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGANACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGNAGCUGAAGUGGAAGUCAGACAGCUACUUCAGCUGGAGCGAC<br>UGGUGGUCUAGCCCCGGAUUCGCCAUCCAAAAGAUCAGGGUGAAGGCCGGAG<br>AGACACAGAAGAAAGUGAUCUUCUGCAGCCGGGAGAAGGUAAGCCACCUGCA<br>GAAGGGCNAGGCUCCCGCCGUGUUCGUCAAGUGCCACGACAAGUCCCUGAAC<br>AAGAAGUCCGGCUGAUAAUAGGCUGGAGCCUCGGUGGCCAUGCUUCUUGCCC<br>CUUGGGCCUCCCCCCAGCCCCUCCUCCCCUUCCUGCACCCGUACCCCCGUGGU<br>CUUUGAAUAAAGUCUGAGUGGGCGGC |
| 185 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGCCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU |

TABLE 2-continued

Sequence optimized sequences for wild type human LPL

| SEQ ID NO | Name | Sequence |
|---|---|---|
| | | GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCUAGCUUCUUGCCC<br>CUUGGGCCUCCCCCCAGCCCCUCCUCCCCUUCCUGCACCCGUACCCCCUCCAU<br>AAAGUAGGAAACACUACAGUGGUCUUUGAAUAAAGUCUGAGUGGGCGGC |
| 186 | | GGGAAAUAAGAGAGAAAAGAAGAGUAAGAAGAAAUAUNAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCUAGCUUCUUGCCC<br>CUUGGGCCUCCCCCCAGCCCCUCCUCCCCUUCCUGCACCCGUACCCCCGCAU<br>UAUUACUCACGGUACGAGUGGUCUUUGAAUAAAGUCUGAGUGGGCGGC |
| 187 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCUAGCUUCUUGCCC<br>CUUGGGCCUCCCCCCAGCCCCUCCUCCCCUUCCUGCACCCGUACCCCCGUGGU<br>CUUUGAAUAAAGUCUGAGUGGGCGGC |
| 188 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC |

TABLE 2-continued

Sequence optimized sequences for wild type human LPL

| SEQ ID NO | Name | Sequence |
|---|---|---|
| | | CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCGCUGGAGCCUCGGUGGCCAUGCUUCUUGCCCCUUGGGCCU<br>CCCCCCAGCCCCUCCUCCCCAUUCCUGCACCCGUACCCCCUCCAUAAAGUAGGA<br>AACACUACAGUGGUCUUUGAAUAAAGUCUGAGUGGGCGGC |
| 189 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG<br>GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCAUGCUUCUUGCCC<br>CUUGGGCCUCCCCCCAGCCCCUCCUCCCCUUCCUGCACCCGUACCCCCCGCAU<br>UAUUACUCACGGUACGAGUGGUCUUUGAAUAAAGUCUGAGUGGGCGGC |
| 190 | | GGGAAAUAAGAGAGAAAAGAAGAGUAAGAAGAAAUAUAAGAGCCACCAUGG<br>AGAGCAAGGCCCUGCUGGUGCUGACCCUGGCCGUGUGGCUGCAGAGCCUGAC<br>CGCCAGCCGGGGAGGCGUGGCCGCCGCCGACCAGCGGCGGGACUUCAUCGAC<br>AUCGAGUCCAAGUUCGCCCUGCGGACGCCCGAGGACACCGCCGAAGACACCU<br>GCCACCUGAUCCCCGGCGUCGCCGAGAGCGUGGCCACAUGCCACUUCAACCAC<br>AGCAGCAAGACCUUCAUGGUGAUCCACGGCUGGACCGUGACCGGCAUGUACG<br>AGAGCUGGGUGCCCAAGCUGGUGGCCGCUCUGUACAAGCGGGAGCCCGACAG<br>CAACGUGAUCGUGGUGGACUGGCUGAGCCGGGCCCAGGAGCACUACCCCGUG<br>AGCGCCGGCUACACCAAGCUCGUCGGCCAGGACGUGGCCCGGUUCAUCAACU<br>GGAUGGAGGAGGAGUUCAACUACCCGCUGGACAACGUGCACCUGCUGGGCUA<br>CAGCCUGGGCGCCCACGCCGCCGGCAUCGCCGGCAGCCUCACCAACAAGAAGG<br>UGAACCGGAUCACCGGCCUGGACCCCGCCGGCCCCAACUUCGAGUACGCCGAG |

TABLE 2-continued

Sequence optimized sequences for wild type human LPL

| SEQ ID NO | Name | Sequence |
|---|---|---|
| | | GCGCCCAGCAGGCUCUCGCCCGACGACGCCGACUUCGUGGACGUGCUGCACAC<br>CUUCACCCGGGGCUCUCCCGGACGGAGCAUCGGCAUCCAGAAGCCCGUGGGC<br>CACGUGGACAUCUACCCCAACGGCGGCACCUUCCAGCCCGGCUGCAACAUCGG<br>CGAGGCCAUCCGGGUGAUCGCCGAGCGGGGUCUGGGCGACGUGGACCAGCUG<br>GUGAAGUGCAGCCACGAGCGGAGCAUUCACCUGUUCAUCGAUAGCCUGCUGA<br>ACGAGGAGAACCCCUCCAAAGCAUACCGGUGCAGUAGUAAGGAGGCCUUCGA<br>GAAGGGCCUGUGCCUGAGCUGCCGGAAGAACAGAUGCAACAACCUUGGGUAC<br>GAGAUCAACAAGGUGCGGGCCAAGAGAUCUUCCAAGAUGUACCUGAAGACCC<br>GGAGCCAGAUGCCCUACAAGGUGUUCCACUACCAGGUGAAGAUCCACUUCAG<br>CGGCACCGAAAGCGAAACUCACACCAACCAGGCCUUUGAAAUCAGCCUGUAC<br>GGCACCGUGGCCGAGUCUGAGAACAUCCCUUUCACACUGCCCGAGGUGAGCA<br>CUAACAAGACCUACAGCUUCCUGAUCUACACCGAGGUGGACAUUGGCGAGCU<br>GCUGAUGCUGAAGCUGAAGUGGAAGUCAGACAGCUACUUCAGCUGGAGCGAC<br>UGGUGGUCUAGCCCCGGAUUCGCCAUCCAGAAGAUCAGGGUGAAGGCCGGAG<br>AGACACAGAAGAAAGUGAUCUUCUGCAGCCGGGAGAAGGUAAGCCACCUGCA<br>GAAGGGCAAGGCUCCCGCCGUGUUCGUCAAGUGCCACGACAAGUCCCUGAAC<br>AAGAAGUCCGGCUGAUAAUAGGCUGGAGCCUCGGUGGCCAUGCUUCUUGCCC<br>CUUGGGCCUCCCCCCAGCCCCUCCUCCCCUUCCUGCACCCGUACCCCCGUGGU<br>CUUUGAAUAAAGUCUGAGUGGGCGGC |

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a LPL polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type LPL is about 23.23%. The uracil or thymine content of a sequence disclosed herein, i.e., its total uracil or thymine content is abbreviated herein as % $U_{TL}$ or % $T_{TL}$.

A uracil- or thymine-modified sequence encoding a LPL polypeptide of the invention can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or (% $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

In some embodiments, the % $U_{TM}$ of a uracil-modified sequence encoding a LPL polypeptide of the invention is below 300%, below 295%, below 290%, below 285%, below 280%, below 275%, below 270%, below 265%, below 260%, below 255%, below 250%, below 245%, below 240%, below 235%, below 230%, below 225%, below 220%, below 215%, below 200%, below 195%, below 190%, below 185%, below 180%, below 175%, below 170%, below 165%, below 160%, below 155%, below 150%, below 145%, below 140%, below 139%, below 138%, below 137%, below 136%, below 135%, below 134%, below 133%, below 132%, below 131%, below 130%, below 129%, below 128%, below 127%, below 126%, below 125%, below 124%, below 123%, below 122%, below 121%, below 120%, below 119%, below 118%, below 117%, below 116%, or below 115%.

In some embodiments, the % $U_{TM}$ of a uracil-modified sequence encoding a LPL polypeptide of the invention is above 100%, above 101%, above 102%, above 103%, above 104%, above 105%, above 106%, above 107%, above 108%, above 109%, above 110%, above 111%, above 112%, above 113%, above 114%, above 115%, above 116%, above 117%, above 118%, above 119%, above 120%, above 121%, above 122%, above 123%, above 124%, above 125%, or above 126%, above 127%, above 128%, above 129%, or above 130%, above 131%, above 132%, above 133%, above 134%, above 135%, above 136%, above 137%, or above 138%.

In some embodiments, the % $U_{TM}$ of a uracil-modified sequence encoding a LPL polypeptide of the invention is between 131% and 133%, between 130% and 134%, between 129% and 135%, between 128% and 136%, between 127% and 137%, between 126% and 138%, between 125% and 139%, between 124% and 140%, between 123% and 141%, between 122% and 142%, between 121% and 143%, between 120% and 144%, or between 119% and 145%.

In some embodiments, the % $U_{TM}$ of a uracil-modified sequence encoding a LPL polypeptide of the invention is between about 125% and about 139%, e.g., between 125% and 138%.

In some embodiments, a uracil-modified sequence encoding a LPL polypeptide of the invention has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if the polypeptide, e.g., wild type LPL, has, e.g., 12, 13, 14, 15, 16, 17, 18, 19, 20, 21, 22, or 23 phenylalanines, the absolute minimum number of uracil pairs (UU) that a uracil-modified sequence encoding the polypeptide, e.g., wild type LPL, can contain is 12, 13, 14, 15, 16, 17, 18, 19, 20, 21, 22, or 23, respectively.

Wild type LPL contains 38 uracil pairs (UU), 15 uracil triplets (UUU), three uracil quadruplets (UUUU), and one uracile quintuplet (UUUUU). In some embodiments, a uracil-modified sequence encoding a LPL polypeptide of the invention has a reduced number of uracil triplets (UUU) with respect to the wild-type nucleic acid sequence. In some embodiments, a uracil-modified sequence encoding a LPL polypeptide of the invention contains 14, 13, 12, 11, 10, 9, 8, 7, 6, 5, 4, 3, 2, 1, or no uracil triplets (UUU). In some embodiments, a uracil-modified sequence encoding a LPL polypeptide of the invention has a reduced number of uracil quadruplets (UUUU) with respect to the wild-type nucleic acid sequence. In some embodiments, a uracil-modified sequence encoding a LPL polypeptide of the invention contains 2, 1, or no uracil quadruplets (UUUU). In some embodiments, a uracil-modified sequence encoding a LPL polypeptide of the invention has a reduced number of uracil quintuplets (UUUUU) with respect to the wild-type nucleic acid sequence. In some embodiments, a uracil-modified sequence encoding a LPL polypeptide of the invention contains no uracil quintuplets (UUUUU).

In some embodiments, a uracil-modified sequence encoding a LPL polypeptide has a reduced number of uracil pairs (UU) with respect to the number of uracil pairs (UU) in the wild-type nucleic acid sequence. In some embodiments, a uracil-modified sequence encoding a LPL polypeptide of the invention has a number of uracil pairs (UU) corresponding to the minimum possible number of uracil pairs (UU) in the wild-type nucleic acid sequence, e.g., 17 uracil pairs in the case of wild type LPL.

In some embodiments, a uracil-modified sequence encoding a LPL polypeptide of the invention has at least 1, 2, 3, 4, 5, 6, 7, 8, 9, 10, 11, 12, 13, 14, 15, 16, or 17 uracil pairs (UU) less than the number of uracil pairs (UU) in the wild-type nucleic acid sequence. In some embodiments, a uracil-modified sequence encoding a LPL polypeptide of the invention has between 13 and 29 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, the polynucleotide of the invention comprises a uracil-modified sequence encoding a LPL polypeptide disclosed herein. In some embodiments, the uracil-modified sequence encoding a LPL polypeptide comprises at least one chemically modified nucleobase, e.g., 5-methoxyuracil. In some embodiments, at least 95% of a nucleobase (e.g., uracil) in a uracil-modified sequence encoding a LPL polypeptide of the invention are modified nucleobases. In some embodiments, at least 95% of uracil in a uracil-modified sequence encoding a LPL polypeptide is 5-methoxyuracil. In some embodiments, the polynucleotide comprising a uracil-modified sequence further comprises a miRNA binding site, e.g., a miRNA binding site that binds to miR-142. In some embodiments, the polynucleotide comprising a uracil-modified sequence is formulated with a delivery agent, e.g., a lipid having Formula (I), (IA), (II), (IIa), (IIb), (IIe), (IId) or (IIe), e.g., any of Compounds 1-232.

In some embodiments, the polynucleotide of the invention comprises an open reading frame (ORF) encoding a LPL polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding LPL are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a LPL polypeptide. In some embodiments, when applied locally, regions of the reference nucleic acid sequence can be modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a LPL polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a LPL polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a LPL polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a LPL polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a LPL polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, a sequence optimized nucleic acid encoding a LPL polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

Modified Nucleotide Sequences Encoding LPL Polypeptides

In some embodiments, the polynucleotide (e.g., a RNA, e.g., an mRNA) of the invention comprises a chemically modified nucleobase. The invention includes modified polynucleotides comprising a polynucleotide described herein (e.g., a polynucleotide comprising a nucleotide sequence encoding a LPL polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a LPL polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can by synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

In some embodiments, a polynucleotide of the present invention (e.g., a polynucleotide comprising a nucleotide sequence encoding a LPL polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

In some embodiments, the polynucleotides of the present invention are chemically modified. As used herein in reference to a polynucleotide, the terms "chemical modification" or, as appropriate, "chemically modified" refer to modification with respect to adenosine (A), guanosine (G), uridine (U), or cytidine (C) ribo- or deoxyribonucleosides in one or more of their position, pattern, percent or population. Generally, herein, these terms are not intended to refer to the ribonucleotide modifications in naturally occurring 5'-terminal mRNA cap moieties.

In some embodiments, the polynucleotides of the present invention can have a uniform chemical modification of all or any of the same nucleoside type or a population of modifications produced by mere downward titration of the same starting modification in all or any of the same nucleoside type, or a measured percent of a chemical modification of all any of the same nucleoside type but with random incorporation, such as where all uridines are replaced by a uridine analog, e.g., pseudouridine or 5-methoxyuridine. In another embodiment, the polynucleotides can have a uniform chemical modification of two, three, or four of the same nucleoside type throughout the entire polynucleotide (such as all uridines and all cytosines, etc. are modified in the same way).

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Tri fluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azido-cytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methyl pseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-0-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil;

5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenylpseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamylqueuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA is a uracil-modified sequence comprising an ORF encoding a LPL polypeptide, wherein the mRNA comprises a chemically modified nucleobase, e.g., 5-methoxyuracil. In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that an mRNA provides suitable protein expression levels while inducing little to no immune response. In some embodiments, the uracil content of the ORF is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140% of the theoretical minimum uracil content in the corresponding wild-type ORF (% Utm). In other embodiments, the uracil content of the ORF is between about 117% and about 134% or between 118% and 132% of the % UTM. In some embodiments, the uracil content of the ORF encoding a LPL polypeptide is about 115%, about 120%, about 125%, about 130%, about 135%, about 140%, about 145%, or about 150% of the % Utm. In this context, the term "uracil" can refer to 5-methoxyuracil and/or naturally occurring uracil.

In some embodiments, the uracil content in the ORF of the mRNA encoding a LPL polypeptide of the invention is less than about 50%, about 40%, about 30%, about 20%, about 15%, or about 12% of the total nucleobase content in the ORF. In some embodiments, the uracil content in the ORF is between about 12% and about 25% of the total nucleobase content in the ORF. In other embodiments, the uracil content in the ORF is between about 15% and about 17% of the total nuclebase content in the ORF. In one embodiment, the uracil content in the ORF of the mRNA encoding a LPL polypeptide is less than about 20% of the total nucleobase content in the open reading frame. In this context, the term "uracil" can refer to 5-methoxyuracil and/or naturally occurring uracil.

In further embodiments, the ORF of the mRNA encoding a LPL polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the LPL polypeptide. In some embodiments, the ORF of the mRNA encoding a LPL polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the LPL polypeptide. In a particular embodiment, the ORF of the mRNA encoding the LPL polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the LPL polypeptide contains no non-phenylalanine uracil pairs and/or triplets.

In further embodiments, the ORF of the mRNA encoding a LPL polypeptide of the invention comprises 5-methoxyuracil and has an adjusted uracil content containing less uracil-rich clusters than the corresponding wild-type nucleotide sequence encoding the LPL polypeptide. In some embodiments, the ORF of the mRNA encoding the LPL polypeptide of the invention contains uracil-rich clusters that are shorter in length than corresponding uracil-rich clusters in the corresponding wild-type nucleotide sequence encoding the LPL polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the LPL polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the LPL polypeptide is substituted with an alternative codon having a codon frequency lower than the codon frequency of the substituted codon in the synonymous codon set.

In some embodiments, the adjusted uracil content, LPL polypeptide-encoding ORF of the 5-methoxyuracil-comprising mRNA exhibits expression levels of LPL when administered to a mammalian cell that are higher than expression levels of LPL from the corresponding wild-type mRNA. In other embodiments, the expression levels of LPL when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of LPL when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, LPL is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the LPL polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500- fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, LPL polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a LPL polypeptide but does not comprise 5-methoxyuracil under the same conditions, or relative to the immune response induced by an mRNA that encodes for a LPL polypeptide and that comprises 5-methoxyuracil but that does not have adjusted uracil content under the same conditions. The innate immune response can be manifested by increased expression of pro-inflammatory cytokines, activation of intracellular PRRs (RIG-1, MDA5, etc), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a LPL polypeptide but does not comprise 5-methoxyuracil, or to an mRNA that encodes a LPL polypeptide and that comprises 5-methoxyuracil but that does not have adjusted uracil content. In some embodiments, the interferon is IFN-3. In some embodiments, cell death frequency cased by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a LPL polypeptide but does not comprise 5-methoxyuracil, or an mRNA that encodes for a LPL polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a LPL polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the LPL polypeptide is less than about 23% of the total nucleobase content in the ORF. In some embodiments, the ORF that encodes the LPL polypeptide is further modified to decrease G/C content of the ORF (absolute or relative) by at least about 40%, as compared to the corresponding wild-type ORF. In yet other embodiments, the ORF encoding the LPL polypeptide contains less than 20 non-phenylalanine uracil pairs and/or triplets. In some embodiments, at least one codon in the ORF of the mRNA encoding the LPL polypeptide is further substituted with an alternative codon having a codon frequency lower than the codon frequency of the substituted codon in the synonymous codon set. In some embodiments, the expression of the LPL polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the LPL polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, $—CH_2—O—N(CH_3)—CH_2—$, $—CH_2—N(CH_3)—N(CH_3)—CH_2—$, $—CH_2—NH—CH_2—$, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, $—N(CH_3)—CH_2—CH_2—$, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $—O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); “locked” nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

The polynucleotides of the invention (e.g., a polynucleotide comprising a nucleotide sequence encoding a LPL polypeptide or a functional fragment or variant thereof) can include a combination of modifications to the sugar, the nucleobase, and/or the internucleoside linkage. These combinations can include any one or more modifications described herein.

In some embodiments the LPL nucleic acids described herein are not one or more of the LPL nucleic acids in Table 3. In other embodiments the LPL nucleic acids described herein are not a nucleic acid having 95% or greater sequence identity to one or more of the LPL nucleic acids in Table 3.

TABLE 3

| Sequence | SEQ ID NO |
|---|---|
| tttaacgtga atcgatgtaa acctgtgttt ggtgcttaga cagggggccc ccgggtagag tggaacccct taagctaagc<br>gaacaggagc ctaacaaagc aaatttttcc gtctgccctt tccccctctt ctcgttggca gggttgatcc tcattactgt<br>ttgctcaaac gtttagaagt gaatttaggt ccctcccccc aacttatgat tttatagcca ataggtgatg aggtttattt gcatatttcc<br>agtcacataa gcagccttgg cgtgaaaaca gtgtcagact cgattccccc tcttcctcct cctcaaggga aagctgccca<br>cttctagctg ccctgccatc ccctttaaag ggcgacttgc tcagcgccaa accgcggctc cagccctctc cagcctccgg<br>ctcagccggc tcatcagtcg gtccgcgcct tgcagctcct ccagagggac gcgccccgag atggagagca aagccctgct<br>cgtgctgact ctggccgtgt ggctccagag tctgaccgcc tcccgcggag gggtggccgc cgccgaccaa agaagagatt<br>ttatcgacat cgaaagtaaa tttgccctaa ggacccctga agacacagct gaggacactt gccacctcat tcccggagta<br>gcagagtccg tggctacctg tcatttcaat cacagcagca aaaccttcat ggtgatccat ggctggacgg taacaggaat<br>gtatgagagt tgggtgccaa aacttgtggc cgccctgtac aagagagaac cagactccaa tgtcattgtg gtggactggc<br>tgtcacgggc tcaggagcat tacccagtgt ccgcgggcta caccaaactg gtgggacagg atgtggcccg gtttatcaac<br>tggatggagg aggagtttaa ctaccctctg gacaatgtcc atctcttggg atacagcctt ggagcccatg ctgctggcat<br>tgcaggaagt ctgaccaata agaaagtcaa cagaattact ggcctcgatc cagctggacc taactttgag tatgcagaag<br>ccccgagtcg tctttctcct gatgatgcag attttgtaga cgtcttacac acattcacca gagggtcccc tggtcgaagc<br>attggaatcc agaaaccagt tgggcatgtt gacatttacc cgaatggagg tacttttcag ccaggatgta acattggaga<br>agctatccgc gtgattgcag agagaggact tggagatgtg gaccagctag tgaagtgctc ccacgagcgc tccattcatc<br>tcttcatcga ctctctgttg aatgaagaaa atccaagtaa ggcctacagg tgcagttcca aggaagcctt tgagaaaggg<br>ctctgcttga gttgtagaaa gaaccgctgc aacaatctgg gctatgagat caataaagtc agagccaaaa gaagcagcaa<br>aatgtacctg aagactcgtt ctcagatgcc ctacaaagtc ttccattacc aagtaaagat tcatttttct gggactgaga<br>gtgaaaccca taccaatcag gcctttgaga tttctctgta tggcaccgtg gccgagagtg agaacatccc attcactctg<br>cctgaagttt ccacaaataa gacctactcc ttcctaattt acacagaggt agatattgga gaactactca tgttgaagct<br>caaatggaag agtgattcat actttagctg gtcagactgg tggagcagtc ccggcttcgc cattcagaag atcagagtaa<br>aagcaggaga gactcagaaa aaggtgatct tctgttctag ggagaaagtg tctcatttgc agaaaggaaa ggcacctgcg<br>gtatttgtga aatgccatga caagtctctg aataagaagt caggctgaaa ctgggcgaat ctacagaaca aagaacggca<br>tgtgaattct gtgaagaatg aagtggagga agtaactttt acaaaacata cccagtgttt ggggtgtttc aaaagtggat<br>tttcctgaat attaatccca gccctaccct tgttagttat tttaggagac agtctcaagc actaaaaagt ggctaattca<br>atttatgggg tatagtggcc aaatagcaca tcctccaacg ttaaaagaca gtggatcatg aaaagtgctg ttttgtcctt<br>tgagaaagaa ataattgttt gagcgcagag taaaataagg ctccttcatg tggcgtattg ggccatagcc tataattggt<br>tagaacctcc tattttaatt ggaattctgg atctttcgga ctgaggcctt ctcaaacttt actctaagtc tccaagaata<br>cagaaaatgc ttttccgcgg cacgaatcag actcatctac acagcagtat gaatgatgtt ttagaatgat tccctcttgc<br>tattggaatg tggtccagac gtcaaccagg aacatgtaac ttggagaggg acgaagaaag ggtctgataa acacagaggt<br>tttaaacagt ccctaccatt ggcctgcatc atgacaaagt tacaaattca aggagatata aaatctagat caattaattc<br>ttaataggct ttatcgttta ttgcttaatc cctctctccc ccttcttttt tgtctcaaga ttatattata ataatgttct ctgggtaggt<br>gttgaaaatg agcctgtaat cctcagctga cacataattt gaatggtgca gaaaaaaaaa aagaaaccgt aattttatta<br>ttagattctc caaatgattt tcatcaattt aaaatcattc aatatctgac agttactctt cagttttagg cttaccttgg tcatgcttca<br>gttgtacttc cagtgcgtct cttttgttcc tggctttgac atgaaaagat aggtttgagt tcaaattttg cattgtgtga gcttctacag<br>attttagaca aggaccgttt ttactaagta aaagggtgga gaggttcctg ggtggattcc ctaagcagtg cttgtaaacc<br>atcgcgtgca atgagccaga tggagtacca tgagggttgc tatttgttgt ttttaacaac taatcaagag tgagtgaaca<br>actatttata aactagatct cctatttttc agaatgctct tctacgtata aatatgaaat gataaagatg tcaaatatct<br>cagaggctat agctgggaac ccgactgtga aagtatgtga tatctgaaca catactagaa agctctgcat gtgtgttgtc<br>cttcagcata attcggaagg gaaaacagtc gatcaaggga tgtattggaa catgtcggag tagaaattgt tcctgatgtg<br>ccagaacttc gaccctttct ctgagagaga tgatcgtgcc tataaatagt aggaccaatg ttgtgattaa catcatcagg<br>cttggaatga attctctcta aaaataaaat gatgtatgat ttgttgttgg catccccttt attaattcat taaatttctg gatttgggtt<br>gtgacccagg gtgcattaac ttaaaagatt cactaaagca gcacatagca ctgggaactc tggctccgaa aaactttgtt<br>atatatatca aggatgttct ggctttacat tttatttatt agctgtaaat acatgtgtgg atgtgtaaat ggagcttgta<br>catattggaa aggtcattgt ggctatctgc atttataaat gtgtggtgct aactgtatgt gtctttatca gtgatggtct<br>cacagagcca actcactctt atgaaatggg ctttaacaaa acaagaaaga aacgtactta actgtgtgaa gaaatggaat<br>cagcttttaa taaaattgac aacattttat taccac | 85 |

TABLE 3 -continued

| Sequence | SEQ ID NO |
|---|---|
| atggagagca aggccctgct ggtgctgacc ctggccgtgt ggctgcagag cctgaccgcc agccgcggcg gcgtggccgc<br>cgccgaccag cgccgcgact tcatcgacat cgagagcaag ttcgccctgc gcacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagcgcgagc ccgacagcaa<br>cgtgatcgtg gtggactggc tgagccgcgc ccaggagcac taccccgtga gcgccggcta caccaagctg gtgggccagg<br>acgtggcccg cttcatcaac tggatggagg aggagttcaa ctacccctg gacaacgtgc acctgctggg ctacagcctg<br>ggcgcccacg ccgccggcat cgccggcagc ctgaccaaca agaaggtgaa ccgcatcacc ggcctggacc ccgccggccc<br>caacttcgag tacgccgagg cccccagccg cctgagcccc gacgacgccg acttcgtgga cgtgctgcac accttcaccc<br>gcggcagccc cggccgcagc atcggcatcc agaagcccgt gggccacgtg gacatctacc ccaacggcgg caccttccag<br>cccggctgca acatcggcga ggccatccgc gtgatcgccg agcgcggcct gggcgacgtg gaccagctgg tgaagtgcag<br>ccacgagcgc agcatccacc tgttcatcga cagcctgctg aacgaggaga accccagcaa ggcctaccgc tgcagcagca<br>aggaggcctt cgagaagggc ctgtgcctga gctgccgcaa gaaccgctgc aacaacctgg gctacgagat caacaaggtg<br>cgcgccaagc gcagcagcaa gatgtacctg aagacccgca gccagatgcc ctacaaggtg ttccactacc aggtgaagat<br>ccacttcagc ggcaccgaga gcgagaccca caccaaccag gccttcgaga tcagcctgta cggcaccgtg gccgagagcg<br>agaacatccc cttcaccctg cccgaggtga gcaccaacaa gacctacagc ttcctgatct acaccgaggt ggacatcggc<br>gagctgctga tgctgaagct gaagtggaag agcgacagct acttcagctg gagcgactgg tggagcagcc ccggcttcgc<br>catccagaag atccgcgtga aggccggcga gacccagaag aaggtgatct tctgcagccg cgagaaggtg agccacctgc<br>agaagggcaa ggcccccgcc gtgttcgtga agtgccacga caagagcctg aacaagaaga gcggc | 86 |
| atggagagca aggccctgct ggtgctgacc ctggccgtgt ggctgcagag cctgaccgcc agcagaggcg gcgtggccgc<br>cgccgaccag agaagagact tcatcgacat cgagagcaag ttcgccctga gaacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagagagagc ccgacagcaa<br>cgtgatcgtg gtggactggc tgagcagagc ccaggagcac taccccgtga gcgccggcta caccaagctg gtgggccagg<br>acgtggccag attcatcaac tggatggagg aggagttcaa ctacccctg gacaacgtgc acctgctggg ctacagcctg<br>ggcgcccacg ccgccggcat cgccggcagc ctgaccaaca agaaggtgaa cagaatcacc ggcctggacc ccgccggccc<br>caacttcgag tacgccgagg cccccagcag actgagcccc gacgacgccg acttcgtgga cgtgctgcac accttcacca<br>gaggcagccc cggcagaagc atcggcatcc agaagcccgt gggccacgtg gacatctacc ccaacggcgg caccttccag<br>cccggctgca acatcggcga ggccatcaga gtgatcgccg agagaggcct gggcgacgtg gaccagctgg tgaagtgcag<br>ccacgagaga agcatccacc tgttcatcga cagcctgctg aacgaggaga accccagcaa ggcctacaga tgcagcagca<br>aggaggcctt cgagaagggc ctgtgcctga gctgcagaaa gaacagatgc aacaacctgg gctacgagat caacaaggtg<br>agagccaaga gaagcagcaa gatgtacctg aagaccagaa gccagatgcc ctacaaggtg ttccactacc aggtgaagat<br>ccacttcagc ggcaccgaga gcgagaccca caccaaccag gccttcgaga tcagcctgta cggcaccgtg gccgagagcg<br>agaacatccc cttcaccctg cccgaggtga gcaccaacaa gacctacagc ttcctgatct acaccgaggt ggacatcggc<br>gagctgctga tgctgaagct gaagtggaag agcgacagct acttcagctg gagcgactgg tggagcagcc ccggcttcgc<br>catccagaag atcagagtga aggccggcga gacccagaag aaggtgatct tctgcagcag agagaaggtg agccacctgc<br>agaagggcaa ggcccccgcc gtgttcgtga agtgccacga caagagcctg aacaagaaga gcggctag | 87 |
| atggagtcca aagcactgct cgttctcacc ctagcagtgt ggctgcagag cctgactgcc tcgcggggag gagttgctgc<br>ggccgaccag cgccgggact ttatcgacat cgagtctaaa ttcgccctgc gcaccccaga ggatactgcc gaagacacct<br>gtcatctaat cccaggggtt gccgagagcg tagccacatg ccatttcaac cactcttcca aaacattcat ggtcatccac<br>ggttggacag tgactggtat gtacgagagc tgggtgccaa agctcgtggc agctctgtac aagagagaac cggattctaa<br>cgtgatcgtc gtggattggc tgagcagagc ccaggaacac tatccagtgt ctgccgggta tacaaaactc gtcggccagg<br>atgtggccag gttcattaac tggatggagg aagaattcaa ttaccctttg gacaacgttc atctgcttgg gtactcactg<br>ggtgcacatg ccgccggtat cgccggttct ttgactaaca aaaaggtgaa caggatcact gggttagacc cggcaggccc<br>taactttgag tacgccgaag caccaagccg gctctcccca gatgatgctg atttcgttga tgtcctacac actttcacac<br>gcgggtcccc cggccgttct atcggaattc agaagccagt tggccatgtt gatatctacc ctaatggggg tacttttcag<br>ccaggctgta acatcgggga ggccattaga gttatagcag agaggggcct cggagacgtc gaccagttgg tgaagtgcag<br>tcatgaacgc tcgatccatc tgttcatcga ttccctgctg aatgaggaga acccgagcaa ggcatataga tgttcctcca<br>aagaggcctt tgagaagggg ctctgcttgt cctgtaggaa gaaccgatgc aacaacttgg gttacgagat aaacaaggta<br>cgtgctaaga ggtcttctaa aatgtatctg aagacgcgga gtcagatgcc ctacaaggtc tttcattacc aagtcaaaat<br>acatttctct gggactgaat cagagacgca tacgaaccaa gcctttgaaa tcagcttgta tggtactgtg gctgagagtg<br>agaatatccc gtttaccctt ccagaagttt caaccaataa aacttatagc tttctgatct acactgaggt agacattgga<br>gaactgctga tgttgaaatt gaagtggaaa agcgacagct acttctcctg gagcgactgg tggtcctcgc ccggcttcgc<br>cattcagaag atcagggtta aggccgggga gacgcagaag aaagttattt tctgttctag ggagaaggtt tctcaccttc<br>aaaagggaaa agcccccgca gttttcgtga aatgccatga taaaagcttg aacaaaaagt ccggatag | 88 |
| atggagagca aggccctgct ggtgctgacc ctggccgtgt ggctgcagag cctgacagcc agcagaggag gagtggccgc<br>tgctgaccag aggcgggact tcattgatat tgagagcaag tttgccctgc ggaccccaga ggacacagct gaggacacct<br>gccacctgat ccctggggtg gccgagagcg tggccacctg ccacttcaac cacagcagca agaccttcat ggtgatccac<br>ggctggacag tgacaggcat gtatgagagc tgggtgccca agctggtggc cgccctgtac aagcgggagc cagacagcaa<br>tgtgattgtg gtggactggc tgagccgggc ccaggagcac taccctgtgt ctgctggcta caccaagctg gtgggccagg<br>atgtggcccg cttcatcaac tggatggagg aggagttcaa ctacccctg gacaacgtgc acctgctggg ctacagcctg<br>ggcgcccacg ccgccggcat tgctggcagc ctgaccaaca agaaggtgaa ccgcatcacc ggcctggacc ctgctggccc<br>caactttgaa tatgcagagg cccccagccg gctgagccca gatgatgctg actttgtgga tgtgctgcac accttcaccc<br>ggggcagccc tggccgcagc atcggcatcc agaagcctgt gggccacgtg gacatctacc caaatggagg caccttccag<br>cccggctgca acattggaga ggccatccgg gtgattgctg agcggggcct gggagatgtg gaccagctgg tgaagtgcag<br>ccatgagagg agcatccacc tgttcatcga cagcctgctg aatgaggaga accccagcaa ggcctaccgc tgcagcagca<br>aggaggcctt tgagaagggc ctgtgcctga gctgcaggaa gaaccgctgc aacaacctgg gctatgagat caacaaggtg<br>cgggccaaga ggagcagcaa gatgtacctg aagaccagga gccagatgcc ctacaaggtg ttccactacc aggtgaagat<br>ccacttcagc ggcacagaga gcgagaccca caccaaccag gcctttgaga tcagcctgta tggaacagtg gccgagagcg<br>agaacatccc cttcaccctg cctgaggtgt ccaccaacaa gacctacagc ttcctgatct acacagaggt ggacattgga<br>gagctgctga tgctgaagct gaagtggaag agtgacagct acttctcctg gagcgactgg tggagcagcc ctggctttgc<br>catccagaag atccgggtga aggccgggga gacccagaag aaggtgatct tctgcagccg ggagaaggtg agccacctgc<br>agaagggcaa ggccccagct gtgtttgtga agtgccacga caagagcctg aacaagaaga gcggctag | 89 |

TABLE 3 -continued

| Sequence | SEQ ID NO |
|---|---|
| atggagagca aggccctgct ggtgctgacc ctggccgtgt ggctgcagtc actgactgct tctagaggag gagtggcggc<br>agccgaccag cgccgggact tcattgacat tgaatcaaag tttgctctcc gcactccaga ggacacagca gaagatacct<br>gccatctgat tccaggggtc gccgagtcag ttgctacatg ccatttcaat catagctcca agacattcat ggtgatccac<br>gggtggacag tgacaggcat gtatgaaagc tgggttccta aattggtcgc cgcgctatat aaacgagagc cagatagcaa<br>cgtgattgta gtggattggt tgtcacgggc tcaggaacat taccccgtat ctgccggcta caccaagctc gtgggacaag<br>atgtggcaag attcatcaac tggatggagg aggaattcaa ttaccccttg gacaatgttc atctgaggg atattcactg<br>ggagcgcatg ctgccgggat cgctggaagc ctgacaaaca agaaagtgaa tagaattacc ggcctggacc ctgcggggcc<br>aaactttgaa tatgcagaag ctcctagcag actgagtccg gacgacgcag attttgtaga cgtccttcat actttcacta<br>ggggctctcc cggcagatcc attggcatcc agaagcccgt tggacatgtg gatatctatc ccaacggagg gacatttcag<br>cccggttgta acatcgggga agccatcagg gtaattgccg aacgcggtct cggcgatgtg gatcagcttg tgaagtgctc<br>tcacgaacgc tccatacatc tatttatcga tagccttcta aatgaggaga acccttcaaa agcataccgt tggagttcca<br>aggaggcatt tgagaagggt ctgtgtctgt cttgccgaaa gaatcggtgt aataacctcg gatacgagat taataaggtt<br>cgggccaaga ggtcctctaa gatgtattta aagaccagat cacagatgcc atacaaagtc ttccattatc aggtgaaaat<br>tcacttcagt ggaaccgaat cagagacaca tactaaccag gcctttgaaa ttagccttta tggtaccgtc gcggagtcag<br>agaacattcc tttcacgtta cccgaggtgt ccaccaacaa gacatactcc tttctcatct acacagaggt agatatcgga<br>gagttgctga tgctgaagct gaaatggaaa agcgattcct atttttcttg gtcggattgg tggagcagcc ccgggtttgc<br>aatccagaag attcgggtga aggctggcga gacccagaag aaggtcattt tttgctctcg tgaaaaagtc tcgcaccttc<br>aaaaaggcaa ggctcccgca gtatttgtga agtgccatga caaaagtctt aataaaaaat ccggatag | 90 |
| atggagtcta aggccctcct tgtacttaca ctggctgtgt ggcttcagtc cctgacagct tccaggggtg gcgttgctgc<br>agcagatcag cgacgggatt ttattgacat tgagagtaaa tttgccctgc gtactcccga ggatacagcc gaagatacct<br>gtcatttgat ccctggagtc gccgagagcg tggctacctg tcatttcaac cattctagca aaacatttat ggtgatacac<br>gggtggacag tcacaggaat gtatgagagc tgggtgccca aattagtggc tgctctgtac aagagggaac ctgactctaa<br>cgtcattgtc gtagattggc tgtcccgggc tcaagagcat taccccgtgt ctgccggtta taccaagctg gtcggccagg<br>atgttgctcg cttcataaat tggatggagg aagagttcaa ttaccctctg gataacgttc acctgctagg gtactcacta<br>ggggctcacg ctgctggaat cgcgggatcg ttgaccaaca aaaaagtcaa ccgaatcacc ggcctcgacc ctgcaggccc<br>aaattttgag tatgccgaag ccccaagcag actgtccccc gacgatgcgg acttcgtgga tgtgctgcac acgtttacaa<br>gaggaagccc agggagaagc atcggcatcc agaagccagt gggacatgtg gacatttacc caaacggcgg tactttccag<br>ccagggtgta atataggggga ggccatacgg gtgatcgccg aacgcggtct gggggatgtg gaccagttag tgaaatgttc<br>ccatgaacgt agcatccatt tatttatcga ttccctcctg aacgaggaga accccagcaa ggcataccgg tgctccagta<br>aggaggcgtt tgaaaagggg ctttgtctga gctgtcgaaa gaataggtgc aacaatttgg gatacgagat caataaagtc<br>agggcaaagc gttctagcaa gatgtacctt aaaactagaa gccagatgcc ttataaggtg tttcattatc aagttaagat<br>ccacttctct ggaacagaat cggagacaca caccaatcaa gcttttgaaa tttctcttta tggtacagtc gctgaaagcg<br>aaaatattcc tttcaccctg cccgaggtca gtaccaataa aacctattcc tttctgatct atacagaagt cgacattgga<br>gagctgctga tgctgaagct caagtggaaa tcagacagct acttctcctg gagcgattgg tggagcagcc ccggattcgc<br>cattcagaag atcagagtca aggccggtga aacccagaaa aaagtgatct tttgttccag agagaaagtc agtcacttgc<br>agaagggaaa agcccctgcg gtcttcgtaa aatgtcacga taagagcctg aacaaaaaaa gtgggtag | 91 |
| auggagucca aggcacugcu agugcugaca cuagccgucu gguugcagag ccuaaccgca agcagaggag<br>gggucgcagc ugcagaccaa cgacgggauu uuauugauau cgaauccaaa uucgcccuua ggacaccaga<br>agauacagcc gaggacacau gucacuugau cccuggggguu gccgaguccg uugccacuug ccacuucaau<br>cacaguagca aaaccuuuau ggucauacac ggcuggacag uuacuggaau guacgaaagu uggguuccaa<br>agcugguugc ggccuuauau aaaagagaac cagauucaaa cgucaucguc guugacuggc ugucaagagc<br>ucaggagcau uaucccguuu ccgcagggua cacuaaguua gugggucagg auguggcucg cuucaucaac<br>uggauggaag aagaguuuaa uuacccauua gauaacgugc accuuuuggg cuauucccug ggugcccacg<br>cugcuggcau ugcuggcucc cucacaaaca agaaagugaa uagaaucacc ggccuggacc cagcagggcc<br>gaacuuugaa uaugccgaag cgcccaguag acucucuccg gacgaugcgg auuucgucga cguccugcau<br>accuuuacac gaggaucccc uggucgaucg auaggcauac agaagccggu uggucacgug gacaucuauc<br>ccaaugggggg gacguuccag cccgggugua acauuggaga agccaucaga guuaucgccg agcggggccu<br>uggggacgug gaucagcucg ugaaaugcag ucacgaacgu uccauacacc uguuuaucga uagucuacug<br>aacgaagaaa aucccagcaa ggccuaccgg ugcagcagua aagaagcuuu ugaaaaaggc uuaugucuga<br>gcugccgaaa aaaucggugc aauaauuugg gguacgaaau aaacaaaguu cgcgcuaaga gaagcuccaa<br>gauguaccug aagacuagau cccagaugcc uuacaaggua uuccauuacc aagugaagau ccauuuuucc<br>ggaacagaaa gcgaaaccca caccaaccag gccuuugaga uuagccugua uggcaccgua gcugaauccg<br>agaacauccc cuuuacgcug cccgaaguaa guacuaauaa aaccuacagc uuucugauuu auacagaagu<br>ggauauuggc gaacugcuga ugcugaagcu gaaguggaag ucagacagcu acuuuucgug gagcgacugg<br>uggucuuccc ccggauuugc aauacagaaa aucaggguga aagccggaga gacacagaaa aaggugaucu<br>ucuguagcag agaaaaggua agucaucugc agaaggguaa ggcuccagcg guguuuguca agugccauga<br>caaaucccug aauaaaaagu ccggcuag | 92 |
| auggagucaa aagcucuucu uguguugacu cucgccgucu ggcugcaguc ccugaccgcc ucgagaggag<br>gaguggcagc agccgaccag agacgcgauu uuauugauau agaauccaag uuugcccucc guacccccga<br>agauacugca gaggauaccu gucaucuuau cccagguguu gcagaguccg uugcuaccug ucacuucaau<br>cauaguucca aaaccuucau ggugauccac ggauggacug uaacaggaau guacgaguca ugggucccaa<br>aacugguggc cgcucucuau aaaagagaac cggauucuaa cguuauugug guugacuggc ugucuagggc<br>ucaagaacau uaccccguga gugcagguua uaccaagcug guugggcagg acguugcgag auuuauuaau<br>uggauggaag aagaguucaa uuacccacug gacaaugugc accugcucgg cuacucccuu ggcgcacacg<br>ccgcaggcau ugccggguca cugaccaaua aaaaaguaaa ccgcaucaca ggucuggacc cagccggucc<br>gaacuuugaa uaugccgagg cucccucacg acuguccccc gaugacgcag auuucgucga uguucugcac<br>acguuuacua gaggaagccc ugggcgcagc auagguauuc aaaaacccgu aggacaugug gauaucuacc<br>caaauggagg cacguuccag ccuggaugua auaucgguga ggcuauccgc gucauagccg aaagaggccu<br>gggggacgua gaccagcuag ugaagugcag ccacgagcgc aguauccauu uauucaucga uucccugcug<br>aaugaagaga auccaucuaa ggcuuauagg ugcucaagca aagaagccuu cgaaaaagga cuuugccuuu<br>cgugcagaaa aaaucguugc aauaaccucg guuaugagau uaauaaaguc agagcuaaga gaucuucuaa<br>gauguaucug aagacccgau cucaaaugcc uuauaaaguu uuccacuacc aggucaagau acacuucagc<br>ggcaccgaau cagagacuca cacuaaucag gcuuuugaga ucuccuugua uggcacaguu gccgagucag | 93 |

TABLE 3 -continued

| Sequence | SEQ ID NO |
|---|---|
| aaaauauucc cuuuacacuc ccagaaguca gcacgaacaa aaccuauucc uuuuuaauuu auaccgaggu<br>cgacaucggu gaacugcuca ugcuaaaacu gaaauggaag ucagauucuu acuucucgug gagcgauugg<br>uggagcagcc caggauuugc uauacagaaa auuagaguua aagccgguga aacccagaag aaagugaucu<br>uuuguucaag agaaaagguu ucucaccugc aaaaggguaa agccccugcc guguucguga aaugccauga<br>uaagucacug aauaaaaagu ccggcuag | |
| atggagtcga aggcgttgct tgtcctgacc cttgcggtct ggctccagtc cctgaccgcg tcgagaggtg gagtggctgc<br>agctgatcag cgaagagatt tcattgacat cgaatcgaag tttgccctga gaactcccga agatacggca gaggatacgt<br>gtcatctgat cccaggcgtt gcagaatcgg tcgcaacttg tcatttcaat cactcgagca agaccttcat ggtaatccac<br>gggtggaccg tgactggaat gtatgaaagc tgggtcccaa agctggtcgc ggccctgtac aagcgagagc cagattcgaa<br>cgttatcgtg gtggattggc tttccagagc acaagaacac tatcctgtct cggcaggtta cactaagctc gtgggacaag<br>acgtggcccg cttcatcaac tggatggaag aagaattcaa ttacccgctg gacaacgtcc accttttggg ttactcactg<br>ggtgcacacg cggcaggcat tgctgggtcg ttgaccaaca agaaagtgaa tcgtattacc ggccttgatc cagcaggtcc<br>aaactttgaa tacgcggaag ccccttcgag actgagtcct gacgatgcag attttgtgga cgtgctgcac acctttacta<br>ggggttcacc aggccggtcc ataggcattc agaagcctgt gggacatgtg gacatctacc caaacggagg cacctttcaa<br>cccggatgca atatcggtga agcaattagg gtcatagcag aaagggggtt gggtgacgtg gatcagcttg tgaaatgttc<br>ccatgagcgc tctatacacc tgttcatcga ctcacttctg aatgaagaaa atccgtcgaa ggcctacaga tgctcctcga<br>aggaagcatt cgaaaagggg ctgtgtctgt cctgccgcaa gaacagatgc aataaccttg gttacgagat caacaaagtg<br>cgcgccaagc ggtcctcaaa aatgtacctt aaaacgcgat cacagatgcc ctacaaggtt tttcattacc aagtcaaaat<br>tcacttttcg ggcactgagt cggagactca taccaaccaa gcatttgaaa ttagcctgta cggaactgtg gcggagagcg<br>aaaacattcc ctttaccctc cccgaagtct ctaccaacaa aacctactcg ttcttgatct acaccgaagt ggacattgga<br>gagcttttga tgctcaaact caagtggaag tccgattctt acttctcctg gagcgattgg tggagctctc caggtttcgc<br>aattcaaaag attcgcgtca aggcgggcga gactcagaaa aaagtcatct tttgttccag agagaaagtg tcgcatttgc<br>aaaagggaaa agcgcctgcg gtgttcgtga aatgtcatga taagagcctt aacaagaagt cagga | 94 |
| atggagtcta aggcacttct cgtgctgacc ctcgctgtct ggctgcagag tctgaccgcg tcacgcggcg gggtggcggc<br>agcagatcaa cgacgagact ttattgacat tgagtcaaaa tttgccctga gaactccaga ggacaccgcc gaagacacgt<br>gtcatctaat ccccggcgtg gccgagtcag ttgccacctg tcacttcaac cactccagca aaacattcat ggtaattcat<br>ggatggaccg tgacaggaat gtacgaaagt tgggttccta agttagtcgc tgccctatat aagcgggagc ccgacagtaa<br>cgttatcgtg gtcgattggc tgagcagggc gcaggagcat tatcctgtga gtgctggata taccaagtta gttgggcaag<br>acgtggcccg cttcataaat tggatggagg aggaatttaa ttaccctctg gacaacgtgc accttttggg ttactccttg<br>ggtgcacacg ctgctggtat agcagggtcc ctcaccaata agaaggttaa tcgaatcacc ggactagacc ctgctggacc<br>aaacttcgaa tatgctgagg caccgtcccg cctgtccccc gatgatgccg atttcgttga cgtgctgcac acctttacca<br>ggggaagtcc gggaagaagc attggcatcc aaaaaccggt cggtcacgtg gacatctatc ccaatggagg caccttccag<br>cccggatgta acatcgggga ggcaattcgc gttatcgccg agagaggcct cggcgacgtc gaccagctgg tcaagtgtag<br>tcatgagcgc tccattcacc tgttcattga ctccctcctc aatgaggaga atccgagtaa agcttacaga tgttcatcga<br>aggaggcatt cgagaagggc ctttgcctgt cctgtcggaa gaataggtgt aataatcttg gttacgagat aaataaggtc<br>cgggccaagc gctcttccaa gatgtacctc aaaactcggt cccagatgcc atataaagtg tttcactatc aagtgaaaat<br>tcatttctcc ggtactgaat ctgagactca caccaaccag gccttcgaga tcagcctgta tggcactgtt gcagaaagtg<br>aaaacattcc cttcacactc cccgaggtgt ctaccaacaa gacctacagt tttctaatct acacggaggt ggatattggc<br>gaactgttga tgcttaagct gaagtggaaa agcgacagct attttagttg gagcgactgg tggagttccc cggggtttgc<br>cattcagaaa attagagtca aggcggggga aactcagaag aaggtgatct tctgcagtag ggaaaaggtg agccatctgc<br>agaaggggaa ggcccctgca gtattcgtaa agtgccacga caaaagtttg aacaaaaagt caggt | 95 |
| aacagtttgt atgctggaag agttctgaaa agatctctga gggctggaag tgctaaggac aatttcataa agaagaaaga<br>agagatttta tcgacatcga aagtaaattt gccctaagga cccctgaaga cacagctgag gacacttgcc acctcattcc<br>cggagtagca gagtccgtgg ctacctgtca tttcaatcac agcagcaaaa ccttcatggt gatccatggc tggacggtaa<br>caggaatgta tgagagttgg gtgccaaaac ttgtggccgc cctgtacaag agagaaccag actccaatgt cattgtggtg<br>gactggctgt cacgggctca ggagcattac ccagtgtccg cgggctacac caaactggtg ggacaggatg tggcccggtt<br>tatcaactgg atggaggagg agtttaacta ccctctggac aatgtccatc tcttgggata cagccttgga gcccatgctg<br>ctggcattgc aggaagtctg accaataaga aagtcaacag aattactggc ctcgatccag ctggacctaa ctttgagtat | 96 |
| atggtgatcc acggctggac cgtgaccggc atgtacgaga gctgggtgcc caagctggtg gccgccctgt acaagcgcga<br>gcccgacagc aacgtgatcg tggtggactg gctgagccgc gcccaggagc actaccccgt gagcgccggc tacaccaagc<br>tggtgggcca ggacgtggcc cgcttcatca actggatgga ggaggagttc aactaccccc tggacaacgt gcacctgctg<br>ggctacagcc tgggcgccca cgccgccggc atcgccggca gcctgaccaa caagaaggtg aaccgcatca ccggcctgga<br>ccccgccggc cccaacttcg agtac | 97 |
| atggtgatcc acggctggac cgtgaccggc atgtacgaga gctgggtgcc caagctggtg gccgccctgt acaagagaga<br>gcccgacagc aacgtgatcg tggtggactg gctgagcaga gcccaggagc actaccccgt gagcgccggc tacaccaagc<br>tggtgggcca ggacgtggcc agattcatca actggatgga ggaggagttc aactaccccc tggacaacgt gcacctgctg<br>ggctacagcc tgggcgccca cgccgccggc atcgccggca gcctgaccaa caagaaggtg aacagaatca ccggcctgga<br>ccccgccggc cccaacttcg agtactag | 98 |
| atggtcattc atgggtggac tgtgacaggt atgtatgaat cttgggtccc caaattagtc gcggctcttt ataagcggga<br>gcctgatagc aacgtgatag ttgtcgactg gttgagtcga gcccaggagc actatcctgt gagcgcagga tataccaaat<br>tggtcggcca agacgtcgcg agatttatca actggatgga agaggaattt aactatcccc ttgataacgt gcacctcctg<br>gggtactcct tgggcgctca tgctgccggc atcgctggca gcttaaccaa taagaaggtc aaccggatta ctggcctgga<br>tcccgccggc ccaaacttcg agtactag | 99 |
| atggtgatcc acggctggac agtgacaggc atgtatgaga gctgggtgcc caagctggtg gccgccctgt acaagcggga<br>gccagacagc aatgtgattg tggtggactg gctgagccgg gcccaggagc actaccctgt gtctgctggc tacaccaagc<br>tggtgggcca ggatgtggcc cgcttcatca actggatgga ggaggagttc aactaccccc tggacaacgt gcacctgctg<br>ggctacagcc tgggcgccca cgccgccggc attgctggca gcctgaccaa caagaaggtg aaccgcatca ccggcctgga<br>ccctgctggc cccaactttg agtactag | 100 |

TABLE 3 -continued

| Sequence | SEQ ID NO |
|---|---|
| atggtgatcc acggctggac cgtgaccggc atgtacgaga gctgggtacc taagctggtg gctgccctct ataaacgcga<br>acctgatagc aatgtcatcg tggtggattg gttgtccaga gcacaggaac attacccagt ttccgcagga tacaccaagc<br>tcgtcggaca ggacgtggcc cgctttatca attggatgga agaagagttt aactaccctc tcgataacgt gcaccttctg<br>ggctacagcc tcggcgccca cgctgcagga atagcaggaa gcctgactaa taaaaaggtg aaccgcatca ctggcctcga<br>cccagcaggc cccaattttg agtacta | 101 |
| atggttattc acggatggac tgtgactggt atgtacgagt catgggttcc caaactcgtc gcggcactgt acaagcgaga<br>gccagattca aacgtgatcg ttgtggattg gctgagcagg gctcaagagc attaccccgt ttctgctggc tacaccaaac<br>ttgtcggcca agatgtagcg aggtttatca actggatgga ggaggaattt aactaccctt tggacaatgt ccaccttctg<br>ggctactctt taggcgcaca tgcagccgga attgccggaa gcctcaccaa taagaaggtt aacaggatca ccggcttgga<br>ccccgctggg ccaaattttg aatactag | 102 |
| augguuaucc auggcuggac ugugacuggc auguacgaaa guuggguucc aaaacuggug gccgcccuuu<br>acaaacgcga gccggaauucu aaugugauug ucgucgauug gcuuucucgc gcacaggagc auuaccccgu<br>gucggcagga uauacuaaau ugguugguca ggauguggca agauuuauua acuggaugga ggaggaauuc<br>aacuaccccc uugauaacgu gcaccuguua ggguauaguc ugggugccca cgccgccggu aucgcuggcu<br>cacucacaaa uaagaagguc aaucgaauca ccggccuuga cccugccggg cccaauuuug aguauuag | 103 |
| augguuaucc auggcuggac ugugacuggc auguacgaaa guuggguucc aaaacuggug gccgcccuuu<br>acaaacgcga gccggauucu aaugugauug ucgucgauug gcuuucucgc gcacaggagc auuaccccgu<br>gucggcagga uauacuaaau ugguugguca ggauguggca agauuuauua acuggaugga ggaggaauuc<br>aacuaccccc uugauaacgu gcaccuguua ggguauaguc ugggugccca cgccgccggu aucgcuggcu<br>cacucacaaa uaagaagguc aacagaauca ccggcuuaga uccagcaggc ccaaacuuug aauacuag | 104 |
| aaactttccc tccttggaaa acagtcacat aagcagcctt ggcgtgaaaa cagtgtcaga ctcgattccc cctcttcctc<br>ctcctcaagg gaaagctgcc cacttctagc tgccctgcca tcccctttaa agggcgactt gctcagcgcc aaaccgcggc<br>tccagccctc tccagcctcc ggctcagccg gctcatcagt cggtccgcgc cttgcagctc ctccagaggg acgcgccccg<br>agatggagag caaagccctg ctcgtgctga ctctggccgt gtggctccag agtctgaccg cctcccgcgg aggggtggcc<br>gccgccgacc aaagaagaga ttttatcgac atcgaaagta aatttgccct aaggacccct gaagacacag ctgaggacac<br>ttgccacctc attcccggag tagcagagtc cgtggctacc tgtcatttca atcacagcag caaaaccttc atggtgatcc<br>atggctggac ggtaacagga atgtatgaga gttgggtgcc aaaacttgtg gccgccctgt acaagagaga accagactc | 105 |
| atggagagca aggccctgct ggtgctgacc ctggccgtgt ggctgcagag cctgaccgcc agccgcggcg gcgtggccgc<br>cgccgaccag cgccgcgact tcatcgacat cgagagcaag ttcgccctgc gcacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagcgcgagc ccgacagc | 106 |
| atggagagca aggccctgct ggtgctgacc ctggccgtgt ggctgcagag cctgaccgcc agcagaggcg gcgtggccgc<br>cgccgaccag agaagagact tcatcgacat cgagagcaag ttcgccctga gaacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagagagagc ccgacagcta g | 107 |
| atggaatcta aggcactact ggtgctaact ctcgcagtgt ggctgcagag tctgaccgcc tcacgagggg gagttgccgc<br>cgctgaccag cggagggact tcattgacat cgaatctaaa tttgcattga gaactccgga agatacagct gaggatacat<br>gccacttaat tccgggtgtt gccgagtccg tcgccacttg ccacttcaac cattcctcca aaaccttcat ggtgatccat<br>ggatggacag ttacggggat gtacgagtct tgggtgccta aactggtcgc tgccttgtac aagagagagc ccgacagcta g | 108 |
| atggagagca aggccctgct ggtgctgacc ctggccgtgt ggctgcagag cctgacagcc agcagaggag gagtggccgc<br>tgctgaccag aggcgggact tcattgatat tgagagcaag tttgccagc ggaccccaga ggacacagct gaggacacct<br>gccacctgat ccctggggtg gccgagagcg tggccacctg ccacttcaac cacagcagca agaccttcat ggtgatccac<br>ggctggacag tgacaggcat gtatgagagc tgggtgccca agctggtggc cgccctgtac aagcgggagc caacagcta g | 109 |
| atggagagca aggccctgct ggtgctgacc ctggccgtgt ggctgcagtc tctgaccgca agtcgcggtg gtgttgccgc<br>tgcagaccag cgaagggact ttatagatat cgaatctaaa ttcgctcttc gaaccccgaa agataccgca gaggacactt<br>gtcacctcat tcccggcgtt gccgaatctg tggctacttg tcatttcaat cattcctcaa aaactttcat ggtgattcat<br>ggttggaccg ttacagggat gtatgaaagt tgggtcccaa agcttgttgc tgccctgtat aagagagagc ccgactccta g | 110 |
| atggagagca aggcactcct cgtcttgact ctggccgtgt ggctgcagtc cctcaccgcc agtcggggtg gggttgcagc<br>cgctgaccag cgtcgcgact ttattgacat cgaatcaaag ttcgcccttc gcacccccga agacacagct gaggacacct<br>gccatctgat acccggagta gctgagagtg tcgccacttg tcacttcaat cactccagca agactttcat ggtgatccac<br>ggatggacgg taaccggaat gtatgagagc tgggtgccca agttagtagc cgcactgtac aagagagagc cggattccta g | 111 |
| auggaaucga aagcuuuacu gguccugacg cuggccgucu ggcuucaaag uuuaaccgcc uccaggggag<br>gcguugccgc cgcagaucag aggcgugauu uuauugacau cgagucuaaa uuugcauuac gcacaccaga<br>ggauacugcc gaagauaccu gucacuuaau ccccggcgua gccgagagcg uggccacuug ccauuucaac<br>cauaguucaa aaaccuuuau ggucauucac ggcuggaccg ucaccgguau guacgaaucu ugggugccua<br>aacuggucgc ugcacuguac aagcgggaac cagauucuua g | 112 |
| auggaaucga aagcuuuacu gguccugacg cuggccgucu ggcuucaaag uuuaaccgcc uccaggggag<br>gcguugccgc cgcagaucag aggcgugauu uuauugacau cgagucuaaa uuugcauuac gcacaccaga<br>ggauacugcc gaagauaccu gucacuuaau ccccggcgua gccgagagcg uggccacuug ccauuucaac<br>cauaguucaa aaaccuuuau ggucauucac ggcuggaccg ucaccgguau guacgaaucu ugggugccua<br>aacuggucgc ugcacuguac aaacgcgaac cagauucuua g | 113 |
| gacaaacagg attcgtcaaa agagaggtgt attaaagtgc cgatcaaatg taatttaaca gctaaacttt ccctccttgg<br>aaaacaggga aagctgccca cttctagctg ccctgccatc ccctttaaag ggcgacttgc tcagcgccaa accgcggctc | 114 |

TABLE 3 -continued

| Sequence | SEQ ID NO |
|---|---|
| cagccctctc cagcctccgg ctcagccggc tcatcagtcg gtccgcgcct tgcagctcct ccagagggac gcgccccgag<br>atggagagca aagccctgct cgtgctgact ctggccgtgt ggctccagag tctgaccgcc tcccgcggag gggtggccgc<br>cgccgaccaa agaagagatt ttatcgacat cgaaagtaaa tttgccctaa ggacccctga agacacagct gaggacactt<br>gccacctcat tcccggagta gcagagtccg tggctacctg tcatttcaat cacagcagca aaaccttcat ggtgatccat<br>ggctggacgg taacaggaat gtatgagagt tgggtgccaa aacttgtggc cgccctgtac aagagagaac cagactccaa<br>tgtcattgtg gtggactggc tgtcacgggc tcaggagcat tacccagtgt ccgcgggcta caccaaact | |
| atggagagca aggccctgct ggtgctgacc ctggccgtgt ggctgcagag cctgaccgcc agccgcggcg gcgtggccgc<br>cgccgaccag cgccgcgact tcatcgacat cgagagcaag ttcgccctgc gcacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagcgcgagc ccgacagcaa<br>cgtgatcgtg gtggactggc tgagccgcgc ccaggagcac taccccgtga gcgccggcta caccaagctg | 115 |
| atggagagca aggccctgct ggtgctgacc ctggccgtgt ggctgcagag cctgaccgcc agcagaggcg gcgtggccgc<br>cgccgaccag agaagagact tcatcgacat cgagagcaag ttcgccctga gaacccccga ggacaccgcc gaggacacct<br>gccacctgat ccccggcgtg gccgagagcg tggccacctg ccacttcaac cacagcagca agaccttcat ggtgatccac<br>ggctggaccg tgaccggcat gtacgagagc tgggtgccca agctggtggc cgccctgtac aagagagagc ccgacagcaa<br>cgtgatcgtg gtggactggc tgagcagagc ccaggagcac taccccgtga gcgccggcta caccaagctg tag | 116 |
| atggagagca aagccttgtt agtgctcaca ctggcggttt ggctccagag cctgacggcc tcaagagggg gcgttgcagc<br>cgccgatcag aggcgcgatt tcatcgacat tgaatctaaa tttgcactcc gaacgcccga ggatacggcc gaggacacat<br>gtcacttgat tcccggcgtc gctgagagcg tggctacttg tcactttaat catagcagta aaactttcat ggtgattcat<br>gggtggaccg tgaccggcat gtatgagtca tgggtaccta aactggtggc ggcactgtac aaacgggagc cagattctaa<br>cgtcatcgtc gtcgattggt tgtcccgtgc acaggaacac tacccagtga gtgcaggata caccaagctg tag | 117 |
| atggagagca aggccctgct ggtgctgacc ctggccgtgt ggctgcagag cctgacagcc agcagaggag gagtggccgc<br>tgctgaccag aggcgggact tcattgatat tgagagcaag tttgccctgc ggaccccaga ggacacagct gaggacacct<br>gccacctgat ccctggggtg gccgagagcg tggccacctg ccacttcaac cacagcagca agaccttcat ggtgatccac<br>ggctggacag tgacaggcat gtatgagagc tgggtgccca agctggtggc cgccctgtac aagcgggagc cagacagcaa<br>tgtgattgtg gtggactggc tgagccgggc ccaggagcac taccctgtgt ctgctggcta caccaagctg tag | 118 |
| atggagagca aggccctgct ggtgctgacc ctggccgtgt ggctgcaatc tcttaccgcc tctaggggag gcgtggccgc<br>agccgaccaa aggcgcgatt ttatcgacat agagtcgaag ttcgctctga ggacccccga ggacacagct gaggatacat<br>gtcacctcat tccgggagtg gcggaatccg tcgccacttg ccactttaac cattcatcca aaactttcat ggtaattcat<br>ggatggaccg tcactggaat gtatgaaagc tgggtgccta agctggtcgc cgccctttac aagagagaac cagacagcaa<br>cgtgattgtt gttgattggt tgtccagagc ccaagaacac tacccagtgt ccgccgggta taccaagctt tag | 119 |
| atggaaagca aagccctgct tgtgctgact ctggccgtgt ggttgcagag tctgaccgcc tccaggggcg gtgttgcagc<br>ggcagaccaa aggagagact ttattgatat cgaatcaaaa tttgctctga gaactccaga ggataccgcc gaggacacct<br>gccaccttat tccgggtgtc gccgaatccg tggccacttg ccacttcaac catagttcaa agactttcat ggtgatacac<br>ggctggactg tcacaggcat gtacgagagt tgggtgccaa agctggtcgc tgcactgtat aagagggagc ccgactccaa<br>cgtcattgtg gtggactggc tgtctcgggc acaggagcat tatcccgttt ctgctgggta caccaaactc tag | 120 |
| auggaaagua aagcacuacu gguccucacc uuagcuguau ggcugcaguc uuugacagcg agccgcgggg<br>ggguggcagc ugcagaccaa cgccgggauu ucauugacau agaaagcaaa uuugccuuac gcaccccaga<br>agacacagcu gaagauacuu gccaucucau ccccggcgua gcugaaagcg uggcuaccug ucacuuuaac<br>cacaguucca agaccuucau ggugauccac ggcuggacug ucacaggaau guacgaguca ugggugccga<br>agcugguggc ggccuuguau aaacgcgagc cugacaguaa ugucauagug guggacuggc ugagccgagc<br>ccaagagcac uaccccguga gugcuggaua uacaaaacug uag | 121 |
| auggaaagca aagcccuguu agugcucacc cuggccguau ggcugcaguc ucugacagcu agccguggug<br>gcguugccgc ugcugaccag cguagggacu uuaucgauau ugaguccaaa uuugcccucc gcacaccuga<br>agauaccgcc gaggacaccu gucaucucau acccggcguc gcugaaagcg uugcuaccug ccacuuuaac<br>cauucgucca agaccuuuau ggugauccac ggguggacag uuaccgguau guacgagucg uggguccccca<br>aacuagucgc ugcccuuuac aagagagagc cugauucuaa cgugaucguc guugacuggu ugagcagagc<br>ccaggagcac uaccccguau cggcugggua cacaaagcug uag | 122 |
| atggagagca aagccctgct cgtgctgact ctggccgccg ccgaccaaag aagagatttt atcgacatcg aaagtaaatt<br>tgccctaagg acccctgaag acacagctga ggacacttgc cacctcattc ccggagtagc agagtccgtg gctacctgtc<br>atttcaatca cagcagcaaa accttcatgg tgatccatgg ctggacggta acaggaatgt atgagagttg ggtgccaaaa<br>cttgtggccg ccctgtacaa gagagaacca gactccaatg tcattgtggt ggactggctg tcacgggctc aggagcatta<br>cccagtgtcc gcgggctaca ccaaactggt gggacaggat gtggcccggt ttatcaactg gatggaggag gagtttaact<br>accctctgga caatgtccat ctcttgggat acagccttgg agcccatgct gctggcattg caggaagtct gaccaataag<br>aaagtcaaca gaattactgg cctcgatcca gctggaccta actttgagta tgcagaagcc ccgagtcgtc tttctcctga<br>tgatgcagat tttgtagacg tcttacacac attcaccaga gggtcccctg gtcgaagcat tggaatccag aaaccagttg<br>ggcatgttga catttacccg aatggaggta cttttcagcc aggatgtaac attggagaag ctatccgcgt gattgcagag<br>agaggacttg gagatgtgga ccagctagtg aagtgctccc acgagcgctc cattcatctc ttcatcgact ctctgttgaa<br>tgaagaaaat ccaagtaagg cctacaggtg cagttccaag gaagcctttg agaaagggct ctgcttgagt tgtagaaaga<br>accgctgcaa caatctgggc tatgagatca ataaagtcag agccaaaaga agcagcaaaa tgtacctgaa gactcgttct<br>cagatgccct acaaagtctt ccattaccaa gtaaagattc atttttctgg gactgagagt gaaacccata ccaatcaggc<br>ctttgagatt tctctgtatg gcaccgtggc cgagagtgag aacatcccat tcactctgcc tgaagtttcc acaaataaga<br>cctactcctt cctaatttac acagaggtag atattggaga actactcatg ttgaagctca aatggaagag tgattcatac<br>tttagctggt cagactggtg gagcagtccc ggcttcgcca ttcagaagat cagagtaaaa gcaggagaga ctcagaaaaa<br>ggtgatcttc tgttctaggg agaaagtgtc tcatttgcag aaaggaaagg cacctgcggt atttgtgaaa tgccatgaca<br>agtctctgaa taagaagtca ggctgaaact gggcgaatct acagaacaaa gaacggcatg tgaattctgt gaagaatgaa<br>gtggaggaag taacttttac aaaacatacc cagtgtttgg ggtgtttcaa aagtggattt tcctgaatat taatcccagc | 123 |

TABLE 3 -continued

| Sequence | SEQ ID NO |
|---|---|
| cctacccttg ttagttattt taggagacag tctcaagcac taaaaagtgg ctaattcaat ttatggggta tagtggccaa<br>atagcacatc ctccaacgtt aaaagacagt ggatcatgaa aagtgctgtt ttgtcctttg agaaagaaat aattgtttga<br>gcgcagagta aaataaggct ccttcatgtg gcgtattggg ccatagccta taattggtta gaacctccta ttttaattgg<br>aattctggat ctttcggact gaggccttct caaactttac tctaagtctc caagaataca gaaaatgctt ttccgcggca<br>cgaatcagac tcatctacac agcagtatga atgatgtttt agaatgattc cctcttgcta ttggaatgtg gtccagacgt<br>caaccaggaa catgtaactt ggagagggac gaagaaaggg tctgataaac acagaggttt taaacagtcc ctaccattgg<br>cctgcatcat gacaaagtta caaattcaag gagatataaa atctagatca attaattctt aataggcttt atcgtttatt<br>gcttaatccc tctctccccc ttcttttttg tctcaagatt atattataat aatgttctct gggtaggtgt tgaaaatgag cctgtaatcc<br>tcagctgaca cataatttga atggtgcaga aaaaaaaaaa gaaaccgtaa ttttattatt agattctcca aatgattttc<br>atcaatttaa aatcattcaa tatctgacag ttactcttca gttttaggct taccttggtc atgcttcagt tgtacttcca gtgcgtctct<br>tttgttcctg gctttgacat gaaaagatag gtttgagttc aaattttgca ttgtgtgagc ttctacagat tttagacaag<br>gaccgttttt actaagtaaa agggtggaga ggttcctggg gtggattcct aagcagtgct tgtaaaccat cgcgtgcaat<br>gagccagatg gagtaccatg agggttgcta tttgttgttt ttaacaacta atcaagagtg agtgaacaac tatttataaa<br>ctagatctcc tatttttcag aatgctcttc tacgtataaa tatgaaatga taaagatgtc aaatatctca gaggctatag<br>ctgggaaccc gactgtgaaa gtatgtgata tctgaacaca tactagaaag ctctgcatgt gtgttgtcct tcagcataat<br>tcggaaggga aaacagtcga tcaagggatg tattggaaca tgtcggagta gaaattgttc ctgatgtgcc agaacttcga<br>ccctttctct gagagagatg atcgtgccta taaatagtag gaccaatgtt gtgattaaca tcatcaggct tggaatgaat<br>tctctctaaa aataaaatga tgtatgattt gttgttggca tccccttat taattcatta aatttctgga tttgggttgt gacccagggt<br>gcattaactt aaaagattca ctaaagcagc acatagcact gggaactctg gctccgaaaa actttgttat atatatcaag<br>gatgttctgg ctttacattt tatttattag ctgtaaatac atgtgtggat gtgtaaatgg agcttgtaca tattggaaag<br>gtcattgtgg ctatctgcat ttataaatgt gtggtgctaa ctgtatgtgt ctttatcagt gatggtctca cagagccaac<br>tcactcttat gaaatgggct ttaacaaaac aagaaagaaa cgtacttaac tgtgtgaaga aatggaatca gcttttaata<br>aaattgacaa cattttatta ccaca | |
| atggagagca aggccctgct ggtgctgacc ctggccgccg ccgaccagag aagagacttc atcgacatcg agagcaagtt<br>cgccctgaga acccccgagg acaccgccga ggacacctgc cacctgatcc ccggcgtggc cgagagcgtg gccacctgcc<br>acttcaacca cagcagcaag accttcatgg tgatccacgg ctggaccgtg accggcatgt acgagagctg ggtgcccaag<br>ctggtggccg ccctgtacaa gagagagccc gacagcaacg tgatcgtggt ggactggctg agcagagccc aggagcacta<br>ccccgtgagc gccggctaca ccaagctggt gggccaggac gtggccagat tcatcaactg gatggaggag gagttcaact<br>acccccctgga caacgtgcac ctgctgggct acagcctggg cgcccacgcc gccggcatcg ccggcagcct gaccaacaag<br>aaggtgaaca gaatcaccgg cctggacccc gccggcccca acttcgagta cgccgaggcc cccagcagac tgagccccga<br>cgacgccgac ttcgtggacg tgctgcacac cttcaccaga ggcagccccg gcagaagcat cggcatccag aagcccgtgg<br>gccacgtgga catctacccc aacggcggca ccttccagcc cggctgcaac atcggcgagg ccatcagagt gatcgccgag<br>agaggcctgg gcgacgtgga ccagctggtg aagtgcagcc acgagagaag catccacctg ttcatcgaca gcctgctgaa<br>cgaggagaac cccagcaagg cctacagatg cagcagcaag gaggccttcg agaagggcct gtgcctgagc tgcagaaaga<br>acagatgcaa caacctgggc tacgagatca acaaggtgag agccaagaga agcagcaaga tgtacctgaa gaccagaagc<br>cagatgccct acaaggtgtt ccactaccag gtgaagatcc acttcagcgg caccgagagc gagacccaca ccaaccaggc<br>cttcgagatc agcctgtacg gcaccgtggc cgagagcgag aacatcccct tcaccctgcc cgaggtgagc accaacaaga<br>cctacagctt cctgatctac accgaggtgg acatcggcga gctgctgatg ctgaagctga agtggaagag cgacagctac<br>ttcagctgga gcgactggtg gagcagcccc ggcttcgcca tccagaagat cagagtgaag gccggcgaga cccagaagaa<br>ggtgatcttc tgcagcagag agaaggtgag ccacctgcag aagggcaagg cccccgccgt gttcgtgaag tgccacgaca<br>agagcctgaa caagaagagc ggctag | 124 |
| atggagtcaa aagctctgct tgtgctgact ctggctgcag cagatcagcg cagagacttt attgatattg agtccaagtt<br>cgctcttcgt actcccgaag acactgccga agacacctgc cacctgatcc cgggcgtcgc cgagtctgtg gccacctgcc<br>atttcaatca ctcatcaaaa accttcatgg taatccacgg ctggacggtc accgggatgt atgagtcctg ggtgcccaaa<br>ctggtggccg cattgtataa gagagagcca gatagcaatg tcatagtggt ggactggctt tcgcgtgctc aggagcacta<br>tccggtttcc gctgggtaca caaaactcgt cggccaggat gtcgcacggt ttatcaattg gatggaagaa gaatttaatt<br>acccactgga caatgtccat ctcctagggt attcgctcgg agcccacgct gcaggtatcg ctggctcact gacgaacaaa<br>aaggtgaacc gcatcaccgg gctcgacccg gcgggtccaa actttgaata tgccgaggct cccagtaggc ttagtccaga<br>cgacgccgat ttcgtggacg tcctgcatac cttcacaagg ggcagtccgg ggaggtcgat tggcattcag aagcccgtgg<br>gccacgtgga catatatcca aatggtggga cctttcagcc cggatgcaat atcggagagg cgattagggt catcgccgaa<br>cggggtcttg gcgacgttga tcagctagtt aaatgcagtc acgagcgcag tattcattta tttatagatt ctctcctcaa<br>cgaagagaat ccctcgaagg cctatcggtg tagctctaag gaagcttttg agaagggact gtgccttagt tgcaggaaga<br>accgatgcaa taatctgggc tatgaaatca ataaggtgcg agcaaagaga agctcaaaaa tgtacctgaa gacccgcagc<br>cagatgccat acaaagtttt ccactaccaa gtgaagattc atttctctgg cacggagagc gagacacaca ctaaccaggc<br>cttcgagata tcgttatatg gcacagtcgc agaatctgag aatatcccat ttacgcttcc cgaagtatct acaaacaaga<br>catactcatt cctgatatac accgaagtgg acattggaga gctactgatg ttgaaattga agtggaagag tgactcctat<br>ttctcttgga gcgattggtg gtcgtctccc ggcttcgcta tccagaaaat acgcgtaaag gcaggtgaaa cccagaaaaa<br>ggtcattttc tgctcaagag aaaaggtcag ccacctacag aagggcaagg cccctgcagt tttcgtgaag tgtcatgata<br>agtctcttaa caagaagtcg ggtag | 125 |
| atggagagca aggccctgct ggtgctgacc ctggccgctg ctgaccagag gcgggacttc attgatattg agagcaagtt<br>tgccctgcgg accccagagg acacagctga ggacacctgc cacctgatcc ctggggtggc cgagagcgtg gccacctgcc<br>acttcaacca cagcagcaag accttcatgg tgatccacgg ctggacagtg acaggcatgt atgagagctg ggtgcccaag<br>ctggtggccg ccctgtacaa gcgggagcca gacagcaatg tgattgtggt ggactggctg agccgggccc aggagcacta<br>ccctgtgtct gctggctaca ccaagctggt gggccaggat gtggcccgct tcatcaactg gatggaggag gagttcaact<br>accccctgga caacgtgcac ctgctgggct acagcctggg cgcccacgcc gccggcattg ctggcagcct gaccaacaag<br>aaggtgaacc gcatcaccgg cctggaccct gctggcccca actttgaata tgcagaggcc cccagccggc tgagcccaga<br>tgatgctgac tttgtggatg tgctgcacac cttcacccgg ggcagccctg gccgcagcat cggcatccag aagcctgtgg<br>gccacgtgga catctaccca aatggaggca ccttccagcc cggctgcaac attggagagg ccatccgggt gattgctgag<br>cggggcctgg gagatgtgga ccagctggtg aagtgcagcc atgagaggag catccacctg ttcatcgaca gcctgctgaa<br>tgaggagaac cccagcaagg cctaccgctg cagcagcaag gaggcctttg agaagggcct gtgcctgagc tgcaggaaga<br>accgctgcaa caacctgggc tatgagatca acaaggtgcg ggccaagagg agcagcaaga tgtacctgaa gaccaggagc<br>cagatgccct acaaggtgtt ccactaccag gtgaagatcc acttcagcgg cacagagagc gagacccaca ccaaccaggc<br>ctttgagatc agcctgtatg gaacagtggc cgagagcgag aacatcccct tcaccctgcc tgaggtgtcc accaacaaga | 126 |

TABLE 3 -continued

| Sequence | SEQ ID NO |
|---|---|
| cctacagctt cctgatctac acagaggtgg acattggaga gctgctgatg ctgaagctga agtggaagag tgacagctac<br>ttctcctgga gcgactggtg gagcagccct ggctttgcca tccagaagat ccgggtgaag gccggggaga cccagaagaa<br>ggtgatcttc tgcagccggg agaaggtgag ccacctgcag aagggcaagg ccccagctgt gtttgtgaag tgccacgaca<br>agagcctgaa caagaagagc ggctag | |
| atggagagca aggccctgct ggtgctgacc ctggccgccg ccgaccagag aagagacttt atagacattg aatcaaaatt<br>cgcactccgt accccagagg ataccgcaga ggatacttgt cacctgattc ctggagttgc tgaaagtgtc gcaacctgtc<br>actttaacca ctcttccaag actttcatgg tgatccatgg ctggacagtg acaggcatgt acgagtcctg ggtgcccaaa<br>ctagtggccg ccctgtataa acgcgagcct gattcgaatg tgatagtggt tgattggctc agcagagctc aggagcatta<br>cccagtgtcc gcagggtata ccaagctggt gggccaggat gtggccagat ttattaattg gatggaggaa gaattcaatt<br>atcctctgga caatgtccac ttacttggtt acagcttagg cgcacacgca gctggcatcg caggctcctt gacaaataag<br>aaagtaaatc gtattaccgg actggatccg gctggcccaa acttcgaata cgcagaggcg ccatcaagat tgagccctga<br>tgatgctgac tttgttgacg ttttgcacac ctttacgaga ggttctccag gaagatctat cgggatccag aaacctgttg<br>gacacgtgga catttaccct aatggcggta cctttcagcc cgggtgtaat atcggcgaag caatccgggt aatagcagag<br>cgggggctgg gcgatgtaga ccagttagtg aaatgctctc acgagcggtc tattcacctg tttatcgact ccctcctgaa<br>tgaggaaaat cccagcaagg cgtaccggtg ttcctcgaag gaggcctttg agaaaggcct gtgcctgtcc tgccgaaaaa<br>accggtgcaa taatttagga tatgagatta ataaagtgcg tgccaaacgc agcagcaaaa tgtacctgaa gacccgcagt<br>cagatgccat ataaagtatt ccactatcaa gtgaaaatcc actttagcgg gaccgaaagc gagacccaca ccaaccaggc<br>ttttgaaatc tcactgtatg gaaccgtagc tgaaagtgaa aacatcccct ttactctgcc agaggtctct actaataaga<br>cctactcgtt cctcatatat accgaggtgg atataggcga gcttctgatg ttgaaactta agtggaagtc cgacagttat<br>ttctcttgga gcgactggtg gtctagtcca ggcttcgcca ttcagaaaat ccgggtcaag gctggcgaga cgcaaaaaaa<br>ggtgatcttt tgctcgaggg agaaggtgtc ccacctacaa aagggcaaag cgcccgctgt ctttgtgaag tgtcacgaca<br>agagcctaaa caagaaatct ggctag | 127 |
| atggaatcca aagcactgct ggtgctgacg ctggccgctg cagatcagcg ccgtgacttt atcgatatag agtccaaatt<br>tgctctgcgc accccctgagg atactgcgga ggacacctgc catctgatac caggagtggc cgagagcgtg gctacctgcc<br>actttaacca tagctctaag acttttatgg tcatccacgg atggacagtg accggcatgt atgaaagttg ggttccaaaa<br>ttggttgccg ctttgtacaa acgggaaccc gattctaacg tgatcgttgt tgactggctc tcaagggctc aggaacacta<br>ccccgtgtcc gcagggtata cgaagttggt gggacaagat gttgctagat ttataaactg gatggaggag gagtttaatt<br>accccctgga taacgtccat ttattggggt attctttagg ggcacacgct gcgggtatcg ctgggtcctt aaccaataag<br>aaggtgaacc ggatcaccgg attggatcca gccggaccga acttcgagta cgcggaagct ccatccaggc tgtcacctga<br>cgatgctgac tttgtggacg ttctccatac cttcacacgc ggaagcccgg gtcggtcaat cggaattcag aagcctgtcg<br>gccacgtgga tatctatcca aacgggggaa cctttcagcc cggatgtaac atcggggagg ccatcagagt tatcgccgaa<br>cgcggactgg gggatgtgga tcagctggtg aagtgtagcc atgagcggag tatacatctg tttattgact ctctgctaaa<br>tgaagagaat ccatccaaag catatcggtg tagcagtaag gaagcctttg agaagggcct gtgtttgagc tgtcgcaaaa<br>accgttgcaa caacctcgga tatgagatta acaaagtccg cgctaaaagg tctagtaaga tgtatctcaa aacgagaagt<br>cagatgcctt acaaggtgtt ccattaccaa gtgaaaatac acttcagcgg aactgagtct gagacccaca caaaccaggc<br>gttcgaaatc agcctctacg gcacggtcgc tgaatctgag aacatcccct tcactctgcc tgaagtctca acaaacaaga<br>catactcctt cctcatttac acggaggtgg acattggaga actgctgatg ctgaagctga aatggaaatc agacagctat<br>ttcagctggt ctgattggtg gtcttcacca ggctttgcca ttcagaaaat tagggttaag gccggtgaga cacagaagaa<br>agtcattttt tgctcgcgcg agaaagtttc tcacctccaa aaaggcaagg ctcctgctgt gtttgtcaaa tgccacgaca<br>agagcttaaa taagaaatct ggctag | 128 |
| auggaaagua aggcacuacu cguuuugaca cuagccgccg cugaucagcg cagagacuuu aucgauaucg<br>aaucuaaauu cgcuuugcgc acccccgaag acacugcuga agauacaugc caccuuaucc cuggggugggc<br>ugaauccguc gccacuugcc auuucaacca uucaagcaag acuuucaugg ugauccacgg auggacgguc<br>acaggcaugu acgaauccug ggugcccaag cucgucgcug cccuguacaa gagagaacca gacuccaaug<br>ucauuguugu cgacuggcug agcagggcuc aggaacauua ucccgugucu gcuggauaca caaagcuggu<br>cgggcaagac guagccagau uuaucaacug gauggaggag gaauuuaacu acccgcugga caacguacau<br>cugcuugguu auuccuuagg ggcccacgcc gccgggauug cagggucucu gacgaacaaa aaggucaauc<br>ggauuaccgg gcucgaucca gccgguccaa auuucgaaua cgcugaagcg ccuucaagac uguccccaga<br>ugaugcagau uucguggaug uccuacacac guuuacuaga ggaucaccag gacgcaguau cggaauccaa<br>aaacccgucg gacacgugga uaucuauccc aauggaggaa cuuuccaacc gggauguaau auuggugagg<br>ccaucagggu gauugccgaa cgugguuugg gagacguuga ucaacuggug aaguguagcc acgaaaggag<br>uauucaucug uuuauugacu cacuucugaa ugaggagaac cccucaaaag cuuacaggug uucaucaaag<br>gaggcauuug agaaaggccu uugucugucg ugcaggaaga aucgauguaa uaaucucgga uacgaaauua<br>acaagguuag ggcgaagcgg aguaguaaga uguauuuaaa gacccguagu cagaugcccu acaaggucuu<br>ccacuaucaa gugaaaaucc acuuuucggg caccgaaucc gaaacacaca ccaaccaggc cuucgagauu<br>ucuuuauaug ggaccguggc cgaaagugag aauauaccuu ucacauuacc cgaggugucu acaaacaaga<br>cguauuccuu cuuaauuuac acagaaguug acauaggcga gcugcuaaug cugaagcuaa aguggaagag<br>cgauucguau uucaguuggu cagacuggug guccagccca ggauuugcaa uccagaaaau ucgcgucaaa<br>gccggugaga cacaaaaaaa aguuauauuc uguucuaggg aaaaagugag ccaucuucag aaagguaagg<br>ccccagccgu cuuuguuaag ugccacgaca agucccuaaa uaaaaaguca ggcuag | 129 |
| auggaaucua aggcacugcu uguguugacc uuggcugccg cugaucagag gagagacuuc aucgauauug<br>aaagcaaauu cgcccuucgc acuccugagg auacugcuga ggauacaugc cauuuaaucc ccggcguagc<br>ugagagcguu gcuacguguc acuucaacca caguucaaaa acuuucaugg uaauucacgg cuggacagua<br>accggcaugu augagagcug gguuccaaag uuaguagccg cccuuuacaa acgugaaccc gacuccaaug<br>ugauaguugu agauuggcug ucccgugccc aagaacacua ccccguuuca gcuggauaca caaaacucgu<br>aggacaggac guggcccgcu uuauuaacug gauggaggag gaguucaauu acccacugga uaauguacau<br>uugcuaggau acucacuggg ggcccacgca gccggcaucg cuggcaguuu aacaaacaag aaggugaaua<br>gaauuacagg ccuggauccc gcuggcccga acuucgagua cgccgaggcc ccuucacgcc ugagcccuga<br>ugacgcggac uucgucgacg ugcugcacac cuucacacgc gggucaccag gacguucuau ugguauccag<br>aaacccgucg ggcacgucga caucuaucca aaugggggaa ccuuucaacc cggaugcaau auuggcgaag<br>caaucagagu cauagcugag agaggauugg gagacgugga ccagcucgug aaauguuccc acgaacguuc<br>aauacaccua uuuaucgacu cccuacugaa ugaggagaac ccaagcaagg cauaccguug cagcucuaag | 130 |

TABLE 3 -continued

| Sequence | SEQ ID NO |
|---|---|
| gaggccuucg aaaaaggauu gugccuguca ugucgaaaaa accgcuguaa uaaucucggc uacgaaauua acaaaguacg cgcaaaacgg aguucuaaaa uguaccuuaa gacccggagu cagaugcccu auaaaguuuu ucauuaccag guuaagaucc auuuuuccgg gacagagucu gaaacucaca ccaaccaagc cuuugaaaua agccuuuacg guacaguugc ugagucggag aacauucccu uuacccuucc agagguuagu acuaacaaga cauacagcuu ccuaauauac acugaaguag acauuggaga acuucugaug cuuaaacuca aauggaaguc ugauaguuac uuuaguuggu ccgacuggug gagcucccca ggcuucgcaa uucaaaaaau ccgcgucaaa gcaggcgaga cccaaaagaa aguuauuuuc ugcucaaggg agaaggucag ccauuuacag aaaggaaaag cccccgcggu cuucgucaag ugccaugaua aaucacugaa caaaaaguca ggguag | |
| ccgtctgccc tttcccccctc ttctcgttgg cagggttgat cctcattact gtttgctcaa acgtttagaa gtgaatttag gtccctcccc ccaacttatg attttatagc caataggtga tgaggtttat ttgcatattt ccagtcacat aagcagcctt ggcgtgaaaa cagtgtcaga ctcgattccc cctcttcctc ctcctcaagg gaaagctgcc cacttctagc tgccctgcca tcccctttaa agggcgactt gctcagcgcc aaaccgcggc tccagccctc tccagcctcc ggctcagccg gctcatcagt cggtccgcgc cttgcagctc ctccagaggg acgcgccccg agatggagag caaagccctg ctcgtgctga ctctggccgt gtggctccag agtctgaccg cctcccgcgg aggggtggcc gccgccgacc aaagaagaga ttttatcgac atcgaaagta aatttgccct aaggacccct gaagacacag ctgaggacac ttgccacctc attcccggag tagcagagtc cgtggctacc tgtcatttca atcacagcag caaaaccttc atggtgatcc atggctggac ggtaacagga atgtatgaga gttgggtgcc aaaacttgtg gccgccctgt acaagagaga accagactcc aatgtcattg tggtggactg gctgtcacgg gctcaggagc attacccagt gtccgcgggc tacaccaaac tggtgggaca ggatgtggcc cggtttatca actggatgga ggaggagttt aactaccctc tggacaatgt ccatctcttg ggatacagcc ttggagccca tgctgctggc attgcaggaa gtctgaccaa taagaaagtc aacagaatta ctggcctcga tccagctgga cctaactttg agtatgcaga agccccgagt cgtctttctc ctgatgatgc agattttgta gacgtcttac acacattcac cagagggtcc cctggtcgaa gcattggaat ccagaaacca gttgggcatg ttgacattta cccgaatgga ggtacttttc agccaggatg taacattgga gaagctatcc gcgtgattgc agagagagga cttggagatg tggaccagct agtgaagtgc tcccacgagc gctccattca tctcttcatc gactctctgt tgaatgaaga aaatccaagt aaggcctaca ggtgcagttc caaggaagcc tttgagaaag ggctctgctt gagttgtaga aagaaccgct gcaacaatct gggctatgag atcaataaag tcagagccaa aagaagcagc aaaatgtacg aagactcgtt ctcagatgcc ctacaaagtc ttccattacc aagtaaagat tcatttttct gggactgaga gtgaaaccca taccaatcag gcctttgaga tttctctgta tggcaccgtg gccgagagtg agaacatccc attcactctg cctgaagttt ccacaaataa gacctactcc ttcctaattt acacagaggt agatattgga gaactactca tgttgaagct caaatggaag agtgattcat actttagctg gtcagactgg tggagcagtc ccggcttcgc cattcagaag atcagagtaa aagcaggaga gactcagaaa aaggtgatct tctgttctag ggagaaagtg tctcatttgc agaaaggaaa ggcacctgcg ttgtatttgtga aatgccatga caagtctctg aataagaagt caggctgaaa ctgggcgaat ctacagaaca aagaacggca tgtgaattct gtgaagaatg aagtggagga agtaactttt acaaaacata cccagtgttt ggggtgtttc aaaagtggat tttcctgaat attaatccca gccctaccct tgttagttat tttaggagac agtctcaagc actaaaaagt ggctaattca atttatgggg tatagtggcc aaatagcaca tcctccaacg ttaaaagaca gtggatcatg aaaagtgatg ttttgtcctt tgagaaagaa ataattgttt gagcgcagag taaaataagg ctccttcatg tggcgtattg ggccatagcc tataattggt tagaacctcc tattttaatt ggaattctgg atctttcgga ctgaggcctt ctcaaacttt actctaagtc tccaagaata cagaaaatgc ttttccgcgg cacgaatcag actcatctac acagcagtat gaatgatgtt ttagaatgat tccctcttgc tattggaatg tggtccagac gtcaaccagg aacatgtaac ttggagaggg acgaagaaag ggtctgataa acacagaggt tttaaacagt ccctaccatt ggcctgcatc atgacaaagt tacaaattca aggagatata aaatctagat caattaattc ttaataggct ttatcgttta ttgcttaatc cctctctccc ccttcttttt tgtctcaaga ttatattata ataatgttct ctgggtaggt gttgaaaatg agcctgtaat cctcagctga cacataattt gaatggtgca gaaaaaaaaa aagaaaccgt aattttatta ttagattctc caaatgattt tcatcaattt aaaatcattc aatatctgac agttactctt cagttttagg cttaccttgg tcatgcttca gttgtacttc cagtgcgtct cttttgttcc tggctttgac atgaaaagat aggtttgagt tcaaattttg cattgtgtga gcttctacag attttagaca aggaccgttt ttactaagta aaagggtgga gaggttcctg gggtggattc ctaagcagtg cttgtaaacc atcgcgtgca atgagccaga tggagtacca tgagggttgc tatttgttgt ttttaacaac taatcaagag tgagtgaaca actatttata aactagatct cctatttttc agaatgctct tctacgtata aatatgaaat gataaagatg tcaaatatct cagaggctat agctgggaac ccgactgtga aagtatgtga tatctgaaca catactagaa agctctgcat gtgtgttgtc cttcagcata attcggaagg gaaaacagtc gatcaaggga tgtattggaa catgtcggag tagaaattgt tcctgatgtg ccagaacttc gaccctttct ctgagagaga tgatcgtgcc tataaatagt aggaccaatg ttgtgattaa catcatcagg cttggaatga attctctcta aaaataaaat gatgtatgat ttgttgttgg catccccttt attaattcat taaatttctg gatttgggtt gtgacccagg gtgcattaac ttaaaagatt cactaaagca gcacatagca ctgggaactc tggctccgaa aaactttgtt atatatatca aggatgttct ggctttacat tttatttatt agctgtaaat acatgtgtgg atgtgtaaat ggagcttgta catattggaa aggtcattgt ggctatctgc atttataaat gtgtggtgct aactgtatgt gtctttatca gtgatggtct cacagagcca actcactctt atgaaatggg ctttaacaaa acaagaaaga aacgtactta actgtgtgaa gaaatggaat cagcttttaa taaaattgac aacattttat taccaca | 131 |
| atggtgatcc acggctggac cgtgaccggc atgtacgaga gctgggtgcc caagctggtg gccgccctgt acaagagaga gcccgacagc aacgtgatcg tggtggactg gctgagcaga gcccaggagc actacccgt gagcgccggc tacaccaagc tggtgggcca ggacgtggcc agattcatca actggatgga ggaggagttc aactaccccc tggacaacgt gcacctgctg ggctacagcc tgggcgccca cgccgccggc atcgccggca gcctgaccaa caagaaggtg aacagaatca ccggcctgga ccccgccggc cccaacttcg agtacgccga ggcccccagc agactgagcc ccgacgacgc cgacttcgtg gacgtgctgc acaccttcac cagaggcagc cccggcagaa gcatcggcat ccagaagccc gtgggccacg tggacatcta ccccaacggc ggcaccttcc agcccggctg caacatcggc gaggccatca gagtgatcgc cgagagaggc ctgggcgacg tggaccagct ggtgaagtgc agccacgaga gaagcatcca cctgttcatc gacagcctgc tgaacgagga gaaccccagc aaggcctaca gatgcagcag caaggaggcc ttcgagaagg gcctgtgcct gagctgcaga aagaacagat gcaacaacct gggctacgag atcaacaagg tgagagccaa gagaagcagc aagatgtacg aggacagctt cagcgacgcc ctgcagagcc tgcccctgcc cagcaaggac agcttcttct gggactag | 132 |
| atggtgatcc acgggtggac tgtcacaggc atgtacgaaa gctgggtgcc gaagctggtt gctgcattgt ataaaagaga gcccgattct aatgtgatcg tggttgattg gctcagtaga gcccaggaac actatcctgt atccgctgga tacacgaagc tggtcgggca agatgtagca cgatttatca actggatgga agaggaattc aattatccac ttgataatgt tcacttactg ggatactctc tgggcgcaca cgcagcaggt atcgctggta gcctcaccaa taagaaagtt aaccgaatta caggattgga tcctgcaggg cccaattttg agtacgccga ggctcctagc aggctctctc cagatgacgc tgactttgtc gatgttctgc acactttcac ccgcggttcg cccggcagat ccataggcat ccaaaagcca gtgggtcacg ttgacattta ccctaacggc gggacatttc aacctgggtg caacataggc gaggcgatca gagtcattgc tgagagggga ctgggtgacg tegatcaget | 133 |

TABLE 3 -continued

| Sequence | SEQ ID NO |
|---|---|
| cgttaagtgc tcacacgaga ggtccatcca tctgtttatc gattcgcttc tcaacgaaga gaatcccagc aaggcgtaca<br>gatgcagctc aaaagaggca tttgaaaaag ggctatgcct gagctgtcga aagaaccggt gtaataattt gggctacgaa<br>atcaataaag tgagggctaa gaggagctcc aagatgtatg aggacagttt ttccgatgcc ctacagtccc tgccgcttcc<br>cagcaaagac agcttcttct gggattag | |
| atggtgatcc acggctggac agtgacaggc atgtatgaga gctgggtgcc caagctggtg gccgccctgt acaagcggga<br>gccagacagc aatgtgattg tggtggactg gctgagccgg gcccaggagc actaccctgt gtctgctggc tacaccaagc<br>tggtgggcca ggatgtggcc cgcttcatca actggatgga ggaggagttc aactaccccc tggacaacgt gcacctgctg<br>ggctacagcc tgggcgccca cgccgccggc attgctggca gcctgaccaa caagaaggtg aaccgcatca ccggcctgga<br>ccctgctggc cccaactttg aatatgcaga ggcccccagc cggctgagcc cagatgatgc tgactttgtg gatgtgctgc<br>acaccttcac ccggggcagc cctggccgca gcatcggcat ccagaagcct gtgggccacg tggacatcta cccaaatgga<br>ggcaccttcc agcccggctg caacattgga gaggccatcc gggtgattgc tgagcggggc ctgggagatg tggaccagct<br>ggtgaagtgc agccatgaga ggagcatcca cctgttcatc gacagcctgc tgaatgagga gaaccccagc aaggcctacc<br>gctgcagcag caaggaggcc tttgagaagg gcctgtgcct gagctgcagg aagaaccgct gcaacaacct gggctatgag<br>atcaacaagg tgcgggccaa gaggagcagc aagatgtatg aggacagctt cagtgatgcc ctgcagagcc tgcccctgcc<br>cagcaaggac agcttcttct gggactag | 134 |
| atggtgatcc acggctggac cgtgaccggc atgtacgaga gctgggttcc gaagctagta gctgccctgt acaagagaga<br>acccgactcc aacgtgatcg ttgtggactg gctttctaga gcgcaggagc attatccagt ctctgcgggg tacacaaaac<br>tggtgggcca ggacgtcgcc aggttcatta actggatgga ggaggaattt aactacccgc tggacaacgt gcatctcctg<br>gggtacagcc tcggggccca cgctgcggga attgccggct cgcttactaa caagaaggtg aaccggatca ctggcttaga<br>ccccgccggt cccaactttg agtacgccga agcacccagt cggctctccc cagatgatgc ggactttgtg gatgttctgc<br>acacctttac tagaggctcc cccgggcgct caatcggcat tcagaagcct gtcggccatg tggacatcta tccgaatggg<br>ggaacttttc agccaggctg caatataggt gaggccattc gggtgatcgc agaacgggga ttgggggacg tagatcagtt<br>agtgaagtgt tcacatgaga gatccatcca tctgtttata gactccttgc tgaacgaaga gaacccttca aaagcttatc<br>gctgtagttc taaggaagcc ttcgagaaag ggttgtgcct ctcgtgtcga aagaaccggt gtaacaacct agggtacgag<br>attaacaagg tgagagccaa acggagctcc aagatgtatg aggacagctt cagcgatgca ctgcagagct tgccattacc<br>gtctaaggat tctttttttct gggattag | 135 |
| atggttattc atgggtggac cgtcactggg atgtatgaaa gctgggtgcc gaaacttgtc gcagccttat acaagagaga<br>accggattcc aacgttatag tggtcgactg gctatctcgt gcccaggaac attaccctgt gtccgcaggt tatactaagc<br>tggttggaca ggacgtggcc cgattcatca actggatgga ggaggaattc aactatccac tggacaacgt gcacctactg<br>ggatactccc tgggtgccca cgccgctgga attgcaggat ctctgacaaa taagaaagtt aacagaatta ccggcctgga<br>tccagcagga cccaacttcg agtacgcgga agcaccatct cggctgagcc ccgatgacgc agatttcgtg gacgttctgc<br>atacctttac aaggggaagt ccagggcgtt ctattggcat tcagaaaccg gtcggtcatg tggacattta tccaaacggc<br>ggtacgtttc agccaggctg taacatcggc gaggctatcc gagtgattgc agaaagaggc ttgggagatg tggatcagtt<br>ggtaaagtgc tcccacgagc gctctatcca cctttttatc gactctctgc tcaacgagga aaaccccagc aaagcttatc<br>gctgctcttc taaggaagcg ttcgaaaagg ggctctgctt gagttgccgc aagaatcggt gtaataattt gggttatgaa<br>atcaacaaag tgcgagccaa gaggtctagc aaaatgtatg aggattcatt ttcagatgca ctgcaaagcc tgcctctgcc<br>ttctaaggac tccttcttct gggactag | 136 |
| auggugaucc acggguggac ugucacugga auguacgagu ccugggugcc aaaguuaguu gcagcgcuuu<br>auaagagaga accugauagc aacguuauug uggucgacug gcugucccgc gcccaagagc acuacccagu<br>gucugcgggu uauacuaagc ugguagggca ggauguggca cgguuuauaa auuggaugga ggaagaguuu<br>aauuaucccc ucgacaaugu gcaucugcuc ggcuauagcu ugggagcgca cgcagcaggg aucgcgggaa<br>gucuaaccaa uaagaaggug aaucgcauua cagggcuuga uccugccggc ccaaacuuug aauaugcuga<br>agcccccuca cggcugagcc cugacgacgc agauuuuguc gauguccugc acacuuucac acgcggcucu<br>ccuggcagau cuaucggcau ucaaaaaccc gugggccaug uagauauuua ucccaaugga ggcacauuuc<br>aaccuggaug caacauagga gaggcaauaa ggguaauugc cgaaaggggc cugggcgacg uugaucagcu<br>ugugaaaugc ucacacgagc guagcaucca cuuguucauc gacagccugu ugaaugagga gaaccccagc<br>aaagccuaca ggugcucaag uaaggaggcu uuugaaaaag gucuuugucu uagcugccga aaaaaccgau<br>gcaacaaucu gggcuaugaa aucaauaaag uaagggccaa gcgguccuca aaaauguacg aagacucuuu<br>uucggaugca cugcagagcc ugccguugcc aucaaaagac aguuuuuucu gggacuag | 137 |
| auggugauuc auggauggac ggugacaggu auguacgaga guuggguucc aaaacuggug gcggcucugu<br>auaaacgaga accugacagc aaugugaucg ucguugauug gcugaguaga gcacaggagc acuaccccgu<br>gucagcugga uacacuaaac ucguagguca ggauguggcc cguuuuauaa acuggaugga agaggaguuc<br>aauuauccac uggauaacgu ccauuuacuu ggcuacagcc ugggagccca ugccgcaggc aucgccgggu<br>cauugacaaa uaagaaaguc aaccguauua cgggcuuaga uccugccggc ccaaauuucg aauaugccga<br>agcuccuagu cgauugucac cggaugaugc ugacuucguc gaugugcugc acacuuucac cagaggcuca<br>cccgguagau ccaucgguau ccagaagcca gugggacacg uggacauuua uccaaacgga gggacauuuc<br>agccaggcug uaauauuggc gaggcuauca gggugauugc agagcgcggc uuaggugacg uggaucaauu<br>ggucaagugu ucgcacgaaa gaucaauuca ccuuuucauc gauagucugc uuaacgagga aaacccauca<br>aaggcauauc ggugcuccag uaaagaagca uuugaaaagg gauugugccu gucuugcaga aagaaccgau<br>gcaacaauuu gggguaugag auuaauaaag uuagagcuaa aaggagcagu aaaauguacg aagacuccuu<br>cucggacgcu uuacaaagcc ucccucuccc auccaaggau uccuucuucu gggauuag | 138 |

Untranslated Regions (UTRs)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the invention comprising an open reading frame (ORF) encoding a LPL polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the LPL polypeptide. In some embodiments, the UTR is heterologous to the ORF encoding the LPL polypeptide. In some embodiments, the polynucleotide comprises two or more 5'UTRs or functional fragments thereof, each of which have the same or different nucleotide sequences. In some embodiments, the polynucleotide comprises two or more 3'UTRs or functional fragments thereof, each of which have the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO: 84), where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial $H^+$-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety. UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5'UTR and/or a 3'UTR selected from any of the UTRs disclosed herein. In some embodiments, the 5'UTR and or the 3'UTR comprise:

| Name | SEQ ID NO: |
|---|---|
| 5'UTR-001 (Upstream UTR) | 35 |
| 5'UTR-002 (Upstream UTR) | 36 |
| 5'UTR-003 (Upstream UTR) | 37 |
| 5'UTR-004 (Upstream UTR) | 38 |
| 5'UTR-005 (Upstream UTR) | 39 |
| 5'UTR-006 (Upstream UTR) | 40 |
| 5'UTR-007 (Upstream UTR) | 41 |
| 5'UTR-008 (Upstream UTR) | 42 |
| 5'UTR-009 (Upstream UTR) | 43 |
| 5'UTR-010 (Upstream UTR) | 44 |
| 5'UTR-011 (Upstream UTR) | 45 |
| 5'UTR-012 (Upstream UTR) | 46 |
| 5'UTR-013 (Upstream UTR) | 47 |
| 5'UTR-014 (Upstream UTR) | 48 |
| 5'UTR-015 (Upstream UTR) | 49 |
| 5'UTR-016 (Upstream UTR) | 50 |
| 5'UTR-017 (Upstream UTR) | 51 |
| 5'UTR-018 (Upstream UTR) | 52 |
| 142-3p 5'UTR-001 (Upstream UTR including miR142-3p binding site) | 53 |
| 142-3p 5'UTR-002 (Upstream UTR including miR142-3p binding site) | 54 |
| 142-3p 5'UTR-003 (Upstream UTR including miR142-3p binding site) | 55 |
| 142-3p 5'UTR-004 (Upstream UTR including miR142-3p binding site) | 56 |
| 142-3p 5'UTR-005 (Upstream UTR including miR142-3p binding site) | 57 |
| 142-3p 5'UTR-006 (Upstream UTR including miR142-3p binding site) | 58 |
| 142-3p 5'UTR-007 (Upstream UTR including miR142-3p binding site) | 59 |
| 3'UTR-001 (Creatine Kinase UTR) | 60 |
| 3'UTR-002 (Myoglobin UTR) | 61 |
| 3'UTR-003 (α-actin UTR) | 62 |
| 3'UTR-004 (Albumin UTR) | 63 |
| 3'UTR-005 (α-globin UTR) | 64 |
| 3'UTR-006 (G-CSF UTR) | 65 |
| 3'UTR-007 (Col1a2; collagen, type I, alpha 2 UTR) | 66 |
| 3'UTR-008 (Col6a2; collagen, type VI, alpha 2 UTR) | 67 |
| 3'UTR-009 (RPN1; ribophorin I UTR) | 68 |
| 3'UTR-010 (LRP1; low density lipoprotein receptor-related protein 1 UTR) | 69 |
| 3'UTR-011 (Nnt1; cardiotrophin-like cytokine factor 1 UTR) | 70 |
| 3'UTR-012 (Col6a1; collagen, type VI, alpha 1 UTR) | 71 |
| 3'UTR-013 (Calr; calreticulin UTR) | 72 |
| 3'UTR-014 (Col1a1; collagen, type I, alpha 1 UTR) | 73 |
| 3'UTR-015 (Plod1; procollagen-lysine, 2-oxoglutarate 5-dioxygenase 1 UTR) | 74 |
| 3'UTR-016 (Nucb1; nucleobindin 1 UTR) | 75 |

-continued

| Name | SEQ ID NO: |
|---|---|
| 3'UTR-017 (α-globin) | 76 |
| 3'UTR-018 | 77 |
| 3' UTR with miR 142-3p binding site | 191 |
| 3' UTR with miR 126-3p binding site | 192 |
| 3' UTR with miR 142-3p and miR 126-3p binding sites | 193 |
| 3' UTR with 3 miR 142-3p binding sites | 194 |
| 3'UTR with miR 142-5p binding site | 195 |
| 3'UTR with 3 miR 142-5p binding sites | 196 |
| 3'UTR with 2 miR 142-5p binding sites and 1 miR 142-3p binding site | 197 |
| 3'UTR with miR 142-3p binding site, P1 insertion | 198 |
| 3'UTR with miR 142-3p binding site, P2 insertion | 199 |
| 3'UTR with miR 142-3p binding site, P3 insertion | 200 |
| 3'UTR with miR 155-5p binding site | 201 |
| 3' UTR with 3 miR 155-5p binding sites | 202 |
| 3'UTR with 2 miR 155-5p binding sites and 1 miR 142-3p binding site | 203 |

In certain embodiments, the 5'UTR and/or 3'UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 35-59 and/or 3'UTR sequences comprises any of SEQ ID NOs: 60-77 and 191-203, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

"Translational enhancer polynucleotide" or "translation enhancer polynucleotide sequence" refer to a polynucleotide that includes one or more of the TEE provided herein and/or known in the art (see. e.g., U.S. Pat. Nos. 6,310,197, 6,849,405, 7,456,273, 7,183,395, US2009/0226470, US2007/0048776, US2011/0124100, US2009/0093049, US2013/0177581, WO2009/075886, WO2007/025008, WO2012/009644, WO2001/055371, WO1999/024595, EP2610341A1, and EP2610340A1; the contents of each of which are incorporated herein by reference in their entirety), or their variants, homologs, or functional derivatives. In some embodiments, the polynucleotide of the invention comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence.

In some embodiments, a 5'UTR and/or 3'UTR comprising at least one TEE described herein can be incorporated in a monocistronic sequence such as, but not limited to, a vector system or a nucleic acid vector.

In some embodiments, a 5'UTR and/or 3'UTR of a polynucleotide of the invention comprises a TEE or portion thereof described herein. In some embodiments, the TEEs in the 3'UTR can be the same and/or different from the TEE located in the 5'UTR.

In some embodiments, a 5'UTR and/or 3'UTR of a polynucleotide of the invention can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In one embodiment, the 5'UTR of a polynucleotide of the invention can include 1-60, 1-55, 1-50, 1-45, 1-40, 1-35, 1-30, 1-25, 1-20, 1-15, 1-10, 9, 8, 7, 6, 5, 4, 3, 2, or 1 TEE sequences. The TEE sequences in the 5'UTR of the polynucleotide of the invention can be the same or different TEE sequences. A combination of different TEE sequences in the 5'UTR of the polynucleotide of the invention can include combinations in which more than one copy of any of the different TEE sequences are incorporated.

In some embodiments, the 5'UTR and/or 3'UTR comprises a spacer to separate two TEE sequences. As a non-limiting example, the spacer can be a 15 nucleotide spacer and/or other spacers known in the art. As another non-limiting example, the 5'UTR and/or 3'UTR comprises a TEE sequence-spacer module repeated at least once, at least twice, at least 3 times, at least 4 times, at least 5 times, at least 6 times, at least 7 times, at least 8 times, at least 9 times, at least 10 times, or more than 10 times in the 5'UTR and/or 3'UTR, respectively. In some embodiments, the 5'UTR and/or 3'UTR comprises a TEE sequence-spacer module repeated 1, 2, 3, 4, 5, 6, 7, 8, 9, or 10 times.

In some embodiments, the spacer separating two TEE sequences can include other sequences known in the art that can regulate the translation of the polynucleotide of the invention, e.g., miR sequences described herein (e.g., miR binding sites and miR seeds). As a non-limiting example, each spacer used to separate two TEE sequences can include a different miR sequence or component of a miR sequence (e.g., miR seed sequence).

In some embodiments, a polynucleotide of the invention comprises a miR and/or TEE sequence. In some embodiments, the incorporation of a miR sequence and/or a TEE sequence into a polynucleotide of the invention can change the shape of the stem loop region, which can increase and/or decrease translation. See e.g., Kedde et al., Nature Cell Biology 2010 12(10):1014-20, herein incorporated by reference in its entirety).

MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

In one embodiment, a polynucleotide of the invention can include at least one miRNA-binding site in the 5'UTR and/or 3'UTR in order to regulate cytotoxic or cytoprotective mRNA therapeutics to specific cells such as, but not limited to, normal and/or cancerous cells. In another embodiment, a polynucleotide of the invention can include two, three, four, five, six, seven, eight, nine, ten, or more miRNA-binding sites in the 5'-UTR and/or 3'-UTR in order to regulate cytotoxic or cytoprotective mRNA therapeutics to specific cells such as, but not limited to, normal and/or cancerous cells.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the invention.

To further drive the selective degradation and suppression in APCs and macrophage, a polynucleotide of the invention can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-5481, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the invention to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

As a non-limiting example, miRNA binding sites for miRNAs that are over-expressed in certain cancer and/or tumor cells can be removed from the 3'UTR of a polynucleotide of the invention, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from TABLE 4, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from TABLE 4, including any combination thereof. In some embodiments, the miRNA binding site binds to miR-142 or is complementary to miR-142. In some embodiments, the miR-142 comprises SEQ ID NO:30. In some embodiments, the miRNA binding site binds to miR-142-3p or miR-142-5p. In some embodiments, the miR-142-3p binding site comprises SEQ ID NO:32. In some embodiments, the miR-142-5p binding site comprises SEQ ID NO:34. In some embodiments, the miRNA binding site comprises a nucleotide sequence at least 80%, at least 85%, at least 90%, at least 95%, or 100% identical to SEQ ID NO:32 or SEQ ID NO:34.

TABLE 4 miR-142 and milt-142 binding sites

| SEQ ID NO. | Description | Sequence |
|---|---|---|
| 30 | 42 | GACAGUGCAGUCACCCAUAAAGUAGAAAG CACUACUAACAGCACUGGAGGGUGUAGUG UUUCCUACUUUAUGGAUGAGUGUACUGUG |
| 31 | 42-3p | UGUAGUGUUUCCUACUUUAUGGA |
| 32 | 42-3p binding site | UCCAUAAAGUAGGAAACACUACA |
| 33 | 42-5p | CAUAAAGUAGAAAGCACUACU |
| 34 | 42-5p binding site | AGUAGUGCUUUCUACUUUAUG |

In some embodiments, a miRNA binding site is inserted in the polynucleotide of the invention in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the invention can be engineered to include more than one miRNA site expressed in different tissues or different cell types of a subject. As a non-limiting example, a polynucleotide of the invention can be engineered to include miR-192 and miR-122 to regulate expression of the polynucleotide in the liver and kidneys of a subject. In another embodiment, a polynucleotide of the invention can be engineered to include more than one miRNA site for the same tissue.

In some embodiments, the expression of a polynucleotide of the invention can be controlled by incorporating at least one miR binding site in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable amino lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A *Pumilio*-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example, a polynucleotide of the invention can include at least one miR-122 binding site in order to dampen expression of an encoded polypeptide of interest in the liver. As another non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a wild type LPL or LPL-S447Stop protein polypeptide (e.g., the wild-type sequence, functional fragment, or variant thereof) and (ii) a miRNA binding site (e.g., a miRNA binding site that binds to miR-142).

In some embodiments, the polynucleotide of the invention comprises a uracil-modified sequence encoding a LPL polypeptide disclosed herein and a miRNA binding site disclosed herein, e.g., a miRNA binding site that binds to miR-142. In some embodiments, the uracil-modified sequence encoding a LPL polypeptide comprises at least one chemically modified nucleobase, e.g., 5-methoxyuracil. In some embodiments, at least 95% of a type of nucleobase (e.g., uricil) in a uracil-modified sequence encoding a LPL polypeptide of the invention are modified nucleobases. In some embodiments, at least 95% of uricil in a uracil-modified sequence encoding a LPL polypeptide is 5-methoxyuridine. In some embodiments, the polynucleotide comprising a nucleotide sequence encoding a LPL polypeptide disclosed herein and a miRNA binding site is formulated with a delivery agent, e.g., a lipid having the Formula (I), (IA), (II), (IIa), (IIb), (IIe), (IId) or (IIe), e.g., any of Compounds 1-232.

3' UTRs

In certain embodiments, a polynucleotide of the present invention (e.g., a polynucleotide comprising a nucleotide sequence encoding a LPL polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

Regions Having a 5' Cap

The invention also includes a polynucleotide that comprises both a 5' Cap and a polynucleotide of the present invention (e.g., a polynucleotide comprising a nucleotide sequence encoding a LPL polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a LPL polypeptide) incorporate a cap moiety.

In some embodiments, polynucleotides of the present invention (e.g., a polynucleotide comprising a nucleotide sequence encoding a LPL polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7G$-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dicucleotide form of a cap analog known in the art and/or described herein. Non-limiting examples of a N7-(4-chlorophenoxyethyl) substituted dicucleotide form of a cap analog include a N7-(4-chlorophenoxyethyl)-G(5')ppp(5')G and a N7-(4-chlorophenoxyethyl)-$m^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a LPL polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

In some embodiments, the polynucleotides of the present disclosure (e.g., a polynucleotide comprising a nucleotide sequence encoding a LPL polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

Start Codon Region

The invention also includes a polynucleotide that comprises both a start codon region and the polynucleotide described herein (e.g., a polynucleotide comprising a nucleotide sequence encoding a LPL polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miR binding site. The perfect complement of a miR binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

Stop Codon Region

The invention also includes a polynucleotide that comprises both a stop codon region and the polynucleotide described herein (e.g., a polynucleotide comprising a nucleotide sequence encoding a LPL polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

Insertions and Substitutions

The invention also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example, the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

Polynucleotide Comprising an mRNA Encoding a LPL Polypeptide

In certain embodiments, a polynucleotide of the present disclosure, for example a polynucleotide comprising an mRNA nucleotide sequence encoding a LPL polypeptide, comprises from 5' to 3' end:

(i) a 5' cap provided above;
(ii) a 5' UTR, such as the sequences provided above;
(iii) an open reading frame encoding a LPL polypeptide, e.g., a sequence optimized nucleic acid sequence encoding LPL disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g, a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type LPL or LPL-S447Stop.

Methods of Making Polynucleotides

The present disclosure also provides methods for making a polynucleotide of the invention (e.g., a polynucleotide comprising a nucleotide sequence encoding a LPL polypeptide) or a complement thereof.

In some aspects, a polynucleotide (e.g., a RNA, e.g., an mRNA) disclosed herein, and encoding a LPL polypeptide, can be constructed using in vitro transcription. In other aspects, a polynucleotide (e.g., a RNA, e.g., an mRNA) disclosed herein, and encoding a LPL polypeptide, can be constructed by chemical synthesis using an oligonucleotide synthesizer.

In other aspects, a polynucleotide (e.g., a RNA, e.g., an mRNA) disclosed herein, and encoding a LPL polypeptide is made by using a host cell. In certain aspects, a polynucleotide (e.g., a RNA, e.g., an mRNA) disclosed herein, and encoding a LPL polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a LPL polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a LPL polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M2671, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L6991, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase $\alpha$ (pol $\alpha$) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 78 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention.

For Example, polymerase chain reaction (PCR), strand displacement amplification (SDAnucleic acid sequence-based amplification (NASBA), also called transcription mediated amplification (TMA), and rolling-circle amplification (RCA), can be utilized in the manufacture of one or more regions of the polynucleotides of the present invention.

Assembling polynucleotides or nucleic acids by a ligase is also widely used. DNA or RNA ligases promote intermolecular ligation of the 5' and 3' ends of polynucleotide chains through the formation of a phosphodiester bond.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a LPL polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. U.S. Pat. No. 8,999,380 or U.S. Pat. No. 8,710,200, all of which are herein incorporated by reference in their entireties.

c. Purification of Polynucleotides Encoding LPL

Purification of the polynucleotides described herein (e.g., a polynucleotide comprising a nucleotide sequence encoding a LPL polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a LPL polypeptide) removes impurities that can reduce or remove an unwanted immune response, e.g., reducing cytokine activity.

In some embodiments, the polynucleotide of the invention (e.g., a polynucleotide comprising a nucleotide sequence encoding a LPL polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a LPL polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded LPL protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a LPL polypeptide comprising one or more of the point mutations known in the art.

In some embodiments, the use of RP-HPLC purified polynucleotide increases LPL protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of LPL protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional LPL protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of LPL protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable LPL activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional LPL in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding LPL

In some embodiments, the polynucleotides of the present invention (e.g., a polynucleotide comprising a nucleotide sequence encoding a LPL polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a LPL polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a LPL polypeptide. In some embodiments, the polynucleotide further comprises a miRNA binding site, e.g., a miRNA binding site that binds miR-142, and/or miR-126.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* $21^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an IVT polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a LPL polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent, (e.g., a compound having the Formula (I), (IA), (II), (IIa), (IIb), (IIc), (IId) or (IIe), e.g., any of Compounds 1-232).

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, M D, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER® 188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc. and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs)

concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

Delivery Agents a. Lipid Compound

The present disclosure provides pharmaceutical compositions with advantageous properties. For example, the lipids described herein (e.g. those having any of Formula (I), (IA), (II), (IIa), (IIb), (IIe), (IId), (IIe), (III), (IV), (V), or (VI) may be advantageously used in lipid nanoparticle compositions for the delivery of therapeutic and/or prophylactic agents to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

The disclosure relates to novel lipids and lipid nanoparticle compositions including a novel lipid. The disclosure also provides methods of delivering a therapeutic and/or prophylactic to a mammalian cell, specifically delivering a therapeutic and/or prophylactic to a mammalian organ, producing a polypeptide of interest in a mammalian cell, and treating a disease or disorder in a mammal in need thereof. For example, a method of producing a polypeptide of interest in a cell involves contacting a nanoparticle composition comprising an mRNA with a mammalian cell, whereby the mRNA may be translated to produce the polypeptide of interest. A method of delivering a therapeutic and/or prophylactic to a mammalian cell or organ may involve administration of a nanoparticle composition including the therapeutic and/or prophylactic to a subject, in which the administration involves contacting the cell or organ with the composition, whereby the therapeutic and/or prophylactic is delivered to the cell or organ.

In one set of embodiments, lipid nanoparticles (LNPs) are provided. In one embodiment, a lipid nanoparticle comprises lipids including an ionizable lipid, a structural lipid, a phospholipid, and mRNA. Each of the LNPs described herein may be used as a formulation for the mRNA described herein. In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid:about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino or cationic lipid and the structural lipid is a neutral lipid, and the sterol is a cholesterol. In some embodiments, the LNP has a molar ratio of 50:38.5:10:1.5 of ionizable lipid: cholesterol:PEG2000-DMG:DSPC.

a. Lipid Compound

The present disclosure provides pharmaceutical compositions with advantageous properties. In particular, the present application provides pharmaceutical compositions comprising:

(a) a polynucleotide comprising a nucleotide sequence encoding a LPL polypeptide; and (b) a delivery agent.

In some embodiments, the delivery agent comprises a lipid compound having the Formula (I)

(I)

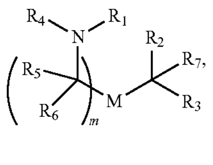

wherein $R_1$ is selected from the group consisting of $C_{530}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, $—(CH_2)_nCHQR$, CHQR, $CQ(R)_2$, and unsubstituted $C_{16}$ alkyl, where Q is selected from a carbocycle, heterocycle, OR, $O(CH_2)_nN(R)_2$, C(O)OR, OC(O)R, $CX_3$, $CX_2H$, $CXH_2$, CN, $N(R)_2$, $C(O)N(R)_2$, N(R)C(O)R, $N(R)S(O)_2R$, $N(R)C(O)N(R)_2$, $N(R)C(S)N(R)_2$, $N(R)R_8$, $O(CH_2)_nOR$, $N(R)C(=NR_9)N(R)_2$, $N(R)C(=CHR_9)N(R)_2$, $OC(O)N(R)_2$, N(R)C(O)OR, —N(OR)C(O)R, $N(OR)S(O)_2R$, N(OR)C(O)OR, $N(OR)C(O)N(R)_2$, $N(OR)C(S)N(R)_2$, $—N(OR)C(=NR_9)N(R)_2$, $N(OR)C(=CHR_9)N(R)_2$, $C(=NR_9)N(R)_2$, $C(=NR_9)R$, —C(O)N(R)OR, and $C(R)N(R)_2C(O)OR$, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In some embodiments, a subset of compounds of Formula (I) includes those in which $R_1$ is selected from the group consisting of $C_{520}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, —$(CH_2)_nCHQR$, CHQR, $CQ(R)_2$, and unsubstituted $C_{16}$ alkyl, where Q is selected from a carbocycle, heterocycle, OR, $O(CH_2)_nN(R)_2$, C(O)OR, OC(O)R, $CX_3$, $CX_2H$, $CXH_2$, CN, $N(R)_2$, $C(O)N(R)_2$, N(R)C(O)R, $N(R)S(O)_2R$, $N(R)C(O)N(R)_2$, N(R)C(S) $N(R)_2$, and —$C(R)N(R)_2C(O)OR$, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of C12 alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof, wherein alkyl and alkenyl groups may be linear or branched.

In some embodiments, a subset of compounds of Formula (I) includes those in which when $R_4$ is $(CH_2)_nQ$, $(CH_2)_nCHQR$, CHQR, or $CQ(R)_2$, then (i) Q is not $N(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{530}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, —$(CH_2)_nCHQR$, CHQR, $CQ(R)_2$, and unsubstituted $C_{16}$ alkyl, where Q is selected from a $C_{36}$ carbocycle, a 5- to 14-membered heteroaryl having one or more heteroatoms selected from N, O, and S, OR, $O(CH_2)_nN(R)_2$, C(O)OR, OC(O)R, $CX_3$, $CX_2H$, $CXH_2$, CN, —$C(O)N(R)_2$, N(R)C(O)R, $N(R)S(O)_2R$, $N(R)C(O)N(R)_2$, $N(R)C(S)N(R)_2$, —$CRN(R)_2C(O)$ OR, —$N(R)R_8$, —$O(CH_2)_nOR$, —N(R)C(=$NR_9$)N $(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —N(OR)C (S)$N(R)_2$, —N(OR)C(=$NR_9$)$N(R)_2$, —N(OR)C (=$CHR_9$)$N(R)_2$, —C(=$NR_9$) $N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{13}$ alkyl, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which $R_1$ is selected from the group consisting of $C_{530}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, —$(CH_2)_nCHQR$, CHQR, $CQ(R)_2$, and unsubstituted $C_{16}$ alkyl, where Q is selected from a $C_{36}$ carbocycle, a 5- to 14-membered heteroaryl having one or more heteroatoms selected from N, O, and S, OR, $O(CH_2)_nN(R)_2$, C(O)OR, OC(O)R, $CX_3$, $CX_2H$, $CXH_2$, CN, —$C(O)N(R)_2$, N(R)C(O)R, $N(R)S(O)_2R$, $N(R)C(O)N(R)_2$, $N(R)C(S)N(R)_2$, —$CRN(R)_2C(O)$ OR, and a 5- to 14-membered heterocycloalkyl having one or more heteroatoms selected from N, O, and S which is substituted with one or more substituents selected from oxo (=O), OH, amino, and $C_{13}$ alkyl, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of C13 alkyl, C23 alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{520}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, $—(CH_2)_nCHQR$, CHQR, $CQ(R)_2$, and unsubstituted $C_{16}$ alkyl, where Q is selected from a $C_{36}$ carbocycle, a 5- to 14-membered heterocycle having one or more heteroatoms selected from N, O, and S, OR, $O(CH_2)$~$N(R)_2$, C(O)OR, OC(O)R, $CX_3$, $CX_2H$, $CXH_2$, —CN, $C(O)N(R)_2$, N(R)C(O)R, $N(R)S(O)_2R$, $N(R)C(O)N(R)_2$, $N(R)C(S)N(R)_2$, $—CRN(R)_2C(O)OR$, $N(R)R_8$, $O(CH_2)_nOR$, $N(R)C(=NR_9)N(R)_2$, $N(R)C(=CHR_9)N(R)_2$, $—OC(O)N(R)_2$, N(R)C(O)OR, N(OR)C(O)R, $N(OR)S(O)_2R$, N(OR)C(O)OR, $—N(OR)C(O)N(R)_2$, $N(OR)C(S)N(R)_2$, $N(OR)C(=NR_9)N(R)_2$, $N(OR)C(=CHR_9)N(R)_2$, $—C(=NR_9)R$, C(O)N(R)OR, and $C(=NR_9)N(R)_2$, and each n is independently selected from 1, 2, 3, 4, and 5; and when Q is a 5- to 14-membered heterocycle and (i) $R_4$ is $(CH_2)_nQ$ in which n is 1 or 2, or (ii) $R_4$ is $(CH_2)_nCHQR$ in which n is 1, or (iii) $R_4$ is CHQR, and $—CQ(R)_2$, then Q is either a 5- to 14-membered heteroaryl or 8- to 14-membered heterocycloalkyl;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{520}$ alkyl, $C_{520}$ alkenyl, R*YR", YR", and R"M'R';

$R_2$ and $R^3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, $—(CH_2)_nCHQR$, CHQR, $CQ(R)_2$, and unsubstituted $C_{16}$ alkyl, where Q is selected from a $C_{36}$ carbocycle, a 5- to 14-membered heterocycle having one or more heteroatoms selected from N, O, and S, OR, $O(CH_2)_nN(R)_2$, C(O)OR, OC(O)R, $CX_3$, $CX_2H$, $CXH_2$, —CN, $C(O)N(R)_2$, N(R)C(O)R, $N(R)S(O)_2R$, $N(R)C(O)N(R)_2$, $N(R)C(S)N(R)_2$, $—CRN(R)_2C(O)OR$, and each n is independently selected from 1, 2, 3, 4, and 5; and when Q is a 5- to 14-membered heterocycle and (i) $R_4$ is $(CH_2)_nQ$ in which n is 1 or 2, or (ii) $R_4$ is $(CH_2)_nCHQR$ in which n is 1, or (iii) $R_4$ is CHQR, and $CQ(R)_2$, then Q is either a 5- to 14-membered heteroaryl or 8- to 14-membered heterocycloalkyl;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), $C_H(OH)$, P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{530}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, —$(CH_2)_n$CHQR, CHQR, $CQ(R)_2$, and unsubstituted $C_{16}$ alkyl, where Q is selected from a $C_{36}$ carbocycle, a 5- to 14-membered heteroaryl having one or more heteroatoms selected from N, O, and S, —OR, $O(CH_2)_nN(R)_2$, C(O)OR, OC(O)R, $CX_3$, $CX_2H$, $CXH_2$, CN, —$C(O)N(R)_2$, N(R)C(O)R, $N(R)S(O)_2R$, $N(R)C(O)N(R)_2$, $N(R)C(S)N(R)_2$, —$CRN(R)_2C(O)$OR, $N(R)R_8$, —$O(CH_2)_n$OR, N(R)C(=$NR_9$)$N(R)_2$, N(R)C(=$CHR_9$)$N(R)_2$, —$OC(O)N(R)_2$, —N(R)C(O)OR, N(OR)C(O)R, $N(OR)S(O)_2R$, N(OR)C(O)OR, —$N(OR)C(O)N(R)_2$, $N(OR)C(S)N(R)_2$, N(OR)C(=$NR_9$)$N(R)_2$, N(OR)C(=$CHR_9$)$N(R)_2$, —C(=$NR_9$)R, C(O)N(R)OR, and C(=$NR_9$)$N(R)_2$, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{3-14}$ alkyl and $C_{3-14}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{520}$ alkyl, $C_{520}$ alkenyl, R*YR", YR", and R"M'R';

$R_2$ and $R_3$ are independently selected from the group consisting of H, $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of a $C_{36}$ carbocycle, $(CH_2)_nQ$, —$(CH_2)_n$CHQR, CHQR, $CQ(R)_2$, and unsubstituted $C_{16}$ alkyl, where Q is selected from a $C_{36}$ carbocycle, a 5- to 14-membered heteroaryl having one or more heteroatoms selected from N, O, and S, —OR, $O(CH_2)_nN(R)_2$, C(O)OR, OC(O)R, $CX_3$, $CX_2H$, $CXH_2$, CN, —$C(O)N(R)_2$, N(R)C(O)R, $N(R)S(O)_2R$, $N(R)C(O)N(R)_2$, $N(R)C(S)N(R)_2$, —$CRN(R)_2C(O)$OR, and each n is independently selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), $C_H$(OH), P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{3-14}$ alkyl and $C_{3-14}$ alkenyl;

each R* is independently selected from the group consisting of $C_{112}$ alkyl and $C_{212}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{53}$o alkyl, $C_{520}$ alkenyl, R*YR", YR", and R"M'R';

$R_2$ and $R_3$ are independently selected from the group consisting of H, $C_{214}$ alkyl, $C_{214}$ alkenyl, R*YR", YR", and R*OR", or $R_2$ and $R_3$, together with the atom to which they are attached, form a heterocycle or carbocycle;

$R_4$ is $(CH_2)$~Q or $(CH_2)$CHQR, where Q is $N(R)_2$, and n is selected from 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{112}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{520}$ alkyl, $C_{520}$ alkenyl, R*YR", YR", and R"M'R';

$R_2$ and $R_3$ are independently selected from the group consisting of H, $C_{214}$ alkyl, $C_{214}$ alkenyl, R*YR", YR", and R*OR", or $R_2$ and $R_3$, together with the atom to which they are attached, form a heterocycle or carbocycle;

$R_4$ is $(CH_2)_nQ$ or $(CH_2)_n$CHQR, where Q is $N(R)_2$, and n is selected from 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{118}$ alkyl, $C_{218}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_1$12 alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{530}$ alkyl, $C_{520}$ alkenyl, R*YR", YR", and R"M'R';

$R_2$ and $R_3$ are independently selected from the group consisting of $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of $(CH_2)_nQ$, $(CH_2)_nCHQR$, CHQR, and $—CQ(R)_2$, where Q is $N(R)_2$, and n is selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, —S—S—, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{1-18}$ alkyl, $C_{2-18}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{112}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{520}$ alkyl, $C_{520}$ alkenyl, R*YR", YR", and R"M'R';

$R_2$ and $R_3$ are independently selected from the group consisting of $C_{114}$ alkyl, $C_{214}$ alkenyl, R*YR", YR", and R*OR", or $R_2$ and $R_3$, together with the atom to which they are attached, form a heterocycle or carbocycle;

$R_4$ is selected from the group consisting of $(CH_2)_nQ$, $(CH_2)_nCHQR$, CHQR, and $—CQ(R)_2$, where Q is $N(R)_2$, and n is selected from 1, 2, 3, 4, and 5;

each $R_5$ is independently selected from the group consisting of $C_{13}$ alkyl, $C_{23}$ alkenyl, and H;

each $R_6$ is independently selected from the group consisting of $C_{13}$ alkyl, $C_{23}$ alkenyl, and H;

M and M' are independently selected from C(O)O, OC(O), C(O)N(R'), —N(R')C(O), C(O), C(S), C(S)S, SC(S), CH(OH), P(O)(OR')O, $S(O)_2$, an aryl group, and a heteroaryl group;

$R_7$ is selected from the group consisting of $C_{13}$ alkyl, $C_{23}$ alkenyl, and H;

each R is independently selected from the group consisting of $C_{13}$ alkyl, $C_{23}$ alkenyl, and H;

each R' is independently selected from the group consisting of $C_{1-18}$ alkyl, $C_{2-18}$ alkenyl, R*YR", YR", and H;

each R" is independently selected from the group consisting of $C_{314}$ alkyl and $C_{314}$ alkenyl;

each R* is independently selected from the group consisting of $C_{112}$ alkyl and $C_{112}$ alkenyl;

each Y is independently a $C_{36}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

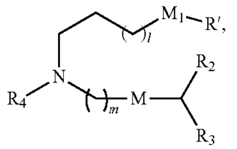

(IA)

or a salt or stereoisomer thereof, wherein 1 is selected from 1, 2, 3, 4, and 5; m is selected from 5, 6, 7, 8, and 9; $M_1$ is a bond or M'; $R_4$ is unsubstituted $C_{13}$ alkyl, or $—(CH_2)_nQ$, in which Q is OH, $NHC(S)N(R)_2$, $NHC(O)N(R)_2$, N(R)C(O)R, $N(R)S(O)_2R$, $—N(R)R_8$, $NHC(=NR_9)N(R)_2$, $NHC(=CHR_9)N(R)_2$, $OC(O)N(R)_2$, N(R)C(O)OR, heteroaryl, or heterocycloalkyl; M and M' are independently selected from C(O)O, OC(O), —C(O)N(R'), P(O)(OR')O, —S—S—, an aryl group, and a heteroaryl group; and $R_2$ and $R_3$ are independently selected from the group consisting of H, $C_{114}$ alkyl, and $C_{214}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9;

$M_1$ is a bond or M';

$R_4$ is unsubstituted $C_{13}$ alkyl, or $(CH_2)_nQ$, in which Q is OH, $NHC(S)N(R)_2$, or $—NHC(O)N(R)_2$;

M and M' are independently selected from C(O)O, OC(O), C(O)N(R'), —P(O)(OR')O, an aryl group, and a heteroaryl group; and $R_2$ and $R_3$ are independently selected from the group consisting of H, $C_{114}$ alkyl, and $C_{214}$ alkenyl.

In certain embodiments, a subset of compounds of Formula (I) includes those of Formula (II):

(II)

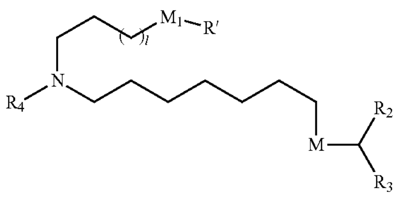

or a salt or stereoisomer thereof, wherein l is selected from 1, 2, 3, 4, and 5; $M_1$ is a bond or M'; $R_4$ is unsubstituted $C_3$ alkyl, or $(CH_2)_nQ$, in which n is 2, 3, or 4, and Q is OH, $NHC(S)N(R)_2$, $NHC(O)N(R)_2$, N(R)C(O)R, $N(R)S(O)_2R$, $N(R)R_8$, $—NHC(=NR_9)N(R)_2$, $NHC(=CHR_9)N(R)_2$, $—OC(O)N(R)_2$, N(R)C(O)OR, heteroaryl, or heterocycloalkyl; M and M' are independently selected from C(O)O, OC(O), C(O)N(R'), P(O)(OR')O, —S—S—, an aryl group, and a heteroaryl group; and $R_2$ and $R_3$ are independently selected from the group consisting of H, $C_{114}$ alkyl, and $C_{214}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{13}$ alkyl, or $(CH_2)_nQ$, in which n is 2, 3, or 4, and Q is OH, $—NHC(S)N(R)_2$, or $NHC(O)N(R)_2$;

M and M' are independently selected from C(O)O, OC(O), C(O)N(R'), —P(O)(OR')O, an aryl group, and a heteroaryl group; and $R_2$ and $R_3$ are independently selected from the group consisting of H, $C_{114}$ alkyl, and $C_{214}$ alkenyl.

In some embodiments, the compound of Formula (I) is of the Formula (IIa), (IIa)

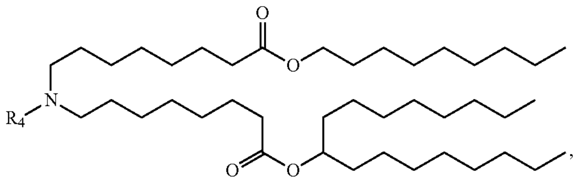

or a salt thereof, wherein $R_4$ is as described above.

In some embodiments, the compound of Formula (I) is of the Formula (IIb), (IIb)

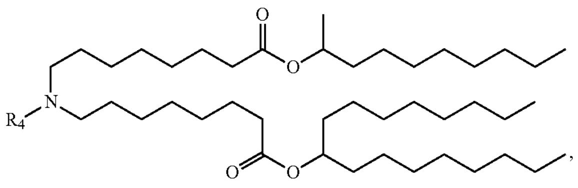

or a salt thereof, wherein $R_4$ is as described above.

In some embodiments, the compound of Formula (I) is of the Formula (IIc), (IIc)

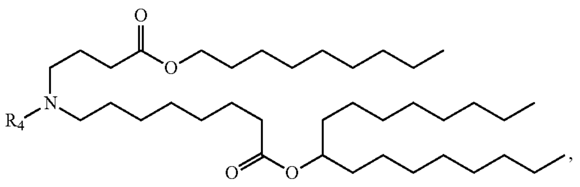

or a salt thereof, wherein $R_4$ is as described above.

In some embodiments, the compound of Formula (I) is of the Formula (IIe):

(IIe)

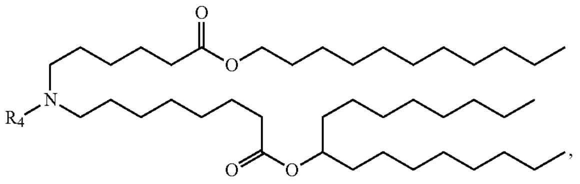

or a salt thereof, wherein $R_4$ is as described above.

In some embodiments, the compound of Formula (IIa), (IIb), (IIc), or (IIe) comprises an $R_4$ which is selected from $(CH_2)_nQ$ and $(CH_2)_nCHQR$, wherein Q, R and n are as defined above.

In some embodiments, Q is selected from the group consisting of OR, OH, $—O(CH_2)_nN(R)_2$, OC(O)R, $CX_3$, CN, N(R)C(O)R, N(H)C(O)R, $N(R)S(O)_2R$, $N(H)S(O)_2R$, $N(R)C(O)N(R)_2$, $N(H)C(O)N(R)_2$, N(H)C(O)N(H)(R), $N(R)C(S)N(R)_2$, $N(H)C(S)N(R)_2$, N(H)C(S)N(H)(R), and a heterocycle, wherein R is as defined above. In some aspects, n is 1 or 2. In some embodiments, Q is OH, $NHC(S)N(R)_2$, or $NHC(O)N(R)_2$.

In some embodiments, the compound of Formula (I) is of the Formula (IId), (IId)

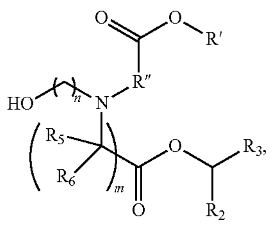

or a salt thereof, wherein $R_2$ and $R_3$ are independently selected from the group consisting of $C_{514}$ alkyl and $C_{514}$ alkenyl, n is selected from 2, 3, and 4, and R', R", $R_5$, $R_6$ and m are as defined above.

In some aspects of the compound of Formula (IId), $R_2$ is $C_8$ alkyl. In some aspects of the compound of Formula (IId), $R_3$ is $C_5C_9$ alkyl. In some aspects of the compound of Formula (IId), m is 5, 7, or 9. In some aspects of the compound of Formula (IId), each $R_5$ is H. In some aspects of the compound of Formula (IId), each $R_6$ is H.

In another aspect, the present application provides a lipid composition (e.g., a lipid nanoparticle (LNP)) comprising: (1) a compound having the Formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a LPL polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "$C_{114}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "$C_{214}$ alkenyl" means a linear or branched hydrocarbon including 2-14 carbon atoms and at least one double bond. An alkenyl group can include one, two, three, four, or more double bonds. For example, $C_{18}$ alkenyl can include one or more double bonds. A $C_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "$C_{36}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O, OC(O), C(O)N(R'), N(R')C(O), C(O), C(S), C(S)S, SC(S), CH(OH), —P(O)(OR')O, $S(O)_2$, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR or OC(O)R), an aldehyde (e.g., C(O)H), a carbonyl (e.g., C(O)R, alternatively represented by C═O), an acyl halide (e.g., C(O)X, in which X is a halide selected from bromide, fluoride, chloride, and iodide), a carbonate (e.g., OC(O)OR), an alkoxy (e.g., OR), an acetal (e.g., $C(OR)_2R''''$, in which each OR are alkoxy groups that can be the same or different and R'''' is an alkyl or alkenyl group), a phosphate (e.g., $P(O)_4^{3}$), a thiol (e.g., SH), a sulfoxide (e.g., S(O)R), a sulfinic acid (e.g., —S(O)OH), a sulfonic acid (e.g., $S(O)_2OH$), a thial (e.g., C(S)H), a sulfate (e.g., $S(O)_4^{2}$), a sulfonyl (e.g., $S(O)_2$), an amide (e.g., $C(O)NR_2$, or N(R)C(O)R), an azido (e.g., $N_3$), a nitro (e.g., $NO_2$), a cyano (e.g., CN), an isocyano (e.g., NC), an acyloxy (e.g., OC(O)R), an amino (e.g., $NR_2$, NRH, or $NH_2$), a carbamoyl (e.g., $OC(O)NR_2$, OC(O)NRH, or —$OC(O)NH_2$), a sulfonamide (e.g., $S(O)_2NR_2$, $S(O)_2NRH$, $S(O)_2NH_2$, $N(R)S(O)_2R$, —$N(H)S(O)_2R$, $N(R)S(O)_2H$, or $N(H)S(O)_2H$), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a $C_{16}$ alkyl group can be further substituted with one, two, three, four, five, or six substituents as described herein.

The compounds of any one of formulae (I), (IA), (II), (IIa), (IIb), (IIc), (IId), and (IIe) include one or more of the following features when applicable.

In some embodiments, $R_4$ is selected from the group consisting of a $C_{36}$ carbocycle, $(CH_2)_nQ$, $(CH_2)_nCHQR$, CHQR, and $CQ(R)_2$, where Q is selected from a $C_{36}$ carbocycle, 5- to 14-membered aromatic or non-aromatic heterocycle having one or more heteroatoms selected from N, O, S, and P, OR, $O(CH_2)_nN(R)_2$, C(O)OR, OC(O)R, $CX_3$, —$CX_2H$, $CXH_2$, CN, $N(R)_2$, $C(O)N(R)_2$, N(R)C(O)R, $N(R)S(O)_2R$, $N(R)C(O)N(R)_2$, —$N(R)C(S)N(R)_2$, and $C(R)N(R)_2C(O)OR$, and each n is independently selected from 1, 2, 3, 4, and 5.

In another embodiment, $R_4$ is selected from the group consisting of a $C_{36}$ carbocycle, $(CH_2)_nQ$, $(CH_2)_nCHQR$, CHQR, and $CQ(R)_2$, where Q is selected from a $C_{36}$ carbocycle, a 5- to 14-membered heteroaryl having one or more heteroatoms selected from N, O, and S, OR, $O(CH_2)_nN(R)_2$, C(O)OR, OC(O)R, $CX_3$, $CX_2H$, $CXH_2$, CN, —$C(O)N(R)_2$, N(R)C(O)R, $N(R)S(O)_2R$, $N(R)C(O)N(R)_2$, $N(R)C(S)N(R)_2$, —$C(R)N(R)_2C(O)OR$, and a 5- to 14-membered heterocycloalkyl having one or more heteroatoms selected from N, O, and S which is substituted with one or more substituents selected from oxo (═O), OH, amino, and $C_{13}$ alkyl, and each n is independently selected from 1, 2, 3, 4, and 5.

In another embodiment, $R_4$ is selected from the group consisting of a $C_{36}$ carbocycle, $(CH_2)_nQ$, $(CH_2)_nCHQR$, CHQR, and $CQ(R)_2$, where Q is selected from a $C_{36}$ carbocycle, a 5- to 14-membered heterocycle having one or more heteroatoms selected from N, O, and S, OR, $O(CH_2)_nN(R)_2$, C(O)OR, OC(O)R, $CX_3$, $CX_2H$, $CXH_2$, CN, $—C(O)N(R)_2$, N(R)C(O)R, $N(R)S(O)_2R$, $N(R)C(O)N(R)_2$, $N(R)C(S)N(R)_2$, $—C(R)N(R)_2C(O)OR$, and each n is independently selected from 1, 2, 3, 4, and 5; and when Q is a 5- to 14-membered heterocycle and (i) $R_4$ is $(CH_2)_nQ$ in which n is 1 or 2, or (ii) $R_4$ is $(CH_2)_nCHQR$ in which n is 1, or (iii) $R_4$ is CHQR, and $CQ(R)_2$, then Q is either a 5- to 14-membered heteroaryl or 8- to 14-membered heterocycloalkyl.

In another embodiment, $R_4$ is selected from the group consisting of a $C_{36}$ carbocycle, $(CH_2)_nQ$, $(CH_2)_nCHQR$, CHQR, and $CQ(R)_2$, where Q is selected from a $C_{36}$ carbocycle, a 5- to 14-membered heteroaryl having one or more heteroatoms selected from N, O, and S, OR, $O(CH_2)_nN(R)_2$, C(O)OR, OC(O)R, $CX_3$, $CX_2H$, $CXH_2$, CN, $—C(O)N(R)_2$, N(R)C(O)R, $N(R)S(O)_2R$, $N(R)C(O)N(R)_2$, $N(R)C(S)N(R)_2$, $—C(R)N(R)_2C(O)OR$, and each n is independently selected from 1, 2, 3, 4, and 5.

In another embodiment, $R_4$ is unsubstituted $C_{14}$ alkyl, e.g., unsubstituted methyl.

In certain embodiments, the disclosure provides a compound having the Formula (I), wherein $R_4$ is $(CH_2)_nQ$ or $(CH_2)_nCHQR$, where Q is $N(R)_2$, and n is selected from 3, 4, and 5.

In certain embodiments, the disclosure provides a compound having the Formula (I), wherein $R_4$ is selected from the group consisting of $(CH_2)_nQ$, $(CH_2)_nCHQR$, CHQR, and $CQ(R)_2$, where Q is $N(R)_2$, and n is selected from 1, 2, 3, 4, and 5.

In certain embodiments, the disclosure provides a compound having the Formula (I), wherein $R_2$ and $R_3$ are independently selected from the group consisting of $C_{214}$ alkyl, $C_{214}$ alkenyl, R*YR", YR", and R*OR", or $R_2$ and $R_3$, together with the atom to which they are attached, form a heterocycle or carbocycle, and $R_4$ is $(CH_2)_nQ$ or $(CH_2)_nCHQR$, where Q is $N(R)_2$, and n is selected from 3, 4, and 5.

In certain embodiments, $R_2$ and $R_3$ are independently selected from the group consisting of $C_{214}$ alkyl, $C_{214}$ alkenyl, R*YR", YR", and R*OR", or $R_2$ and $R_3$, together with the atom to which they are attached, form a heterocycle or carbocycle.

In some embodiments, $R_1$ is selected from the group consisting of $C_{520}$ alkyl and $C_{520}$ alkenyl.

In other embodiments, $R_1$ is selected from the group consisting of R*YR", YR", and R"M'R'.

In certain embodiments, $R_1$ is selected from R*YR" and YR". In some embodiments, Y is a cyclopropyl group. In some embodiments, R* is $C_8$ alkyl or $C_8$ alkenyl. In certain embodiments, R" is $C_{312}$ alkyl. For example, R" can be $C_3$ alkyl. For example, R" can be $C_{48}$ alkyl (e.g., $C_4$, $C_5$, $C_6$, $C_7$, or $C_8$ alkyl).

In some embodiments, $R_1$ is $C_{520}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{520}$ alkenyl. In certain embodiments, $R_1$ is $C_{18}$ alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

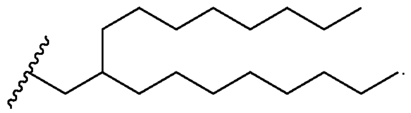 [SMILES: *CC(CCCCCCCC)CCCCCCCC]

In certain embodiments, $R_1$ is unsubstituted $C_{520}$ alkyl or $C_{520}$ alkenyl. In certain embodiments, R' is substituted $C_{520}$ alkyl or $C_{520}$ alkenyl (e.g., substituted with a $C_{36}$ carbocycle such as 1-cyclopropylnonyl).

In other embodiments, $R_1$ is R"M'R'.

In some embodiments, R' is selected from R*YR" and YR". In some embodiments, Y is $C_{38}$ cycloalkyl. In some embodiments, Y is $C_{61}o$ aryl. In some embodiments, Y is a cyclopropyl group. In some embodiments, Y is a cyclohexyl group.

In certain embodiments, R* is $C_1$ alkyl.

In some embodiments, R" is selected from the group consisting of $C_{3-12}$ alkyl and $C_{312}$ alkenyl. In some embodiments, R" adjacent to Y is $C_1$ alkyl. In some embodiments, R" adjacent to Y is $C_{49}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

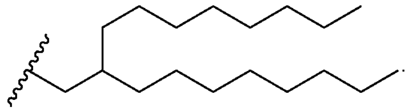 [SMILES: *CC(CCCCCCCC)CCCCCCCC]

In certain embodiments, R' is unsubstituted $C_{11}s$ alkyl. In certain embodiments, R' is substituted $C_{118}$ alkyl (e.g., $C_{115}$ alkyl substituted with a $C_{36}$ carbocycle such as 1-cyclopropylnonyl).

In some embodiments, R" is selected from the group consisting of $C_{314}$ alkyl and $C_{314}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is C(O)O. In some embodiments, M' is OC(O).

In other embodiments, M' is an aryl group or heteroaryl group. For example, M' can be selected from the group consisting of phenyl, oxazole, and thiazole.

In some embodiments, M is C(O)O In some embodiments, M is OC(O). In some embodiments, M is C(O)N(R'). In some embodiments, M is P(O)(OR')O.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{13}$ alkyl (e.g., methyl, ethyl, propyl, or i-propyl).

In some embodiments, $R_2$ and $R_3$ are independently $C_{514}$ alkyl or $C_{514}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{17}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from $(CH_2)_nQ$ and $(CH_2)_nCHQR$.

In some embodiments, Q is selected from the group consisting of OR, OH, —$O(CH_2)_nN(R)_2$, OC(O)R, $CX_3$, CN, N(R)C(O)R, N(H)C(O)R, $N(R)S(O)_2R$, $N(H)S(O)_2R$, $N(R)C(O)N(R)_2$, $N(H)C(O)N(R)_2$, N(H)C(O)N(H)(R), $N(R)C(S)N(R)_2$, $N(H)C(S)N(R)_2$, N(H)C(S)N(H)(R), C(R) $N(R)_2C(O)OR$, a carbocycle, and a heterocycle.

In certain embodiments, Q is OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (═O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{610}$ aryl (such as phenyl) or $C_{36}$ cycloalkyl.

In some embodiments, n is 1. In other embodiments, n is 2. In further embodiments, n is 3. In certain other embodiments, n is 4. For example, $R_4$ can be —$(CH_2)_2OH$. For example, $R_4$ can be $(CH_2)_3OH$. For example, $R_4$ can be $(CH_2)_4OH$. For example, $R_4$ can be benzyl. For example, $R_4$ can be 4-methoxybenzyl.

In some embodiments, $R_4$ is a $C_{36}$ carbocycle. In some embodiments, $R_4$ is a $C_{36}$ cycloalkyl. For example, $R_4$ can be cyclohexyl optionally substituted with e.g., OH, halo, $C_{16}$ alkyl, etc. For example, $R_4$ can be 2-hydroxycyclohexyl.

In some embodiments, R is H.

In some embodiments, R is unsubstituted $C_{13}$ alkyl or unsubstituted $C_{23}$ alkenyl. For example, $R_4$ can be $CH_2CH(OH)CH_3$ or $CH_2CH(OH)CH_2CH_3$.

In some embodiments, R is substituted $C_{13}$ alkyl, e.g., $CH_2OH$. For example, $R_4$ can be $CH_2CH(OH)CH_2OH$.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{320}$ carbocycle (e.g., $C_{318}$ carbocycle, $C_{315}$ carbocycle, $C_{312}$ carbocycle, or $C_{310}$ carbocycle), either aromatic or non-aromatic. In some embodiments, $R_2$ and $R_3$, together with the atom to which they are attached, form a $C_{36}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{36}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{36}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{715}$ carbocycle, such as a cycloheptyl, cyclopentadecanyl, or naphthyl group.

In some embodiments, $R_4$ is selected from $(CH_2)_nQ$ and $(CH_2)_nCHQR$. In some embodiments, Q is selected from the group consisting of OR, OH, $O(CH_2)_nN(R)_2$, —OC(O)R, $CX_3$, CN, N(R)C(O)R, N(H)C(O)R, $N(R)S(O)_2R$, $N(H)S(O)_2R$, —$N(R)C(O)N(R)_2$, $N(H)C(O)N(R)_2$, N(H)C(O)N(H)(R), $N(R)C(S)N(R)_2$, $N(H)C(S)N(R)_2$, N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{36}$ carbocycle, such as a phenyl group. In certain embodiments, the heterocycle or $C_{36}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of Formula (I) is selected from the group consisting of:

(Compound 1)

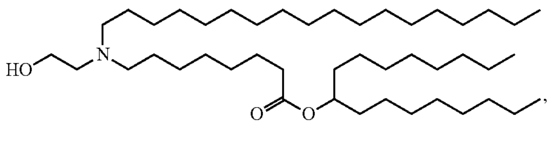

, (Compound 2)

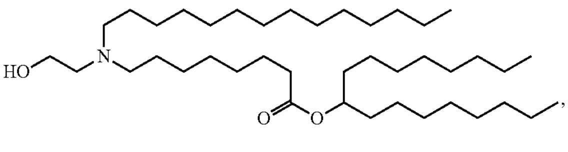

,

-continued
(Compound 3)
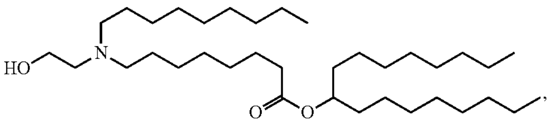
(Compound 4)
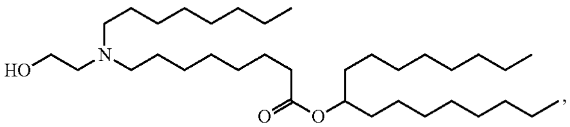
(Compound 5)
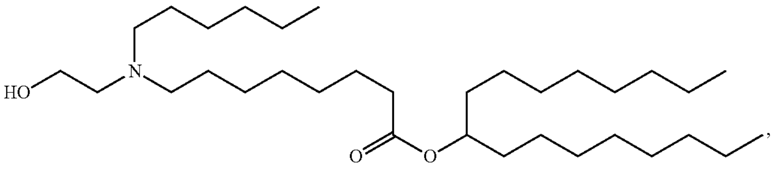
(Compound 6)
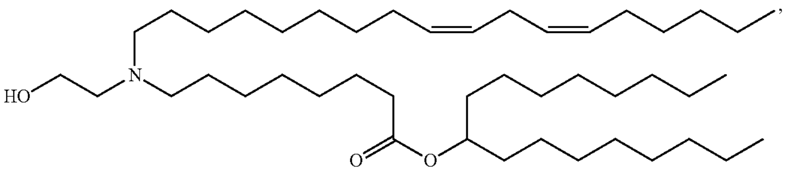
(Compound 7)
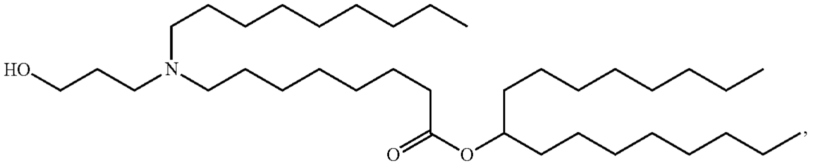
(Compound 8)
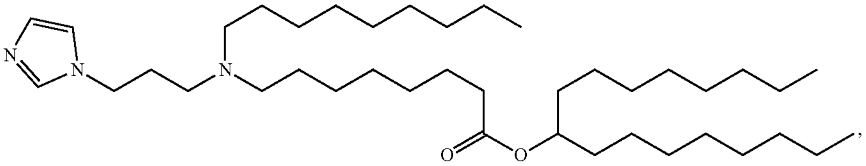
(Compound 9)
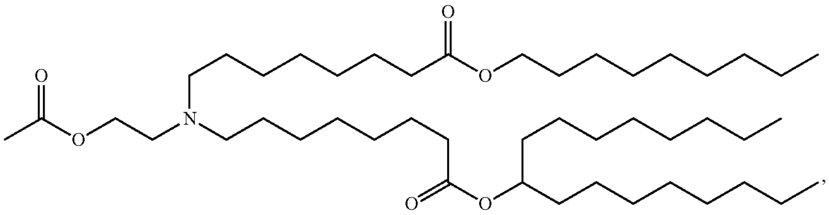
(Compound 10)
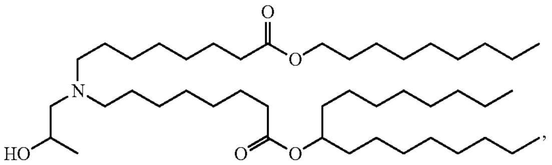
(Compound 11)
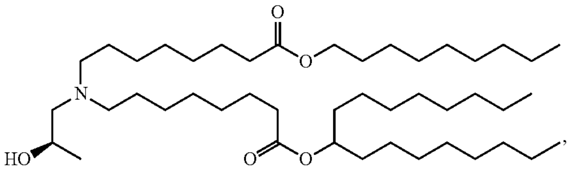
(Compound 12)
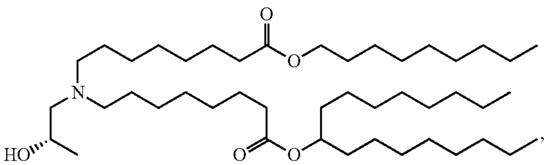
(Compound 13)
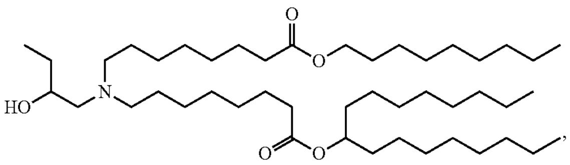

-continued
(Compound 14)
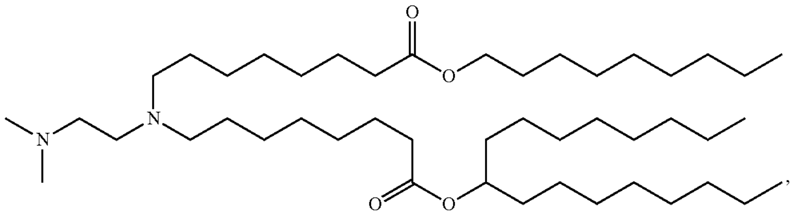
(Compound 15)
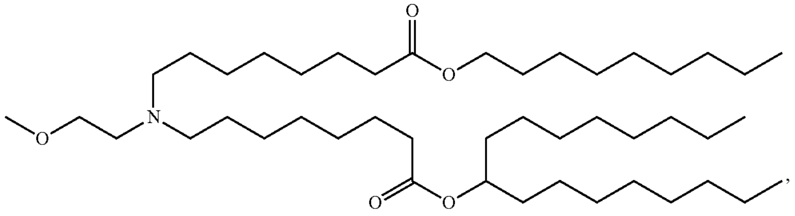
(Compound 16)
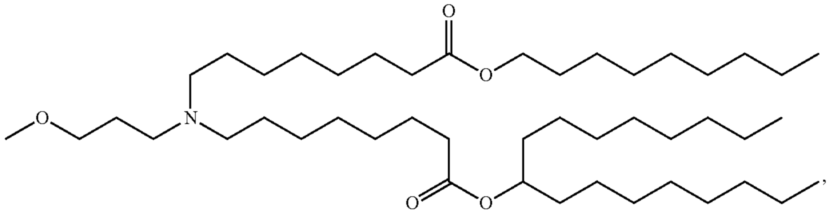
(Compound 17)
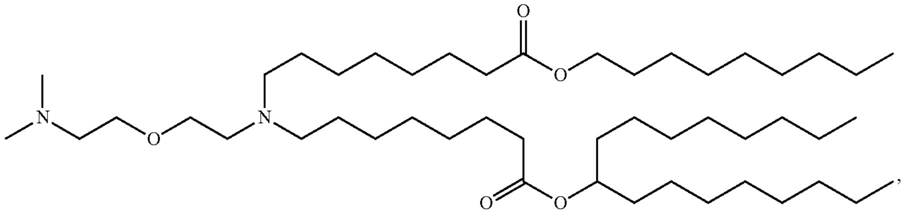
(Compound 18)
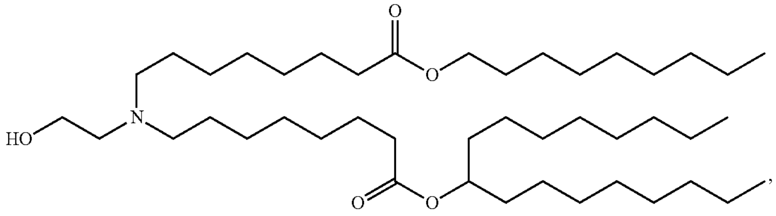
(Compound 19)
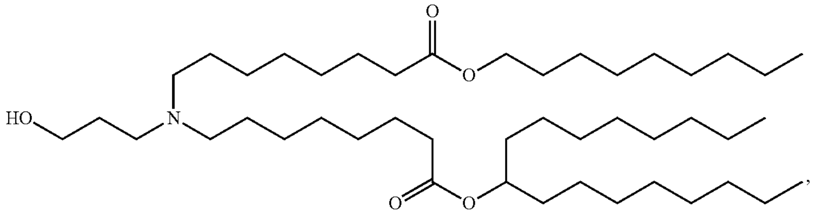
(Compound 20)
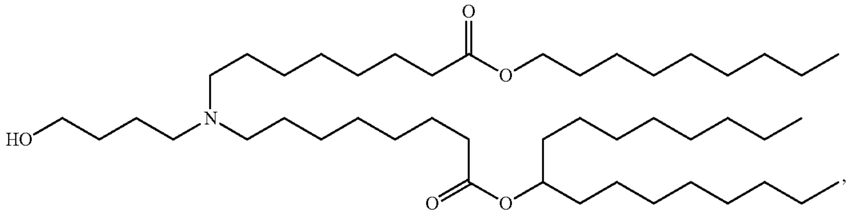

-continued
(Compound 21)
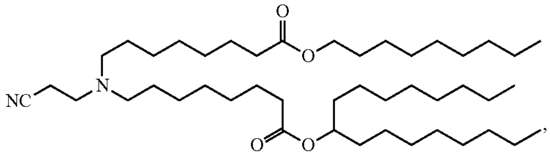,
(Compound 22)
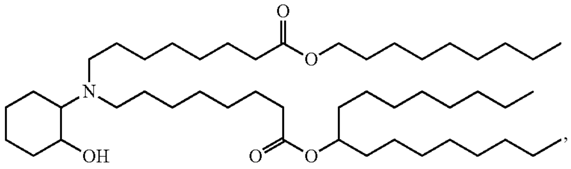,
(Compound 23)
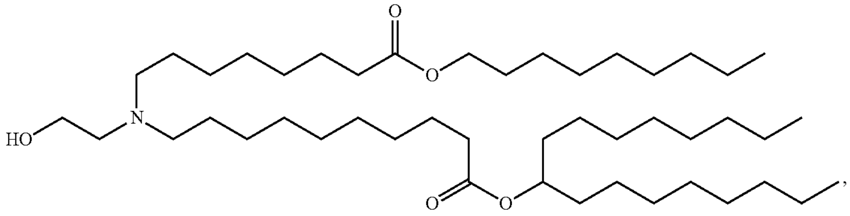,
(Compound 24)
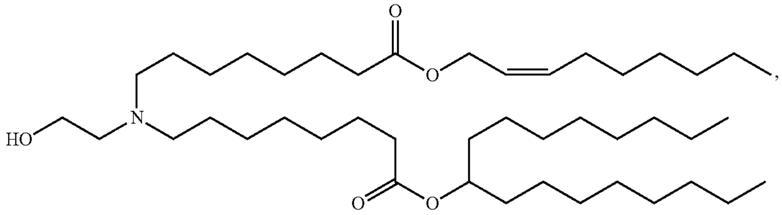,
(Compound 25)
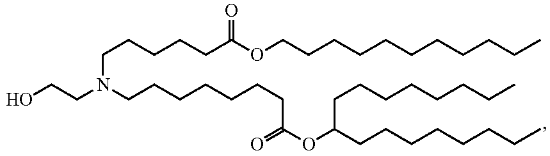,
(Compound 26)
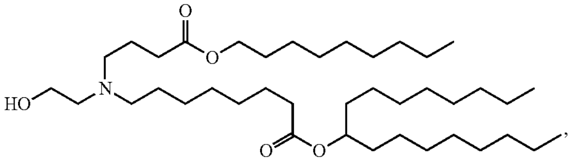,
(Compound 27)
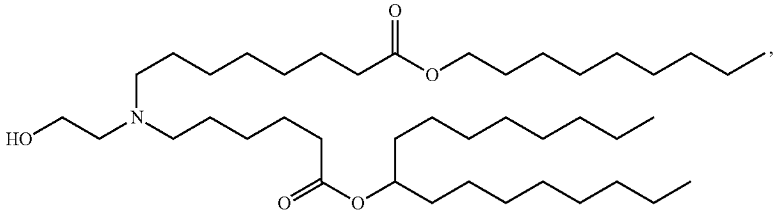,
(Compound 28)
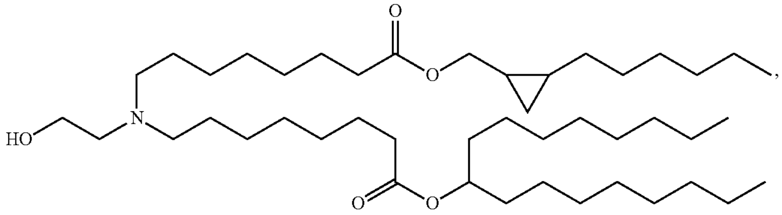,
(Compound 29)
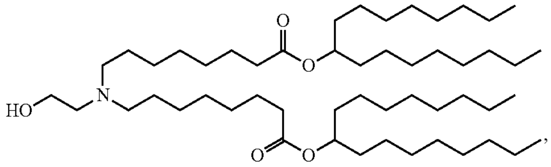,
(Compound 30)
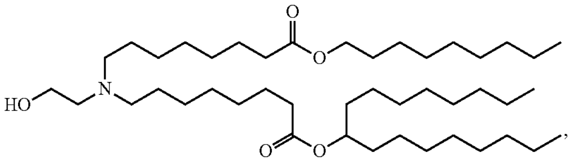, -continued
(Compound 31)
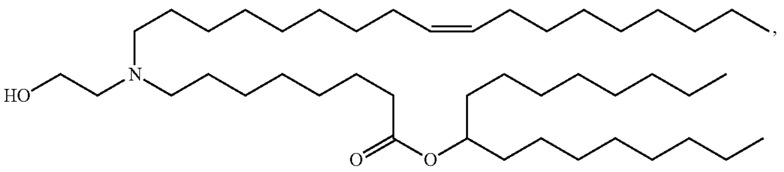
(Compound 32)
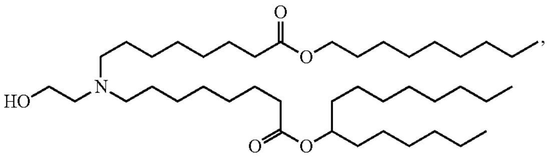
(Compound 33)
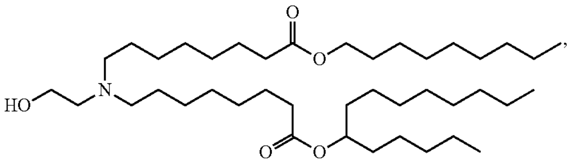
(Compound 34)
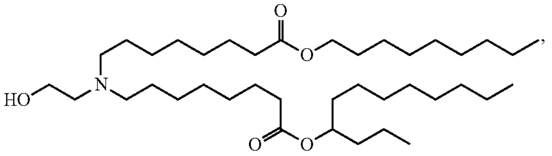
(Compound 35)
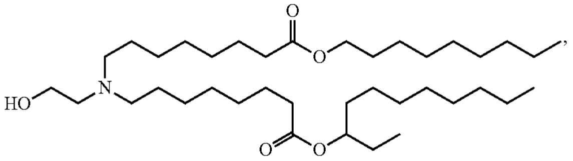
(Compound 36)
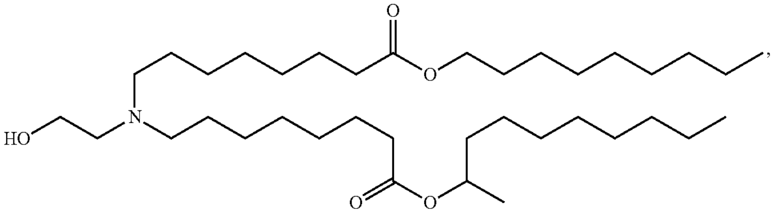
(Compound 37)
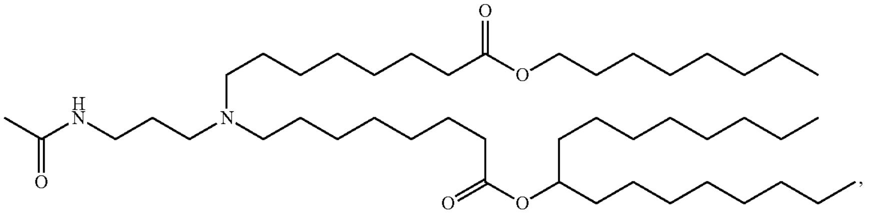
(Compound 38)
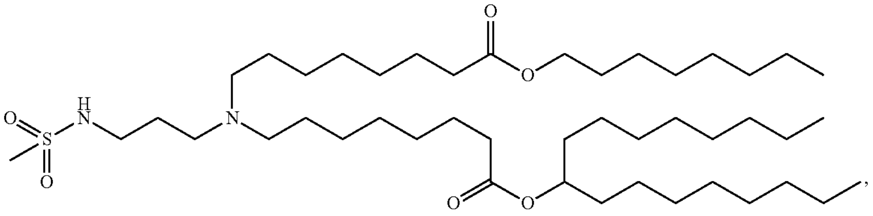
(Compound 39)
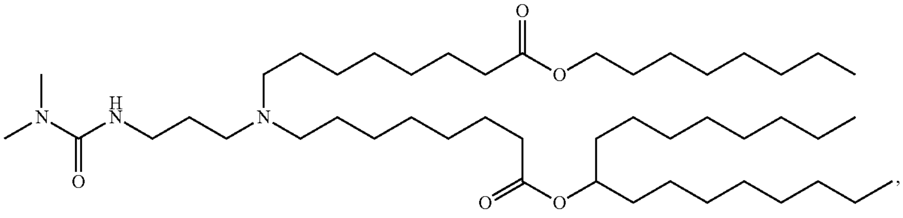

-continued
(Compound 40)
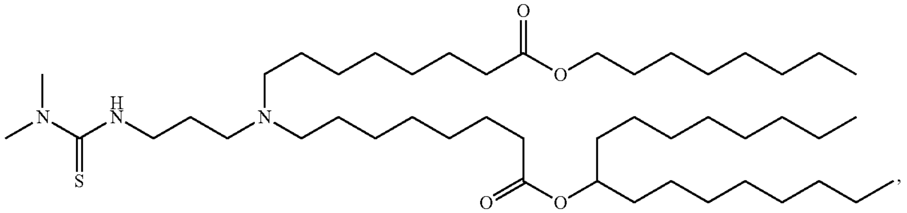
(Compound 41)
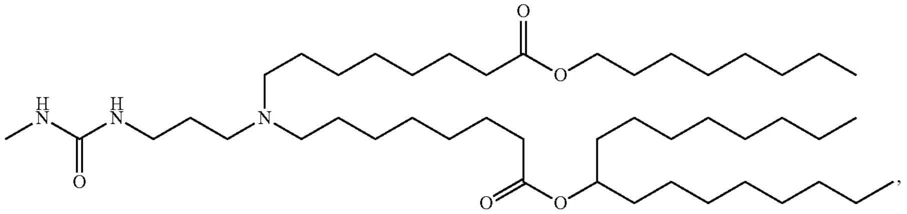
(Compound 42)
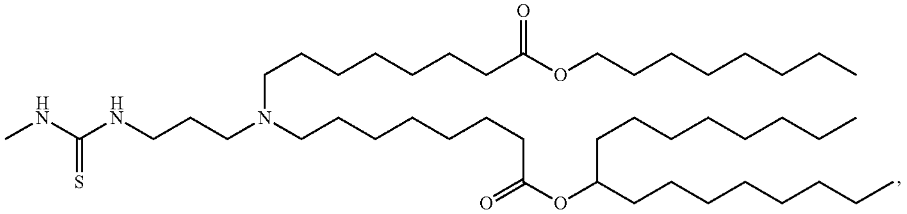
(Compound 43)
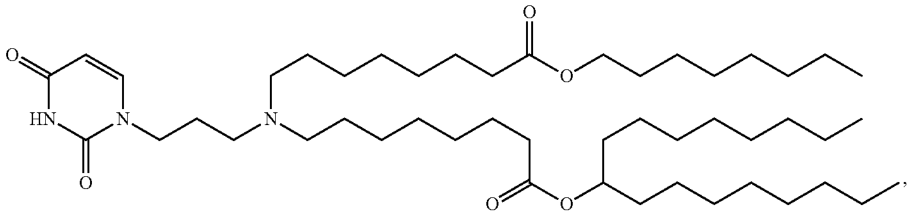
(Compound 44)
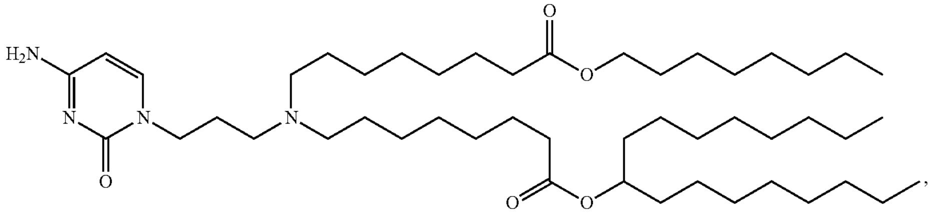
(Compound 45)
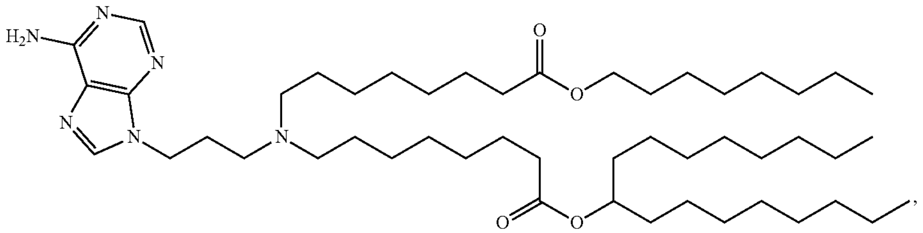
(Compound 46)
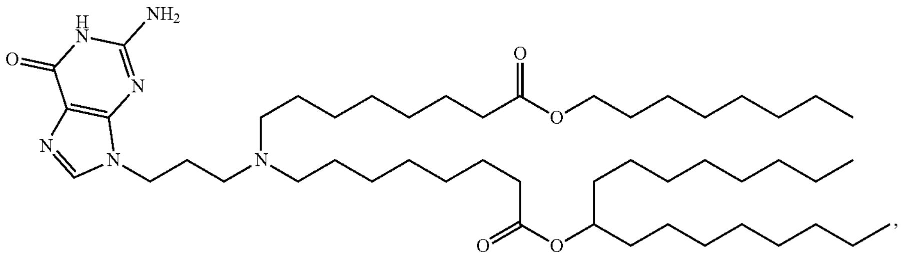

-continued
(Compound 47)
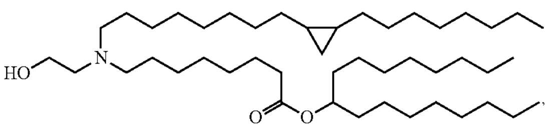
,
(Compound 48)
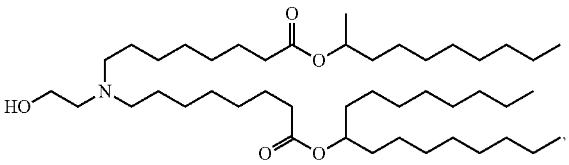
,
(Compound 49)
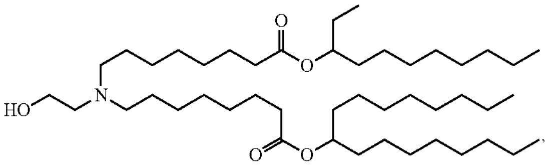
,
(Compound 50)
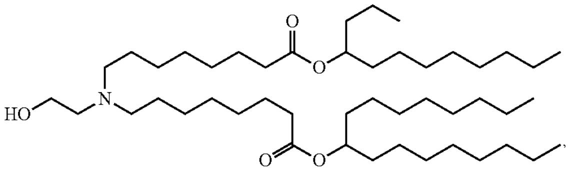
,
(Compound 51)
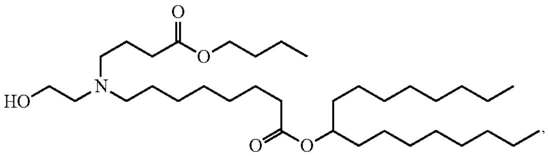
,
(Compound 52)
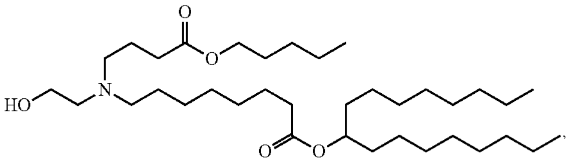
,
(Compound 53)
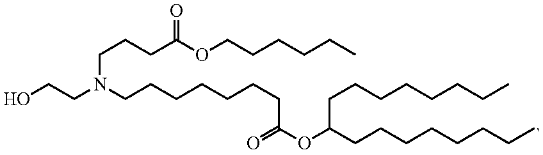
,
(Compound 54)
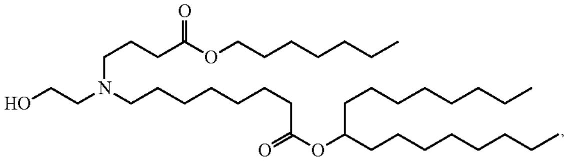
,
(Compound 55)
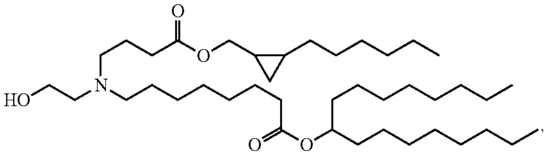
,
(Compound 56)
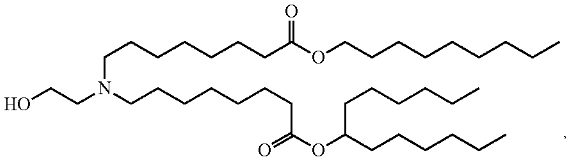
,
(Compound 57)
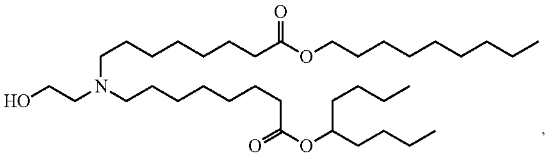
,
(Compound 58)
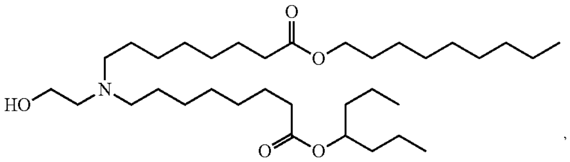
,
(Compound 59)
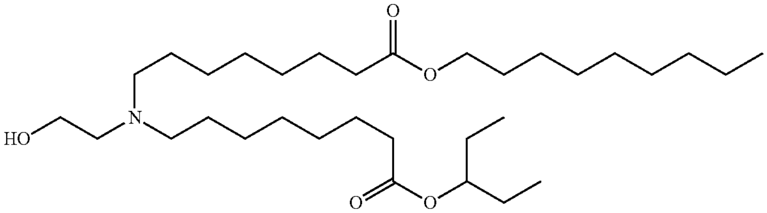
,
(Compound 60)
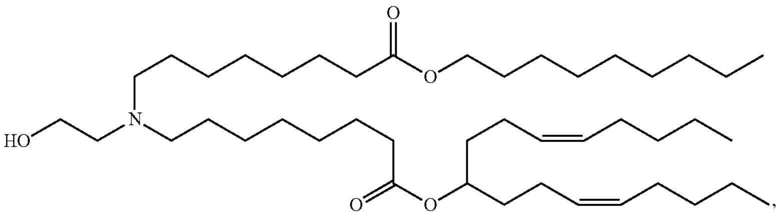
, -continued
(Compound 61)
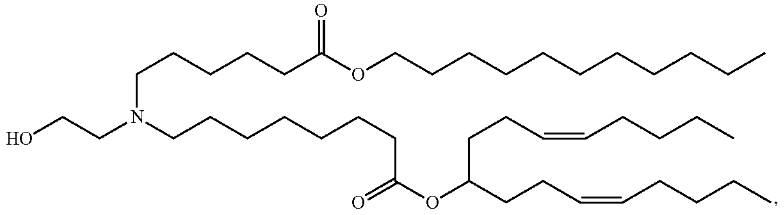
(Compound 62)
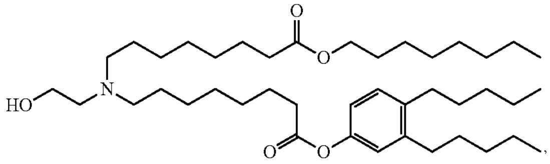
(Compound 63)
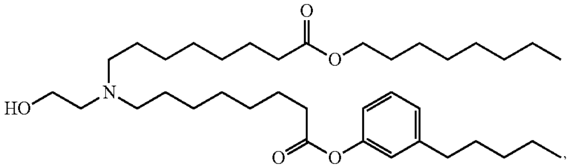
(Compound 64)
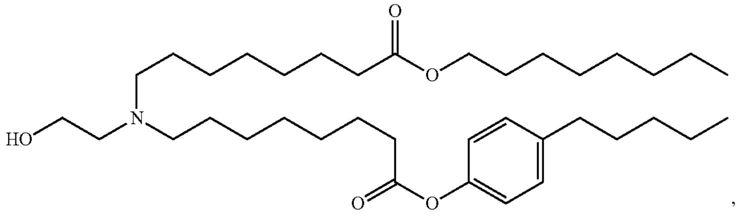
(Compound 65)
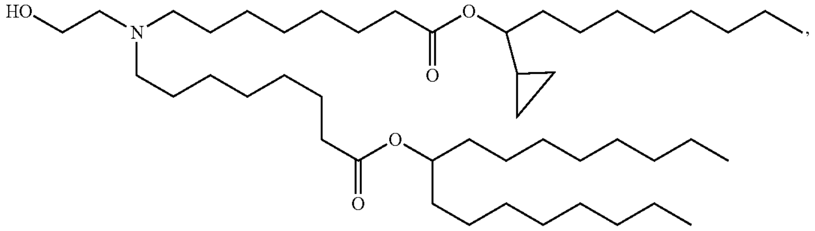
(Compound 66)
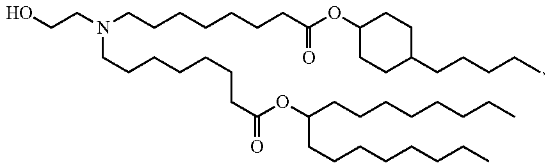
(Compound 67)
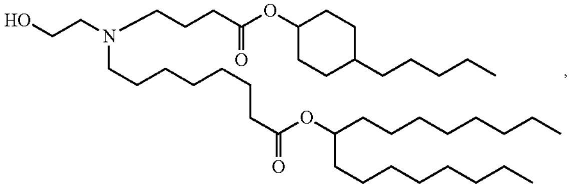
(Compound 68)
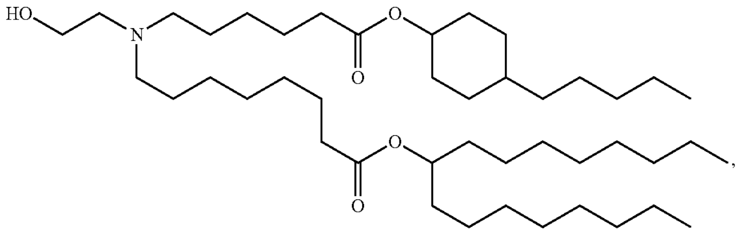
(Compound 69)
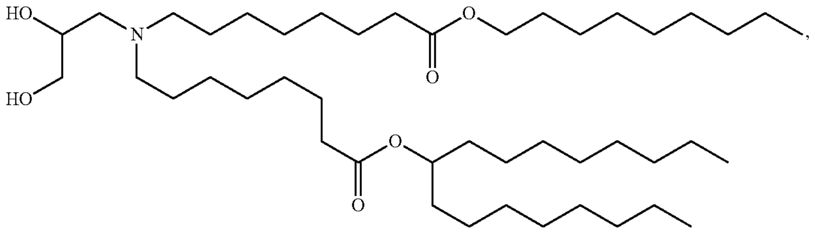

-continued
(Compound 70)
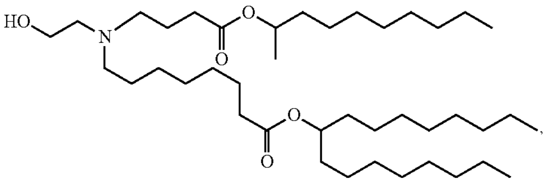
(Compound 71)
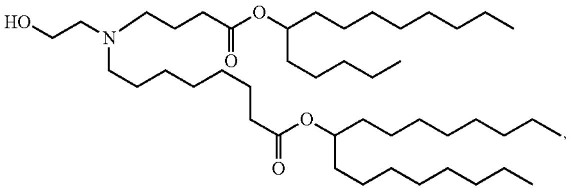
(Compound 72)
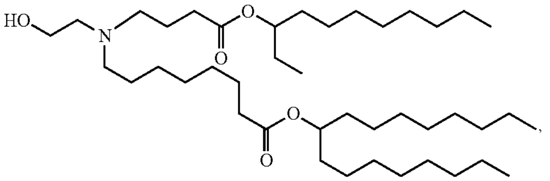
(Compound 73)
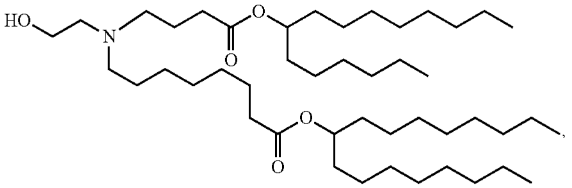
(Compound 74)
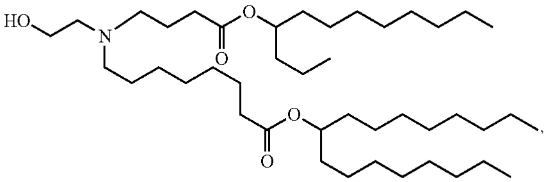
(Compound 75)
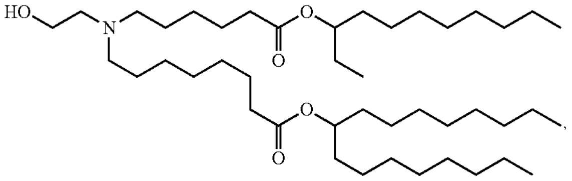
(Compound 76)
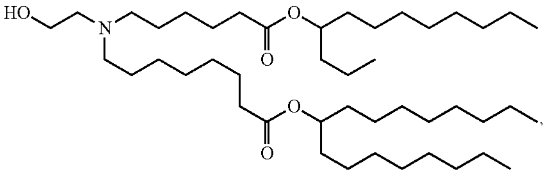
(Compound 77)
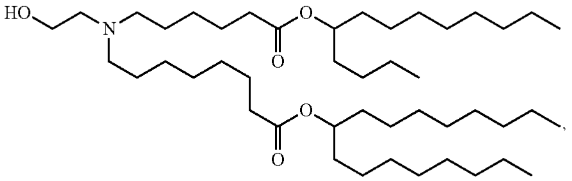
(Compound 78)
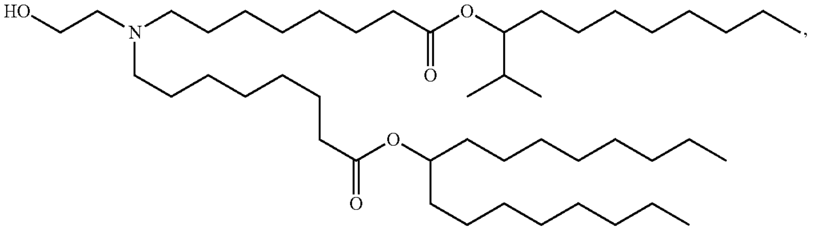
(Compound 79)
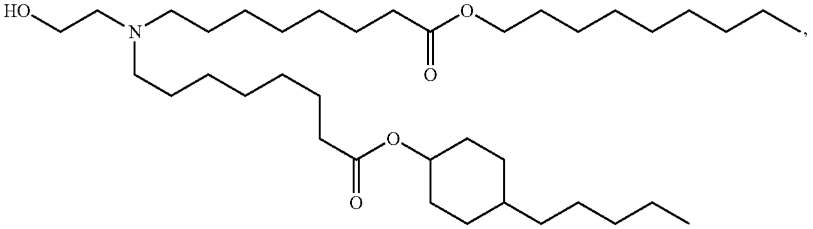
(Compound 80)
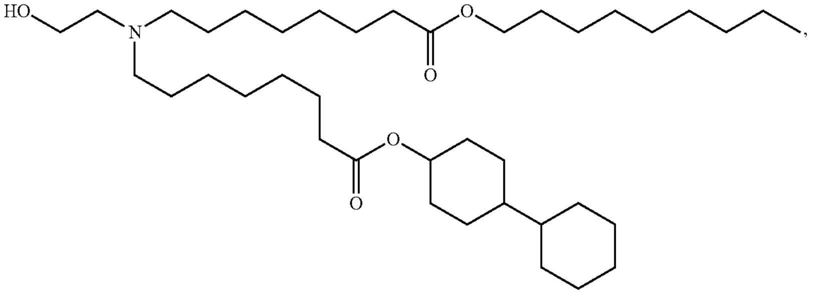

-continued
(Compound 81)
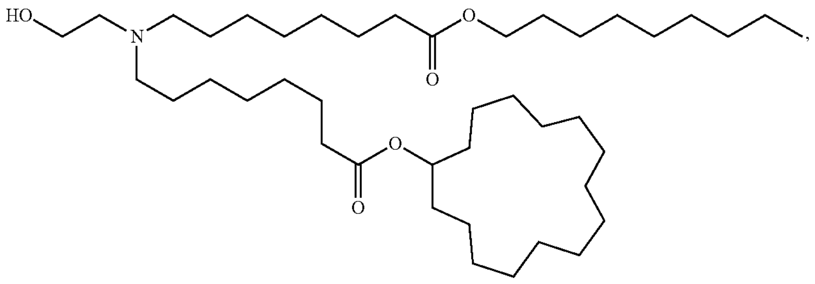
(Compound 82)
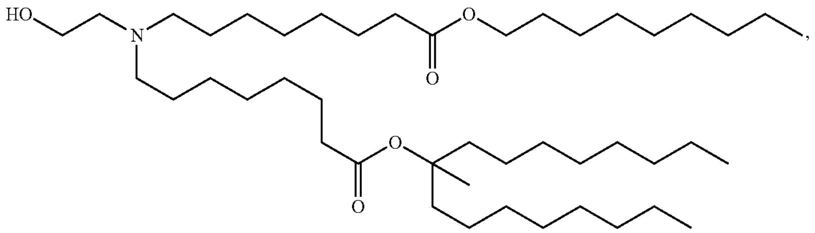
(Compound 83)
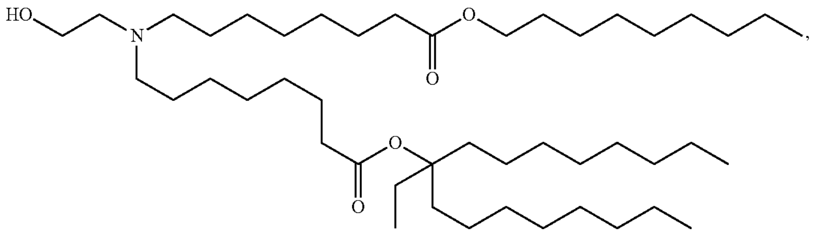
(Compound 84)
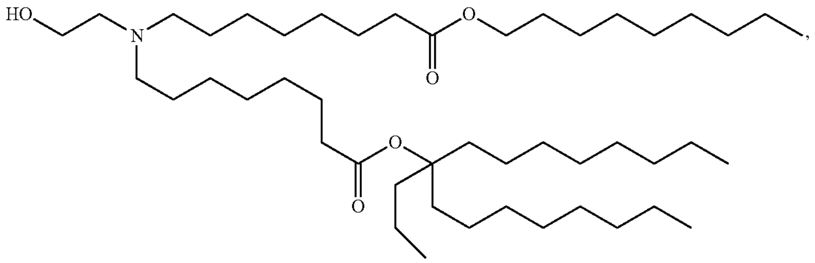
(Compound 85)
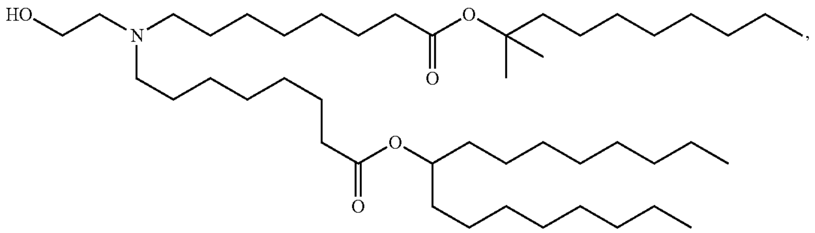
(Compound 86)
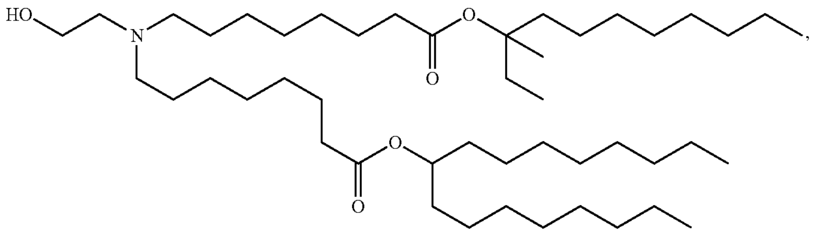

-continued
(Compound 87)
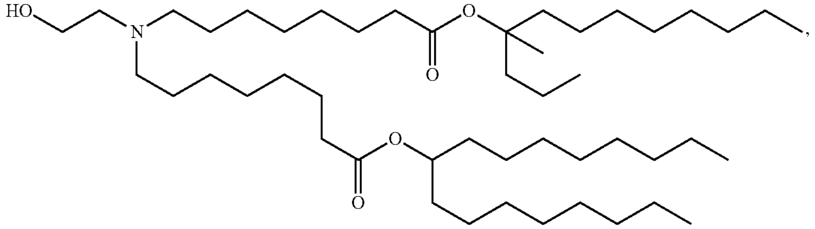
(Compound 88)
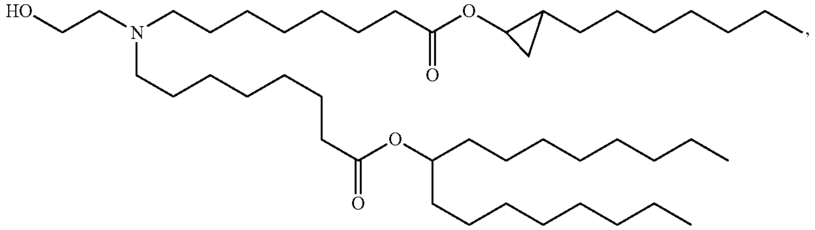
(Compound 89)
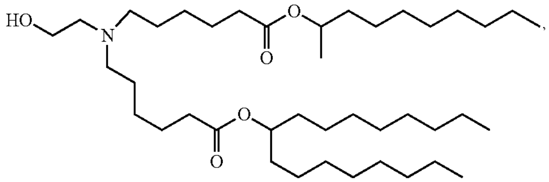
(Compound 90)
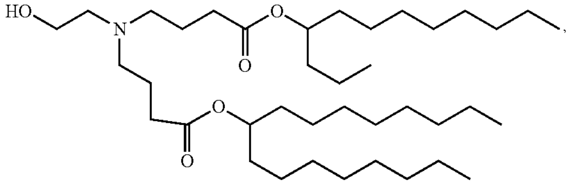
(Compound 91)
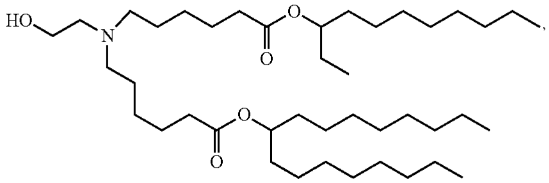
(Compound 92)
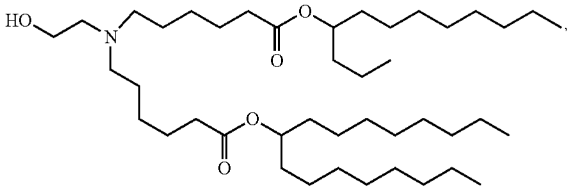
(Compound 93)
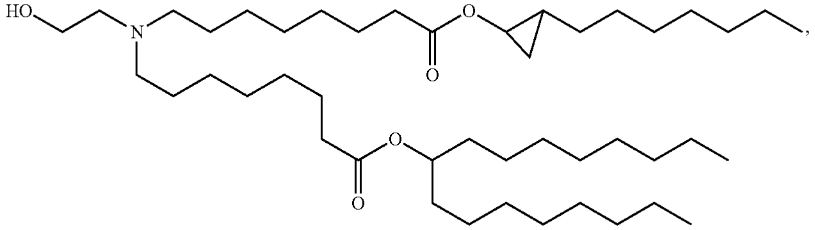
(Compound 94)
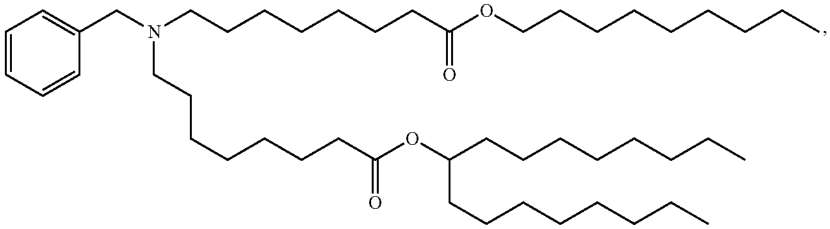
(Compound 95)
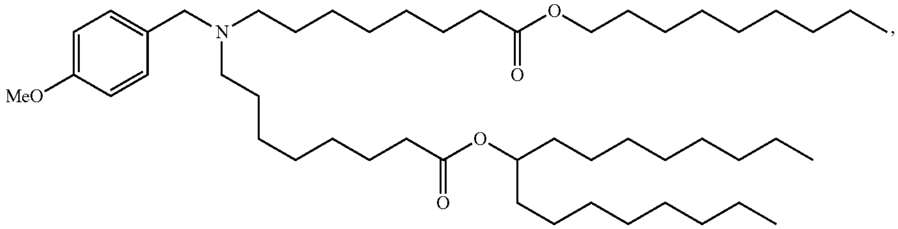

-continued
(Compound 96)
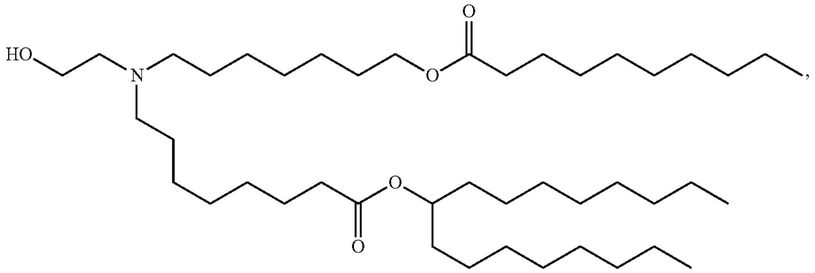
(Compound 97)
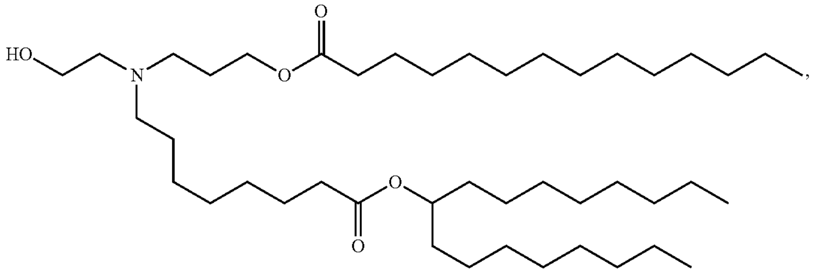
(Compound 98)
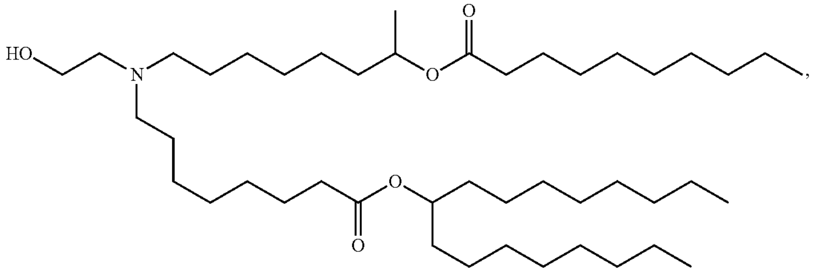
(Compound 99)
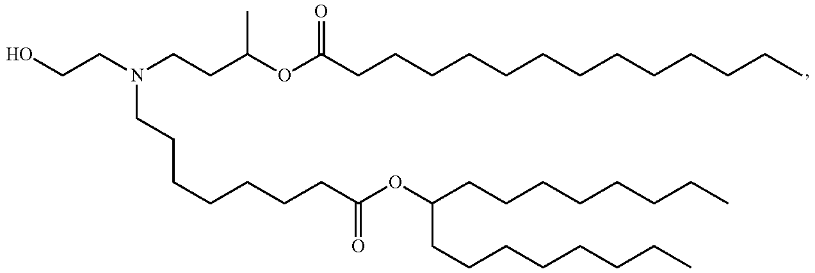
(Compound 100)
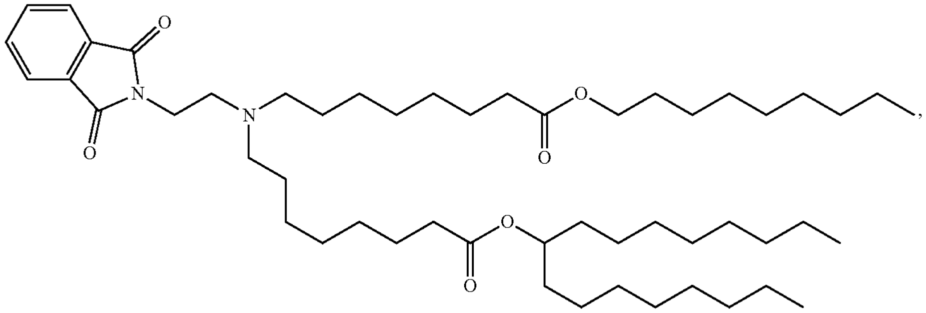

-continued
(Compound 101)
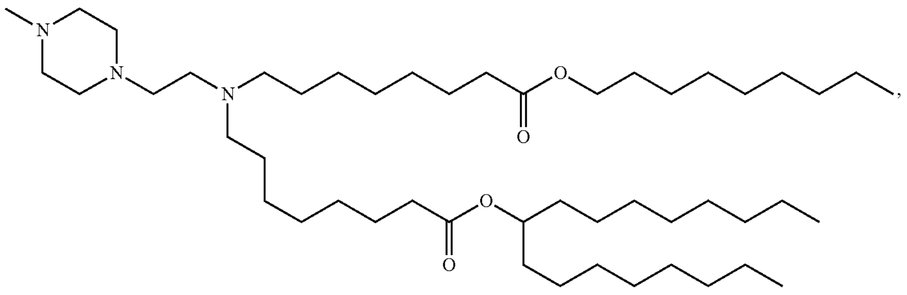
(Compound 102)
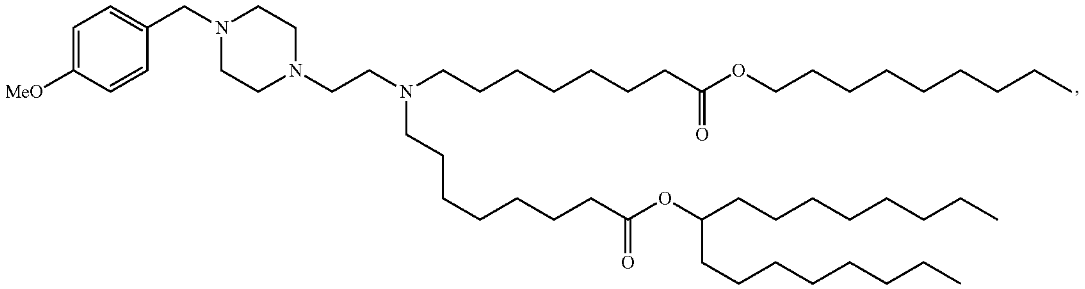
(Compound 103)
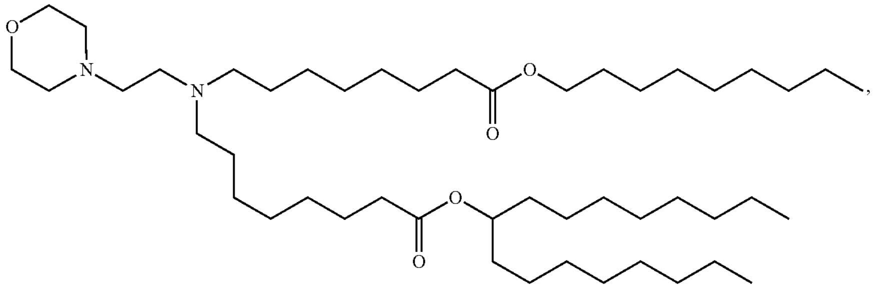
(Compound 104)
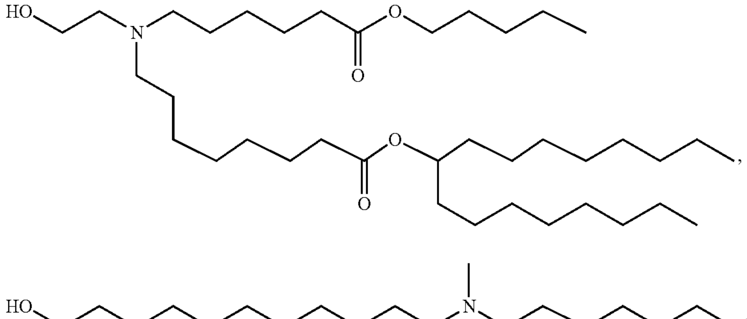
(Compound 105)
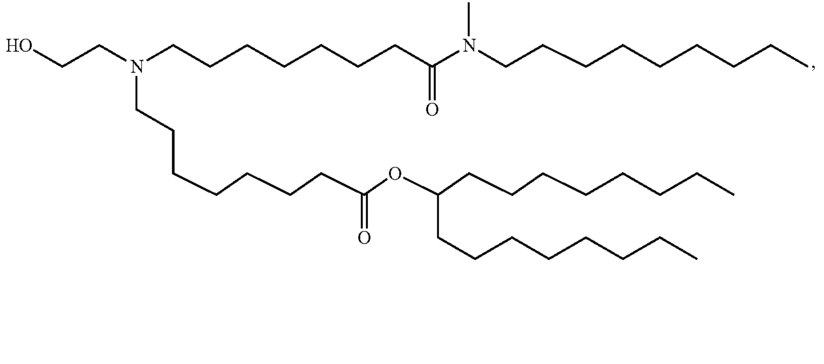

-continued
(Compound 106)
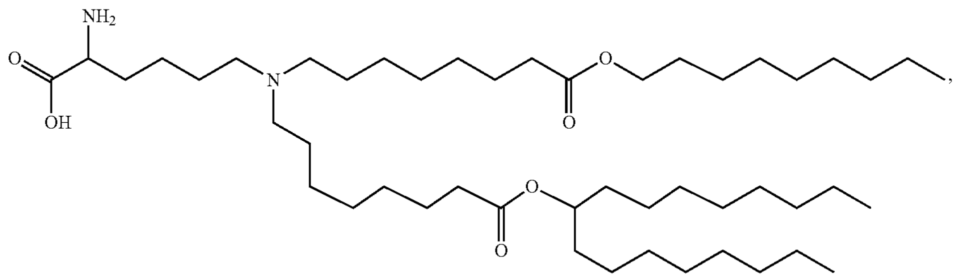
(Compound 107)
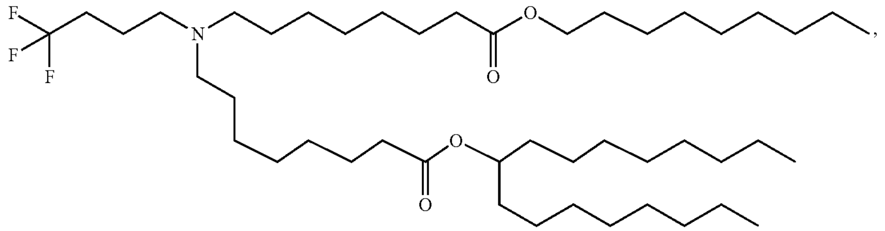
(Compound 108)
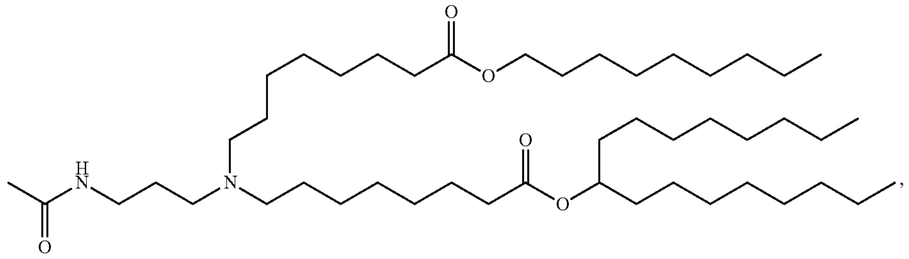
(Compound 109)
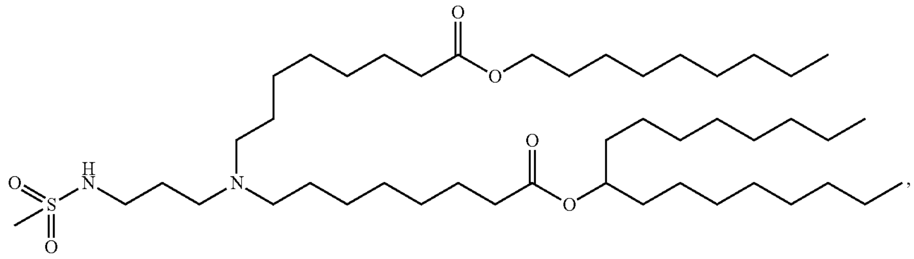
(Compound 110)
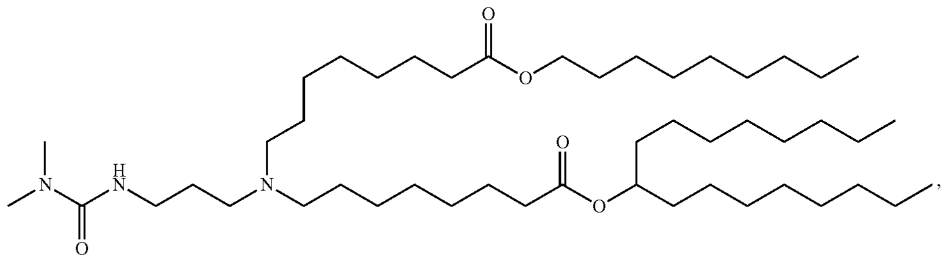
(Compound 111)
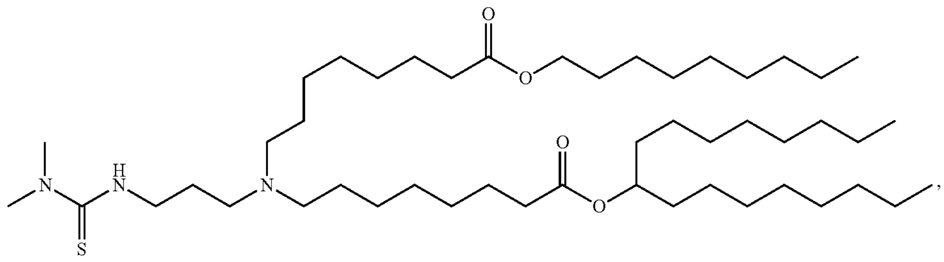

-continued
(Compound 112)
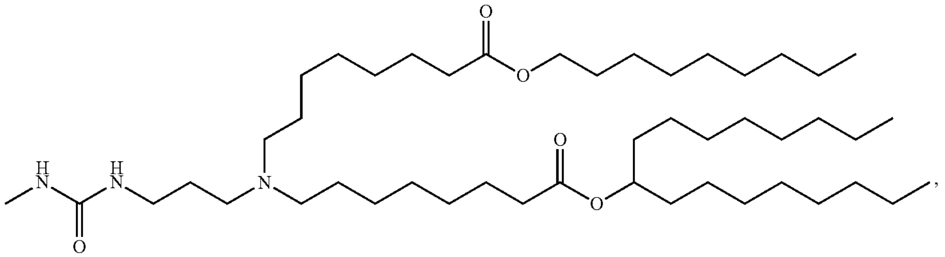
(Compound 113)
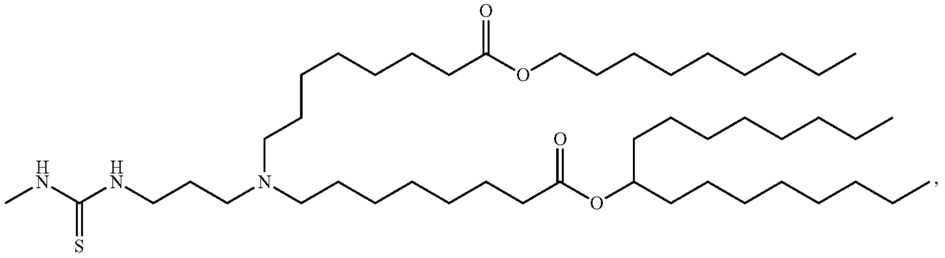
(Compound 114)
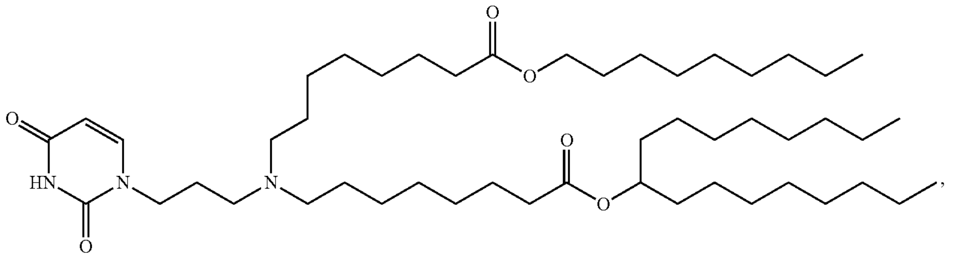
(Compound 115)
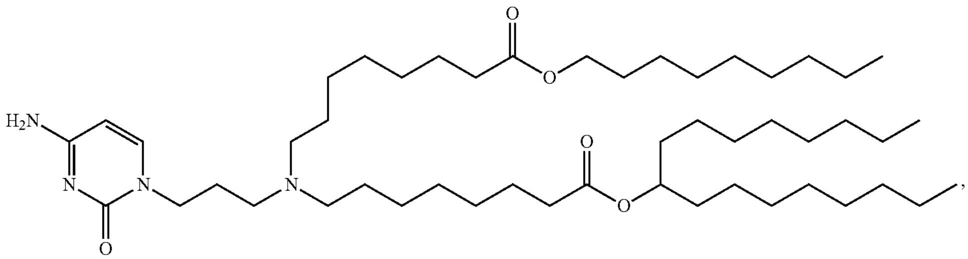
(Compound 116)
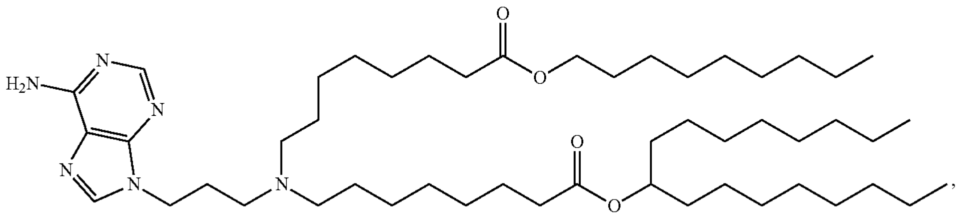
(Compound 117)
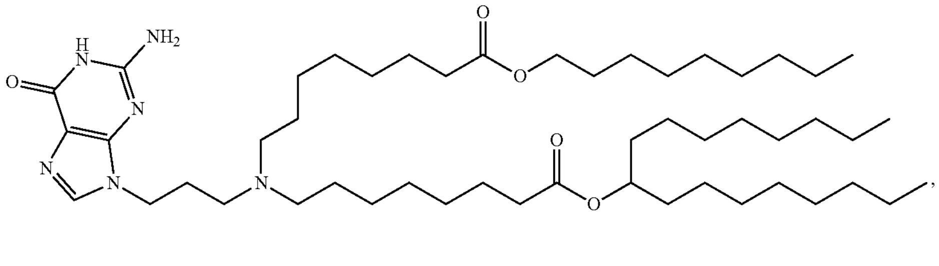

-continued
(Compound 118)
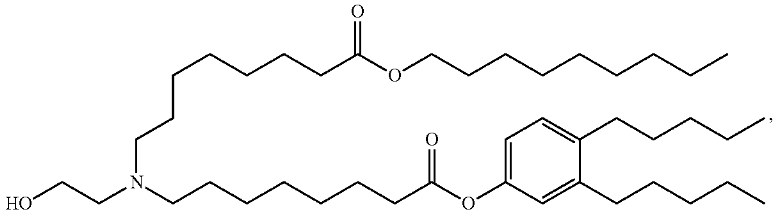
(Compound 119)
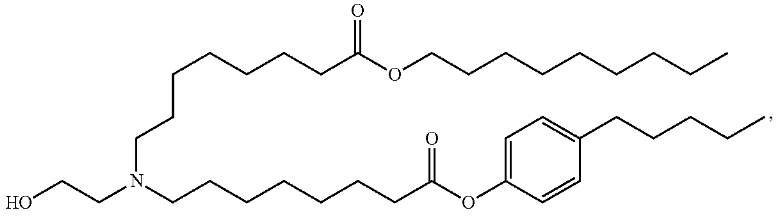
(Compound 120)
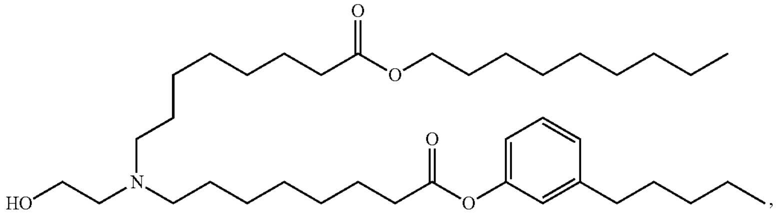
(Compound 121)
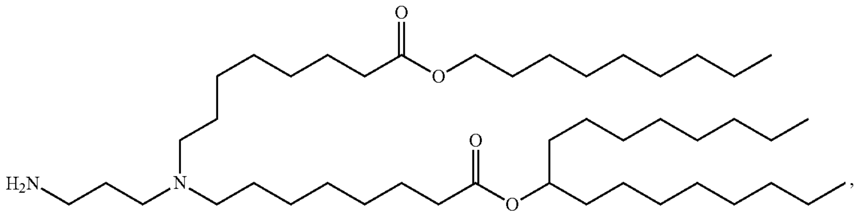
(Compound 122)
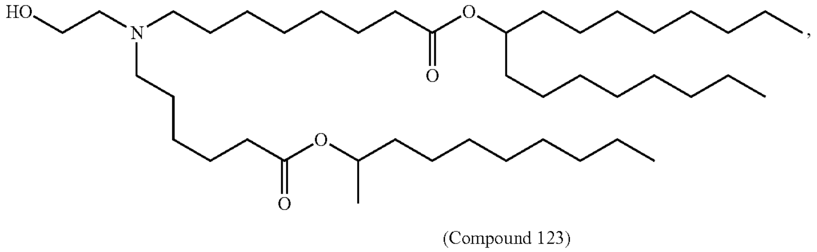
(Compound 123)
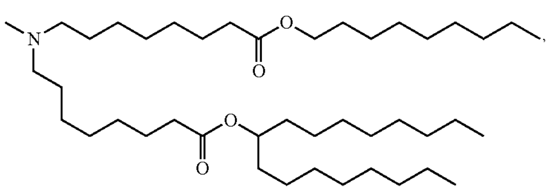
(Compound 124)
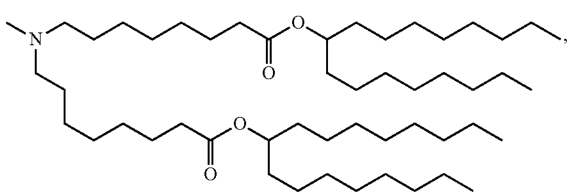
(Compound 125)
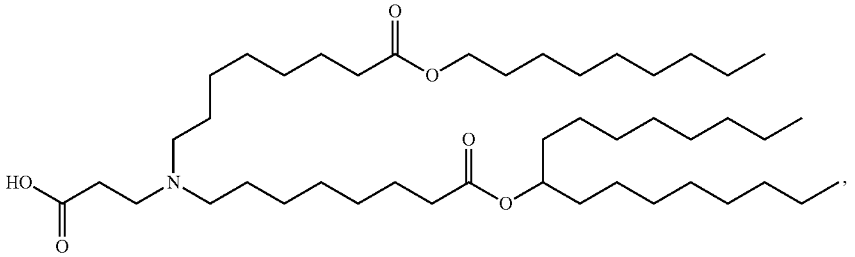

-continued
(Compound 126)
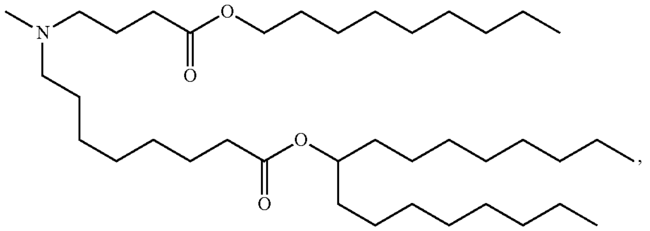
(Compound 127)
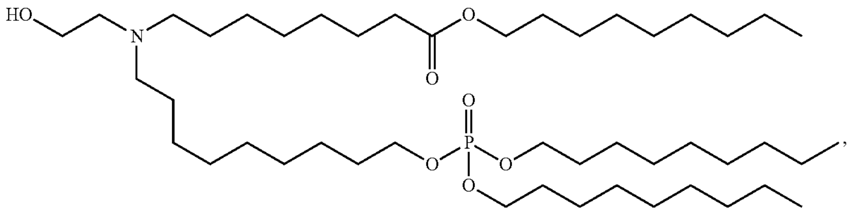
(Compound 128)
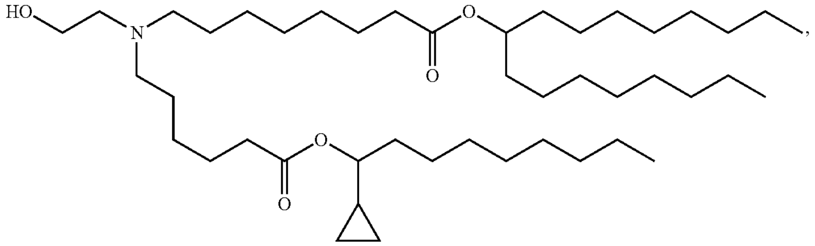
(Compound 129)
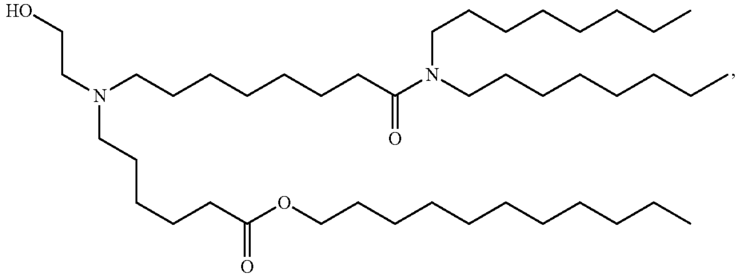
(Compound 130)
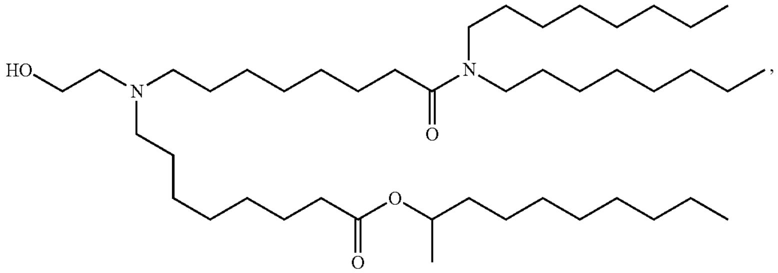
(Compound 131)
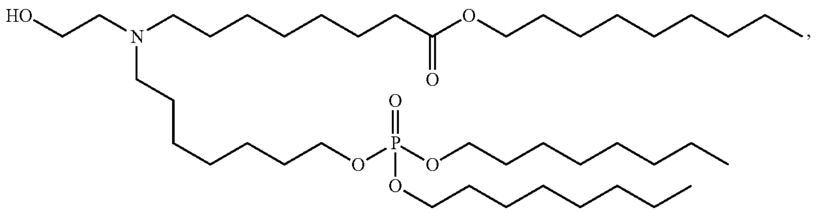

-continued
(Compound 132)
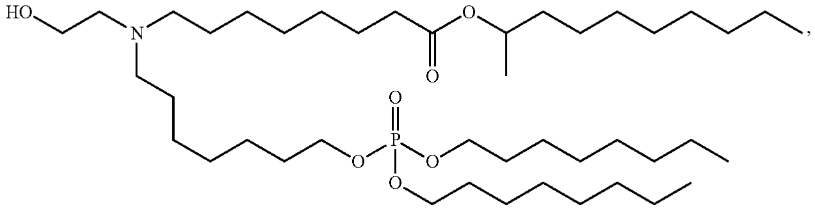
(Compound 133)
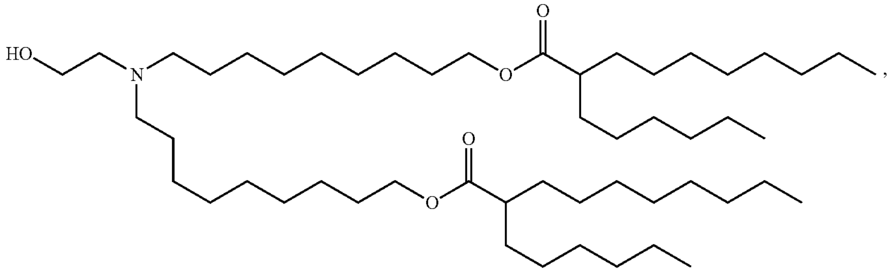
(Compound 134)
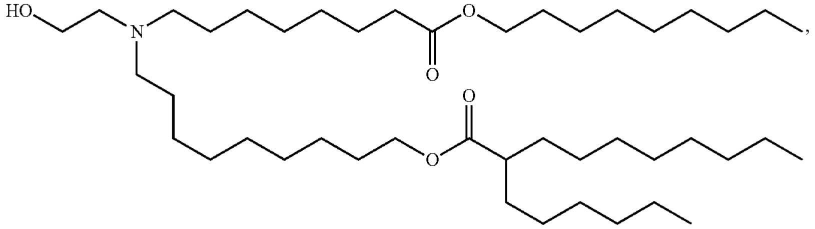
(Compound 135)
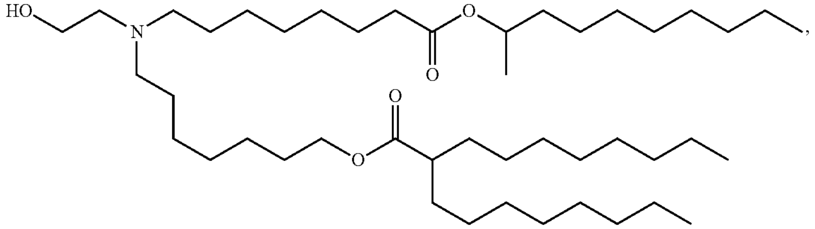
(Compound 136)
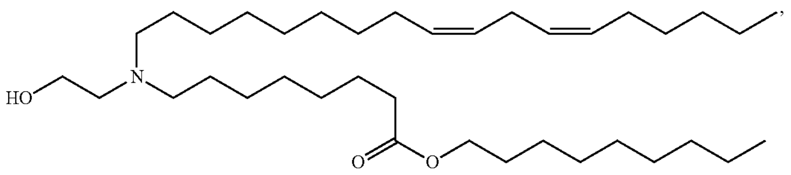
(Compound 137)
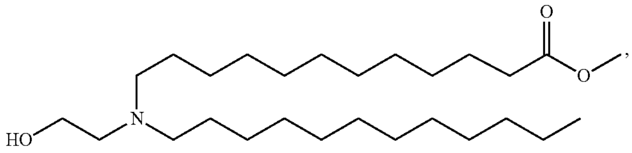
(Compound 138)
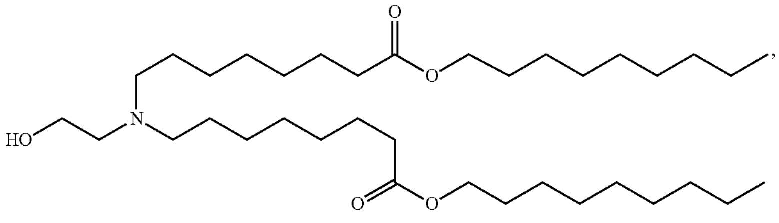

-continued
(Compound 139)
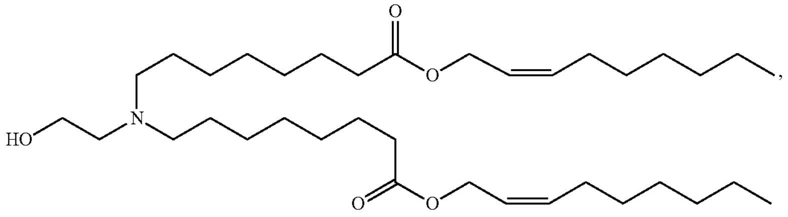
(Compound 140)
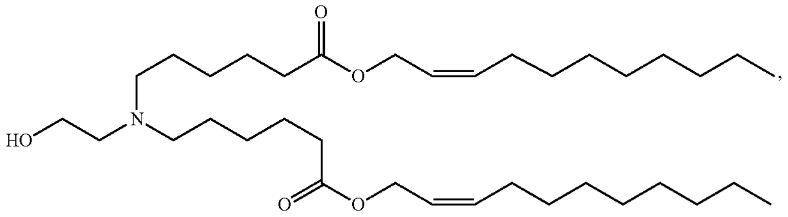
(Compound 141)
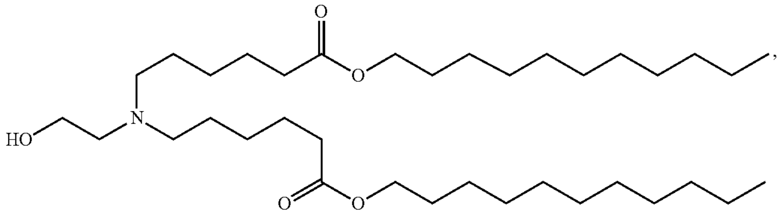
(Compound 142)
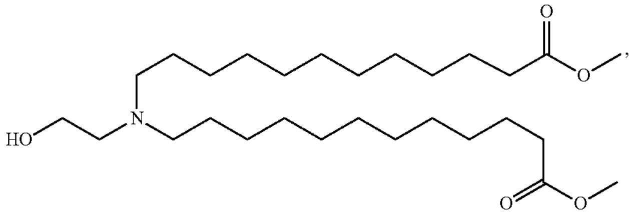
(Compound 143)
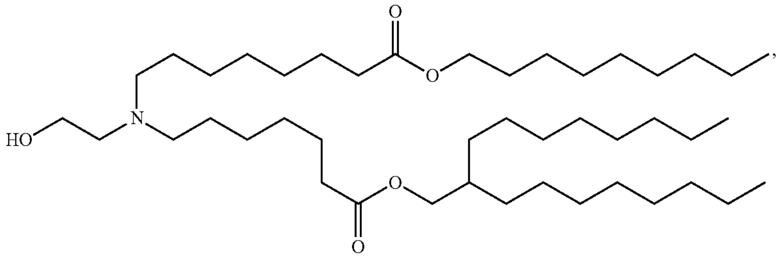
(Compound 144)
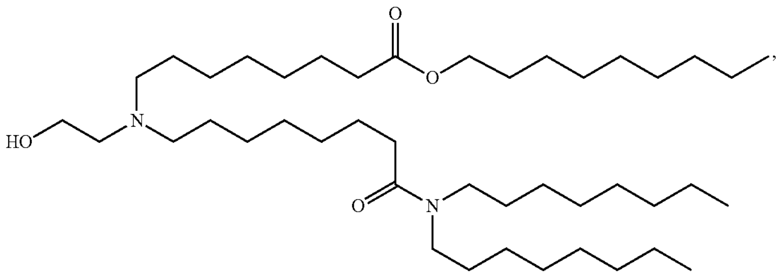

-continued
(Compound 145)
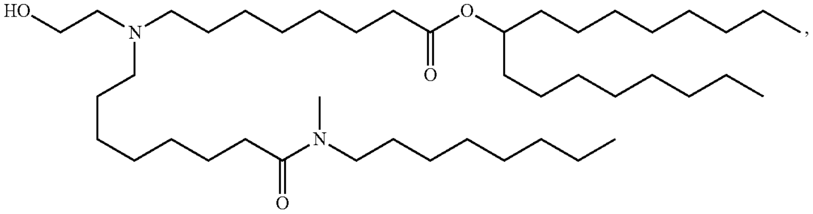
(Compound 146)
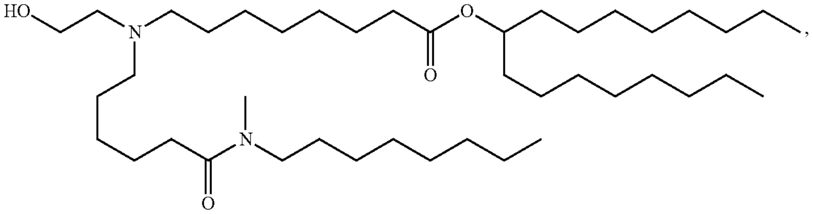
(Compound 147)
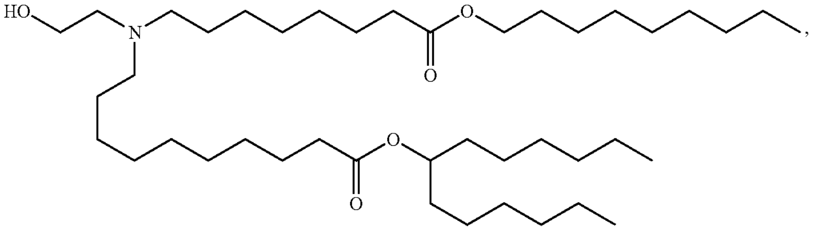
(Compound 148)
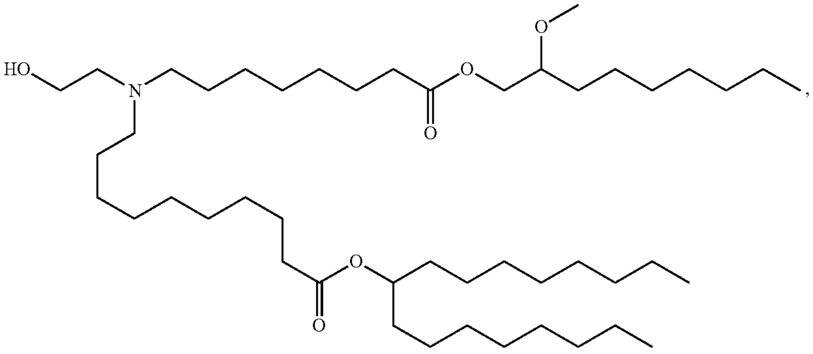
(Compound 149)
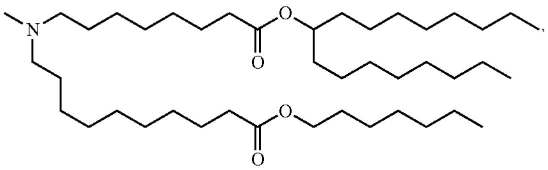
(Compound 150)
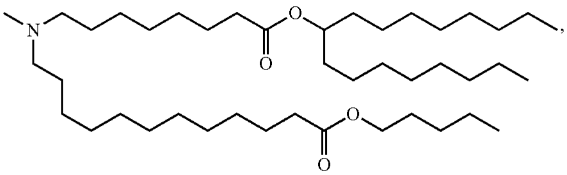
(Compound 151)
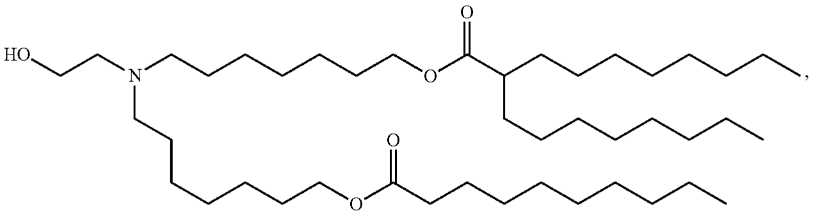

-continued
(Compound 152)
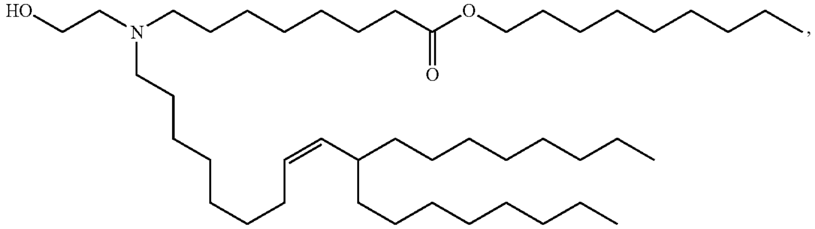
(Compound 153)
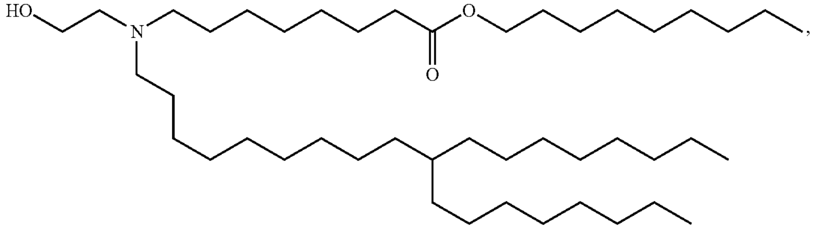
(Compound 154)
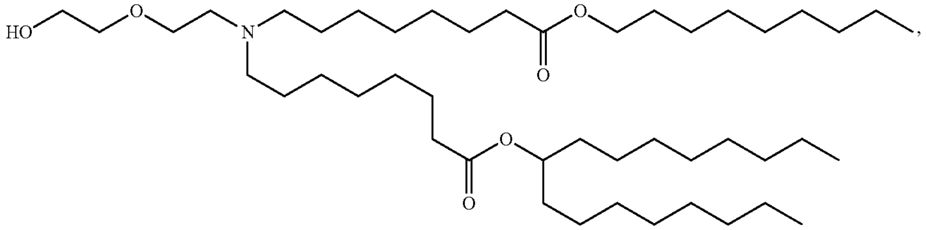
(Compound 155)
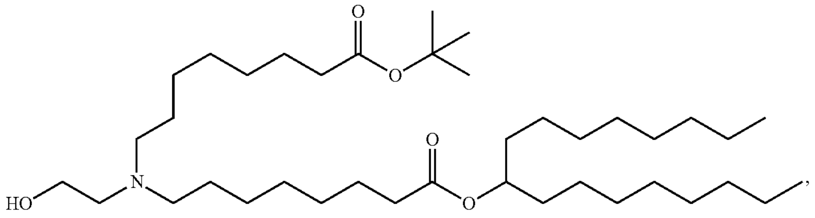
(Compound 156)
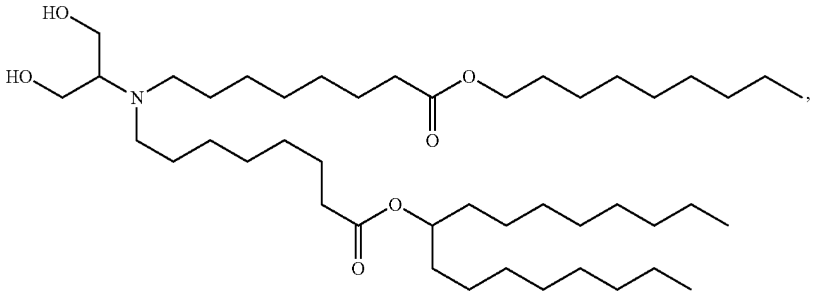
(Compound 157)
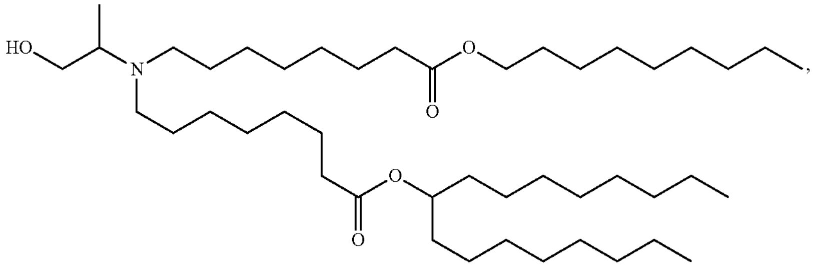

-continued
(Compound 158)
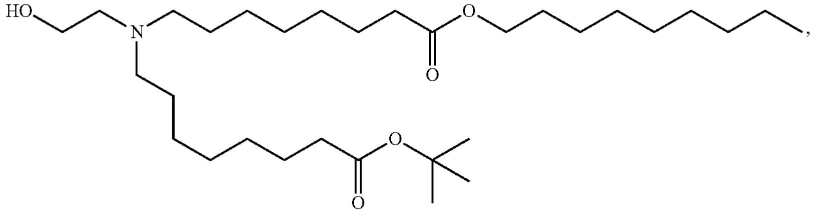
(Compound 159)
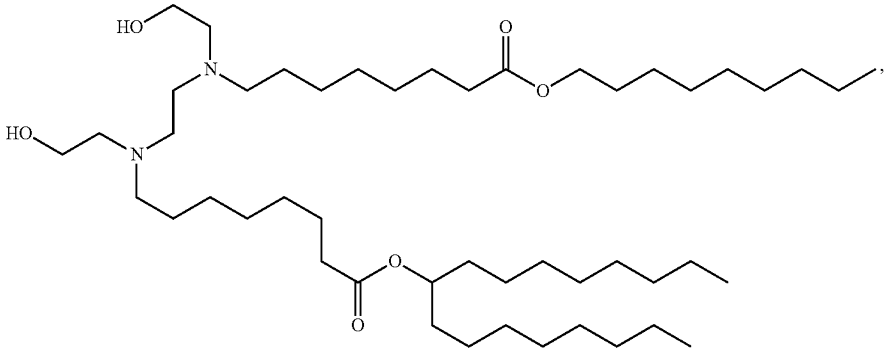
(Compound 160)
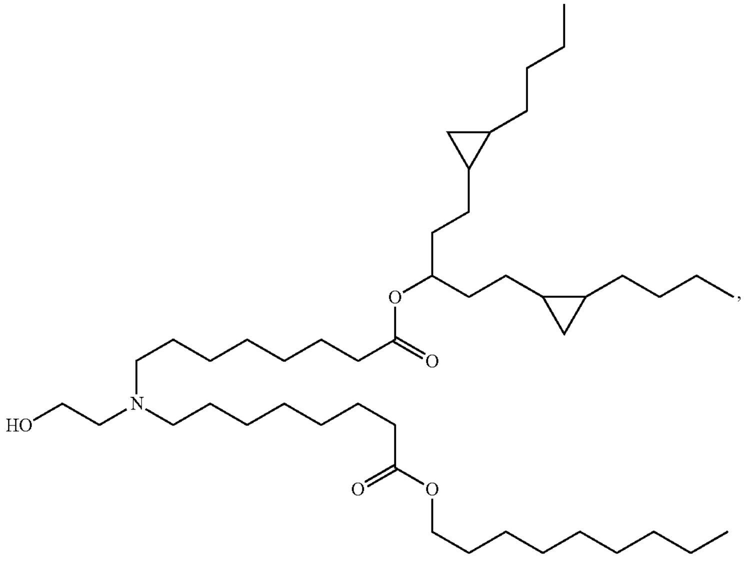
(Compound 161)
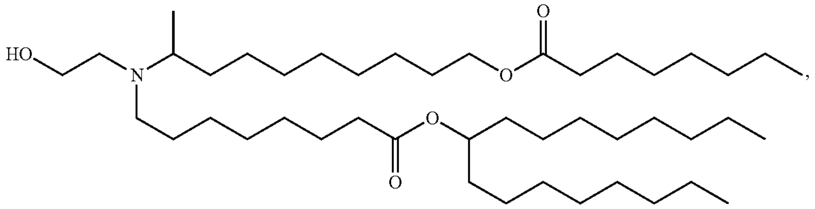
(Compound 162)
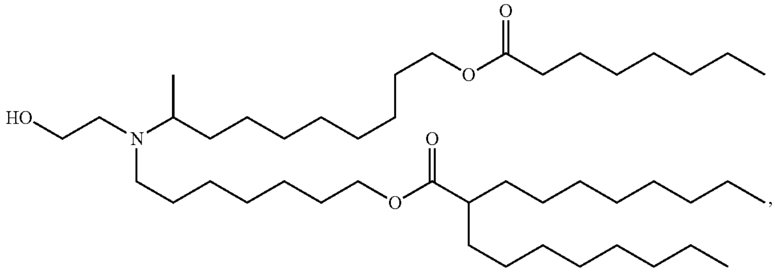

-continued
(Compound 163)
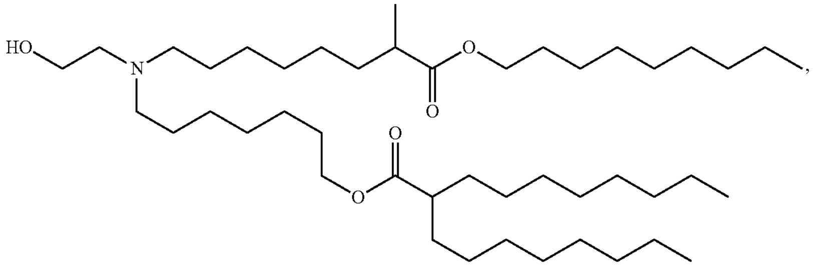
(Compound 164)
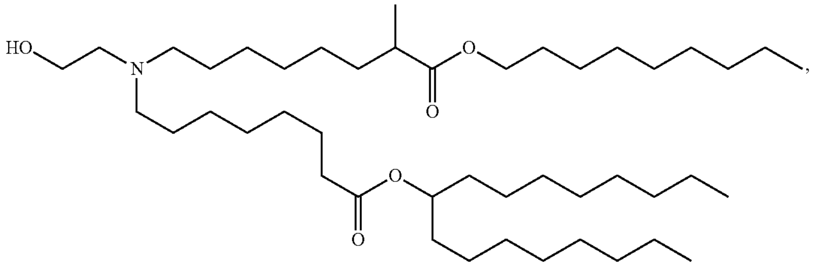
(Compound 165)
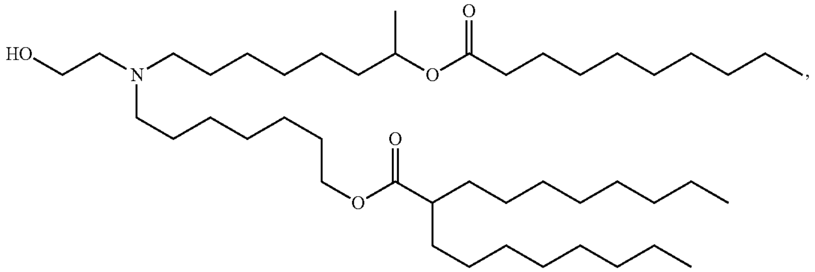
(Compound 166)
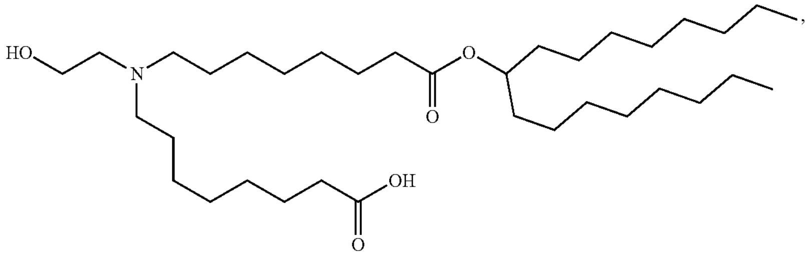
(Compound 167)
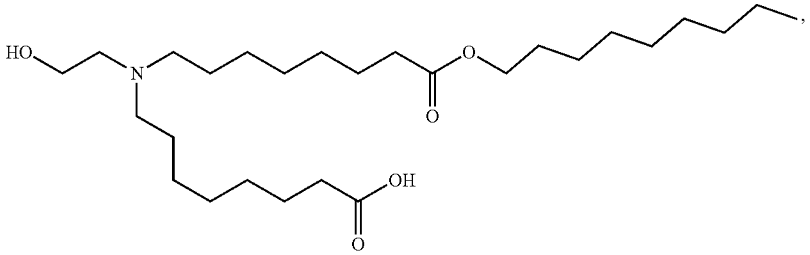

-continued
(Compound 168)
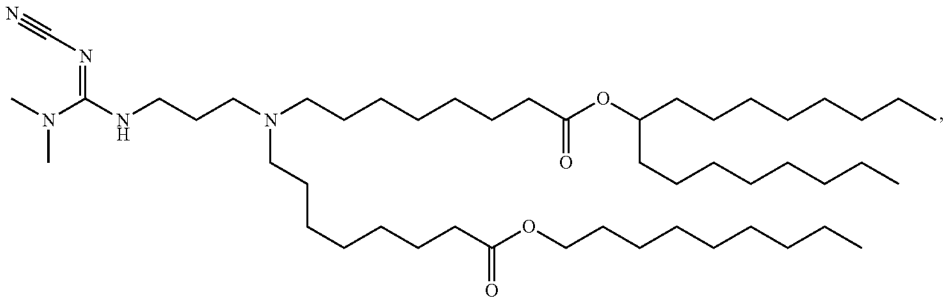
(Compound 169)
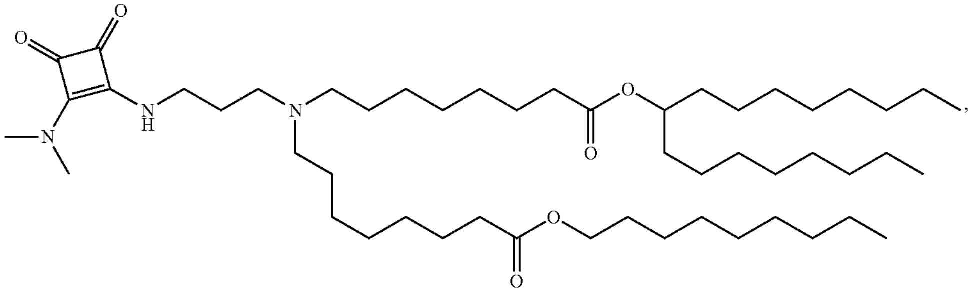
(Compound 170)
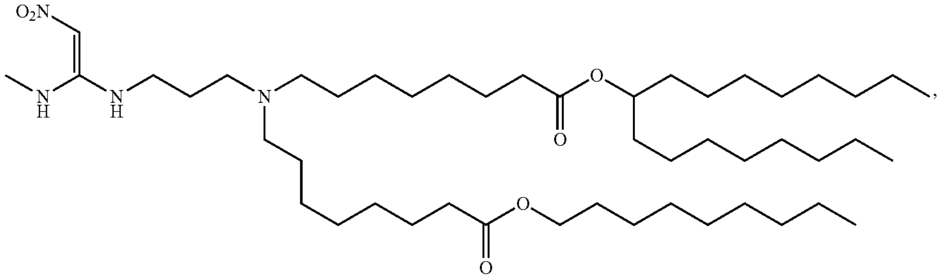
(Compound 171)
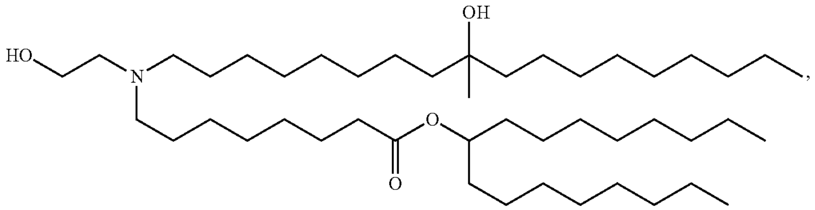
(Compound 172)
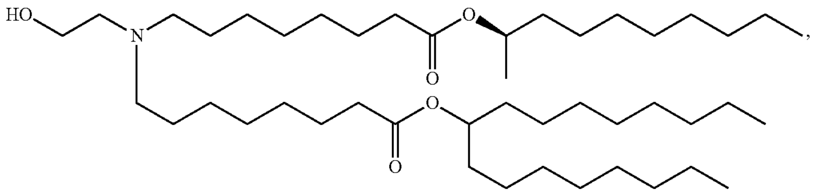
(Compound 173)
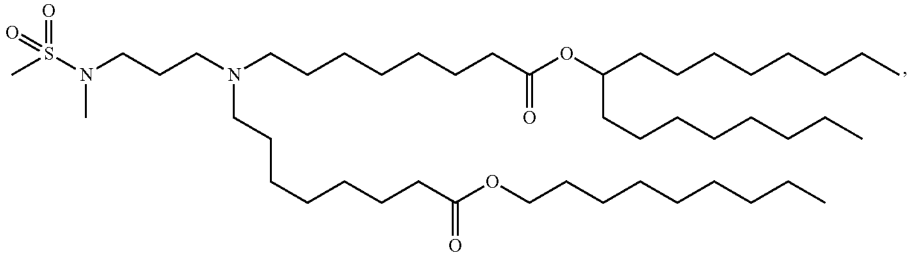

-continued
(Compound 174)
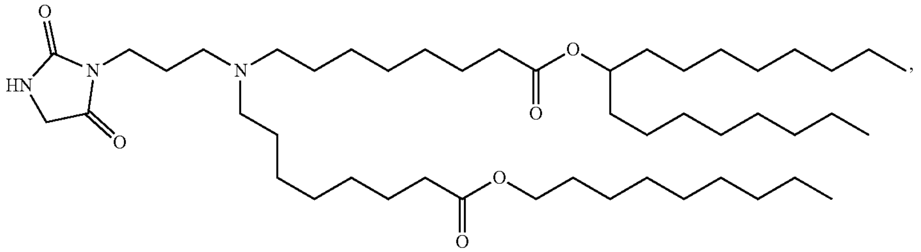
(Compound 175)
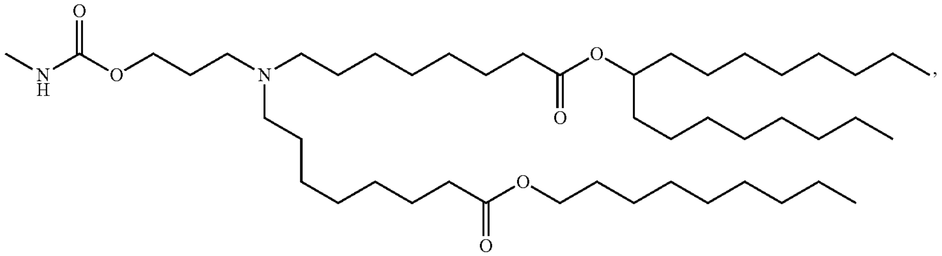
(Compound 176)
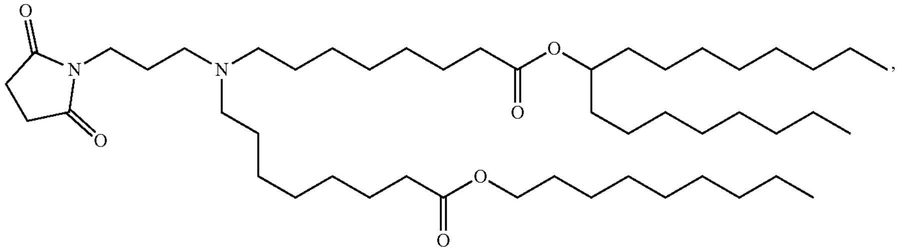
(Compound 177)
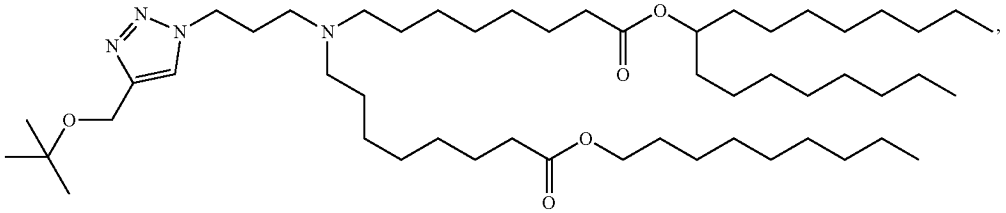
(Compound 178)
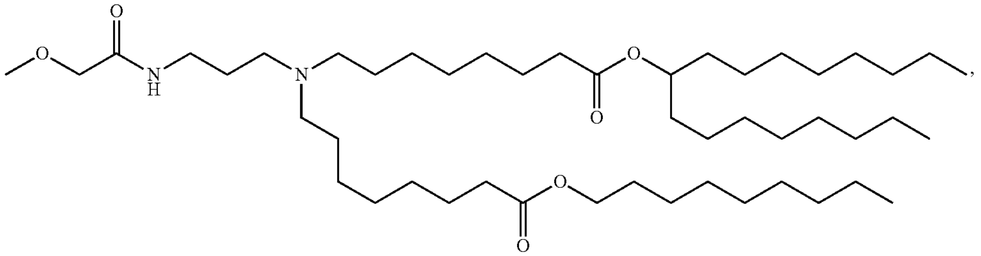
(Compound 179)
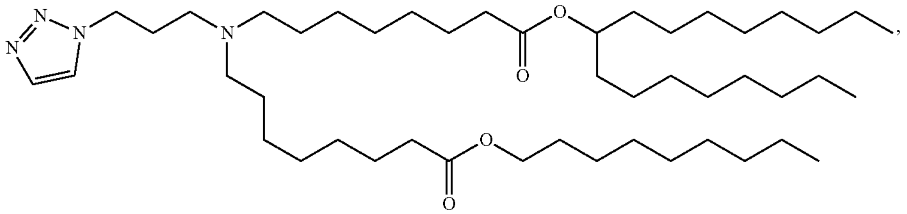

-continued
(Compound 180)
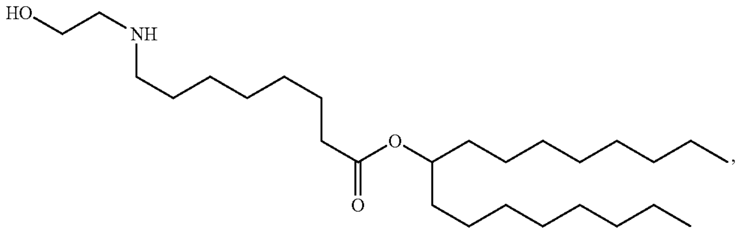
(Compound 181)
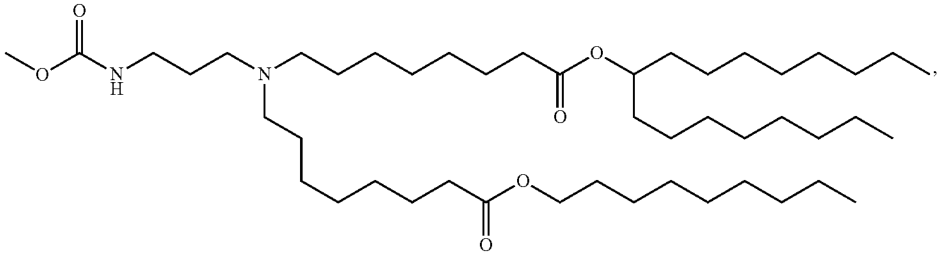
(Compound 182)
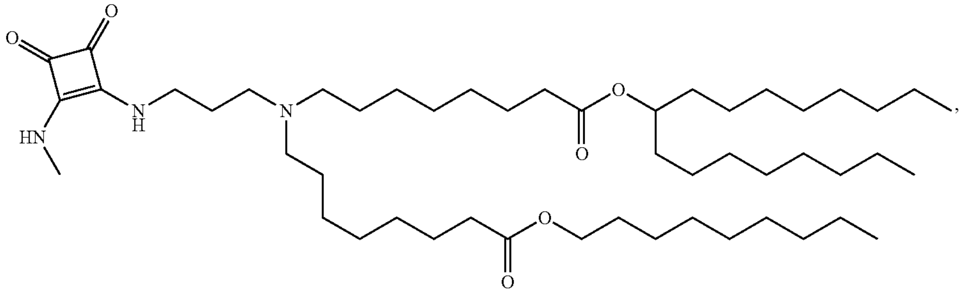
(Compound 183)
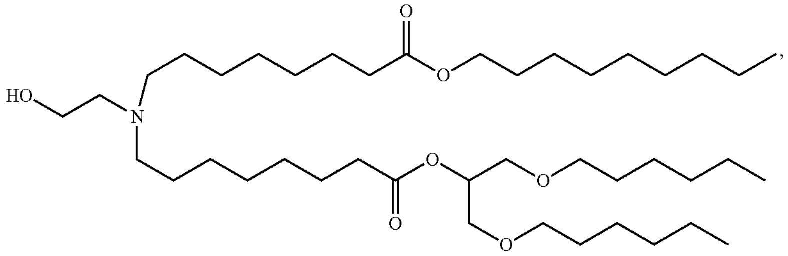
(Compound 184)
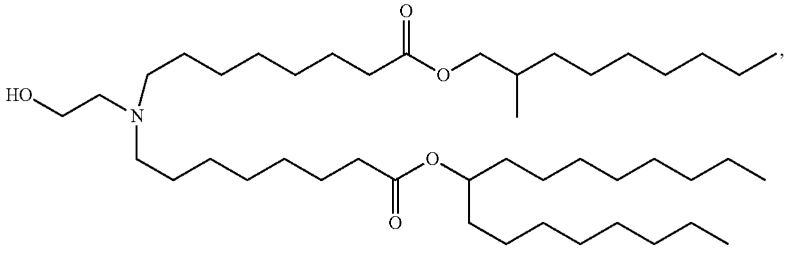
(Compound 185)
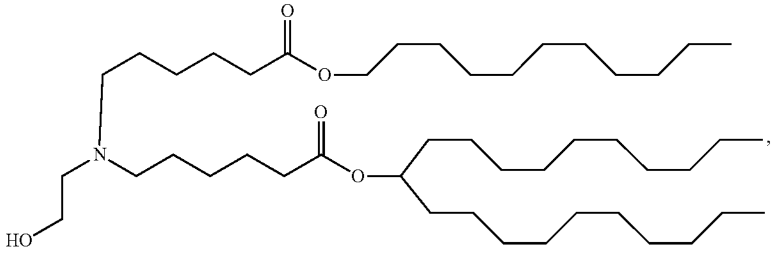

-continued
(Compound 186)
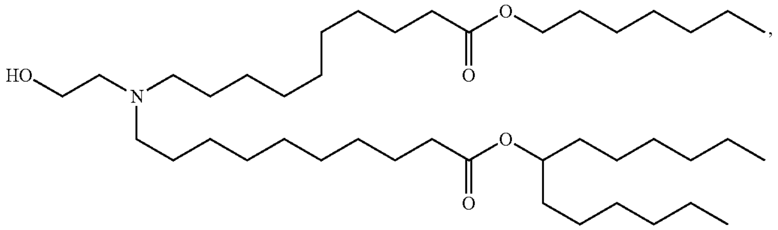
(Compound 187)
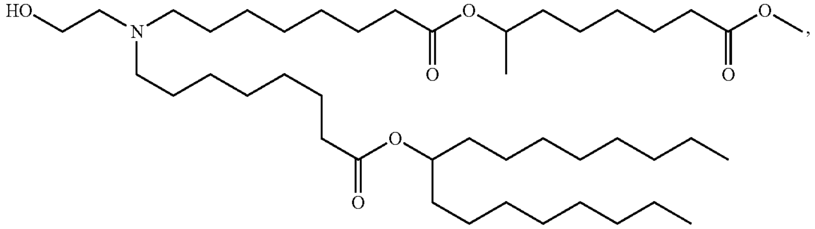
(Compound 188)
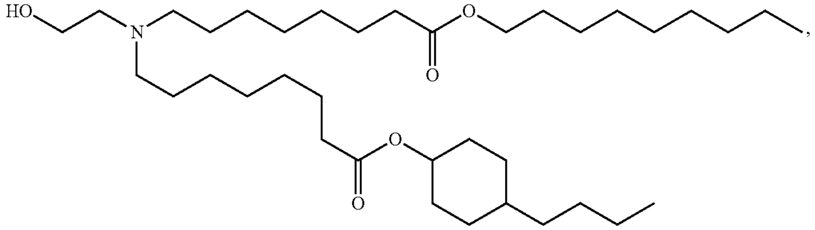
(Compound 189)
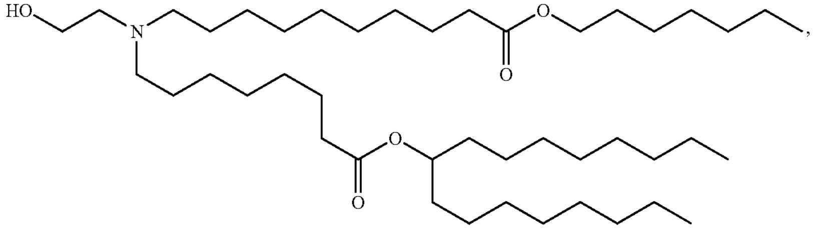
(Compound 190)
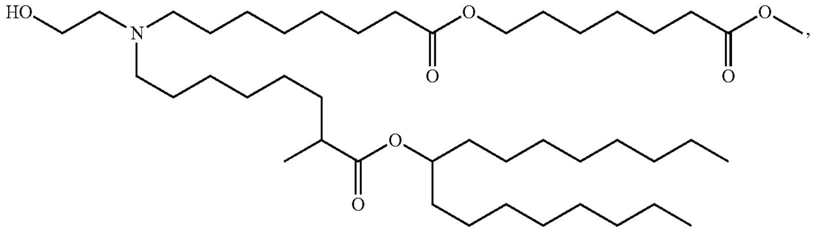
(Compound 191)
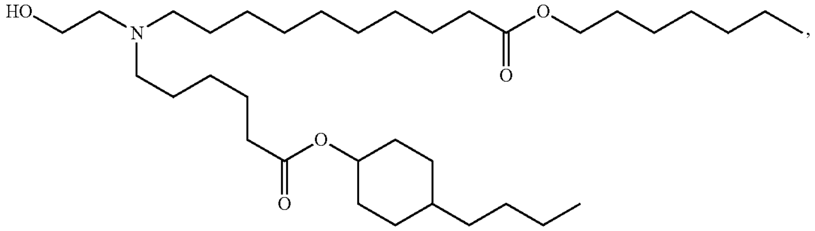

-continued
(Compound 192)
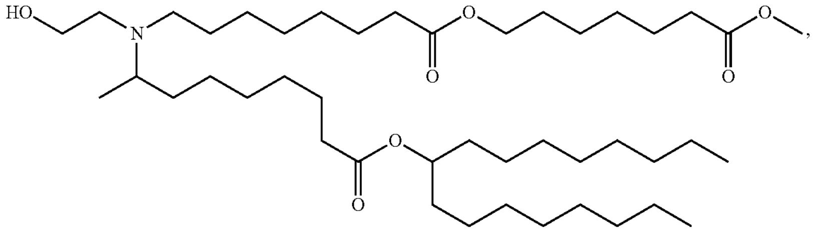
(Compound 193)
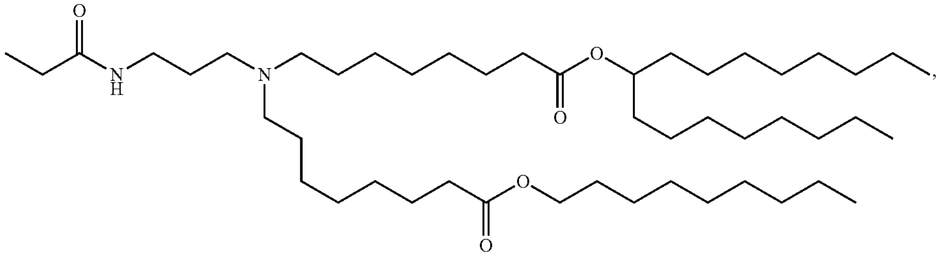
(Compound 194)
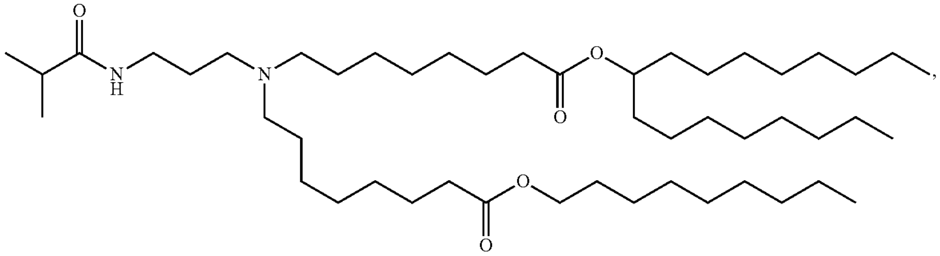
(Compound 195)
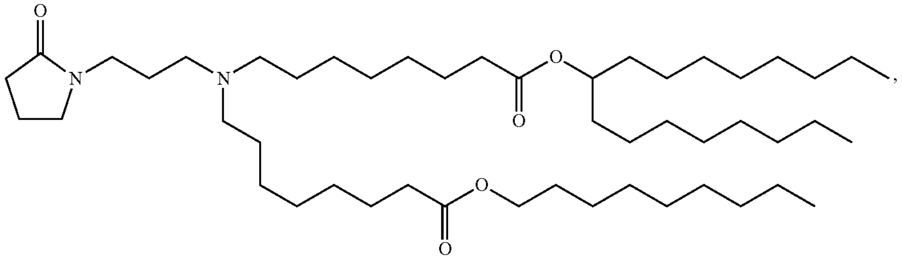
(Compound 196)
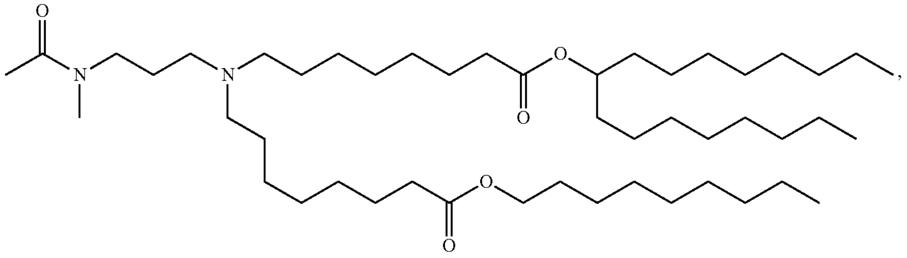
(Compound 197)
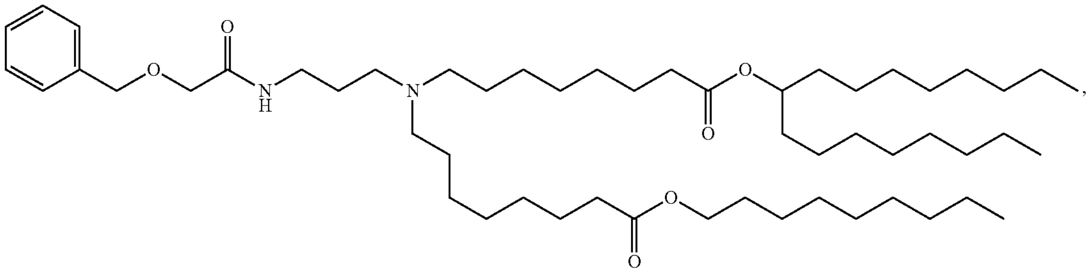

-continued
(Compound 198)
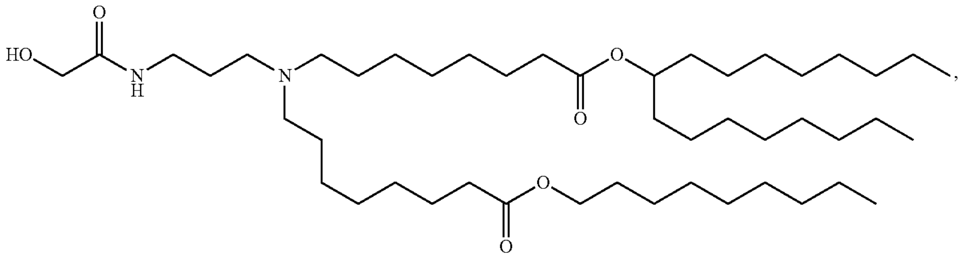
,
(Compound 199)
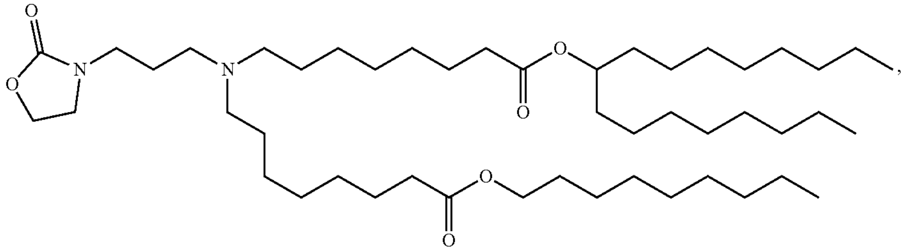
,
(Compound 200)
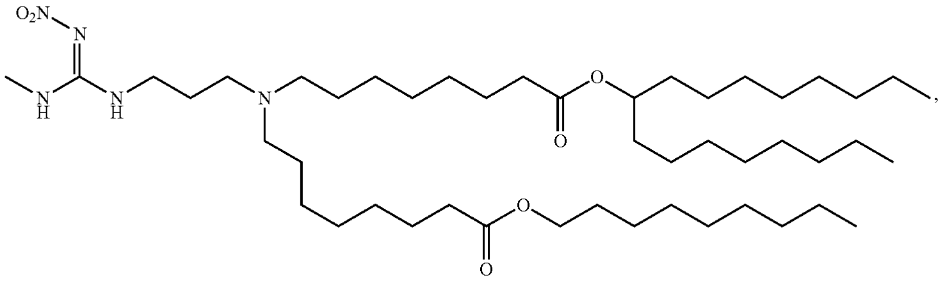
,
(Compound 201)
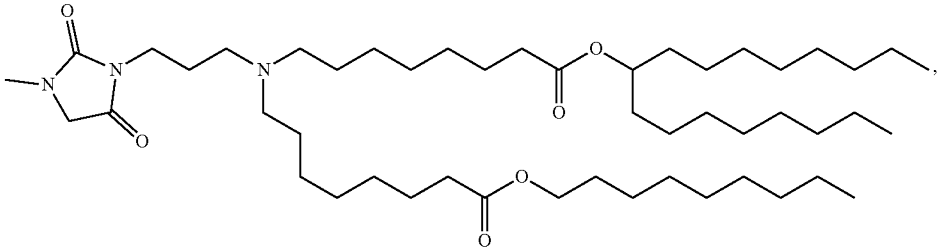
,
(Compound 202)
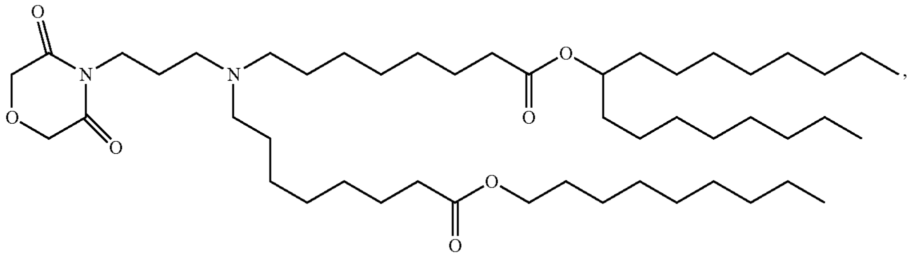
,
(Compound 203)
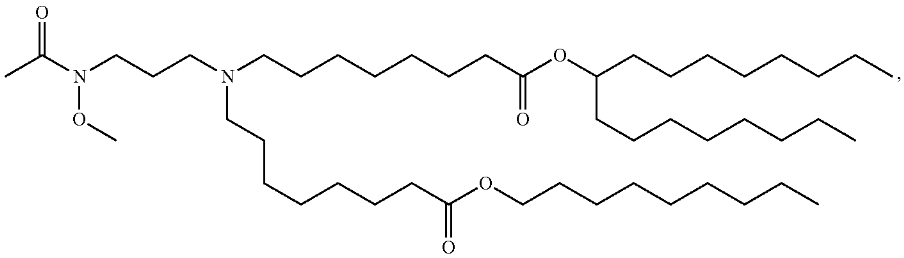
, -continued
(Compound 204)
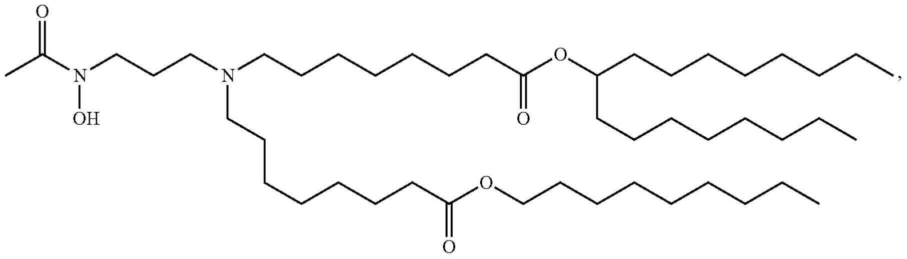
(Compound 205)
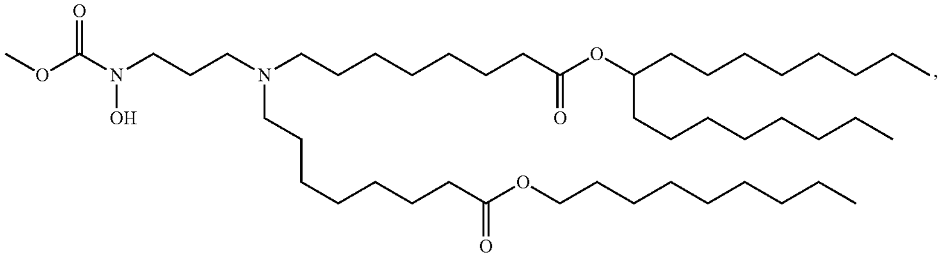
(Compound 206)
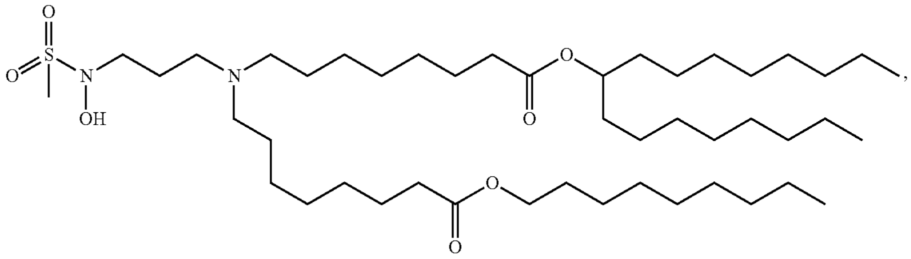
(Compound 207)
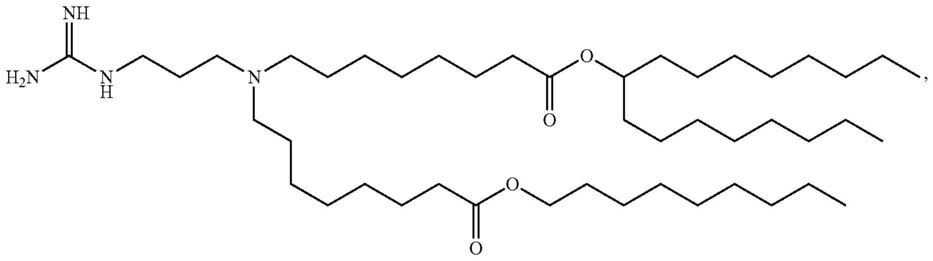
(Compound 208)
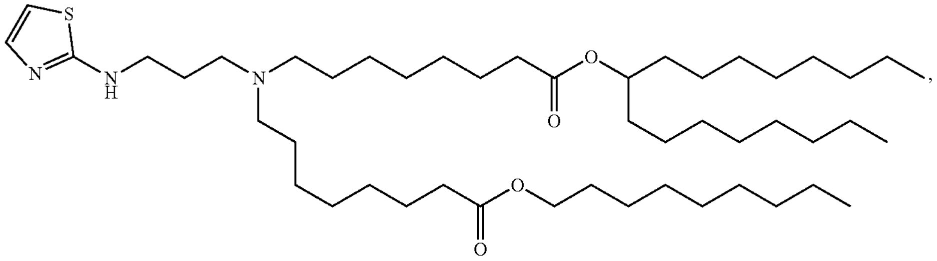
(Compound 209)
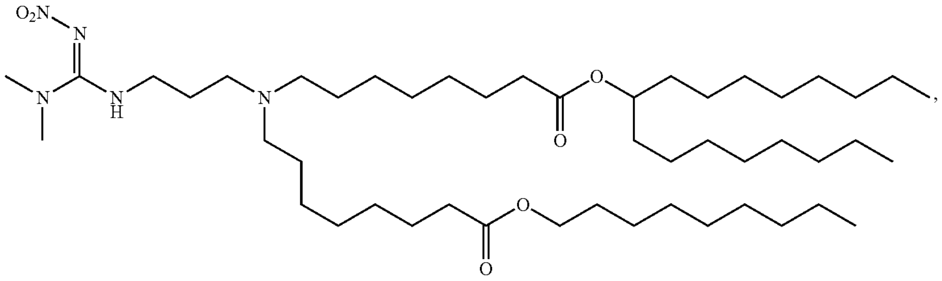

-continued
(Compound 210)
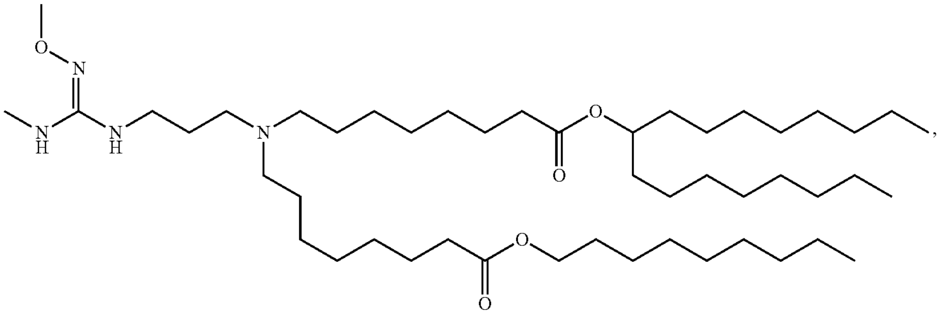
(Compound 211)
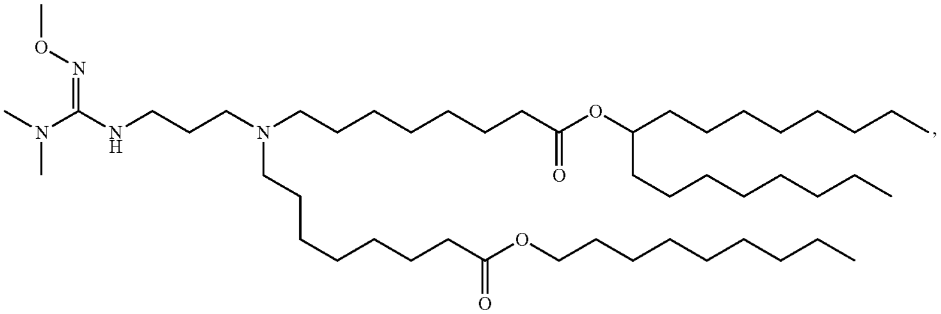
(Compound 212)
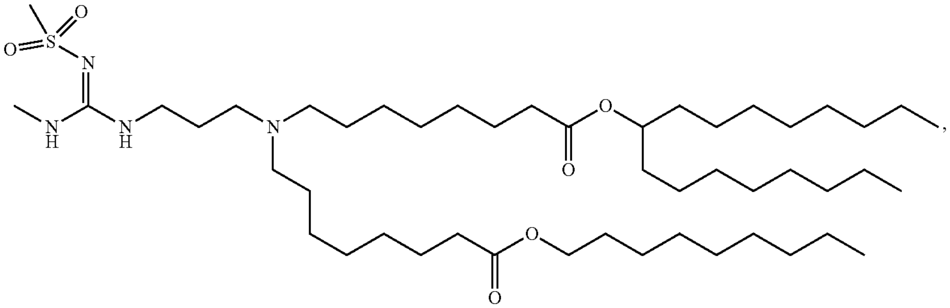
(Compound 213)
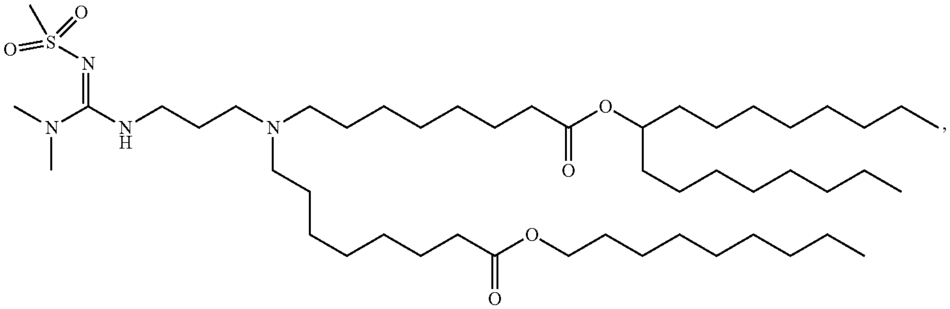
(Compound 214)
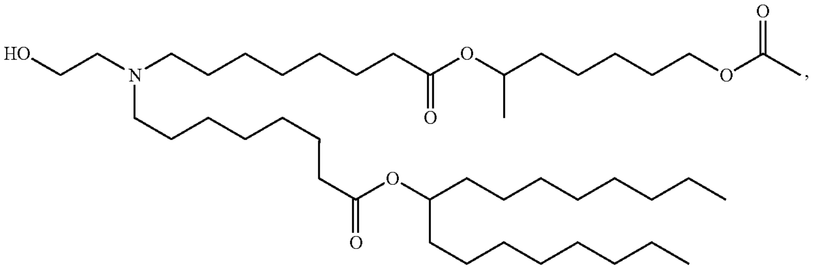

-continued
(Compound 215)
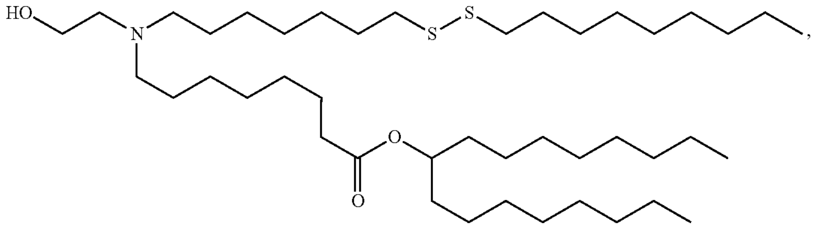
(Compound 216)
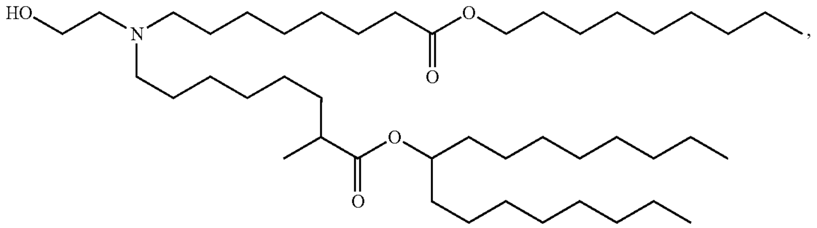
(Compound 217)
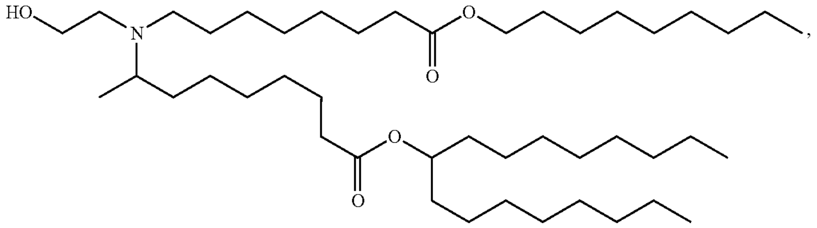
(Compound 218)
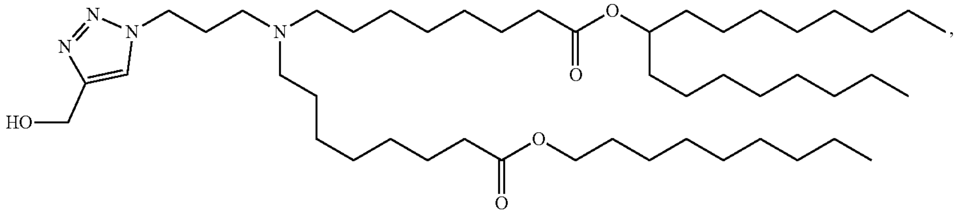
(Compound 219)
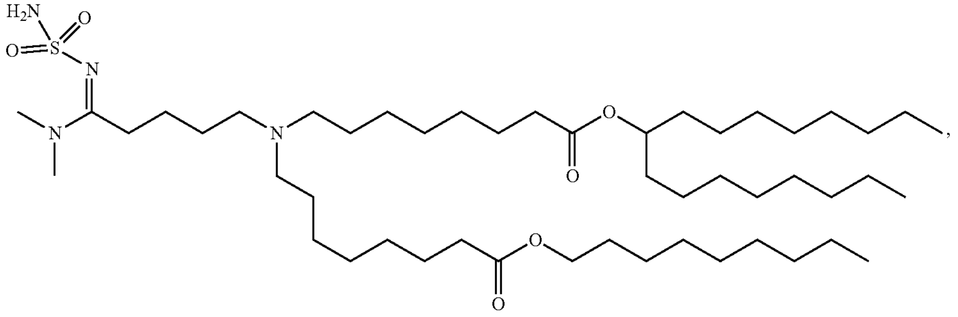
(Compound 220)
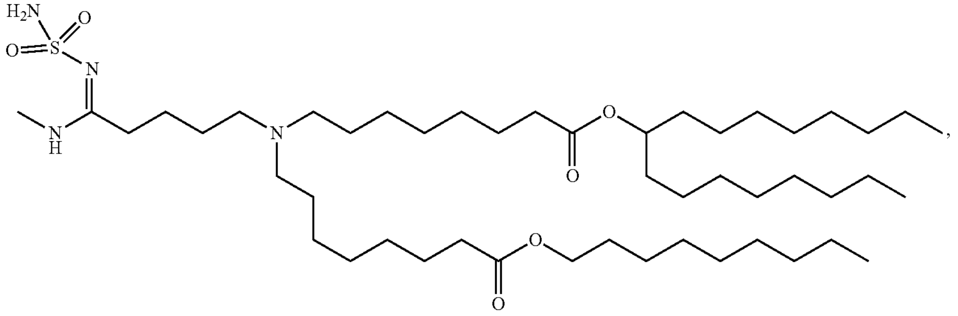

-continued
(Compound 221)
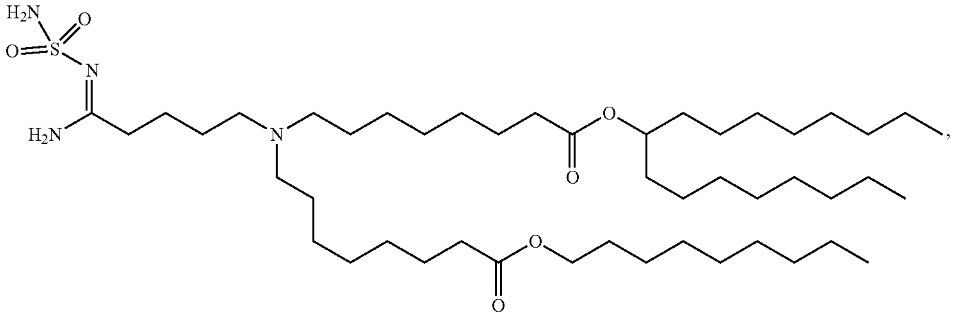
(Compound 222)
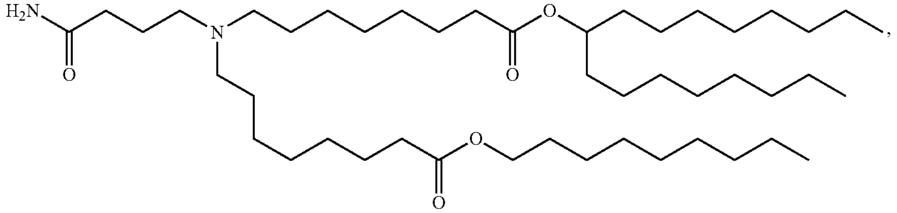
(Compound 223)
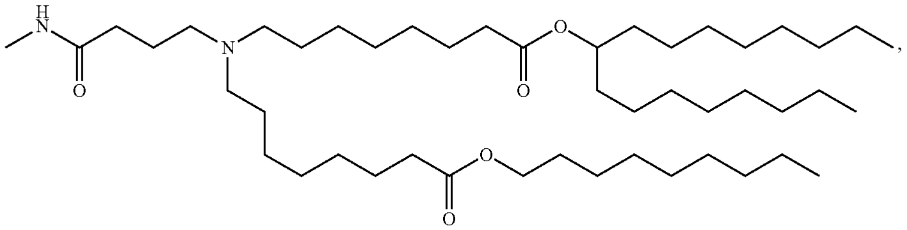
(Compound 224)
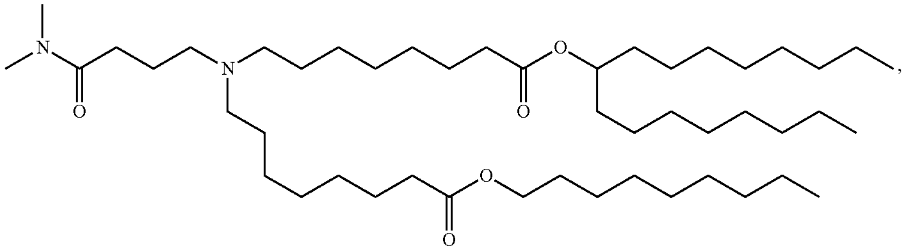
(Compound 225)
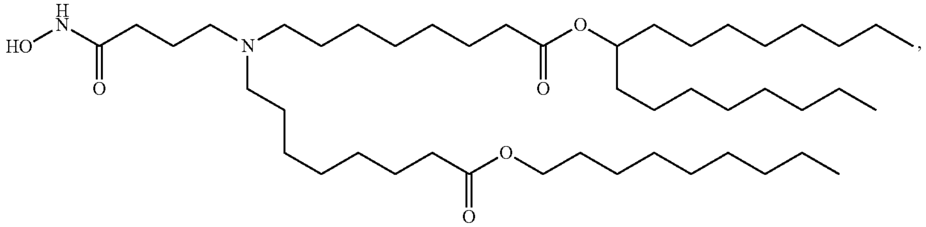
(Compound 226)
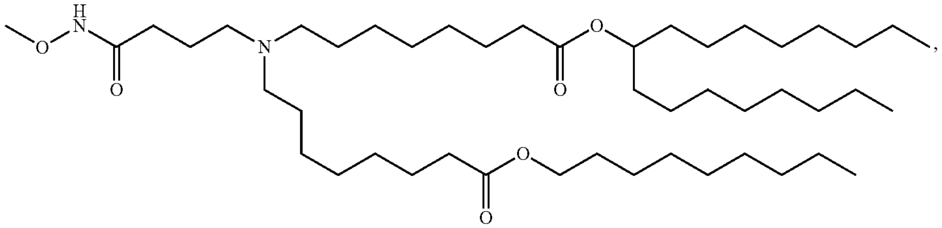

-continued (Compound 227)

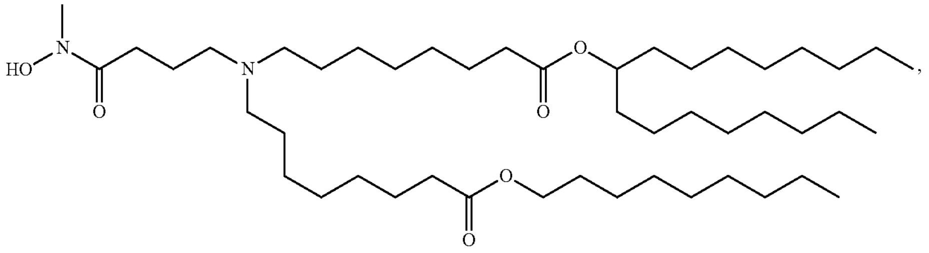

(Compound 228)

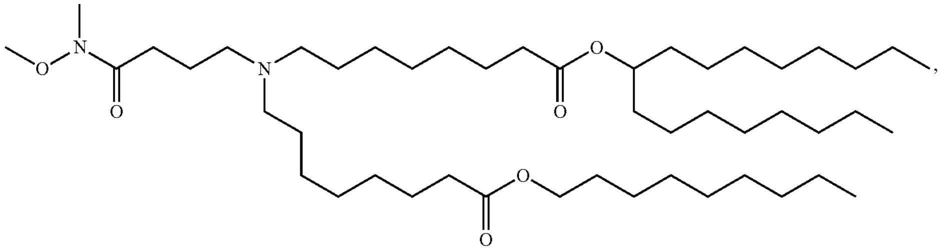

(Compound 229)

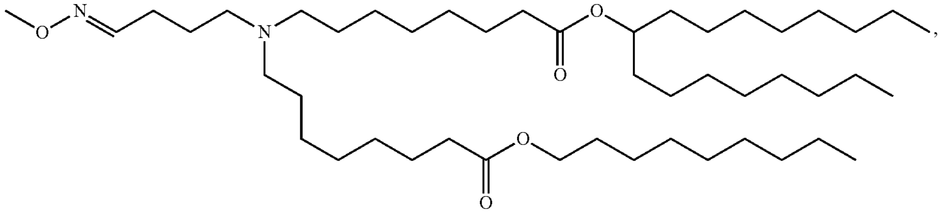

(Compound 230)

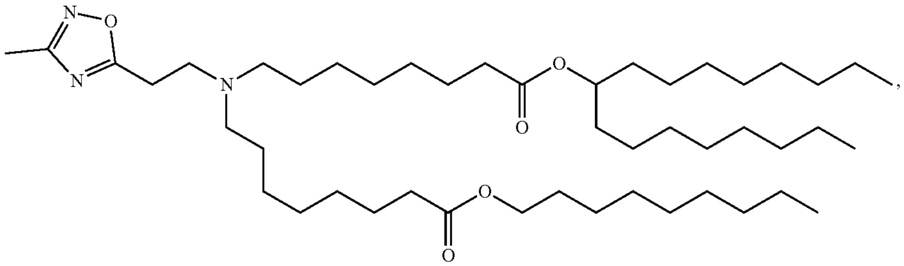

(Compound 231)

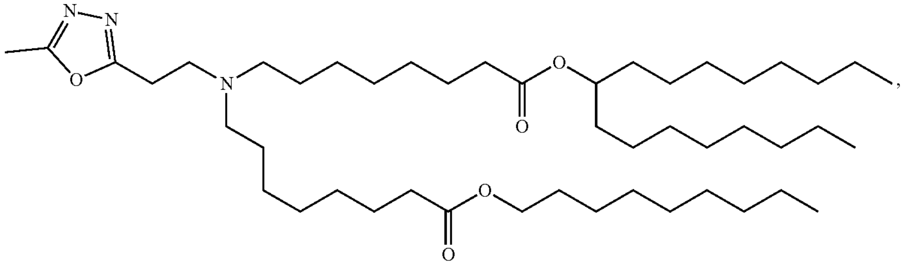

(Compound 232)

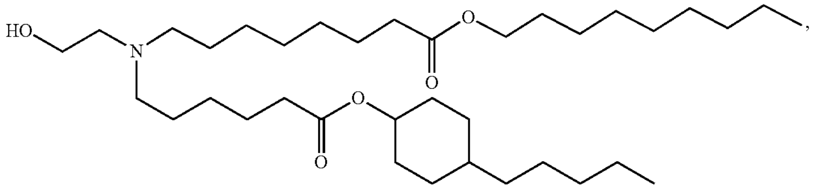

and salts or stereoisomers thereof.

In other embodiments, the compound of Formula (I) is selected from the group consisting of Compound 1-Compound 232, or salt or stereoisomers thereof.

In some embodiments ionizable lipids including a central piperazine moiety are provided. The lipids described herein may be advantageously used in lipid nanoparticle compositions for the delivery of therapeutic and/or prophylactic agents to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprises a reference lipid (e.g., MC3, KC2, or DLinDMA) and the same therapeutic or prophylactic agent.

In some embodiments, the delivery agent comprises a lipid compound having the Formula (III)

(III)

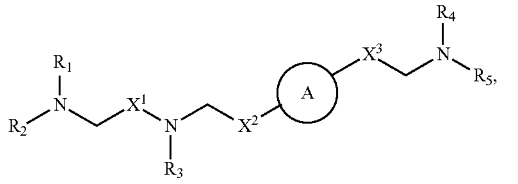

or salts or stereoisomers thereof, wherein ring A is

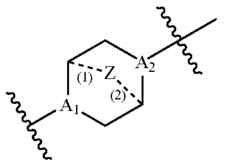

or

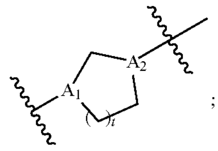

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of C(O)O, OC(O), —OC(O)O, C(O)N(R'), N(R')C(O), C(O), C(S), C(S)S, SC(S), CH(OH), P(O)(OR')O, $—S(O)_2$, an aryl group, and a heteroaryl group;

$X^1$, $X^2$, and $X^3$ are independently selected from the group consisting of a bond, $—CH_2$, $(CH_2)_2—$, CHR, CHY, C(O), C(O)O, OC(O), $—C(O)—CH_2—$, $—CH_2—C(O)—$, $C(O)O—CH_2$, $OC(O)—CH_2$, $CH_2—C(O)O$, $CH_2—OC(O)$, CH(OH), C(S), and CH(SH;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

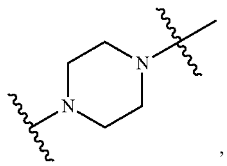 [SMILES: *N1CCN(*)CC1]

, then i) at least one of $X^1$, $X^2$, and $X^3$ is not $—CH_2—$; and/or ii) at least one of $R_1$, $R_2$, $R_3$, $R_4$, and $R_5$ is —R"MR'.

In some embodiments, the compound is of any of formulae (IIIa1)-(IIIa6):

(IIIa1)

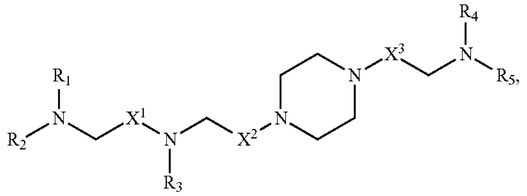

(IIIa2)

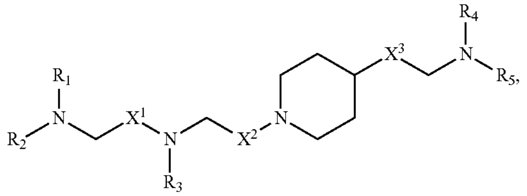

(IIIa3)

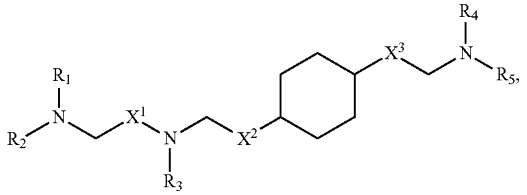

(IIIa4)

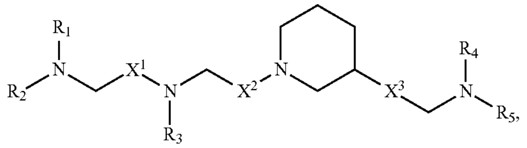

(IIIa5)

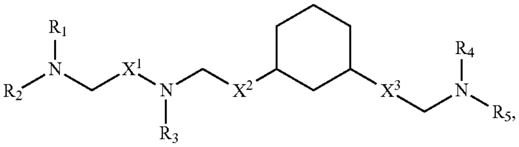

or (IIIa6)

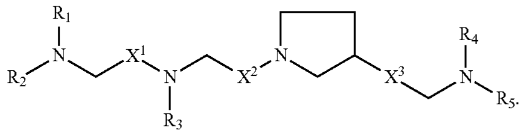

The compounds of Formula (III) or any of (IIIa1)-(IIIa6) include one or more of the following features when applicable.

In some embodiments, ring A is

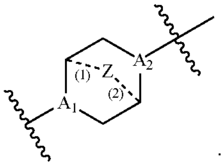

.

In some embodiments, ring A is

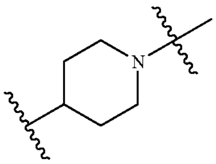

or

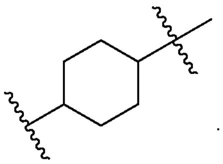

.

In some embodiments, ring A is

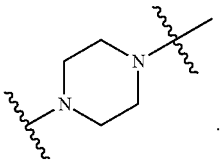 [SMILES: *N1CCN(*)CC1]

.

In some embodiments, ring A is

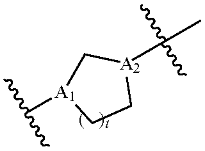

In some embodiments, ring A is

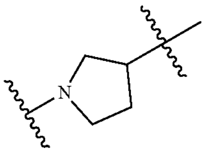

,

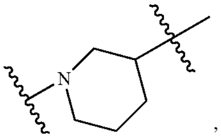

, or

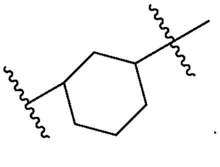

.

In some embodiments, ring A is

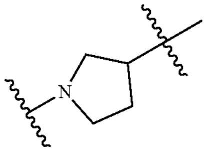

or

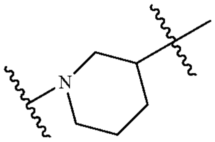

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O, OC(O), —C(O)—$CH_2$—, —$CH_2$—C(O)—, —C(O)O—$CH_2$, OC(O)—$CH_2$, $CH_2$—C(O)O, or $CH_2$—OC(O).

In some embodiments, $X^3$ is —C(O)—, —C(O)O—, —OC(O)—, —C(O)—$CH_2$—, —$CH_2$—C(O)—, C(O)O—$CH_2$, OC(O)—$CH_2$, $CH_2$—C(O)O, or $CH_2$—OC(O). In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:
(Compound 233)
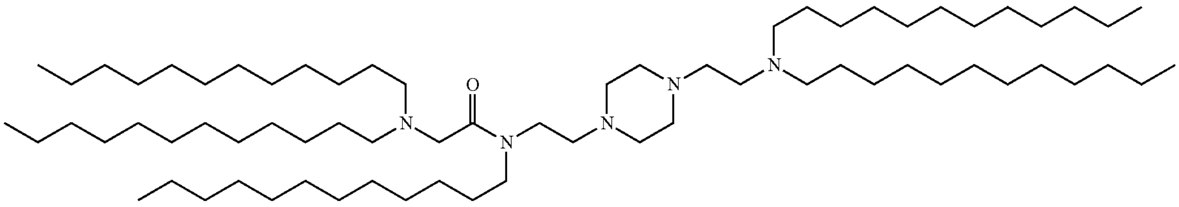,
(Compound 234)
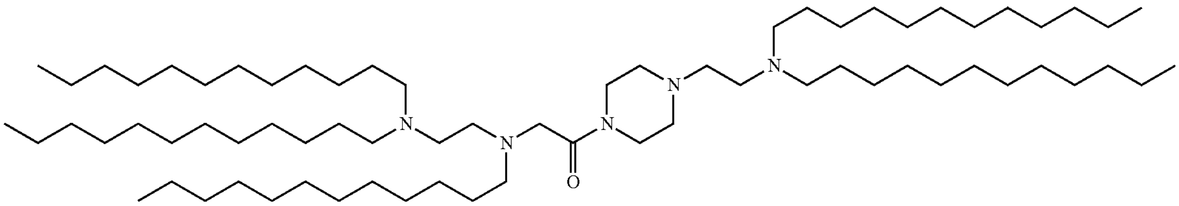,
(Compound 235)
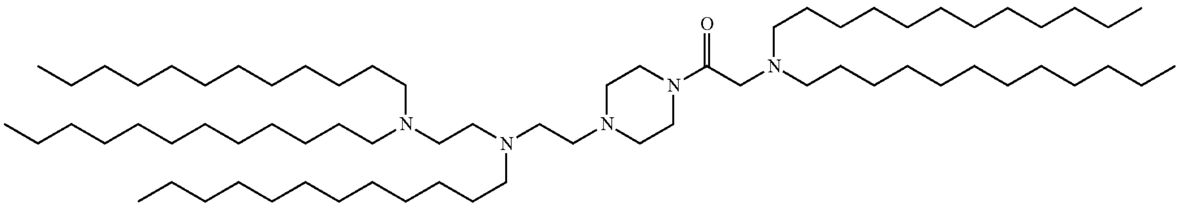,
(Compound 236)
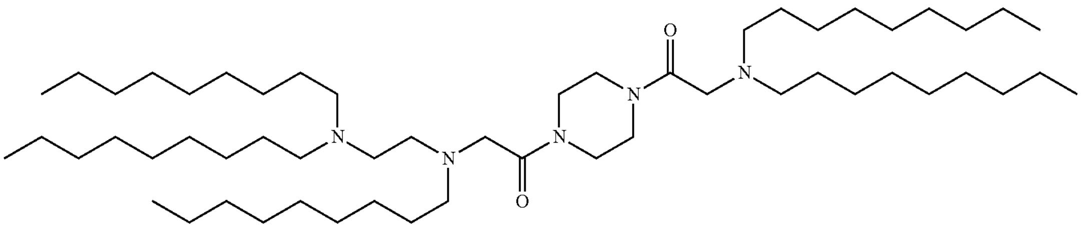,
(Compound 237)
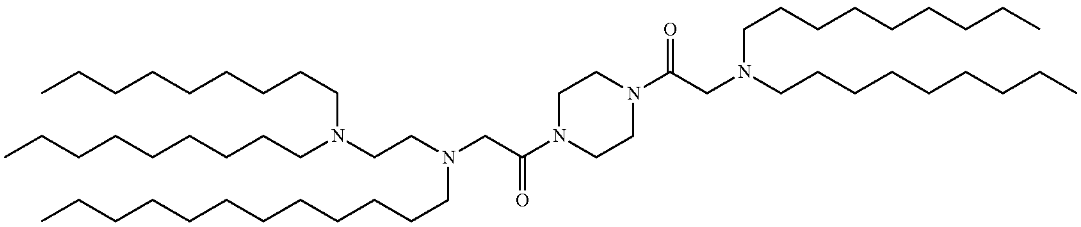,
(Compound 238)
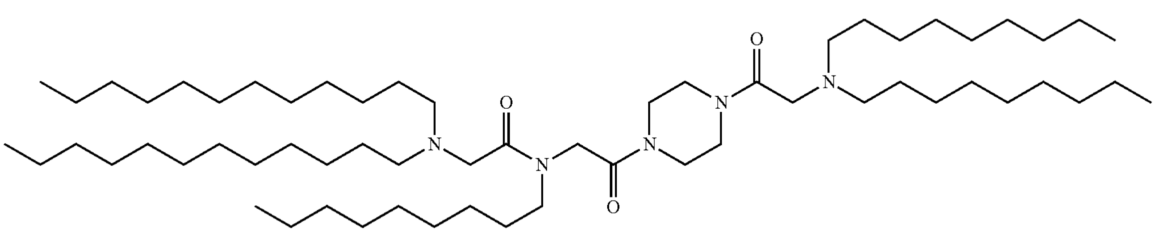, -continued
(Compound 239)
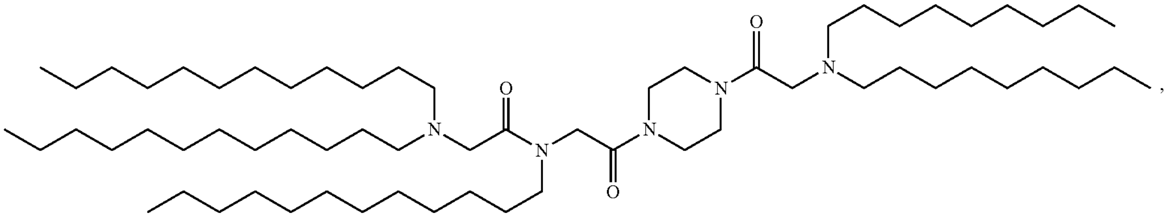
(Compound 240)
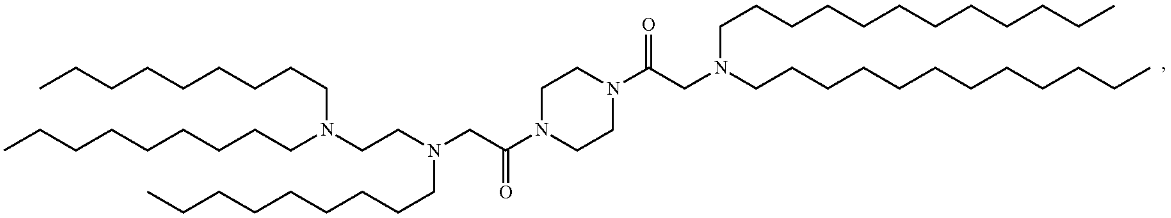
(Compound 241)
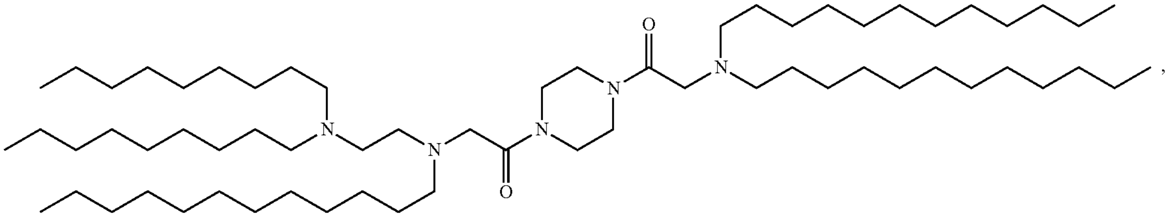
(Compound 242)
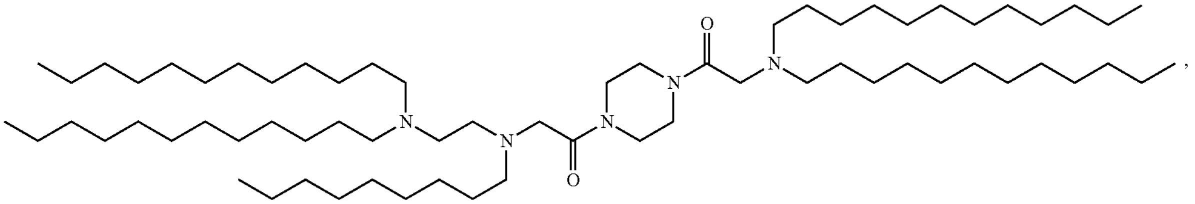
(Compound 243)
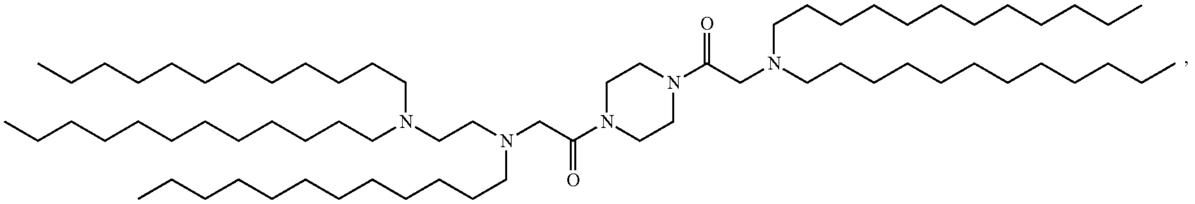
(Compound 244)
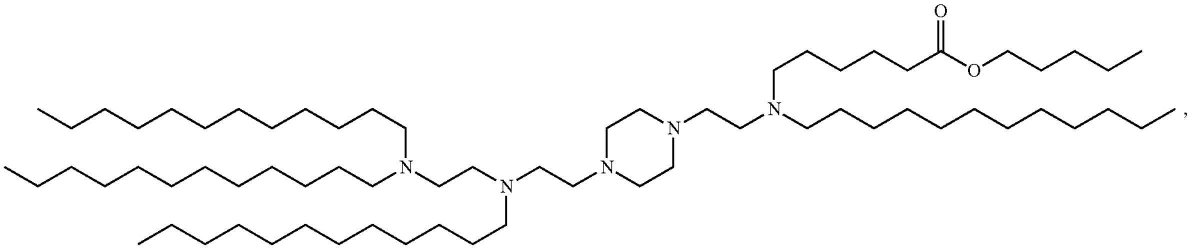

-continued
(Compound 245)
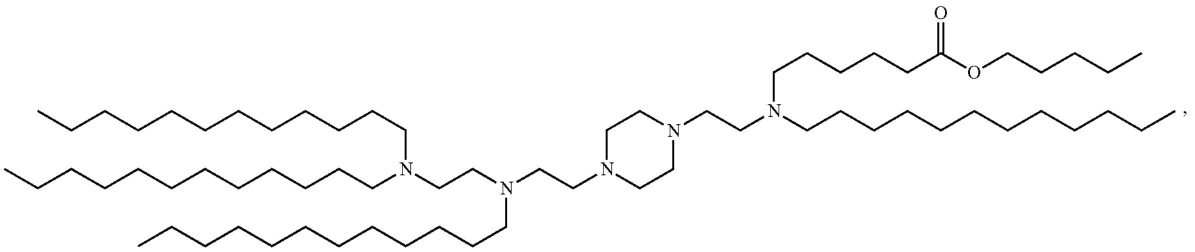
(Compound 246)
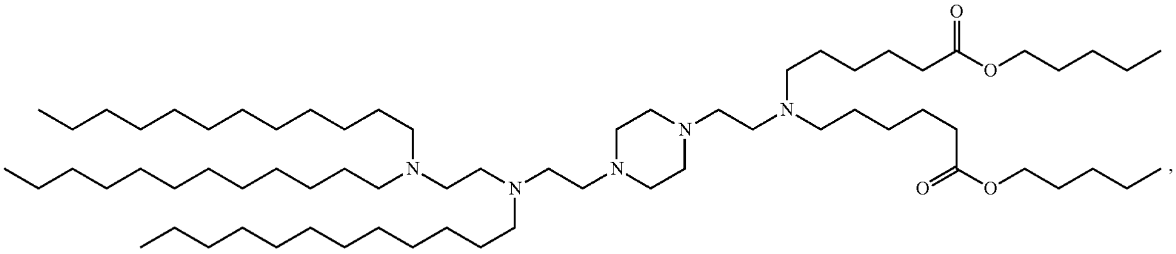
(Compound 247)
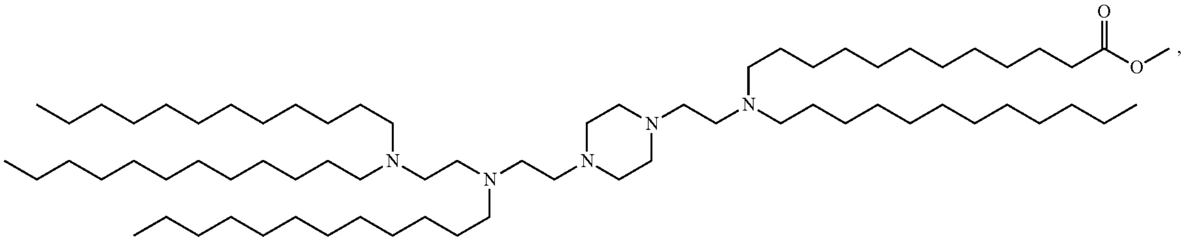
(Compound 248)
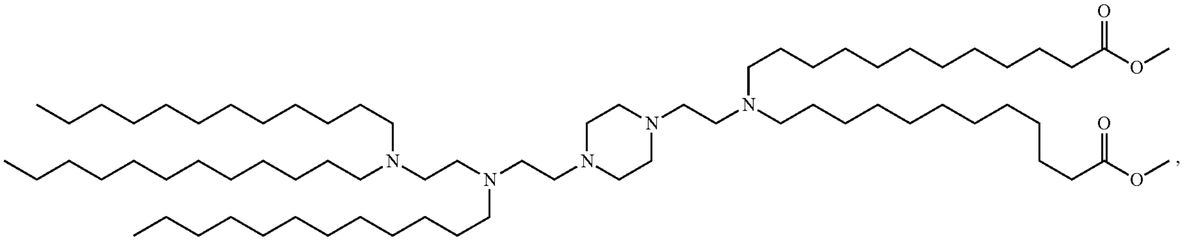
(Compound 274)
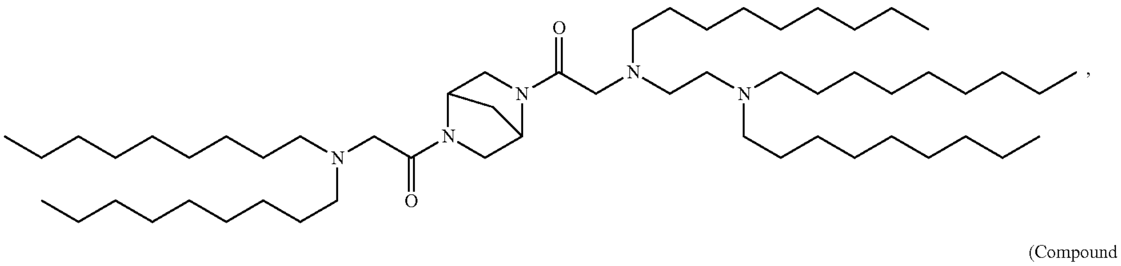
(Compound 275)
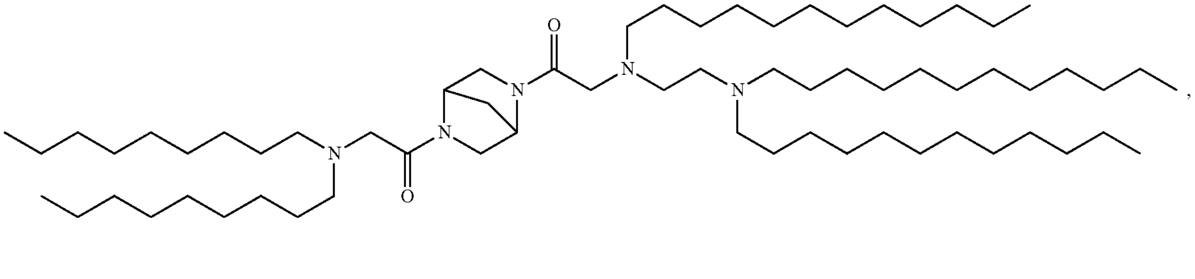

-continued
(Compound 276)
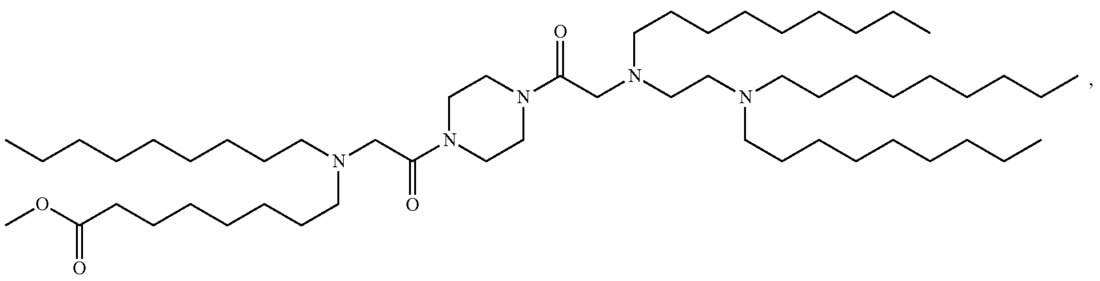
(Compound 277)
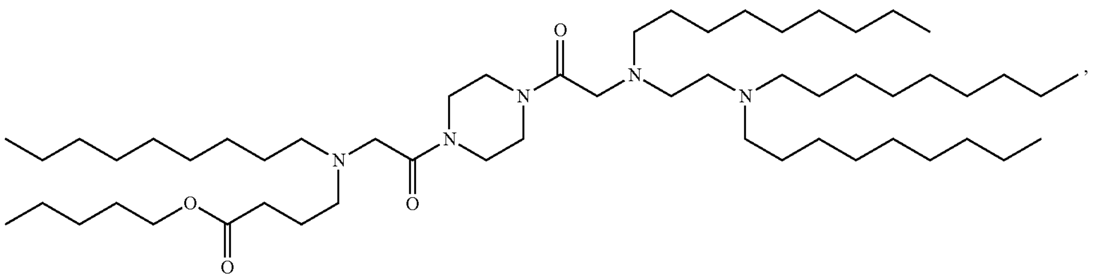
(Compound 278)
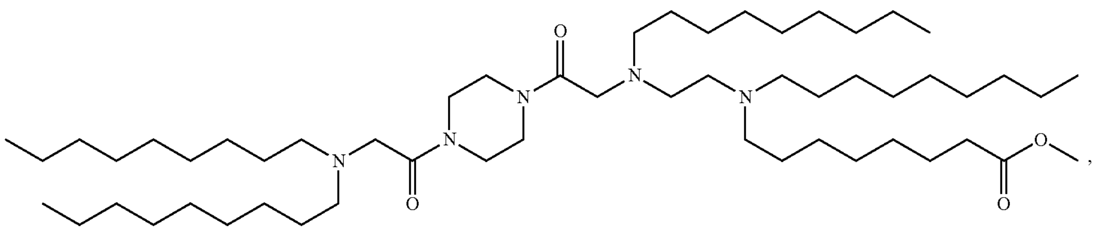
(Compound 279)
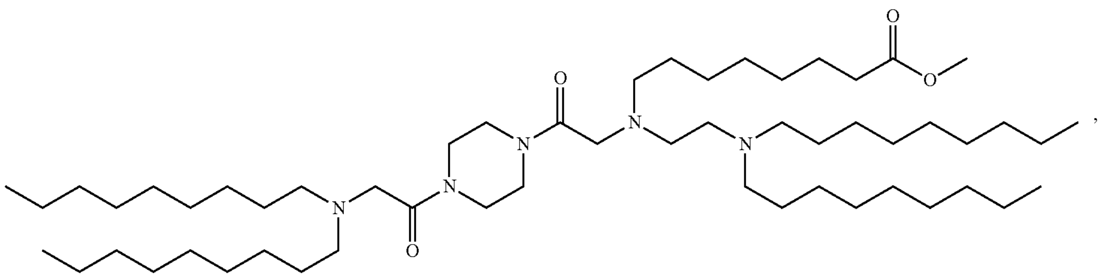
(Compound 280)
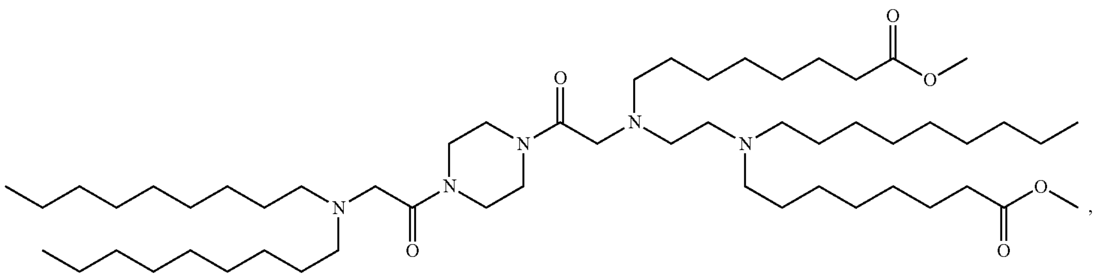

-continued
(Compound 281)
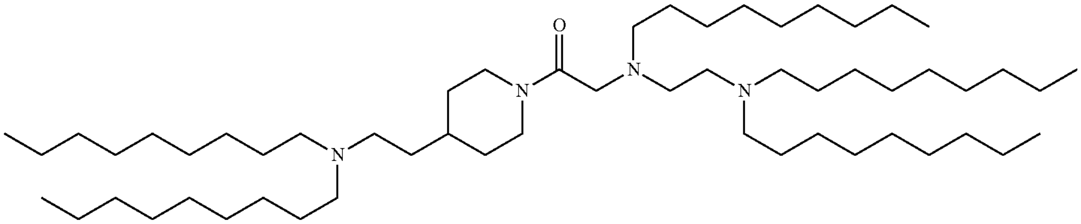
,
(Compound 282)
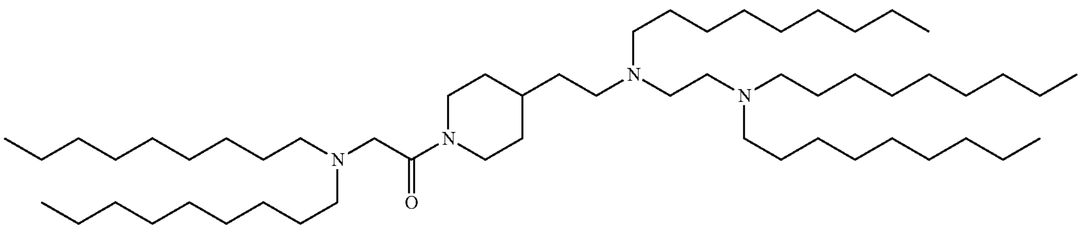
,
(Compound 283)
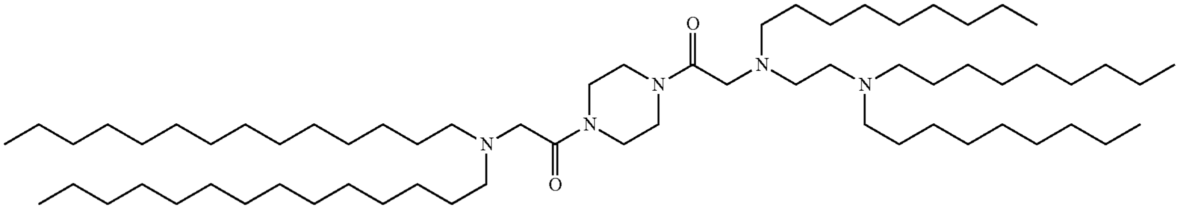
,
(Compund 284)
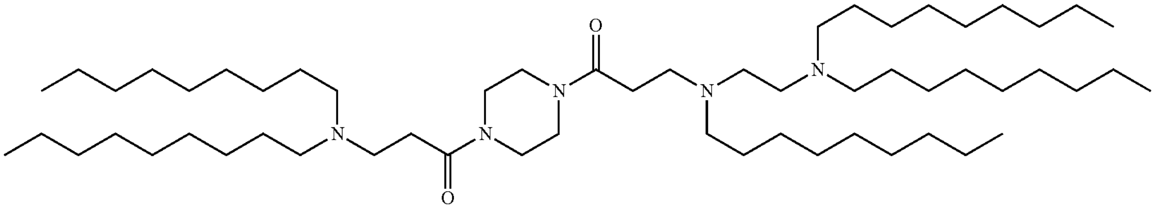
,
(Compound 285)
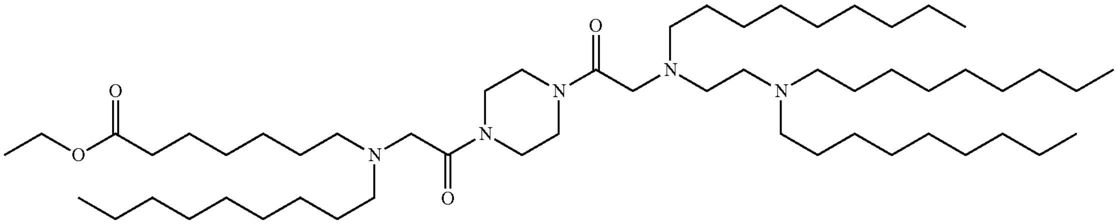
,
(Compound 286)
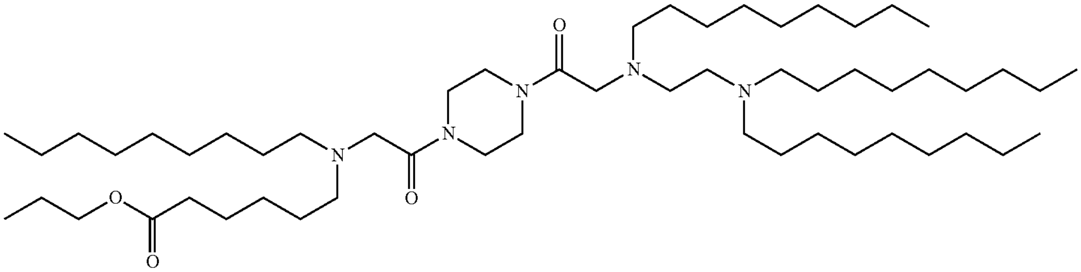
, -continued
(Compound 287)
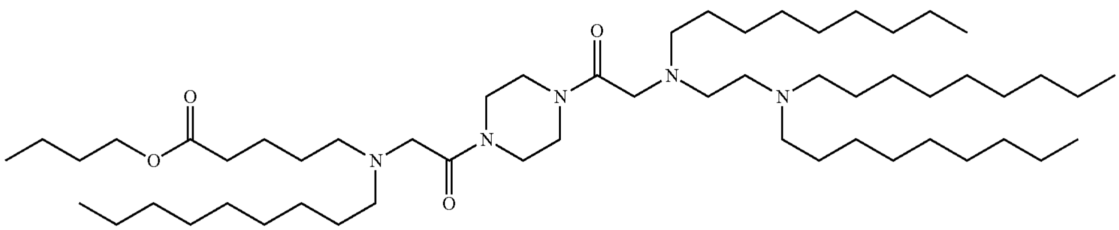
,
(Compound 288)
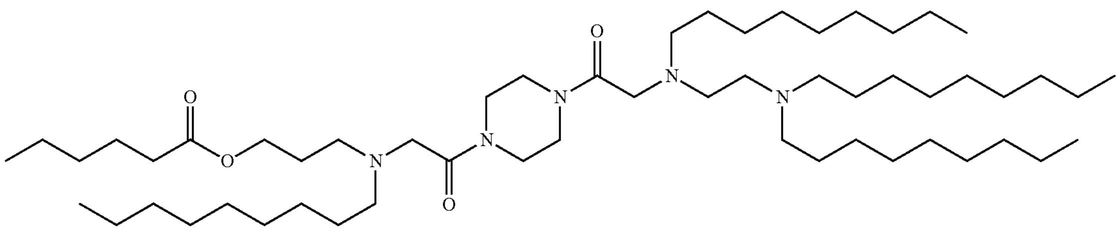
,
(Compound 289)
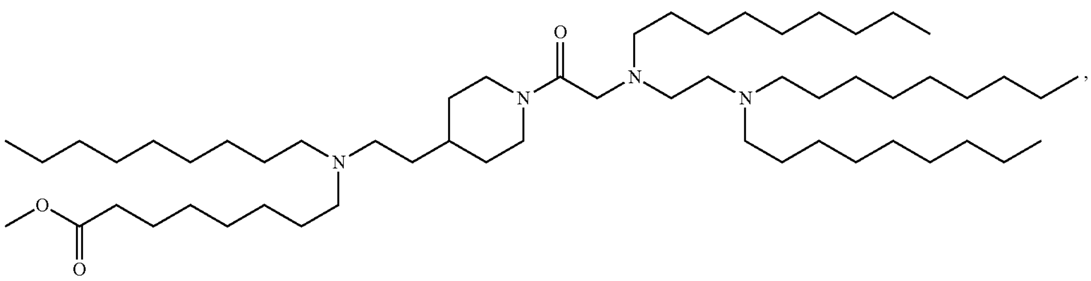
,
(Compound 290)
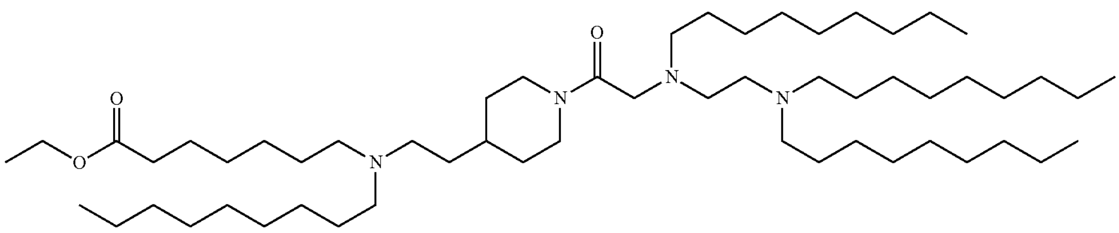
,
(Compound 291)
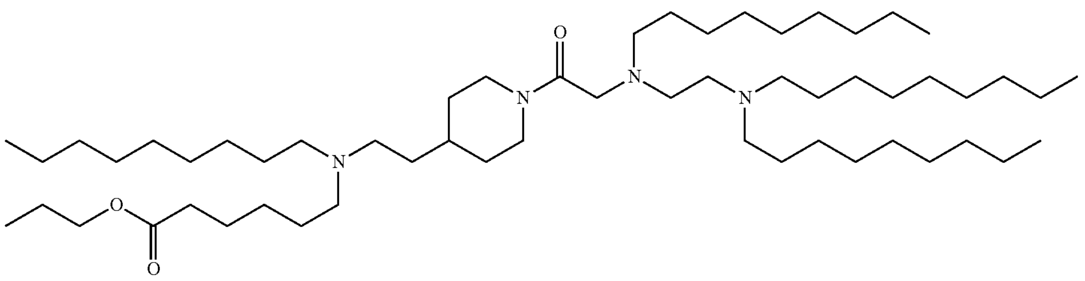
,
(Compound 292)
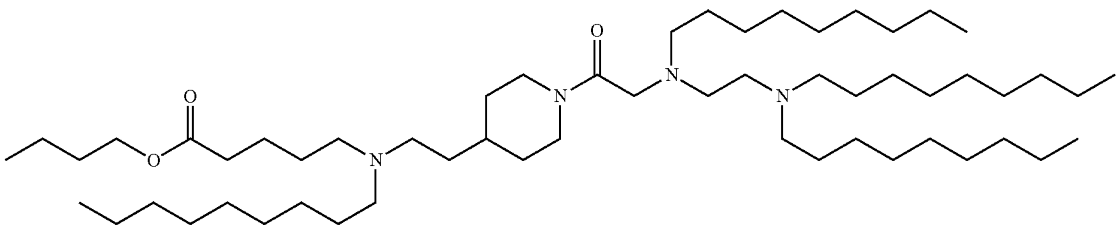
, -continued
(Compound 293)
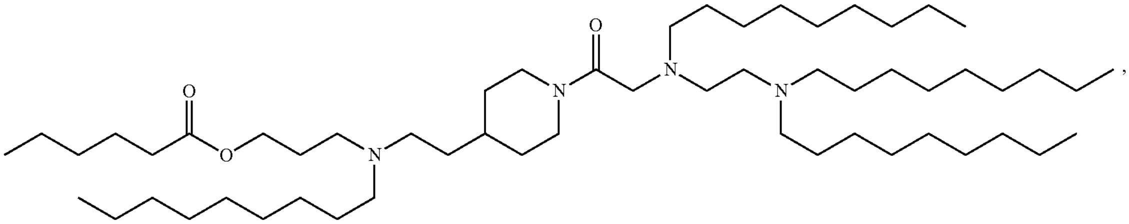
(Compound 294)
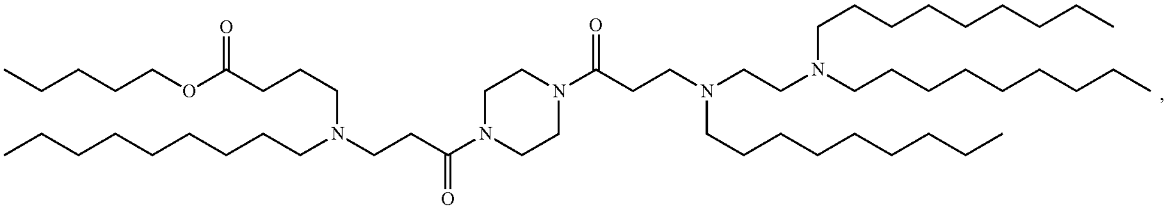
(Compound 295)
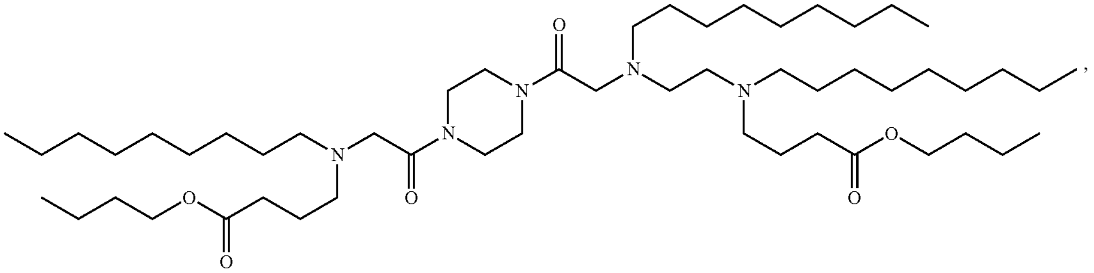
(Compound 296)
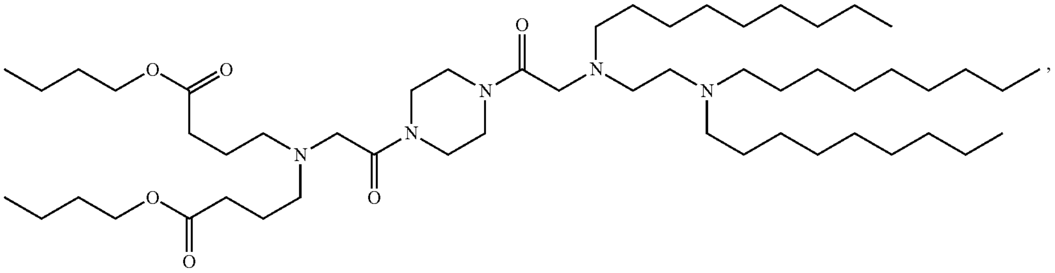
(Compound 297)
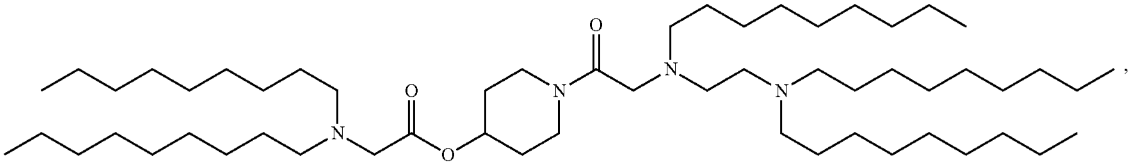
(Compound 298)
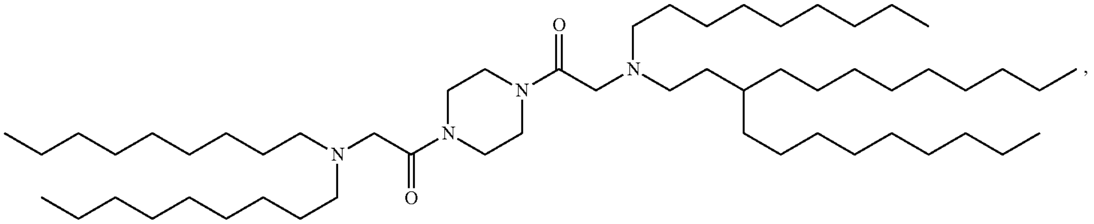

-continued
(Compound 300)
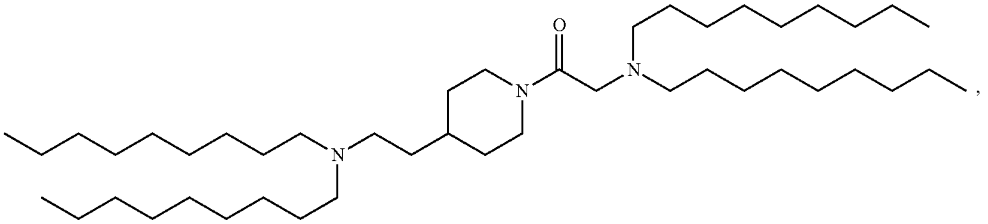
(Compound 301)
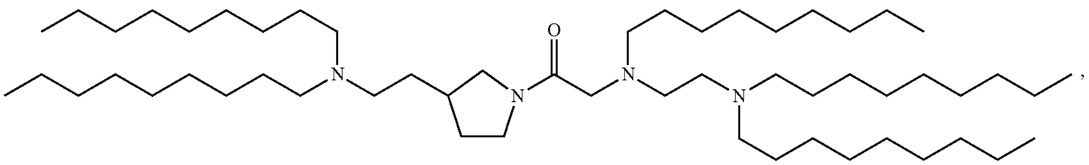
(Compound 302)
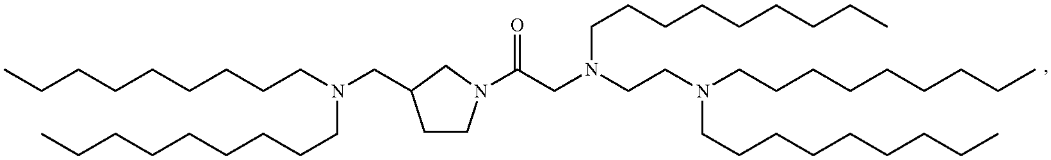
(Compound 303)
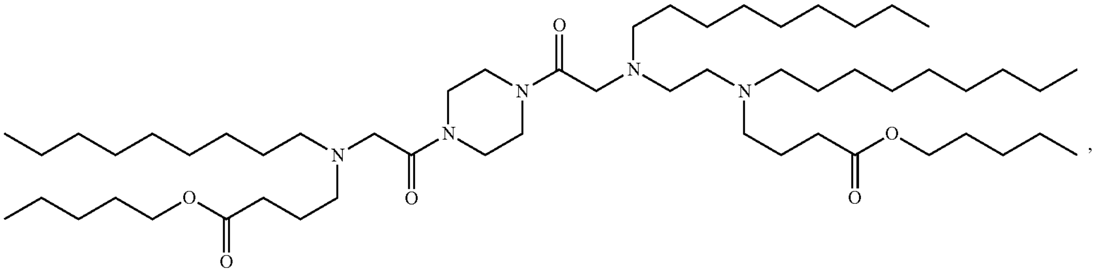
(Compound 304)
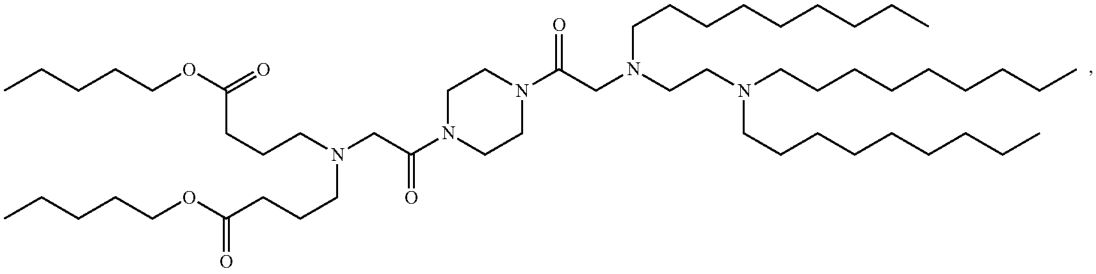
(Compound 305)
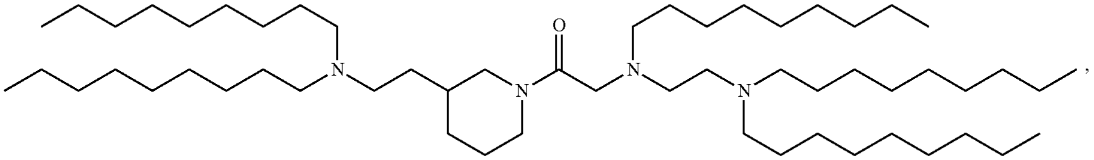
(Compound 306)
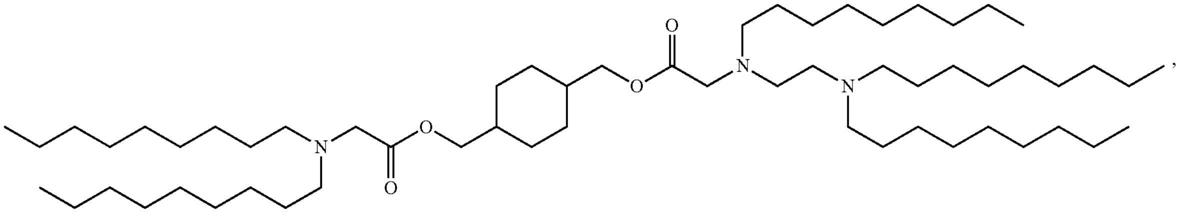

-continued
(Compound 307)
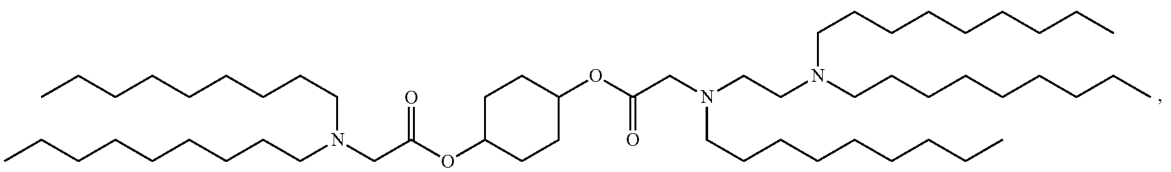
(Compound 308)
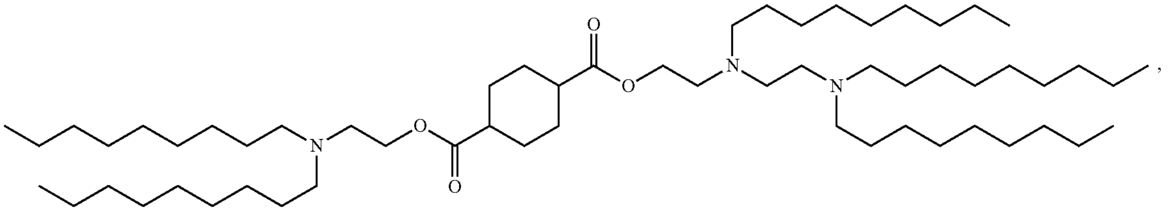
(Compound 310)
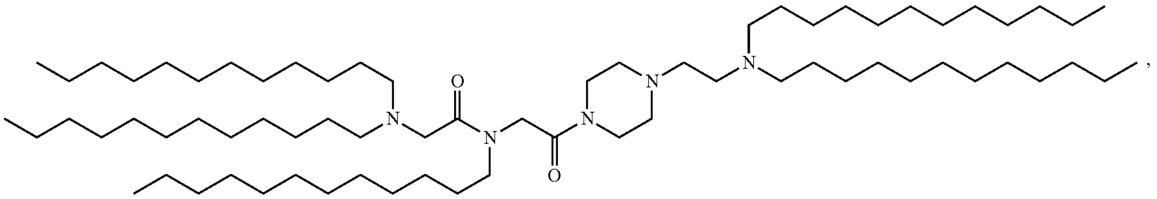
(Compound 311)
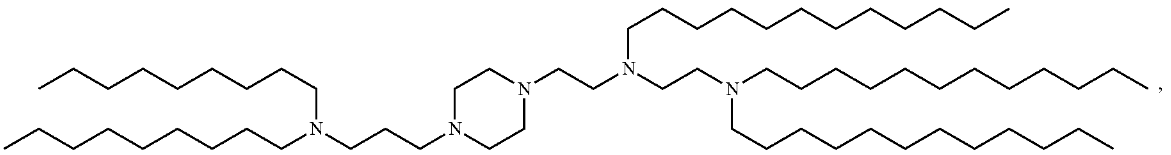
(Compound 312)
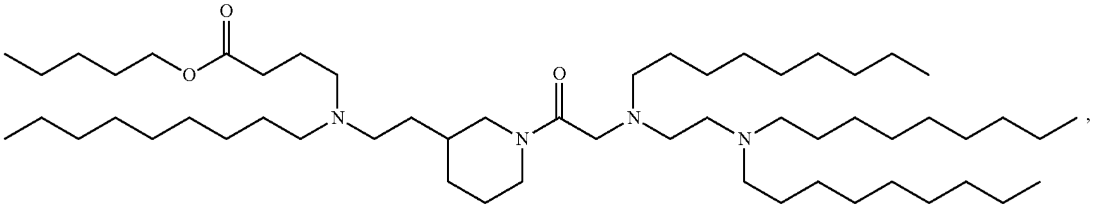
(Compound 313)
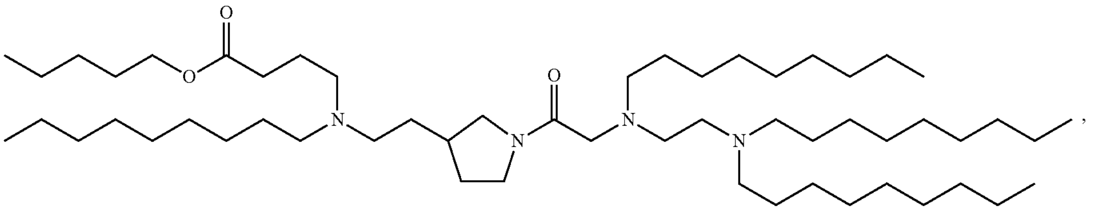
(Compound 314)
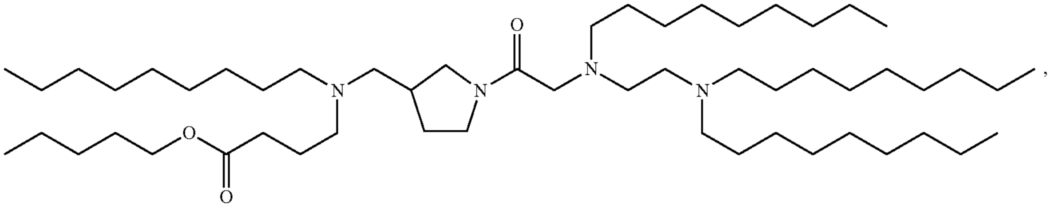

-continued
(Compound 315)
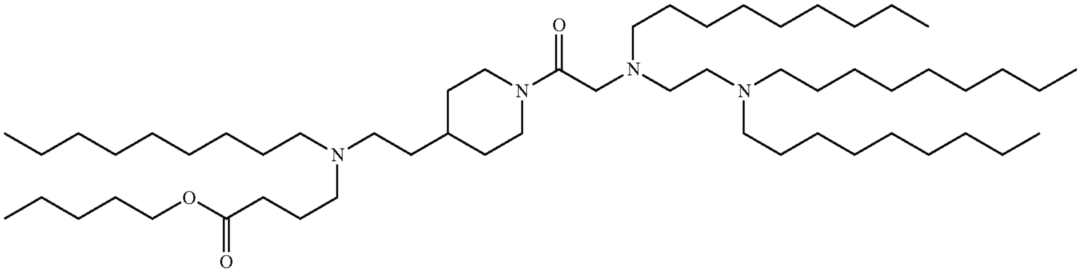
,
(Compound 316)
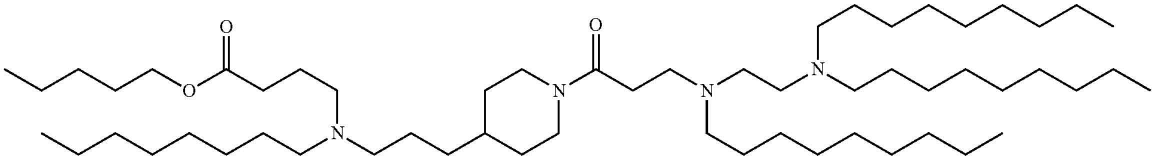
,
(Compound 317)
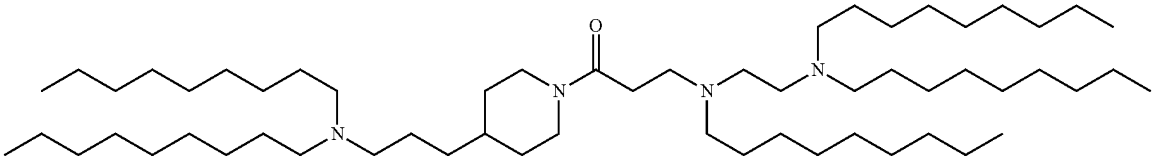
,
(Compound 318)
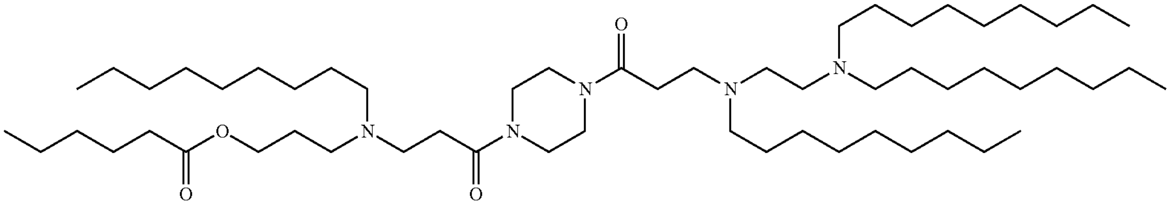
,
(Compound 319)
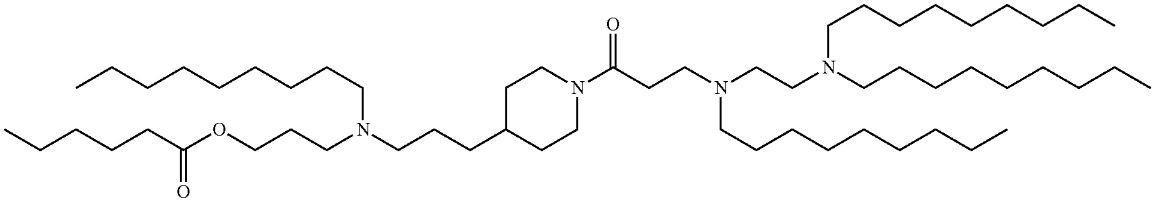
,
(Compound 320)
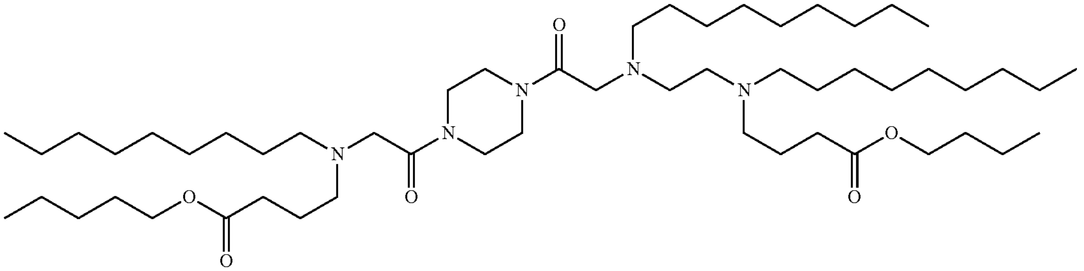
, -continued
(Compound 321)
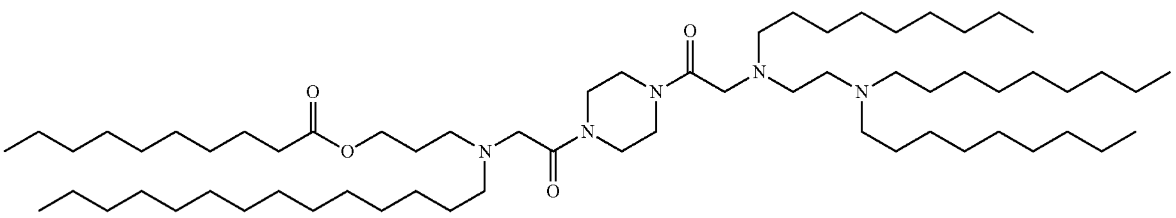
,
(Compound 322)
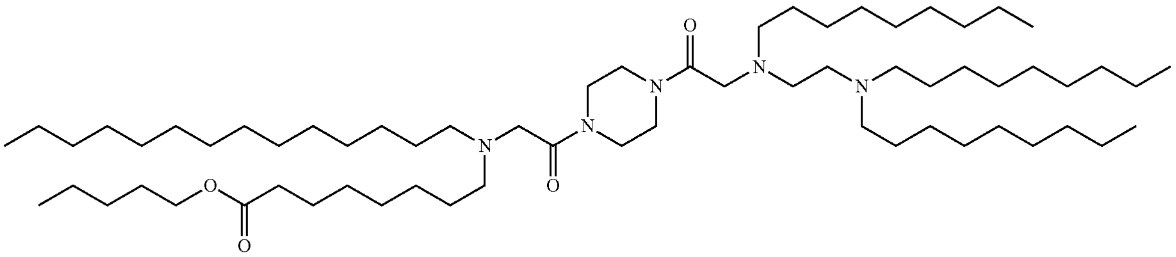
,
(Compound 323)
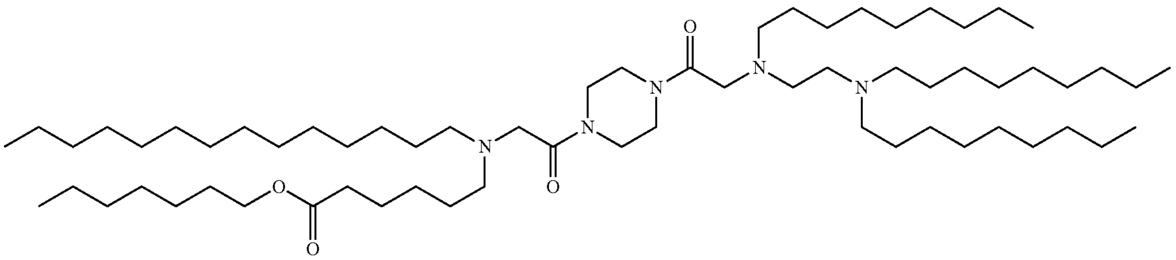
,
(Compound 324)
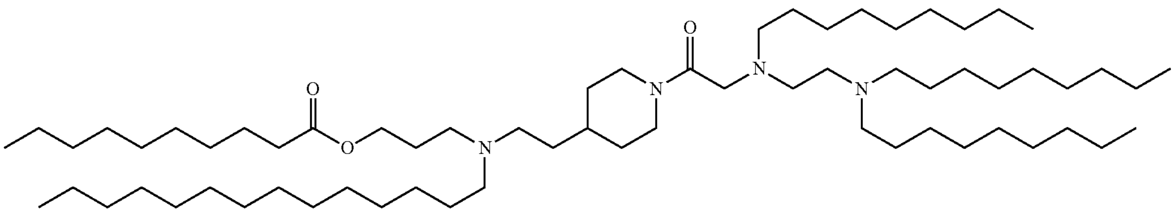
,
(Compound 325)
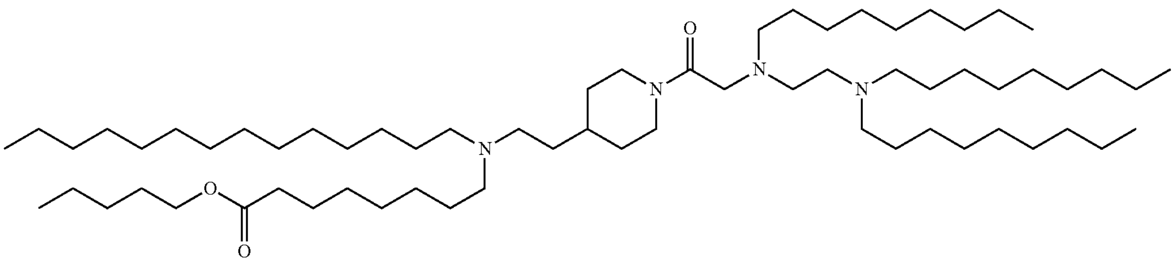
,
(Compound 326)
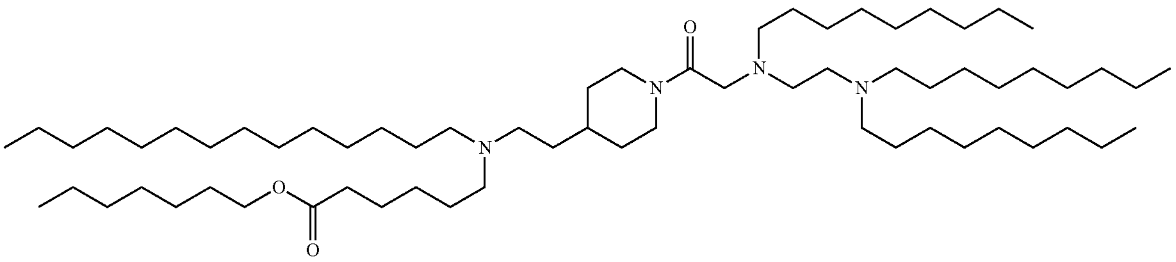
, -continued
(Compound 327)
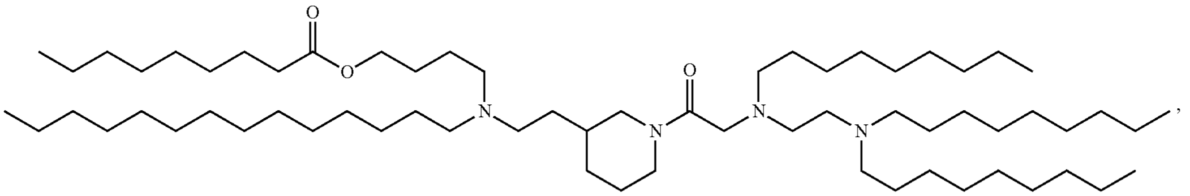
(Compound 328)
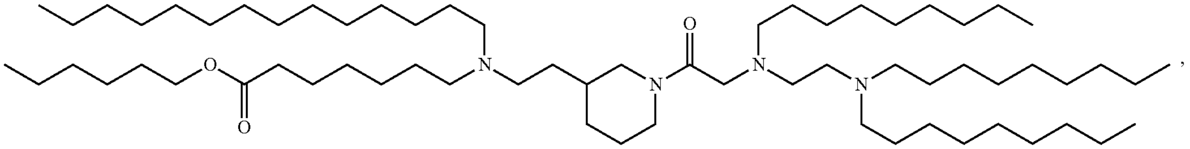
(Compound 329)
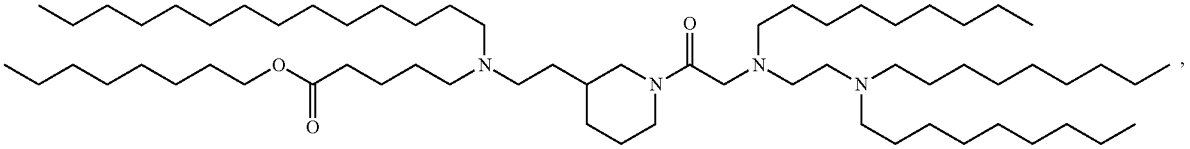
(Compound 330)
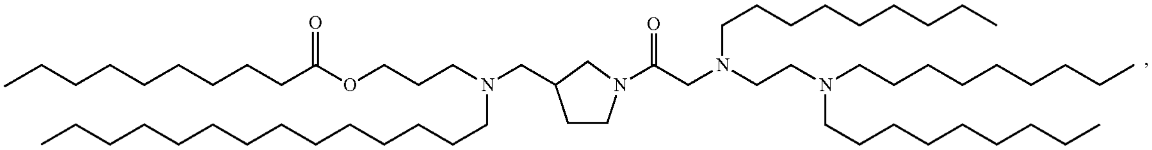
(Compound 331)
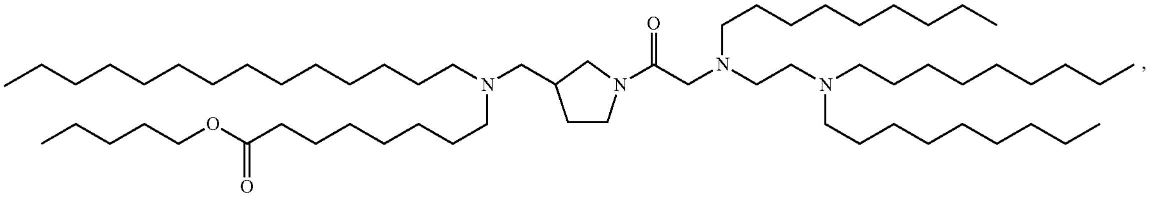
(Compound 332)
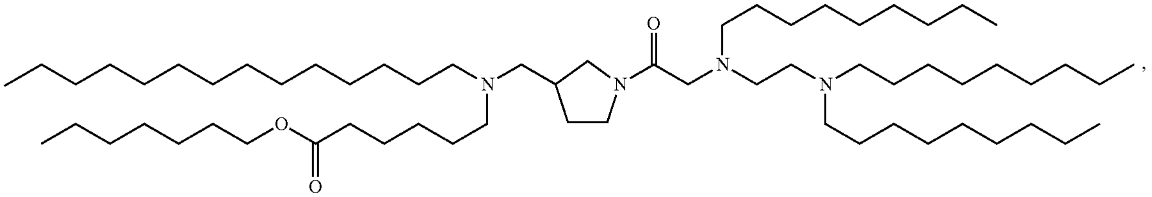
(Compound 333)
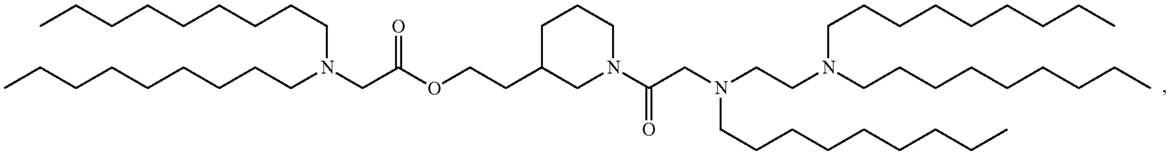
(Compound 334)
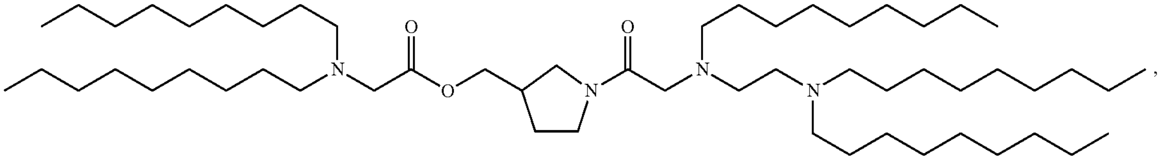

-continued
(Compound 335)
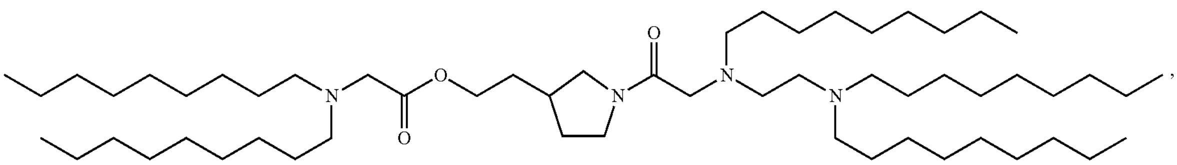
(Compound 336)
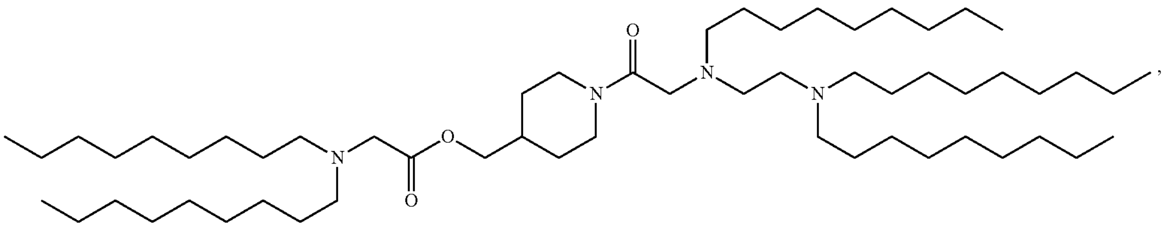
(Compound 337)
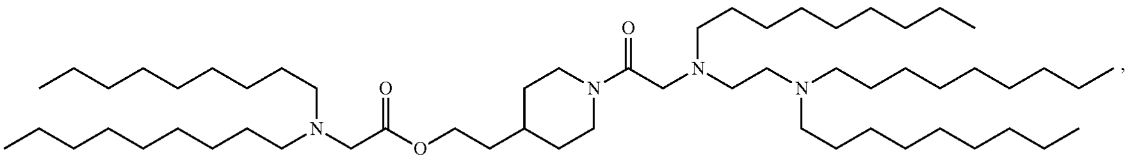
(Compound 338)
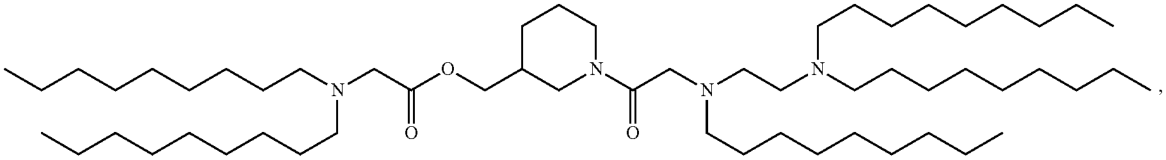
(Compound 339)
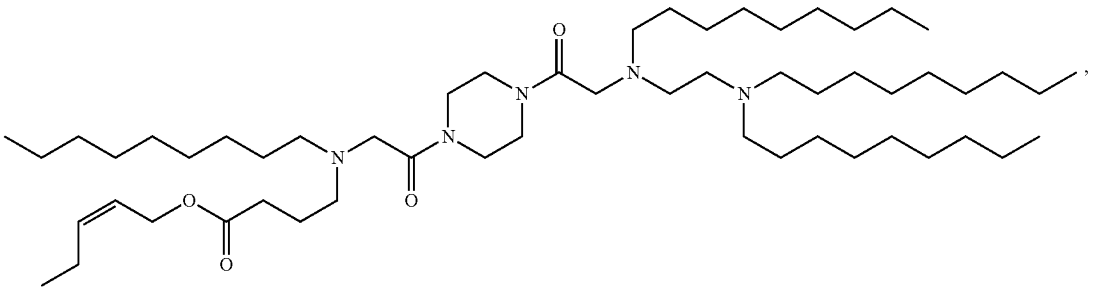
(Compound 340)
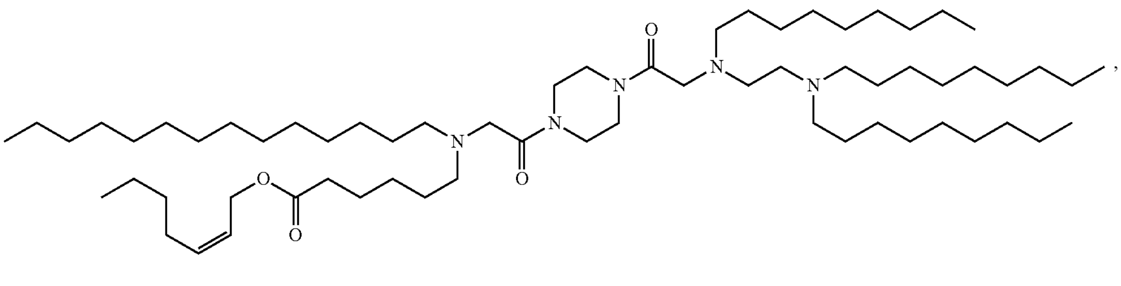
, and -continued (Compound 341)

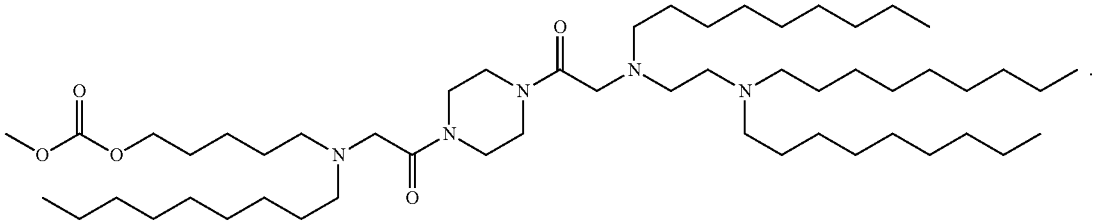

In some embodiments, the delivery agent comprises Compound 236.

In some embodiments, the delivery agent comprises a compound having the Formula (IV)

(IV)

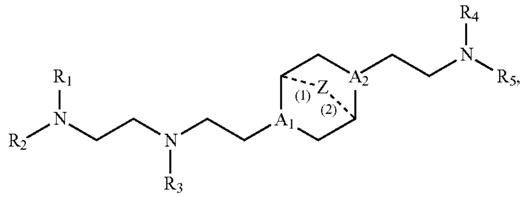

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{620}$ alkyl and $C_{6-20}$ alkenyl;

wherein when ring A is

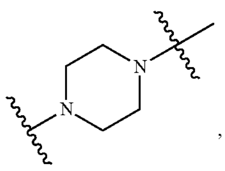 [SMILES: *N1CCN(*)CC1]

, then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

(IVa)

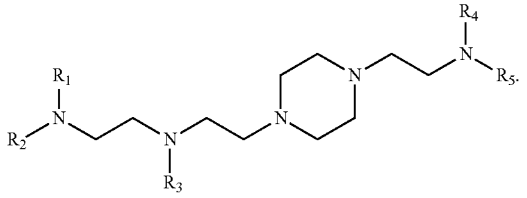

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are Cis alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:
(Compound 249)
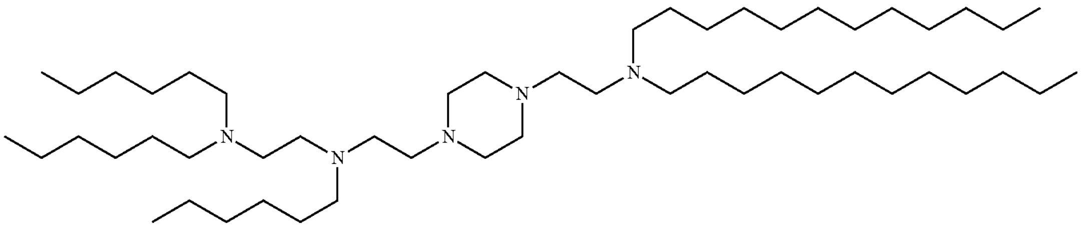
,
(Compound 250)
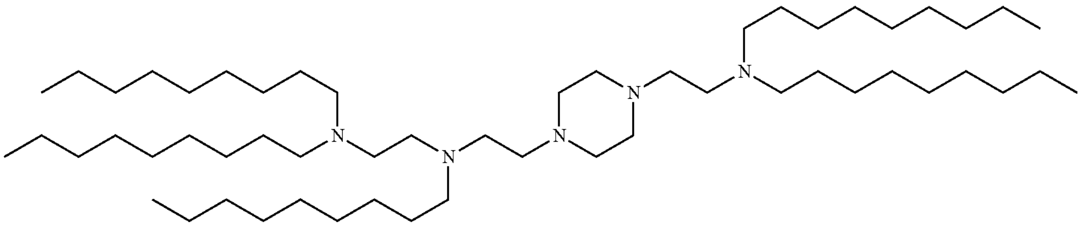
,
(Compound 251)
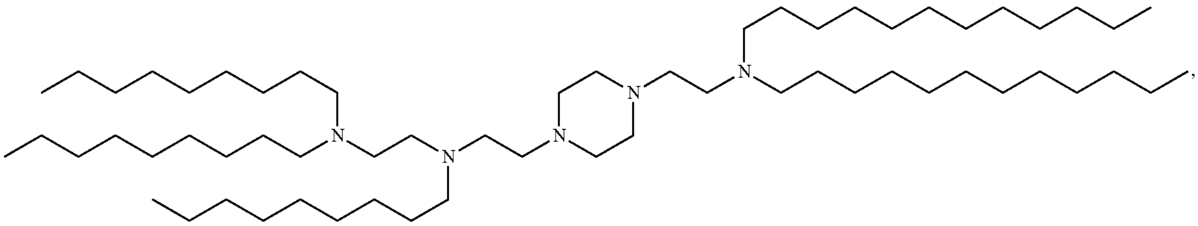
,
(Compound 252)
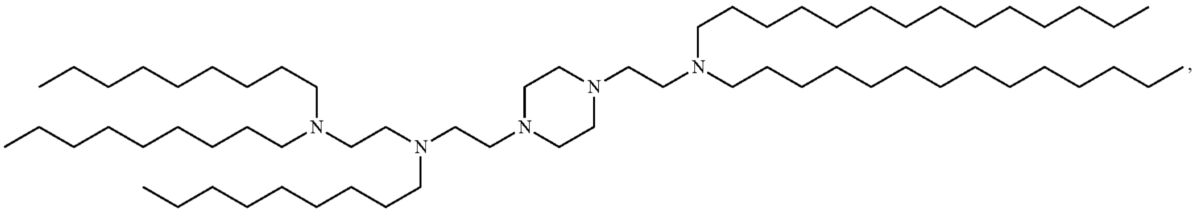
,
(Compound 253)
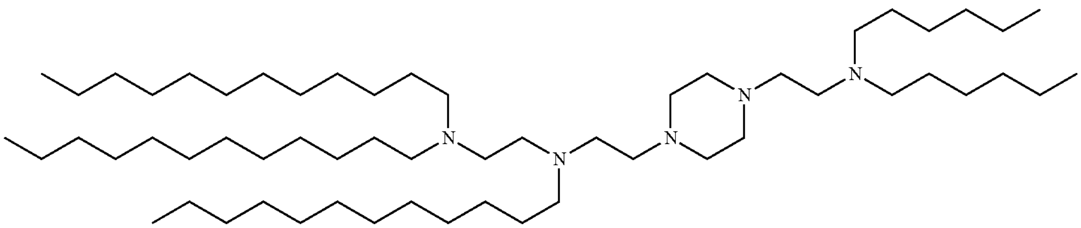
,
(Compound 254)
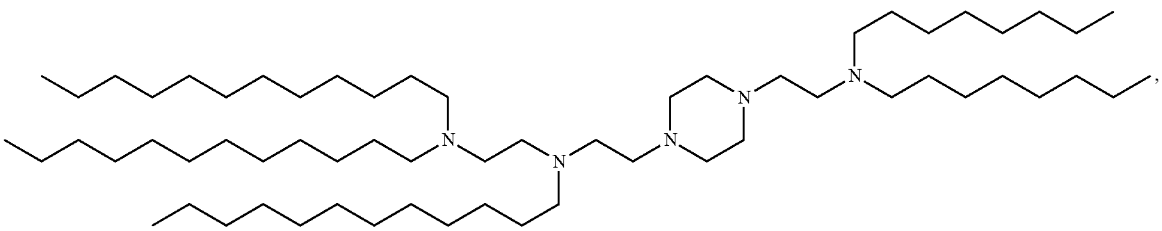
, -continued
(Compound 255)
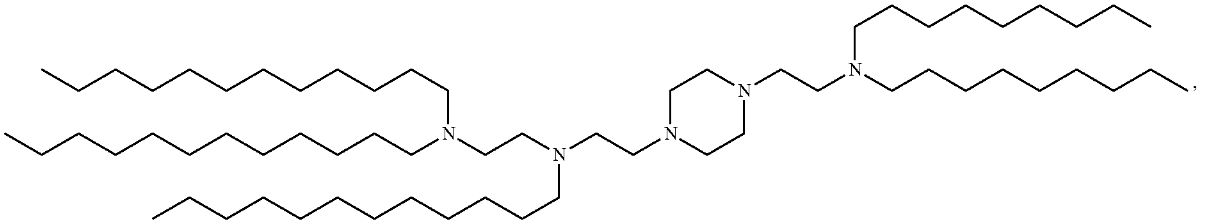
(Compound 256)
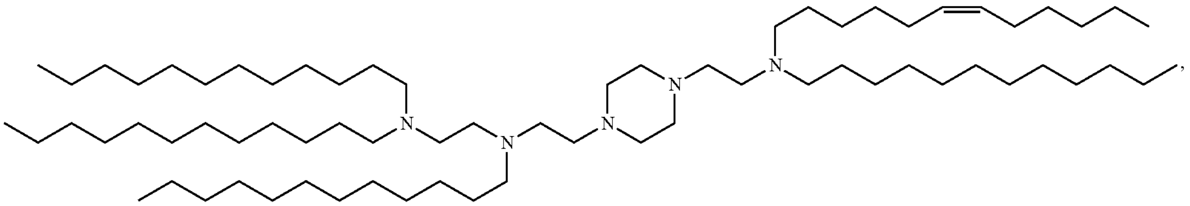
(Compound 257)
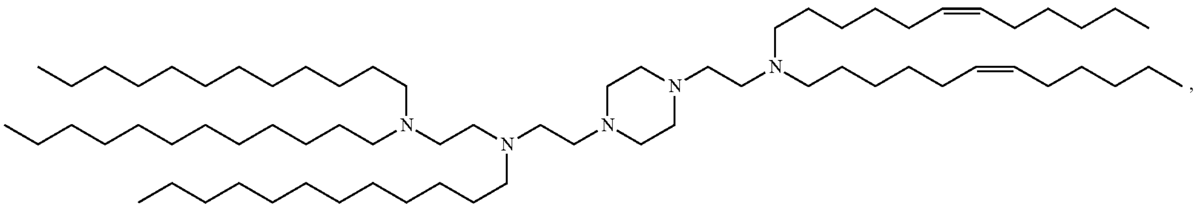
(Compound 258)
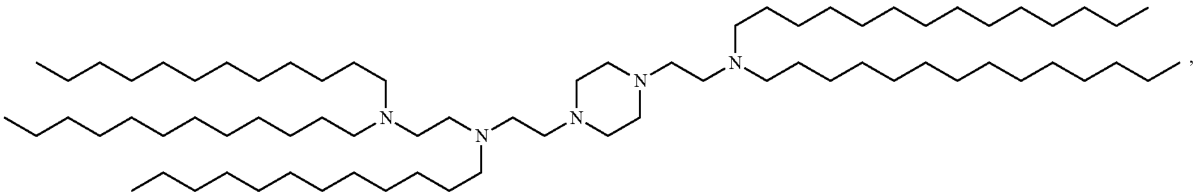
(Compound 259)
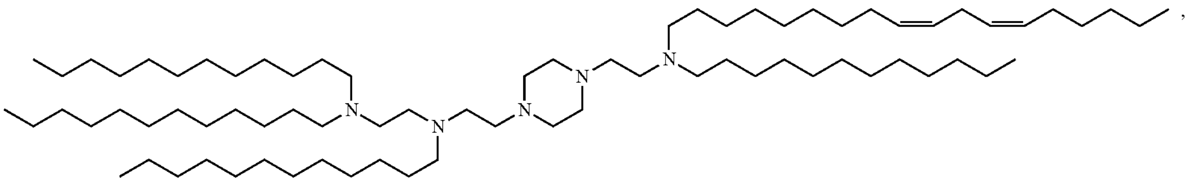
(Compound 260)
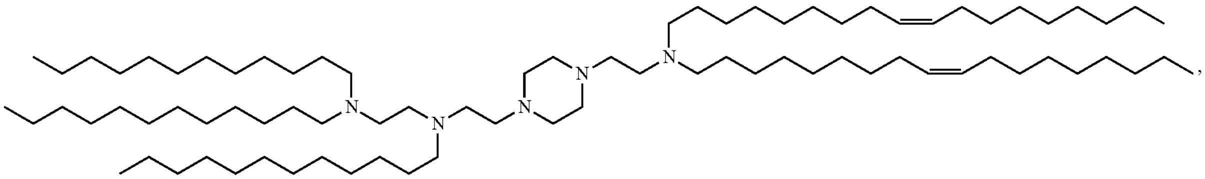
(Compound 261)
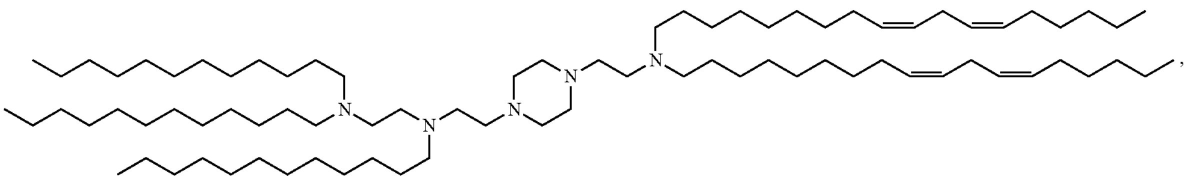

-continued (Compound 262)

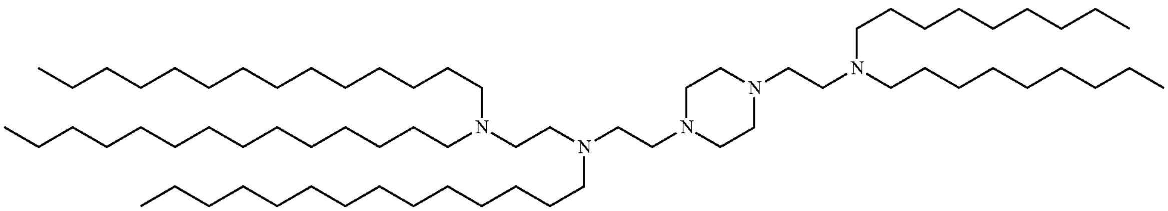

, (Compound 263)

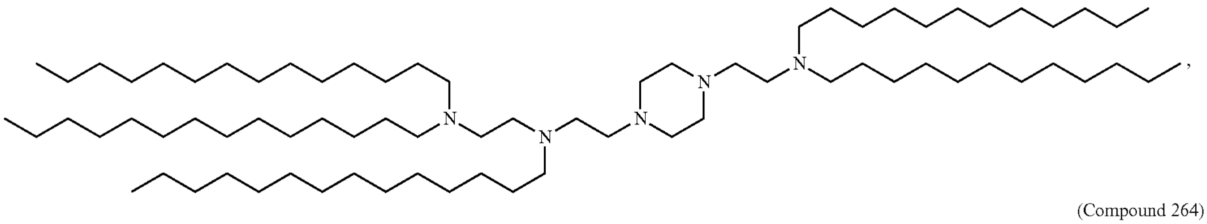

, (Compound 264)

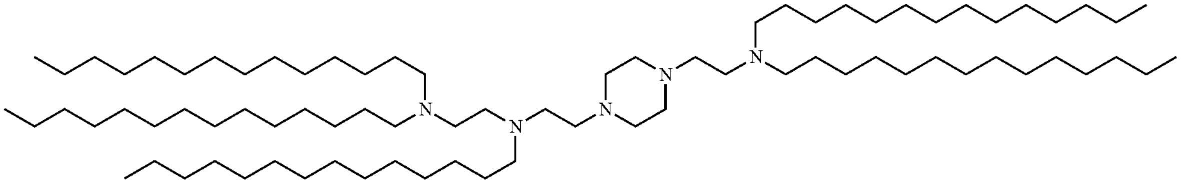

, (Compound 265)

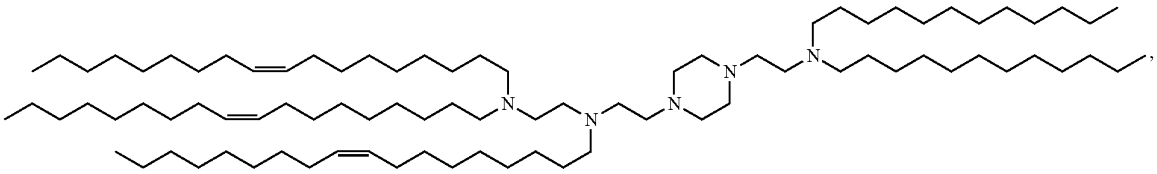

, and (Compound 266)

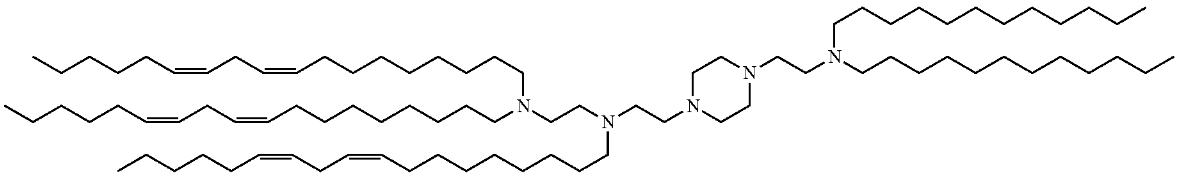

.

In other embodiments, the delivery agent comprises a compound having the Formula (V)

(V)

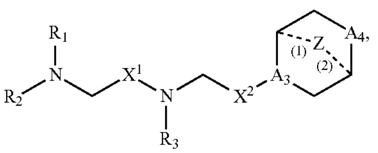

or salts or stereoisomers thereof, in which $A_3$ is CH or N;

$A_4$ is $CH_2$ or NH; and at least one of $A_3$ and $A_4$ is N or NH;

is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from C(O)O, OC(O), C(O)N(R'), N(R')C(O), —C(O), C(S), C(S)S, SC(S), CH(OH), P(O)(OR')O, $S(O)_2$, an aryl group, and a heteroaryl group;

$X^1$ and $X^2$ are independently selected from the group consisting of $CH_2$, $(CH_2)_2$, —CHR, CHY, C(O), C(O)O, OC(O), —C(O)—$CH_2$—, —$CH_2$—C(O)—, C(O)$OCH_2$, OC(O)$CH_2$, —$CH_2$—C(O)O, $CH_2$OC(O), CH(OH), C(S), and CH(SH);

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of Formula (Va):

(Va)

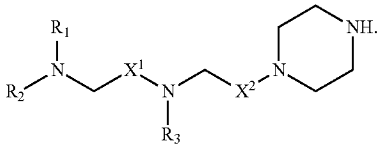

The compounds of Formula (V) or (Va) include one or more of the following features when applicable.

In some embodiments, Z is $CH_2$.

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not $—CH_2—$. For example, in certain embodiments, $X^1$ is not $—CH_2—$. In some embodiments, at least one of $X^1$ and $X^2$ is —C(O)—.

In some embodiments, $X^2$ is —C(O)—, C(O)O, OC(O), $—C(O)—CH_2—$, $—CH_2—C(O)—$, $—C(O)O—CH_2$, $OC(O)—CH_2$, $CH_2—C(O)O$, or $CH_2—OC(O)$.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In some embodiments, the compound is selected from the group consisting of:

(Compound 267)

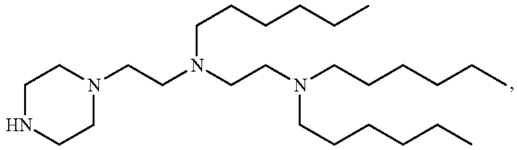

, (Compound 268)

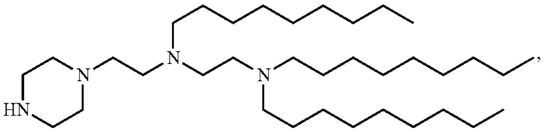

, (Compound 269)

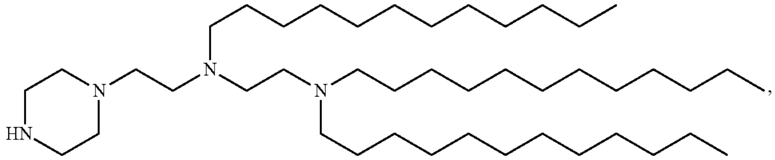

, (Compound 270)

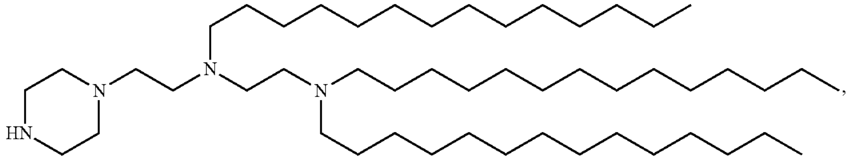

, (Compound 271)

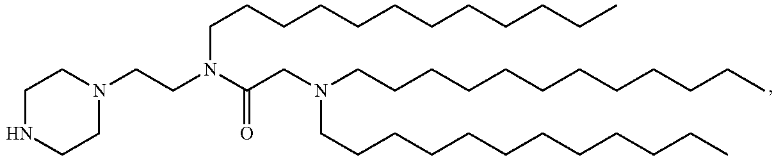

, (Compound 272)

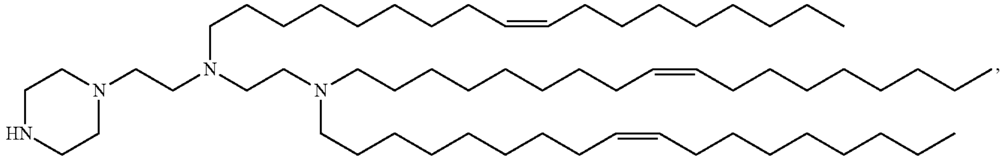

, (Compound 273)

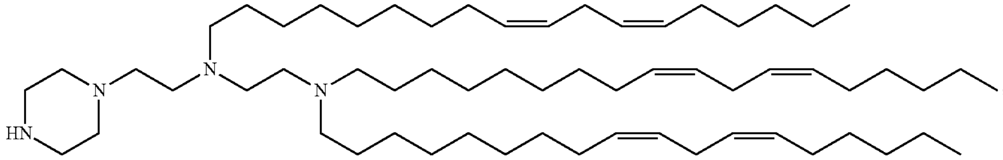

, and

-continued (Compound 309)

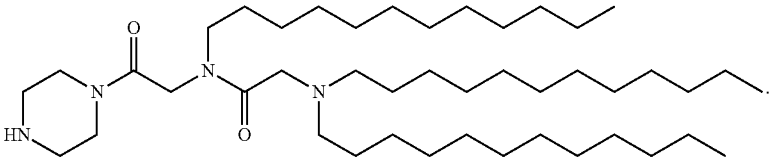

In other embodiments, the delivery agent comprises a compound having the Formula (VI):

(VI)

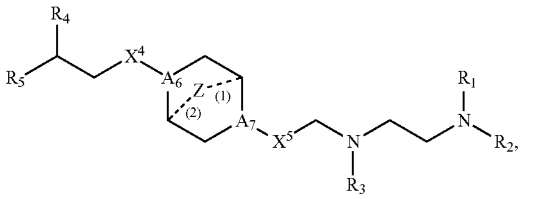

or salts or stereoisomers thereof, in which $A_6$ and $A_7$ are each independently selected from CH or N, wherein at least one of $A_6$ and $A_7$ is N;

Z is $CH_2$ or absent wherein when Z is $CH_2$, the dashed lines (1) and (2) each represent a single bond; and when Z is absent, the dashed lines (1) and (2) are both absent;

$X^4$ and $X^5$ are independently selected from the group consisting of —$CH_2$—, $CH_2)_2$—, CHR, CHY, C(O), C(O)O, OC(O), —C(O)—$CH_2$—, —$CH_2$—C(O)—, C(O)O$CH_2$, OC(O)—$CH_2$, —$CH_2$—C(O)O, $CH_2$—OC(O), CH(OH), C(S), and CH(SH);

$R_1$, $R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";

each M is independently selected from the group consisting of C(O)O, OC(O), —C(O)N(R'), N(R')C(O), C(O), C(S), C(S)S, SC(S), $C_H$(OH), P(O)(OR')O, $S(O)_2$ an aryl group, and a heteroaryl group;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is-$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'. In some embodiments, the compound is (Compound 299)

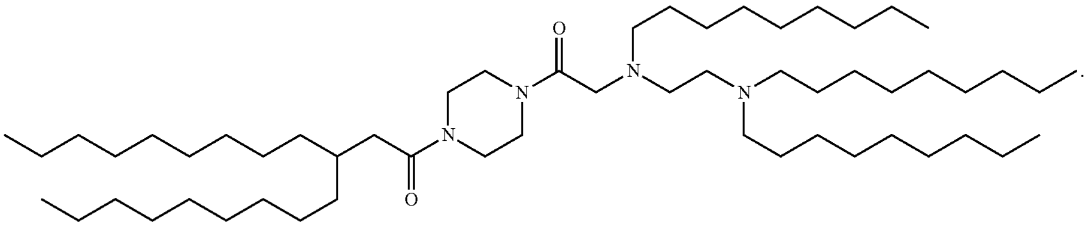

In other embodiments, the delivery agent comprises a compound having the formula:

(Compound 324)

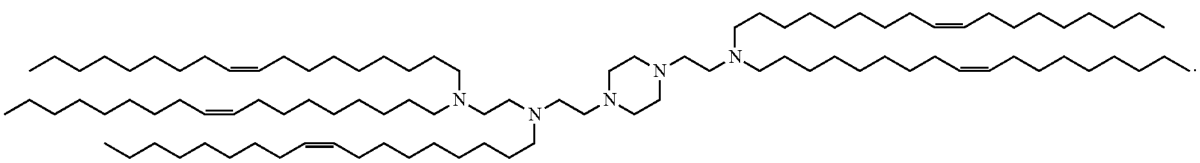

Amine moieties of the lipid compounds disclosed herein can be protonated under certain conditions. For example, the central amine moiety of a lipid according to Formula (I) is typically protonated (i.e., positively charged) at a pH below the pKa of the amino moiety and is substantially not charged at a pH above the pKa. Such lipids can be referred to ionizable amino lipids.

In one specific embodiment, the ionizable amino lipid is Compound 18.

In some embodiments, the amount the ionizable amino lipid, e.g., compound of Formula (I) ranges from about 1 mol % to 99 mol % in the lipid composition.

In one embodiment, the amount of the ionizable amino lipid, e.g., compound of Formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of Formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of Formula (I) is about 50 mol % in the lipid composition.

In addition to the ionizable amino lipid disclosed herein, e.g., compound of Formula (I), the lipid composition of the pharmaceutical compositions disclosed herein can comprise additional components such as phospholipids, structural lipids, PEG-lipids, and any combination thereof.

b. Additional Components in the Lipid Composition (i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:

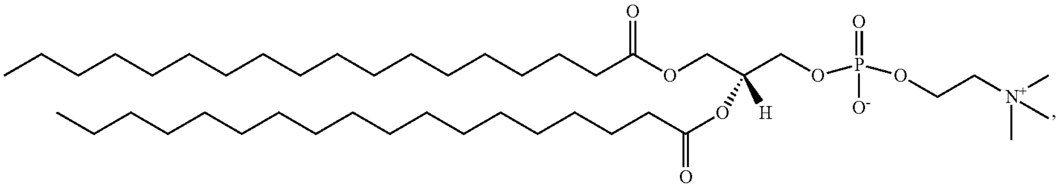

-continued
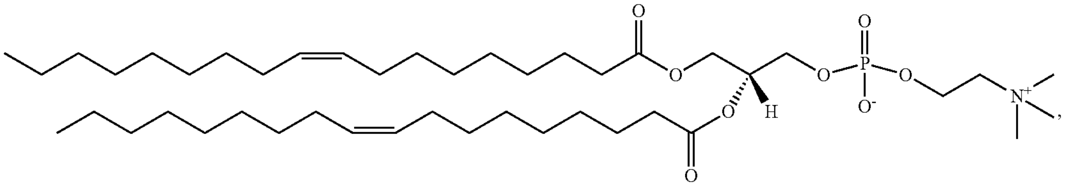
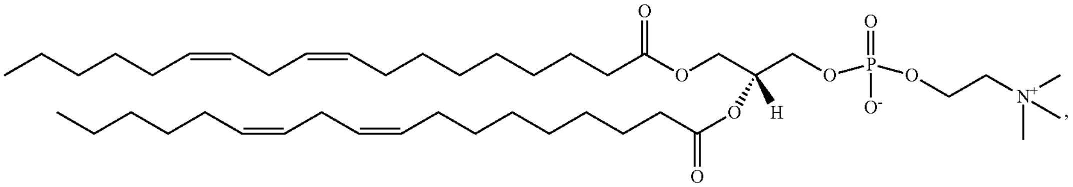
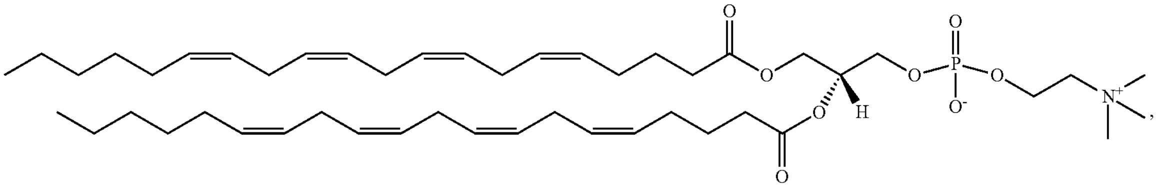
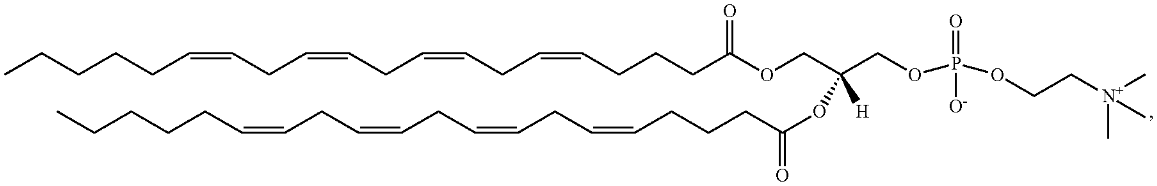
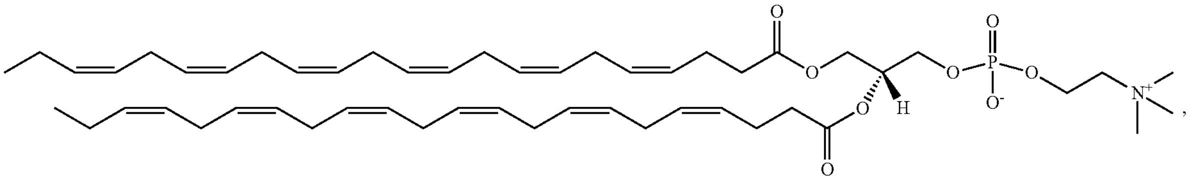
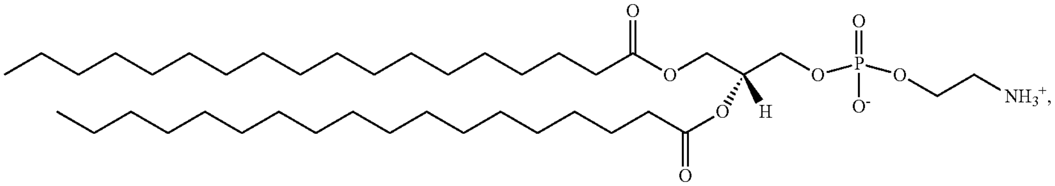
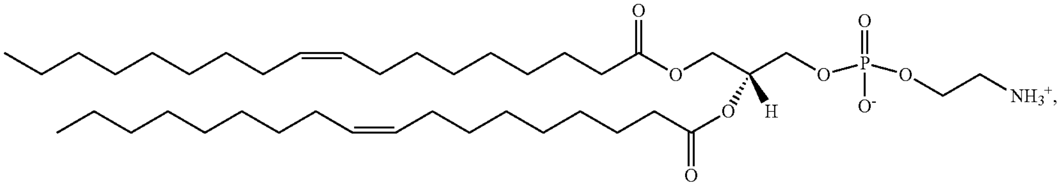
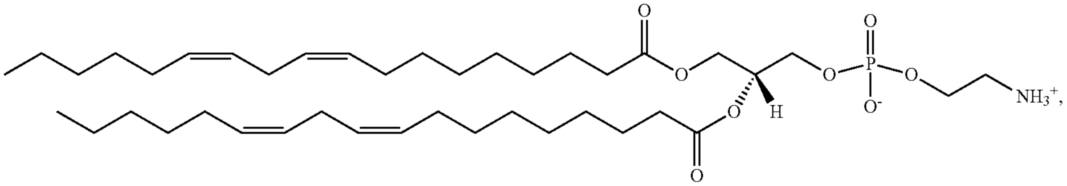
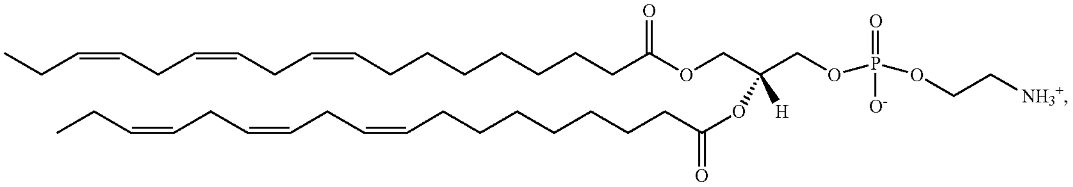

-continued

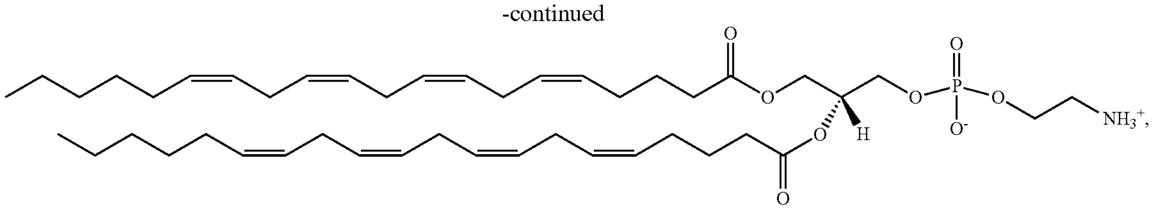

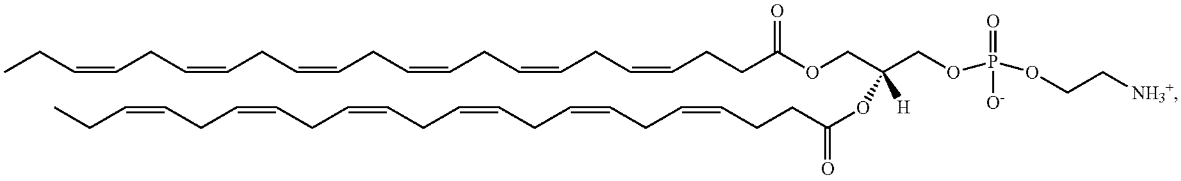

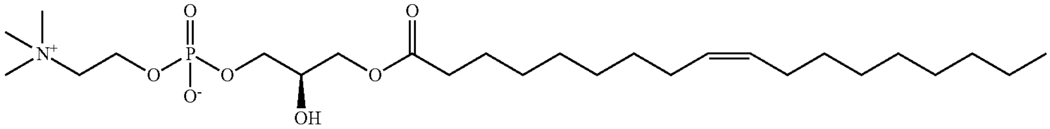

,

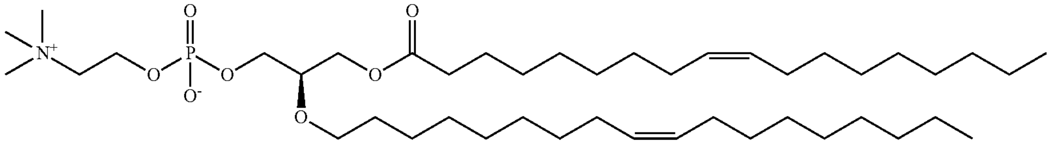

,

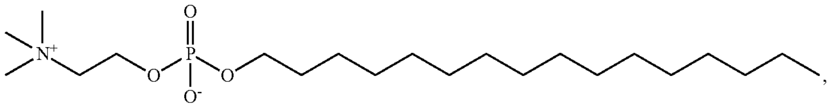

,

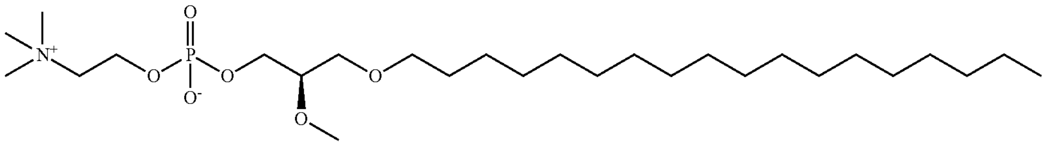

, and

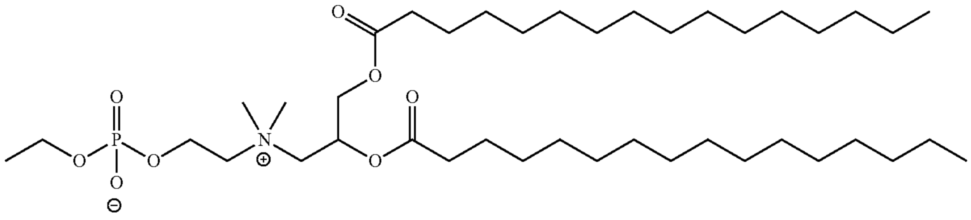

.

In certain embodiments, a phospholipid useful or potentially useful in the present invention is an analog or variant of DSPC. In certain embodiments, a phospholipid useful or potentially useful in the present invention is a compound of Formula (IX):

(IX)

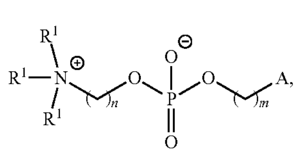

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

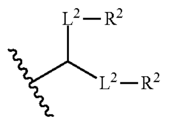

or

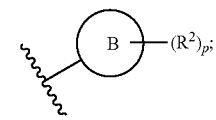

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, —$OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $—NR^NC(O)N(R^N)$, C(O)O, OC(O), OC(O)O, $OC(O)N(R^N)$, $NR^NC(O)O$, C(O)S, SC(O), $—C(═NR^N)$, $C(═NR^N)N(R^N)$, $NR^NC(═NR^N)$, $NR^NC(═NR^N)N(R^N)$, C(S), $C(S)N(R^N)$, $—NR^NC(S)$, $NR^NC(S)N(R^N)$, S(O), OS(O), S(O)O, OS(O)O, $OS(O)_2$, $S(O)_2O$, $OS(O)_2O$, $—N(R^N)S(O)$, $S(O)N(R^N)$, $N(R^N)S(O)N(R^N)$, $OS(O)N(R^N)$, $N(R^N)S(O)O$, $S(O)_2$, $—N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

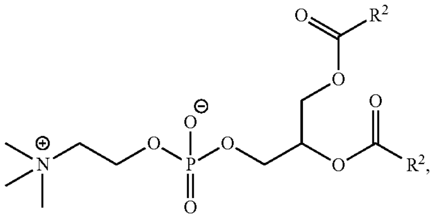

wherein each instance of $R^2$ is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

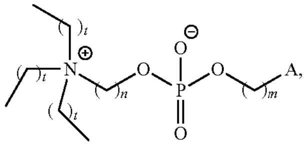

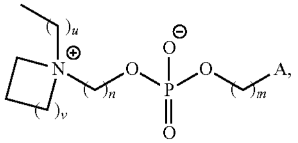

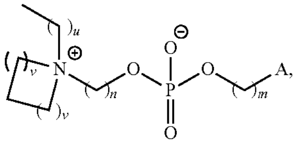

-continued

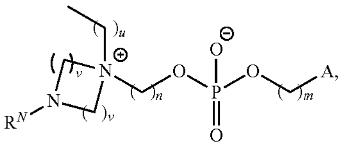

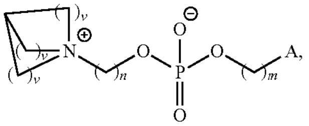

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

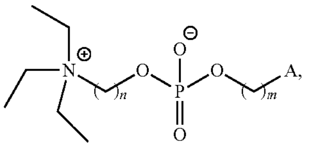

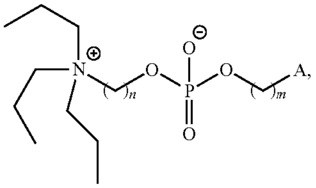

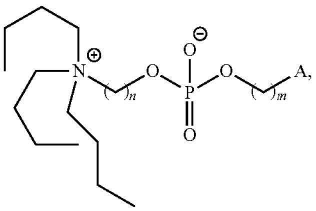

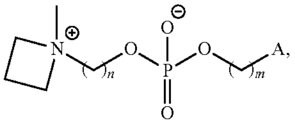

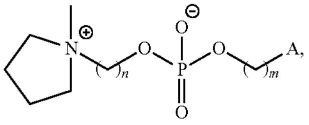

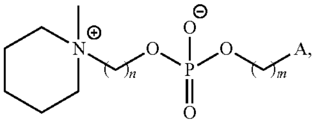

-continued
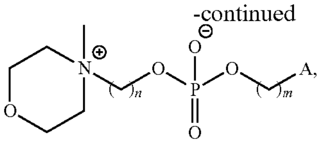
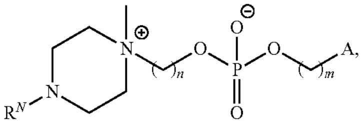
-continued
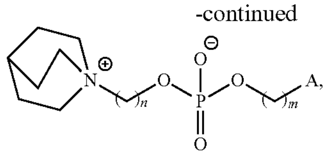
or a salt thereof.
In certain embodiments, a compound of Formula (IX) is one of the following:
(Compound 400)
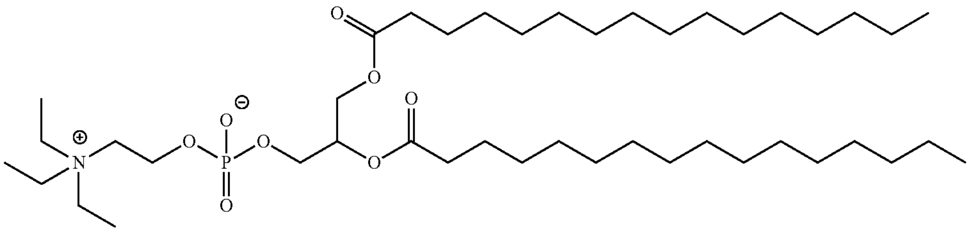
(Compound 401)
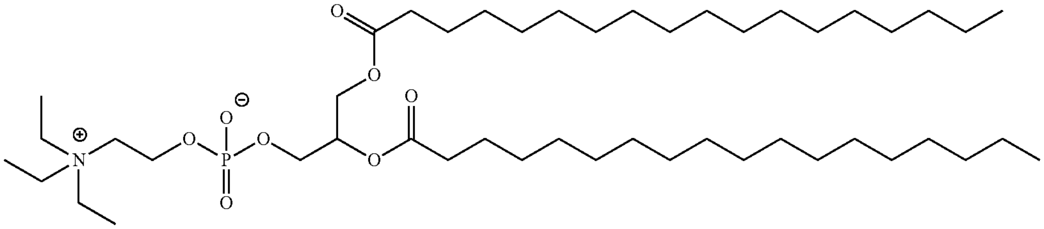
(Compound 402)
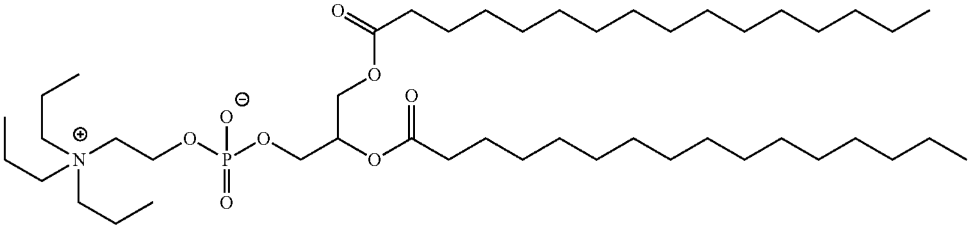
(Compound 403)
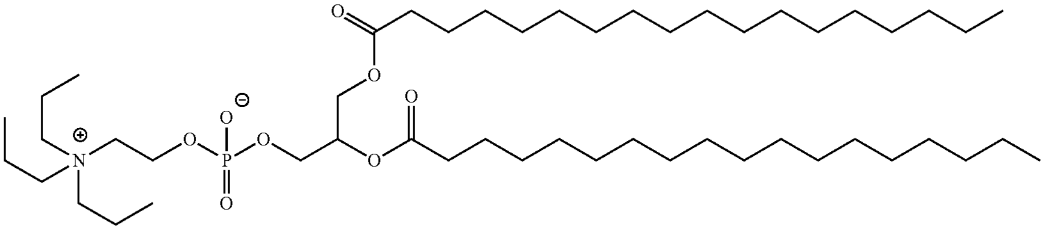
(Compound 404)
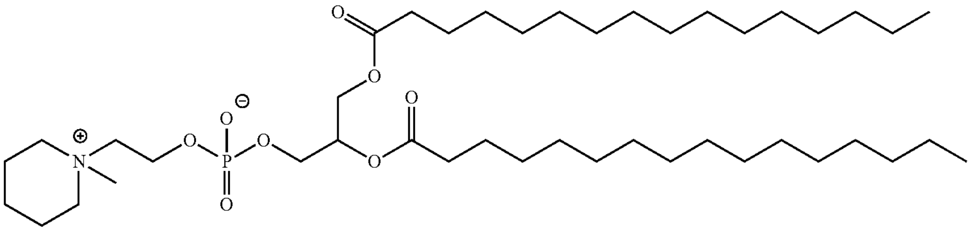

-continued
(Compound 405)
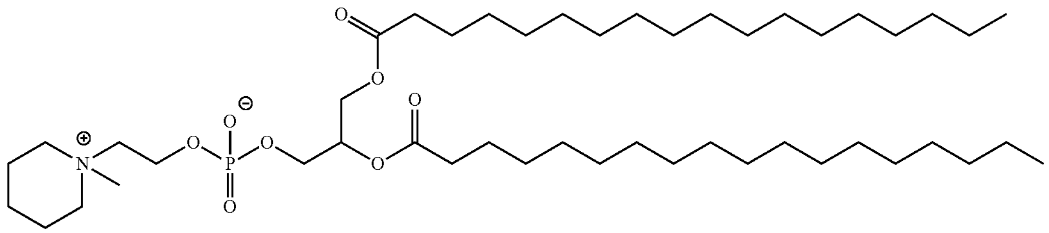
(Compound 406)
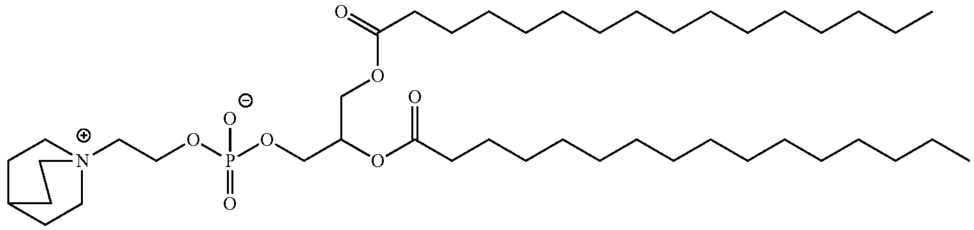
(Compound 407)
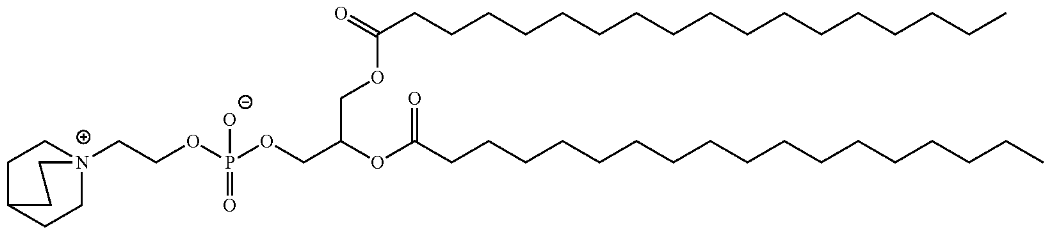
(Compound 408)
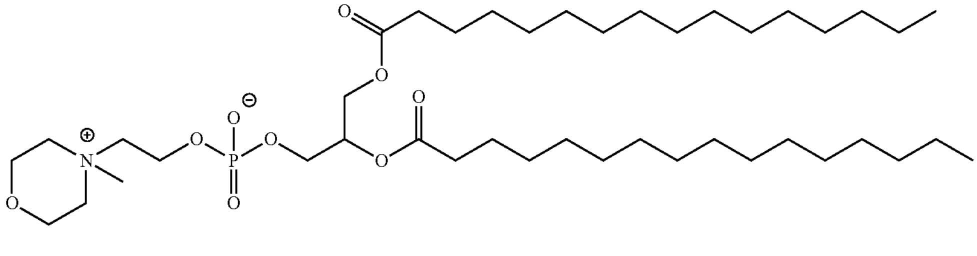

-continued (Compound 409)

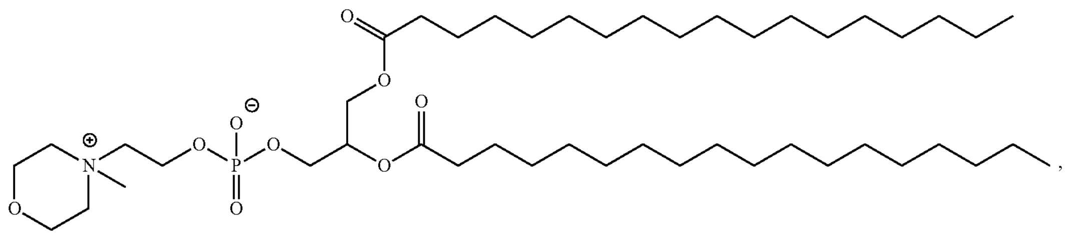

or a salt thereof.

In certain embodiments, a compound of Formula (IX) is of Formula (IX-a):

(IX-a)

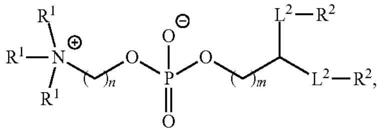

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

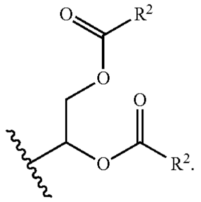

In certain embodiments, the compound of Formula (IX-a) is of one of the following formulae:

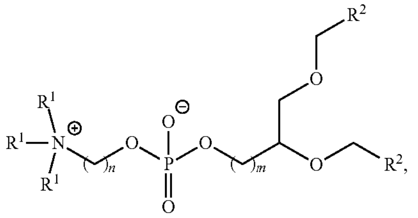

-continued

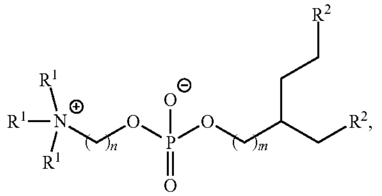

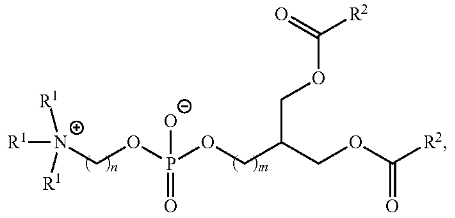

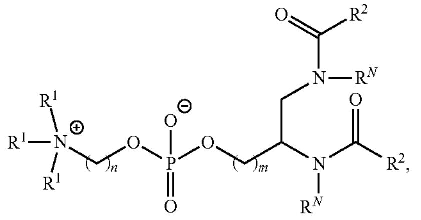

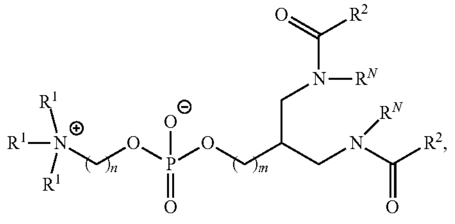

or a salt thereof.

In certain embodiments, a compound of Formula (IX) is one of the following:

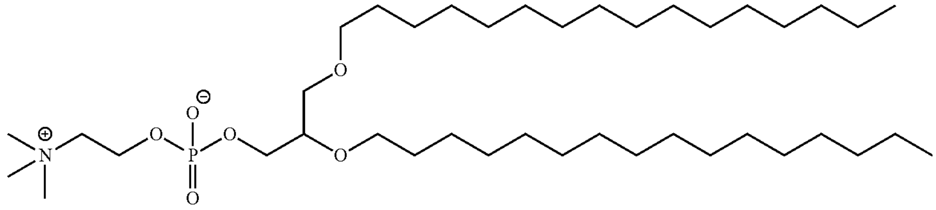

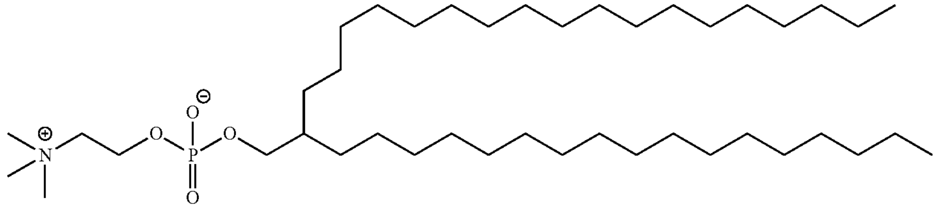

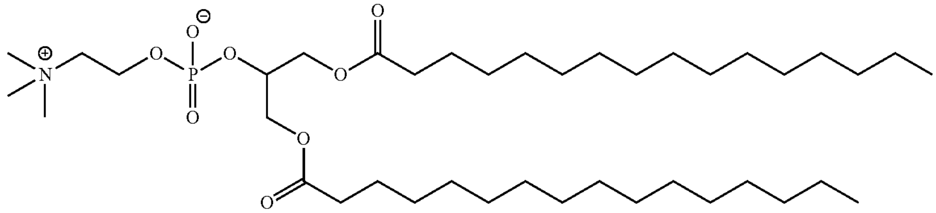

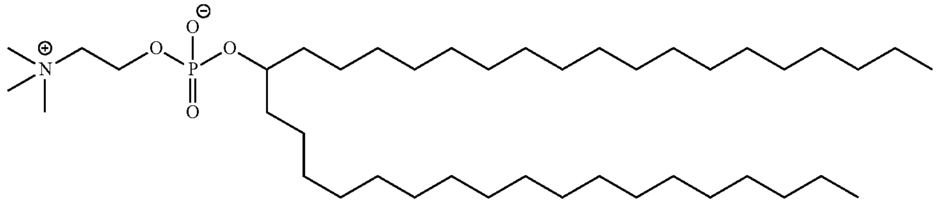

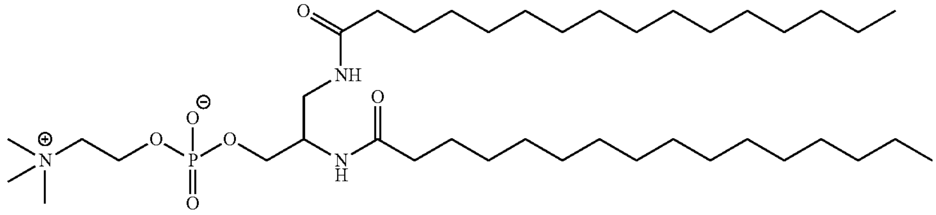, or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

(IX-b)

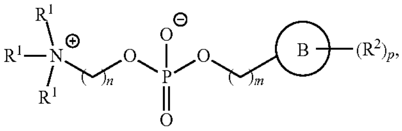

(IX-b), or a salt thereof.

In certain embodiments, the compound of Formula (IX-b) is of Formula (IX-b-1):

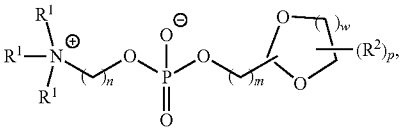
(IX-b-1)

or a salt thereof, wherein:

w is 0, 1, 2, or 3.

In certain embodiments, the compound of Formula (IX-b) is of Formula (IX-b-2):

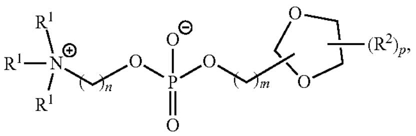
(IX-b-2)

or a salt thereof.

In certain embodiments, the compound of Formula (IX-b) is of Formula (IX-b-3):

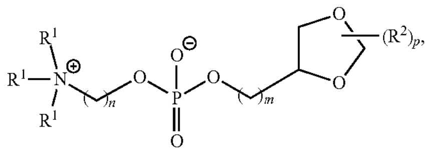
(IX-b-3)

or a salt thereof.

In certain embodiments, the compound of Formula (IX-b) is of Formula (IX-b-4):

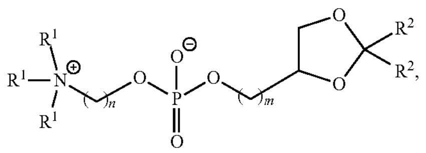
(IX-b-4)

or a salt thereof.

In certain embodiments, the compound of Formula (IX-b) is one of the following:

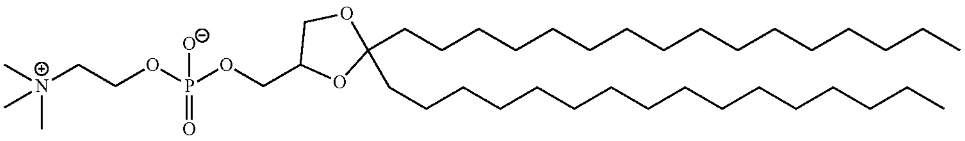

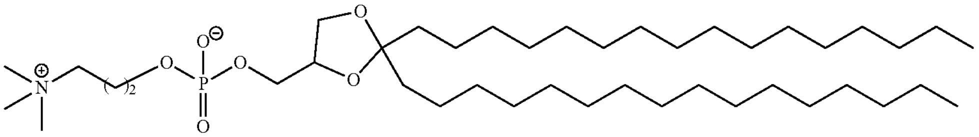

-continued

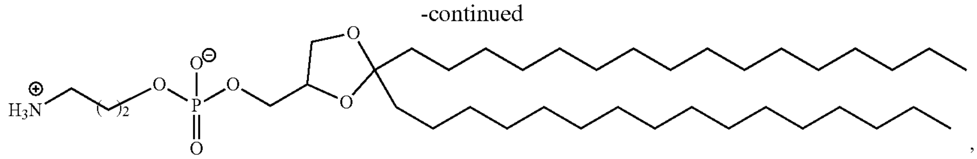

, or salts thereof.

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $—NR^NC(O)N(R^N)$, C(O)O, OC(O), OC(O)O, $OC(O)N(R^N)$, $NR^NC(O)O$, C(O)S, SC(O), $—C(═NR^N)$, $C(═NR^N)N(R^N)$, $NR^NC(═NR^N)$, $NR^NC(═NR^N)N(R^N)$, C(S), $C(S)N(R^N)$, $—NR^NC(S)$, $NR^NC(S)N(R^N)$, S(O), OS(O), S(O)O, OS(O)O, $OS(O)_2$, $S(O)_2O$, $OS(O)_2O$, $—N(R^N)S(O)$, $S(O)N(R^N)$, $N(R^N)S(O)N(R^N)$, $OS(O)N(R^N)$, $N(R^N)S(O)O$, $S(O)_2$, $—N(R^N)S(O)_2$, $S(O)_2N(R^N)$, $N(R^N)S(O)_2N(R^N)$, $OS(O)_2N(R^N)$, or $N(R^N)S(O)_2O$.

In certain embodiments, the compound of Formula (IX) is of Formula (IX-c):

(IX-c)

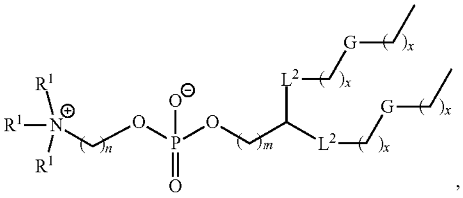

, or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(═NR^N)$, $C(═NR^N)N(R^N)$, $NR^NC(═NR^N)$, $NR^NC(═NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $—N(R^N)S(O)$, $S(O)N(R^N)$, $N(R^N)S(O)N(R^N)$, $OS(O)N(R^N)$, $N(R^N)S(O)O$, $S(O)_2$, $—N(R^N)S(O)_2$, $S(O)_2N(R^N)$, $N(R^N)S(O)_2N(R^N)$, $OS(O)_2N(R^N)$, or $N(R^N)S(O)_2O$. Each possibility represents a separate embodiment of the present invention.

In certain embodiments, the compound of Formula (IX-c) is of Formula (IX-c-1):

(IX-c-1)

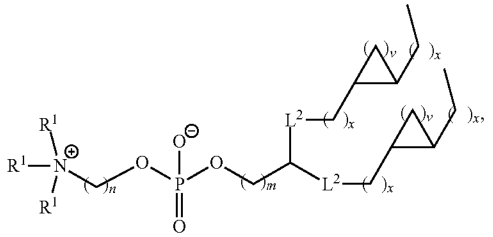

or salt thereof, wherein:

each instance of v is independently 1, 2, or 3.

In certain embodiments, the compound of Formula (IX-c) is of Formula (IX-c-2):

(IX-c-2)

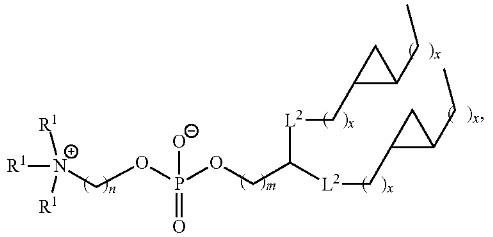

or a salt thereof.

In certain embodiments, the compound of Formula (IX-c) is of the following formula:

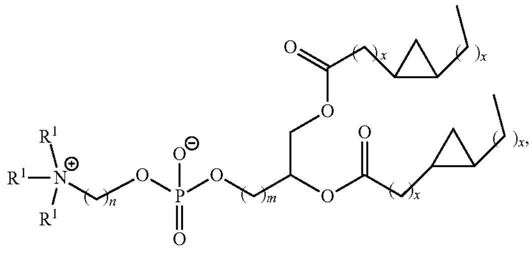

or a salt thereof.

In certain embodiments, the compound of Formula (IX-c) is the following:

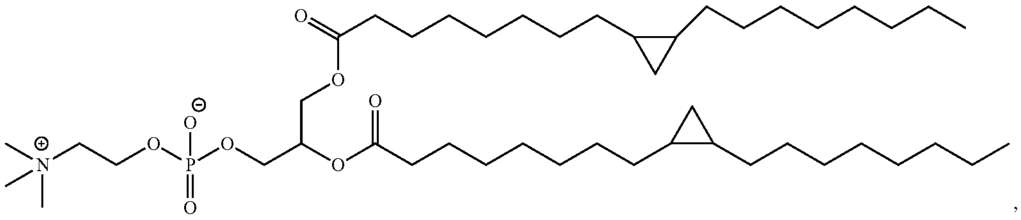 [SMILES: CCCCCCCCC1CC1CCCCCCCC(=O)OCC(COP(=O)([O-])OCC[N+](C)(C)C)OC(=O)CCCCCCCC1CC1CCCCCCCC]

, or a salt thereof.

In certain embodiments, the compound of Formula (IX-c) is of Formula (IX-c-3):

(IX-c-3)

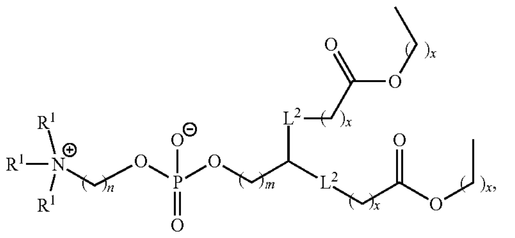

or a salt thereof.

In certain embodiments, the compound of Formula (IX-c) is of the following formulae:

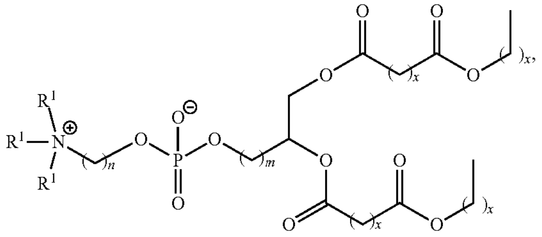

or a salt thereof.

In certain embodiments, the compound of Formula (IX-c) is the following:

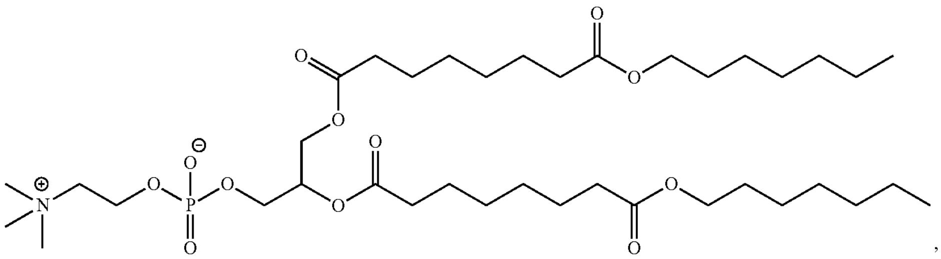 [SMILES: CCCCCCCOC(=O)CCCCCCC(=O)OCC(COP(=O)([O-])OCC[N+](C)(C)C)OC(=O)CCCCCCC(=O)OCCCCCCC]

, or a salt thereof.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:
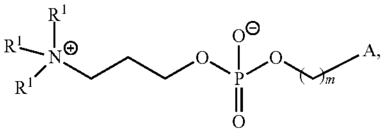
-continued
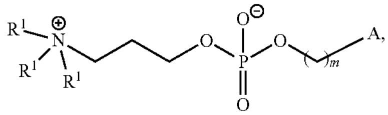
or a salt thereof.
In certain embodiments, a compound of Formula (IX) is one of the following:
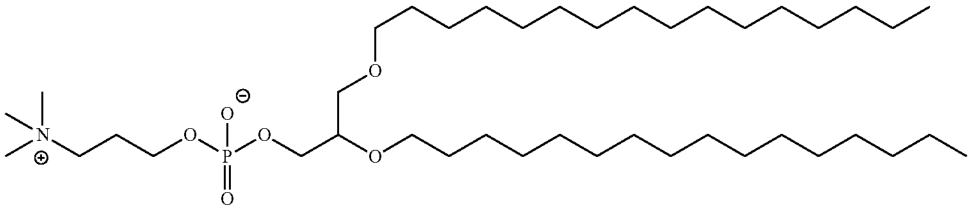
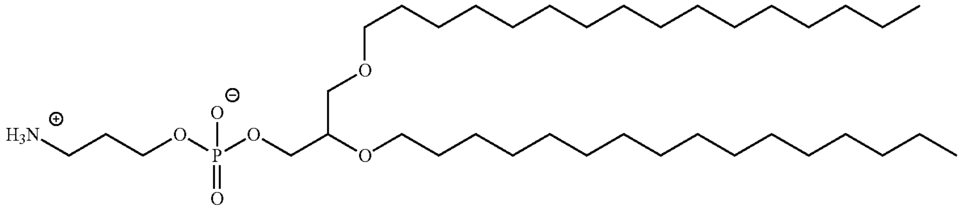
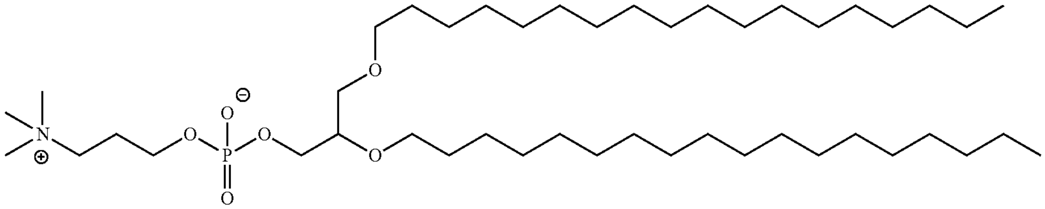
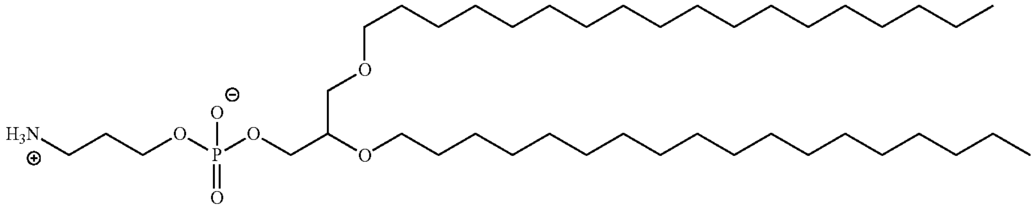
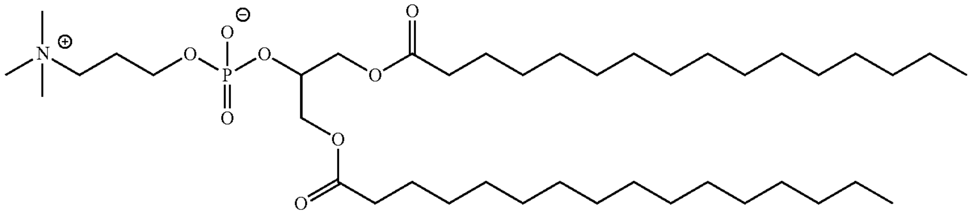
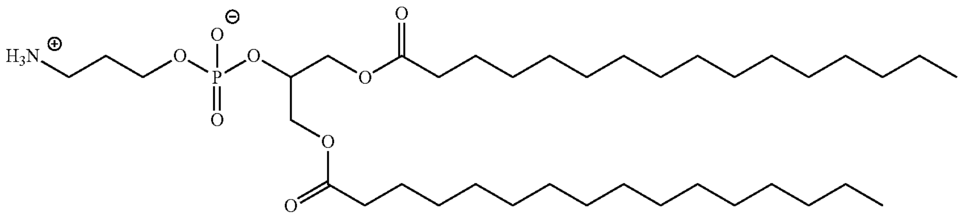

-continued
(Compound 411)
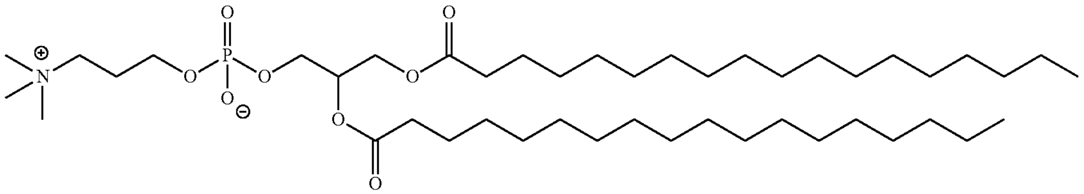
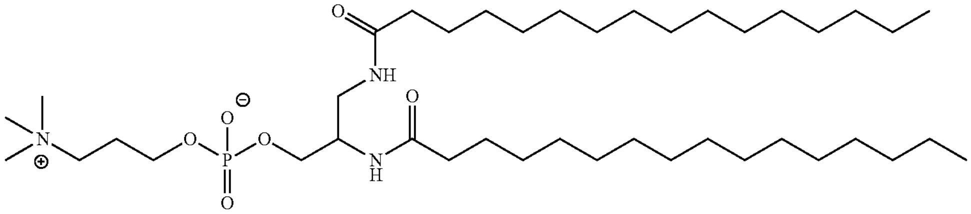
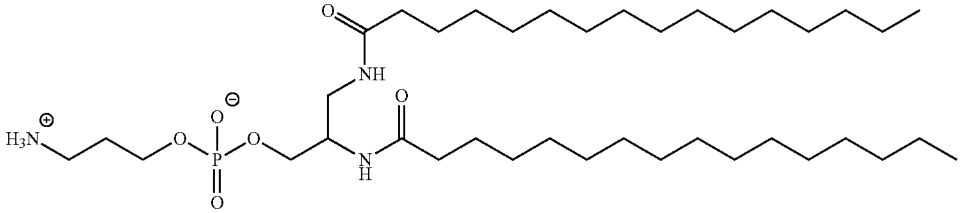
(Compound 412)
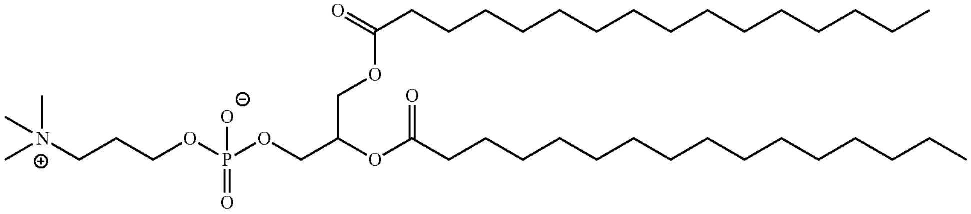
(Compound 413)
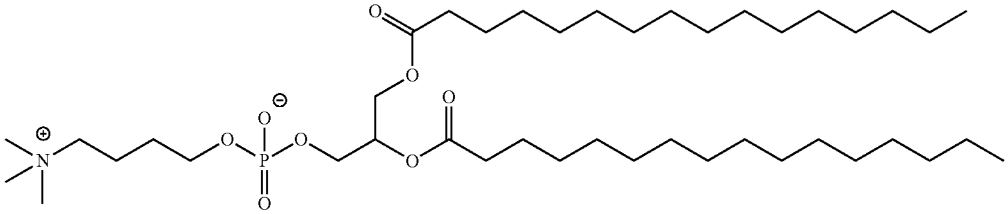
(Compound 414)
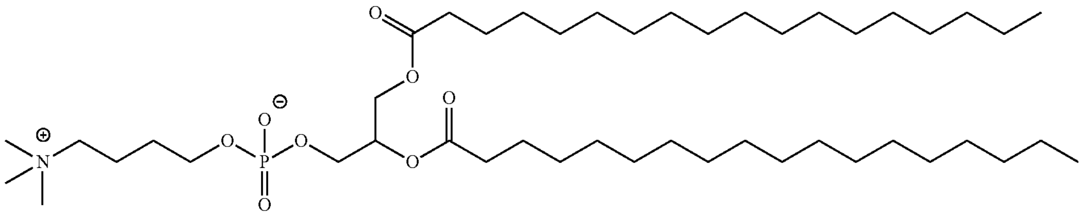
,
or salts thereof.
Alternative Lipids
In certain embodiments, an alternative lipid is used in place of a phospholipid of the invention. Non-limiting examples of such alternative lipids include the following:

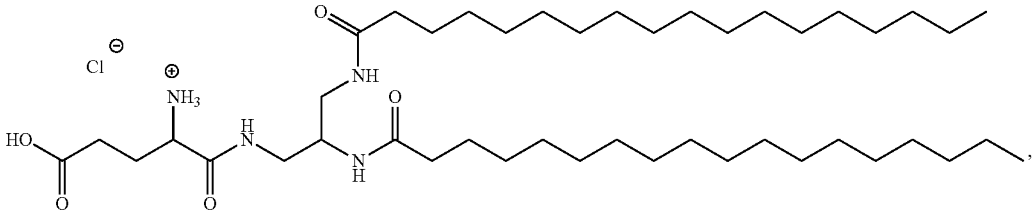
,

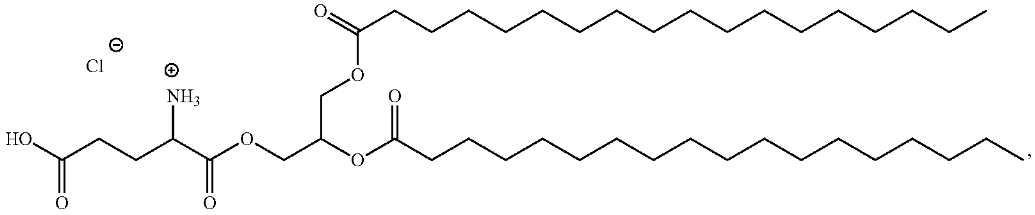
,

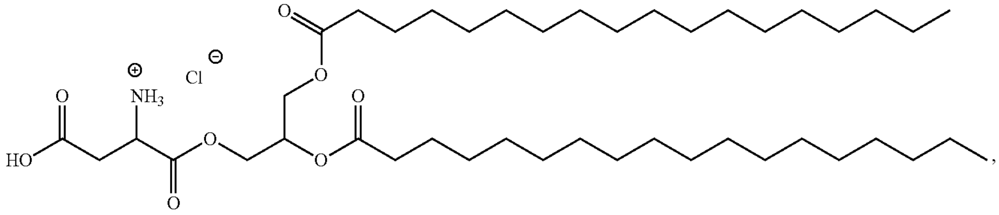
,

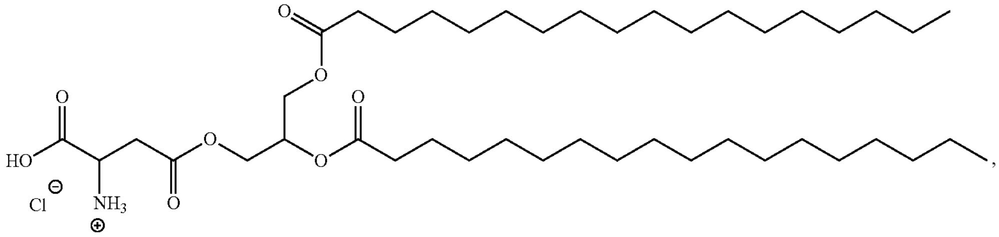
,

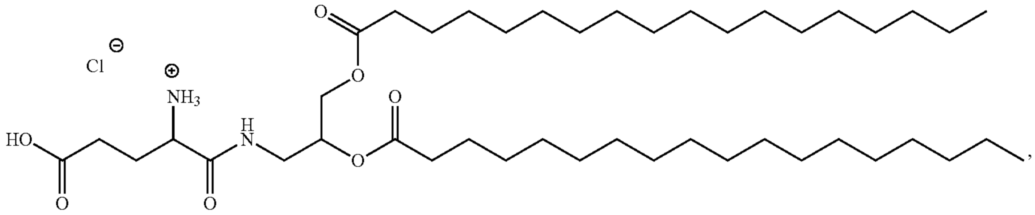
,

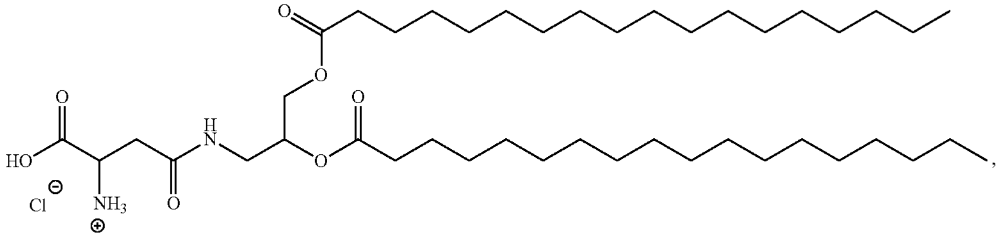
, and

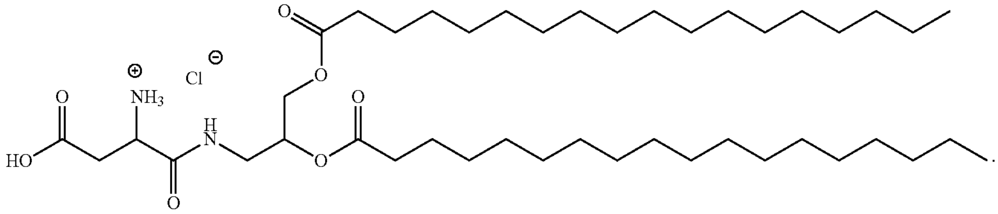
.

(ii) Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

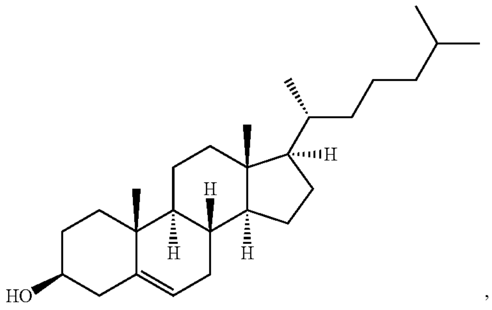

,

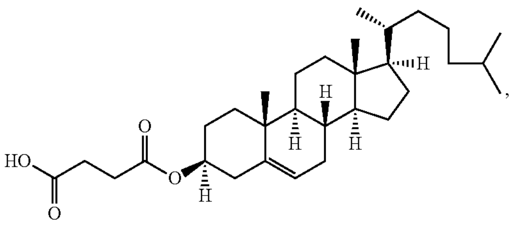

, and

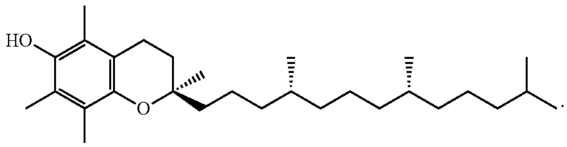

.

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

(iii) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In one embodiment, the PEG-lipid is $PEG_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

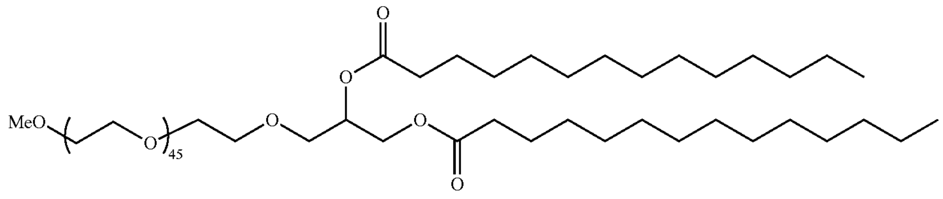

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

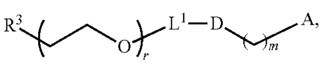

(VII)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, —OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

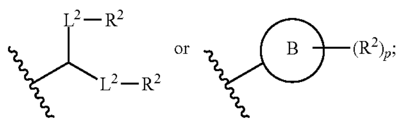

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, —$OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, —$NR^NC(O)N(R^N)$, C(O)O, OC(O), OC(O)O, $OC(O)N(R^N)$, $NR^NC(O)O$, C(O)S, SC(O), —$C({=}NR^N)$, $C({=}NR^N)N(R^N)$, $NR^NC({=}NR^N)$, $NR^NC({=}NR^N)N(R^N)$, C(S), $C(S)N(R^N)$, —$NR^NC(S)$, $NR^NC(S)N(R^N)$, S(O), OS(O), S(O)O, OS(O)O, $OS(O)_2$, $S(O)_2O$, $OS(O)_2O$, —$N(R^N)S(O)$, $S(O)N(R^N)$, $N(R^N)S(O)N(R^N)$, $OS(O)N(R^N)$, $N(R^N)S(O)O$, $S(O)_2$, —$N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is —$OR^O$, and $R^O$ is hydrogen). In certain embodiments, the compound of Formula (VII) is of Formula (VII-OH):

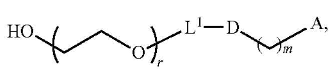

(VII-OH)

or a salt thereof.

In certain embodiments, D is a moiety obtained by click chemistry (e.g., triazole). In certain embodiments, the compound of Formula (VII) is of Formula (VII-a-1) or (VII-a-2):

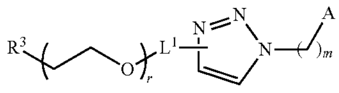

(VII-a-1)

or

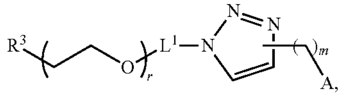

(VII-a-2)

or a salt thereof.

In certain embodiments, the compound of Formula (VII) is of one of the following formulae:
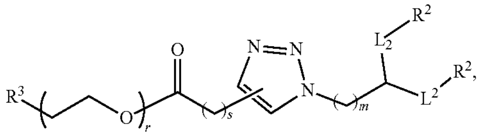
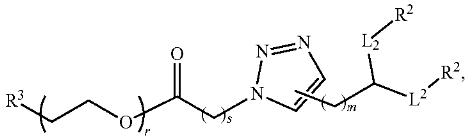
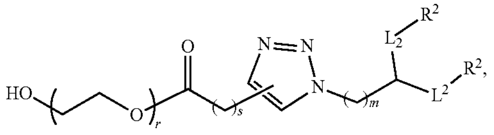
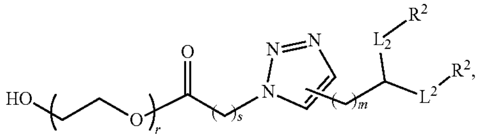
or a salt thereof, wherein
s is 0, 1, 2, 3, 4, 5, 6, 7, 8, 9, or 10.
In certain embodiments, the compound of Formula (VII) is of one of the following formulae:
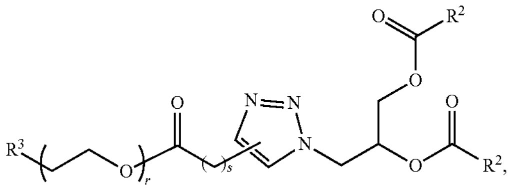
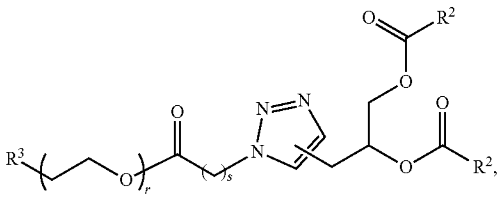
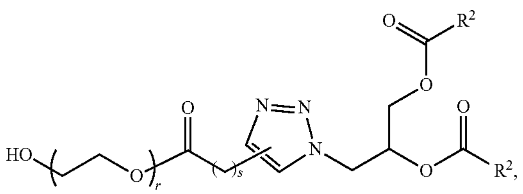
-continued
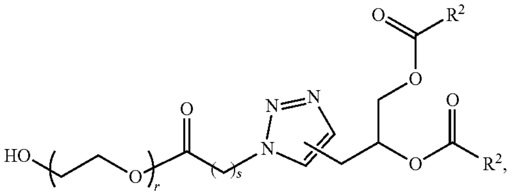
or a salt thereof.
In certain embodiments, a compound of Formula (VII) is of one of the following formulae:
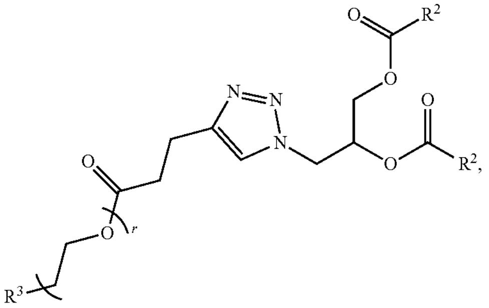
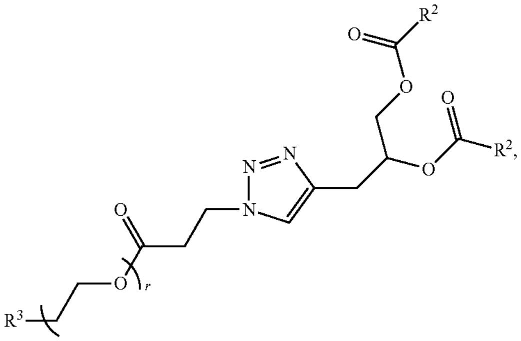
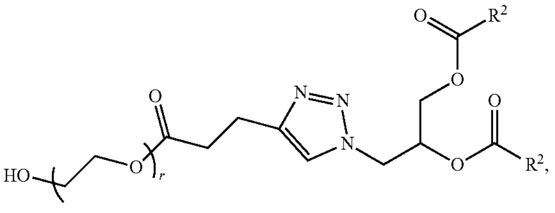
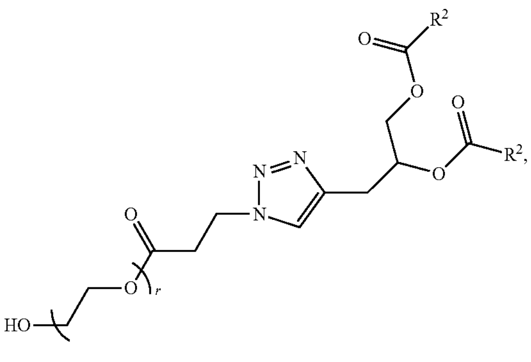
or a salt thereof.

In certain embodiments, a compound of Formula (VII) is of one of the following formulae:

(Compound 415)

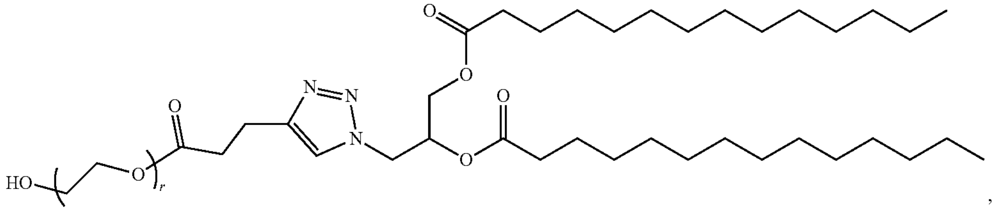

, (Compound 416)

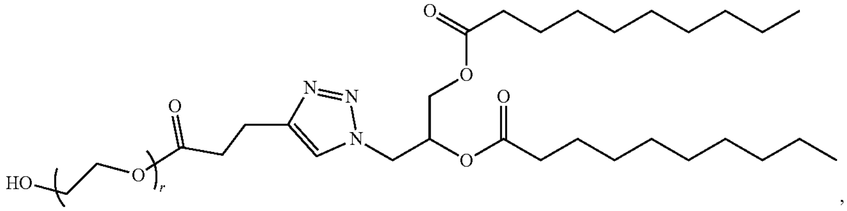

, (Compound 417)

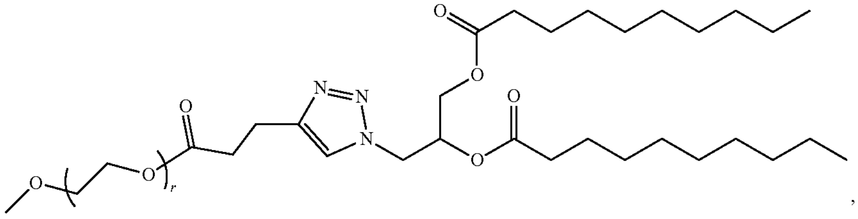

, (Compound 418)

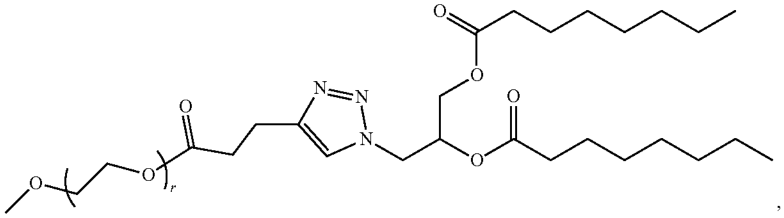

, or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

(VII-b-1)

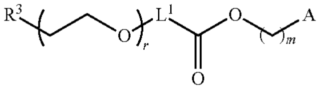

(VII-b-2)

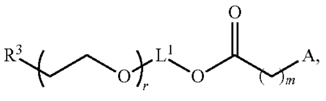

or a salt thereof.

In certain embodiments, a compound of Formula (VII) is of Formula (VII-b-1-OH) or (VII-b-2-OH):

(VII-b-1-OH)

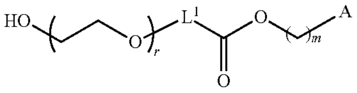

(VII-b-2-OH)

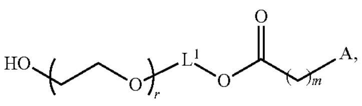

or a salt thereof.

In certain embodiments, the compound of Formula (VII) is of one of the following formulae:

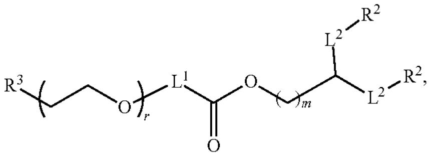

-continued
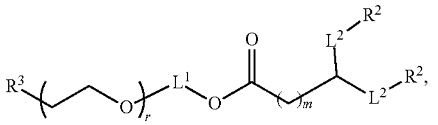
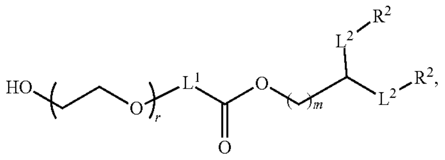
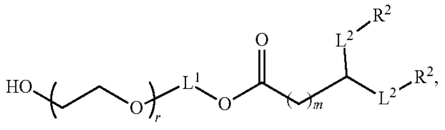
or a salt thereof.
In certain embodiments, a compound of Formula (VII) is of one of the following formulae:
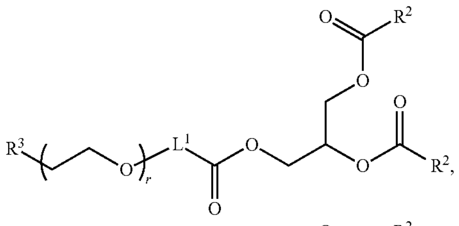
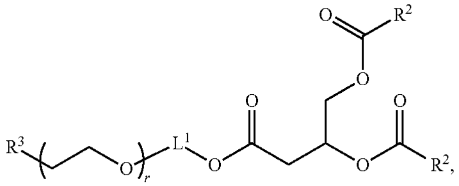
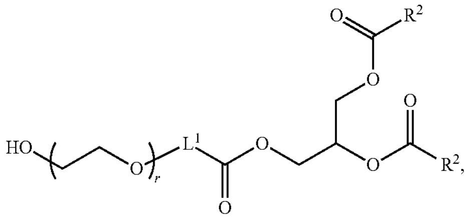
-continued
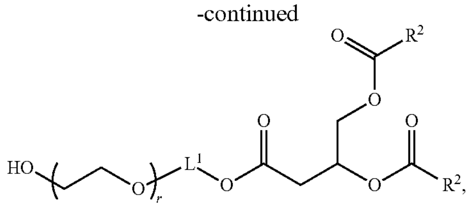
or a salt thereof.
In certain embodiments, a compound of Formula (VII) is of one of the following formulae:
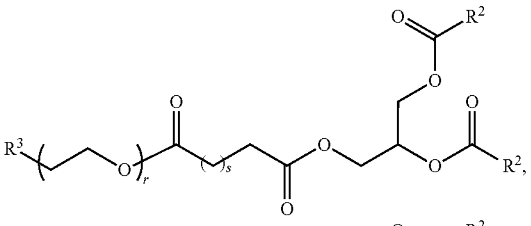
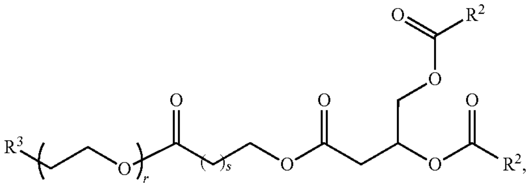
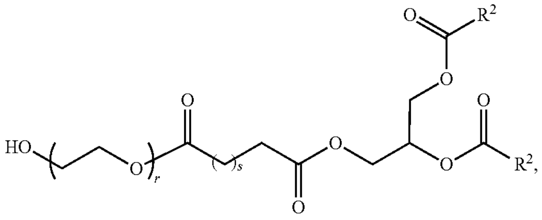
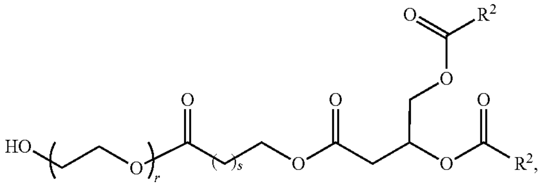
or a salt thereof.
In certain embodiments, a compound of Formula (VII) is of one of the following formulae:
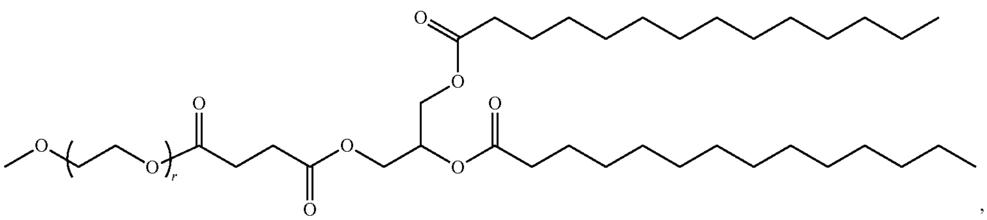
, -continued

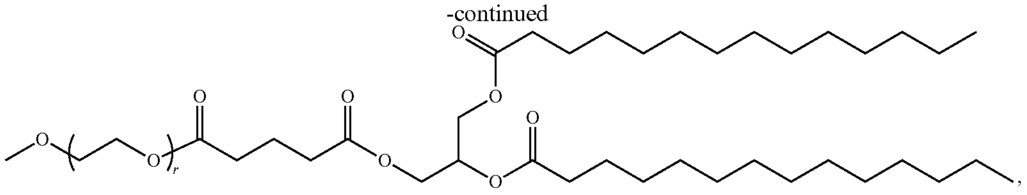

or salts thereof.

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

(VIII)

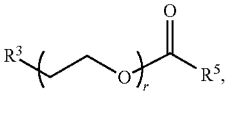

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —$N(R^N)$, O, S, C(O), $C(O)N(R^N)$, $NR^NC(O)$, $NR^NC(O)N(R^N)$, C(O)O, OC(O), OC(O)O, —$OC(O)N(R^N)$, $NR^NC(O)O$, C(O)S, SC(O), $C(=NR^N)$, $C(=NR^N)N(R^N)$, $NR^NC(=NR^N)$, —$NR^NC(=NR^N)N(R^N)$, C(S), $C(S)N(R^N)$, $NR^NC(S)$, $NR^NC(S)N(R^N)$, S(O) OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, —$OS(O)N(R^N)$, $N(R^N)S(O)O$, $S(O)_2$, $N(R^N)S(O)_2$, $S(O)_2N(R^N)$, $N(R^N)S(O)_2N(R^N)$, —$OS(O)_2N(R^N)$, or $N(R^N)S(O)_2O$; and each instance of $R^N$ is independently hydrogen, optionally substituted alkyl, or a nitrogen protecting group.

In certain embodiments, the compound of Formula (VIII) is of Formula (VIII-OH):

(VIII-OH)

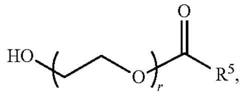

or a salt thereof. In some embodiments, r is 45.

In certain embodiments, a compound of Formula (VIII) is of one of the following formulae:

(Compound 419)

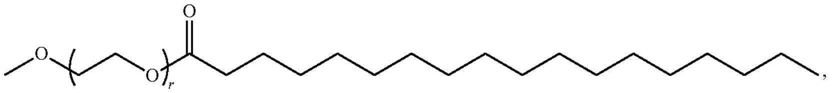

(Compound 420)

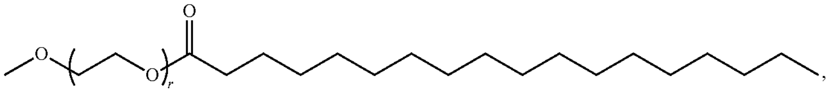

(Compound 421)

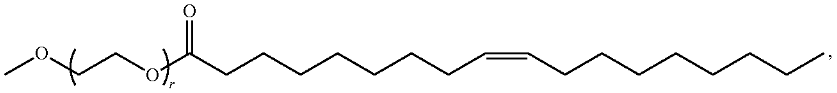

(Compound 422)

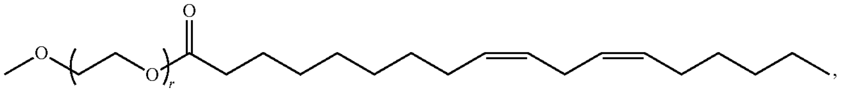

(Compound 423)

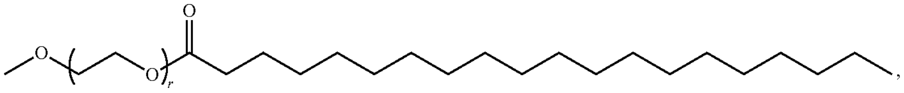

(Compound 424)

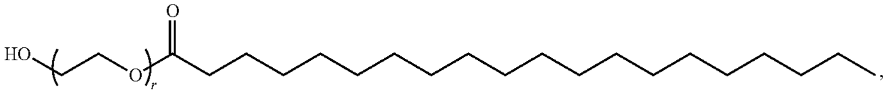

-continued (Compound 425)

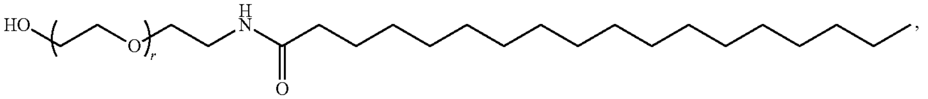

(Compound 426)

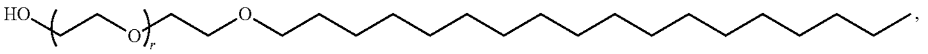

or a salt thereof. In some embodiments, r is 45.

In yet other embodiments the compound of Formula (VIII) is:

(Compound 427)

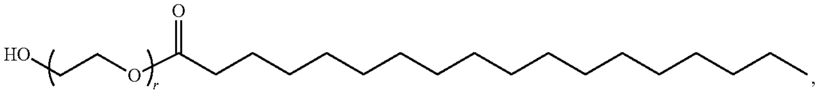

or a salt thereof.

In one embodiment, the compound of Formula (VIII) is (Compound 428)

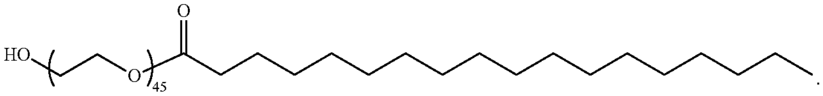

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

(iv) Other Ionizable Amino Lipids

The lipid composition of the pharmaceutical composition disclosed herein can comprise one or more ionizable amino lipids in addition to a lipid according to Formula (I), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), (13Z,165Z)—N,N-dimethyl-3-nonydocosa-13-16-dien-1-amine (L608), 2-({8-[(3p)-cholest-5-en-3-yloxy]octyl}oxy)-N,N-dimethyl-3-[(9Z,12Z)-octadeca-9,12-di en-1-yloxy]propan-1-amine (Octyl-CLinDMA), (2R)-2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

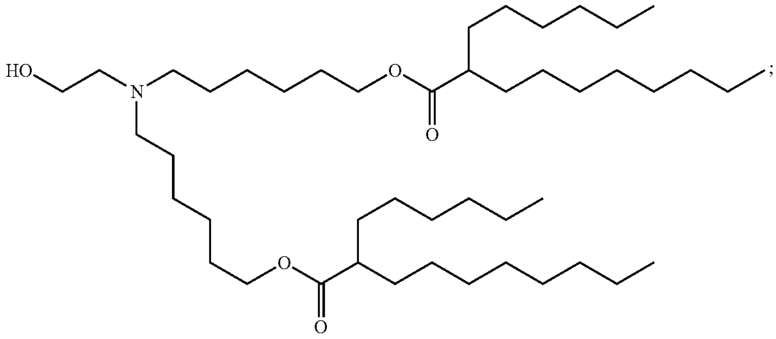
;
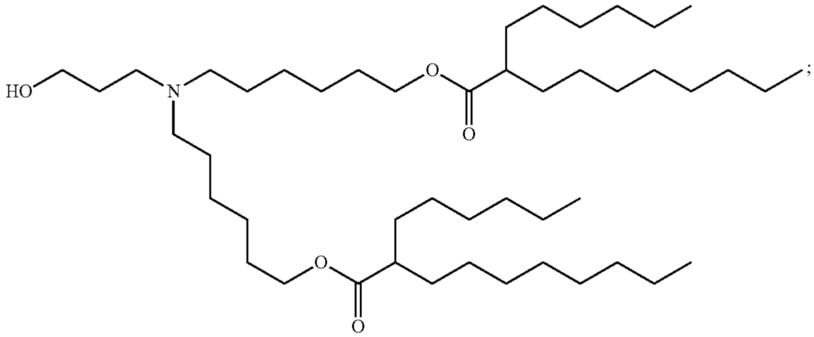
;
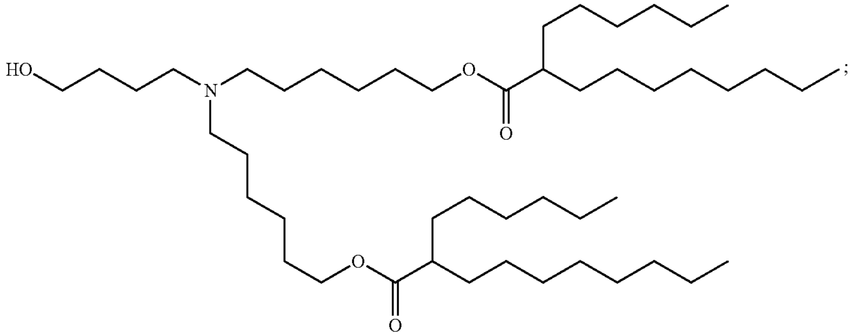
;
and any combination thereof.
Ionizable lipids can also be the compounds disclosed in International Publication No. WO 2015/199952 A1, hereby incorporated by reference in its entirety. For example, the ionizable amino lipids include, but not limited to:
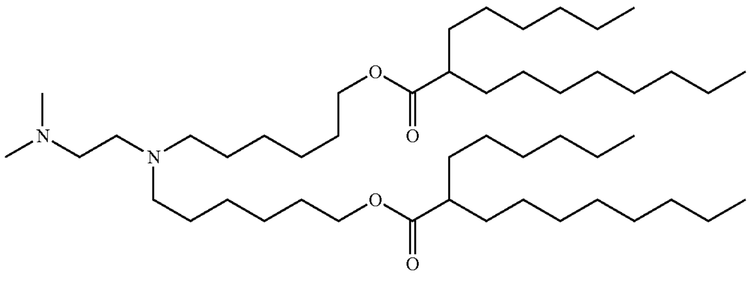
;

-continued
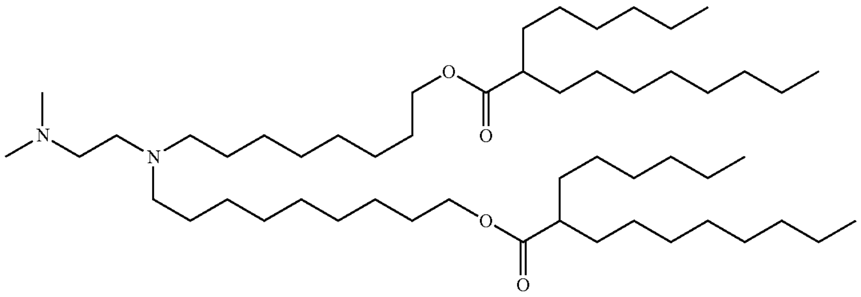
;
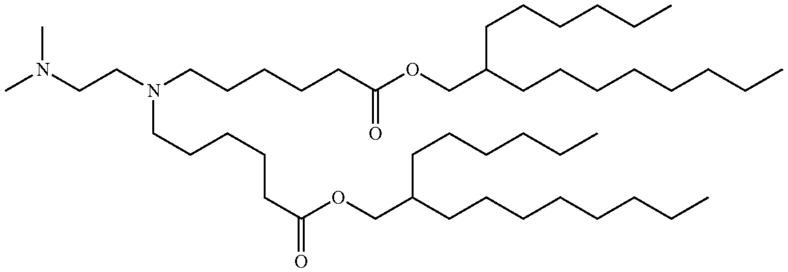
;
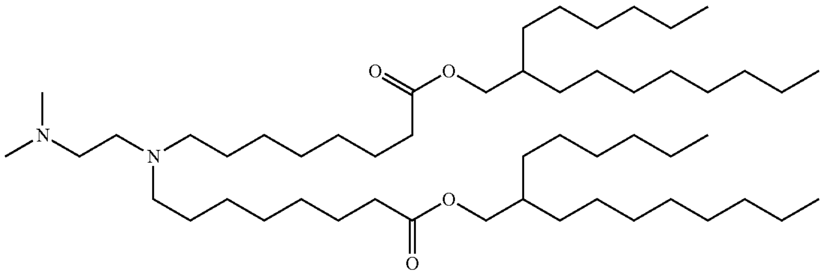
;
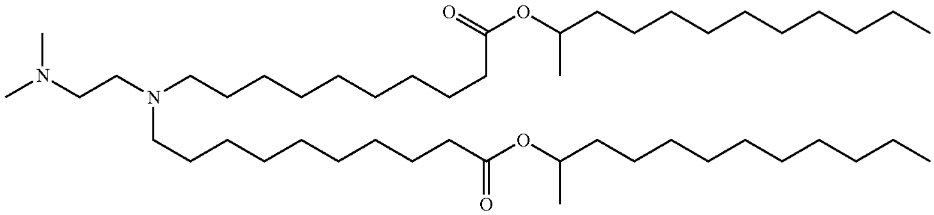
;
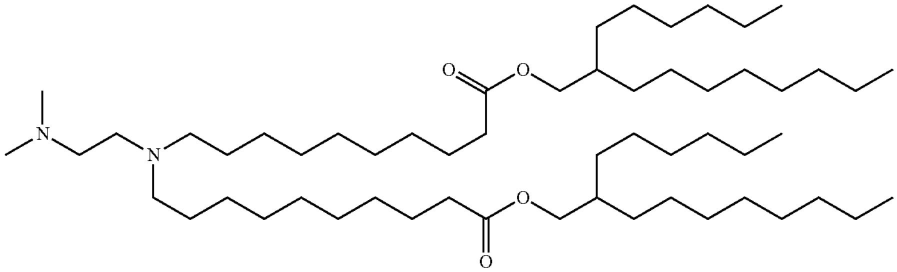
;
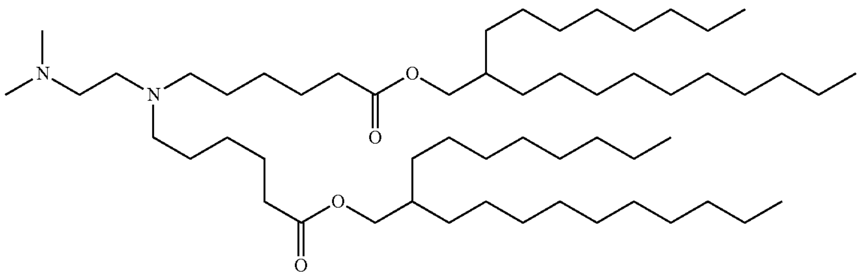
;

-continued

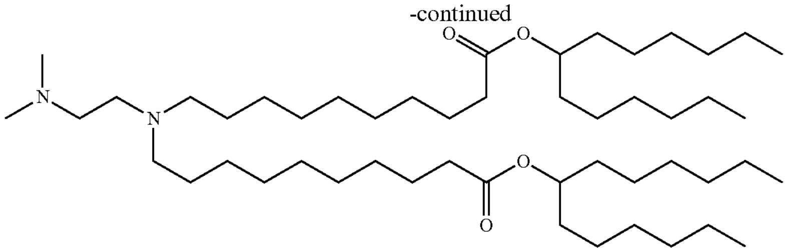

;

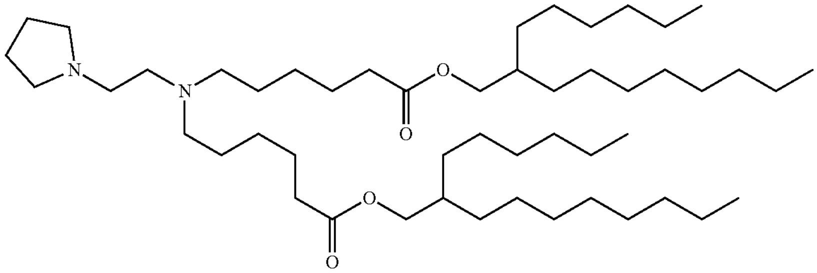

;

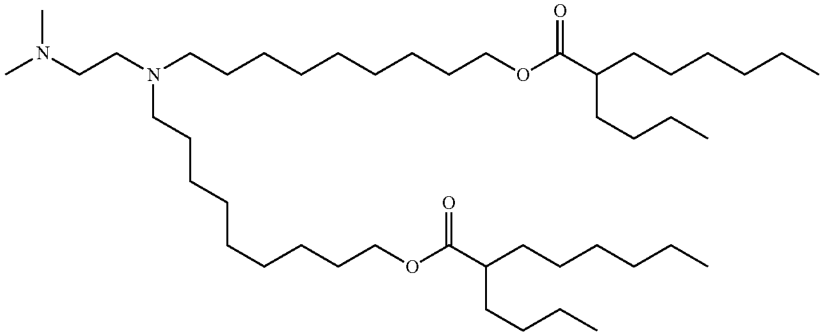

;

and any combination thereof.

(v) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

In another aspect, the present application provides a lipid composition (e.g., a lipid nanoparticle (LNP)) comprising: (1) a compound having the Formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a LPL polypeptide, e.g., a polynucleotide encapsulated therein.

Pharmacokinetics/Pharmacodynamics

Pharmacokinetics of LPL polypeptides are described in further detail in Example 23. The results demonstrate that introduction of the 5-methoxy uridine (mo5U)-modified hLPL mRNAs formulated in Compound 18 in Zucker fa/fa rats leads to expression of the encoded protein (e.g., LPL) within about 1 hour, with a steady level of protein expression such that maximum plasma concentration for the protein can be reached, for example, within about 2-6 hours, or about 4 hours. The half life of the encoded LPL protein can be, for example, about 10-18 hours, or about 12 hours. Pharmacokinetics of the constructs of the present disclosure can be measured using an ELISA or any method known in the art (Shepard et al., Int J Obesity, 24(2):187-94 (2000); Desager et al., Atherosclerosis, 124:S65-73 (1996)). For example, the pharmacokinetics (pK) of different constructs may be measured by assaying plasma samples with an ELISA. Accordingly, in one embodiment, the post-heparin plasma concentration of hLPL one hour after administration is greater than 3.0 μg/mL. In other embodiments, the post-heparin plasma concentration of hLPL is greater that 0.2, 0.4, 0.6, 0.8, 1.0, 1.2, 1.4, 1.6, 1.8, 2.0, 2.2, 2.4, 2.6, 2.8, or 3.0 μg/mL. In some embodiments, the post-heparin plasma concentration of hLPL is maintained for at least 1.5, 2.0, 2.5, 3.0, 3.5, 4.0, 4.5, or 5.0 hours.

Accordingly, in one aspect of the present disclosure provides a method for providing an LPL polypeptide to a subject, comprising administering to the subject intravenously a first dose of an mRNA (mRNA) encapsulated in an LNP, wherein the mRNA encodes the LPL polypeptide; and administering to the subject intravenously a second dose of the mRNA encapsulated in an LNP about 7 days following administration of the first dose. In some embodiments, the second dose is administered 3, 4, 5, 6, 8, 9, 10, 11, or 12 days following administration of the first dose. In other embodiments, 3, 4, 5, 6, 7, 8, 9, 10, or more doses of the LPL LNP formulation are administered.

Pharmacodynamics (pD) may also be measured by any method known in the art. In some embodiments, pD is measured as the percent change in plasma triglycerides over baseline level following administration of the LPL LNP formulation. In some embodiments, administration of the LPL LNP formulation causes a reduction in triglyceride levels greater than 100% of baseline. In other embodiments, the reduction of triglycerides is at least 90%, 85%, 80%, 75%, 70%, 65%, 60%, 55%, or 50% of baseline.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, Cig alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''''$, in which each OR are alkoxy groups that can be the same or different and R'''' is an alkyl or alkenyl group), a phosphate (e.g., $P(O)_4^{3}—$), a thiol (e.g., —SH), a sulfoxide (e.g., —S(O)R), a sulfinic acid (e.g., —S(O)OH), a sulfonic acid (e.g., $—S(O)_2OH$), a thial (e.g., —C(S)H), a sulfate (e.g., $S(O)_4^{2}—$), a sulfonyl (e.g., $—S(O)_2—$), an amide (e.g., $—C(O)NR_2$, or —N(R)C(O)R), an azido (e.g., $—N_3$), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

About, Approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean +/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

As used herein, the term "delivering" means providing an entity to a destination. For example, delivering a therapeutic and/or prophylactic to a subject may involve administering a nanoparticle composition including the therapeutic and/or prophylactic to the subject (e.g., by an intravenous, intramuscular, intradermal, or subcutaneous route). Administration of a nanoparticle composition to a mammal or mammalian cell may involve contacting one or more cells with the nanoparticle composition.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model). In certain embodiments, a nanoparticle composition including a compound according to Formula (I), (IA), (II), (IIa), (IIb), (IIc), (IId) or (IIe) has substantively the same level of delivery enhancement regardless of administration routes. For example, certain compounds disclosed herein exhibit similar delivery enhancement when they are used for delivering a therapeutic and/or prophylactic either intravenously or intramuscularly. In other embodiments, certain compounds disclosed herein (e.g., a compound of Formula (IA) or (II), such as Compound 18, 25, 30, 60, 108-112, or 122) exhibit a higher level of delivery enhancement when they are used for delivering a therapeutic and/or prophylactic intramuscularly than intravenously.

As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. For example, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a nanoparticle composition including a lipid component and an RNA.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the "polydispersity index" is a ratio that describes the homogeneity of the particle size distribution of a system. A small value, e.g., less than 0.3, indicates a narrow particle size distribution.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, and mixtures thereof.

As used herein, a "single unit dose" is a dose of any therapeutic administered in one dose/at one time/single route/single point of contact, i.e., single administration event.

As used herein, a "split dose" is the division of single unit dose or total daily dose into two or more doses.

As used herein, a "total daily dose" is an amount given or prescribed in 24 hour period. It may be administered as a single unit dose.

As used herein, "size" or "mean size" in the context of nanoparticle compositions refers to the mean diameter of a nanoparticle composition.

As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

As used herein "target tissue" refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The term "therapeutic agent" or "prophylactic agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "transfection" refers to the introduction of a species (e.g., an RNA) into a cell. Transfection may occur, for example, in vitro, ex vivo, or in vivo.

As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the "zeta potential" is the electrokinetic potential of a lipid, e.g., in a particle composition.

In one specific embodiment, the compound of Formula (I) is Compound 18.

In some embodiments, the amount the compound of Formula (I) ranges from about 1 mol % to 99 mol % in the lipid composition.

In one embodiment, the amount of compound of Formula (I) is at least about 1, 2, 3, 4, 5, 6, 7,8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the compound of Formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the compound of Formula (I) is about 50 mol % in the lipid composition.

In addition to the compound of Formula (I), the lipid composition of the pharmaceutical compositions disclosed herein can comprise additional components such as phospholipids, structural lipids, quaternary amine compounds, PEG-lipids, and any combination thereof.

In some embodiments, the largest dimension of a nanoparticle composition is 1 m or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

When a molecule comprising polyethylene glycol (i.e. PEG) is used, it may be used as a stabilizer. In some embodiments, the molecule comprising polyethylene glycol may be polyethylene glycol conjugated to a lipid and thus may be provided as PEG-c-DOMG or PEG-DMG, for example. Certain of the LNPs provided herein comprise no or low levels of PEGylated lipids, including no or low levels of alkyl-PEGylated lipids, and may be referred to herein as being free of PEG or PEGylated lipid. Thus, some LNPs comprise less than 0.5 mol % PEGylated lipid. In some instances, PEG may be an alkyl-PEG such as methoxy-PEG. Still other LNPs comprise non-alkyl-PEG such as hydroxy- PEG, and/or non-alkyl-PEGylated lipids such as hydroxy-PEGylated lipids. The PEGylated lipid may be a Cmpd420, a Cmpd396, a Cmpd394, Cmpd397, Cmpd395, Cmpd417, Cmpd418, or Cmpd419.

Certain of the LNPs provided herein comprise an ionizable lipid, such as an ionizable amino or ionizable cationic lipid, a phospholipid, a structural lipid, and optionally a stabilizer (e.g., a molecule comprising polyethylene glycol) which may or may not be provided conjugated to another lipid.

In one embodiment, formulations comprising the polynucleotides and lipid nanoparticles described herein can comprise 0.15 mg/ml to 2 mg/ml of the polynucleotide described herein (e.g., mRNA). In some embodiments, the formulation can further comprise 10 mM of citrate buffer and the formulation can additionally comprise up to 10% w/w of sucrose (e.g., at least 1% w/w, at least 2% w/w/, at least 3% w/w, at least 4% w/w, at least 5% w/w, at least 6% w/w, at least 7% w/w, at least 8% w/w, at least 9% w/w or 10% w/w).

Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a compound of Formula (I) as described herein, and (ii) a polynucleotide encoding a LPL polypeptide. In such nanoparticle composition, the lipid composition disclosed herein can encapsulate the polynucleotide encoding a LPL polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

Nanoparticle compositions of the present disclosure comprise at least one compound according to Formula (I), (IA), (II), (IIa), (IIb), (IIc), (IId) or (IIe). For example, the nanoparticle composition can include one or more of Compounds 1-232. Nanoparticle compositions can also include a variety of other components. For example, the nanoparticle composition can include one or more other lipids in addition to a lipid according to Formula (I) or (II), for example (i) at least one phospholipid, (ii) at least one structural lipid, (iii) at least one PEG-lipid, or (iv) any combination thereof. Inclusion of structural lipid can be optional, for example when lipids according to formula III are used in the lipid nanoparticle compositions of the invention.

In some embodiments, the nanoparticle composition comprises a compound of formula (I), (e.g., Compounds 18, 25, 26 or 48). In some embodiments, the nanoparticle composition comprises a compound of formula (I) (e.g., Compounds 18, 25, 26 or 48) and a phospholipid (e.g., DSPC).

In some embodiments, the nanoparticle composition comprises a compound of formula (III) (e.g., Compound 236). In some embodiments, the nanoparticle composition comprises a compound of formula (III) (e.g., Compound 236) and a phospholipid (e.g., DOPE or DSPC).

In some embodiments, the nanoparticle composition comprises a lipid composition consisting or consisting essentially of compound of formula (I) (e.g., Compounds 18, 25, 26 or 48). In some embodiments, the nanoparticle composition comprises a lipid composition consisting or consisting essentially of a compound of formula (I) (e.g., Compounds 18, 25, 26 or 48) and a phospholipid (e.g., DSPC).

In some embodiments, the nanoparticle composition comprises a lipid composition consisting or consisting essentially of compound of formula (III) (e.g., Compound 236). In some embodiments, the nanoparticle composition comprises a lipid composition consisting or consisting essentially of a compound of formula (III) (e.g., Compound 236) and a phospholipid (e.g., DOPE or DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable lipid and the structural lipid is a neutral lipid, and the sterol is a cholesterol. In some embodiments, the LNP has a molar ratio of 50:38.5:10:1.5 of ionizable lipid:cholesterol:DSPC: PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18:Phospholipid:Cholesterol: Compound 428. In some embodiments, the LNP has a molar ratio of 50:38.5:10:1.5 of Compound 18:DSPC:Cholesterol: Compound 428.

In some embodiments, the LNP has a molar ratio of 50:38.5:10:1.5 of Compound 236:Phospholipid:Cholesterol: Compound 428. In some embodiments, the LNP has a molar ratio of 50:38.5:10:1.5 of Compound 236:DSPC:Cholesterol:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a LPL polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a LPL polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SLTV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is a cationic or an ionizable lipid. In some embodiments, lipid nanoparticle formulations further comprise other components, including a phospholipid, a structural lipid, a quaternary amine compound, and a molecule capable of reducing particle aggregation, for example a PEG or PEG-modified lipid.

Cationic and ionizable lipids can include those as described in, e.g., Intl. Pub. Nos. WO2015199952, WO 2015130584, WO 2015011633, and WO2012040184 WO2013126803, WO2011153120, WO2011149733, WO2011090965, WO2011043913, WO2011022460, WO2012061259, WO2012054365, WO2012044638, WO2010080724, WO201021865, WO2008103276, and WO2013086373; U.S. Pat. Nos. 7,893,302, 7,404,969, 8,283,333, and 8,466,122; and U.S. Pub. Nos. US2010224447, US20120295832, US20150315112, US20100036115, US20120202871, US20130064894, US20130129785, US20130150625, US20130178541, US20130123338 and US20130225836, each of which is herein incorporated by reference in its entirety. In some embodiments, the amount of the cationic and ionizable lipids in the lipid composition ranges from about 0.01 mol % to about 99 mol %.

Exemplary ionizable lipids include, but not limited to, any one of Compounds 1-232 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl]eptadecan-8-amine, 1-[(1S, 2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl} cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0.1 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US201 0262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigitial micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut fir Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 un, greater than 600 nm, greater than 650 nm, greater than 700 nm, greater than 750 nm, greater than 800 nm, greater than 850 nm, greater than 900 nm, greater than 950 nm or greater than 1000 un.

In some embodiments, the polynucleotides can be delivered using smaller LNPs. Such particles can comprise a diameter from below 0.1 μm up to 100 nm such as, but not limited to, less than 0.1 μm, less than 1.0 m, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177, 274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art, the polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

w. Conjugates

In some embodiments, the compositions or formulations of the present disclosure comprise the polynucleotides described herein (e.g., a polynucleotide comprising a nucleotide sequence encoding a LPL polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835.393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

Methods of Use

The polynucleotides, pharmaceutical compositions and formulations described above are used in the preparation, manufacture and therapeutic use of to treat and/or prevent LPL-related diseases, disorders or conditions. In some embodiments, the polynucleotides, compositions and formulations of the invention are used to treat and/or prevent hyperlipidemia.

In some embodiments, the polynucleotides, pharmaceutical compositions and formulations of the invention are used in methods for reducing the levels of triglycerides, chylomicrons, and/or VLDL in a subject in need thereof. For instance, one aspect of the invention provides a method of alleviating the symptoms of hyperlipidemia in a subject comprising the administration of a composition or formulation comprising a polynucleotide encoding LPL to that subject (e.g, an mRNA encoding a LPL polypeptide).

In some embodiments, the polynucleotides, pharmaceutical compositions and formulations of the invention are used to reduce the level of a metabolite associated with hyperlipidemia (e.g., the substrate or product, i.e., triglycerides, chylomicrons, and VLDL), the method comprising administering to the subject an effective amount of a polynucleotide encoding a LPL polypeptide.

In some embodiments, the administration of an effective amount of a polynucleotide, pharmaceutical composition or formulation of the invention reduces the levels of a biomarker of hyperlipidemia, e.g., triglycerides, chylomicrons, and/or VLDL. In some embodiments, the administration of the polynucleotide, pharmaceutical composition or formulation of the invention results in reduction in the level of one or more biomarkers of hyperlipidemia, e.g., triglycerides, chylomicrons, and/or VLDL, within a short period of time after administration of the polynucleotide, pharmaceutical composition or formulation of the invention.

Replacement therapy is a potential treatment for hyperlipidemia. Thus, in certain aspects of the invention, the polynucleotides, e.g., mRNA, disclosed herein comprise one or more sequences encoding a LPL polypeptide that is suitable for use in gene replacement therapy for hyperlipidemia. In some embodiments, the present disclosure treats a lack of LPL or LPL activity, or decreased or abnormal LPL activity in a subject by providing a polynucleotide, e.g., mRNA, that encodes a LPL polypeptide to the subject. In some embodiments, the polynucleotide is sequence-optimized. In some embodiments, the polynucleotide (e.g., an mRNA) comprises a nucleic acid sequence (e.g., an ORF) encoding a LPL polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142.

In some embodiments, the administration of a composition or formulation comprising polynucleotide, pharmaceutical composition or formulation of the invention to a subject results in a decrease in tryglycerides in cells to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of LPL in cells of the subject. In some embodiments, administering the polynucleotide, pharmaceutical composition or formulation of the invention results in an increase of LPL enzymatic activity in the subject. For example, in some embodiments, the polynucleotides of the present invention are used in methods of administering a composition or formulation comprising an mRNA encoding a LPL polypeptide to a subject, wherein the method results in an increase of LPL enzymatic activity in at least some cells of a subject.

In some embodiments, the administration of a composition or formulation comprising an mRNA encoding a LPL polypeptide to a subject results in an increase of LPL enzymatic activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the activity level expected in a normal subject, e.g., a human not suffering from hyperlipidemia.

In some embodiments, the administration of the polynucleotide, pharmaceutical composition or formulation of the invention results in expression of LPL protein in at least some of the cells of a subject that persists for a period of time sufficient to allow significant triglycerides, chylomicrons, and/or VLDL metabolism to occur.

In some embodiments, the expression of the encoded polypeptide is increased. In some embodiments, the polynucleotide increases LPL expression levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the LPL expression level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 5 to 29, 80 to 83, and 148 (See TABLE 2), wherein the polynucleotide encodes an LPL polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

Compositions and Formulations for Use

Certain aspects of the invention are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a LPL polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site); and (ii) a delivery agent comprising a compound having Formula (I), e.g., any of Compounds 1-232 (e.g., Compound 18, 25, 26 or 48).

In some embodiments, the uracil or thymine content of the ORF relative to the theoretical minimum uracil or thymine content of a nucleotide sequence encoding the LPL polypeptide (% $U_{TM}$ or % $T_{TM}$), is between about 100% and about 150%.

In some embodiments, the polynucleotides, compositions or formulations above are used to treat and/or prevent a LPL-related diseases, disorders or conditions, e.g., hyperlipidemia.

Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a LPL polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a LPL polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

Kits and Devices a. Kits

The invention provides a variety of kits for conveniently and/or effectively using the claimed nucleotides of the present invention. Typically, kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minute period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type LPL sequence) with another amino acid residue. An amino acid can be substituted in a parent or reference sequence (e.g., a wild type LPL polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue, i.e., In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, symptoms, sequelae, or any effects causing a decrease in the quality of life of a patient of hyperlipidemia are considered associated with hyperlipidemia and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a LPL peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding a LPL peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a LPL polypeptide, and a second part (e.g., genetically fused to the first part) comprising a second therapeutic protein (e.g., a protein with a distinct enzymatic activity, an antigen binding moiety, or a moiety capable of extending the plasma half life of LPL, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-orithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a LPL deficiency), an effective amount of an agent is, for example, an amount of mRNA expressing sufficient LPL to ameliorate, reduce, eliminate, or prevent the signs or symptoms associated with the LPL deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, “encapsulation” can refer to complete, substantial, or partial enclosure, confinement, surrounding, or encasement.

Encodedprotein cleavage signal: As used herein, “encoded protein cleavage signal” refers to the nucleotide sequence that encodes a protein cleavage signal.

Engineered: As used herein, embodiments of the invention are “engineered” when they are designed to have a feature or property, whether structural or chemical, that varies from a starting point, wild type or native molecule.

Enhanced Delivery: As used herein, the term “enhanced delivery” means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, “exosome” is a vesicle secreted by mammalian cells or a complex involved in RNA degradation.

Expression: As used herein, “expression” of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term “ex vivo” refers to events that occur outside of an organism (e.g., animal, plant, or microbe or cell or tissue thereof). Ex vivo events can take place in an environment minimally altered from a natural (e.g., in vivo) environment.

Feature: As used herein, a “feature” refers to a characteristic, a property, or a distinctive element. When referring to polypeptides, “features” are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a “formulation” includes at least a polynucleotide and one or more of a carrier, an excipient, and a delivery agent.

Fragment: A “fragment,” as used herein, refers to a portion. For example, fragments of proteins can comprise polypeptides obtained by digesting full-length protein isolated from cultured cells. In some embodiments, a fragment is a subsequences of a full length protein (e.g., LPL) wherein N-terminal, and/or C-terminal, and/or internal subsequences have been deleted. In some preferred aspects of the present invention, the fragments of a protein of the present invention are functional fragments.

Functional: As used herein, a “functional” biological molecule is a biological molecule in a form in which it exhibits a property and/or activity by which it is characterized. Thus, a functional fragment of a polynucleotide of the present invention is a polynucleotide capable of expressing a functional LPL fragment. As used herein, a functional fragment of LPL refers to a fragment of wild type LPL or LPL-S447Stop (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

Helper Lipid: As used herein, the term “helper lipid” refers to a compound or molecule that includes a lipidic moiety (for insertion into a lipid layer, e.g., lipid bilayer) and a polar moiety (for interaction with physiologic solution at the surface of the lipid layer). Typically, the helper lipid is a phospholipid. A function of the helper lipid is to “complement” the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term “homology” refers to the overall relatedness between polymeric molecules, e.g. between nucleic acid molecules (e.g. DNA molecules and/or RNA molecules) and/or between polypeptide molecules. Generally, the term “homology” implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be “homologous” to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term “homologous” necessarily refers to a comparison between at least two sequences (polynucleotide or polypeptide sequences).

Identity: As used herein, the term “identity” refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C-X-C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (11-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin- MC3-DMA (MC3) and (1 3Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition.

LPL Associated Disease: As use herein the terms "LPL-associated disease" or "LPL-associated disorder" refer to diseases or disorders, respectively, which result from aberrant LPL activity (e.g., decreased activity or increased activity). As a non-limiting example, familial lipoprotein lipase deficiency (FLLD) and hyperlipidemia are LPL associated diseases.

The terms "LPL enzymatic activity," "LPL activity," and "lipoprotein lipase activity" are used interchangeably in the present disclosure and refer to LPL's ability to (1) hydrolyze triglycerides in lipoproteins, such as those found in chylomicrons and very low-density lipoproteins (VLDL) or (2) serve as a ligand/bridging factor for receptor-mediated cellular uptake of chylomicron remnants, cholesterol-rich lipoproteins, or free fatty acids.

Accordingly, a fragment or variant retaining or having LPL enzymatic activity or LPL activity refers to a fragment or variant that has measurable (1) enzymatic activity hydrolyzing triglycerides in lipoproteins or (2) receptor-mediated cellular uptake of chylomicron remnants, cholesterol-rich lipoproteins, or free fatty acids.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (coin), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences,* $17^{th}$ ed., Mack Publishing Company, Easton, Pa., 1985, p. 1418*, Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more signs or symptoms, features, or clinical manifestations of a particular infection, disease, disorder, and/or condition; partially or completely delaying onset of one or more signs or symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine (ψ) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine (ψm).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragement or a variant thereof. In some embodiments, the reference nucleic acid sequence is a previously sequence optimized nucleic acid sequence.

Salts: In some aspects, the pharmaceutical composition for intratumoral delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more signs or symptoms of the disease, disorder, and/or condition.

Susceptible to: An individual who is "susceptible to" a disease, disorder, and/or condition has not been diagnosed with and/or can not exhibit signs or symptoms of the disease, disorder, and/or condition but harbors a propensity to develop a disease or its signs or symptoms. In some embodiments, an individual who is susceptible to a disease, disorder, and/or condition (for example, cancer) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues can include the liver and the spleen.

The presence of a therapeutic agent in an off-target issue can be the result of: (i) leakage of a polynucleotide from the administration site to peripheral tissue or distant off-target tissue (e.g., liver) via diffusion or through the bloodstream (e.g., a polynucleotide intended to express a polypeptide in a certain tissue would reach the liver and the polypeptide would be expressed in the liver); or (ii) leakage of an polypeptide after administration of a polynucleotide encoding such polypeptide to peripheral tissue or distant off-target tissue (e.g., liver) via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a LPL polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs or symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve signs or symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence).

Transfection: As used herein, "transfection" refers to the introduction of a polynucleotide into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more signs or symptoms or features of a disease, e.g., hyperlipidemia. For example, “treating” hyperlipidemia can refer to diminishing signs or symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, “unmodified” refers to any substance, compound or molecule prior to being changed in some way. Unmodified can, but does not always, refer to the wild type or native form of a biomolecule. Molecules can undergo a series of modifications whereby each modified molecule can serve as the “unmodified” starting molecule for a subsequent modification.

Uracil: Uracil is one of the four nucleobases in the nucleic acid of RNA, and it is represented by the letter U. Uracil can be attached to a ribose ring, or more specifically, a ribofuranose via a β-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a “uracil” or a “uridine.”

Uridine Content: The terms “uridine content” or “uracil content” are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms “uridine-modified sequence” refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms “uridine-modified sequence” and “uracil-modified sequence” are considered equivalent and interchangeable.

A “high uridine codon” is defined as a codon comprising two or three uridines, a “low uridine codon” is defined as a codon comprising one uridine, and a “no uridine codon” is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms “uridine enriched” and grammatical variants refer to the increase in uridine content (expressed in absolute value or as a percentage value) in a sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms “uridine rarefied” and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as “substitutional variants.” The substitutions can be single, where only one amino acid in the molecule has been substituted, or they can be multiple, where two or more amino acids have been substituted in the same molecule. If amino acids are inserted or deleted, the resulting variant would be an “insertional variant” or a “deletional variant” respectively.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as “a,” “an,” and “the” can mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term “comprising” is intended to be open and permits but does not require the inclusion of additional elements or steps. When the term “comprising” is used herein, the term “consisting of” is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Manufacture of Polynucleotides

According to the present disclosure, the manufacture of polynucleotides and or parts or regions thereof may be accomplished utilizing the methods taught in International Application WO2014/152027 entitled "Manufacturing Methods for Production of RNA Transcripts", the contents of which is incorporated herein by reference in its entirety.

Purification methods may include those taught in International Application WO2014/152030 and WO2014/152031, each of which is incorporated herein by reference in its entirety.

Detection and characterization methods of the polynucleotides may be performed as taught in WO2014/144039, which is incorporated herein by reference in its entirety.

Characterization of the polynucleotides of the disclosure may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, WO2014/144711 and WO2014/144767, the contents of each of which is incorporated herein by reference in its entirety.

Example 2

Chimeric Polynucleotide Synthesis

Introduction

According to the present disclosure, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)

(b) 5' triphosphate segment which may include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) is treated with cordycepin and then with pyrophosphatase to create the 5'monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3

PCR for cDNA Production

PCR procedures for the preparation of cDNA can be performed using 2×KAPA HIFI™ HotStart ReadyMix by Kapa Biosystems (Woburn, MA). This system includes 2×KAPA ReadyMix12.5 μl; Forward Primer (10 μM) 0.75 μl; Reverse Primer (10 μM) 0.75 μl; Template cDNA-100 ng; and $dH_2O$ diluted to 25.0 μl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-$T_{120}$ for a poly-$A_{120}$ in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 μg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 4

In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:

Template cDNA—1.0 μg

10× transcription buffer (400 mM Tris-HCl pH 8.0, 190 mM $MgCl_2$, 50 mM DTT, 10 mM Spermidine)—2.0 μl Custom NTPs (25 mM each)—7.2 μl RNase Inhibitor—20 U T7 RNA polymerase—3000 U $dH_2O$ Up to 20.0 μl, and Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 μg of RNA. Following the cleanup, the RNA can be quantified using the NanoDrop and analyzed by agarose gel electrophoresis to confirm the RNA is the proper size and that no degradation of the RNA has occurred.

Example 5

Enzymatic Capping

Capping of a polynucleotide can be performed with a mixture includes: IVT RNA 60 μg-180 μg and $dH_2O$ up to 72 μl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 6

PolyA Tailing Reaction

Without a poly-T in the cDNA, a poly-A tailing reaction must be performed before cleaning the final product. This can be done by mixing Capped IVT RNA (100 l); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubating at 37° C. for 30 min. If the poly-A tail is already in the transcript, then the tailing reaction can be skipped and proceed directly to cleanup with Ambion's MEGACLEAR™ kit (Austin, TX) (up to 500 μg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 7

Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs, Ipswich, MA). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 8

Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 9

Agarose Gel Electrophoresis of Modified RNA or RT PCR Products

Individual polynucleotides (200-400 ng in a 20 μl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 10

Nanodrop Modified RNA Quantification and UV Spectral Data

Modified polynucleotides in TE buffer (1 μl) can be used for Nanodrop UV absorbance readings to quantitate the yield of each polynucleotide from a chemical synthesis or in vitro transcription reaction.

Example 11

Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 12

Method of Screening for Protein Expression

Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 13

Synthesis of mRNA Encoding LPL

Sequence optimized polynucleotides encoding LPL polypeptides, i.e., SEQ ID NO: 1 or 3, are synthesized and characterized as described in Examples 1 to 12. mRNAs encoding both human LPL are prepared for Examples 14-19 described below, and are synthesized and characterized as described in Examples 1 to 12.

An mRNA encoding human LPL is constructed, e.g., by using the ORF sequence provided in SEQ ID NO: 2 or 4. The mRNA sequence includes both 5' and 3' UTR regions (see, e.g., SEQ ID NOs: 79 and 141, respectively). In a construct, the 5'UTR and 3'UTR sequences are:

```
5'UTR
                                                (SEQ ID NO: 79)
TCAAGCTTTTGGACCCTCGTACAGAAGCTAATACGACTCACTATAGGGA

AATAAGAGAGAAAAGAAGAGTAAGAAGAAATATAAGAGCCACC
```

-continued

3'UTR (SEQ ID NO: 141)

TGATAATAGGCTGGAGCCTCGGTGGCCATGCTTCTTGCCCCTTGGGCCT

CCCCCCAGCCCCTCCTCCCCTTCCTGCACCCGTACCCCCGTGGTCTTTG

AATAAAGTCTGAGTGGGCCGC

The LPL mRNA sequence is prepared as modified mRNA. Specifically, during in vitro translation, modified mRNA is generated using 5-methoxy-UTP to ensure that the mRNAs contain 100% 5-methoxy-uridine instead of uridine. Further, LPL-mRNA is synthesized with a primer that introduces a polyA-tail, and a Cap 1 structure is generated on both mRNAs using Vaccinia Virus Capping Enzyme and a 2'-O methyl-transferase to generate: m7G(5')ppp(5')G-2'-O-methyl.

Example 14

Detecting Endogenous LPL Expression In Vitro

LPL expression is characterized in a variety of cell lines derived from both mice and human sources. Cell are cultured in standard conditions and cell extracts are obtained by placing the cells in lysis buffer. For comparison purposes, appropriate controls are also prepared. To analyze LPL expression, lysate samples are prepared from the tested cells and mixed with lithium dodecyl sulfate sample loading buffer and subjected to standard Western blot analysis. For detection of LPL, the antibody used is a commercial anti-LPL antibody. For detection of a load control, the antibody used is anti-citrase synthase (rabbit polyclonal; PA5-22126; Thermo-Fisher Scientific®). To examine the localization of endogenous LPL, immunofluorescence analysis is performed on cells. LPL expression is detected using a commercial anti-LPL. The location of specific organelles can be detected with existing commercial products. For example, mitochondria can be detected using Mitotracker, and the nucleus can be stained with DAPI. Image analysis is performed on a Zeiss ELYRA imaging system.

Endogenous LPL expression can be used as a base line to determine changes in LPL expression resulting from transfection with mRNAs comprising nucleic acids encoding LPL.

Example 15

In Vitro Expression of LPL in HeLa Cells

To measure in vitro expression of human LPL in HeLa cells, those cells are seeded on 12-well plates (BD Biosciences, San Jose, USA) one day prior to transfection. mRNA formulations comprising human LPL or a GFP control are transfected using 800 ng mRNA and 2 μL Lipofectamin 2000 in 60 μL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze LPL expression, equal loads of each lysate (24 g) are prepared in a loading buffer and subjected to standard Western blot analysis. For detection of LPL, a commercial anti-LPL antibody is used according to the manufacturer's instructions.

Example 16

In Vitro LPL Activity in HeLa Cells

An in vitro LPL activity assay is performed to determine whether LPL exogenously-expressed after introduction of mRNA comprising a LPL sequence is active.

Expression Assay

HeLa cells are transfected with mRNA formulations comprising human LPL or a GFP control. Cells are transfected with Lipofectamin 2000 and lysed as described in Example 14 above. Appropriate controls are also prepared.

Activity Assay

To assess whether exogenous LPL can function, an in vitro activity assay is performed using transfected HeLa cell lysates as the source of enzymatic activity. To begin, lysate is mixed LPL substrate. The reaction is stopped by adding 100 g/L TCA and vortexing. The reaction tubes are then centrifuged at 13,000 g for 1 min, and the supernatant is analyzed for the presence of labeled enzymatic products resulting from the activity of LPL using HPLC-based separation and quantification. Specifically, 20 μL of each activity reaction supernatant are analyzed using a HPLC system equipped with a Quaternary-Pump, a Multi-sampler, a Thermostated Column-Compartment, a Poroshell EC-C18 120 HPLC-column and a Radiometric Detector controlled by OpenLAB Chromatography Data System, all used according to the manufacturers' recommendations.

Example 17

Measuring In Vitro Expression of LPL in Cells

Cells from normal subjects and FLLD patients are examined for their capacity to express exogenous LPL. Cells are transfected with mRNA formulations comprising human LPL, mouse LPL, or a GFP control via electroporation using a standard protocol. Each construct is tested separately. After incubation, cells are lysed and protein concentration in each lysate is measured using a suitable assay, e.g., by BCA assay. To analyze LPL expression, equal loads of each lysate are prepared in a loading buffer and subjected to standard Western blot analysis. For detection of LPL, an anti-LPL is used. For detection of a load control, the antibody used is anti-citrase synthase (rabbit polyclonal; MA5-17625; Pierce®).

Example 18

Measuring In Vitro LPL Activity in Lysates

Expression

Cells from normal human subjects and FLLD patients are cultured. Cells are transfected with mRNA formulations comprising human LPL, mouse LPL, or a GFP control via electroporation using a standard protocol.

Activity Assay

To assess whether exogenous LPL function, an in vitro activity assay is performed using transfected cell lysates as the source of enzymatic activity. Lysate containing expressed LPL protein is incubated with labeled LPL substrate, and the activity of LPL is quantified by measuring the levels of labeled products resulting from the enzymatic activity of LPL.

Example 19

In Vivo LPL Expression in Animal Models

To assess the ability of LPL-containing mRNA's to facilitate LPL expression in vivo, mRNA encoding human LPL is introduced into C57B/L6 mice. C57B/L6 mice are injected intravenously with either control mRNA (NT-FIX) or human LPL mRNA. The mRNA is formulated in lipid nanoparticles for delivery into the mice. Mice are sacrificed after 24 or 48 hrs. and LPL protein levels in liver lysates are determined by capillary electrophoresis (CE). Citrate synthase expression is examined for use as a load control. For control NT-FIX injections, 4 mice are tested for each time point. For human LPL mRNA injections, 6 mice are tested for each time point. Treatment with mRNA encoding LPL is expected to reliably induce expression of LPL.

Example 20

Human LPL Mutant and Chimeric Constructs

A polynucleotide of the present invention can comprise at least a first region of linked nucleosides encoding human LPL, which can be constructed, expressed, and characterized according to the examples above. Similarly, the polynucleotide sequence can contain one or more mutations that results in the expression of a LPL with increased or decreased activity. Furthermore, the polynucleotide sequence encoding LPL can be part of a construct encoding a chimeric fusion protein.

Example 21

Synthesis of Compounds According to Formula (I)

A. General Considerations

All solvents and reagents used were obtained commercially and used as such unless noted otherwise. $^{1}H$ NMR spectra were recorded in $CDCl_3$, at 300 K using a Bruker Ultrashield 300 MHz instrument. Chemical shifts are reported as parts per million (ppm) relative to TMS (0.00) for $^{1}H$. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 μm, and a gradient of 65 to 100% acetonitrile in water with 0.1% TFA over 5 minutes at 1.2 mL/min. Injection volume was 5 μL and the column temperature was 80° C. Detection was based on electrospray ionization (ESI) in positive mode using Waters SQD mass spectrometer (Milford, MA, USA) and evaporative light scattering detector.

The representative procedures described below are useful in the synthesis of Compounds 1-232.

The following abbreviations are employed herein:

THF: Tetrahydrofuran
DMAP: 4-Dimethylaminopyridine
LDA: Lithium Diisopropylamide
rt: Room Temperature
DME: 1,2-Dimethoxyethane
n-BuLi: n-Butyllithium B. Compound 2: Heptadecan-9-yl 8-((2-hydroxyethyl)(tetradecyl)amino) octanoate Representative Procedure 1:

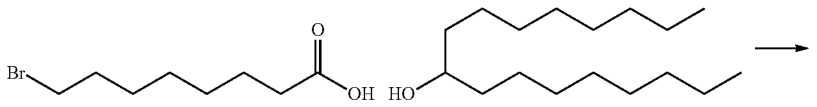

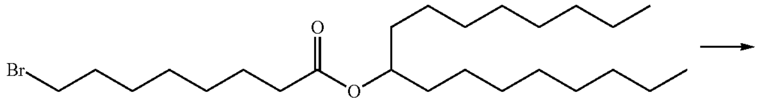

heptadecan-9-yl 8-bromooctanoate

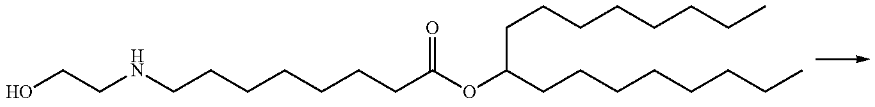

heptadecan-9-yl 8-((2-hydroxyethyl)amino)octanoate

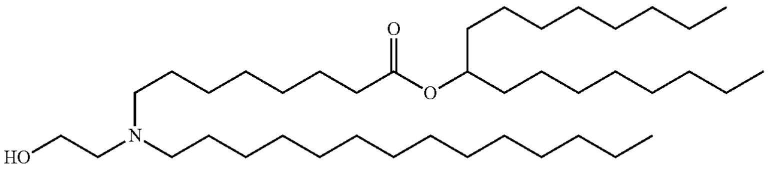

heptadecan-9-yl 8-((2-hydroxyethyl)(tetradecyl)amino)octanoate eptadecan-9-yl 8-((2-hydroxyethyl)(tetradecyl)amino)octanoate

Heptadecan-9-yl 8-bromooctanoate (Method A)

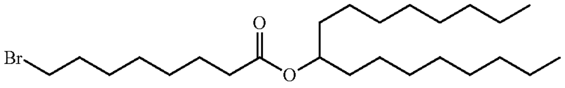 [SMILES: CCCCCCCCC(CCCCCCCC)OC(=O)CCCCCCCBr]

To a solution of 8-bromooctanoic acid (1.04 g, 4.6 mmol) and heptadecan-9-ol (1.5 g, 5.8 mmol) in dichloromethane (20 mL) was added N-(3-dimethylaminopropyl)-N'-ethylcarbodiimide hydrochloride (1.1 g, 5.8 mmol), N,N-diisopropylethylamine (3.3 mL, 18.7 mmol) and DMAP (114 mg, 0.9 mmol). The reaction was allowed to stir at rt for 18 h. The reaction was diluted with dichloromethane and washed with saturated sodium bicarbonate. The organic layer was separated and washed with brine, and dried over $MgSO_4$. The organic layer was filtered and evaporated in vacuo. The residue was purified by silica gel chromatography (0-10% ethyl acetate in hexanes) to obtain heptadecan-9-yl 8-bromooctanoate (875 mg, 1.9 mmol, 41%).

$^1$H NMR (300 MHz, $CDCl_3$) δ: ppm 4.89 (m, 1H); 3.42 (m, 2H); 2.31 (m, 2H); 1.89 (m, 2H); 1.73-1.18 (br. m, 36H); 0.88 (m, 6H).

Heptadecan-9-yl 8-((2-hydroxyethyl)amino)octanoate (Method B)

Chemical Formula: $C_{41}H_{83}NO_3$
Molecular Weight: 638.12

A solution of heptadecan-9-yl 8-((2-hydroxyethyl)amino) octanoate (125 mg, 0.28 mmol), 1-bromotetradecane (94 mg, 0.34 mmol) and N,N-diisopropylethylamine (44 mg, 0.34 mmol) in ethanol was allowed to stir at 65° C. for 18 h. The reaction was cooled to rt and solvents were evaporated in vacuo. The residue was taken-up in ethyl acetate and saturated sodium bicarbonate. The organic layer was separated, dried over $Na_2SO_4$ and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)(tetradecyl)amino)octanoate (89 mg, 0.14 mmol, 50%). UPLC/ELSD: RT=3.61 min. MS (ES): m/z (MH) 638.91 for $C_{41}H_{83}NO_3$. $^1$H NMR (300 MHz, $CDCl_3$) δ: ppm 4.86 (p, 1H); 3.72-3.47 (br. m, 2H); 2.78-2.40 (br. m, 5H); 2.28 (t, 2H); 1.70-1.40 (m, 10H); 1.38-1.17 (br. m, 54H); 0.88 (m, 9H).

Synthesis of Intermediates:

Intermediate A: 2-Octyldecanoic acid

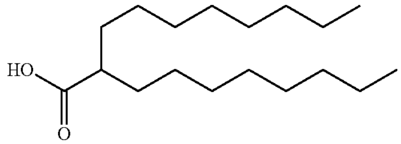

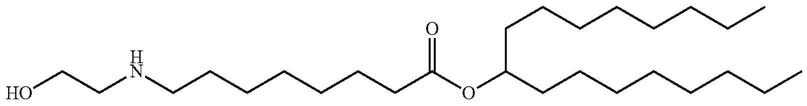 [SMILES: CCCCCCCCC(CCCCCCCC)OC(=O)CCCCCCCNCCO]

A solution of heptadecan-9-yl 8-bromooctanoate (3.8 g, 8.2 mmol) and 2-aminoethan-1-ol (15 mL, 248 mmol) in ethanol (3 mL) was allowed to stir at 62° C. for 18 h. The reaction mixture was concentrated in vacuo and the residue was taken-up in ethyl acetate and water. The organic layer was separated and washed with water, brine and dried over $Na_2SO_4$. The mixture was filtered and evaporated in vacuo. The residue was purified by silica gel chromatography (0-100% (mixture of 1% $NH_4OH$, 20% MeOH in dichloromethane) in dichloromethane) to obtain heptadecan-9-yl 8-((2-hydroxyethyl)amino)octanoate (3.1 g, 7 mmol, 85%). UPLC/ELSD: RT=2.67 min. MS (ES): m/z ($MH^+$) 442.68 for $C_{27}H_{55}NO_3$.

$^1$H NMR (300 MHz, $CDCl_3$) δ: ppm 4.89 (p, 1H); 3.67 (t, 2H); 2.81 (t, 2H); 2.65 (t, 2H); 2.30 (t, 2H); 2.05 (br. m, 2H); 1.72-1.41 (br. m, 8H); 1.40-1.20 (br. m, 30H); 0.88 (m, 6H).

Heptadecan-9-yl 8-((2-hydroxyethyl)(tetradecyl) amino)octanoate (Method C)

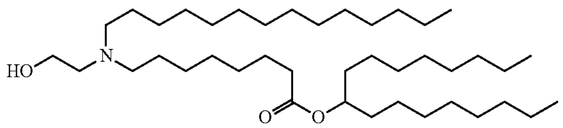 [SMILES: CCCCCCCCCCCCCCN(CCO)CCCCCCCC(=O)OC(CCCCCCCC)CCCCCCCC]

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at rt for 30 min. After this time 1-iodooctane (5 g, 20.8 mmol) was added and the reaction mixture was heated at 45° C. for 6 h. The reaction was quenched with 1N HCl (10 mL). The organic layer was dried over $MgSO_4$, filtered and evaporated in vacuo. The residue was purified by silica gel chromatography (0-20% ethyl acetate in hexanes) to yield 2-octyldecanoic acid (1.9 g, 6.6 mmol, 38%). $^1$H NMR (300 MHz, $CDCl_3$) δ: ppm 2.38 (br. m, 1H); 1.74-1.03 (br. m, 28H); 0.91 (m, 6H).

Intermediate B: 7-Bromoheptyl 2-octyldecanoate

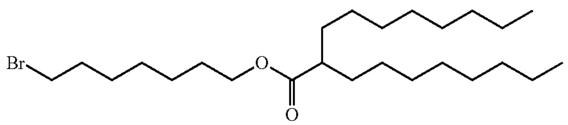 [SMILES: CCCCCCCCC(CCCCCCCC)C(=O)OCCCCCCCBr]

7-bromoheptyl 2-octyldecanoate was synthesized using Method A from 2-octyldecanoic acid and 7-bromoheptan-1-ol. $^{1}H$ NMR (300 MHz, $CDCl_3$) δ: ppm 4.09 (br. m, 2H); 3.43 (br. m, 2H); 2.48-2.25 (br. m, 1H); 1.89 (br. m, 2H); 1.74-1.16 (br. m, 36H); 0.90 (m, 6H).

Intermediate C: (2-Hexylcyclopropyl)methanol

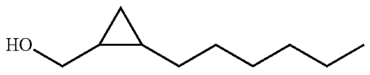

A solution of diethyl zinc (20 mL, 20 mmol, 1 M in hexanes), in dichloromethane (20 mL) was allowed to cool to −40° C. for 5 min. Then a solution of diiodomethane (3.22 mL, 40 mmol) in dichloromethane (10 mL) was added dropwise. After the reaction was allowed to stir for 1 h at −40° C., a solution of trichloro-acetic acid (327 mg, 2 mmol) and DME (1 mL, 9.6 mmol) in dichloromethane (10 mL) was added. The reaction was allowed to warm to −15° C. and stir at this temperature for 1 h. A solution of (Z)-non-2-en-1-ol (1.42 g, 10 mmol) in dichloromethane (10 mL) was then added to the −15° C. solution. The reaction was then slowly allowed to warm to rt and stir for 18 h. After this time saturated $NH_4Cl$ (200 mL) was added and the reaction was extracted with dichloromethane (3×), washed with brine, and dried over $Na_2SO_4$. The organic layer was filtered, evaporated in vacuo and the residue was purified by silica gel chromatography (0-50% ethyl acetate in hexanes) to yield (2-hexylcyclopropyl)methanol (1.43 g, 9.2 mmol, 92%). $^{1}H$ NMR (300 MHz, $CDCl_3$) S: ppm 3.64 (m, 2H); 1.57-1.02 (m, 12H); 0.99-0.80 (m, 4H); 0.72 (m, 1H), 0.00 (m, 1H).

C. Compound 18: Heptadecan-9-yl 8-((2-hydroxyethyl)(8-(nonyloxy)-8-oxooctyl)amino) octanoate

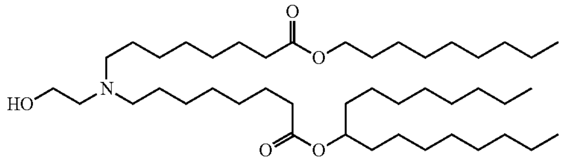 [SMILES: CCCCCCCCCOC(=O)CCCCCCCN(CCO)CCCCCCCC(=O)OC(CCCCCCCC)CCCCCCCC]

Chemical Formula: $C_{44}H_{87}NO_5$

Molecular Weight: 710.18

Compound 18 was synthesized according to the general procedure and Representative Procedure 1 described above.

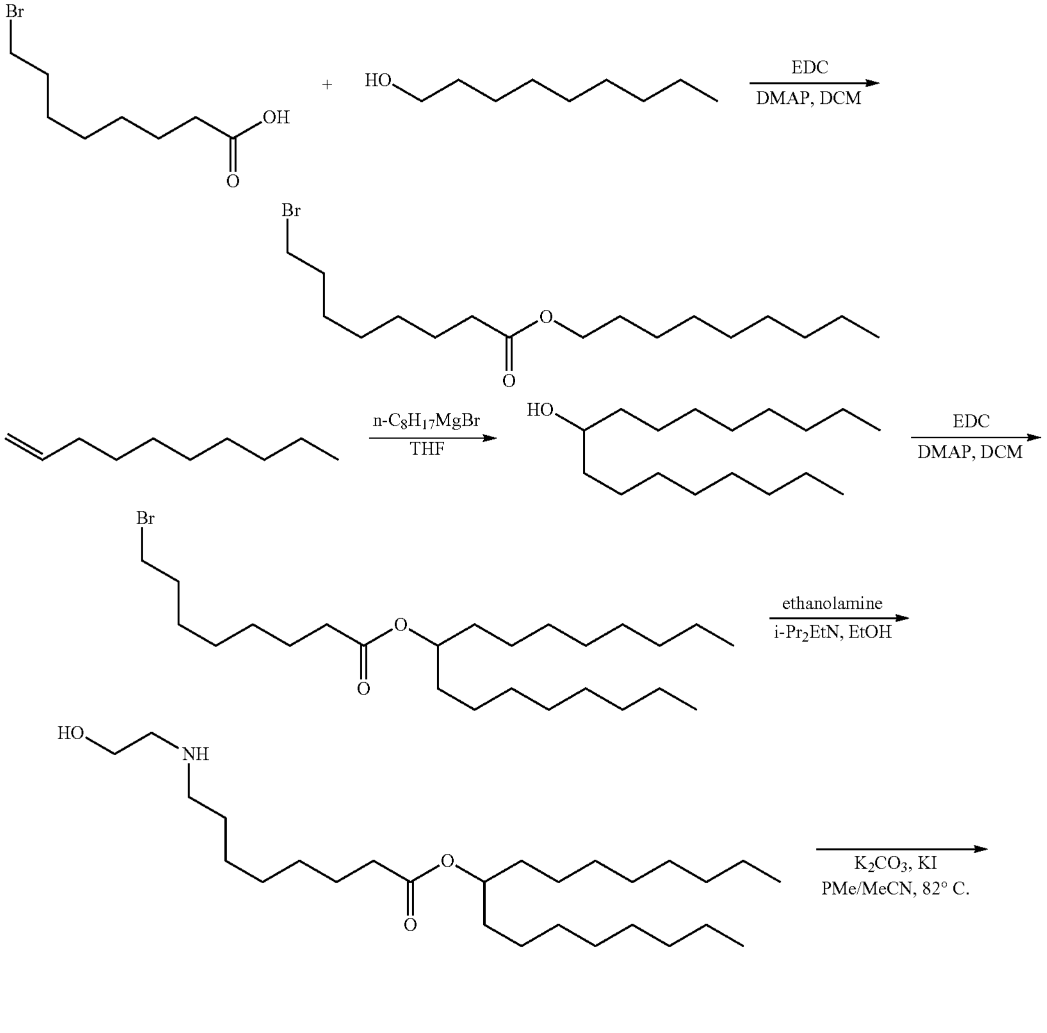

-continued

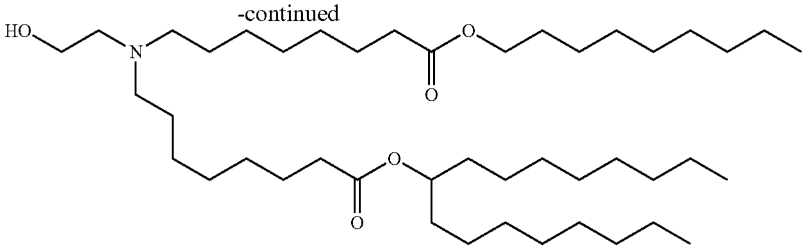

UPLC/ELSD: RT=3.59 min. MS (ES): m/z ($MH^+$) 710.89 for $C_{44}H_{87}NO_5$. $^1H$ NMR (300 MHz, $CDCl_3$) δ: ppm 4.86 (m, 1H); 4.05 (t, 2H); 3.53 (br. m, 2H); 2.83-2.36 (br. m, 5H); 2.29 (m, 4H); 0.96-1.71 (m, 64H); 0.88 (m, 9H).

TABLE 6

Characteristics of nanoparticle compositions including compounds according to Formula (I), (IA), (II), (IIa), (IIb), (IIc), (IId) or (IIe)

| Compound | Formulation | Size (nm) | PDI | EE (%) |
|---|---|---|---|---|
| 6 | Compound 6:DSPC:Chol:PEG-DMG (50:10:38.5:1.5) | 70.5 | 0.082 | 97.84 |
| 18 | Compound 18:DSPC:Chol:PEG-DMG (50:10:38.5:1.5) | 78.6 | 0.095 | 97.34 |
| MC3 | MC3:DSPC:Chol:PEG-DMG (50:10:38.5:1.5) | 73.7 | 0.114 | 97.22 |

TABLE 7

Evaluation of nanoparticle compositions including compounds according to Formula (I), (IA), (II), (IIa), (IIb), (IIc), (IId) or (IIe).

| | hEPO expression (pg/ml) | | | Cytokine expression (pg/ml) | |
|---|---|---|---|---|---|
| | | | | IP-10 | IL-6 |
| Compound | 3 h | 6 h | 24 h | (6 h) | (6 h) |
| 6 | 2.31E+06 | 3.17E+06 | 1.11E+06 | 116.66 | 10.15 |
| 18 | 3.00E+06 | 3.38E+06 | 1.80E+06 | 299.93 | 10.16 |
| MC3 | 1.57E+06 | 1.83E+06 | 0.81E+06 | 117.94 | 19.85 |

TABLE 8

Evaluation of nanoparticle compositions including compounds according to Formula (I), (IA), (II), (IIa), (IIb), (IIc), (IId) or (IIe).

| Compound | Fold increase in hEPO concentration relative to MC3 |
|---|---|
| 18 | 8.6 |
| 25 | 7.1 |
| 30 | 9.2 |
| 108 | 3.7 |
| 109 | 5.3 |
| 110 | 1.2 |
| 111 | 10.6 |

TABLE 8-continued

Evaluation of nanoparticle compositions including compounds according to Formula (I), (IA), (II), (IIa), (IIb), (IIc), (IId) or (IIe).

| Compound | Fold increase in hEPO concentration relative to MC3 |
|---|---|
| 112 | 1.6 |
| 60 | 11.2 |
| 122 | 10.7 |
| MC3 | 1 |

TABLE 9

Comparison of nanoparticle compositions including compounds according to Formula (I), (IA), (II), (IIa), (IIb), (IIc), (IId) or (IIe).

| | Compound 6 | Compound 18 | MC3 |
|---|---|---|---|
| Average hEPO concentration (pg/ml, 6 h) | $3.17 \times 10^6$ | $3.38 \times 10^6$ | $1.83 \times 10^6$ |
| Fold increase in hEPO concentration relative to MC3 | 1.73 | 1.85 | 1 |
| Average total flux (6 h, ffluc) | $7.60 \times 10^9$ | $2.13 \times 10^{10}$ | $6.59 \times 10^9$ |
| Fold increase in average total flux relative to MC3 | 1.15 | 3.23 | 1 |

D. Compound 136: Nonyl 8-((2-hydroxyethyl)((9Z, 12Z)-octadeca-9,12-dien-1-yl)amino)octanoate Representative Procedure 2:

Nonyl 8-bromooctanoate (Method A)

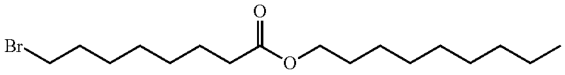 [SMILES: CCCCCCCCCOC(=O)CCCCCCCBr]

To a solution of 8-bromooctanoic acid (5 g, 22 mmol) and nonan-1-ol (6.46 g, 45 mmol) in dichloromethane (100 mL) were added N-(3-Dimethylaminopropyl)-N'-ethylcarbodiimide hydrochloride (4.3 g, 22 mmol) and DMAP (547 mg, 4.5 mmol). The reaction was allowed to stir at rt for 18 h. The reaction was diluted with dichloromethane and washed with saturated sodium bicarbonate. The organic layer was separated and washed with brine, dried over $MgSO_4$. The organic layer was filtered and evaporated under vacuum. The residue was purified by silica gel chromatography (0-10% ethyl acetate in hexanes) to obtain nonyl 8-bromooctanoate (6.1 g, 17 mmol, 77%).

$^1H$ NMR (300 MHz, $CDCl_3$) δ: ppm 4.06 (t, 2H); 3.40 (t, 2H); 2.29 (t, 2H); 1.85 (m, 2H); 1.72-0.97 (m, 22H); 0.88 (m, 3H).

Nonyl 8-((2-hydroxyethyl)amino)octanoate

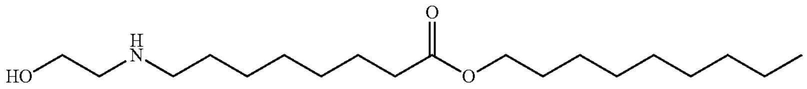 [SMILES: CCCCCCCCCOC(=O)CCCCCCCNCCO]

A solution of nonyl 8-bromooctanoate (1.2 g, 3.4 mmol) and 2-aminoethan-1-ol (5 mL, 83 mmol) in ethanol (2 mL) was allowed to stir at 62° C. for 18 h. The reaction mixture was concentrated in vacuum and the residue was extracted with ethyl acetate and water. The organic layer was separated and washed with water, brine and dried over $Na_2SO_4$. The organic layer was filtered and evaporated in vacuo. The residue was purified by silica gel chromatography (0-100% (mixture of 1% $NH_4OH$, 20% MeOH in dichloromethane) in dichloromethane) to obtain nonyl 8-((2-hydroxyethyl) amino)octanoate (295 mg, 0.9 mmol, 26%).

UPLC/ELSD: RT=1.29 min. MS (ES): m/z ($MH^+$) 330.42 for $C_{19}H_{39}NO_3$ $^1H$ NMR (300 MHz, $CDCl_3$) δ: ppm 4.07 (t, 2H); 3.65 (t, 2H); 2.78 (t, 2H); 2.63 (t, 2H); 2.32-2.19 (m, 4H); 1.73-1.20 (m, 24H); 0.89 (m, 3H)

Nonyl 8-((2-hydroxyethyl)((9Z,12Z)-octadeca-9,12-dien-1-yl)amino)octanoate

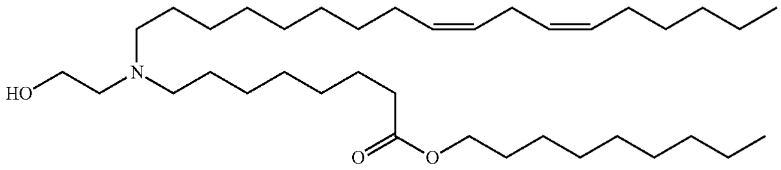 [SMILES: CCCCC/C=C\C/C=C\CCCCCCCCN(CCO)CCCCCCCC(=O)OCCCCCCCCC]

Chemical Formula: $C_{37}H_{71}NO_3$

Molecular Weight: 577.98

A solution of nonyl 8-((2-hydroxyethyl)amino)octanoate (150 mg, 0.46 mmol), (6Z,9Z)-18-bromooctadeca-6,9-diene (165 mg, 0.5 mmol) and N,N-diisopropylethylamine (65 mg, 0.5 mmol) in ethanol (2 mL) was allowed to stir at reflux for 48 h. The reaction was allowed to cool to rt and solvents were evaporated under vacuum. The residue was purified by silica gel chromatography (0-10% MeOH in dichloromethane) to obtain nonyl 8-((2-hydroxyethyl)((9Z,12Z)-octadeca-9,12-dien-1-yl)amino)octanoate (81 mg, 0.14 mmol, 30%) as a HBr salt.

UPLC/ELSD: RT=3.24 min. MS (ES): m/z ($MH^+$) 578.64 for $C_{37}H_{71}NO_3$ $^1H$ NMR (300 MHz, $CDCl_3$) δ: ppm 10.71 (br., 1H); 5.36 (br. m, 4H); 4.04 (m, 4H); 3.22-2.96 (br. m, 5H); 2.77 (m, 2H); 2.29 (m, 2H); 2.04 (br. m, 4H); 1.86 (br. m, 4H); 1.66-1.17 (br. m, 40H); 0.89 (m, 6H)

E. Compound 138: Dinonyl 8,8'-((2-hydroxyethyl)azanediyl)dioctanoate

Representative Procedure 3:

Dinonyl 8,8'-((2-hydroxyethyl)azanediyl)dioctanoate

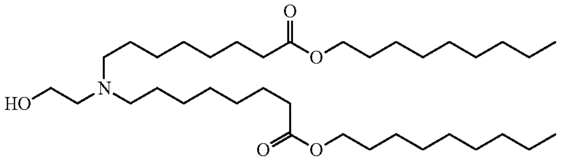 [SMILES: CCCCCCCCCOC(=O)CCCCCCCN(CCO)CCCCCCCC(=O)OCCCCCCCCC]

Chemical Formula: $C_{36}H_{71}NO_5$
Molecular Weight: 597.97

A solution of nonyl 8-bromooctanoate (200 mg, 0.6 mmol) and 2-aminoethan-1-ol (16 mg, 0.3 mmol) and N,N-diisopropylethylamine (74 mg, 0.6 mmol) in THF/$CH_3CN$ (1:1) (3 mL) was allowed to stir at 63° C. for 72 h. The reaction was cooled to rt and solvents were evaporated under vacuum. The residue was extracted with ethyl acetate and saturated sodium bicarbonate. The organic layer was separated, dried over $Na_2SO_4$ and evaporated under vacuum. The residue was purified by silica gel chromatography (0-10% MeOH in dichloromethane) to obtain dinonyl 8,8'-((2-hydroxyethyl)azanediyl)dioctanoate (80 mg, 0.13 mmol, 43%).

UPLC/ELSD: RT=3.09 min. MS (ES): m/z ($MH^+$) 598.85 for $C_{36}H_{71}NO_5$ $^1H$ NMR (300 MHz, $CDCl_3$) δ: ppm 4.05 (m, 4H); 3.57 (br. m, 2H); 2.71-2.38 (br. m, 6H); 2.29 (m, 4H), 1.71-1.01 (br. m, 49H), 0.88 (m, 6H).

All other compounds of Formula (I) of this disclosure can be obtained by a method analogous to Representative Procedures 1-3 as described above.

Example 22

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining a lipid according to Formula (I), a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 m sterile filters (Sarstedt, Nimbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotideused in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the TABLE 5 below.

TABLE 5

| Exemplary Formulations of Nanoparticles | |
|---|---|
| Composition (mol %) | Components |
| 40:20:38.5:1.5 | Compound:Phospholipid:Chol:PEG-DMG |
| 45:15:38.5:1.5 | Compound:Phospholipid:Chol:PEG-DMG |
| 50:10:38.5:1.5 | Compound:Phospholipid:Chol:PEG-DMG |
| 55:5:38.5:1.5 | Compound:Phospholipid:Chol:PEG-DMG |
| 60:5:33.5:1.5 | Compound:Phospholipid:Chol:PEG-DMG |
| 45:20:33.5:1.5 | Compound:Phospholipid:Chol:PEG-DMG |
| 50:20:28.5:1.5 | Compound:Phospholipid:Chol:PEG-DMG |
| 55:20:23.5:1.5 | Compound:Phospholipid:Chol:PEG-DMG |
| 60:20:18.5:1.5 | Compound:Phospholipid:Chol:PEG-DMG |
| 40:15:43.5:1.5 | Compound:Phospholipid:Chol:PEG-DMG |
| 50:15:33.5:1.5 | Compound:Phospholipid:Chol:PEG-DMG |
| 55:15:28.5:1.5 | Compound:Phospholipid:Chol:PEG-DMG |
| 60:15:23.5:1.5 | Compound:Phospholipid:Chol:PEG-DMG |
| 40:10:48.5:1.5 | Compound:Phospholipid:Chol:PEG-DMG |
| 45:10:43.5:1.5 | Compound:Phospholipid:Chol:PEG-DMG |
| 55:10:33.5:1.5 | Compound:Phospholipid:Chol:PEG-DMG |
| 60:10:28.5:1.5 | Compound:Phospholipid:Chol:PEG-DMG |
| 40:5:53.5:1.5 | Compound:Phospholipid:Chol:PEG-DMG |
| 45:5:48.5:1.5 | Compound:Phospholipid:Chol:PEG-DMG |
| 50:5:43.5:1.5 | Compound:Phospholipid:Chol:PEG-DMG |
| 40:20:40:0 | Compound:Phospholipid:Chol:PEG-DMG |
| 45:20:35:0 | Compound:Phospholipid:Chol:PEG-DMG |
| 50:20:30:0 | Compound:Phospholipid:Chol:PEG-DMG |
| 55:20:25:0 | Compound:Phospholipid:Chol:PEG-DMG |
| 60:20:20:0 | Compound:Phospholipid:Chol:PEG-DMG |
| 40:15:45:0 | Compound:Phospholipid:Chol:PEG-DMG |
| 45:15:40:0 | Compound:Phospholipid:Chol:PEG-DMG |
| 50:15:35:0 | Compound:Phospholipid:Chol:PEG-DMG |
| 55:15:30:0 | Compound:Phospholipid:Chol:PEG-DMG |
| 60:15:25:0 | Compound:Phospholipid:Chol:PEG-DMG |
| 40:10:50:0 | Compound:Phospholipid:Chol:PEG-DMG |
| 45:10:45:0 | Compound:Phospholipid:Chol:PEG-DMG |
| 50:10:40:0 | Compound:Phospholipid:Chol:PEG-DMG |
| 55:10:35:0 | Compound:Phospholipid:Chol:PEG-DMG |
| 60:10:30:0 | Compound:Phospholipid:Chol:PEG-DMG |

Example 23

Augmentation of Lipoprotein Lipase (LPL) for the Treatment of Severe Hypertriglyceridemia (HTG)

Lipoprotein lipase (LPL) is the pivotal enzyme responsible for the hydrolysis of circulating triglycerides. It is anchored to the inner walls of blood vessels, where it breaks down circulating triglycerides into non-esterified fatty acids and glycerol. Primary hypertriglyceridemia (HTG) occurs when there are defects in LPL or genes relating to LPL or lipoprotein clearance/uptake, such as apoCII, apoCIII, apoAV, GPIHBP1, and LMF1, among others. Secondary HTG is associated with obesity, metabolic syndrome, diabetes, alcohol abuse, renal disease, and certain medications, including anti-psychotics and anti-retrovirals.

Severe HTG, defined as fasting triglyceride levels above 500 mg/dL, is common, affecting 1,7% of the US population, approximately 3 million individuals. The prevalence of severe HTG (triglycerides greater than 1,000 mg/dL) is likely higher in the US than in Europe, with an estimated prevalence of 1:250 (Ford et al., USA NHANES 1999-2004) to 1:2,654 (Valdivielso et al., 2009, Spain ICARIA). At levels of triglycerides greater than 2,000 mg/dL, the prevalence was found to be 1:1,893 (Christian et al, 2011, USA NHANES).

At triglyceride levels above 1,000 mg/dL, acute pancreatitis (AP) may result. The incidence of acute pancreatitis ranges from 4.9-73.4/10,000 worldwide, and its hospitalization rate is rising. It is estimated that HTG accounts for up to 10% of acute pancreatitis attacks. Epidemiology studies have shown that lower circulating triglyceride levels are associated with a reduced incidence of HTG-AP. Furthermore, HTG is an independent risk factor for cardiovascular disease. The standard-of-care for HTG includes dietary restrictions, exercise, fibrates, omega-3, and niacin.

Existing HTG treatments focus on reducing the risk of coronary heart disease, as the two have been shown to be associated with one another. Changes in triglyceride concentrations have been shown to change the risk of coronary heart disease, but a causal link has not been established. For mild to moderate HTG, statins are usually recommended. For those with triglycerides above 1000 mg/dL, other triglyceride-lowering treatments are administered. Fibrates have shown a 20-50% reduction in triglycerides, with the greatest benefit being realized in more severely affected patients. However, in cases of non-severe HTG, treatment elevates the risk of pancreatitis. Nicotinic acid can decrease TG by 15-25%, but may worsen glucose tolerance in diabetic patients and may be harmful when combined with statins. Omega-3 (fish oil) yields a 50% reduction in TG, but the first generation preparations may raise LDL. GLYBERA®, which was approved in Europe after multiple attempts and is not currently approved in the US, is only focused on LPLD patients, and not HTG broadly. It has shown limited (if any) short term efficacy and no longer term efficacy. In contrast, the present disclosure shows a 50% improvement when combined with standard-of-care recommendations (diet, exercise, etc.) compared to omega-3/fibrate treatment.

Additionally, it has been suggested that there is a link between HTG and cerebrovascular disease. These correlations may result in an asymmetric upside to the LPL treatment.

A. Intravenous Administration: Rat Study

Zucker fa/fa rats were administered a single intravenous (IV) dose of 0.5 mg/kg 5-methoxy uridine (mo5U)-modified WT-hLPL modRNA/Compound 18 formulation or eGFP-(5-methoxy uridine (mo5U)-modified)-miR-126 and the concentration of hLPL was measured by ELISA (as an indication of pharmacokinetics) and the percent change in triglyceride levels from baseline was measured (as an indication of pharmacodynamics). The following was noted: significant hLPL expression as early as one hour after administration, which was sustained after LNP administration, a signifincant reduction in plasma triglycerides levels (over 65%), and that plasma triglycerides rebound 5 days after injection, suggesting that a weekly dosing frequency may be needed (FIGS. 4 and 7). Further, significant hLPL expression was seen after six hours, and then sustained at 24 hours after LNP administration (FIG. 7). The same protocol was used to examine hLPL expression in Zycker fa/fa rats administered a single IV dose of 0.5 mg/kg hLPL-WT-miR-126 or hLPL-WT-miR-142 and −126. Both constructs were shown to result in significant hLPL expression after six hours. Of the two, the hLPL-WT-miR-126 was shown to result in higher hLPL expression (FIG. 8).

Zucker fa/fa obese diabetic rats with high levels of triglycerides underwent a three-week repeat IV dose of 5-methoxy uridine (mo5U)-modified hLPL mRNAs/Compound 18 formulation (2 doses per week). The formulations tested were as follows: NT-FIX-N1-methyl pseudouridine (m1Ψ)-modified (0.5 mg/kg), hLPL-WT-5-methoxy uridine (mo5U)-modified (0.05, 0.2, and 0.5 mg/kg), and hLPL-S447X-5-methoxy uridine (mo5U)-modified (0.2 mg/kg). The concentration of hLPL was measured by ELISA (as an indication of pharmacokinetics; FIG. 5) and the percent change in triglyceride levels from baseline was measured (as an indication of pharmacodynamics; FIG. 6). The results showed dose-dependent LPL mRNA levels in the liver and spleen and significant hLPL expression six hours after the sixth LNP administration.

B. Dose Range Finding Studies

Dose range finding (DRF) studies using surrogate Compound 18 are in progress to further examine the Compound 18 programs. One month of a DRF study, consisting of one dose per week (5 total doses) in adult rat was performed in order to measure hematology, clinical chemistry, and full pathology. No adverse events were reported and the clinical chemistry was normal. Additionally, one month of GLP dose studies, consisting of five doses (one per week) via IV infusion will be administered to rats in order to examine safety pharmacology measures, including central nervous system (rats) and cardiovascular system (monkeys), such as heart rate, blood pressure, and EKG readings. Furthermore, gene toxicity studies were be undertaken, in vitro, using a 4 strain Ames test, and in vitro micronucleous hPBMCs. The Ames data suggests Compound 18 does not have mutagenic potential. An in vivo mouse micronucleus assay will also be performed to further investigate the Compound 18/5-methoxy uridine (mo5U) modification chemistry.

Example 24

In Vivo Screening of Ob/Ob and CD-1 Mice Using 5-Methoxy Uridine (mo5U)-Modified LDL mRNA Experiment In order to examine the effects of different LPL variants in mouse models, the following experiments were performed. For the experiments, 8-10 week-old ob/ob (obese diabetic model) or CD-1 (wild-type) mice were used. Two days prior to the test injection (day −2), plasma was collected from the mice ("pre-bleed"). The injection (day 0) consisted of a single IV injection at a concentration of 0.5 mg/kg. The formulations tested were: $LPL^{S447X}$ mRNA/MC3 (n=3/mRNA), LPL-WT mRNA/MC3 (n=3/mRNA), $LPL^{R324A}$ mRNA/MC3 (n=3/mRNA), and $LPL^{R324A/S447X}$ mRNA/MC3 (n=3/mRNA). All were modified with 5-methoxy uridine (mo5U). Plasma was collected about four hours later ("pre-heparin"). Both the pre-heparin and the pre-bleed samples were assayed for triglyceride (TG) levels. After the pre-heparin sample was drawn, the subjects were administered 100 units/kg of heparin. Ten minutes later, plasma was collected ("post-heparin") and later analyzed for hLPL concentration.

Results

In a first experiment, a single IV dose of 0.5 mg/kg 5-methoxy uridine (mo5U)-modified $LPL^{S447X}$ mRNA/MC3 formulation in ob/ob mice showed a similar level of hLPL expression from variants 2, 4, 6, and 10, as compared to 5-methoxy uridine (mo5U)-modified LPL-WT-v10 at 4 hours after LNP administration. The same group showed hLPL activity that was less than or equal to N1-methyl pseudouridine (m1Ψ)-modified LPL-WT.

Next, a single IV dose of 0.5 mg/kg 5-methoxy uridine (mo5U)-modified LPL-WT mRNA/MC3 formulation in ob/ob mice showed significant hLPL expression from variants 11, 14, and 15, four hours after LNP administration. Note that hLPL expression from variant 11 was shown to correlate with its activity.

To confirm the results regarding variant 11 above, a single IV dose of 0.5 mg/kg 5-methoxy uridine (mo5U)-modified LPL-WT mRNA/MC3 formulation in CD-1 mice was analyzed. The results confirmed the significant hLPL expression and activity from variant 11 four hours after LNP administration. The percent change in triglycerides in CD-1 mice six hours after 0.5 mg/kg injections of either hLPL-WT-miR-126 or saline is shown in FIG. 16.

Then, 5-methoxy uridine (mo5U)-modified $LPL^{R324A}$ mRNA/MC3 formulations were tested. A single IV dose of 0.5 mg/kg 5-methoxy uridine (mo5U)-modified $LPL^{R324A}$ mRNA/MC3 formulation in CD-1 mice showed very low hLPL expression and activity four hours after LNP administration. Likewise, a single IV dose of 0.5 mg/kg 5-methoxy uridine (mo5U)-modified $LPL^{R324A/S447X}$ mRNA/MC3 formulation in CD-1 mice showed very low hLPL expression and generally decreased activity four hours after LNP administration.

Example 25

Intralipid Challenge Before hLPL-WT-miR-126 mRNA Injection in Sprague Dawley Rats Sprague-Dawley rats were surgically implanted with catheters (Taconic). Plasma samples were taken one day before administration and directly prior to administration of either hLPL-WT-miR-126 mRNA or eGFP-miR-126 mRNA. The rats were also subjected to an 8-10 hour fast prior to the injection. One hour following the injection, the rats were given a 20% Intralipid (10 μL/g) or chylomicron IV infusion via the jugular vein. Plasma TGs were analyzed at each time point (one day before injection, just before injection, 5 minutes, 15 minutes, 20 minutes, 30 minutes, 45 minutes, 1 hour, 2 hours, 3 hours, and ten minutes after a heparin injection following the 3 hour point). The results are shown in FIG. 9. The straight intralipid infusion resulted in persistently higher TG levels, as compared to the intralipid infusion 1 hour following the 0.5 mg/kg hLPL-WT-miR-126 mRNA injection.

Example 26 hLPL Bio-Distribution

CD-1 mice 12 weeks of age were given three 0.5 mg/kg IV injections of either saline (n=5), NT-FIX mRNA (control, n=5), or 5-methoxy uridine (mo5U)-modified LPL-WT mRNA. The injections were given 1.25 days apart, and six hours after each injection, samples were taken. One day before the injection and pre-heparin, samples were taken and analyzed for plasma triglycerides. After the heparin administration, the heart, liver, soleus muscle, and epididymal fat were analyzed using immunohistochemistry and Western blotting.

Levels of LPL were higher in the liver in the LPL group as compared to the other two groups, while they were less than or equivalent to levels of the other two groups in epididymal fat (FIG. 10). The results of the Western blot are given in FIG. 11.

Example 27

Pharmacokinetic/Pharmacodynamics Study in HTG Cynomolgus Macaque

The pharmacokinetic and pharmacodynamics of different LPL mRNA formulations were examined in Cynomolgus macaques. Relatively old (12-18 year-old) NHPs with diabetes and high levels of triglyceride were used. Four different formulations were tested (n=3 NHPs/formulation), including: N1-methyl pseudouridine (m1Ψ)-modified NT-FIX mRNA, 5-methoxy uridine (moSU)-modified hLPL- WT mRNA, 5-methoxy uridine (mo5U)-modified hLPL$^{S447X}$ mRNA (a gain-of-function mutation without the last two amino acids), and 5-methoxy uridine (mo5U)-modified eGFP mRNA. Each mRNA construct was formulated in Compound 18-containing lipid nanoparticles. The subjects were administered the selected formulation for one hour intravenously. Sera were collected six, 12, and 24 hours following the infusion, as well as 2 weeks, 1 week, 3 days, and one day prior to the infusion. Pre-bleeds were collected for lipid measurements, then heparin was administered (100U/kg) and then blood was collected for LPL measurements. A six-hour fast preceded each collection point. There was no discernable difference in the post-heparin serum concentration of LPL between the treated and control groups (FIG. 12). There was also no appreciable difference in triglycerides and cholesterol between the treated and control groups (FIGS. 13A-13C). A summary of TG levels, and cholesterol change is given in FIG. 15; as serum triglycerides decreased, HDL levels increased and LDL levels decreased.

Example 28

Other Studies

An hLPL-specific signature peptide was identified with LC-MS/MS (AQEHYPVSAGYT*K$^{C13-N15}$; SEQ ID NO: 144) and detected in hLPL-dosed NHP sera (FIG. 14). It was then calibrated for hLPL quantitation.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A pharmaceutical composition comprising a lipid nanoparticle, wherein the lipid nanoparticle comprises a compound having the Formula (IA)

(IA)

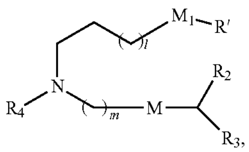

or a salt or stereoisomer thereof, wherein l is selected from 1, 2, 3, 4, and 5;

m is selected from 5, 6, 7, 8, and 9;

$M_1$ is a bond or M';

$R_4$ is unsubstituted $C_{1-3}$ alkyl, or —$(CH_2)_nQ$, wherein n is 1, 2, 3, 4, or 5 and Q is OH, —NHC(S)N$(R)_2$, or —NHC(O)N$(R)_2$;

M and M' are independently selected from —C(O)O—, —OC(O)—, —C(O)N(R')—, —OP(O)(OR')O—, an aryl group, and a heteroaryl group;

$R_2$ and $R_3$ are independently selected from the group consisting of H, $C_{1-14}$ alkyl, and $C_{2-14}$ alkenyl;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl; and each Y is independently a $C_{3-6}$ carbocycle;

wherein the lipid nanoparticle comprises an mRNA that comprises an open reading frame (ORF) encoding a lipoprotein lipase (LPL) polypeptide.

2. The pharmaceutical composition of claim 1, wherein m is 5, 7, or 9.

3. The pharmaceutical composition of claim 1, wherein the compound is of Formula (II)

(II)

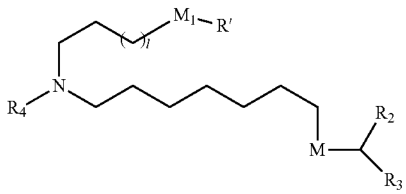

or a salt or stereoisomer thereof, wherein $R_4$ is unsubstituted $C_{1-3}$ alkyl, or —$(CH_2)_nQ$, in which n is 2, 3, or 4, and Q is OH, —NHC(S)N$(R)_2$, or —NHC(O)N$(R)_2$.

4. The pharmaceutical composition of claim 1, wherein $M_1$ is M'.

5. The pharmaceutical composition of claim 4, wherein M and M' are independently —C(O)O— or —OC(O)—.

6. The pharmaceutical composition of claim 1, wherein l is 1, 3, or 5.

7. A pharmaceutical composition comprising a lipid nanoparticle, wherein the lipid nanoparticle comprises a compound selected from the group consisting of:

(Compound 1)

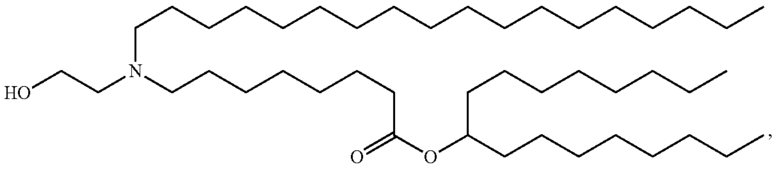

, (Compound 2)

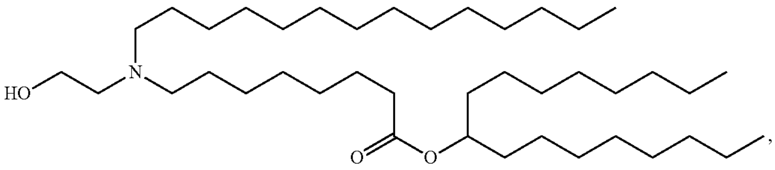

, (Compound 3)

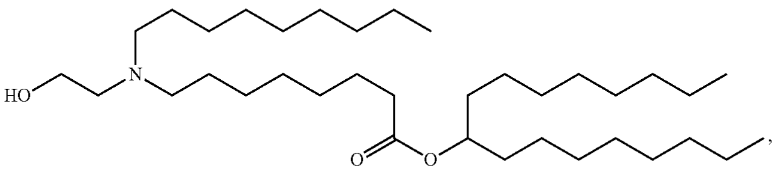

, (Compound 4)

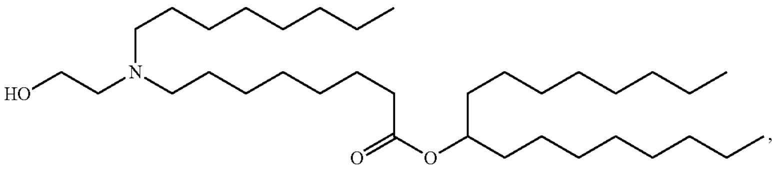

,

-continued
(Compound 5)
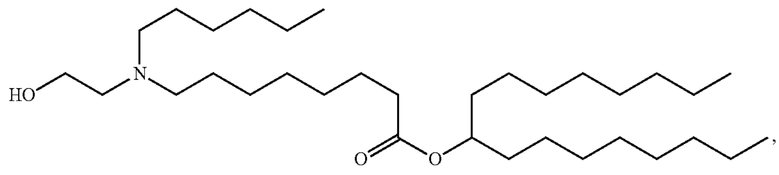
,
(Compound 6)
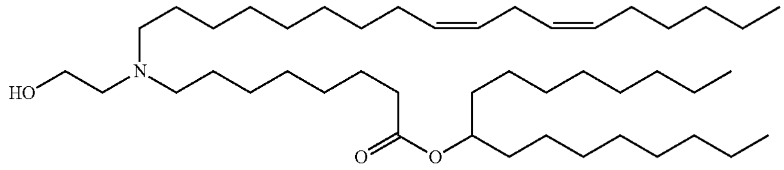
,
(Compound 7)
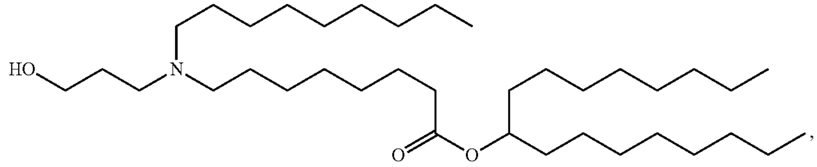
,
(Compound 18)
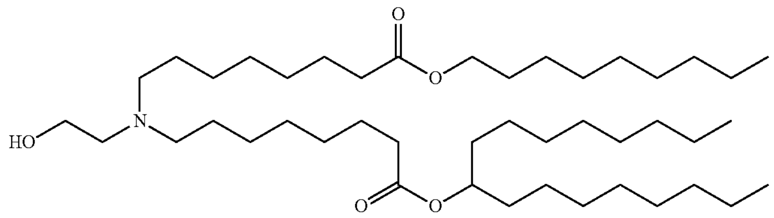
,
(Compound 19)
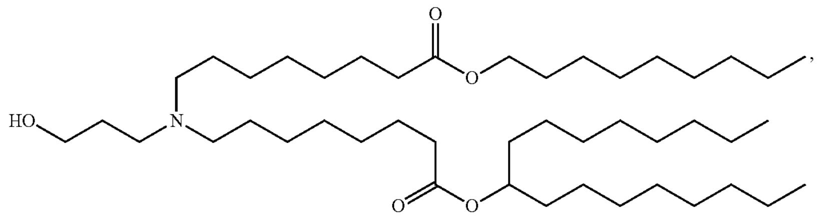
,
(Compound 20)
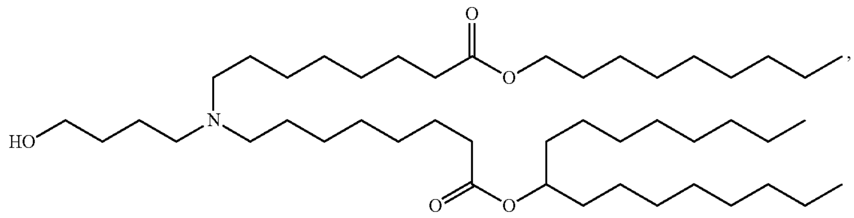
,
(Compound 23)
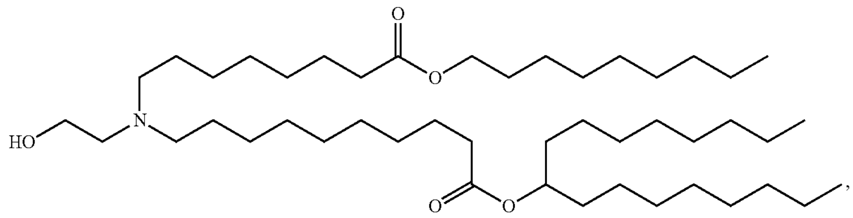
, -continued
(Compound 24)
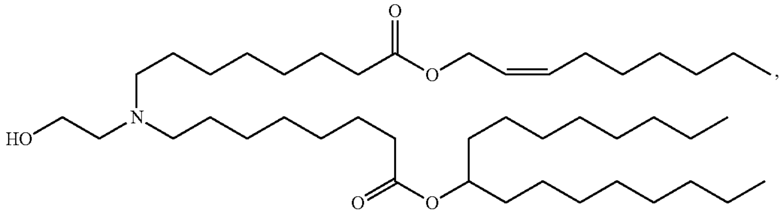
(Compound 25)
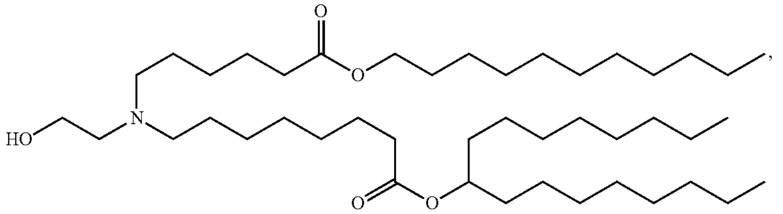
(Compound 26)
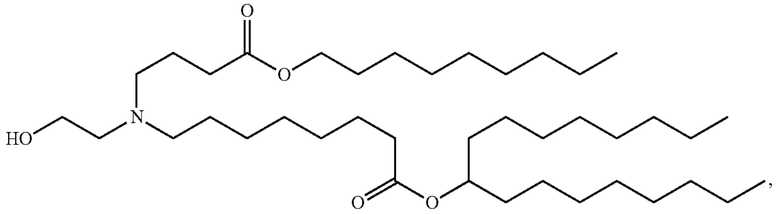
(Compound 27)
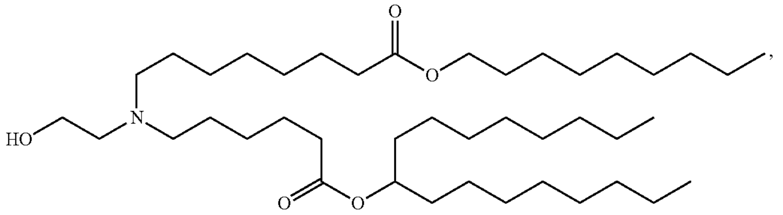
(Compound 28)
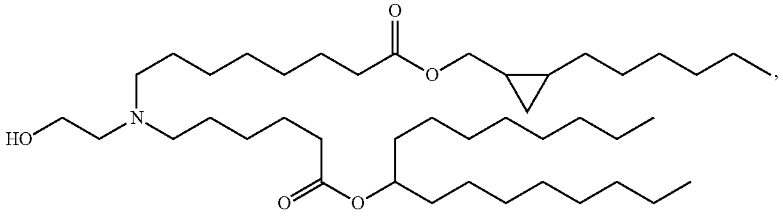
(Compound 29)
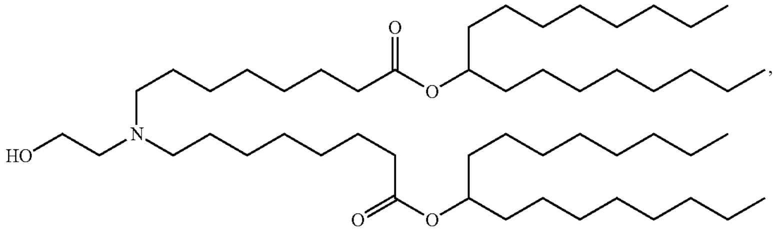
(Compound 30)
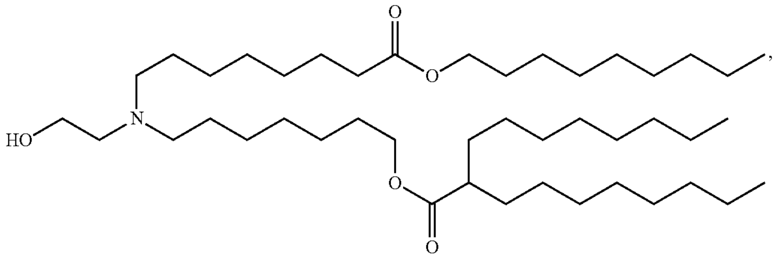

-continued
(Compound 31)
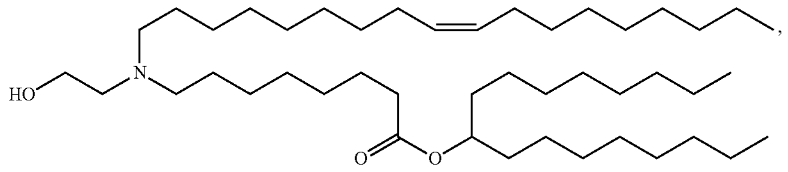
(Compound 32)
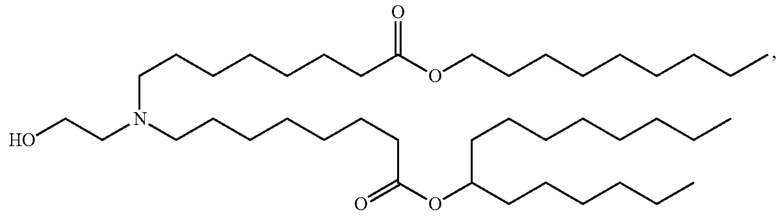
(Compound 33)
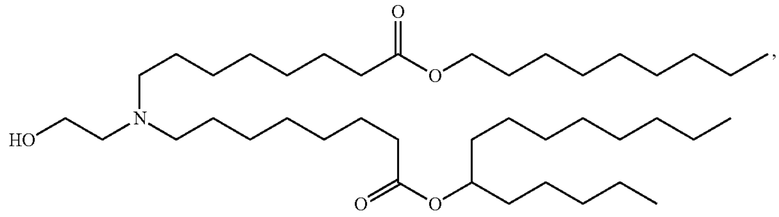
(Compound 34)
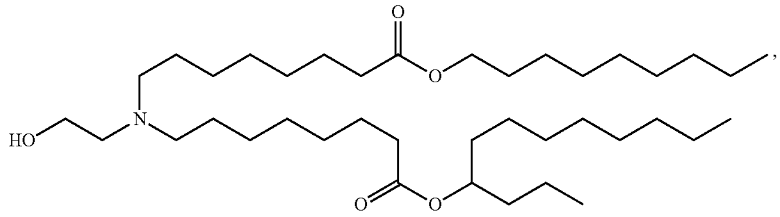
(Compound 35)
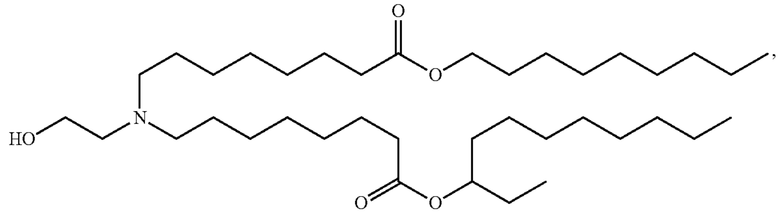
(Compound 36)
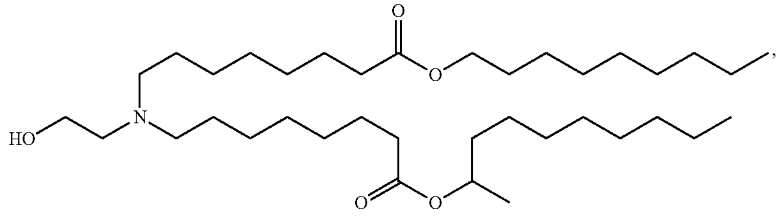
(Compound 39)
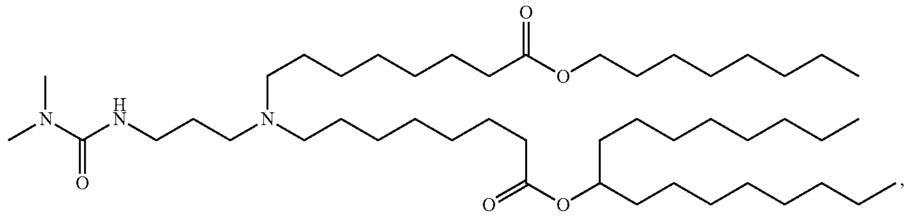

-continued
(Compound 40)
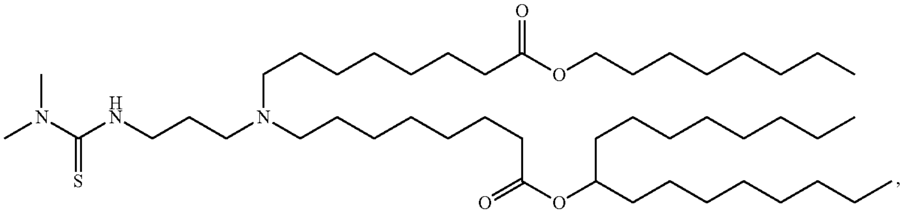
(Compound 41)
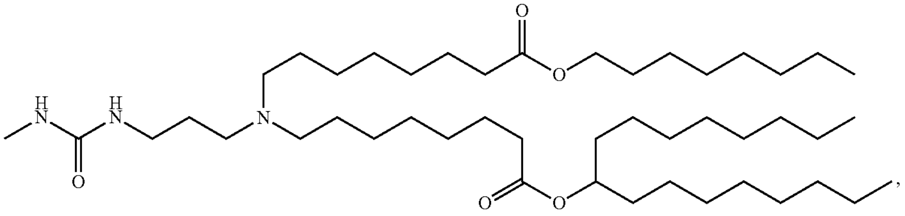
(Compound 42)
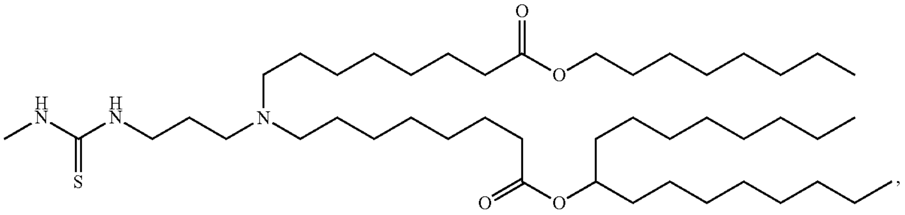
(Compound 47)
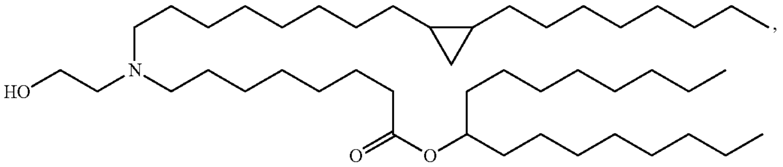
(Compound 48)
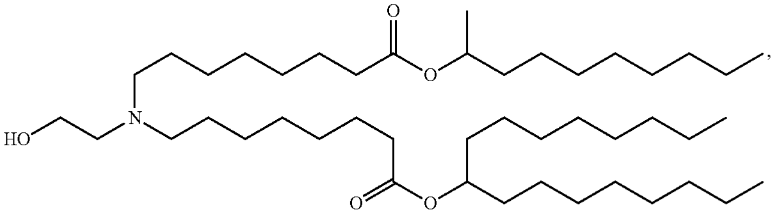
(Compound 49)
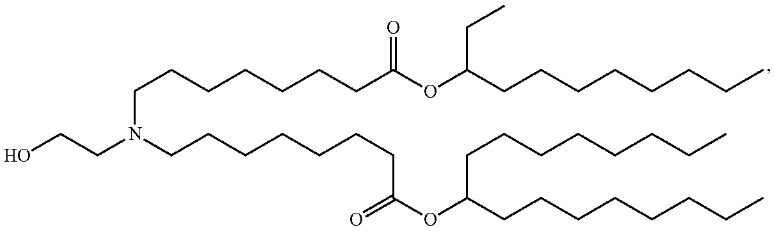
(Compound 50)
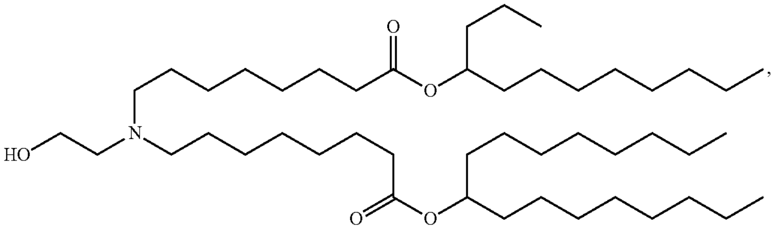

-continued
(Compound 51)
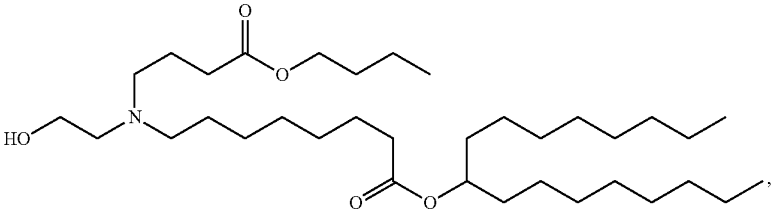
(Compound 52)
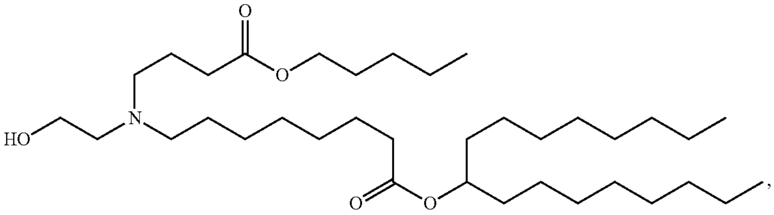
(Compound 53)
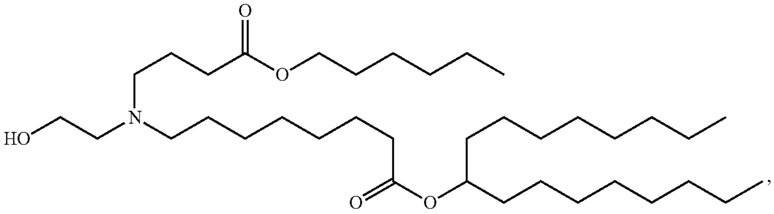
(Compound 54)
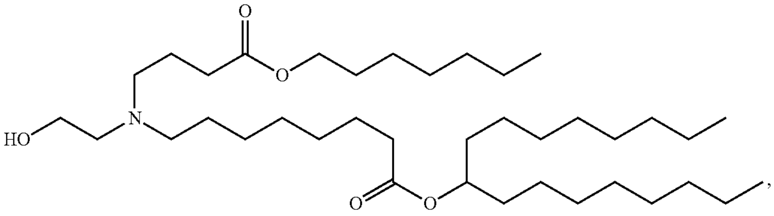
(Compound 55)
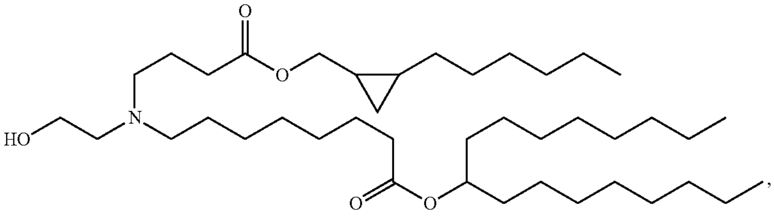
(Compound 56)
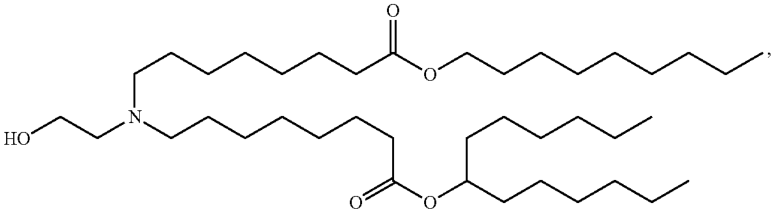
(Compound 57)
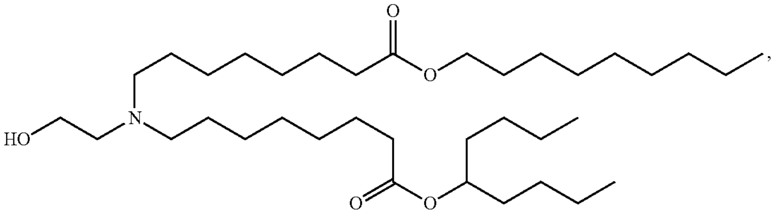

-continued
(Compound 58)
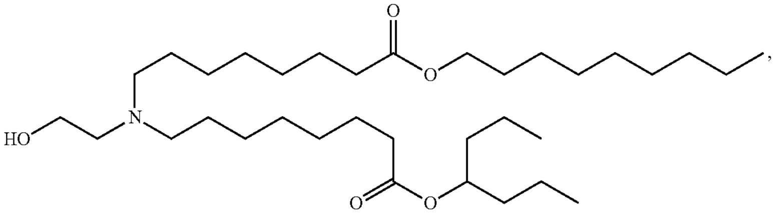
(Compound 59)
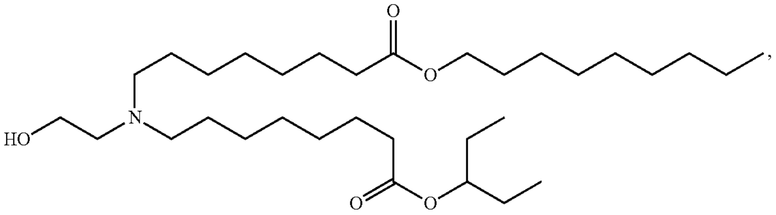
(Compound 60)
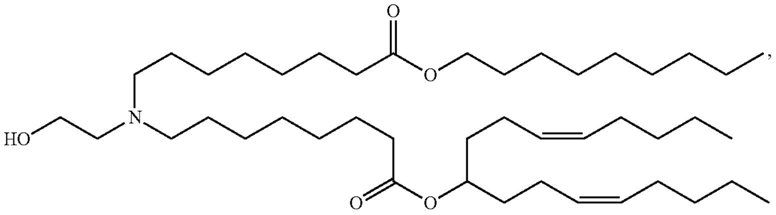
(Compound 61)
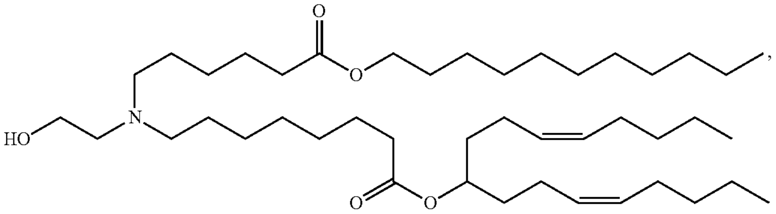
(Compound 63)
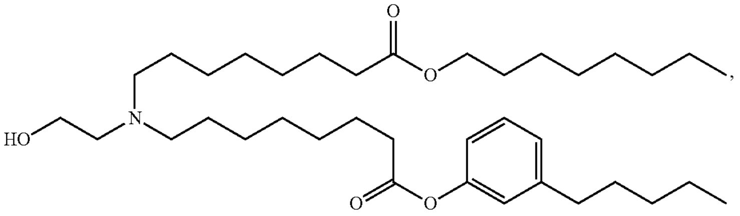
(Compound 64)
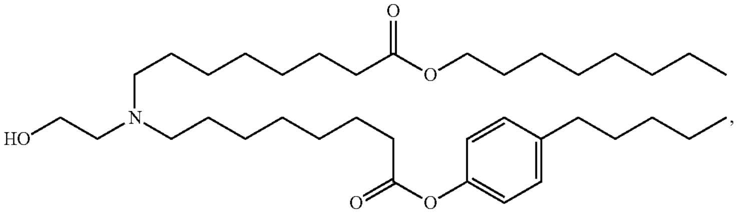
(Compound 66)
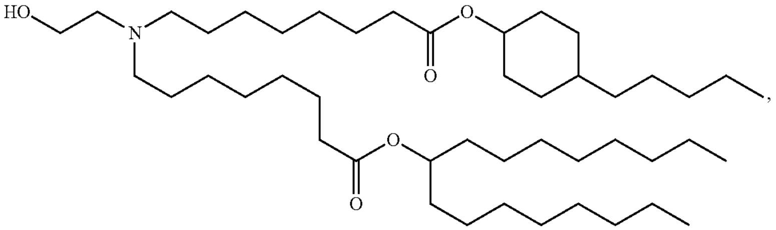

-continued
(Compound 67)
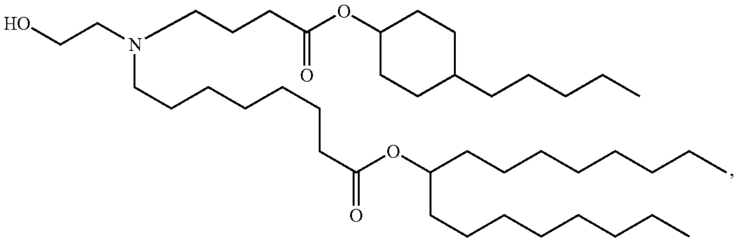
(Compound 68)
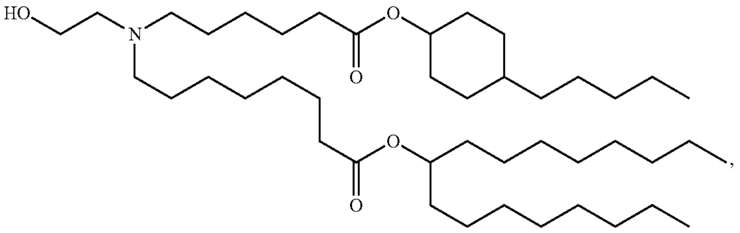
(Compound 70)
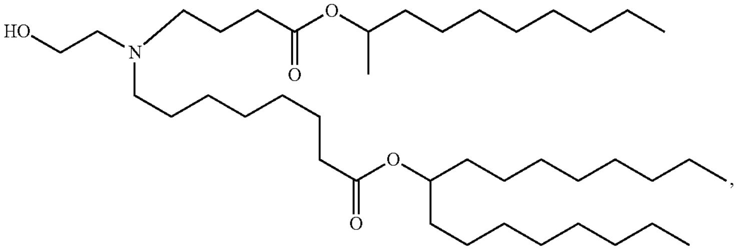
(Compound 71)
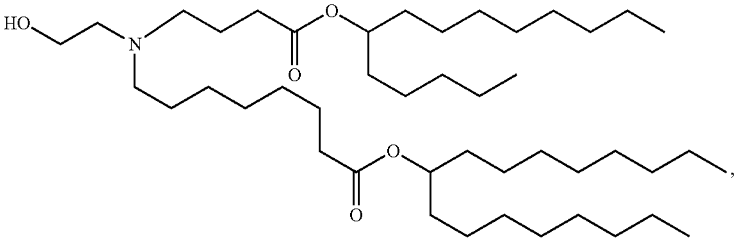
(Compound 72)
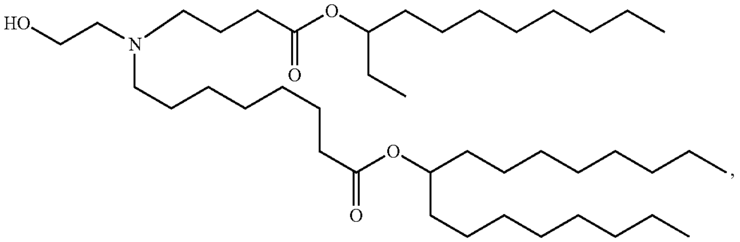
(Compound 73)
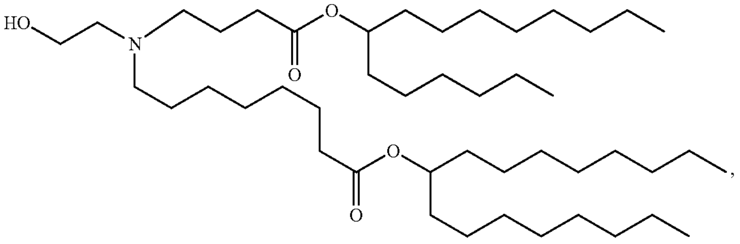

-continued
(Compound 74)
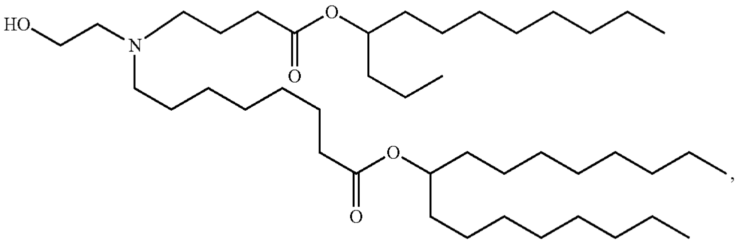
(Compound 75)
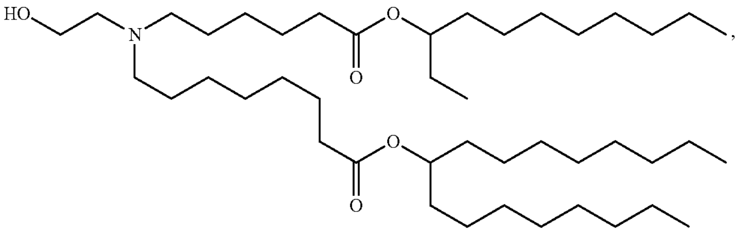
(Compound 76)
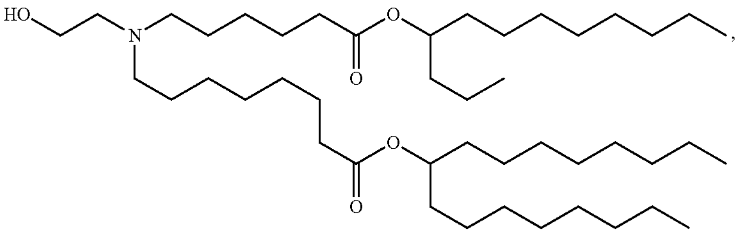
(Compound 77)
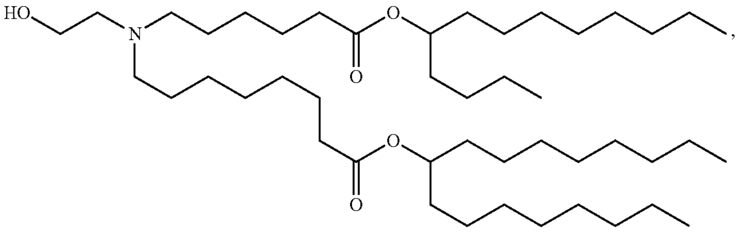
(Compound 78)
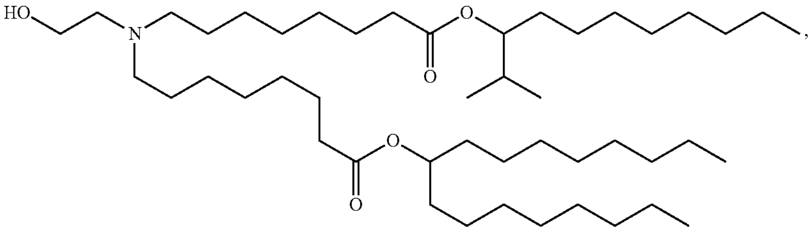
(Compound 79)
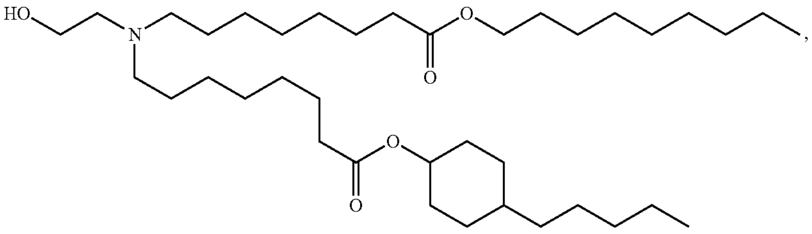

-continued
(Compound 82)
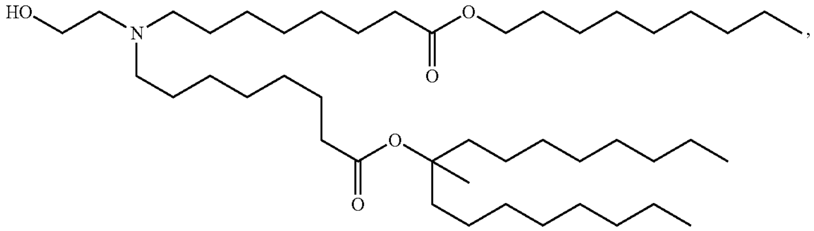
(Compound 85)
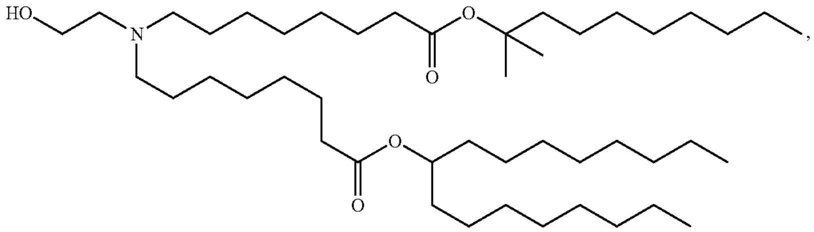
(Compound 86)
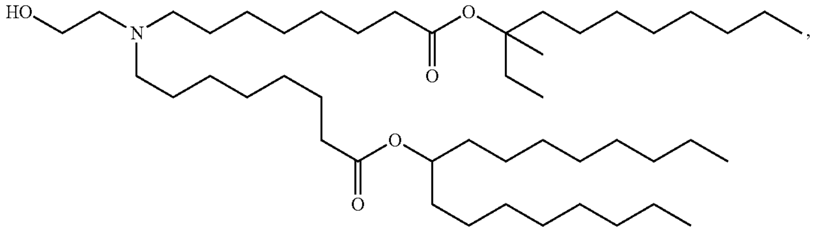
(Compound 87)
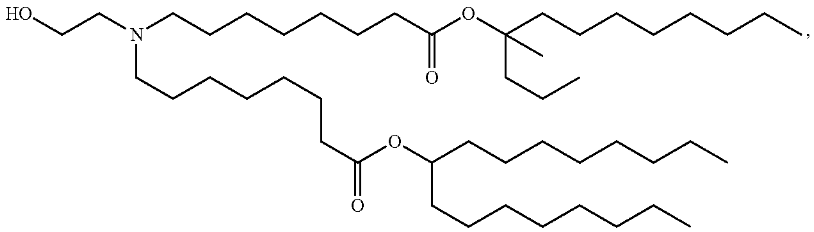
(Compound 88)
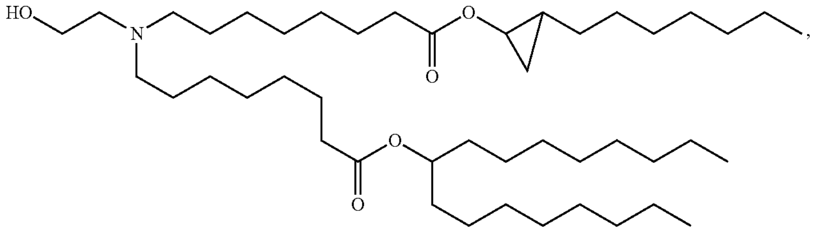
(Compound 89)
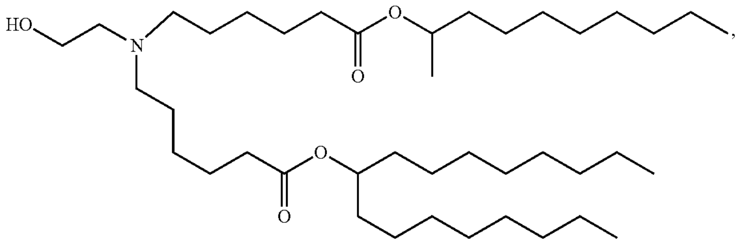

-continued
(Compound 90)
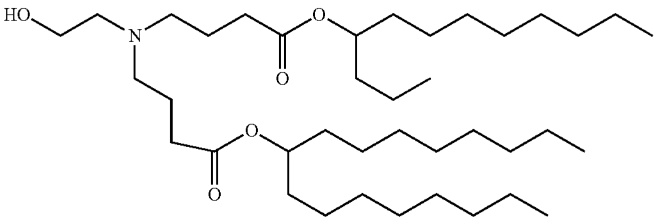
(Compound 91)
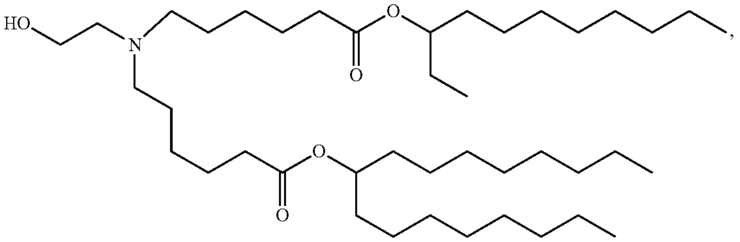
(Compound 92)
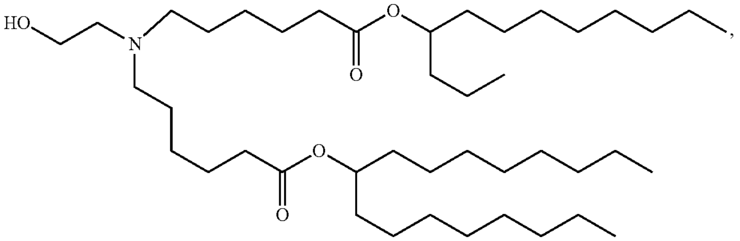
(Compound 93)
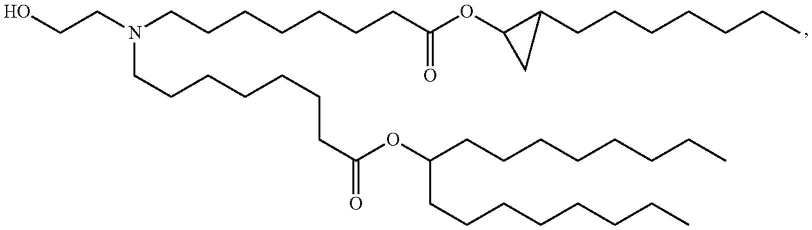
(Compound 96)
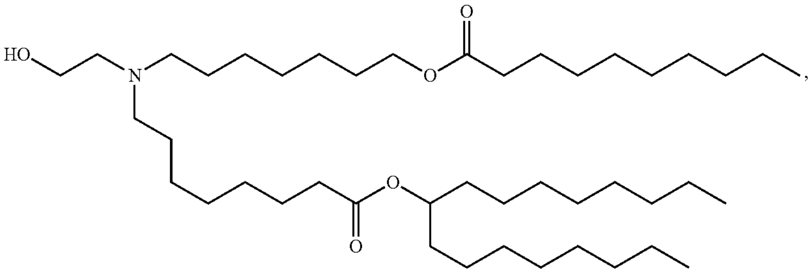
(Compound 97)
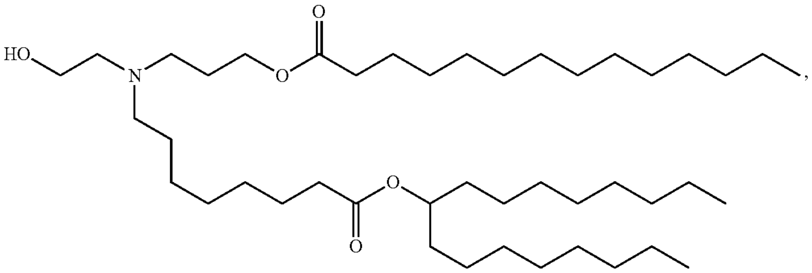

-continued
(Compound 104)
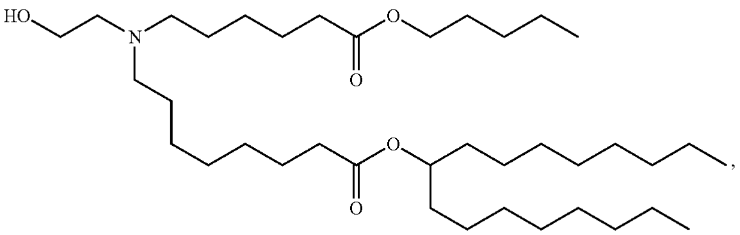
(Compound 105)
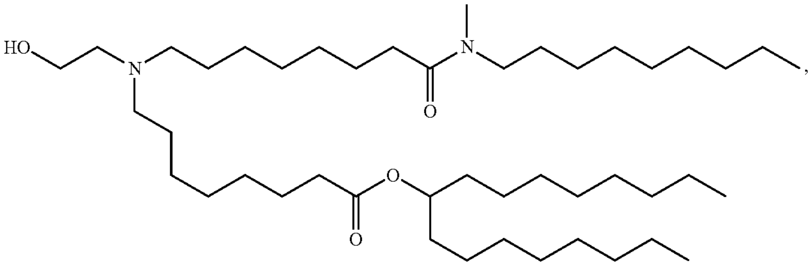
(Compound 110)
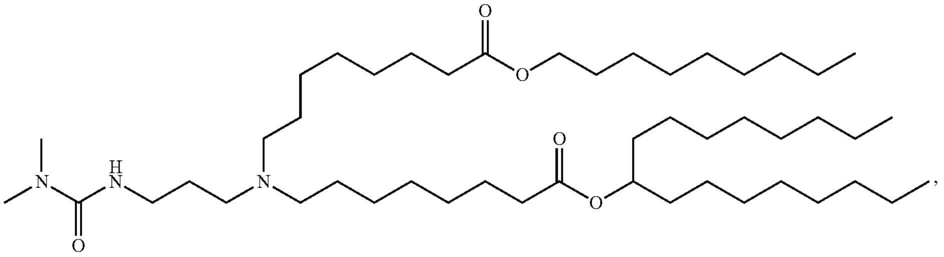
(Compound 111)
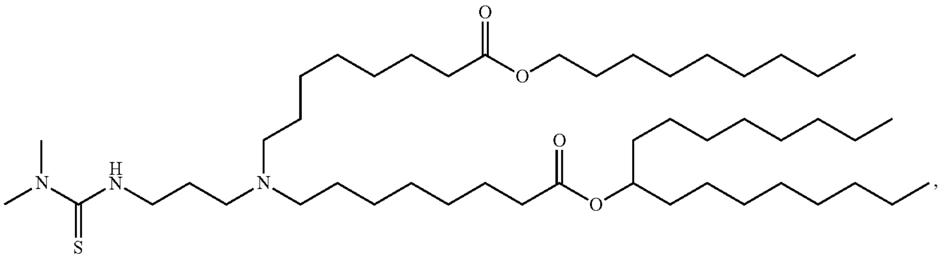
(Compound 112)
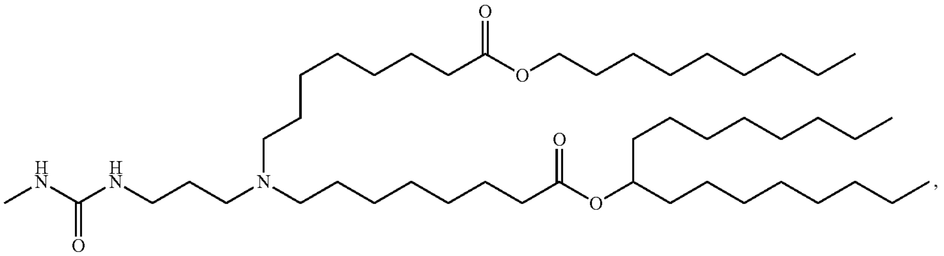
(Compound 113)
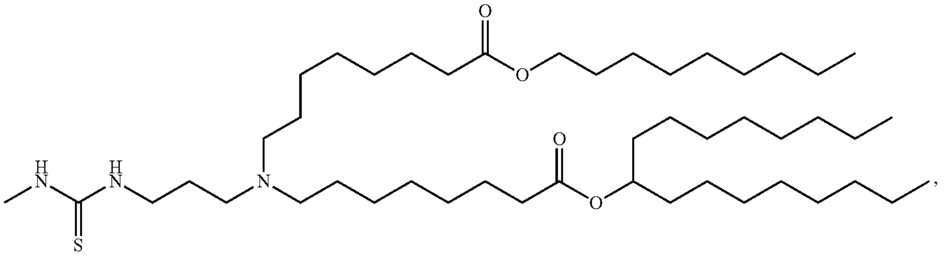

-continued
(Compound 119)
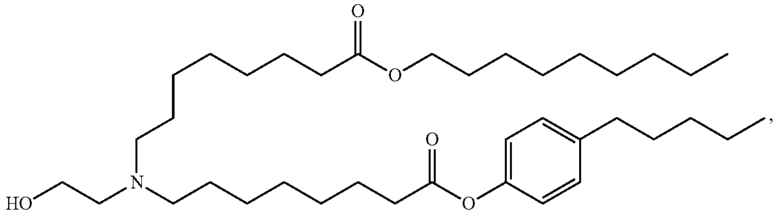
,
(Compound 120)
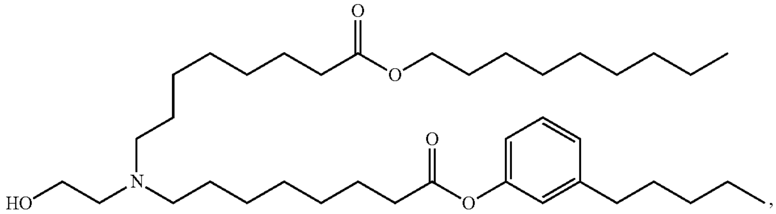
,
(Compound 122)
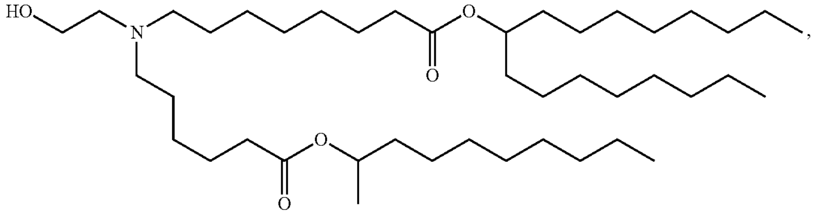
,
(Compound 123)
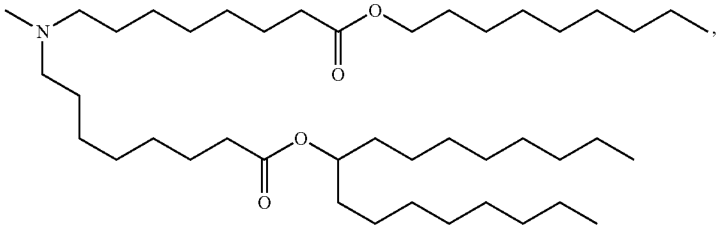
,
(Compound 124)
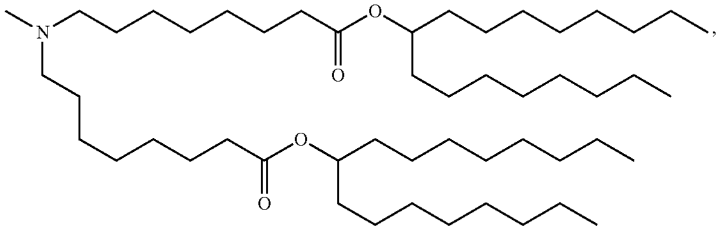
,
(Compound 126)
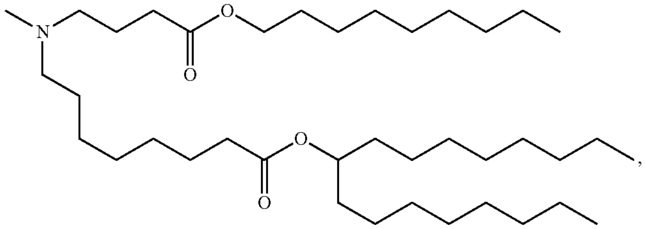
,
(Compound 127)
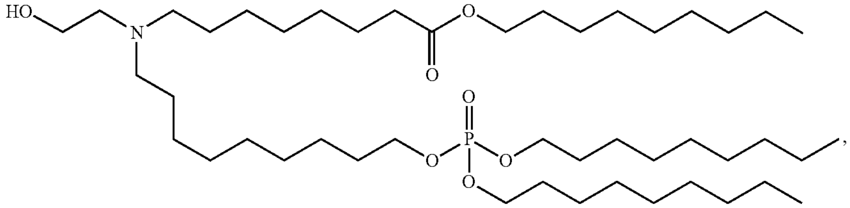
, -continued
(Compound 129)
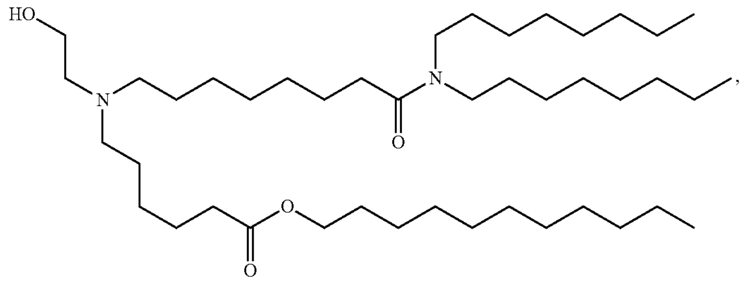
(Compound 130)
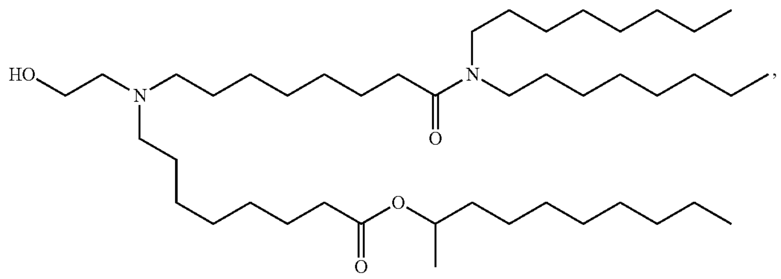
(Compound 131)
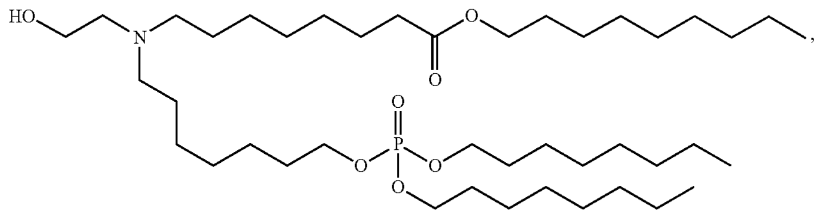
(Compound 132)
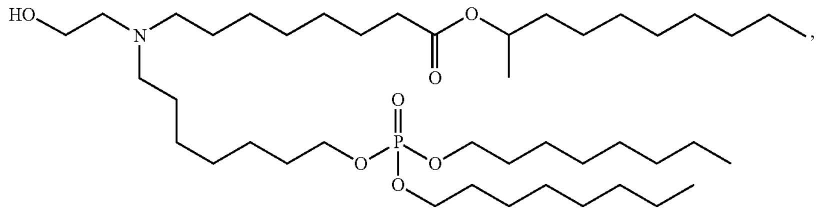
(Compound 133)
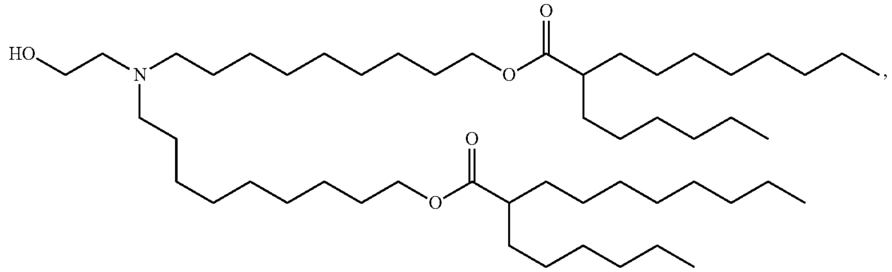
(Compound 134)
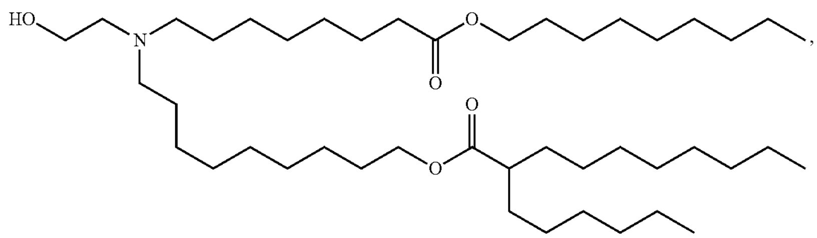

-continued
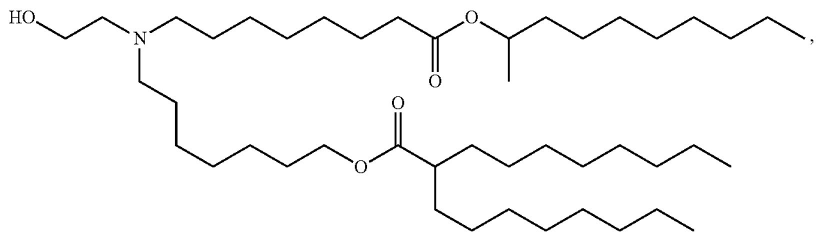
(Compound 135)
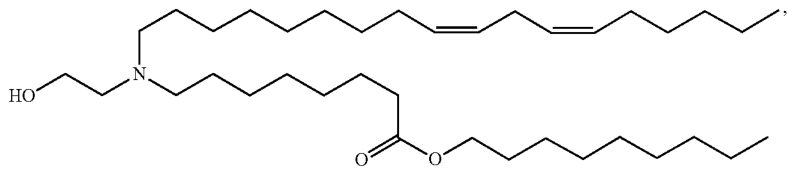
(Compound 136)
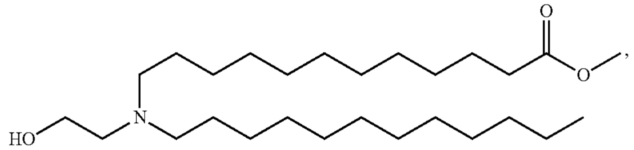
(Compound 137)
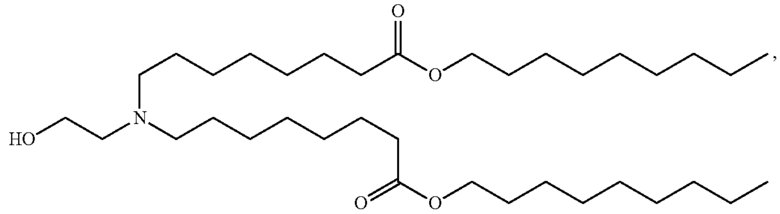
(Compound 138)
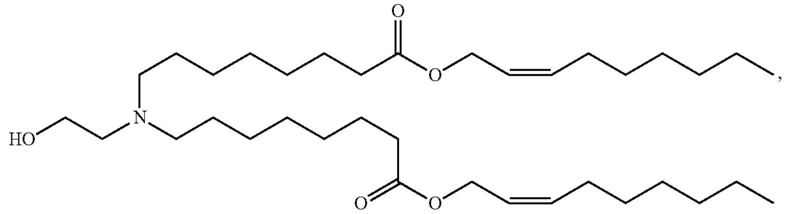
(Compound 139)
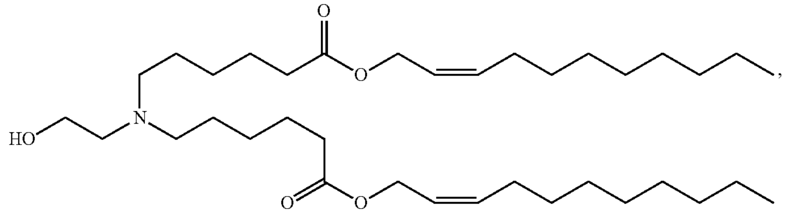
(Compound 140)
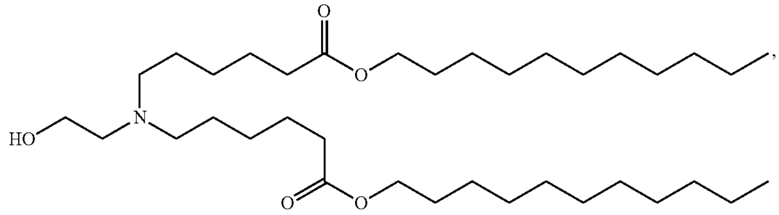
(Compound 141)

-continued
(Compound 142)
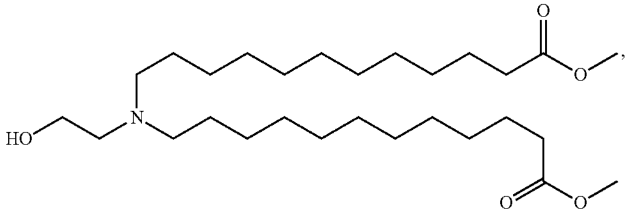
(Compound 143)
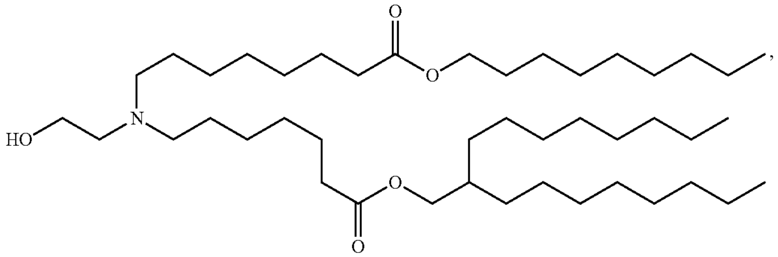
(Compound 144)
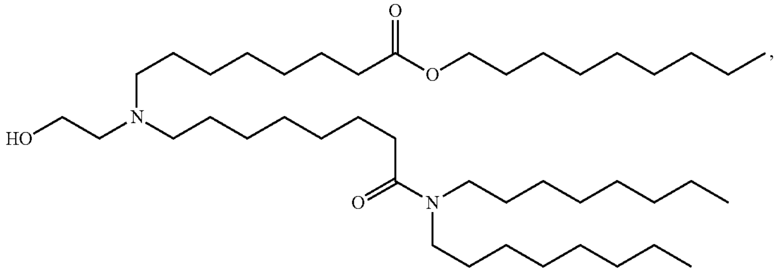
(Compound 145)
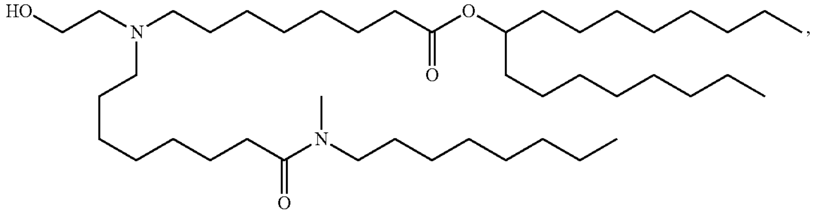
(Compound 146)
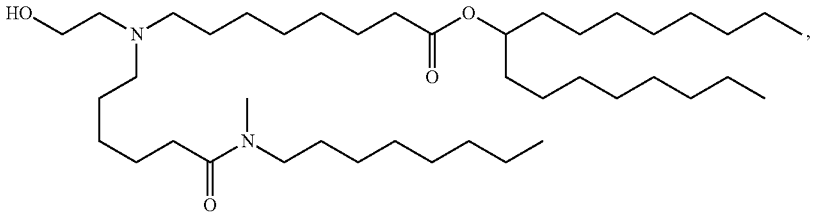
(Compound 147)
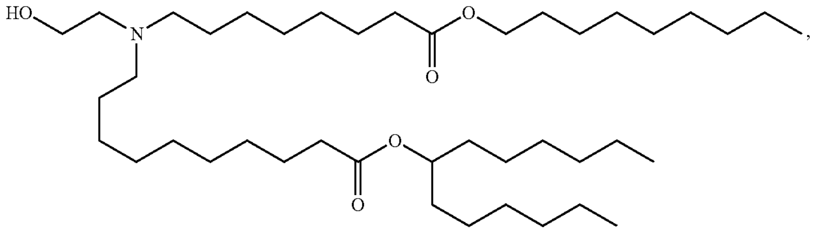

-continued
(Compound 149)
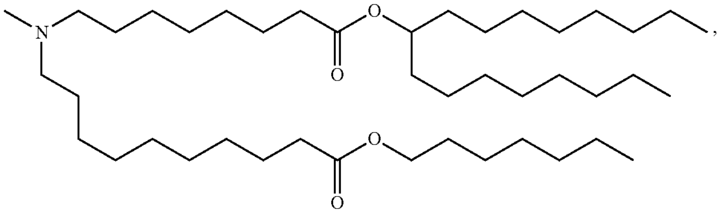
(Compound 150)
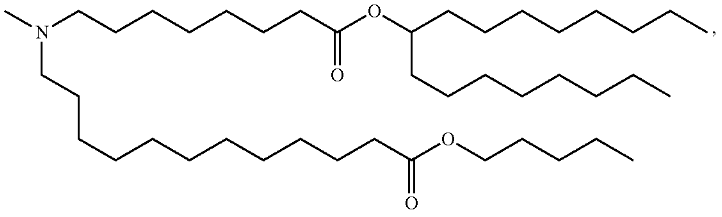
(Compound 151)
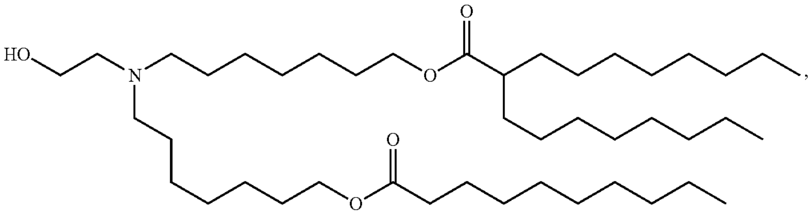
(Compound 153)
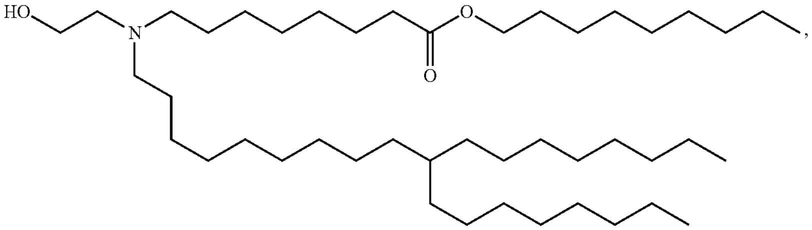
(Compound 154)
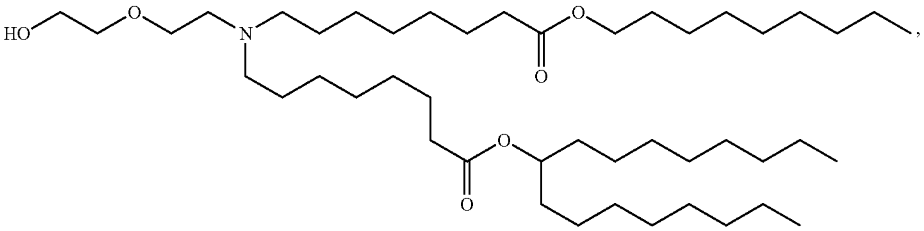
(Compound 155)
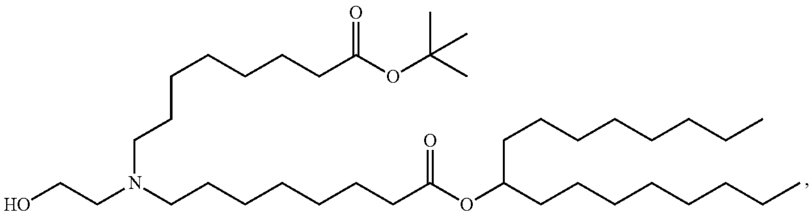
(Compound 158)
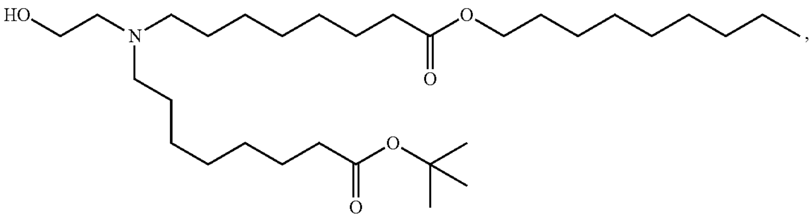

-continued
(Compound 166)
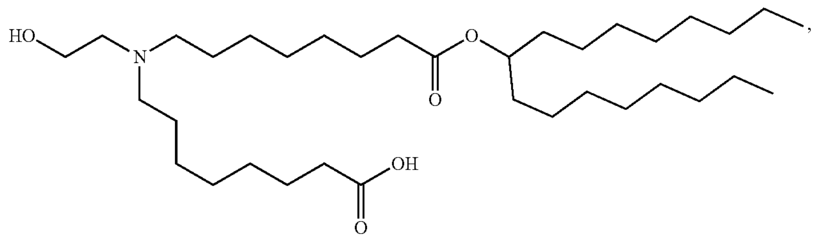
(Compound 167)
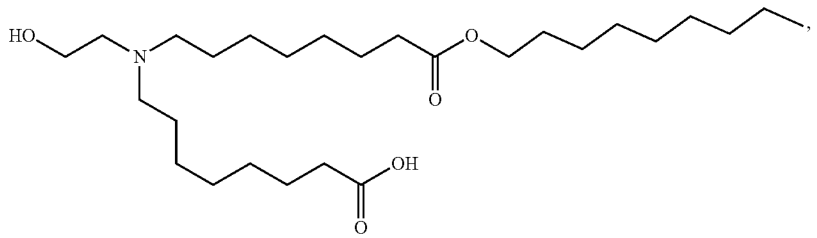
(Compound 172)
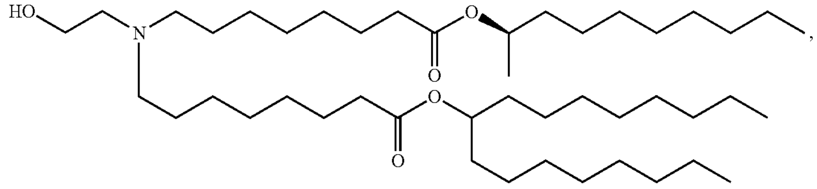
(Compound 184)
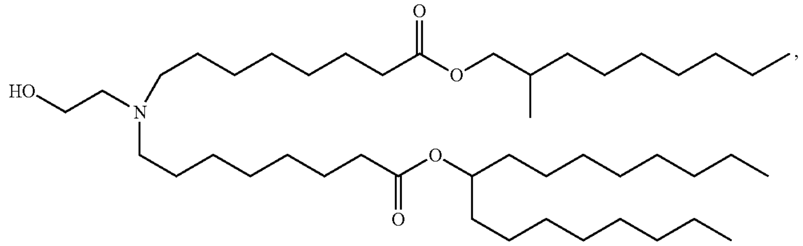
(Compound 185)
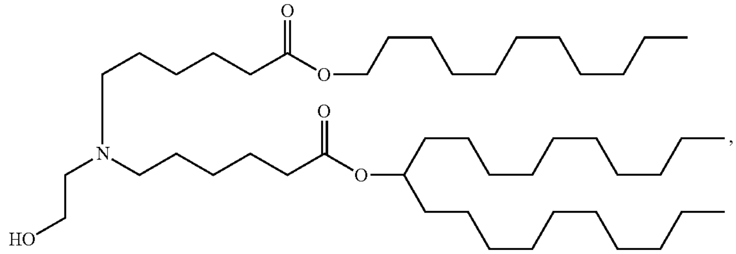
(Compound 186)
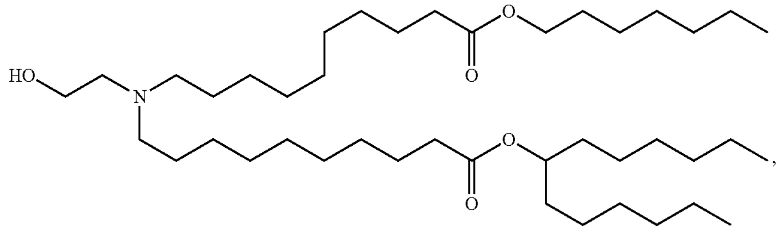

-continued (Compound 188)

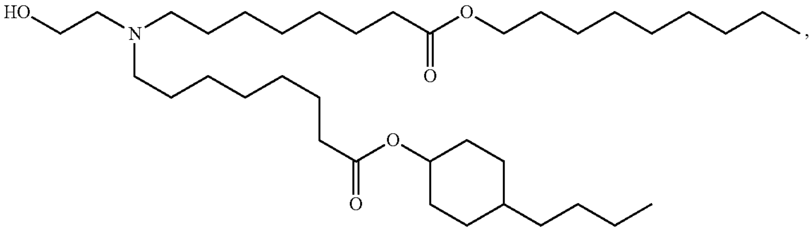

(Compound 189)

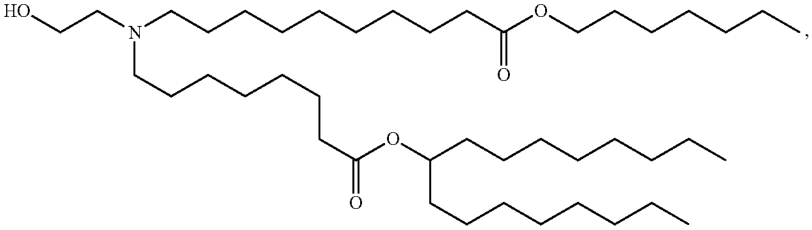

(Compound 191)

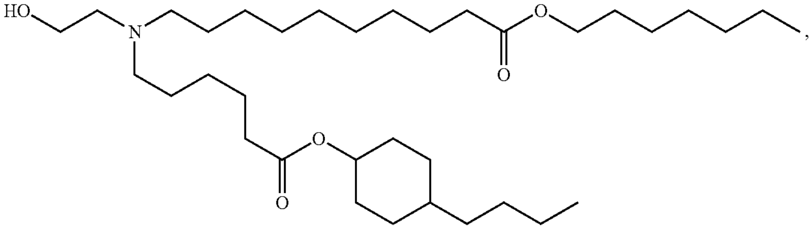

(Compound 232)

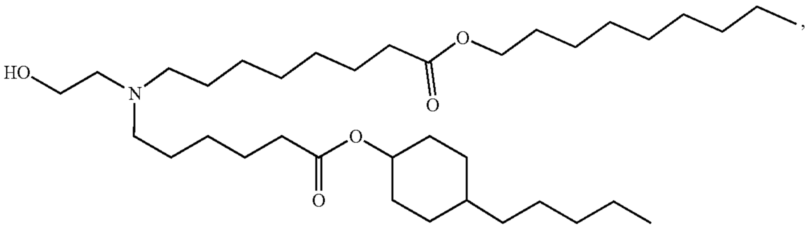

or a salt or stereoisomer thereof, wherein the lipid nanoparticle comprises an mRNA that comprises an open reading frame (ORF) encoding a lipoprotein lipase (LPL) polypeptide.

8. The pharmaceutical composition of claim 1, wherein the compound is (Compound 18)

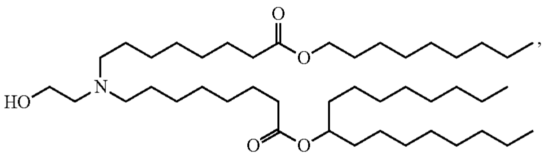

or a salt thereof.

9. A method of treating hyperlipidemia in a human subject in need thereof, comprising administering to the human subject a therapeutically effective amount of the pharmaceutical composition of claim 1.

10. The method of claim 9, wherein the pharmaceutical composition when administered as a single intravenous dose is sufficient to:

(i) reduce the subject's plasma lipids at least 2-fold, at least 5-fold, at least 10-fold, at least 20-fold or at least 50-fold as compared to a reference starting level for at least 24 hours, at least 48 hours, at least 72 hours, at least 96 hours, or at least 120 hours post-administration;

(ii) reduce the subject's plasma lipids at least 30%, least 25%, at least 20%, at least 10%, at least 5% or at least 15% as compared to a baseline reference starting level for at least 24 hours, at least 48 hours, at least 72 hours, at least 96 hours, or at least 120 hours post-administration;

(iii) increase serum levels of:

(a) ApoB to within least at 10-fold, at least within 5-fold, at least within 2-fold, or at least within 1.5-fold as compared to a normal ApoB serum level within at least 24 hours, at least 48 hours, at least 72 hours, at least 96 hours, or at least 120 hours post-administration, or (b) high-density lipoprotein cholesterol (HDLc) or HDL to within at least 10-fold, at least within 5-fold, at least within 2-fold, or at least within 1.5-fold, as compared to a normal HDLc or HDL serum level, for at least 24 hours, at least 48 hours, at least 72 hours, at least 96 hours, or at least 120 hours post-administration;

(iv) maintain serum LPL activity levels at a normal physiological level or a supraphysiological level for at least 24 hours, at least 48 hours, at least 72 hours, at least 96 hours, or at least 120 hours post-administration, and/or (v) increase and maintain serum LPL activity levels at 10% or more than the baseline reference serum LPL activity level for at least 24 hours, at least 48 hours, at least 72 hours, or at least 96 hours post-administration.

11. The pharmaceutical composition of claim 1, wherein the lipid nanoparticle comprises Compound 18, DSPC, Cholesterol, and Compound 428, wherein Compound 18 is

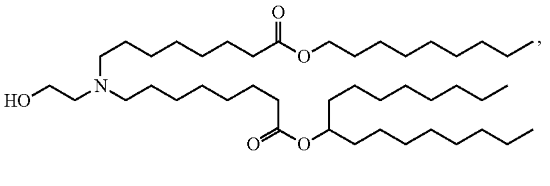 [SMILES: CCCCCCCCCOC(=O)CCCCCCCN(CCO)CCCCCCCC(=O)OC(CCCCCCCC)CCCCCCCC]

and wherein Compound 428 is

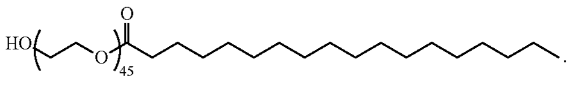

12. The pharmaceutical composition of claim 1, wherein the lipid nanoparticle comprises from about 45 mol % to about 55 mol % of ionizable lipid.

13. The pharmaceutical composition of claim 1, wherein the lipid nanoparticle comprises from about 35 mol % to about 40 mol % of structural lipid.

14. The pharmaceutical composition of claim 1, wherein the lipid nanoparticle comprises from about 2 mol % to about 4 mol % of PEG lipid.

15. A method of reducing plasma lipid levels in a human subject in need thereof, comprising administering to the human subject an effective amount of the pharmaceutical composition of claim 1.

16. A method of increasing serum LPL activity in a human subject in need thereof, comprising administering to the human subject an effective amount of the pharmaceutical composition of claim 1.

17. The method of claim 9, wherein the human subject has a LPL deficiency.

18. A method of reducing plasma lipid levels in a human subject in need thereof, comprising administering to the human subject an effective amount of the pharmaceutical composition of claim 3.

19. A method of increasing serum LPL activity in a human subject in need thereof, comprising administering to the human subject an effective amount of the pharmaceutical composition of claim 3.

20. A method of treating hyperlipidemia in a human subject in need thereof, comprising administering to the human subject a therapeutically effective amount of the pharmaceutical composition of claim 3.

21. The method of claim 20, wherein the human subject has a LPL deficiency.

22. A method of reducing plasma lipid levels in a human subject in need thereof, comprising administering to the human subject an effective amount of the pharmaceutical composition of claim 8.

23. A method of increasing serum LPL activity in a human subject in need thereof, comprising administering to the human subject an effective amount of the pharmaceutical composition of claim 8.

24. A method of treating hyperlipidemia in a human subject in need thereof, comprising administering to the human subject a therapeutically effective amount of the pharmaceutical composition of claim 8.

25. The method of claim 24, wherein the human subject has a LPL deficiency.

26. A method of reducing plasma lipid levels in a human subject in need thereof, comprising administering to the human subject an effective amount of the pharmaceutical composition of claim 11.

27. A method of increasing serum LPL activity in a human subject in need thereof, comprising administering to the human subject an effective amount of the pharmaceutical composition of claim 11.

28. A method of treating hyperlipidemia in a human subject in need thereof, comprising administering to the human subject a therapeutically effective amount of the pharmaceutical composition of claim 11.

29. The method of claim 28, wherein the human subject has a LPL deficiency.

30. The pharmaceutical composition of claim 1, wherein the LPL polypeptide comprises SEQ ID NO:1.

31. The pharmaceutical composition of claim 1, wherein the LPL polypeptide comprises SEQ ID NO:1.

32. The pharmaceutical composition of claim 3, wherein the LPL polypeptide comprises SEQ ID NO:1.

33. The pharmaceutical composition of claim 7, wherein the LPL polypeptide comprises SEQ ID NO:1.

34. The pharmaceutical composition of claim 8, wherein the LPL polypeptide comprises SEQ ID NO:1.

35. The pharmaceutical composition of claim 11, wherein the LPL polypeptide comprises SEQ ID NO:1.

36. The method of claim 9, wherein the LPL polypeptide comprises SEQ ID NO:1.

37. The method of claim 15, wherein the LPL polypeptide comprises SEQ ID NO:1.

38. The method of claim 16, wherein the LPL polypeptide comprises SEQ ID NO:1.

39. The method of claim 17, wherein the LPL polypeptide comprises SEQ ID NO:1.

40. The method of claim 18, wherein the LPL polypeptide comprises SEQ ID NO:1.

41. The method of claim 19, wherein the LPL polypeptide comprises SEQ ID NO:1.

42. The method of claim 20, wherein the LPL polypeptide comprises SEQ ID NO:1.

43. The method of claim 21, wherein the LPL polypeptide comprises SEQ ID NO:1.

44. The method of claim 22, wherein the LPL polypeptide comprises SEQ ID NO:1.

45. The method of claim 23, wherein the LPL polypeptide comprises SEQ ID NO:1.

46. The method of claim 24, wherein the LPL polypeptide comprises SEQ ID NO:1.

47. The method of claim 25, wherein the LPL polypeptide comprises SEQ ID NO:1.

48. The method of claim 26, wherein the LPL polypeptide comprises SEQ ID NO:1.

49. The method of claim 27, wherein the LPL polypeptide comprises SEQ ID NO:1.

50. The method of claim 28, wherein the LPL polypeptide comprises SEQ ID NO:1.

51. The method of claim 29, wherein the LPL polypeptide comprises SEQ ID NO:1.

52. The pharmaceutical composition of claim 1, wherein the compound is of Formula (IIa), (IIb), (IIc), or (IIe):

(IIa)

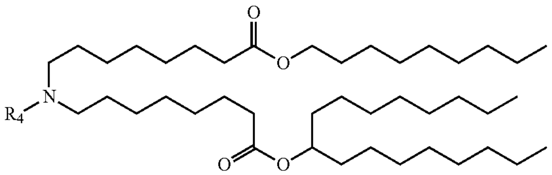

, (IIb)

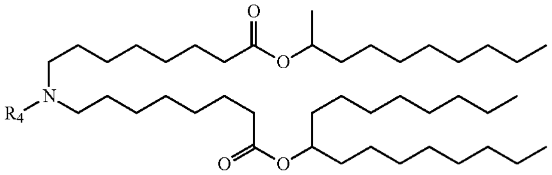

, (IIc)

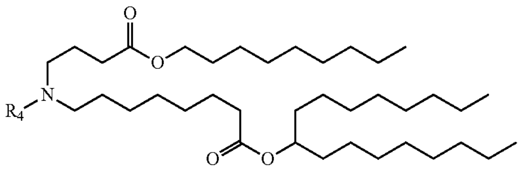

, or (IIe)

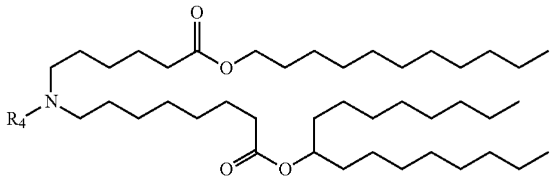

, or a salt or stereoisomer thereof.

53. The pharmaceutical composition of claim 1, wherein the lipid nanoparticle further comprises a phospholipid, a structural lipid, and a PEG lipid.

54. The pharmaceutical composition of claim 53, wherein the phospholipid is selected from:

1,2-dilinoleoyl-sn-glycero-3-phosphocholine (DLPC),
1,2-dimyristoyl-sn-glycero-phosphocholine (DMPC),
1,2-dioleoyl-sn-glycero-3-phosphocholine (DOPC),
1,2-dipalmitoyl-sn-glycero-3-phosphocholine (DPPC),
1,2-distearoyl-sn-glycero-3-phosphocholine (DSPC),
1,2-diundecanoyl-sn-glycero-phosphocholine (DUPC),
1-palmitoyl-2-oleoyl-sn-glycero-3-phosphocholine (POPC),
1,2-di-O-octadecenyl-sn-glycero-3-phosphocholine (18:0 Diether PC),
1-oleoyl-2-cholesterylhemisuccinoyl-sn-glycero-3-phosphocholine (OChemsPC),
1-hexadecyl-sn-glycero-3-phosphocholine (C16 Lyso PC),
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine,
1,2-dioleoyl-sn-glycero-3-phosphoethanolamine (DOPE),
1,2-diphytanoyl-sn-glycero-3-phosphoethanolamine (ME 16:0 PE),
1,2-distearoyl-sn-glycero-3-phosphoethanolamine,
1,2-dilinoleoyl-sn-glycero-3-phosphoethanolamine,
1,2-dilinolenoyl-sn-glycero-3-phosphoethanolamine,
1,2-diarachidonoyl-sn-glycero-3-phosphoethanolamine,
1,2-didocosahexaenoyl-sn-glycero-3-phosphoethanolamine,
1,2-dioleoyl-sn-glycero-3-phospho-rac-(1-glycerol) sodium salt (DOPG),
sphingomyelin, and any mixtures thereof.

55. The pharmaceutical composition of claim 53, wherein the structural lipid is selected from cholesterol, fecosterol, sitosterol, ergosterol, campesterol, stigmasterol, brassicasterol, tomatidine, ursolic acid, alpha-tocopherol, and any mixtures thereof.

* * * * *